(12) United States Patent
Mohammadi et al.

(10) Patent No.: US 10,174,090 B2
(45) Date of Patent: Jan. 8, 2019

(54) FGF21 PROTEIN WITH ENHANCED BINDING AFFINITY FOR β-KLOTHO FOR THE TREATMENT OF TYPE II DIABETES, OBESITY, AND RELATED METABOLIC DISORDERS

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/283,862

(22) Filed: Oct. 3, 2016

(65) Prior Publication Data

US 2017/0096462 A1 Apr. 6, 2017

Related U.S. Application Data

(63) Continuation of application No. 13/784,289, filed on Mar. 4, 2013, now Pat. No. 9,475,856.

(60) Provisional application No. 61/605,961, filed on Mar. 2, 2012.

(51) Int. Cl.
| | |
|---|---|
| A61K 38/18 | (2006.01) |
| C07K 14/50 | (2006.01) |
| A61K 45/06 | (2006.01) |
| G01N 33/74 | (2006.01) |
| A61K 38/00 | (2006.01) |

(52) U.S. Cl.
CPC .......... *C07K 14/50* (2013.01); *A61K 38/1825* (2013.01); *A61K 45/06* (2013.01); *G01N 33/74* (2013.01); *A61K 38/00* (2013.01); *C07K 2319/00* (2013.01); *C07K 2319/21* (2013.01); *G01N 2333/50* (2013.01); *G01N 2500/02* (2013.01); *G01N 2800/042* (2013.01)

(58) Field of Classification Search
None
See application file for complete search history.

(56) References Cited

U.S. PATENT DOCUMENTS

| | | |
|---|---|---|
| 5,132,408 A | 7/1992 | Baird et al. |
| 5,478,804 A | 12/1995 | Calabresi et al. |
| 5,656,458 A | 8/1997 | Barr |
| 6,326,484 B1 | 12/2001 | Gage et al. |
| 6,982,170 B1 | 1/2006 | Maciag et al. |
| 7,491,697 B2 | 2/2009 | Beals et al. |
| 7,582,607 B2 | 9/2009 | Frye et al. |
| 7,622,445 B2 | 11/2009 | Frye et al. |
| 7,655,627 B2 | 2/2010 | Frye et al. |
| 7,956,033 B2 | 6/2011 | Cheng et al. |
| 8,168,591 B2 | 5/2012 | Takada et al. |
| 8,642,546 B2 | 2/2014 | Belouski et al. |
| 8,889,426 B2 | 11/2014 | Mohammadi et al. |
| 8,889,621 B2 | 11/2014 | Mohammadi et al. |
| 8,906,854 B2 | 12/2014 | Jonker et al. |
| 8,951,966 B2 | 2/2015 | Ling et al. |
| 8,999,929 B2 | 4/2015 | Mohammadi et al. |
| 9,072,708 B2 | 7/2015 | Jonker et al. |
| 9,272,017 B2 | 3/2016 | Mohammadi et al. |
| 9,464,126 B2 | 10/2016 | Mohammadi et al. |
| 9,474,785 B2 | 10/2016 | Mohammadi et al. |
| 9,475,856 B2 | 10/2016 | Mohammadi et al. |
| 9,550,820 B2 | 1/2017 | Mohammadi et al. |
| 9,657,075 B2 | 5/2017 | Mohammadi et al. |
| 9,907,830 B2 | 3/2018 | Mohammadi et al. |
| 9,926,355 B2 | 3/2018 | Mohammadi et al. |
| 9,926,356 B2 | 3/2018 | Mohammadi et al. |
| 2004/0259780 A1 | 12/2004 | Glasebrook et al. |
| 2007/0142278 A1 | 6/2007 | Beals et al. |
| 2007/0237768 A1 | 10/2007 | Glaesner et al. |
| 2007/0265200 A1 | 11/2007 | Glaesner et al. |
| 2007/0293430 A1 | 12/2007 | Frye et al. |
| 2007/0299007 A1 | 12/2007 | Frye et al. |
| 2008/0103096 A1 | 5/2008 | Frye et al. |

(Continued)

FOREIGN PATENT DOCUMENTS

| | | |
|---|---|---|
| EP | 0 645 451 B1 | 8/2001 |
| WO | WO 2011/047267 A1 | 4/2011 |

(Continued)

OTHER PUBLICATIONS

Office Action for U.S. Appl. No. 15/598,420 dated Jul. 5, 2018.
Yie et al., "FGF21 N- and C-Termini Play Different Roles in Receptor Interaction and Activation," FEBS Lett. 583:19-24 (2009).
Andrukhova et al., "FGF23 Acts Directly on Renal Proximal Tubules to Induce Phosphaturia Through Activation of the ERK1/2-SGK1 Signaling Pathway," Bone 51(3):621-8 (Jun. 12, 2012).
Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).
Jonker et al., "A PPARgamma-FGF1 Axis Is Required for Adaptive Adipose Remodelling and Metabolic Homeostasis," Nature 485(7398):391-394 (Apr. 22, 2012).

(Continued)

*Primary Examiner* — Christine J Saoud
(74) *Attorney, Agent, or Firm* — LeClairRyan PLLC

(57) ABSTRACT

The present invention relates to chimeric proteins that include an N-terminus coupled to a C-terminus, where the N-terminus includes an N-terminal portion of fibroblast growth factor 21 ("FGF21") and the C-terminus includes a C-terminal portion of fibroblast growth factor 19 ("FGF19"). The present invention also relates to pharmaceutical compositions including chimeric proteins according to the present invention, as well as methods for treating a subject suffering from diabetes, obesity, or metabolic syndrome, methods of treating a subject in need of increased FGF21-βKlotho-FGF receptor complex formation, methods of causing increased FGF21 receptor agonist-βKlotho-FGF receptor complex formation, and methods of screening for compounds with enhanced binding affinity for the βKlotho-FGF receptor complex involving the use of chimeric proteins of the present invention.

32 Claims, 18 Drawing Sheets

Specification includes a Sequence Listing.

(56) References Cited

U.S. PATENT DOCUMENTS

| | | |
|---|---|---|
| 2008/0255045 A1 | 10/2008 | Cujec et al. |
| 2008/0261875 A1 | 10/2008 | Etgen et al. |
| 2009/0111742 A1 | 4/2009 | Kharitonenkov et al. |
| 2009/0118190 A1 | 5/2009 | Beals et al. |
| 2009/0305986 A1 | 12/2009 | Belouski et al. |
| 2010/0062984 A1 | 3/2010 | Kumar et al. |
| 2010/0158914 A1 | 6/2010 | Desnoyers |
| 2010/0184665 A1 | 7/2010 | Suzuki et al. |
| 2010/0216715 A1 | 8/2010 | Tagmose et al. |
| 2010/0285131 A1 | 11/2010 | Belouski et al. |
| 2010/0286042 A1 | 11/2010 | Imamura et al. |
| 2010/0323954 A1 | 12/2010 | Li et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0172401 A1 | 7/2011 | Cujec et al. |
| 2011/0190207 A1 | 8/2011 | Mohammadi et al. |
| 2011/0195077 A1 | 8/2011 | Gass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0184211 A1 | 7/2013 | Mohammadi et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0111821 A1 | 4/2015 | Suh et al. |
| 2015/0343022 A1 | 12/2015 | Jonker et al. |
| 2016/0206695 A1 | 7/2016 | Suh et al. |
| 2017/0029480 A1 | 2/2017 | Mohammadi et al. |
| 2017/0101449 A1 | 4/2017 | Mohammadi et al. |
| 2017/0226172 A1 | 8/2017 | Mohammadi et al. |
| 2017/0355738 A1 | 12/2017 | Mohammadi et al. |
| 2018/0186849 A1 | 7/2018 | Mohammadi et al. |
| 2018/0186850 A1 | 7/2018 | Mohammadi et al. |

FOREIGN PATENT DOCUMENTS

| | | |
|---|---|---|
| WO | WO 2011/130729 A2 | 10/2011 |
| WO | WO 2013/184958 A1 | 12/2013 |
| WO | WO 2013/184960 A2 | 12/2013 |
| WO | WO 2013/184962 A1 | 12/2013 |
| WO | WO 2015/149069 A1 | 10/2015 |

OTHER PUBLICATIONS

Wu et al., "A Unique FGF23 With the Ability to Activate FGFR Signaling Through Both alphaKlotho and betaKlotho," J. Mol. Biol. 418:82-89 (2012).
Beenken & Mohammadi, "The Structural Biology of the FGF19 Subfamily," Adv. Exp. Med. Biol. 728:1-24 (2012).
Wu et al., "C-Terminal Tail of FGF19 Determines its Specificity Toward Klotho Co-Receptors," J. Biol. Chem. 283(48):33304-33309 (2008).
Goetz et al., "Conversion of a Paracrine Fibroblast Growth Factor Into an Endocrine Fibrobalst Growth Factor," J. Biol. Chem. 287(34):29134-29146 (Jun. 25, 2012).
Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).
Olsen et al., "Insights Into the Molecular Basis for Fibroblast Growth Factor Receptor Autoinhibition and Ligand-Binding Promiscuity," Proc. Nat'l. Acad. Sci. USA 101(4):935-940 (2004).
Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).
Wu et al., "Separating Mitogenic and Metabolic Activities of Fibroblast Growth Factor 19 (FGF19)," Proc. Nat'l. Acad. Sci. USA 107(32):14158-14163 (2010).
Wu et al., "FGF19-Induced Hepatocyte Proliferation Is Mediated Through FGFR4 Activation," J. Biol. Chem. 285(8):5165-5170 (2009).
Zhang et al., "Receptor Specificity of the Fibroblast Growth Factor Family," J. Biol. Chem. 281(23):15694-15700 (2006).
PCT Search Report and Written Opinion for PCT/US2013/028888 (dated Jul. 23, 2013).
Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).
Zakrzewska et al., "Increased Protein Stability of FGF1 Can Compensate for its Reduced Affinity for Heparin," J. Biol. Chem. 284(37):25388-403 (2009).
Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780(12):1432-40 (2008).
Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).
Kharitonenkov et al., "The Metabolic State of Diabetic Monkeys is Regulated by Fibroblast Growth Factor-21," Endocrinology 148(2):774-81 (2007).
Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).
Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).
Goetz et al., "Molecular Insights Into the Klotho-Dependent, Endocrine Mode of Action of Fibroblast Growth Factor 19 Subfamily Members," Mol. Cell. Biol. 27(9):3417-3428 (2007).
Beenken, "Structural and Biochemical Studies of FGF-FGFR Complexes," Thesis (Sep. 2011).
Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).
Wu et al., "FGF19 Regulates Cell Proliferation, Glucose and Bile Acid Metabolism Via FGFR4-Dependent and Independent Pathways," PLoS One 6(3):e17868 (Mar. 8, 2011).
Wu et al., "Selective Activation of FGFR4 by an FGF19 Variant Does Not Improve Glucose Metabolism in OB/OB Mice," Proc. Nat'l. Acad. Sci U.S.A. 106(34):14379-84 (2009).
Mohammadi et al., "Structural Basis for Fibroblast Growth Factor Receptor Activation," Cytokine & Growth Factor Reviews 16:107-137 (2005).
Hutley et al., "Fibroblast Growth Factor 1: A Key Regulator of Human Adipogenesis," Diabetes 53:3097-3106 (2004).
Imamura et al., "Recovery of Mitogenic Activity of a Growth Factor Mutant with Nuclear Translocation Sequence," Science 249:1567-1570 (Sep. 28, 1990).
International Search Report and Written Opinion for PCT/US13/44589 (dated Nov. 13, 2013).
International Search Report and Written Opinion for PCT/US13/44594 (dated Nov. 13, 2013).
International Search Report and Written Opinion for PCT/US13/44592 (dated Jan. 17, 2014).
Restriction Requirement for U.S. Appl. No. 13/838,350 (dated Jan. 30, 2014).
Restriction Requirement in U.S. Appl. No. 14/176,992 (dated Mar. 7, 2014).
Office Action in U.S. Appl. No. 13/641,451 (dated Dec. 16, 2013).
Office Action in U.S. Appl. No. 14/176,992 (dated Jun. 26, 2014).

(56) References Cited

OTHER PUBLICATIONS

International Search Report and Written Opinion for PCT/US14/17367 (dated Jun. 18, 2014).
Razzaque, "The FGF23-Klotho Axis: Endocrine Regulation of Phosphate Homeostasis," Nat. Rev. Endocrinol. 5(11):611-19 (2009).
Restriction Requirement in U.S. Appl. No. 13/837,880 (dated Sep. 3, 2014).
Restriction Requirement in U.S. Appl. No. 13/839,051 (dated Sep. 3, 2014).
Office Action in U.S. Appl. No. 13/838,350 (dated Jul. 17, 2014).
Restriction Requirement in U.S. Appl. No. 14/097,056 (dated Aug. 14, 2014).
Office Action in U.S. Appl. No. 13/839,051 (dated Dec. 11, 2014).
Office Action in U.S. Appl. No. 13/838,350 (dated Dec. 11, 2014).
Restriction Requirement in U.S. Appl. No. 13/837,880 (dated Dec. 11, 2014).
Office Action in U.S. Appl. No. 13/837,880, 11 pages (dated Aug. 4, 2015).
Office Action in U.S. Appl. No. 13/839,051, 11 pages (dated Aug. 6, 2015).
Office Action in U.S. Appl. No. 13/838,350, 11 pages (dated Aug. 3, 2015).
Restriction Requirement in U.S. Appl. No. 14/097,116, 9 pages (dated Dec. 11, 2014).
Restriction Requirement in U.S. Appl. No. 14/185,366, 9 pages (dated Jun. 4, 2015).
Office Action in U.S. Appl. No. 14/185,366, 10 pages (dated Jan. 15, 2016).
Abraham et al., "Human Basic Fibroblast Growth Factor: Nucleotide Sequence and Genomic Organization," *EMBO J.* 10:2523-2528 (1986).
Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).
Kurosu et al., "The Klotho Gene Family as a Regulator of Endocrine Fibroblast Growth Factors," Mol Cel Endocrin. 299:72-78 (2009).
Ono et al., "Novel Regulation of Fibroblast Growth Factor 2 (FGF2)-Mediated Cell Growth by Polysialic Acid," J. Biol. Chem. 287(6):3710-3722 (2012).
Schlessinger et al., "Crystal Structure of a Ternary FGF-FGFR-Heparin Complex Reveals a Dual Role for Heparin in FGFR Binding and Dimerization," Molecular Cell 6:743-750 (2000).
Thompson et al., "Energetic Characterization of the Basic Fibroblast Growth Factor-Heparin Interaction: Identification of the Heparin Binding Domains," Biochemistry 33:3831-3840 (1994).
Suh et al., "Endocrinization of FGF1 Produces a Neomorphic and Potent Insulin Sensitizer," Author Manuscript, Nature 513(7518):436-439 (2014).
Beenken et al., "The FGF Family: Biology, Pathophysiology and Therapy," Nat Rev Drug Discov. 8(3):235-53 (Mar. 2009).
Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).
Micanovic et al., "Different Roles of N- and C-Termini in the Functional Activity of FGF21," J. Cell. Physiol. 219:227-234 (2009).
Kharitonenkov et al.,"FGF-21/FGF-21 Receptor Interaction and Activation is Determined by βKlotho," J. Cell. Physiol. 215:1-7 (2008).
Yao et al., "Expression and Pharmacological Evaluation of Fusion Protein FGF21-L-Fc," Acta Pharmaceutica Sinica 46(7):787-92 (2011) (Abstract in English).
Extended European Search Report for European Application No. 13799858.9, 13 pages (dated May 3, 2016).
Office Action in U.S. Appl. No. 13/839,051 (dated May 25, 2016).
Patent Examination Report in Australian Patent Application No. 2014274604 (dated Oct. 16, 2015).
Office Action for Chinese Patent Application No. 201380039848.9 (dated Oct. 8, 2016) (Translation in English).
Pellegrini et al., "Crystal Structure of Fibroblast Growth Factor Receptor Ectodomain Bound to Ligand and Heparin," Nature 407:1029-1034 (2000).
Pellegrini et al., Protein Data Bank, 1E0O, "Crystal Structure of a Ternary FGF1-FGFR2-Heparin Complex," (Released Oct. 23, 2000).
Restriction Requirement in U.S. Appl. No. 13/784,289 (dated Sep. 3, 2014).
Office Action in U.S. Appl. No. 13/784,289 (dated Mar. 4, 2015).
Office Action in U.S. Appl. No. 13/784,289 (dated Nov. 5, 2015).
Second Office Action for Chinese Patent Application No. 201380039848.9 (dated Jun. 8, 2017).
Office Action in U.S. Appl. No. 15/289,447 (dated Jun. 16, 2017).
DiGabriele et al., "Structure of a Heparin-Linked Biologically Active Dimer of Fibroblast Growth Factor," Nature 393(6687):812-7 (1998).
Office Action in U.S. Appl. No. 15/289,544 (dated May 30, 2017).
Crumley et al., Genbank Accession No. 1605206A, acidic fibroblast growth factor (1996).
Unpublished U.S. Appl. No. 15/598,420, filed May 18, 2017.

A
```
FGF19 (169)  L P M V   E E   D L R G H   L E S D M F S S   L   S T D   M   F G L   T   L E A V   F K K - - - - - -
FGF21 (168)  P G L P   A L       - - - - -   P P G I L A P Q   P   D V G   S     L S M   - P S Q G       Y A S - - - - - -
FGF23 (163)  - - E I   P L T - - H F N T P   I P R R H T R S A S   D D S E R D P L N -   V L E P R A R M T   A P A S C S Q E L P
FGF19        - - - - - - - -   - - - - - - - -   - - - - - - - -   - - - - - - - -
FGF21        - - - - - - - -   - - - - - - - -   - - - - - - - -   - - - - - - - -
FGF23 (212)  S A E D N S P M A S   D P L G V V R G G R   V N T H A G G T G P   E G C R P F A K F I
```
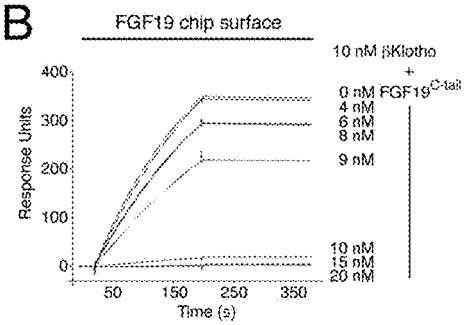
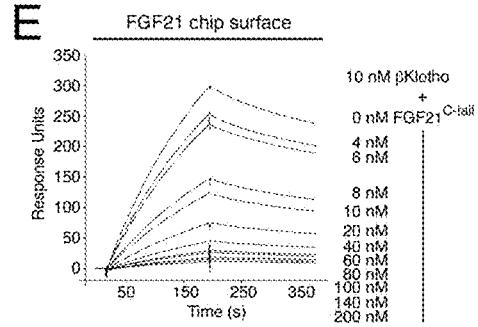
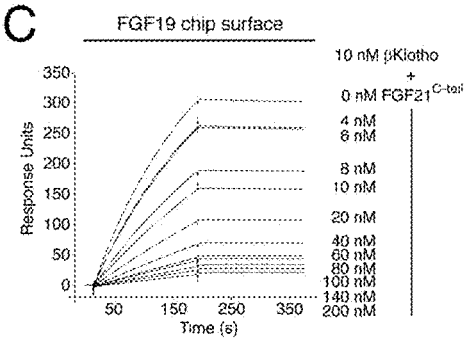
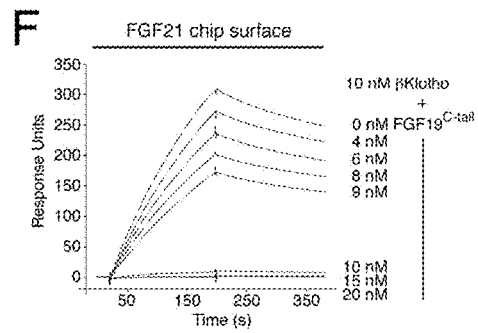
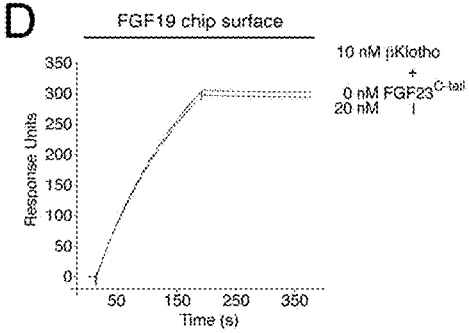
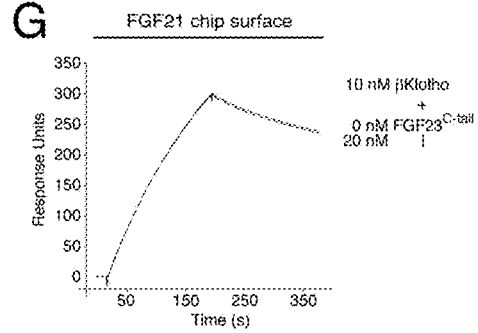
FIGS. 5A-5G

SEQUENCE LISTING

<160> NUMBER OF SEQ ID NOS: 336

<210> SEQ ID NO 1
<211> LENGTH: 216
<212> TYPE: PRT
<213> ORGANISM: Homo sapiens

<400> SEQUENCE: 1

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215

<210> SEQ ID NO 2
<211> LENGTH: 216
<212> TYPE: PRT
<213> ORGANISM: Gorilla gorilla

<400> SEQUENCE: 2

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu

```
            100                 105                 110
Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                    165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215

<210> SEQ ID NO 3
<211> LENGTH: 216
<212> TYPE: PRT
<213> ORGANISM: Pan troglodytes

<400> SEQUENCE: 3

Met Arg Asn Gly Cys Val Val His Val Trp Ile Leu Ala Gly Leu
1               5                   10                  15

Trp Leu Ala Val Ala Gly Arg Pro Leu Ala Phe Ser Asp Ala Gly Arg
                20                  25                  30

His Val His Tyr Cys Trp Gly Asp Pro Ile Pro Leu Arg His Leu Tyr
            35                  40                  45

Thr Ser Gly Pro His Gly Leu Ser Ser Cys Phe Leu Arg Ile Pro Ala
        50                  55                  60

Asn Cys Val Met Asn Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                    165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
            195                 200                 205

Val Arg Ser Pro Ser Phe Glu Lys
        210                 215

<210> SEQ ID NO 4
<211> LENGTH: 216
<212> TYPE: PRT
<213> ORGANISM: Macaca mulatta
```

<400> SEQUENCE: 4

Met Arg Ser Gly Cys Val Val His Ala Trp Ile Leu Ala Ser Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65              70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 5
<211> LENGTH: 216
<212> TYPE: PRT
<213> ORGANISM: Pongo abelii

<400> SEQUENCE: 5

Met Arg Ser Gly Cys Val Val His Ala Trp Ile Leu Ala Gly Leu
1               5                   10                  15

Trp Leu Ala Val Ala Gly Arg Pro Leu Ala Phe Ser Asp Ser Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65              70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
            165                 170                 175

Glu Asp Leu Arg Arg His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
            210                 215

<210> SEQ ID NO 6
<211> LENGTH: 216
<212> TYPE: PRT
<213> ORGANISM: Nomascus leucogenys

<400> SEQUENCE: 6

Met Arg Ser Glu Cys Val Val His Ala Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
            165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
            195                 200                 205

Val Arg Ser Pro Ser Phe Glu Lys
            210                 215

<210> SEQ ID NO 7
<211> LENGTH: 142
<212> TYPE: PRT
<213> ORGANISM: Callithrix jacchus

<400> SEQUENCE: 7

Met Trp Lys Ala Thr Ala Gly Gly Gln Gln Gly Gln Ser Glu Ala Gln
1               5                   10                  15

Met Ser Thr Cys Pro His Val Pro Arg Pro Leu Trp Ile Ala Gln Ser
            20                  25                  30

Cys Leu Phe Ser Leu Gln Leu Gln Tyr Ser Glu Asp Cys Ala Phe
            35                  40                  45

Glu Glu Glu Ile Arg Pro Asp Gly Tyr Asn Val Tyr Trp Ser Glu Lys
 50                  55                  60

His Arg Leu Pro Val Ser Leu Ser Ser Ala Lys Gln Arg Gln Leu Tyr
 65                  70                  75                  80

Lys Lys Arg Gly Phe Leu Pro Leu Ser His Phe Leu Pro Met Leu Pro
                85                  90                  95

Ile Ala Pro Glu Pro Glu Asp Leu Arg Gly His Leu Glu Ser Asp
                100                 105                 110

Val Phe Ser Ser Pro Leu Glu Thr Asp Ser Met Asp Pro Phe Gly Leu
                115                 120                 125

Val Thr Gly Leu Glu Ala Val Asn Ser Pro Ser Phe Glu Lys
    130                 135                 140

<210> SEQ ID NO 8
<211> LENGTH: 219
<212> TYPE: PRT
<213> ORGANISM: Microcebus murinus

<400> SEQUENCE: 8

Met Pro Ser Gly Gln Ser Gly Cys Val Ala Ala Arg Ala Leu Ile Leu
 1               5                  10                  15

Ala Gly Leu Trp Leu Thr Ala Ala Gly Arg Pro Leu Ala Phe Ser Asp
                20                  25                  30

Ala Gly Pro His Val His Tyr Gly Trp Gly Glu Pro Ile Arg Leu Arg
                35                  40                  45

His Leu Tyr Thr Ala Gly Pro His Gly Leu Ser Ser Cys Phe Leu Arg
 50                  55                  60

Ile Arg Ala Asp Gly Ser Val Asp Cys Ala Arg Gly Gln Ser Ala His
 65                  70                  75                  80

Ser Leu Leu Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
                100                 105                 110

Gln Gly Leu Leu Arg Tyr Ser Glu Glu Asp Cys Ala Phe Glu Glu Glu
                115                 120                 125

Ile Arg Pro Asp Gly Tyr Asn Val Tyr Arg Ser Glu Lys His Arg Leu
                130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Thr Gly Asp Leu Arg Asp His Leu Glu Ser Asp Met Phe Ala
                180                 185                 190

Ser Pro Leu Glu Thr Asp Ser Met Asp Pro Phe Gly Ile Ala Thr Arg
                195                 200                 205

Leu Gly Val Val Lys Ser Pro Ser Phe Gln Lys
    210                 215

<210> SEQ ID NO 9
<211> LENGTH: 138
<212> TYPE: PRT
<213> ORGANISM: Choloepus hoffmanni

<400> SEQUENCE: 9

```
Leu Leu Glu Met Lys Ala Val Ala Leu Arg Ala Val Ala Ile Lys Gly
1               5                   10                  15

Val His Ser Ala Leu Tyr Leu Cys Met Asn Ala Asp Gly Ser Leu His
                20                  25                  30

Gly Leu Pro Arg Tyr Ser Ala Glu Asp Cys Ala Phe Glu Glu Glu Ile
            35                  40                  45

Arg Pro Asp Gly Tyr Asn Val Tyr Trp Ser Arg Lys His Gly Leu Pro
    50                  55                  60

Val Ser Leu Ser Ser Ala Lys Gln Arg Gln Leu Tyr Lys Gly Arg Gly
65                  70                  75                  80

Phe Leu Pro Leu Ser His Phe Leu Pro Met Leu Pro Met Thr Pro Ala
                85                  90                  95

Glu Pro Ala Asp Pro Gly Asp Asp Val Glu Ser Asp Met Phe Ser Ser
            100                 105                 110

Pro Leu Glu Thr Asp Ser Met Asp Pro Phe Gly Ile Ala Ser Arg Leu
            115                 120                 125

Glu Leu Val Asn Ser Pro Ser Phe Gln Thr
    130                 135

<210> SEQ ID NO 10
<211> LENGTH: 205
<212> TYPE: PRT
<213> ORGANISM: Ailuropoda melanoleuca

<400> SEQUENCE: 10

Val Leu Ala Gly Leu Cys Leu Ala Val Ala Gly Arg Pro Leu Ala Phe
1               5                   10                  15

Ser Asp Ala Gly Pro His Val His Tyr Gly Trp Gly Glu Pro Ile Arg
                20                  25                  30

Leu Arg His Leu Tyr Thr Ala Gly Pro His Gly Leu Ser Ser Cys Phe
            35                  40                  45

Leu Arg Ile Arg Ala Asp Gly Gly Val Asp Cys Ala Arg Gly Gln Ser
    50                  55                  60

Ala His Ser Leu Val Glu Ile Arg Ala Val Ala Leu Arg Thr Val Ala
65                  70                  75                  80

Ile Lys Gly Val His Ser Val Arg Tyr Leu Cys Met Gly Ala Asp Gly
                85                  90                  95

Arg Met Gln Gly Leu Pro Gln Tyr Ser Ala Gly Asp Cys Ala Phe Glu
            100                 105                 110

Glu Glu Ile Arg Pro Asp Gly Tyr Asn Val Tyr Arg Ser Lys Lys His
            115                 120                 125

Arg Leu Pro Val Ser Leu Ser Gly Ala Lys Gln Arg Gln Leu Tyr Lys
    130                 135                 140

Asp Arg Gly Phe Leu Pro Leu Ser His Phe Leu Pro Met Leu Pro Gly
145                 150                 155                 160

Ser Pro Ala Glu Pro Arg Asp Leu Gln Asp His Ala Glu Ser Asp Gly
            165                 170                 175

Phe Ser Ala Pro Leu Glu Thr Asp Ser Met Asp Pro Phe Gly Ile Ala
            180                 185                 190

Thr Lys Met Gly Leu Val Lys Ser Pro Ser Phe Gln Lys
            195                 200                 205

<210> SEQ ID NO 11
<211> LENGTH: 218
<212> TYPE: PRT
<213> ORGANISM: Sus scrofa
```

<400> SEQUENCE: 11

Met Arg Ser Ala Pro Ser Arg Cys Ala Val Val Arg Ala Leu Val Leu
1               5                   10                  15

Ala Gly Leu Trp Leu Ala Ala Ala Gly Arg Pro Leu Ala Phe Ser Asp
                20                  25                  30

Ala Gly Pro His Val His Tyr Gly Trp Gly Glu Ser Val Arg Leu Arg
            35                  40                  45

His Leu Tyr Thr Ala Ser Pro His Gly Val Ser Ser Cys Phe Leu Arg
    50                  55                  60

Ile His Ser Asp Gly Pro Val Asp Cys Ala Pro Gly Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Arg Tyr Leu Cys Met Gly Ala Asp Gly Lys Met Gln
            100                 105                 110

Gly Gln Thr Gln Tyr Ser Asp Glu Asp Cys Ala Phe Glu Glu Glu Ile
        115                 120                 125

Arg Pro Asp Gly Tyr Asn Val Tyr Trp Ser Lys Lys His His Leu Pro
130                 135                 140

Val Ser Leu Ser Ser Ala Arg Gln Arg Gln Leu Tyr Lys Gly Arg Gly
145                 150                 155                 160

Phe Leu Pro Leu Ser His Phe Leu Pro Met Leu Ser Thr Leu Pro Ala
                165                 170                 175

Glu Pro Glu Asp Leu Gln Asp Pro Phe Lys Ser Asp Leu Phe Ser Leu
            180                 185                 190

Pro Leu Glu Thr Asp Ser Met Asp Pro Phe Arg Ile Ala Ala Lys Leu
        195                 200                 205

Gly Ala Val Lys Ser Pro Ser Phe Tyr Lys
210                 215

<210> SEQ ID NO 12
<211> LENGTH: 218
<212> TYPE: PRT
<213> ORGANISM: Bos Taurus

<400> SEQUENCE: 12

Met Arg Ser Ala Pro Ser Arg Cys Ala Val Val Arg Ala Leu Val Leu
1               5                   10                  15

Ala Gly Leu Trp Leu Ala Ala Ala Gly Arg Pro Leu Ala Phe Ser Asp
                20                  25                  30

Ala Gly Pro His Val His Tyr Gly Trp Gly Glu Ser Val Arg Leu Arg
            35                  40                  45

His Leu Tyr Thr Ala Gly Pro Gln Gly Leu Tyr Ser Cys Phe Leu Arg
    50                  55                  60

Ile His Ser Asp Gly Ala Val Asp Cys Ala Gln Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Asp Ala Asp Gly Lys Met
            100                 105                 110

Gln Gly Leu Thr Gln Tyr Ser Ala Glu Asp Cys Ala Phe Glu Glu Glu
        115                 120                 125

Ile Arg Pro Asp Gly Tyr Asn Val Tyr Trp Ser Arg Lys His His Leu
130                 135                 140

Pro Val Ser Leu Ser Ser Arg Gln Arg Gln Leu Phe Lys Ser Arg
145                 150                 155                 160

Gly Phe Leu Pro Leu Ser His Phe Leu Pro Met Leu Ser Thr Ile Pro
            165                 170                 175

Ala Glu Pro Glu Asp Leu Gln Glu Pro Leu Lys Pro Asp Phe Phe Leu
            180                 185                 190

Pro Leu Lys Thr Asp Ser Met Asp Pro Phe Gly Leu Ala Thr Lys Leu
            195                 200                 205

Gly Ser Val Lys Ser Pro Ser Phe Tyr Asn
            210                 215

<210> SEQ ID NO 13
<211> LENGTH: 192
<212> TYPE: PRT
<213> ORGANISM: Canis lupus familiaris

<400> SEQUENCE: 13

Leu Ala Phe Ser Asp Ala Gly Pro His Val His Ser Phe Trp Gly Glu
1               5                   10                  15

Pro Ile Arg Leu Arg His Leu Tyr Thr Ala Gly Pro His Gly Leu Ser
            20                  25                  30

Ser Cys Phe Leu Arg Ile Arg Ala Asp Gly Gly Val Asp Cys Ala Arg
        35                  40                  45

Gly Gln Ser Ala His Ser Leu Met Glu Met Arg Ala Val Ala Leu Arg
    50                  55                  60

Thr Val Ala Ile Lys Gly Val His Ser Gly Arg Tyr Leu Cys Met Gly
65                  70                  75                  80

Ala Asp Gly Arg Met Gln Gly Leu Pro Gln Tyr Ser Ala Gly Asp Cys
                85                  90                  95

Thr Phe Glu Glu Glu Ile Arg Pro Asp Gly Tyr Asn Val Tyr Trp Ser
            100                 105                 110

Lys Lys His His Leu Pro Ile Ser Leu Ser Ser Ala Lys Gln Arg Gln
        115                 120                 125

Leu Tyr Lys Gly Arg Gly Phe Leu Pro Leu Ser His Phe Leu Pro Ile
    130                 135                 140

Leu Pro Gly Ser Pro Thr Glu Pro Arg Asp Leu Glu Asp His Val Glu
145                 150                 155                 160

Ser Asp Gly Phe Ser Ala Ser Leu Glu Thr Asp Ser Met Asp Pro Phe
                165                 170                 175

Gly Ile Ala Thr Lys Ile Gly Leu Val Lys Ser Pro Ser Phe Gln Lys
            180                 185                 190

<210> SEQ ID NO 14
<211> LENGTH: 218
<212> TYPE: PRT
<213> ORGANISM: Oryctolagus cuniculus

<400> SEQUENCE: 14

Met Arg Arg Ala Pro Ser Gly Gly Ala Ala Arg Ala Leu Val Leu
1               5                   10                  15

Ala Gly Leu Trp Leu Ala Ala Ala Arg Pro Leu Ala Leu Ser Asp
            20                  25                  30

Ala Gly Pro His Leu His Tyr Gly Trp Gly Glu Pro Val Arg Leu Arg
        35                  40                  45

His Leu Tyr Ala Thr Ser Ala His Gly Val Ser His Cys Phe Leu Arg
    50                  55                  60

```
Ile Arg Ala Asp Gly Ala Val Asp Cys Glu Arg Ser Gln Ser Ala His
 65                  70                  75                  80

Ser Leu Leu Glu Ile Arg Ala Val Ala Leu Arg Thr Val Ala Phe Lys
                 85                  90                  95

Gly Val His Ser Ser Arg Tyr Leu Cys Met Gly Ala Asp Gly Arg Met
            100                 105                 110

Arg Gly Gln Leu Gln Tyr Ser Glu Glu Asp Cys Ala Phe Gln Glu Glu
        115                 120                 125

Ile Ser Ser Gly Tyr Asn Val Tyr Arg Ser Thr Thr His His Leu Pro
    130                 135                 140

Val Ser Leu Ser Ser Ala Lys Gln Arg His Leu Tyr Lys Thr Arg Gly
145                 150                 155                 160

Phe Leu Pro Leu Ser His Phe Leu Pro Val Leu Pro Leu Ala Ser Glu
                165                 170                 175

Glu Thr Ala Ala Leu Gly Asp His Pro Glu Ala Asp Leu Phe Ser Pro
            180                 185                 190

Pro Leu Glu Thr Asp Ser Met Asp Pro Phe Gly Met Ala Thr Lys Leu
        195                 200                 205

Gly Pro Val Lys Ser Pro Ser Phe Gln Lys
    210                 215
```

<210> SEQ ID NO 15
<211> LENGTH: 215
<212> TYPE: PRT
<213> ORGANISM: Pteropus vampyrus

<400> SEQUENCE: 15

```
Met Arg Ser Pro Cys Ala Val Ala Arg Ala Leu Val Leu Ala Gly Leu
  1               5                  10                  15

Trp Leu Ala Ser Ala Ala Gly Pro Leu Ala Leu Ser Asp Ala Gly Pro
                 20                  25                  30

His Val His Tyr Gly Trp Gly Glu Ala Ile Arg Leu Arg His Leu Tyr
             35                  40                  45

Thr Ala Gly Pro His Gly Pro Ser Ser Cys Phe Leu Arg Ile Arg Ala
         50                  55                  60

Asp Gly Ala Val Asp Cys Ala Arg Gly Gln Ser Ala His Ser Leu Val
 65                  70                  75                  80

Glu Ile Arg Ala Val Ala Leu Arg Asn Val Ala Ile Lys Gly Val His
                 85                  90                  95

Ser Val Arg Tyr Leu Cys Met Gly Ala Asp Gly Arg Met Leu Gly Leu
            100                 105                 110

Leu Gln Tyr Ser Ala Asp Asp Cys Ala Phe Glu Glu Glu Ile Arg Pro
        115                 120                 125

Asp Gly Tyr Asn Val Tyr His Ser Lys Lys His His Leu Pro Val Ser
    130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Leu Glu
            180                 185                 190

Thr Asp Asp Met Asp Pro Phe Gly Ile Ala Ser Lys Leu Gly Leu Glu
        195                 200                 205

Glu Ser Pro Ser Phe Gln Lys
```

<210> SEQ ID NO 16
<211> LENGTH: 219
<212> TYPE: PRT
<213> ORGANISM: Tursiops truncates

<400> SEQUENCE: 16

Met Arg Ser Ala Pro Ser Arg Cys Ala Val Arg Ala Leu Val Leu
1               5                   10                  15

Ala Gly Leu Trp Leu Ala Ala Ala Gly Arg Pro Leu Ala Phe Ser Asp
            20                  25                  30

Ala Gly Pro His Val His Tyr Gly Trp Gly Glu Ser Val Arg Leu Arg
        35                  40                  45

His Leu Tyr Thr Ala Gly Pro Gln Gly Leu Ser Ser Cys Phe Leu Arg
    50                  55                  60

Ile His Ser Asp Gly Ala Val Asp Cys Ala Pro Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Gly Ala Asp Gly Lys Met
            100                 105                 110

Gln Gly Leu Ser Gln Tyr Ser Ala Glu Asp Cys Ala Phe Glu Glu Glu
        115                 120                 125

Ile Arg Pro Asp Gly Tyr Asn Val Tyr Trp Ser Lys Lys His His Leu
    130                 135                 140

Pro Val Ser Leu Ser Ser Ala Arg Gln Arg Gln Leu Phe Lys Gly Arg
145                 150                 155                 160

Gly Phe Leu Pro Leu Ser His Phe Leu Pro Met Leu Ser Thr Ile Pro
                165                 170                 175

Thr Glu Pro Asp Glu Ile Gln Asp His Leu Lys Pro Asp Leu Phe Ala
            180                 185                 190

Leu Pro Leu Lys Thr Asp Ser Met Asp Pro Phe Gly Leu Ala Thr Lys
        195                 200                 205

Leu Gly Val Val Lys Ser Pro Ser Phe Tyr Lys
    210                 215

<210> SEQ ID NO 17
<211> LENGTH: 219
<212> TYPE: PRT
<213> ORGANISM: Myotis lucifugus

<400> SEQUENCE: 17

Met Gln Ser Ala Trp Ser Arg Arg Val Val Arg Ala Leu Val Leu
1               5                   10                  15

Ala Ser Leu Gly Leu Ala Ser Ala Gly Gly Pro Leu Gly Leu Ser Asp
            20                  25                  30

Ala Gly Pro His Val His Tyr Gly Trp Gly Glu Ser Ile Arg Leu Arg
        35                  40                  45

His Leu Tyr Thr Ser Gly Pro His Gly Pro Ser Ser Cys Phe Leu Arg
    50                  55                  60

Ile Arg Ala Asp Gly Ala Val Asp Cys Ala Arg Gly Gln Ser Ala His
65                  70                  75                  80

Ser Leu Val Glu Ile Arg Ala Val Ala Leu Arg Lys Val Ala Ile Lys
                85                  90                  95

Gly Val His Ser Ala Leu Tyr Leu Cys Met Gly Gly Asp Gly Arg Met

```
            100                 105                 110
Leu Gly Leu Pro Gln Phe Ser Pro Glu Asp Cys Ala Phe Glu Glu Glu
        115                 120                 125

Ile Arg Pro Asp Gly Tyr Asn Val Tyr Arg Ser Gln Lys His Gln Leu
    130                 135                 140

Pro Val Ser Leu Ser Ser Ala Arg Gln Arg Gln Leu Phe Lys Ala Arg
145                 150                 155                 160

Gly Phe Leu Pro Leu Ser His Phe Leu Pro Met Leu Pro Ser Ser Pro
                165                 170                 175

Ala Gly Pro Val Pro Arg Glu Arg Pro Ser Glu Pro Asp Glu Phe Ser
            180                 185                 190

Ser Pro Leu Glu Thr Asp Ser Met Asp Pro Phe Gly Ile Ala Asn Asn
        195                 200                 205

Leu Arg Leu Val Arg Ser Pro Ser Phe Gln Glu
    210                 215
```

<210> SEQ ID NO 18
<211> LENGTH: 185
<212> TYPE: PRT
<213> ORGANISM: Ornithorhynchus anatinus

<400> SEQUENCE: 18

```
Met Leu Ser Cys Val Val Leu Pro Ser Leu Leu Glu Ile Lys Ala Val
1               5                   10                  15

Ala Val Arg Thr Val Ala Ile Lys Gly Val His Ile Ser Arg Tyr Leu
            20                  25                  30

Cys Met Glu Glu Asp Gly Lys Thr Pro Trp Ala Arg Leu Leu Glu Ile
        35                  40                  45

Lys Ala Val Ala Val Arg Thr Val Ala Ile Lys Gly Val His Ser Ser
    50                  55                  60

Arg Tyr Leu Cys Met Glu Glu Asp Gly Lys Leu His Gly Gln Ile Trp
65                  70                  75                  80

Tyr Ser Ala Glu Asp Cys Ala Phe Glu Glu Glu Ile Arg Pro Asp Gly
                85                  90                  95

Tyr Asn Val Tyr Lys Ser Lys Lys Tyr Gly Val Pro Val Ser Leu Ser
            100                 105                 110

Ser Ala Lys Gln Arg Gln Gln Phe Lys Gly Arg Asp Phe Leu Pro Leu
        115                 120                 125

Ser Arg Phe Leu Pro Met Ile Asn Thr Val Pro Val Glu Pro Ala Glu
    130                 135                 140

Phe Gly Asp Tyr Ala Asp Tyr Phe Glu Ser Asp Ile Phe Ser Ser Pro
145                 150                 155                 160

Leu Glu Thr Asp Ser Met Asp Pro Phe Arg Ile Ala Pro Lys Leu Ser
                165                 170                 175

Pro Val Lys Ser Pro Ser Phe Gln Lys
            180                 185
```

<210> SEQ ID NO 19
<211> LENGTH: 212
<212> TYPE: PRT
<213> ORGANISM: Monodelphis domestica

<400> SEQUENCE: 19

```
Met Ala Gln Leu Leu Ala Pro Leu Leu Thr Leu Ala Ala Leu Trp Leu
1               5                   10                  15

Ala Pro Thr Ala Arg Ala Arg Pro Leu Val Asp Ala Gly Pro His Val
```

```
                20                  25                  30
Tyr Tyr Gly Trp Gly Glu Pro Ile Arg Leu Arg His Leu Tyr Thr Ala
            35                  40                  45
Asn Arg His Gly Leu Ala Ser Phe Ser Phe Leu Arg Ile His Arg Asp
    50                  55                  60
Gly Arg Val Asp Gly Ser Arg Ser Gln Ser Ala Leu Ser Leu Leu Glu
65                  70                  75                  80
Ile Lys Ala Val Ala Leu Arg Met Val Ala Ile Lys Gly Val His Ser
                85                  90                  95
Ser Arg Tyr Leu Cys Met Gly Asp Ala Gly Lys Leu Gln Gly Ser Val
            100                 105                 110
Arg Phe Ser Ala Glu Asp Cys Thr Phe Glu Glu Gln Ile Arg Pro Asp
        115                 120                 125
Gly Tyr Asn Val Tyr Gln Ser Pro Lys Tyr Asn Leu Pro Val Ser Leu
    130                 135                 140
Cys Thr Asp Lys Gln Arg Gln Gln Ala His Gly Lys Glu His Leu Pro
145                 150                 155                 160
Leu Ser His Phe Leu Pro Met Ile Asn Ala Ile Pro Leu Glu Ala Glu
                165                 170                 175
Glu Pro Glu Gly Pro Arg Met Leu Ala Ala Pro Leu Glu Thr Asp Ser
            180                 185                 190
Met Asp Pro Phe Gly Leu Thr Ser Lys Leu Leu Pro Val Lys Ser Pro
        195                 200                 205
Ser Phe Gln Lys
    210

<210> SEQ ID NO 20
<211> LENGTH: 220
<212> TYPE: PRT
<213> ORGANISM: Anolis carolinensis

<400> SEQUENCE: 20

Met Cys Arg Arg Ala Leu Pro Leu Leu Gly Ala Leu Leu Gly Leu Ala
1               5                   10                  15
Ala Val Ala Ser Arg Ala Leu Pro Leu Thr Asp Ala Gly Pro His Val
            20                  25                  30
Ser Tyr Gly Trp Gly Glu Pro Val Arg Leu Arg His Leu Tyr Thr Ala
            35                  40                  45
Gly Arg Gln Gly Leu Phe Ser Gln Phe Leu Arg Ile His Ala Asp Gly
    50                  55                  60
Arg Val Asp Gly Ala Gly Ser Gln Asn Arg Gln Ser Leu Leu Glu Ile
65                  70                  75                  80
Arg Ala Val Ser Leu Arg Ala Val Ala Leu Lys Gly Val His Ser Ser
                85                  90                  95
Arg Tyr Leu Cys Met Glu Glu Asp Gly Arg Leu Arg Gly Met Leu Arg
            100                 105                 110
Tyr Ser Ala Glu Asp Cys Ser Phe Glu Glu Met Arg Pro Asp Gly
        115                 120                 125
Tyr Asn Ile Tyr Lys Ser Lys Lys Tyr Gly Val Leu Val Ser Leu Ser
    130                 135                 140
Asn Ala Arg Gln Arg Gln Gln Phe Lys Gly Lys Asp Phe Leu Pro Leu
145                 150                 155                 160
Ser His Phe Leu Pro Met Ile Asn Thr Val Pro Val Glu Ser Ala Asp
                165                 170                 175
```

```
Phe Gly Glu Tyr Gly Asp Thr Arg Gln His Tyr Glu Ser Asp Ile Phe
            180                 185                 190

Ser Ser Arg Leu Glu Thr Asp Ser Met Asp Pro Phe Gly Leu Thr Ser
            195                 200                 205

Glu Val Ser Ser Val Gln Ser Pro Ser Phe Gly Lys
    210                 215                 220

<210> SEQ ID NO 21
<211> LENGTH: 179
<212> TYPE: PRT
<213> ORGANISM: Ochotona princeps

<400> SEQUENCE: 21

Val Arg Ser Arg Gly Ala Met Ala Arg Ala Leu Val Leu Ala Thr Leu
1               5                   10                  15

Trp Leu Ala Ala Thr Gly Arg Pro Leu Ala Leu Ser Asp Ala Gly Pro
            20                  25                  30

His Leu His Tyr Gly Trp Gly Glu Pro Ile Arg Leu Arg His Leu Tyr
        35                  40                  45

Ala Thr Ser Ala His Gly Leu Ser His Cys Phe Leu Arg Ile Arg Thr
    50                  55                  60

Asp Gly Thr Val Asp Cys Glu Arg Ser Gln Ser Ala His Leu Gln Tyr
65                  70                  75                  80

Ser Glu Glu Asp Cys Ala Phe Glu Glu Glu Ile Ser Ser Gly Tyr Asn
                85                  90                  95

Val Tyr Arg Ser Arg Arg Tyr Gln Leu Pro Val Ser Leu Gly Ser Ala
            100                 105                 110

Arg Gln Arg Gln Leu Gln Arg Ser Arg Gly Phe Leu Pro Leu Ser His
        115                 120                 125

Phe Leu Pro Val Leu Pro Ala Ala Ser Glu Glu Val Ala Ala Pro Ala
    130                 135                 140

Asp His Pro Gln Ala Asp Pro Phe Ser Pro Leu Glu Thr Asp Ser Met
145                 150                 155                 160

Asp Pro Phe Gly Met Ala Thr Lys Arg Gly Leu Val Lys Ser Pro Ser
                165                 170                 175

Phe Gln Lys

<210> SEQ ID NO 22
<211> LENGTH: 221
<212> TYPE: PRT
<213> ORGANISM: Cavia porcellus

<400> SEQUENCE: 22

Met Trp Ser Ala Pro Ser Gly Cys Val Val Ile Arg Ala Leu Val Leu
1               5                   10                  15

Ala Gly Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Arg Ser
    50                  55                  60

Arg Cys Phe Leu Arg Ile His Thr Asp Gly Ala Val Asp Cys Val Glu
65                  70                  75                  80

Glu Gln Ser Glu His Cys Leu Leu Glu Ile Arg Ala Val Ala Leu Glu
                85                  90                  95

Thr Val Ala Ile Lys Asp Ile Asn Ser Val Arg Tyr Leu Cys Met Gly
```

```
            100                 105                 110
Pro Asp Gly Arg Met Arg Gly Leu Pro Trp Tyr Ser Glu Glu Asp Cys
            115                 120                 125

Ala Phe Lys Glu Glu Ile Ser Tyr Pro Gly Tyr Ser Val Tyr Arg Ser
            130                 135                 140

Gln Lys His His Leu Pro Ile Val Leu Ser Ser Val Lys Gln Arg Gln
145                 150                 155                 160

Gln Tyr Gln Ser Lys Gly Val Val Pro Leu Ser Tyr Phe Leu Pro Met
                165                 170                 175

Leu Pro Lys Ala Ser Val Glu Pro Ser Asp Glu Glu Ser Ser Val
            180                 185                 190

Phe Ser Leu Pro Leu Lys Thr Asp Ser Met Asp Pro Phe Gly Met Ala
            195                 200                 205

Ser Glu Ile Gly Leu Val Lys Ser Pro Ser Phe Gln Lys
            210                 215                 220

<210> SEQ ID NO 23
<211> LENGTH: 196
<212> TYPE: PRT
<213> ORGANISM: Tupaia belangeri

<400> SEQUENCE: 23

Met Arg Arg Thr Pro Ser Gly Phe Ala Val Ala Arg Val Leu Phe Leu
1               5                   10                  15

Gly Ser Leu Trp Leu Ala Ala Gly Ser Pro Leu Ala Leu Ser Asp
            20                  25                  30

Ala Gly Pro His Val Asn Tyr Gly Trp Asp Glu Ser Ile Arg Leu Arg
            35                  40                  45

His Leu Tyr Thr Ala Ser Pro His Gly Ser Thr Ser Cys Phe Leu Arg
        50                  55                  60

Ile Arg Asp Asp Gly Ser Val Asp Cys Ala Arg Gly Gln Ser Leu His
65                  70                  75                  80

Ser Leu Leu Glu Ile Lys Ala Val Ala Leu Gln Thr Val Ala Ile Lys
                85                  90                  95

Gly Val Tyr Ser Val Arg Tyr Leu Cys Met Asp Ala Asp Gly Arg Met
            100                 105                 110

Gln Gly Leu Ser Thr Lys His Gly Leu Pro Val Ser Leu Ser Ser Ala
            115                 120                 125

Lys Gln Arg Gln Leu Leu Thr Val Arg Gly Phe Pro Ser Leu Pro His
130                 135                 140

Phe Leu Leu Met Met Ala Lys Thr Ser Ala Gly Pro Gly Asn Pro Arg
145                 150                 155                 160

Asp His Pro Gly Ser Asn Thr Phe Ser Leu Pro Leu Glu Thr Asp Ser
                165                 170                 175

Met Asp Pro Phe Gly Met Thr Thr Arg His Gly Leu Val Lys Ser Pro
            180                 185                 190

Ser Phe Gln Asn
        195

<210> SEQ ID NO 24
<211> LENGTH: 218
<212> TYPE: PRT
<213> ORGANISM: Rattus norvegicus

<400> SEQUENCE: 24

Met Ala Arg Lys Trp Ser Gly Arg Ile Val Ala Arg Ala Leu Val Leu
```

```
            1               5                  10                 15
        Ala Thr Leu Trp Leu Ala Val Ser Gly Arg Pro Leu Gln Gln Ser
                    20                 25                 30

Gln Ser Val Ser Asp Glu Gly Pro Leu Phe Leu Tyr Gly Trp Gly Lys
                    35                 40                 45

Ile Thr Arg Leu Gln Tyr Leu Tyr Ser Ala Gly Pro Tyr Val Ser Asn
                50                 55                 60

Cys Phe Leu Arg Ile Arg Ser Asp Gly Ser Val Asp Cys Glu Glu Asp
        65                  70                 75                     80

Gln Asn Glu Arg Asn Leu Leu Glu Phe Arg Ala Val Ala Leu Lys Thr
                        85                 90                 95

Ile Ala Ile Lys Asp Val Ser Ser Val Arg Tyr Leu Cys Met Ser Ala
                    100                105                110

Asp Gly Lys Ile Tyr Gly Leu Ile Arg Tyr Ser Glu Glu Asp Cys Thr
                    115                120                125

Phe Arg Glu Glu Met Asp Cys Leu Gly Tyr Asn Gln Tyr Arg Ser Met
                    130                135                140

Lys His His Leu His Ile Ile Phe Ile Lys Ala Lys Pro Arg Glu Gln
        145                 150                155                    160

Leu Gln Gly Gln Lys Pro Ser Asn Phe Ile Pro Ile Phe His Arg Ser
                        165                170                175

Phe Phe Glu Ser Thr Asp Gln Leu Arg Ser Lys Met Phe Ser Leu Pro
                    180                185                190

Leu Glu Ser Asp Ser Met Asp Pro Phe Arg Met Val Glu Asp Val Asp
                    195                200                205

His Leu Val Lys Ser Pro Ser Phe Gln Lys
                    210                215

<210> SEQ ID NO 25
<211> LENGTH: 218
<212> TYPE: PRT
<213> ORGANISM: Mus musculus

<400> SEQUENCE: 25

Met Ala Arg Lys Trp Asn Gly Arg Ala Val Ala Arg Ala Leu Val Leu
        1               5                  10                 15

Ala Thr Leu Trp Leu Ala Val Ser Gly Arg Pro Leu Ala Gln Gln Ser
                    20                 25                 30

Gln Ser Val Ser Asp Glu Asp Pro Leu Phe Leu Tyr Gly Trp Gly Lys
                    35                 40                 45

Ile Thr Arg Leu Gln Tyr Leu Tyr Ser Ala Gly Pro Tyr Val Ser Asn
                50                 55                 60

Cys Phe Leu Arg Ile Arg Ser Asp Gly Ser Val Asp Cys Glu Glu Asp
        65                  70                 75                     80

Gln Asn Glu Arg Asn Leu Leu Glu Phe Arg Ala Val Ala Leu Lys Thr
                        85                 90                 95

Ile Ala Ile Lys Asp Val Ser Ser Val Arg Tyr Leu Cys Met Ser Ala
                    100                105                110

Asp Gly Lys Ile Tyr Gly Leu Ile Arg Tyr Ser Glu Glu Asp Cys Thr
                    115                120                125

Phe Arg Glu Glu Met Asp Cys Leu Gly Tyr Asn Gln Tyr Arg Ser Met
                    130                135                140

Lys His His Leu His Ile Ile Phe Ile Gln Ala Lys Pro Arg Glu Gln
        145                 150                155                    160
```

```
Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
    210                 215
```

```
<210> SEQ ID NO 26
<211> LENGTH: 227
<212> TYPE: PRT
<213> ORGANISM: Gallus gallus

<400> SEQUENCE: 26
```

```
Met Gly Pro Ala Arg Pro Ala Ala Pro Gly Ala Ala Leu Ala Leu Leu
1               5                   10                  15

Gly Ile Ala Ala Ala Ala Ala Ala Arg Ser Leu Pro Leu Pro Leu Asp
                20                  25                  30

Val Gly Gly Pro His Val Asn Tyr Gly Trp Gly Glu Pro Ile Arg Leu
            35                  40                  45

Arg His Leu Leu His Arg Pro Gly Lys His Gly Leu Phe Ser Cys Phe
        50                  55                  60

Leu Arg Ile Gly Gly Asp Gly Arg Val Asp Ala Val Gly Ser Gln Ser
65                  70                  75                  80

Pro Gln Ser Leu Leu Glu Ile Arg Ala Val Ala Val Arg Thr Val Ala
                85                  90                  95

Ile Lys Gly Val Gln Ser Ser Arg Tyr Leu Cys Met Asp Glu Ala Gly
                100                 105                 110

Arg Leu His Gly Gln Leu Ser Tyr Ser Ile Glu Asp Cys Ser Phe Glu
        115                 120                 125

Glu Glu Ile Arg Pro Asp Gly Tyr Asn Val Tyr Lys Ser Lys Lys Tyr
    130                 135                 140

Gly Ile Ser Val Ser Leu Ser Ser Ala Lys Gln Arg Gln Gln Phe Lys
145                 150                 155                 160

Gly Lys Asp Phe Leu Pro Leu Ser His Phe Leu Pro Met Ile Asn Thr
                165                 170                 175

Val Pro Val Glu Val Thr Asp Phe Gly Glu Tyr Gly Asp Tyr Ser Gln
            180                 185                 190

Ala Phe Glu Pro Glu Val Tyr Ser Ser Pro Leu Glu Thr Asp Ser Met
        195                 200                 205

Asp Pro Phe Gly Ile Thr Ser Lys Leu Ser Pro Val Lys Ser Pro Ser
    210                 215                 220

Phe Gln Lys
225
```

```
<210> SEQ ID NO 27
<211> LENGTH: 237
<212> TYPE: PRT
<213> ORGANISM: Taeniopygia guttata

<400> SEQUENCE: 27
```

```
Met Val Ile Ile Ser Asn Leu Tyr Leu Met Gln Asn Asp Val Met Met
1               5                   10                  15

Asn Met Arg Arg Ala Pro Leu Arg Val His Ala Ala Arg Ser Ser Ala
                20                  25                  30
```

```
Thr Pro Ala Ser Ala Leu Pro Leu Pro Pro Pro Asp Ala Gly Pro His
            35                  40                  45

Leu Lys Tyr Gly Trp Gly Glu Pro Ile Arg Leu Arg His Leu Tyr Thr
 50                  55                  60

Ala Ser Lys His Gly Leu Phe Ser Cys Phe Leu Arg Ile Gly Ala Asp
 65                  70                  75                  80

Gly Arg Val Asp Ala Ala Gly Ser Gln Ser Pro Gln Ser Leu Leu Glu
                 85                  90                  95

Ile Arg Ala Val Ala Val Arg Thr Val Ala Ile Lys Gly Val Gln Ser
             100                 105                 110

Ser Arg Tyr Leu Cys Met Asp Glu Ala Gly Arg Leu His Gly Gln Leu
             115                 120                 125

Arg Asn Ser Thr Glu Asp Cys Ser Phe Glu Glu Ile Arg Pro Asp
130                 135                 140

Gly Tyr Asn Val Tyr Arg Ser Lys Lys His Gly Ile Ser Val Ser Leu
145                 150                 155                 160

Ser Ser Ala Lys Gln Arg Gln Gln Phe Lys Gly Lys Asp Phe Leu Pro
                165                 170                 175

Leu Ser His Phe Leu Pro Met Ile Asn Thr Val Pro Met Glu Ser Ala
             180                 185                 190

Asp Phe Gly Glu Tyr Gly Asp Tyr Ser Gln Ala Phe Glu Ala Glu Ala
             195                 200                 205

Phe Ser Ser Pro Leu Glu Thr Asp Ser Met Asp Pro Phe Gly Ile Ala
             210                 215                 220

Ser Lys Leu Ser Leu Val Lys Ser Pro Ser Phe Gln Asn
225                 230                 235

<210> SEQ ID NO 28
<211> LENGTH: 210
<212> TYPE: PRT
<213> ORGANISM: Danio rerio

<400> SEQUENCE: 28

Met Leu Leu Leu Leu Phe Val Thr Val Cys Gly Ser Ile Gly Val Glu
 1               5                  10                  15

Ser Leu Pro Leu Pro Asp Ser Gly Pro His Leu Ala Asn Asp Trp Ser
                 20                  25                  30

Glu Ala Val Arg Leu Arg His Leu Tyr Ala Ala Arg His Gly Leu His
             35                  40                  45

Leu Gln Ile Asn Thr Asp Gly Glu Ile Ile Gly Ser Thr Cys Lys Ala
 50                  55                  60

Arg Thr Val Ser Leu Met Glu Ile Trp Pro Val Asp Thr Gly Cys Val
 65                  70                  75                  80

Ala Ile Lys Gly Val Ala Ser Ser Arg Phe Leu Cys Met Glu Arg Leu
                 85                  90                  95

Gly Asn Leu Tyr Gly Ser His Ile Tyr Thr Lys Glu Asp Cys Ser Phe
             100                 105                 110

Leu Glu Arg Ile Leu Pro Asp Gly Tyr Asn Val Tyr Phe Ser Ser Lys
             115                 120                 125

His Gly Ala Leu Val Thr Leu Ser Gly Ala Lys Asn Lys Leu His Ser
130                 135                 140

Asn Asp Gly Thr Ser Ala Ser Gln Phe Leu Pro Met Ile Asn Thr Leu
145                 150                 155                 160

Ser Glu Glu His Thr Lys Gln His Ser Gly Glu Gln His Ser Ser Val
                165                 170                 175
```

Asn His Gly Gln Asp His Gln Leu Gly Leu Glu Ile Asp Ser Met Asp
            180                 185                 190

Pro Phe Gly Lys Ile Ser Gln Ile Val Ile Gln Ser Pro Ser Phe Asn
            195                 200                 205

Lys Arg
    210

<210> SEQ ID NO 29
<211> LENGTH: 215
<212> TYPE: PRT
<213> ORGANISM: Xenopus (Silurana) tropicalis

<400> SEQUENCE: 29

Met Trp Lys Thr Leu Pro Trp Ile Leu Val Pro Met Met Val Ala Val
1               5                   10                  15

Leu Tyr Phe Leu Gly Gly Ala Glu Ser Leu Pro Leu Phe Asp Ala Gly
            20                  25                  30

Pro His Met Gln Asn Gly Trp Gly Glu Ser Ile Arg Ile Arg His Leu
        35                  40                  45

Tyr Thr Ala Arg Arg Phe Gly His Asp Ser Tyr Tyr Leu Arg Ile His
    50                  55                  60

Glu Asp Gly Arg Val Asp Gly Asp Arg Gln Gln Ser Met His Ser Leu
65                  70                  75                  80

Leu Glu Ile Arg Ala Ile Ala Val Gly Ile Val Ala Ile Lys Gly Tyr
                85                  90                  95

Arg Ser Ser Leu Tyr Leu Cys Met Gly Ser Glu Gly Lys Leu Tyr Gly
            100                 105                 110

Met His Ser Tyr Ser Gln Asp Asp Cys Ser Phe Glu Glu Glu Leu Leu
        115                 120                 125

Pro Asp Gly Tyr Asn Met Tyr Lys Ser Arg Lys His Gly Val Ala Val
    130                 135                 140

Ser Leu Ser Lys Glu Lys Gln Lys Gln Tyr Lys Gly Lys Gly Tyr
145                 150                 155                 160

Leu Pro Leu Ser His Phe Leu Pro Val Ile Ser Trp Val Pro Met Glu
                165                 170                 175

Pro Thr Gly Asp Val Glu Asp Asp Ile Tyr Arg Phe Pro Phe Asn Thr
            180                 185                 190

Asp Thr Lys Ser Val Ile Asp Ser Leu Asp Thr Leu Gly Leu Met Asp
        195                 200                 205

Phe Ser Ser Tyr His Lys Lys
    210                 215

<210> SEQ ID NO 30
<211> LENGTH: 219
<212> TYPE: PRT
<213> ORGANISM: Otolemur garnettii

<400> SEQUENCE: 30

Met Pro Ser Gly Leu Arg Gly Arg Val Val Ala Gly Ala Leu Ala Leu
1               5                   10                  15

Ala Ser Phe Trp Leu Ala Val Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

```
Val Arg Thr Asp Gly Ala Val Asp Cys Ala Arg Gly Gln Ser Ala His
 65                  70                  75                  80

Ser Leu Leu Glu Ile Arg Ala Val Ala Leu Arg Thr Val Ala Ile Lys
                 85                  90                  95

Gly Val His Ser Ala Arg Tyr Leu Cys Met Gly Ala Asp Gly Arg Met
            100                 105                 110

Gln Gly Leu Pro Gln Tyr Ser Glu Glu Asp Cys Ala Phe Glu Glu Glu
        115                 120                 125

Ile Arg Pro Asp Gly Tyr Asn Val Tyr Trp Ser Glu Lys His Arg Leu
    130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Pro Gly Asp Leu Arg Asp His Leu Glu Ser Asp Met Phe Ser
            180                 185                 190

Leu Pro Leu Glu Thr Asp Ser Met Asp Pro Phe Gly Ile Ala Thr Arg
        195                 200                 205

Leu Gly Val Val Lys Ser Pro Ser Phe Gln Lys
    210                 215

<210> SEQ ID NO 31
<211> LENGTH: 219
<212> TYPE: PRT
<213> ORGANISM: Felis catus

<400> SEQUENCE: 31

Met Arg Ser Ala Pro Ser Gln Cys Ala Val Thr Arg Ala Leu Val Leu
1               5                   10                  15

Ala Gly Leu Trp Leu Ala Ala Ala Gly Arg Pro Leu Ala Phe Ser Asp
                20                  25                  30

Ala Gly Pro His Val His Tyr Gly Trp Gly Pro Ile Arg Leu Arg
            35                  40                  45

His Leu Tyr Thr Ala Gly Pro His Gly Leu Ser Ser Cys Phe Leu Arg
        50                  55                  60

Ile Arg Ala Asp Gly Gly Val Asp Cys Ala Arg Ser Gln Ser Ala His
65                  70                  75                  80

Ser Leu Val Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
            100                 105                 110

Gln Gly Leu Leu Gln Tyr Ser Ala Gly Asp Cys Ala Phe Gln Glu Glu
        115                 120                 125

Ile Arg Pro Asp Gly Tyr Asn Val Tyr Arg Ser Glu Lys His Arg Leu
    130                 135                 140

Pro Val Ser Leu Ser Ser Ala Ile Gln Arg Gln Leu Tyr Lys Gly Arg
145                 150                 155                 160

Gly Phe Leu Pro Leu Ser His Phe Leu Pro Met Leu Pro Gly Ser Pro
                165                 170                 175

Ala Glu Pro Arg Asp Leu Gln Asp His Val Glu Ser Glu Arg Phe Ser
            180                 185                 190

Ser Pro Leu Glu Thr Asp Ser Met Asp Pro Phe Gly Ile Ala Thr Lys
        195                 200                 205

Met Gly Leu Val Lys Ser Pro Ser Phe Gln Lys
```

<210> SEQ ID NO 32
<211> LENGTH: 223
<212> TYPE: PRT
<213> ORGANISM: Pelodiscus sinensis

<400> SEQUENCE: 32

```
Met Trp Arg Ser Leu Cys Lys Ser His Thr Ser Leu Ala Leu Leu Gly
1               5                   10                  15

Leu Cys Phe Ala Val Val Val Arg Ser Leu Pro Phe Ser Asp Ala Gly
            20                  25                  30

Pro His Val Asn Tyr Gly Trp Gly Glu Pro Ile Arg Leu Arg His Leu
        35                  40                  45

Tyr Thr Ala Ser Arg His Gly Leu Phe Asn Tyr Phe Leu Arg Ile Ser
    50                  55                  60

Ser Asp Gly Lys Val Asp Gly Thr Ser Ile Gln Ser Pro His Ser Leu
65                  70                  75                  80

Leu Glu Ile Arg Ala Val Ala Val Arg Thr Val Ala Ile Lys Gly Val
                85                  90                  95

His Ser Ser Arg Tyr Leu Cys Met Glu Glu Asp Gly Lys Leu His Gly
            100                 105                 110

Leu Leu Arg Tyr Ser Thr Glu Asp Cys Ser Phe Glu Glu Glu Ile Arg
        115                 120                 125

Pro Asp Gly Tyr Asn Val Tyr Lys Ser Lys Lys Tyr Gly Ile Ser Val
    130                 135                 140

Ser Leu Ser Ser Ala Lys Gln Arg Gln Gln Phe Lys Gly Lys Asp Phe
145                 150                 155                 160

Leu Pro Leu Ser His Phe Leu Pro Met Ile Asn Thr Val Pro Val Glu
                165                 170                 175

Ser Met Asp Phe Gly Glu Tyr Gly Asp Tyr Ser His Thr Phe Glu Ser
            180                 185                 190

Asp Leu Phe Ser Ser Pro Leu Glu Thr Asp Ser Met Asp Pro Phe Gly
        195                 200                 205

Ile Thr Ser Lys Ile Ser Pro Val Lys Ser Pro Ser Phe Gln Lys
    210                 215                 220
```

<210> SEQ ID NO 33
<211> LENGTH: 217
<212> TYPE: PRT
<213> ORGANISM: Latimeria chalumnae

<400> SEQUENCE: 33

```
Met Leu Gln Ala Leu Tyr Asn Leu Cys Thr Ala Leu Val Leu Phe Lys
1               5                   10                  15

Leu Pro Phe Ala Met Val Gly Tyr Thr Leu Pro Ser Ala Asn Glu Gly
            20                  25                  30

Pro His Leu Asn Tyr Asp Trp Gly Glu Ser Val Arg Leu Lys His Leu
        35                  40                  45

Tyr Thr Ser Ser Lys His Gly Leu Ile Ser Tyr Phe Leu Gln Ile Asn
    50                  55                  60

Asp Asp Gly Lys Val Asp Gly Thr Thr Arg Ser Cys Tyr Ser Leu
65                  70                  75                  80

Leu Glu Ile Lys Ser Val Gly Pro Gly Val Leu Ala Ile Lys Gly Ile
                85                  90                  95

Gln Ser Ser Arg Tyr Leu Cys Val Glu Lys Asp Gly Lys Leu His Gly
```

```
            100             105             110
Ser Arg Thr Tyr Ser Ala Asp Asp Cys Ser Phe Lys Glu Asp Ile Leu
            115             120             125

Pro Asp Gly Tyr Thr Ile Tyr Val Ser Lys Lys His Gly Ser Val Val
130             135             140

Asn Leu Ser Asn His Lys Gln Lys Arg Gln Arg Asn Arg Arg Thr Leu
145             150             155             160

Pro Pro Phe Ser Gln Phe Leu Pro Leu Met Asp Thr Ile Arg Val Glu
            165             170             175

Cys Met Asn Cys Gly Glu His Cys Asp Asp Asn Leu His Asp Glu Leu
            180             185             190

Glu Thr Gly Leu Ser Met Asp Pro Phe Glu Ser Thr Ser Lys Lys Ser
            195             200             205

Phe Gln Ser Pro Ser Phe His Asn Arg
            210             215

<210> SEQ ID NO 34
<211> LENGTH: 219
<212> TYPE: PRT
<213> ORGANISM: Mustela putorius furo

<400> SEQUENCE: 34

Met Arg Ser Ala Ala Ser Arg Cys Ala Val Ala Arg Ala Leu Val Leu
1               5               10              15

Ala Gly Leu Trp Leu Ala Ala Gly Arg Pro Leu Ala Phe Ser Asp
            20              25              30

Ala Gly Pro His Val His Tyr Gly Trp Gly Pro Ile Arg Leu Arg
            35              40              45

His Leu Tyr Thr Ala Gly Pro His Gly Leu Ser Ser Cys Phe Leu Arg
50              55              60

Ile Arg Ala Asp Gly Gly Val Asp Cys Ala Arg Gly Gln Ser Ala His
65              70              75              80

Ser Leu Val Glu Ile Arg Ala Val Ala Leu Arg Thr Val Ala Ile Lys
            85              90              95

Gly Val Tyr Ser Asp Arg Tyr Leu Cys Met Gly Ala Asp Gly Arg Met
            100             105             110

Gln Gly Leu Pro Gln Tyr Ser Ala Gly Asp Cys Ala Phe Glu Glu Glu
            115             120             125

Ile Arg Pro Asp Gly Tyr Asn Val Tyr Arg Ser Lys Lys His Arg Leu
130             135             140

Pro Val Ser Leu Ser Ser Ala Lys Gln Arg Gln Leu Tyr Lys Asp Arg
145             150             155             160

Gly Phe Leu Pro Leu Ser His Phe Leu Pro Met Leu Pro Gly Ser Leu
            165             170             175

Ala Glu Pro Arg Asp Leu Gln Asp His Val Glu Ala Asp Gly Phe Ser
            180             185             190

Ala Pro Leu Glu Thr Asp Ser Met Asp Pro Phe Gly Ile Ala Thr Lys
            195             200             205

Met Gly Leu Val Lys Ser Pro Ser Phe Gln Lys
210             215

<210> SEQ ID NO 35
<211> LENGTH: 218
<212> TYPE: PRT
<213> ORGANISM: Takifugu rubripes
```

<400> SEQUENCE: 35

Ser Ser Thr Arg Ile Ser Gly Asn Met Val Leu Leu Met Leu Pro Ile
1               5                   10                  15

Thr Val Ala Asn Leu Phe Leu Cys Ala Gly Val Leu Ser Leu Pro Leu
            20                  25                  30

Leu Asp Gln Gly Ser His Phe Pro Gln Gly Trp Glu Gln Val Val Arg
        35                  40                  45

Phe Arg His Leu Tyr Ala Ala Ser Ala Gly Leu His Leu Leu Ile Thr
    50                  55                  60

Glu Glu Gly Ser Ile Gln Gly Ser Ala Asp Pro Thr Leu Tyr Ser Leu
65                  70                  75                  80

Met Glu Ile Arg Pro Val Asp Pro Gly Cys Val Ile Arg Gly Ala
                85                  90                  95

Ala Thr Thr Arg Phe Leu Cys Ile Glu Gly Ala Gly Arg Leu Tyr Ser
                100                 105                 110

Ser Gln Thr Tyr Ser Lys Asp Asp Cys Thr Phe Arg Glu Gln Ile Leu
            115                 120                 125

Ala Asp Gly Tyr Ser Val Tyr Arg Ser Val Gly His Gly Ala Leu Val
        130                 135                 140

Ser Leu Gly Asn Tyr Arg Gln Gln Leu Arg Gly Glu Asp Trp Ser Val
145                 150                 155                 160

Pro Thr Leu Ala Gln Phe Leu Pro Arg Ile Ser Ser Leu Asp Gln Asp
                165                 170                 175

Phe Lys Ala Ala Leu Asp Glu Thr Glu Lys Pro Glu Gln Thr Ala Pro
            180                 185                 190

Gln Arg Ser Glu Pro Val Asp Met Val Asp Ser Phe Gly Lys Leu Ser
        195                 200                 205

Gln Ile Ile His Ser Pro Ser Phe His Lys
    210                 215

<210> SEQ ID NO 36
<211> LENGTH: 94
<212> TYPE: PRT
<213> ORGANISM: Equus caballus

<400> SEQUENCE: 36

Ala Ala Gly Arg Pro Leu Ala Leu Ser Asp Ala Gly Pro His Val His
1               5                   10                  15

Tyr Gly Trp Gly Glu Pro Ile Arg Leu Arg His Leu Tyr Thr Ala Gly
            20                  25                  30

Pro His Gly Leu Ser Ser Cys Phe Leu Arg Ile Arg Ala Asp Gly Ala
        35                  40                  45

Val Asp Cys Ala Arg Gly Gln Ser Ala His Ser Leu Val Glu Ile Arg
    50                  55                  60

Ala Val Ala Leu Arg Thr Val Ala Ile Lys Gly Val His Ser Val Arg
65                  70                  75                  80

Tyr Leu Cys Met Gly Ala Asp Gly Arg Met Gln Gly Leu Val
                85                  90

<210> SEQ ID NO 37
<211> LENGTH: 209
<212> TYPE: PRT
<213> ORGANISM: Oryzias latipes

<400> SEQUENCE: 37

Thr Met Leu Leu Ile Val Val Thr Ile Ser Thr Met Val Phe Ser Asp

```
                1               5                   10                  15
            Ser Gly Val Ser Ser Met Pro Leu Ser Asp His Gly Pro His Ile Thr
                            20                  25                  30
            His Ser Trp Ser Gln Val Val Arg Leu Arg His Leu Tyr Ala Val Lys
                            35                  40                  45
            Pro Gly Gln His Val Gln Ile Arg Glu Asp Gly His Ile His Gly Ser
                            50                  55                  60
            Ala Glu Gln Thr Leu Asn Ser Leu Leu Glu Ile Arg Pro Val Ala Pro
            65                  70                  75                  80
            Gly Arg Val Val Phe Arg Gly Val Ala Thr Ser Arg Phe Leu Cys Met
                                85                  90                  95
            Glu Ser Asp Gly Arg Leu Phe Ser Ser His Thr Phe Asp Lys Asp Asn
                            100                 105                 110
            Cys Val Phe Arg Glu Gln Ile Leu Ala Asp Gly Tyr Asn Ile Tyr Ile
                            115                 120                 125
            Ser Asp Gln His Gly Thr Leu Leu Ser Leu Gly Asn His Arg Gln Arg
                            130                 135                 140
            Gln Gln Gly Leu Asp Arg Asp Val Pro Ala Leu Ala Gln Phe Leu Pro
            145                 150                 155                 160
            Arg Ile Ser Thr Leu Gln Gln Gly Val Tyr Pro Val Pro Asp Pro Pro
                            165                 170                 175
            His Gln Met Arg Thr Met Gln Thr Glu Lys Thr Leu Asp Ala Thr Asp
                            180                 185                 190
            Thr Phe Gly Gln Leu Ser Lys Ile Ile His Ser Pro Ser Phe Asn Lys
                            195                 200                 205
            Arg

<210> SEQ ID NO 38
<211> LENGTH: 207
<212> TYPE: PRT
<213> ORGANISM: Xiphophorus maculates

<400> SEQUENCE: 38

Met Phe Val Phe Ile Leu Cys Ile Ala Gly Glu Leu Phe Thr Leu Gly
            1               5                   10                  15
            Val Phe Cys Met Pro Met Met Asp Gln Gly Pro Leu Val Thr His Gly
                            20                  25                  30
            Trp Gly Gln Val Val Arg His Arg His Leu Tyr Ala Ala Lys Pro Gly
                            35                  40                  45
            Leu His Leu Leu Ile Ser Glu Asp Gly Gln Ile His Gly Ser Ala Asp
                            50                  55                  60
            Gln Thr Leu Tyr Ser Leu Leu Glu Ile Gln Pro Val Gly Pro Gly Arg
            65                  70                  75                  80
            Val Val Ile Lys Gly Val Ala Thr Thr Arg Phe Leu Cys Met Glu Ser
                                85                  90                  95
            Asp Gly Arg Leu Tyr Ser Thr Glu Thr Tyr Ser Arg Ala Asp Cys Thr
                            100                 105                 110
            Phe Arg Glu Gln Ile Gln Ala Asp Gly Tyr Asn Val Tyr Thr Ser Asp
                            115                 120                 125
            Ser His Gly Ala Leu Leu Ser Leu Gly Asn Asn Gln Arg His Ser
                            130                 135                 140
            Gly Ser Asp Arg Gly Val Pro Ala Leu Ala Arg Phe Leu Pro Arg Leu
            145                 150                 155                 160
            Asn Thr Leu Gln Gln Ala Val Pro Thr Glu Pro Asp Val Pro Asp Gln
```

```
                165                 170                 175
Leu Ser Pro Glu Lys Val Gln Gln Thr Val Asp Met Val Ala Ser Phe
            180                 185                 190

Gly Lys Leu Ser His Ile Ile His Ser Pro Ser Phe His Lys Arg
        195                 200                 205

<210> SEQ ID NO 39
<211> LENGTH: 220
<212> TYPE: PRT
<213> ORGANISM: Ictidomys tridecemlineatus

<400> SEQUENCE: 39

Met Arg Ser Ala Pro Ser Gly Arg Ala Leu Ala Arg Ala Leu Val Leu
1               5                   10                  15

Ala Ser Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Phe Ser
    50                  55                  60

Asn Cys Phe Leu Arg Ile Arg Thr Asp Gly Ala Val Asp Cys Glu Glu
65                  70                  75                  80

Lys Gln Ser Glu Arg Ser Leu Met Glu Ile Arg Ala Val Ala Leu Glu
                85                  90                  95

Thr Val Ala Ile Lys Asp Ile Asn Ser Val Arg Tyr Leu Cys Met Gly
            100                 105                 110

Ala Asp Gly Arg Ile Gln Gly Leu Pro Arg Tyr Ser Glu Glu Cys
        115                 120                 125

Thr Phe Lys Glu Glu Ile Ser Tyr Asp Gly Tyr Asn Val Tyr Arg Ser
    130                 135                 140

Gln Lys Tyr His Leu Pro Val Val Leu Ser Ser Ala Lys Gln Arg Gln
145                 150                 155                 160

Leu Tyr Gln Ser Lys Gly Val Val Pro Leu Ser Tyr Phe Leu Pro Met
                165                 170                 175

Leu Pro Leu Ala Ser Ala Glu Thr Arg Asp Arg Leu Gly Ser Asp Val
            180                 185                 190

Phe Ser Leu Pro Leu Glu Thr Asp Ser Met Asp Pro Phe Gly Met Ala
        195                 200                 205

Ser Glu Val Gly Leu Lys Ser Pro Ser Phe Gln Lys
    210                 215                 220

<210> SEQ ID NO 40
<211> LENGTH: 203
<212> TYPE: PRT
<213> ORGANISM: Gasterosteus aculeatus

<400> SEQUENCE: 40

Met Leu Leu Leu Leu Val Pro Ala Tyr Val Ala Ser Val Phe Leu Ala
1               5                   10                  15

Leu Gly Val Val Cys Leu Pro Leu Thr Asp Gln Gly Leu His Met Ala
            20                  25                  30

Asp Asp Trp Gly Gln Ser Val Arg Leu Lys His Leu Tyr Ala Ala Ser
        35                  40                  45

Pro Gly Leu His Leu Leu Ile Gly Glu Asp Gly Arg Ile Gln Gly Ser
    50                  55                  60

Ala Gln Gln Ser Pro Tyr Ser Leu Leu Glu Ile Ser Ala Val Asp Pro
```

```
                 65                  70                  75                  80
Gly Cys Val Val Ile Arg Gly Val Ala Thr Ala Arg Phe Leu Cys Ile
                 85                  90                  95
Glu Gly Asp Gly Arg Leu Tyr Ser Ser Asp Thr Tyr Ser Arg Asp Asp
            100                 105                 110
Cys Thr Phe Arg Glu Gln Ile Leu Pro Asp Gly Tyr Ser Val Tyr Val
        115                 120                 125
Ser His Gly His Gly Ala Leu Leu Ser Leu Gly Asn His Arg Gln Arg
    130                 135                 140
Leu Gln Gly Arg Asp His Gly Val Pro Ala Leu Ala Gln Phe Leu Pro
145                 150                 155                 160
Arg Val Ser Thr Met Asp Gln Ala Ser Ala Pro Asp Ala Pro Gly Gln
                165                 170                 175
Thr Ala Thr Glu Thr Glu Glu Pro Val Asp Ser Phe Gly Lys Leu Ser
            180                 185                 190
Gln Ile Ile His Ser Pro Ser Phe His Glu Arg
        195                 200

<210> SEQ ID NO 41
<211> LENGTH: 208
<212> TYPE: PRT
<213> ORGANISM: Oreochromis niloticus

<400> SEQUENCE: 41

Met Leu Leu Leu Ile Val Ser Ile Val Asn Met Leu Phe Gly Val
1               5                  10                  15
Gly Met Val Cys Met Pro Leu Ser Asp Asn Gly Pro His Ile Ala His
                20                  25                  30
Gly Trp Ala Gln Val Val Arg Leu Arg His Leu Tyr Ala Thr Arg Pro
            35                  40                  45
Gly Met His Leu Leu Ile Ser Glu Gly Gly Gln Ile Arg Gly Ser Ala
        50                  55                  60
Val Gln Thr Leu His Ser Leu Met Glu Ile Arg Pro Val Gly Pro Gly
65                  70                  75                  80
Arg Val Val Ile Arg Gly Val Ala Thr Ala Arg Phe Leu Cys Ile Glu
                85                  90                  95
Asp Asp Gly Thr Leu Tyr Ser Ser His Ala Tyr Ser Arg Glu Asp Cys
            100                 105                 110
Ile Phe Arg Glu Gln Ile Leu Pro Asp Gly Tyr Asn Ile Tyr Ile Ser
        115                 120                 125
Asp Arg His Gly Val Leu Leu Ser Leu Gly Asn His Arg Gln Arg Leu
    130                 135                 140
Gln Gly Leu Asp Arg Gly Asp Pro Ala Leu Ala Gln Phe Leu Pro Arg
145                 150                 155                 160
Ile Ser Thr Leu Asn Gln Ile Pro Ser Pro Gly Ala Asn Ile Gly Asp
                165                 170                 175
His Met Lys Val Ala Lys Thr Glu Glu Pro Val Asp Thr Ile Asp Ser
            180                 185                 190
Phe Gly Lys Phe Ser Gln Ile Ile Asp Ser Pro Ser Phe His Lys Arg
        195                 200                 205

<210> SEQ ID NO 42
<211> LENGTH: 152
<212> TYPE: PRT
<213> ORGANISM: Meleagris gallopavo
```

<400> SEQUENCE: 42

Val Gly Asn Gln Ser Pro Gln Ser Ile Leu Glu Ile Thr Ala Val Asp
1               5                   10                  15

Val Gly Ile Val Ala Ile Lys Gly Leu Phe Ser Gly Arg Tyr Leu Ala
            20                  25                  30

Met Asn Lys Arg Gly Arg Leu Tyr Ala Ser Leu Ser Tyr Ser Ile Glu
        35                  40                  45

Asp Cys Ser Phe Glu Glu Ile Arg Pro Gly Tyr Asn Val Tyr
    50                  55                  60

Lys Ser Lys Lys Tyr Gly Ile Ser Val Ser Leu Ser Ser Ala Lys Gln
65                  70                  75                  80

Arg Gln Gln Phe Lys Gly Lys Asp Phe Leu Pro Leu Ser His Phe Leu
                85                  90                  95

Pro Met Ile Asn Thr Val Pro Val Glu Val Thr Asp Phe Gly Glu Tyr
                100                 105                 110

Gly Asp Tyr Ser Gln Ala Phe Glu Pro Glu Val Tyr Ser Ser Pro Leu
            115                 120                 125

Glu Thr Asp Ser Met Asp Pro Phe Gly Ile Thr Ser Lys Leu Ser Pro
            130                 135                 140

Val Lys Ser Pro Ser Phe Gln Lys
145                 150

<210> SEQ ID NO 43
<211> LENGTH: 216
<212> TYPE: PRT
<213> ORGANISM: Papio anubis

<400> SEQUENCE: 43

Met Arg Ser Gly Cys Val Val His Ala Trp Ile Leu Ala Ser Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Ile Arg Pro
            115                 120                 125

Asp Gly Tyr Asn Val Tyr Arg Ser Gln Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly Pro Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

-continued

Val Arg Ser Pro Ser Phe Glu Lys
    210                 215

<210> SEQ ID NO 44
<211> LENGTH: 216
<212> TYPE: PRT
<213> ORGANISM: Saimiri boliviensis boliviensis

<400> SEQUENCE: 44

Met Arg Ser Gly Cys Val Val His Ala Trp Ile Leu Ala Gly Leu
1               5                   10                  15

Trp Leu Ala Val Val Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Ser Pro His Gly Leu Ser Ser Cys Phe Leu Arg Ile Arg Ser
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Ser Arg Tyr Leu Cys Met Gly Ala Asp Gly Arg Leu Gln Gly Leu
            100                 105                 110

Phe Gln Tyr Ser Glu Glu Asp Cys Ala Phe Glu Glu Ile Arg Pro
            115                 120                 125

Asp Gly Tyr Asn Val Tyr Leu Ser Glu Lys His Arg Leu Pro Val Ser
            130                 135                 140

Leu Ser Ser Ala Lys Gln Arg Gln Leu Tyr Lys Lys Arg Gly Phe Leu
145                 150                 155                 160

Pro Leu Ser His Phe Leu Pro Met Leu Pro Arg Ala Pro Glu Glu Pro
                165                 170                 175

Asp Asp Leu Arg Gly His Leu Glu Ser Asp Val Phe Ser Ser Pro Leu
            180                 185                 190

Glu Thr Asp Ser Met Asp Pro Phe Gly Leu Val Thr Gly Leu Glu Ala
            195                 200                 205

Val Asn Ser Pro Ser Phe Glu Lys
    210                 215

<210> SEQ ID NO 45
<211> LENGTH: 216
<212> TYPE: PRT
<213> ORGANISM: Pteropus alecto

<400> SEQUENCE: 45

Met Arg Ser Pro Cys Ala Val Ala Arg Ala Leu Val Leu Ala Gly Leu
1               5                   10                  15

Trp Leu Ala Ser Ala Ala Gly Pro Leu Ala Leu Ser Asp Ala Gly Pro
            20                  25                  30

His Val His Tyr Gly Trp Gly Glu Ala Ile Arg Leu Arg His Leu Tyr
        35                  40                  45

Thr Ala Gly Pro His Gly Pro Ser Ser Cys Phe Leu Arg Ile Arg Ala
    50                  55                  60

Asp Gly Ala Val Asp Cys Ala Arg Gly Gln Ser Ala His Ser Leu Val
65                  70                  75                  80

Glu Ile Arg Ala Val Ala Leu Arg Asn Val Ala Ile Lys Gly Val His
                85                  90                  95

Ser Val Arg Tyr Leu Cys Met Gly Ala Asp Gly Arg Met Leu Gly Leu
            100                 105                 110

Leu Gln Tyr Ser Ala Asp Asp Cys Ala Phe Glu Glu Ile Arg Pro
        115                 120                 125

Asp Gly Tyr Asn Val Tyr His Ser Lys Lys His His Leu Pro Val Ser
        130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Pro Leu
            180                 185                 190

Glu Thr Asp Asp Met Asp Pro Phe Gly Ile Ala Ser Lys Leu Gly Leu
            195                 200                 205

Glu Glu Ser Pro Ser Phe Gln Lys
            210                 215

<210> SEQ ID NO 46
<211> LENGTH: 245
<212> TYPE: PRT
<213> ORGANISM: Myotis davidii

<400> SEQUENCE: 46

Met Ser Gly Gln Asn Ser Gly Arg His Gly Ser Arg Pro Gly Leu Asp
1               5                   10                  15

Glu Glu Pro Glu Pro Gly Pro Leu Glu Leu Arg Ala Leu Gly Ser Thr
            20                  25                  30

Arg Ala Asp Pro Gln Leu Cys Asp Phe Leu Glu Asn His Phe Leu Gly
        35                  40                  45

Tyr Thr Cys Leu Glu Leu Asp Ile Cys Leu Ala Thr Tyr Leu Gly Val
    50                  55                  60

Ser His Trp Gly Glu Ser Ile Arg Leu Arg His Leu Tyr Thr Ser Gly
65              70                  75                  80

Pro His Gly Pro Ser Ser Cys Phe Leu Arg Ile Arg Val Asp Gly Ala
                85                  90                  95

Val Asp Cys Ala Arg Gly Gln Ser Ala His Ser Leu Val Glu Ile Arg
            100                 105                 110

Ala Val Ala Leu Arg Lys Val Ala Ile Lys Gly Val His Ser Ala Leu
        115                 120                 125

Tyr Leu Cys Met Glu Gly Asp Gly Arg Met Arg Gly Leu Pro Gln Phe
    130                 135                 140

Ser Pro Glu Asp Cys Ala Phe Glu Glu Ile Arg Pro Asp Gly Tyr
145                 150                 155                 160

Asn Val Tyr Arg Ser Gln Lys His Gln Leu Pro Val Ser Leu Ser Ser
                165                 170                 175

Ala Arg Gln Arg Gln Leu Phe Lys Ala Arg Gly Phe Leu Pro Leu Ser
            180                 185                 190

His Phe Leu Pro Met Leu Pro Ser Pro Ala Glu Pro Val His Arg
        195                 200                 205

Glu Arg Pro Leu Glu Pro Asp Ala Phe Ser Ser Pro Leu Glu Thr Asp
    210                 215                 220

Ser Met Asp Pro Phe Gly Ile Ala Asn Asn Leu Arg Leu Val Lys Ser
225                 230                 235                 240

Pro Ser Phe Gln Lys
                245

<210> SEQ ID NO 47
<211> LENGTH: 250
<212> TYPE: PRT
<213> ORGANISM: Tupaia chinensis

<400> SEQUENCE: 47

Met Arg Arg Thr Trp Ser Gly Phe Ala Val Ala Thr Arg Ala Gly Ser
1               5                   10                  15

Pro Leu Ala Leu Ala Asp Ala Gly Pro His Val Asn Tyr Gly Trp Asp
            20                  25                  30

Glu Ser Ile Arg Leu Arg His Leu Tyr Thr Ala Ser Leu His Gly Ser
        35                  40                  45

Thr Ser Cys Phe Leu Arg Ile Arg Asp Asp Gly Ser Val Gly Cys Ala
    50                  55                  60

Arg Gly Gln Ser Met His Ser Leu Leu Glu Ile Lys Ala Val Ala Leu
65                  70                  75                  80

Gln Thr Val Ala Ile Lys Gly Val Tyr Ser Val Arg Tyr Leu Cys Met
                85                  90                  95

Asp Thr Asp Gly Arg Met Gln Gly Leu Pro Gln Tyr Ser Glu Glu Asp
            100                 105                 110

Cys Thr Phe Glu Glu Glu Ile Arg Ser Asp Gly His Asn Val Tyr Arg
        115                 120                 125

Ser Lys Lys His Gly Leu Pro Val Ser Leu Ser Ser Ala Lys Gln Arg
    130                 135                 140

Gln Leu Tyr Lys Gly Arg Gly Phe Leu Ser Leu Ser His Phe Leu Leu
145                 150                 155                 160

Met Met Pro Lys Thr Ser Ala Gly Pro Gly Asn Pro Arg Asp Gln Arg
                165                 170                 175

Asn Pro Arg Asp Gln Arg Asp Pro Asn Thr Phe Ser Leu Pro Leu Glu
            180                 185                 190

Thr Asp Ser Met Asp Pro Phe Gly Met Thr Thr Arg His Gly Leu Leu
        195                 200                 205

Leu Asp Ser Cys Cys Ala Ser Leu Val Leu Leu Asn Ile Ser Thr Asp
    210                 215                 220

Gly Glu Phe Ser Pro Tyr Gly Asn Ile Leu Arg Pro Ser Phe Arg Phe
225                 230                 235                 240

Lys Leu Phe Lys Met Lys Lys Val Thr Asn
                245                 250

<210> SEQ ID NO 48
<211> LENGTH: 209
<212> TYPE: PRT
<213> ORGANISM: Heterocephalus glaber

<400> SEQUENCE: 48

Met Arg Phe Ser Lys Ser Thr Cys Gly Phe Phe Asn His Gln Arg Leu
1               5                   10                  15

Gln Ala Leu Trp Leu Ser Leu Ser Ser Val Lys Trp Val Leu Asp Ala
            20                  25                  30

Ala Val Glu Gly Arg Pro Ile Arg Leu Arg His Leu Tyr Ala Ala Gly
        35                  40                  45

Pro Tyr Gly Arg Ser Arg Cys Phe Leu Arg Ile His Thr Asp Gly Ala
    50                  55                  60

Val Asp Cys Val Glu Glu Gln Ser Glu His Cys Leu Leu Glu Ile Arg
65                  70                  75                  80

```
Ala Val Ala Leu Glu Thr Val Ala Ile Lys Asp Ile Asn Ser Val Arg
                85                  90                  95
Tyr Leu Cys Met Gly Pro Asp Gly Arg Met Gln Gly Leu Pro Trp Tyr
                100                 105                 110
Ser Glu Glu Asp Cys Ala Phe Lys Glu Ile Ser Tyr Pro Gly Tyr
                115                 120                 125
Ser Val Tyr Arg Ser Gln Lys His His Leu Pro Ile Val Leu Ser Ser
        130                 135                 140
Val Lys Gln Arg Gln Gln Tyr Gln Ser Lys Gly Val Val Pro Leu Ser
145                 150                 155                 160
Tyr Phe Leu Pro Met Leu Pro Lys Ala Ser Val Glu Pro Gly Asp Glu
                165                 170                 175
Glu Glu Ser Ala Phe Ser Leu Pro Leu Lys Thr Asp Ser Met Asp Pro
                180                 185                 190
Phe Gly Met Ala Ser Glu Ile Gly Leu Ala Lys Ser Pro Ser Phe Gln
            195                 200                 205
Lys

<210> SEQ ID NO 49
<211> LENGTH: 13
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (7)..(7)
<223> OTHER INFORMATION: Xaa at position 7 is R or N

<400> SEQUENCE: 49

Thr Gly Leu Glu Ala Val Xaa Ser Pro Ser Phe Glu Lys
1               5                   10

<210> SEQ ID NO 50
<211> LENGTH: 20
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (14)..(14)
<223> OTHER INFORMATION: Xaa at position 14 is R or N

<400> SEQUENCE: 50

Met Asp Pro Phe Gly Leu Val Thr Gly Leu Glu Ala Val Xaa Ser Pro
1               5                   10                  15

Ser Phe Glu Lys
            20

<210> SEQ ID NO 51
<211> LENGTH: 48
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (3)..(3)
<223> OTHER INFORMATION: Xaa at position 3 is M or I
<220> FEATURE:
```

-continued

```
<221> NAME/KEY: MISC_FEATURE
<222> LOCATION: (4)..(4)
<223> OTHER INFORMATION: Xaa at position 4 is V or A
<220> FEATURE:
<221> NAME/KEY: MISC_FEATURE
<222> LOCATION: (13)..(13)
<223> OTHER INFORMATION: Xaa at position 13 is G or R
<220> FEATURE:
<221> NAME/KEY: MISC_FEATURE
<222> LOCATION: (19)..(19)
<223> OTHER INFORMATION: Xaa at position 19 is M or V
<220> FEATURE:
<221> NAME/KEY: MISC_FEATURE
<222> LOCATION: (42)..(42)
<223> OTHER INFORMATION: Xaa at position 42 is R or N

<400> SEQUENCE: 51

Leu Pro Xaa Xaa Pro Glu Glu Pro Glu Asp Leu Arg Xaa His Leu Glu
1               5                   10                  15

Ser Asp Xaa Phe Ser Ser Pro Leu Glu Thr Asp Ser Met Asp Pro Phe
            20                  25                  30

Gly Leu Val Thr Gly Leu Glu Ala Val Xaa Ser Pro Ser Phe Glu Lys
        35                  40                  45

<210> SEQ ID NO 52
<211> LENGTH: 651
<212> TYPE: DNA
<213> ORGANISM: Homo sapiens

<400> SEQUENCE: 52
atgcggagcg ggtgtgtggt ggtccacgta tggatcctgg ccggcctctg gctggccgtg     60
gccgggcgcc ccctcgcctt ctcggacgcg gggccccacg tgcactacgg ctggggcgac    120
cccatccgcc tgcggcacct gtacacctcc ggccccacg gctctccag ctgcttcctg      180 cgcatccgtg ccgacggcgt cgtggactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga aagcaccgc     420 ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a              651

<210> SEQ ID NO 53
<211> LENGTH: 651
<212> TYPE: DNA
<213> ORGANISM: Gorilla

<400> SEQUENCE: 53
atgcggagcg ggtgtgtggt ggtccacgtc tggatcctgg ccggcctctg gctggccgtg     60
gccgggcgcc ccctcgcctt ctcggacgcg gggccccacg tgcactacgg ctggggcgac    120
cccatccgcc tgcggcacct gtacacctcc ggccccacg gctctccag ctgcttcctg      180 cgcatccgtg ccgacggcgt cgtggactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatctga aagcaccgc     420
```

```
ctcccggtct ccctgagcag tgccaaacag cggcagctgt acaagaacag aggctttctt    480
ccgctctctc atttcctgcc catgctgccc atggtcccag aggagcctga ggacctcagg    540
ggccacttgg aatctgacat gttctcttca cccctggaga ccgacagcat ggacccattt    600
gggcttgtca ccggactgga ggccgtgagg agtcctagct ttgagaagta a             651
```

<210> SEQ ID NO 54
<211> LENGTH: 651
<212> TYPE: DNA
<213> ORGANISM: Pan troglodytes

<400> SEQUENCE: 54

```
atgcggaacg ggtgtgtggt ggtccacgtc tggatcctgg ccggcctctg gctggccgtg    60
gccgggcgcc ccctcgcctt ctcggacgcg gggcgccacg tgcactactg ctggggcgac    120
cccatccccc tgcggcacct gtacacctcc ggcccccatg gctctccag ctgcttcctg     180 cgcatccctg cgaactgcgt catgaactgc gcgcggggcc agagcgcgca cagtttgctg    240
gagatcaagg cagtcgctct gcggaccgtg gccatcaagg gcgtgcacag cgtgcggtac    300
ctctgcatgg gcgccgacgg caagatgcag gggctgcttc agtactcgga ggaagactgt    360
gctttcgagg aggagatccg cccagatggc tacaatgtgt accgatccga gaagcaccgc    420
ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a             651
```

<210> SEQ ID NO 55
<211> LENGTH: 651
<212> TYPE: DNA
<213> ORGANISM: Macaca mulatta

<400> SEQUENCE: 55

```
atgaggagcg ggtgtgtggt ggtccacgcc tggatcctgg ccagcctctg gctggccgtg    60
gccgggcgtc ccctcgcctt ctcggacgcg gggcccacg tgcactacgg ctggggcgac     120
cccatccgcc tgcggcacct gtacacctcc ggcccccatg gctctccag ctgcttcctg     180 cgcatccgca ccgacggcgt cgtggactgc gcgcggggcc aaagcgcgca cagtttgctg    240
gagatcaagg cagtagctct gcggaccgtg gccatcaagg gcgtgcacag cgtgcggtac    300
ctctgcatgg gcgccgacgg caagatgcag gggctgcttc agtactcaga ggaagactgt    360
gctttcgagg aggagatccg ccctgatggc tacaatgtat accgatccga gaagcaccgc    420
ctcccggtct ctctgagcag tgccaaacag aggcagctgt acaagaacag aggctttctt    480
ccgctctctc atttcctacc catgctgccc atggcccag aggagcctga ggacctcagg     540
ggccacttgg aatctgacat gttctcttcg cccctggaga ctgacagcat ggacccattt    600
gggcttgtca ccggactgga ggcggtgagg agtcccagct ttgagaaata a             651
```

<210> SEQ ID NO 56
<211> LENGTH: 651
<212> TYPE: DNA
<213> ORGANISM: Pongo abelii

<400> SEQUENCE: 56

```
atgcggagcg ggtgtgtggt ggtccacgcc tggatcctgg ccggcctctg gctggccgtg    60
gccgggcgcc ccctcgcctt ctcggactcg gggcccacg tgcactacgg ctggggcgac     120
```

```
cccatccgcc tgcggcacct gtacacctcc ggcccccacg ggctctccag ctgcttcctg      180
cgcatccgtg ccgacggcgt cgtggactgc gcgcggggcc agagcgcgca cagtttgctg      240
gagatcaagg cagtcgctct gcggaccgtg gccatcaagg cgtgcacag cgtgcggtac       300 ctctgcatgg gcgccgacgg caagatgcag gggctgcttc agtactcgga ggaagactgt      360
gctttcgagg aggagatccg cccagatggc tacaatgtgt accgatccga aagcaccgc       420 ctcccggtct ccctgagcag tgccaaacag cggcagctgt acaagaacag gggctttctt      480
ccgctctctc atttcctgcc catgctgccc atggtcccag aggagcctga ggacctcagg      540
cgccacttgg aatccgacat gttctcttcg cccctggaga ccgacagcat ggacccattt      600
gggcttgtca ccggactgga ggccgtgagg agtcccagct ttgagaaata a               651
```

```
<210> SEQ ID NO 57
<211> LENGTH: 651
<212> TYPE: DNA
<213> ORGANISM: Nomascus leucogenys

<400> SEQUENCE: 57
```

```
atgcggagcg agtgtgtggt ggtccacgcc tggatcctgg ccggcctctg gctggcagtg       60
gccgggcgcc ccctcgcctt ttcggacgcg gggccccacg tgcactacgg ctggggcgac      120
cccatccgtc tgcggcacct gtacacctcc ggccccacg  ggctctccag ctgcttcctg      180
cgcatccgtg ccgacggcgt cgtggactgc gcgcggggcc agagcgcgca cagtttgctg      240
gagatcaagg cagtcgctct gcggaccgtg gccataaagg cgtgcacag cgtgcggtac       300 ctctgcatgg gcgccgacgg caagatgcag gggctgcttc agtattcgga ggaagactgt      360
gctttcgagg aggagatccg cccagatggc tacaatgtgt accgatccga aagcaccgc       420 ctccccgtct ccctgagcag tgccaaacag cggcagctgt ataagaacag aggctttctt      480
ccactctctc atttcctgcc catgctgccc atggtcccag aggagcctga ggacctcagg      540
ggccacttgg aatctgacat gttctcttcg cccctggaga ccgacagcat ggacccattt      600
gggcttgtca ccggactgga ggccgtgagg agtcccagct ttgagaaata a               651
```

```
<210> SEQ ID NO 58
<211> LENGTH: 429
<212> TYPE: DNA
<213> ORGANISM: Callithrix jacchus

<400> SEQUENCE: 58
```

```
atgtggaagg ccaccgctgg tggccagcag ggacagtccg aagcacaaat gtccacatgt       60
ccccatgttc ctcgtcctct gtggattgct cagagctgcc tgttttctct gcagctccag      120
tactcggagg aagactgtgc tttcgaggag gagatccgcc ctgatggcta caatgtgtac      180
tggtccgaga agcaccgcct cccggtctcc ctgagcagcg ccaaacagcg gcagctgtac      240
aagaaacgag gctttcttcc actgtcccat ttcctgccca tgctgccat  agccccagaa      300 gagcctgagg acctcagggg acacctggaa tctgacgtgt tctcttcacc cctggagact      360
gacagcatgg acccatttgg gcttgtcacg ggactggagg cggtgaacag tcccagcttt      420
gagaagtaa                                                              429
```

```
<210> SEQ ID NO 59
<211> LENGTH: 660
<212> TYPE: DNA
<213> ORGANISM: Microcebus murinus
```

<400> SEQUENCE: 59

```
atgccgagcg ggcaaagcgg ttgtgtggcg gcccgcgccc tgatcctggc cggcctctgg      60
ctgaccgcgg ccgggcgccc gctggccttc tccgacgcgg gcccgcacgt gcactacggc     120
tggggcgagc ccatccgcct gcggcacctg tacaccgccg gccccacgg cctctccagc      180
tgcttcctgc gcatccgcgc agacggctcc gtggactgcg cgcggggcca gagcgcacac     240
agtttgctgg agatcagggc ggtcgctctt cggactgtgg ccatcaaggg cgtgcacagc     300
gtgcggtacc tctgcatggg cgcagacggc aggatgcagg ggctgctccg gtactcggag     360
gaagactgtg ccttcgagga ggagatccgc cccgatggct acaacgtgta ccggtctgag     420
aagcaccgcc tgccggtgtc tctgagcagc gccaggcaga ggcagctgta caagggcagg     480
ggcttcctgc cgctctctca cttcctgccc atgctgcccg tgaccccggc agagaccggg     540
gacctcaggg accacttgga gtccgacatg ttcgcttcgc ccctggagac cgacagcatg     600
gacccgtttg ggatcgccac cagacttggg gtggtgaaga gtcccagctt cagaaatga     660
```

<210> SEQ ID NO 60
<211> LENGTH: 415
<212> TYPE: DNA
<213> ORGANISM: Choloepus hoffmanni

<400> SEQUENCE: 60

```
ttgctcgaaa tgaaggcagt ggcgctgcgg gccgtggcca tcaagggcgt gcacagtgct      60
ctgtacctct gcatgaacgc cgacggcagt ctgcacgggc tgcctcggta ctctgcagaa     120
gactgtgctt tgaggagga atccgcccc gacggctaca atgtgtactg gtctaggaag     180
cacggcctcc ctgtctcttt gagcagtgca aaacagaggc agctgtacaa aggcagaggc     240
tttctgcccc tgtcccactt cctgcccatg ctgcccatga cgccggccga gcccgcagac     300
cccggggatg acgtggagtc ggacatgttc tcttcacctc tggaaaccga cagcatggat     360
cctttggaa ttgcctccag acttgagctt gtgaacagtc cagctttcag cataa          415
```

<210> SEQ ID NO 61
<211> LENGTH: 619
<212> TYPE: DNA
<213> ORGANISM: Ailuropoda melanoleuca

<400> SEQUENCE: 61

```
ggtcctagcc ggcctctgcc tggcggtagc cgggcgcccc ctagccttct cggacgcggg      60
gccgcacgtg cactacggct ggggtgagcc catccgccta cggcacctgt acaccgccgg     120
cccccacggc ctctccagct gcttcctgcg catccgtgcc gacggcgggg ttgactgcgc     180
gcggggccag agcgcgcaca gtttggtgga gatcagggca gtcgctctgc ggaccgtggc     240
catcaaggt gtgcacagcg tccggtacct ctgcatgggc gcggacggca ggatgcaagg     300
gctgcctcag tactctgcag gggactgtgc tttcgaggag gagatccgcc ccgacggcta     360
caatgtgtac cggtccaaga agcaccgtct ccccgtctct ctgagcggtg ccaaacagag     420
gcagctttac aaagacagag gctttctgcc cctgtcccac ttcttgccca tgctgcccgg     480
gagcccagca gagcccaggg acctccagga ccatgcggag tcggacgggt tttctgcacc     540
cctagaaaca gacagcatgg acccttttgg gatcgccacc aaaatgggac tagtgaagag     600
tcccagcttc cagaaataa                                                 619
```

<210> SEQ ID NO 62
<211> LENGTH: 660

```
<212> TYPE: DNA
<213> ORGANISM: Sus scrofa

<400> SEQUENCE: 62
atgcggagcg ctccgagccg gtgcgcggtg gtccgcgccc tggtcctggc cggcctctgg      60
ctggccgcag ccgggcgccc cctagccttc tcggatgctg gccgcacgt gcactacggc     120 tggggcgagt cggtccgcct gcggcacctg tacactgcga gtccccacgg cgtctccagc    180
tgcttcctgc gcatccactc agacggcccc gtggactgcg cgccgggaca gagcgcgcac    240
agtttgatgg agatcagggc agtcgcgctg agtaccgtgg cgatcaaggg cgagcgcagc    300
ggccgttacc tctgcatggg cgccgacggc aagatgcaag gcagactca gtactcggat     360 gaggactgtg ctttcgagga ggagatccgc cctgatggct acaacgtgta ctggtccaag    420
aaacaccatc tgcccgtctc tctgagcagc gccaggcaga ggcagctgta caaaggcagg    480
ggcttcctgc gctgtccca ctttctgccc atgctgtcca ctctcccagc cgagccggag     540
gacctccagg accccttcaa gtccgacctg ttttcttttgc ccctggaaac ggacagcatg   600
gaccctttcc ggatcgccgc caaactggga gcggtgaaga gtcccagctt ctataaataa    660

<210> SEQ ID NO 63
<211> LENGTH: 657
<212> TYPE: DNA
<213> ORGANISM: Bos taurus

<400> SEQUENCE: 63
atgcggagcg ctccgagccg gtgcgccgtg gcccgcgccc tggtcctggc tggcctctgg     60
ctggccgcag ccgggcgccc cctggccttc tcggatgcgg gccgcacgt gcactacggc    120 tggggcgagt cggttcgctt gcggcacctg tataccgcgg gcccgcaggg cctctacagc    180
tgctttctgc gcatccactc cgacggcgcc gtggactgcg cgcaggtcca gagcgcgcac    240
agtttgatgg agatcagggc ggtcgctctg agcaccgtag ccatcaaggg cgagcgcagc    300
gtgctgtacc tctgcatgga cgccgacggc aagatgcaag gactgaccca gtactcagcc    360
gaggactgtg ctttcgagga ggagatccgt cctgacggct acaacgtgta ctggtccagg    420
aagcaccatc tcccggtctc cctgagcagc tccaggcaga ggcagctgtt caaaagcagg    480
ggcttcctgc gctgtctca cttcctgccc atgctgtcca ccatcccagc cgaacctgaa     540
gacctccagg aaccctgaa gcctgatttc tttctgcccc tgaaaacaga tagcatggac    600
cctttcgggc tcgccaccaa actgggatcg gtgaagagtc ccagcttcta taattaa       657

<210> SEQ ID NO 64
<211> LENGTH: 579
<212> TYPE: DNA
<213> ORGANISM: Canis lupus familiaris

<400> SEQUENCE: 64
ctagccttct ccgacgcggg gccgcacgtg cactccttct gggggagcc catccgcctg      60 cggcacctgt acaccgccgg cccccacggc ctctccagct gcttcctgcg catccgcgcc    120
gacggcgggg tggactgcgc gcggggccag agcgcgcaca gtctgatgga gatgagggcg    180
gtcgctctgc ggaccgtggc catcaagggc gtgcacagcg gccggtacct ctgcatgggc    240
gccgacggca ggatgcaagg gctgcctcag tactccgccg agactgtac tttcgaggag     300 gagatccgtc ccgatggcta caatgtgtac tggtccaaga agcaccatct ccccatctct    360
ctgagtagtg ccaaacagag gcagctctac aagggcaggg gcttttttgcc cctgtcccac    420
```

| | |
|---|---|
| ttcttaccta tcttgcccgg gagcccaaca gagcccaggg acctggaaga ccatgtggag | 480 |
| tctgacgggt tttctgcatc cctggaaaca gacagcatgg acccttttgg gatcgccacc | 540 |
| aaaattggac tagtgaagag tcccagtttc caaaaataa | 579 |

<210> SEQ ID NO 65
<211> LENGTH: 657
<212> TYPE: DNA
<213> ORGANISM: Oryctolagus cuniculus

<400> SEQUENCE: 65

| | |
|---|---|
| atgcgccgcg cgccgagcgg aggtgccgcg gcccgcgcct tggtcctggc cggcctctgg | 60 |
| ctggccgcgg ccgcgcgccc cttggccttg tccgacgcgg gcccgcatct gcactacggc | 120 |
| tggggcgagc ccgtccgcct gcggcacctg tacgccacca cgcccacgg cgtctcgcac | 180 |
| tgcttcctgc gtatacgcgc cgacggcgcc gtggactgca gcggagcca gagcgcacac | 240 |
| agcttgctgg agatccgagc ggtcgccctg cgcaccgtgg ccttcaaggg cgtgcacagc | 300 |
| tcccgctacc tctgcatggg cgccgacggc aggatgcggg gcagctgca gtactcggag | 360 |
| gaggactgtg ccttccagga ggagatcagc tccggctaca cgtgtaccg ctccacgacg | 420 |
| caccacctgc ccgtgtctct gagcagtgcc aagcagagac acctgtacaa gaccagaggc | 480 |
| ttcctgcccc tctcccactt cctgcccgtg ctgcccctgg cctccgagga ccgcggcc | 540 |
| ctcggcgacc accctgaagc cgacctgttc tccccgcccc tggaaaccga cagcatggac | 600 |
| cccttcggca tggccaccaa gctcgggccg gtgaagagcc ccagctttca gaagtag | 657 |

<210> SEQ ID NO 66
<211> LENGTH: 651
<212> TYPE: DNA
<213> ORGANISM: Pteropus vampyrus

<400> SEQUENCE: 66

| | |
|---|---|
| atgcggagcc cgtgcgctgt ggcccgcgcc ttggtcctgg ccggcctctg gctggcctca | 60 |
| gctgcgggcc ccctcgccct tcggacgcg gggccgcacg tgcactacgg ctggggcgag | 120 |
| gccatccgcc tgcggcacct gtacaccgcc ggcccccacg gcccctccag ctgcttcctg | 180 |
| cgcatccgcg cggatggggc ggtggactgc gcgcggggcc agagcgcgca cagtttggtg | 240 |
| gaaatccggg ctgtcgccct gcggaacgtg gctatcaagg gcgtgcacag cgtccgatac | 300 |
| ctctgcatgg gagccgacgg caggatgcta gggctgcttc agtactccgc tgacgactgc | 360 |
| gccttcgagg aggagatccg cccggacggc tacaacgtgt accactccaa gaagcaccac | 420 |
| ctcccggtct ctctgagcag tgccaagcag aggcaactgt acaaggacag gggcttcctg | 480 |
| cccctgtccc atttcctgcc catgctgccc aggagcccga cagagcccga aacttcgaa | 540 |
| gaccacttgg aggccgacac gttttcctcg cccctggaga cagacgacat ggaccctttt | 600 |
| gggattgcca gtaaattggg gctggaggaa agtcccagct ccagaagta a | 651 |

<210> SEQ ID NO 67
<211> LENGTH: 660
<212> TYPE: DNA
<213> ORGANISM: Tursiops truncatus

<400> SEQUENCE: 67

| | |
|---|---|
| atgcggagcg ctccgagccg gtgcgccgtg gcccgcgccc tggtcctggc cggcctctgg | 60 |
| ctggctgcag ccggggcgcc cctagccttc tcggatgccg gccgcacgt gcactacggc | 120 |
| tggggcgagt ccgtccgcct gcggcacctg tacaccgcgg gtccccaggg cctctccagc | 180 |

```
tgcttcctgc gcatccactc agacggcgcc gtggactgcg cgccggttca gagcgcgcac    240
agtttgatgg agatcagggc agtcgctctg agtaccgtgg ccatcaaggg cgaacgcagc    300
gtcctgtacc tctgcatggg cgccgacggc aaaatgcaag ggctgagtca gtactcagct    360
gaggactgtg cctttgagga ggaaatccgt ccggacggct acaacgtgta ctggtccaag    420
aaacaccacc tcccggtgtc cctgagcagc gccaggcagc ggcagctgtt caaaggcagg    480
ggtttcctgc cgctgtctca cttccttccc atgctgtcca ccatccccac agagcccgat    540
gaaatccagg accacttgaa gcccgatttg tttgctttgc ccctgaaaac agatagcatg    600
gacccatttg ggctcgccac caaactggga gtggtgaaga gtcccagctt ctataagtaa    660

<210> SEQ ID NO 68
<211> LENGTH: 660
<212> TYPE: DNA
<213> ORGANISM: Myotis lucifugus

<400> SEQUENCE: 68
atgcaaagcg cgtggagccg acgcgttgtg gcccgagccc tggtcttggc cagcctcggg     60
ctggcctcag ccgggggggcc cctcggtctt tcggacgctg gccgcacgt gcactacggc    120 tgggggagt ccatccgcct gcgccacctg tacacctccg gcccccacgg cccatccagc    180
tgcttcctgc gcatccgcgc tgacggcgca gtggactgcg cgcggggcca gagcgcgcac    240
agtttggtgg agatcagggc cgtcgccttg cggaaagtgg ccatcaaggg cgtgcacagc    300
gccctgtacc tctgcatggg aggcgacggc aggatgctgg ggctgcctca gttctcgccc    360
gaggactgtg ctttcgagga ggagatccgc ccggacggct acaacgtgta ccggtcccag    420
aagcaccagc tgcccgtctc gctgagcagt gccggcaga ggcagctgtt caaggcccgg    480
ggcttcctgc cgctgtccca cttcctgccc atgctgccca gcagcccgc gggacccgtg    540 ccccagagcc gccccctcgga gccggacgag ttctcttcgc ccctggaaac agacagcatg    600
gacccttttg ggattgccaa caacctgagg ctggtgagaa gtcccagctt tcaggaataa    660

<210> SEQ ID NO 69
<211> LENGTH: 558
<212> TYPE: DNA
<213> ORGANISM: Ornithorhynchus anatinus

<400> SEQUENCE: 69
atgctttcct gtgtggtttt gcctagtctg ctggagatca aggcggtggc cgtgcgcacg     60
gtggccatca aagggggtcca catctctcgg tacctctgca tggaagagga tgggaaaact    120
ccatgggcac gtctgctgga gatcaaggcg gtggccgtgc gcacggtggc catcaaaggg    180
gtccacagct ctcggtacct ctgcatggaa gaggatggaa actccatgg gcagatttgg    240 tattctgcag aagactgtgc ttttgaagag gaaatacgtc cagatggcta caatgtgtat    300
aaatctaaga aatatggtgt tcctgtttct ttaagcagcg ccaaacaaag gcagcaattc    360
aaaggaagag actttctgcc tctttctcgt ttcttgccaa tgatcaacac agtgcctgtg    420
gagccagcag agtttgggga ctatgccgat tactttgaat cagatatatt ttcctcacct    480
ctggaaactg acagcatgga cccatttaga attgcccta aactgtcccc tgtaaagagc    540
cccagctttc agaaataa                                                 558

<210> SEQ ID NO 70
<211> LENGTH: 639
<212> TYPE: DNA
```

<213> ORGANISM: Monodelphis domestica

<400> SEQUENCE: 70

```
atggcccagc tcctggcccc gctcctcacc ctggctgctc tctggctggc cccgacggcg     60
cgtgcccgac cgctggtgga cgccgggcct cacgtctact acggctgggg ggagcccatt    120
cgtctgcggc atctctacac ggccaatcgg cacgggctcg ccagcttctc cttcctccgg    180
atccaccgcg acggccgcgt ggacggcagc cggagtcaga gcgcgctcag tttgctggag    240
atcaaggcgg tagctcttcg gatggtggcg atcaaaggtg tccatagctc tcggtacctg    300
tgtatgggag acgccgggaa actccaggga tcggtgaggt tctcggccga ggactgcacc    360
ttcgaggagc agattcgccc cgacggctac aacgtgtacc agtccccaa gtacaacctc     420
cccgtctcgc tctgcactga caagcagagg cagcaggccc acggcaagga gcacctgccc    480
ctgtcccact tcctgcccat gatcaatgct attcctttgg aggccgagga gcccgagggc    540
cccaggatgt tggcggcgcc tctggagacg gacagcatgg accccttcgg cctcacctcc    600
aagctgttgc cggtcaagag ccccagcttt cagaaataa                          639
```

<210> SEQ ID NO 71
<211> LENGTH: 663
<212> TYPE: DNA
<213> ORGANISM: Anolis carolinensis

<400> SEQUENCE: 71

```
atgtgtcggc gggcgttgcc tctgctgggg gcccttctgg gcttggcggc cgtggcctcc    60
cgcgccctcc cgctcaccga cgccgggccc cacgtcagct acggctgggg ggagcccgtc   120
cggctcaggc acctctacac cgcggggcgg cagggcctct tcagccagtt cctccgcatc   180
cacgccgacg ggagagtcga cggcgccggc agccagaacc ggcagagttt gctggagatc   240
cgcgcggtct cgttgcgcgc cgtggccctc aaaggcgtgc acagctcccg ctacctctgc   300
atggaggagg acgccggct ccgcgggatg ctcagatatt ctgcagaaga ctgttccttt    360
gaagaggaga tgcgtccaga tggctacaat atctacaagt caaagaaata cggagttttg   420
gtctccctaa gtaatgccag acaaagacag caattcaaag gaaagatttt cttcctttg    480
tctcatttct tgccgatgat caacactgtg ccagtggagt ctgcagactt ggagagtat    540
ggtgacacca gcagcatta tgaatcggat attttcagtt cacgtcttga aactgacagc    600
atggacccttt ttggcctcac ttcagaagtg tcatcagtac aaagtcctag ctttgggaaa   660
taa                                                                 663
```

<210> SEQ ID NO 72
<211> LENGTH: 541
<212> TYPE: DNA
<213> ORGANISM: Ochotona princeps

<400> SEQUENCE: 72

```
gtgcggagca ggggagccat ggcccgcgct ctggttctag ccactctctg gctggccgcg    60
acggggcggc cgctggcctt gtccgacgcg gggccgcacc tgcactacgg ctggggcgag   120
cccatccgcc tgcggcacct gtacgccacc agcgcccacg gctctcgca ctgctttttg    180
cgcatccgta ccgacggcac cgtggactgc gagcgcagcc agagcgcgca cactacagta   240
ctcggaggag gactgcgcct tcgaaggaga gatcagctct ggctataacg tgtaccgctc   300
caggaggtac cagctgcccg tgtccctggg cagcgccagg cagaggcagc tgcagcggag   360
ccgtggcttc ctgccctgt cccacttcct gccggtgctg cccgcggcct cggaggaggt    420
```

```
ggcggcccce gctgaccacc cgcaagcaga ccctttctcg ccccctggaga ccgacagcat   480 ggacccattt ggaatggcca ccaagcgggg gctggtgaag agccccagct tccagaagtg   540
a                                                                    541
```

<210> SEQ ID NO 73
<211> LENGTH: 666
<212> TYPE: DNA
<213> ORGANISM: Cavia porcellus

<400> SEQUENCE: 73

```
atgtggagtg cgccgagcgg atgtgtggtg atccgcgccc tggtcctggc tggcctgtgg    60
ctggcggtgg cggggcgccc cctggcccgg cggtctctcg cgctatctga ccaggggccg   120
cacttgtact acggctggga ccagccgatc cgccttcggc acctgtacgc cgcgggcccc   180
tacggccgct cgcgctgctt cctgcgcatt cacacggacg gcgcggtgga ctgcgtcgag   240
gaacagagcg agcactgttt gctggagatc agagcagtcg ctctggagac cgtggccatc   300
aaggacataa acagcgtccg gtacctgtgc atgggccccg acggcaggat gcgggcctg    360 ccctggtatt cggaggagga ctgtgccttc aaggaagaga tcagctaccc gggctacagc   420
gtgtaccgct cccagaagca ccacctcccc atcgtgctga gcagtgtcaa gcagaggcag   480
cagtaccaga gcaagggggt ggtgcccctg tcctacttcc tgcccatgct gcccaaggcc   540
tctgtggagc ccagcgacga ggaggaatcc agcgtgttct cgttgcccct gaagacggac   600
agcatggacc cctttgggat ggccagtgag atcgggctgg tgaagagtcc cagctttcag   660
aagtaa                                                               666
```

<210> SEQ ID NO 74
<211> LENGTH: 593
<212> TYPE: DNA
<213> ORGANISM: Tupaia belangeri

<400> SEQUENCE: 74

```
atgaggagaa caccgagcgg gtttgcagtg gcccgtgtcc tcttcctggg cagccttt gg    60 ctggccgcag ccgggagccc cttggccctg tccgacgccg ggccgcatgt gaactacggc   120
tgggatgagt ccatacgcct gcgacacttg tacaccgcca gcccgcacgg ctccaccagc   180
tgcttcttgc gcatccgtga cgacggctca gtggactgcg cgcggggcca gagttttgcac  240 agtttgctgg agatcaaggc agtcgctttg cagaccgtgg ccatcaaagg cgtgtacagt   300
gtccgctacc tctgcatgga cgccgacggc aggatgcagg gctgggtcc acgaagcacg    360 gcctcccagt ctccctgagc agtgccaagc agaggcagct gttaacggtt aggggctttc   420
cttcccttcc ccacttcctg ctcatgatgg ccaagacttc agcagggcct ggaaacccca   480
gggaccaccc agggtctaac actttctcgt tgcccctgga aactgatagc atggacccat   540
ttgggatgac caccagacat gggctggtga agagtcccag ctttcaaaac taa          593
```

<210> SEQ ID NO 75
<211> LENGTH: 657
<212> TYPE: DNA
<213> ORGANISM: Rattus norvegicus

<400> SEQUENCE: 75

```
atggcgagaa agtggagtgg gcgtattgtg gcccgagctc tggtcctggc cactctgtgg    60
ctggccgtgt ctgggcgtcc cctggtccag caatcccagt ctgtgtcgga tgaaggtcca   120
```

| | |
|---|---:|
| ctctttctct atggctgggg caagattacc cgcctgcagt acctgtactc tgctggtccc | 180 |
| tacgtctcca actgcttcct gcgtatccgg agtgacggct ctgtggactg cgaggaggac | 240 |
| cagaacgaac gaaatctgtt ggagttccgc gcggttgctc tgaagacaat tgccatcaag | 300 |
| gacgtcagca gcgtgcggta cctctgcatg agcgccgacg gcaagatata cgggctgatt | 360 |
| cgctactcgg aggaagactg taccttcagg gaggaaatgg actgtttggg ctacaaccag | 420 |
| tacaggtcca tgaagcacca cctccacatc atcttcatca aggccaagcc cagagagcag | 480 |
| ctccagggcc agaaaccttc aaactttatc cccatatttc accggtcttt ctttgaatcc | 540 |
| acggaccagc tgaggtctaa aatgttctct ctgcccctgg agagcgacag catggatccg | 600 |
| ttcagaatgg tggaggatgt ggaccaccta gtgaagagtc ccagcttcca gaaatga | 657 |

<210> SEQ ID NO 76
<211> LENGTH: 657
<212> TYPE: DNA
<213> ORGANISM: Mus musculus

<400> SEQUENCE: 76

| | |
|---|---:|
| atggcgagaa agtggaacgg gcgtgcggtg gcccgagccc tggtcctggc cactctgtgg | 60 |
| ctggctgtgt ctgggcgtcc cctggctcag caatcccagt ctgtgtcaga tgaagatcca | 120 |
| ctctttctct acggctgggg caagattacc cgcctgcagt acctgtactc cgctggtccc | 180 |
| tatgtctcca actgcttcct ccgaatccgg agcgacggct ctgtggactg cgaggaggac | 240 |
| caaaacgaac gaaatttgtt ggaattccgc gcggtcgctc tgaagacgat tgccatcaag | 300 |
| gacgtcagca gcgtgcggta cctctgcatg agcgcggacg gcaagatata cgggctgatt | 360 |
| cgctactcgg aggaagactg taccttcagg gaggaaatgg actgtttagg ctacaaccag | 420 |
| tacagatcca tgaagcacca tctccatatc atcttcatcc aggccaagcc cagagaacag | 480 |
| ctccaggacc agaaaccctc aaactttatc cccgtgtttc accgctcctt ctttgaaacc | 540 |
| ggggaccagc tgaggtctaa aatgttctcc ctgcccctgg agagtgacag catggatccg | 600 |
| ttcaggatgg tggaggatgt agaccaccta gtgaagagtc ccagcttcca gaaatga | 657 |

<210> SEQ ID NO 77
<211> LENGTH: 684
<212> TYPE: DNA
<213> ORGANISM: Gallus gallus

<400> SEQUENCE: 77

| | |
|---|---:|
| atggggccgg cccgccccgc cgcaccgggc gctgccctgg cgctgctggg gatcgccgcc | 60 |
| gccgccgccg ccgccaggtc cctgccgctg cccgacgtcg ggggtccgca cgtcaactac | 120 |
| ggctggggg aacccatccg gctgcggcac ctactacacc gcccaggcaa gcacgggctc | 180 |
| ttcagctgct tcctgcgcat cggcggcgac ggccgggtgg acgctgtcgg tagccagagc | 240 |
| ccgcagagtc tgtttggaga tccgcgccgt gcggtgcgca ccgtggccat caagggcgtg | 300 |
| cagagctccc gctacctctg catggacgag gcggggcggc tgcacgggca gctcagctat | 360 |
| tccattgagg actgttcctt tgaagaggag attcgtccag acggctacaa cgtgtataaa | 420 |
| tcaaagaaat acgggatatc ggtgtctttg agcagtgcca aacaaagaca gcaattcaaa | 480 |
| ggaaaagatt ttctcccgct gtctcacttc ttacccatga tcaacactgt gccagtggag | 540 |
| gtgacagact ttggtgaata tggtgattac agccaggctt ttgagccaga ggtctactca | 600 |
| tcgcctctcg aaacgacag catggatccc tttgggatca cttccaaact gtctccagtg | 660 |
| aagagcccca gctttcagaa atga | 684 |

<210> SEQ ID NO 78
<211> LENGTH: 714
<212> TYPE: DNA
<213> ORGANISM: Taeniopygia guttata

<400> SEQUENCE: 78

```
atggttatca taagcaatct atatctgatg cagaacgatg ttatgatgaa tatgaggcga      60
gcaccccttc gcgttcacgc tgctcgctct tcggccaccc ctgcctccgc gctgccgctg     120
ccgccgcccg acgccggccc gcacctcaaa tacggctggg gagagcccat ccggctgcgg     180
cacctctaca ccgccagcaa gcacgggctc ttcagctgct cctgcgtat cggcgctgac      240
ggccgggtgg acgcggccgg cagccagagc ccgcagagcc tgctagagat ccgcgccgtg     300
gccgtgcgca ccgtggccat caagggcgtg cagagctccc ggtacctgtg catggacgag     360
gcggggcggc tgcacgggca gctcaggaat ccactgaag actgctcctt tgaggaggag       420
attcgcccag acggctacaa tgtgtataga tctaaaaaac atggaatatc ggtgtctttg     480
agcagtgcca acaaagaca gcagttcaag gggaaagatt ccttcccct gtctcacttc       540
ttgcccatga tcaacactgt gcccatggag tcagcagact ttggtgaata tggtgattac     600
agccaggcct ttgaggcaga ggccttctcc tcacctctgg agacggacag catggacccc     660
tttggcatcg cctccaaact gtccctagtg aagagcccta gcttccaaaa ctga           714
```

<210> SEQ ID NO 79
<211> LENGTH: 633
<212> TYPE: DNA
<213> ORGANISM: Danio rerio

<400> SEQUENCE: 79

```
atgctcctct tactctttgt cactgtttgt ggaagtatcg gcgtggagag cctcccgttg      60
cccgactctg gtccacattt ggcaaatgac tggagtgaag ccgtccggct acgacatctg     120
tacgcagcca gacatggctt acatctgcaa ataaacacag acggagaaat cattggatcc     180
acatgcaaag ctcggacagt aagtttgatg gagatatggc cggtggacac aggctgcgta     240
gccattaagg gagttgcaag ctcccgattt ctttgcatgg aaagactggg aaacctgtac     300
ggatcgcaca tttacactaa agaggactgc tctttttgg aacgcatcct tccagacggc       360
tacaacgtct acttctcgag caaacacgga gctcttgtga ctttaagtgg tgcgaaaaac     420
aagttgcaca gtaacgatgg gacttctgca tcccagttcc tccccatgat caacacactt     480
tcagaggaac acactaaaca gcactcaggg gaacagcact ttctgttaa ccatggacag       540
gaccatcagt tgggccttga aatagacagt atggacccctt tcggaaagat ctctcaaata    600
gtgatccaga gtcccagctt caacaaaaga tga                                   633
```

<210> SEQ ID NO 80
<211> LENGTH: 648
<212> TYPE: DNA
<213> ORGANISM: Xenopus (Silurana) tropicalis

<400> SEQUENCE: 80

```
atgtggaaga ccctgccttg gatttttggtt cccatgatgg tggccgtgct gtatttcctc     60
ggaggggcgg aaagtctgcc gcttttttgat gccgggccgc acatgcagaa cggctggggg    120
gagtcgatca gaattcggca cctgtatacg gccaggagg tcgggcacga cagctactac      180
ctccggatac acgaggatgg cagagtcgat ggtgacaggc aacaaagcat gcacagttta    240
```

```
ttggaaatca gagcaattgc agttggaatt gttgccatta aagggtatcg cagctctctg    300
tacctgtgca tggggtccga gggaaaactc tatggaatgc acagttactc ccaggatgat    360
tgctcttttg aagaggagct tctcccggat ggatacaaca tgtataaatc aaggaaacat    420
ggcgttgctg tctccctaag caaggagaag cagaagcaac aatacaaagg aaagggctac    480
ctcccgttgt cccatttcct acccgtgata agctgggtgc catggagcc accggagat    540 gtagaagatg atatctacag gtttccattc aatacggaca caaaaagtgt cattgacagc    600 cttgatacc tgggactaat ggattttttcg agttatcaca agaaatag    648

<210> SEQ ID NO 81
<211> LENGTH: 660
<212> TYPE: DNA
<213> ORGANISM: Otolemur garnettii

<400> SEQUENCE: 81
atgcccagcg ggctgagagg gcgtgtggta gccggcgccc tggccctggc cagcttctgg    60
ctggccgtgg ccgggcgccc gctggccttc tcggatgccg ccctcacgt gcactacggc    120 tggggtgagc ccatccgcct gcgacacctg tacaccgccg cccccacgg cctctccagc    180 tgcttcctgc gcgtacgcac cgacggtgcg gtagactgcg cgcggggcca gagcgcacac    240
agtttgctgg aaatcagggc cgtcgctctc cggaccgtgg ccatcaaagg cgtgcacagc    300
gcgcggtacc tctgcatggg cgccgacggc aggatgcagg ggctgcctca gtactcggag    360
gaagactgtg cctttgagga ggagatccgg ccagacggct acaacgtcta ctggtctgag    420
aagcaccgcc tgccggtgtc tctgagcagt gcccggcaga ggcagctgta caagggcagg    480
ggctttctgc cgctctctca cttcctgccc atgctgcctg tgaccccagc cgagcccggg    540
gacctcagag accactggaa tccgacatg ttctcttttgc ccctggaaac tgacagcatg    600
gatccatttg ggatcgccac cagactgggc gtggtgaaga gtcccagctt tcagaaatga    660

<210> SEQ ID NO 82
<211> LENGTH: 660
<212> TYPE: DNA
<213> ORGANISM: Felis catus

<400> SEQUENCE: 82
atgcggagcg cgccgagcca gtgcgcggta acccgcgccc tggtcctagc cggtctctgg    60
ctggcagcag ccgggcgccc cctagccttc tcggacgcgg ggcctcacgt gcactacggc    120
tggggtgagc ccatccgcct gcggcacctg tacaccgccg cccccacgg cctctccagc    180 tgcttcctgc gcatccgagc cgacgggggg gttgactgcg cgcggagcca gagcgcgcac    240
agtttggtgg agatcagggc agtcgctctg cggaccgtgg ccatcaaggg cgtgcacagc    300
gtccggtacc tctgcatggg cgccgacggc aggatgcaag ggctgcttca gtactctgct    360
ggggactgtg ccttccaaga ggagatccgc cccgacggct acaatgtgta ccggtccgag    420
aagcaccgtc tccccgtctc tttgagtagt gccatacaga ggcagctgta caagggcaga    480 gggttttttgc ccctgtccca tttcttgccc atgctgcccg gcagcccagc agagcccagg    540
gacctccagg accacgtgga gtcggagagg ttttcttcac ccctggaaac agacagcatg    600
gaccctttgg ggattgccac caaaatgggg ttagtgaaga gtcccagctt ccaaaagtaa    660

<210> SEQ ID NO 83
<211> LENGTH: 672
<212> TYPE: DNA
<213> ORGANISM: Pelodiscus sinensis
```

<400> SEQUENCE: 83

```
atgtggagga gcctgtgcaa atctcacacg tctctggctc tgctgggact ctgctttgcg      60
gtggtcgtga gatctctgcc tttctcggat gcagggccac atgtgaacta ggctggggg     120
gagcctattc gattaaggca cctatacacc gccagcagac acgggctgtt caattacttc    180
ctgaggatca gcagtgatgg caaagtggat ggcaccagca ttcagagtcc tcacagtctg    240
ctggaaatca gggctgtggc agttcgcacg gtggcgatca agggcgtcca cagttcccgg    300
tacctctgca tggaagaaga cgggaagctg catggacttc tcaggtattc tacagaagat    360
tgctcctttg aagaggagat acgcccagat ggctacaatg tatataaatc aaagaaatat    420
ggaatctctg tgtccttaag tagtgccaaa caaagacaac aattcaaagg aaaagacttt    480
cttccattgt ctcacttctt gcctatgatc aatacagtac ctgtggagtc aatggatttt    540
ggagaatatg gtgattatag tcatactttt gaatcagatc tattctcttc acctctcgaa    600
actgacagca tggatccctt tggaatcacc tctaaaatat ctccagtgaa gagccccagc    660
tttcagaaat aa                                                        672
```

<210> SEQ ID NO 84
<211> LENGTH: 654
<212> TYPE: DNA
<213> ORGANISM: Latimeria chalumnae

<400> SEQUENCE: 84

```
atgttacagg cactgtacaa tctctgtaca gctctagttt tgtttaagct tccttttgca     60
atggtggggt acaccctgcc ttctgccaat gaagggcccc atctgaacta tgactgggga    120
gaatctgtaa gactcaaaca tctgtacaca tctagcaagc atggattgat cagttacttt    180
ttacagatca atgatgatgg caaagtagat gggaccacta cacgaagctg ttatagtttg    240
ctcgaaataa aatcagtggg gccaggagtt ttggcaatta aaggcataca gagctccaga    300
taccttttgtg tcgagaagga tggaaaattg catggatcgc gcacttattc agcagacgat    360
tgctccttca aagaggatat actcccagat ggttacacta tctacgtgtc aaagaaacat    420
ggatctgttg ttaatctgag caaccacaaa cagaaacgtc agagaaatcg cagaaccctg    480
cctccatttt ctcagttcct accgcttatg acaccattc gtgtggagtg catgaactgc     540
ggggagcact gtgacgacaa cctgcatgac gagctagaaa caggactgtc catggatccc    600
tttgaaagta catccaaaaa atcctttcag agtcccagct ttcacaatag ataa           654
```

<210> SEQ ID NO 85
<211> LENGTH: 660
<212> TYPE: DNA
<213> ORGANISM: Mustela putorius

<400> SEQUENCE: 85

```
atgcggagcg ccgcgagtcg gtgcgcggta gcccgcgcgc tggtcctagc cggcctttgg      60
ctggccgcag ccgggcgccc cctagccttc tcggacgcgg ggccgcacgt gcactatggc    120
tggggtgagc ccatccgcct acggcacctg tacaccgccg gccccacgg cctctccagc     180
tgcttcctgc gcatccgtgc cgacggcggg gttgactgcg cgcggggcca gagcgcgcac    240
agtttggtgg agatccgggc agtcgctctg cggacggtgg ccatcaaggg cgtgtacagc    300
gaccgctatc tctgcatggg tgcggacggc aggatgcaag ggctgcctca gtactccgcc    360
ggagactgtg ctttcgagga ggagatccgc cctgatggct acaacgtgta ccggtccaag    420
```

```
aagcaccgtc tccccgtctc cctgagcagt gcgaaacaaa ggcagctgta caaggaccgg      480 ggcttttttgc ctctgtccca tttcttgccc atgctgcccg ggagcctggc ggagcccagg      540
gacctccagg accacgtgga ggctgatggg ttttctgccc cctagaaac agacagcatg       600 gaccctttg ggattgccac caaaatggga ctagtgaaga gtcccagctt ccaaaaatga       660

<210> SEQ ID NO 86
<211> LENGTH: 654
<212> TYPE: DNA
<213> ORGANISM: Takifugu rubripes

<400> SEQUENCE: 86
tcatctacaa ggattagtgg aaacatggtt ctcctcatgc tccccatcac cgttgcaaac       60
ctcttcctct gtgctggagt tctctccttg cctttgttgg atcaagggtc tcattttccc      120
caaggctggg aacaggtagt ccgcttcagg cacctgtatg ctgccagtgc agggctgcac      180
ctgctgatca ctgaagaggg ctcgatccaa ggctctgcag atccaacttt atacagcctg      240
atggagatcc gtccggtgga cccaggctgt gttgtcatta gaggagcagc aaccacacgc      300
ttcctctgca tagaaggtgc tggaagactg tactcatcac agacctacag caaagacgac      360
tgtaccttca gagagcaaat cctagcagac ggctacagcg tctacagatc tgtcggacac      420
ggagctctgg tcagtctggg aaactaccgg cagcagctga gggggagga ctggagcgtt       480 ccgacactgg ctcagttcct ccccagaata agttcactgg atcaggactt taaagctgct      540
cttgacgaga ctgagaagcc agaacaaact gcacctcaaa gatcggaacc tgtcgacatg      600
gtggactcat ttgaaaagct ctctcagatc atccacagtc ccagttttca caag            654

<210> SEQ ID NO 87
<211> LENGTH: 282
<212> TYPE: DNA
<213> ORGANISM: Equus caballus

<400> SEQUENCE: 87
gcggccgggc gcccctagc cttgtccgac gctgggccgc acgtgcacta cggctggggc       60
gagccgatcc gcctgcggca cctgtacacc gccggccccc acggcctctc cagctgcttc      120
ctgcgcatcc gcgccgatgg cgccgtggac tgcgcgcggg gccagagcgc gcacagtttg      180
gtggagatca gagcagtcgc tctgcgcacc gtggccatca agggcgtgca cagcgtccgg      240
tacctctgca tgggcgccga cggcaggatg caagggctgg ta                       282

<210> SEQ ID NO 88
<211> LENGTH: 630
<212> TYPE: DNA
<213> ORGANISM: Oryzias latipes

<400> SEQUENCE: 88
accatgctgc tcattgtggt caccatttcc acaatggtgt tttctgactc tggagtttcc       60
agcatgccgc tctctgatca tggaccccac atcactcaca gctggagcca agtggtccgc      120
ctccggcacc tgtacgcggt caagcctgga caacatgtcc agatcagaga ggatggacac      180
atccacggct cagcagaaca aactctgaac agcctgctgg agatccgtcc ggttgctccg      240
ggacgggtgg tcttcagagg agtagccacc tcaaggtttc tgtgcatgga gagcgacggc      300
agactcttct cctcacacac atttgacaag acaactgcg tcttcagaga gcagatcttg       360
gcagacggct acaacatcta catttcagat cagcatggaa ccctgcttag tttgggaaac      420
caccggcaaa ggcagcaggg tttagaccgg gatgttccag ccctggctca gttcctcccc      480
```

```
aggatcagca ccctgcagca gggcgtgtac ccagtgccag acccccccca ccagatgaga    540
acaatgcaaa cagagaagac tctagatgcc acggacacat tgggcaact ctctaaaatc     600 attcacagtc ccagcttcaa caaaagatga                                     630
```

<210> SEQ ID NO 89
<211> LENGTH: 624
<212> TYPE: DNA
<213> ORGANISM: Xiphophorus maculatus

<400> SEQUENCE: 89

```
atgtttgtgt tcattctatg cattgctggt gaactttta ctctgggagt attttgcatg     60
ccaatgatgg accaggggcc acttgtcacc catggctggg gccaggtggt ccggcaccgg    120
catctgtatg cagccaagcc aggactgcac ctactgatca gtgaggatgg acaaatccac    180
ggttccgcag atcaaactct ttacagcctg ctggagatcc aacctgttgg ccccggacgt    240
gttgtgatca aggagtggc aaccacacgc ttcctctgca tggagagcga cggcagattg     300
tactcaactg aaacatacag cagagctgac tgcaccttca gagaacagat ccaggcagac    360
ggctacaacg tctacacctc tgatagccat ggagccctcc tcagtttggg aaacaaccag    420
caaagacaca gcggctcaga ccgtggtgtt ccagctctgg cccgctttct tcccaggtta    480
aacacccttc agcaggccgt ccccacagag ccggatgttc ctgatcagct cagtccagag    540
aaagtacaac agactgtgga catggtggcc tcctttggca agctctctca tataattcac    600
agtcccagct ccataagag atga                                            624
```

<210> SEQ ID NO 90
<211> LENGTH: 663
<212> TYPE: DNA
<213> ORGANISM: Ictidomys tridecemlineatus

<400> SEQUENCE: 90

```
atgcggagcg cgccgagcgg acgtgcctta gcccgcgccc tggtgctggc cagcctctgg    60
ttggcagtgg ccggacgacc cctggcccgg cgctctctgg ctctctccga ccaggggcca    120
cacttgtact atggctggga tcagcccatc cgcctccggc acctgtacgc cgcgggcccc    180
tacggcttct ccaactgttt cctgcgcatc cgcaccgacg cgccgtgga ctgcgaggag     240 aagcagagcg agcgtagttt gatggagatc agggcggtcg ctctggagac tgtggccatc    300
aaggacataa acagcgtccg gtacctctgc atgggcgccg acggcaggat acagggactg    360
cctcggtact cggaggaaga gtgcacgttc aaggaggaga tcagctatga cggctacaac    420
gtgtaccggt cccagaagta ccaccttccc gtggtgctca gcagtgccaa gcagcggcag    480
ctgtaccaga gcaagggcgt ggttcccctg tcctacttcc tgcccatgct gcccctggcc    540
tctgcggaga ccagggaccg cttggaatcc gatgtgttct ctttacctct ggaaactgac    600
agcatggacc cgtttgggat ggccagtgaa gtgggcctga agagcccag cttccagaag     660 taa                                                                  663
```

<210> SEQ ID NO 91
<211> LENGTH: 612
<212> TYPE: DNA
<213> ORGANISM: Gasterosteus aculeatus

<400> SEQUENCE: 91

```
atgctgctgc tgctggtccc cgcgtacgtt gccagtgtgt ttttagctct cggggttgtt    60
```

| | |
|---|---:|
| tgcttgcccc taacagatca gggtctccac atggccgacg actggggcca gtcggtccga | 120 |
| ctcaagcacc tgtacgccgc cagcccggga ctccacctgc tgatcgggga ggatggtcgg | 180 |
| atccaaggct cggcgcagca aagcccctac agcctgctgg agatcagtgc agtggatccg | 240 |
| ggctgtgtgg tcatcagagg agtagcaacc gcacggtttc tctgcatcga aggcgatgga | 300 |
| agactgtact catcggacac ctacagcaga gacgactgca ccttcaggga gcagatcctc | 360 |
| ccggacggct acagcgtcta cgtctcccat ggacacgggg ccctgctcag cctggggaac | 420 |
| cacaggcaga ggctgcaggg tcgagaccac ggcgtgccgg ctctggccca gttcctcccg | 480 |
| agggtcagca ccatggatca ggcctcggcc ccgacgcgc ccgggcagac cgccaccgag | 540 |
| acggaagagc ccgtggactc gtttggaaag ctctctcaga tcattcacag tcccagcttc | 600 |
| cacgagagat ga | 612 |

<210> SEQ ID NO 92
<211> LENGTH: 627
<212> TYPE: DNA
<213> ORGANISM: Oreochromis niloticus

<400> SEQUENCE: 92

| | |
|---|---:|
| atgctgctgc tcctcatcgt atccattgtc aatatgcttt ttggtgttgg aatggtttgc | 60 |
| atgcccctgt cagacaacgg gccccacatc gcccacggct gggcccaggt ggtccggctc | 120 |
| aggcaccttt acgccaccag accgggaatg cacctgctga tcagtgaggg tggacagatc | 180 |
| cgtggttctg ccgtccagac tctgcacagc ctaatggaga ttcgtccagt cggtccaggc | 240 |
| cgtgttgtca tcagaggggt agcaaccgca aggtttctct gcatagaaga cgacggcaca | 300 |
| ctgtactcat cgcacgccta cagcagagag gactgcatct tcagagagca gatcttgcca | 360 |
| gatgggtaca catctacat ctctgacaga catggagtcc tgctcagtct gggaaaccac | 420 |
| cggcaaagac tgcagggctt agaccgagga gatccagccc tggcccagtt cctccccagg | 480 |
| atcagcactc tgaatcaaat cccttcccct ggggcaaaca tcggtgacca catgaaagta | 540 |
| gcaaaaacag aagaacctgt ggacacaata gattcatttg gaaagttctc tcagatcatt | 600 |
| gacagtccca gcttccataa gagatga | 627 |

<210> SEQ ID NO 93
<211> LENGTH: 456
<212> TYPE: DNA
<213> ORGANISM: Meleagris gallopavo

<400> SEQUENCE: 93

| | |
|---|---:|
| gtaggcaatc aatcaccaca gagcatcctt gaaataactg ctgttgatgt cgggatcgtc | 60 |
| gctatcaagg gcttgttctc tggcagatac ctggccatga caaaagggg caggctttat | 120 |
| gcatcactca gctattccat tgaggactgt tcctttgaag aggagattcg tccagatggc | 180 |
| tataacgtgt ataaatcaaa gaaatacgga atatcagtgt ctttgagcag tgccaaacaa | 240 |
| agacaacaat tcaaaggaaa agattttctc ccactgtctc acttcttacc catgatcaac | 300 |
| actgtgccag tggaggtgac agactttggt gaatacggtg attacagcca ggcttttgag | 360 |
| ccagaggtct actcatcgcc tctcgaaacg gacagcatgg atcccttgg gatcacttcc | 420 |
| aaactgtctc cagtgaagag ccccagcttt cagaaa | 456 |

<210> SEQ ID NO 94
<211> LENGTH: 651
<212> TYPE: DNA
<213> ORGANISM: Papio anubis

<400> SEQUENCE: 94

| | | | | | | |
|---|---|---|---|---|---|---|
| atgaggagcg | ggtgtgtggt | ggtccacgcc | tggatcctgg | ccagcctctg | gctggccgtg | 60 |
| gccgggcgtc | ccctcgcctt | ctcggacgcg | gggccccacg | tgcactacgg | ctggggcgac | 120 |
| cccatccgcc | tgcggcacct | gtacacctcc | ggccccacg | gctctccag | ctgcttcctg | 180 |
| cgcatccgca | ccgacggcgt | cgtggactgc | gcgcggggcc | aaagcgcgca | cagtttgctg | 240 |
| gagatcaagg | cagtagctct | gcggaccgtg | gccatcaagg | gcgtgcacag | cgtgcggtac | 300 |
| ctctgcatgg | gcgccgacgg | caagatgcag | gggctgcttc | agtactcaga | ggaagactgt | 360 |
| gctttcgagg | aggagatccg | ccctgatggc | tacaatgtat | accgatccca | gaagcaccgc | 420 |
| ctcccggtct | ccctgagcag | tgccaaacag | cggcagctgt | acaagaacag | aggctttctt | 480 |
| ccgctgtctc | atttcctgcc | catgctgccc | atggccccag | aggagcctga | ggacctcagg | 540 |
| ggccccttgg | aatctgacat | gttctcttcg | cccctggaga | ctgacagcat | ggacccattt | 600 |
| gggcttgtca | ccggactgga | ggcggtgagg | agtcccagct | ttgagaaata | a | 651 |

<210> SEQ ID NO 95
<211> LENGTH: 651
<212> TYPE: DNA
<213> ORGANISM: Saimiri boliviensis boliviensis

<400> SEQUENCE: 95

| | | | | | | |
|---|---|---|---|---|---|---|
| atgcggagcg | ggtgtgtggt | ggtccacgcc | tggatcctgg | ctggcctctg | gctggctgtg | 60 |
| gtcgggcgcc | ccctcgcctt | ctccgatgcg | gggccgcatg | tgcattacgg | ctggggcgac | 120 |
| cccattcgcc | tgcggcacct | gtacacctcc | agcccccacg | gcctctccag | ctgcttcctg | 180 |
| cgcatccgca | gcgacggcgt | cgtggactgc | gcgcggggcc | agagcgcgca | cagtttgctg | 240 |
| gagatcaagg | cagtcgctct | aaggaccgtg | gccatcaagg | gcgtgcacag | ctcgcggtac | 300 |
| ctctgcatgg | gcgccgacgg | caggctgcag | gggctgttcc | agtactcgga | ggaagactgt | 360 |
| gctttcgagg | aggagatccg | ccccgacggc | tacaatgtgt | acctatccga | gaagcaccgc | 420 |
| ctcccggtct | ccctgagcag | cgccaaacag | cggcagctgt | acaagaaacg | aggctttctt | 480 |
| ccgctgtccc | atttcctgcc | catgctgccc | agagccccag | aggagcctga | tgacctcagg | 540 |
| ggccacttgg | aatctgacgt | gttctcttca | cccctggaga | ctgatagcat | ggacccattt | 600 |
| gggcttgtca | cgggactgga | ggcggtgaac | agtcccagct | ttgagaagta | a | 651 |

<210> SEQ ID NO 96
<211> LENGTH: 648
<212> TYPE: DNA
<213> ORGANISM: Pteropus alecto

<400> SEQUENCE: 96

| | | | | | | |
|---|---|---|---|---|---|---|
| atgcgcagcc | cgtgcgcggt | ggcgcgcgcg | ctggtgctgg | cgggcctgtg | gctggcgagc | 60 |
| gcggcgggcc | cgctggcgct | gagcgatgcg | ggcccgcatg | tgcattatgg | ctggggcgaa | 120 |
| gcgattcgcc | tgcgccatct | gtataccgcg | ggcccgcatg | gcccgagcag | ctgctttctg | 180 |
| cgcattcgcg | cggatggcgc | ggtggattgc | gcgcgcggcc | agagcgcgca | tagcctggtg | 240 |
| gaaattcgcg | cggtggcgct | gcgcaacgtg | gcgattaaag | gcgtgcatag | cgtgcgctat | 300 |
| ctgtgcatgg | gcgcggatgg | ccgcatgctg | ggcctgctgc | agtatagcgc | ggatgattgc | 360 |
| gcgtttgaag | aagaaattcg | cccggatggc | tataacgtgt | atcatagcaa | aaaacatcat | 420 |
| ctgccggtga | gcctgagcag | cgcgaaacag | cgccagctgt | ataaagatcg | cggctttctg | 480 |

```
ccgctgagcc attttctgcc gatgctgccg cgcagcccga ccgaaccgga aaactttgaa      540
gatcatctgg aagcggatac ctttagcagc ccgctggaaa ccgatgatat ggatccgttt      600
ggcattgcga gcaaactggg cctggaagaa agcccgagct ttcagaaa                   648
```

```
<210> SEQ ID NO 97
<211> LENGTH: 735
<212> TYPE: DNA
<213> ORGANISM: Myotis davidii

<400> SEQUENCE: 97
atgagcggcc agaacagcgg ccgccatggc agccgcccgg cctggatga agaaccggaa       60 ccgggcccgc tggaactgcg cgcgctgggc agcacccgcg cggatccgca gctgtgcgat      120
tttctggaaa accatttttct gggctatacc tgcctggaac tggatatttg cctggcgacc    180
tatctgggcg tgagccattg gggcgaaagc attcgcctgc ccatctgta taccagcggc      240 ccgcatggcc cgagcagctg ctttctgcgc attcgcgtgg atggcgcggt ggattgcgcg     300
cgcggccaga gcgcgcatag cctggtggaa attcgcgcgg tggcgctgcg caaagtggcg     360
attaaaggcg tgcatagcgc gctgtatctg tgcatggaag gcgatggccg catgcgcggc     420
ctgccgcagt ttagcccgga agattgcgcg tttgaagaag aaattcgccc ggatggctat     480
aacgtgtatc gcagccagaa acatcagctg ccggtgagcc tgagcagcgc gcgccagcgc    540
cagctgttta aagcgcgcgg cttctctgccg ctgagccatt ttctgccgat gctgccgagc    600
agcccggcgg aaccggtgca tcgcgaacgc ccgctggaac cggatgcgtt tagcagcccg    660
ctggaaaccg atagcatgga tccgtttggc attgcgaaca acctgcgcct ggtgaaaagc    720
ccgagctttc agaaa                                                     735
```

```
<210> SEQ ID NO 98
<211> LENGTH: 750
<212> TYPE: DNA
<213> ORGANISM: Tupaia chinensis

<400> SEQUENCE: 98
atgcgccgca cctggagcgg ctttgcggtg gcgacccgcg cgggcagccc gctggcgctg     60
gcggatgcgg gcccgcatgt gaactatggc tgggatgaaa gcattcgcct gcgccatctg    120
tataccgcga gcctgcatgg cagcaccagc tgctttctgc gcattcgcga tgatggcagc    180
gtgggctgcg cgcgcggcca gagcatgcat agcctgctgg aaattaaagc ggtggcgctg    240
cagaccgtgg cgattaaagg cgtgtatagc gtgcgctatc tgtgcatgga taccgatggc    300
cgcatgcagg gcctgccgca gtatagcgaa gaagattgca cctttgaaga gaaaattcgc    360
agcgatggcc ataacgtgta tcgcagcaaa aaacatggcc tgccggtgag cctgagcagc    420
gcgaaacagc gccagctgta taaaggccgc ggctttctga gcctgagcca ttttctgctg    480
atgatgccga aaaccagcgc gggcccgggc aacccgcgcg atcagcgcaa cccgcgcgat    540
cagcgcgatc cgaacacctt tagcctgccg ctggaaaccg atagcatgga tccgtttggc    600
atgaccaccc gccatggcct gctgctggat agctgctgcg cgagcctggt gctgctgaac    660
attagcaccg atggcgaatt tagcccgtat ggcaacattc tgcgcccgag ctttcgctttt   720 aaactgttta aaatgaaaaa agtgaccaac                                     750
```

```
<210> SEQ ID NO 99
<211> LENGTH: 627
<212> TYPE: DNA
<213> ORGANISM: Heterocephalus glaber
```

<400> SEQUENCE: 99

```
atgcgcttta gcaaaagcac ctgcggcttt tttaaccatc agcgcctgca ggcgctgtgg      60
ctgagcctga gcagcgtgaa atgggtgctg gatgcggcgg tggaaggccg cccgattcgc     120
ctgcgccatc tgtatgcggc gggcccgtat ggccgcagcc gctgctttct gcgcattcat     180
accgatggcg cggtggattg cgtggaagaa cagagcgaac attgcctgct ggaaattcgc     240
gcggtggcgc tggaaaccgt ggcgattaaa gatattaaca gcgtgcgcta tctgtgcatg     300
ggcccggatg ccgcatgca gggcctgccg tggtatagcg aagaagattg cgcgtttaaa     360
gaagaaatta gctatccggg ctatagcgtg tatcgcagcc agaaacatca tctgccgatt     420
gtgctgagca gcgtgaaaca cgccagcag tatcagagca aaggcgtggt gccgctgagc     480
tattttctgc cgatgctgcc gaaagcgagc gtggaaccgg cgatgaaga agaaagcgcg     540
tttagcctgc cgctgaaaac cgatagcatg gatccgtttg gcatggcgag cgaaattggc     600
ctggcgaaaa gcccgagctt tcagaaa                                         627
```

<210> SEQ ID NO 100
<211> LENGTH: 209
<212> TYPE: PRT
<213> ORGANISM: Homo sapiens

<400> SEQUENCE: 100

```
Met Asp Ser Asp Glu Thr Gly Phe Glu His Ser Gly Leu Trp Val Ser
  1               5                  10                  15
Val Leu Ala Gly Leu Leu Leu Gly Ala Cys Gln Ala His Pro Ile Pro
             20                  25                  30
Asp Ser Ser Pro Leu Leu Gln Phe Gly Gly Gln Val Arg Gln Arg Tyr
         35                  40                  45
Leu Tyr Thr Asp Asp Ala Gln Gln Thr Glu Ala His Leu Glu Ile Arg
     50                  55                  60
Glu Asp Gly Thr Val Gly Gly Ala Ala Asp Gln Ser Pro Glu Ser Leu
 65                  70                  75                  80
Leu Gln Leu Lys Ala Leu Lys Pro Gly Val Ile Gln Ile Leu Gly Val
             85                  90                  95
Lys Thr Ser Arg Phe Leu Cys Gln Arg Pro Asp Gly Ala Leu Tyr Gly
            100                 105                 110
Ser Leu His Phe Asp Pro Glu Ala Cys Ser Phe Arg Glu Leu Leu Leu
        115                 120                 125
Glu Asp Gly Tyr Asn Val Tyr Gln Ser Glu Ala His Gly Leu Pro Leu
    130                 135                 140
His Leu Pro Gly Asn Lys Ser Pro His Arg Asp Pro Ala Pro Arg Gly
145                 150                 155                 160
Pro Ala Arg Phe Leu Pro Leu Pro Gly Leu Pro Pro Ala Leu Pro Glu
                165                 170                 175
Pro Pro Gly Ile Leu Ala Pro Gln Pro Pro Asp Val Gly Ser Ser Asp
            180                 185                 190
Pro Leu Ser Met Val Gly Pro Ser Gln Gly Arg Ser Pro Ser Tyr Ala
        195                 200                 205
Ser
```

<210> SEQ ID NO 101
<211> LENGTH: 209
<212> TYPE: PRT
<213> ORGANISM: Pongo abelii

<400> SEQUENCE: 101

```
Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser
```

<210> SEQ ID NO 102
<211> LENGTH: 209
<212> TYPE: PRT
<213> ORGANISM: Pan troglodytes

<400> SEQUENCE: 102

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
130                 135                 140
```

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Thr
            195                 200                 205

Ser

<210> SEQ ID NO 103
<211> LENGTH: 209
<212> TYPE: PRT
<213> ORGANISM: Canis lupus familiaris

<400> SEQUENCE: 103

Met Gly Trp Ala Glu Ala Gly Phe Glu His Leu Gly Leu Trp Val Pro
1               5                   10                  15

Val Leu Ala Val Leu Leu Leu Glu Ala Cys Arg Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
            85                  90                  95

Lys Thr Ser Arg Phe Leu Cys Gln Gly Pro Asp Gly Thr Leu Tyr Gly
            100                 105                 110

Ser Leu His Phe Asp Pro Val Ala Cys Ser Phe Arg Glu Leu Leu Leu
            115                 120                 125

Glu Asp Gly Tyr Asn Ile Tyr His Ser Glu Thr Leu Gly Leu Pro Leu
130                 135                 140

Arg Leu Arg Pro His Asn Ser Ala Tyr Arg Asp Leu Ala Pro Arg Gly
145                 150                 155                 160

Pro Ala Arg Phe Leu Pro Leu Pro Gly Leu Leu Pro Ala Pro Pro Glu
            165                 170                 175

Pro Pro Gly Ile Leu Ala Pro Glu Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 104
<211> LENGTH: 209
<212> TYPE: PRT
<213> ORGANISM: Bos Taurus

<400> SEQUENCE: 104

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
            35                  40                  45

-continued

Leu Tyr Thr Asp Asp Ala Gln Glu Thr Glu Ala His Leu Glu Ile Arg
            50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly
                100                 105                 110

Ser Leu His Phe Asp Pro Lys Ala Cys Ser Phe Arg Glu Leu Leu Leu
                115                 120                 125

Glu Asp Gly Tyr Asn Val Tyr Gln Ser Glu Thr Leu Gly Leu Pro Leu
                130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Ala Pro Pro Asp
                165                 170                 175

Pro Pro Gly Ile Leu Ala Pro Glu Pro Pro Asp Val Gly Ser Ser Asp
                180                 185                 190

Pro Leu Ser Met Val Gly Pro Ser Tyr Gly Arg Ser Pro Ser Tyr Thr
                195                 200                 205

Ser

<210> SEQ ID NO 105
<211> LENGTH: 209
<212> TYPE: PRT
<213> ORGANISM: Equus caballus

<400> SEQUENCE: 105

Met Asp Trp Asp Lys Thr Gly Phe Lys Tyr Gln Gly Leu Trp Val Pro
1               5                   10                  15

Val Leu Ala Val Leu Leu Gly Ala Cys Gln Ser His Pro Ile Pro
                20                  25                  30

Asp Ser Ser Pro Leu Leu Gln Phe Gly Gly Gln Val Arg Gln Arg His
                35                  40                  45

Leu Tyr Thr Asp Asp Ala Gln Glu Thr Glu Ala His Leu Glu Ile Arg
            50                  55                  60

Ala Asp Gly Thr Val Ala Gly Ala Val His Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
                100                 105                 110

Ser Leu His Phe Asp Pro Val Ala Cys Ser Phe Arg Glu Leu Leu Leu
                115                 120                 125

Glu Asp Gly Tyr Asn Val Tyr Gln Ser Glu Thr Leu Gly Leu Pro Leu
                130                 135                 140

Arg Leu Pro His His Ser Ser Pro Tyr Gln Asp Pro Ala Pro Arg Ala
145                 150                 155                 160

Pro Ala Arg Phe Leu Pro Leu Pro Gly Phe Pro Pro Ala Pro Pro Glu
                165                 170                 175

Pro Pro Gly Ile Pro Ala Pro Glu Pro Pro Asp Val Gly Ser Ser Asp
                180                 185                 190

Pro Leu Ser Met Val Gly Pro Ser Arg Ser Arg Ser Pro Ser Tyr Thr
                195                 200                 205

Ser

<210> SEQ ID NO 106
<211> LENGTH: 209
<212> TYPE: PRT
<213> ORGANISM: Ailuropoda melanoleuca

<400> SEQUENCE: 106

Met Gly Trp Asp Glu Ala Arg Ser Glu Gln Leu Gly Leu Trp Val Pro
1               5                   10                  15

Val Leu Ala Val Leu Leu Leu Glu Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Ala Ile Arg
    50                  55                  60

Ala Asp Gly Thr Val Val Gly Ala Ala Ser Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

Ser Val Arg Phe Asp Pro Val Ala Cys Ser Phe Arg Glu Leu Leu Leu
        115                 120                 125

Glu Asp Gly Tyr Asn Ile Tyr His Ser Glu Thr Leu Gly Leu Pro Leu
    130                 135                 140

Arg Leu Pro Ala His Asn Ser Pro Tyr Arg Asp Ser Ala Pro Arg Gly
145                 150                 155                 160

Pro Ala Arg Phe Leu Pro Leu Pro Gly Leu Leu Pro Val Pro Pro Asp
                165                 170                 175

Pro Pro Gly Ile Leu Gly Pro Glu Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 107
<211> LENGTH: 209
<212> TYPE: PRT
<213> ORGANISM: Oryctolagus cuniculus

<400> SEQUENCE: 107

Met Asp Trp Gly Lys Ala Lys Cys Arg Pro Gly Leu Trp Val Pro
1               5                   10                  15

Ala Leu Ala Ala Leu Leu Leu Gly Ala Cys Gln Ala His Pro Ile Pro
            20                  25                  30

Asp Ser Ser Pro Leu Leu Gln Phe Gly Asp Gln Val Arg Gln His
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Gln Met Lys Ala Leu Gln Pro Gly Ile Ile Gln Ile Leu Gly Val
                85                  90                  95

Gln Thr Ser Arg Phe Leu Cys Gln Arg Pro Asp Gly Thr Leu Tyr Gly

```
                    100                 105                 110
Ser Leu His Phe Asp Arg Glu Ala Cys Ser Phe Arg Glu Leu Leu Arg
            115                 120                 125

Glu Asp Gly Tyr Asn Val Tyr Leu Ser Glu Ala Leu Gly Leu Pro Leu
        130                 135                 140

Arg Leu Ser Pro Gly Ser Pro Arg Arg Ala Pro Ala Pro Arg Gly
145                 150                 155                 160

Pro Ala Arg Phe Leu Pro Leu Pro Gly Leu Pro Asp Leu Pro Glu
                165                 170                 175

Pro Pro Gly Leu Leu Ala Ala Ala Pro Pro Asp Val Asp Ser Pro Asp
            180                 185                 190

Pro Leu Ser Met Val Gln Pro Ala Leu Asp Gln Ser Pro Ser Tyr Thr
            195                 200                 205

Ser
```

<210> SEQ ID NO 108
<211> LENGTH: 209
<212> TYPE: PRT
<213> ORGANISM: Gorilla gorilla

<400> SEQUENCE: 108

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser
```

<210> SEQ ID NO 109
<211> LENGTH: 209
<212> TYPE: PRT
<213> ORGANISM: Nomascus leucogenys

<400> SEQUENCE: 109

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Ala Ala Asp Gln Ser Pro Glu Ser Leu
65                  70                  75                  80

Leu Gln Leu Lys Ala Leu Lys Pro Gly Val Ile Gln Ile Leu Gly Val
            85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
            165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 110
<211> LENGTH: 209
<212> TYPE: PRT
<213> ORGANISM: Procavia capensis

<400> SEQUENCE: 110

Met Asp Trp Ala Lys Phe Gly Ile Glu His Pro Gly Leu Trp Val Pro
1               5                   10                  15

Val Met Ala Val Leu Leu Leu Gly Ala Cys Gln Gly Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala His Arg Ser Pro Glu Ser Leu
65                  70                  75                  80

Leu Glu Leu Lys Ala Leu Lys Pro Gly Ile Ile Gln Ile Leu Gly Val
            85                  90                  95

Lys Thr Ser Arg Phe Leu Cys Gln Gly Pro Asp Gly Val Leu Tyr Gly
            100                 105                 110

Ser Leu Arg Phe Asp Pro Val Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

Arg Leu Pro Ser His Asn Ser Pro Gln Arg Asp Leu Ala Ser Arg Val
145                 150                 155                 160

```
Pro Ala Arg Phe Leu Pro Leu Pro Gly Arg Leu Thr Val Leu Pro Glu
            165                 170                 175

Pro Ser Gly Val Leu Gly Pro Glu Pro Pro Asp Val Asp Ser Ser Asp
        180                 185                 190

Pro Leu Ser Met Val Gly Pro Ser Gln Gly Arg Ser Pro Ser Tyr Ala
        195                 200                 205

Ser

<210> SEQ ID NO 111
<211> LENGTH: 209
<212> TYPE: PRT
<213> ORGANISM: Cavia porcellus

<400> SEQUENCE: 111

Met Asp Trp Ala Arg Thr Glu Cys Glu Arg Pro Arg Leu Trp Val Ser
1               5                   10                  15

Met Leu Ala Ile Leu Leu Val Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Asp Thr Glu Val His Leu Glu Ile Arg
    50                  55                  60

Ala Asp Gly Ser Val Arg Gly Ile Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Arg Thr Ser Arg Phe Leu Cys Gln Arg Pro Asp Gly Ser Leu Tyr Gly
            100                 105                 110

Ser Leu His Phe Asp Pro Glu Ala Cys Ser Phe Arg Glu Leu Leu Leu
        115                 120                 125

Ala Asp Gly Tyr Asn Val Tyr Lys Ser Glu Ala His Gly Leu Pro Leu
    130                 135                 140

His Leu Leu Arg Gly Asp Ser Leu Ser Gln Glu Pro Ala Pro Pro Gly
145                 150                 155                 160

Pro Ala Arg Phe Leu Pro Leu Pro Gly Leu Pro Ala Thr Pro Pro Glu
            165                 170                 175

Pro Pro Arg Met Leu Pro Pro Gly Pro Pro Asp Val Gly Ser Ser Asp
        180                 185                 190

Pro Leu Ser Met Val Gly Pro Leu Trp Asp Arg Ser Pro Ser Tyr Thr
        195                 200                 205

Ser

<210> SEQ ID NO 112
<211> LENGTH: 209
<212> TYPE: PRT
<213> ORGANISM: Tupaia belangeri

<400> SEQUENCE: 112

Met Gly Trp Asp Lys Ala Arg Phe Glu His Leu Gly Ala Trp Ala Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60
```

```
Ala Asp Gly Thr Val Val Gly Ala Ala His Gln Ser Pro Glu Ser Leu
 65                  70                  75                  80

Leu Glu Leu Lys Ala Leu Lys Pro Gly Val Ile Gln Ile Leu Gly Val
             85                  90                  95

Lys Thr Ser Arg Phe Leu Cys Gln Arg Pro Asp Gly Ala Leu Tyr Gly
        100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
130                 135                 140

Arg Leu Pro Pro His Asp Ser Pro His Arg Asp Arg Thr Pro Arg Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
                180                 185                 190

Pro Leu Ser Met Met Gly Pro Ser Gln Gly Gln Ser Pro Ser Tyr Ala
            195                 200                 205

Ser

<210> SEQ ID NO 113
<211> LENGTH: 210
<212> TYPE: PRT
<213> ORGANISM: Sorex araneus

<400> SEQUENCE: 113

Met Val Trp Asp Lys Ala Arg Gly Gln Gln Leu Gly Leu Trp Ala Pro
  1               5                  10                  15

Met Leu Leu Gly Leu Leu Leu Gly Ala Cys Gln Ala His Pro Leu Pro
             20                  25                  30

Asp Ser Ser Pro Leu Leu Gln Phe Gly Gly Gln Val Arg Leu Arg Phe
        35                  40                  45

Leu Tyr Thr Asp Asp Ala Gln Arg Thr Gly Ala His Leu Glu Ile Arg
 50                  55                  60

Ala Asp Gly Thr Val Gln Gly Ala Ala His Arg Thr Pro Glu Cys Leu
 65                  70                  75                  80

Leu Glu Leu Lys Ala Leu Lys Pro Gly Val Ile Gln Ile Leu Gly Val
             85                  90                  95

Ser Thr Ser Arg Phe Leu Cys Gln Arg Pro Asp Gly Val Leu Tyr Gly
        100                 105                 110

Ser Leu Arg Phe Asp Pro Glu Ala Cys Ser Phe Arg Glu Leu Leu Leu
        115                 120                 125

Gln Asp Gly Tyr Asn Val Tyr Gln Ser Glu Ala Leu Gly Leu Pro Leu
130                 135                 140

Tyr Leu His Pro Pro Ser Ala Pro Val Ser Gln Glu Pro Ala Ser Arg
145                 150                 155                 160

Gly Ala Val Arg Phe Leu Pro Leu Pro Gly Leu Pro Pro Ala Ser Leu
                165                 170                 175

Glu Pro Pro Arg Pro Pro Ala Pro Val Pro Pro Asp Val Gly Ser Ser
            180                 185                 190

Asp Pro Leu Ser Met Val Gly Pro Pro Glu Arg His Ser Pro Ser Tyr
            195                 200                 205

Thr Ser
    210
```

```
<210> SEQ ID NO 114
<211> LENGTH: 208
<212> TYPE: PRT
<213> ORGANISM: Ictidomys tridecemlineatus

<400> SEQUENCE: 114
```

| | | | | | | | | | | | | | | | |
|---|---|---|---|---|---|---|---|---|---|---|---|---|---|---|---|
| Met | Asp | Trp | Val | Lys | Ala | Lys | Leu | Glu | Pro | Leu | Gly | Leu | Trp | Val | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Val | Leu | Ala | Ala | Leu | Val | Leu | Gly | Ala | Cys | Gln | Ala | Tyr | Pro | Ile | Pro |
| | | | 20 | | | | | 25 | | | | | 30 | | |

| | | | | | | | | | | | | | | | |
|---|---|---|---|---|---|---|---|---|---|---|---|---|---|---|---|
| Asp | Ser | Ser | Pro | Leu | Leu | Gln | Phe | Gly | Gly | Gln | Val | Arg | Gln | Arg | Tyr |
| | | 35 | | | | | 40 | | | | | 45 | | | |

| | | | | | | | | | | | | | | | |
|---|---|---|---|---|---|---|---|---|---|---|---|---|---|---|---|
| Leu | Tyr | Thr | Asp | Asp | Ala | Gln | Glu | Thr | Glu | Ala | His | Leu | Glu | Ile | Arg |
| | 50 | | | | | 55 | | | | | 60 | | | | |

| | | | | | | | | | | | | | | | |
|---|---|---|---|---|---|---|---|---|---|---|---|---|---|---|---|
| Ala | Asp | Gly | Thr | Val | Val | Gly | Ala | Ala | His | Gln | Ser | Pro | Glu | Ser | Leu |
| 65 | | | | | 70 | | | | | 75 | | | | | 80 |

| | | | | | | | | | | | | | | | |
|---|---|---|---|---|---|---|---|---|---|---|---|---|---|---|---|
| Leu | Glu | Leu | Lys | Ala | Leu | Lys | Pro | Gly | Val | Ile | Gln | Ile | Leu | Gly | Val |
| | | | | 85 | | | | | 90 | | | | | 95 | |

| | | | | | | | | | | | | | | | |
|---|---|---|---|---|---|---|---|---|---|---|---|---|---|---|---|
| Lys | Thr | Ser | Arg | Phe | Leu | Cys | Gln | Arg | Pro | Asp | Gly | Val | Leu | Tyr | Gly |
| | | | 100 | | | | | 105 | | | | | 110 | | |

| | | | | | | | | | | | | | | | |
|---|---|---|---|---|---|---|---|---|---|---|---|---|---|---|---|
| Ser | Leu | His | Phe | Asp | Pro | Glu | Ala | Cys | Ser | Phe | Arg | Glu | Gln | Leu | Leu |
| | | 115 | | | | | 120 | | | | | 125 | | | |

| | | | | | | | | | | | | | | | |
|---|---|---|---|---|---|---|---|---|---|---|---|---|---|---|---|
| Glu | Asp | Gly | Tyr | Asn | Val | Tyr | Gln | Ser | Glu | Ser | His | Gly | Leu | Pro | Val |
| | 130 | | | | | 135 | | | | | 140 | | | | |

| | | | | | | | | | | | | | | | |
|---|---|---|---|---|---|---|---|---|---|---|---|---|---|---|---|
| Arg | Leu | Pro | Pro | Asn | Ser | Pro | Tyr | Arg | Asp | Pro | Ala | Pro | Pro | Gly | Pro |
| 145 | | | | | 150 | | | | | 155 | | | | | 160 |

| | | | | | | | | | | | | | | | |
|---|---|---|---|---|---|---|---|---|---|---|---|---|---|---|---|
| Ala | Arg | Phe | Leu | Pro | Leu | Pro | Gly | Leu | Pro | Pro | Ala | Ala | Leu | Glu | Pro |
| | | | | 165 | | | | | 170 | | | | | 175 | |

| | | | | | | | | | | | | | | | |
|---|---|---|---|---|---|---|---|---|---|---|---|---|---|---|---|
| Pro | Gly | Ile | Leu | Gly | Pro | Glu | Pro | Pro | Asp | Val | Gly | Ser | Ser | Asp | Pro |
| | | | 180 | | | | | 185 | | | | | 190 | | |

| | | | | | | | | | | | | | | | |
|---|---|---|---|---|---|---|---|---|---|---|---|---|---|---|---|
| Leu | Ser | Met | Val | Gly | Pro | Leu | Gln | Gly | Arg | Ser | Pro | Ser | Tyr | Ala | Ser |
| | | | | 195 | | | | | 200 | | | | | 205 | |

```
<210> SEQ ID NO 115
<211> LENGTH: 208
<212> TYPE: PRT
<213> ORGANISM: Loxodonta Africana

<400> SEQUENCE: 115
```

| | | | | | | | | | | | | | | | |
|---|---|---|---|---|---|---|---|---|---|---|---|---|---|---|---|
| Met | Asp | Trp | Ala | Lys | Phe | Gly | Leu | Glu | His | Pro | Gly | Leu | Trp | Val | Pro |
| 1 | | | | 5 | | | | | 10 | | | | | 15 | |

| | | | | | | | | | | | | | | | |
|---|---|---|---|---|---|---|---|---|---|---|---|---|---|---|---|
| Val | Met | Ala | Val | Leu | Leu | Leu | Gly | Ala | Cys | Gln | Gly | His | Pro | Ile | Pro |
| | | | 20 | | | | | 25 | | | | | 30 | | |

| | | | | | | | | | | | | | | | |
|---|---|---|---|---|---|---|---|---|---|---|---|---|---|---|---|
| Asp | Ser | Ser | Pro | Leu | Leu | Gln | Phe | Gly | Gly | Gln | Val | Arg | Gln | Arg | Tyr |
| | | 35 | | | | | 40 | | | | | 45 | | | |

| | | | | | | | | | | | | | | | |
|---|---|---|---|---|---|---|---|---|---|---|---|---|---|---|---|
| Leu | Tyr | Thr | Asp | Asp | Gln | Glu | Thr | Glu | Ala | His | Leu | Glu | Ile | Arg | Ala |
| | 50 | | | | | 55 | | | | | 60 | | | | |

| | | | | | | | | | | | | | | | |
|---|---|---|---|---|---|---|---|---|---|---|---|---|---|---|---|
| Asp | Gly | Thr | Val | Ala | Gly | Ala | Ala | His | Arg | Ser | Ser | Glu | Ser | Leu | Leu |
| 65 | | | | | 70 | | | | | 75 | | | | | 80 |

| | | | | | | | | | | | | | | | |
|---|---|---|---|---|---|---|---|---|---|---|---|---|---|---|---|
| Glu | Leu | Lys | Ala | Leu | Lys | Pro | Gly | Ile | Ile | Gln | Ile | Leu | Gly | Val | Lys |
| | | | | 85 | | | | | 90 | | | | | 95 | |

| | | | | | | | | | | | | | | | |
|---|---|---|---|---|---|---|---|---|---|---|---|---|---|---|---|
| Thr | Ser | Arg | Phe | Leu | Cys | Gln | Gly | Pro | Asp | Gly | Val | Leu | Tyr | Gly | Ser |
| | | | 100 | | | | | 105 | | | | | 110 | | |

| | | | | | | | | | | | | | | | |
|---|---|---|---|---|---|---|---|---|---|---|---|---|---|---|---|
| Leu | His | Phe | Asp | Pro | Ala | Ala | Cys | Ser | Phe | Arg | Glu | Leu | Leu | Leu | Glu |
| | | 115 | | | | | 120 | | | | | 125 | | | |

-continued

Asp Gly Tyr Asn Val Tyr Trp Ser Glu Ala His Gly Leu Pro Ile Arg
            130                 135                 140

Leu Pro Ser His Asn Ser Pro Tyr Arg Asp Pro Ala Ser Arg Val Pro
145                 150                 155                 160

Ala Arg Phe Leu Pro Leu Pro Gly Leu Leu Pro Met Leu Gln Glu Pro
                165                 170                 175

Pro Gly Val Leu Ala Pro Glu Pro Pro Asp Val Asp Ser Ser Asp Pro
            180                 185                 190

Leu Ser Met Val Gly Pro Ser Gln Gly Arg Ser Pro Ser Tyr Ala Ser
                195                 200                 205

<210> SEQ ID NO 116
<211> LENGTH: 208
<212> TYPE: PRT
<213> ORGANISM: Sus scrofa

<400> SEQUENCE: 116

Met Gly Trp Ala Glu Ala Lys Phe Glu Arg Leu Gly Leu Trp Val Pro
1               5                   10                  15

Val Leu Ala Val Leu Leu Gly Ala Cys Gln Ala Arg Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
50                  55                  60

Asp Gly Thr Val Ala Gly Val Ala Arg Gln Ser Pro Glu Ser Leu Leu
65                  70                  75                  80

Glu Leu Lys Ala Leu Lys Pro Gly Val Ile Gln Ile Leu Gly Val Gln
                85                  90                  95

Thr Ser Arg Phe Leu Cys Gln Gly Pro Asp Gly Arg Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala Leu Gly Leu Pro Leu Arg
    130                 135                 140

Leu Pro Pro His Arg Ser Ser Asn Arg Asp Leu Ala Pro Arg Gly Pro
145                 150                 155                 160

Ala Arg Phe Leu Pro Leu Pro Gly Leu Pro Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser His Gly Arg Ser Pro Ser Tyr Thr Ser
                195                 200                 205

<210> SEQ ID NO 117
<211> LENGTH: 208
<212> TYPE: PRT
<213> ORGANISM: Felis catus

<400> SEQUENCE: 117

Met Asp Trp Asp Glu Ala Gly Ser Gln Arg Leu Gly Leu Trp Val Val
1               5                   10                  15

Leu Gly Val Leu Leu Pro Glu Ala Cys Gln Ala His Pro Ile Pro Asp
            20                  25                  30

Ser Ser Pro Leu Leu Gln Phe Gly Gly Gln Val Arg Gln Arg Phe Leu
        35                  40                  45

```
Tyr Thr Asp Asp Ala Gln Glu Thr Glu Val His Leu Glu Ile Lys Ala
    50                  55                  60

Asp Gly Thr Val Val Gly Thr Ala Arg Arg Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Gly Pro Asp Gly Thr Leu Tyr Gly Ser
                100                 105                 110

Leu Arg Phe Asp Pro Ala Ala Cys Ser Phe Arg Glu Leu Leu Leu Glu
                115                 120                 125

Asp Gly Tyr Asn Ile Tyr His Ser Glu Thr Leu Gly Leu Pro Leu Arg
                130                 135                 140

Leu Pro Pro His Asn Ser Pro Tyr Arg Asp Leu Ala Pro Arg Ala Pro
145                 150                 155                 160

Ala Arg Phe Leu Pro Leu Pro Gly Leu Leu Pro Ala Pro Pro Glu Pro
                165                 170                 175

Pro Gly Ile Leu Ala Pro Glu Pro Pro Asp Val Gly Ser Ser Asp Pro
                180                 185                 190

Leu Ser Met Val Gly Pro Ser Gln Gly Arg Ser Pro Ser Tyr Ala Ser
                195                 200                 205

<210> SEQ ID NO 118
<211> LENGTH: 208
<212> TYPE: PRT
<213> ORGANISM: Otolemur garnettii

<400> SEQUENCE: 118

Asp Lys Ala Arg Thr Gly Phe Lys His Pro Gly Pro Trp Phe Pro Leu
1               5                   10                  15

Leu Ala Val Leu Leu Leu Gly Ala Cys Gln Ala His Pro Ile Pro Asp
                20                  25                  30

Ser Ser Pro Leu Leu Gln Phe Gly Gly Gln Val Arg Gln Arg Tyr Leu
                35                  40                  45

Tyr Thr Asp Asp Ala Gln Glu Thr Glu Ala His Leu Glu Ile Arg Glu
    50                  55                  60

Asp Gly Thr Val Val Gly Ala Ala Gln Gln Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Arg Pro Asp Gly Gly Leu Tyr Gly Ser
                100                 105                 110

Leu Tyr Phe Asp Pro Lys Ala Cys Ser Phe Arg Glu Leu Leu Leu Glu
                115                 120                 125

Asp Gly Tyr Asn Val Tyr Trp Ser Glu Thr Tyr Gly Leu Pro Leu His
                130                 135                 140

Leu Pro Pro Ala Asn Ser Pro Tyr Trp Gly Pro Ser Leu Arg Ser Pro
145                 150                 155                 160

Ala Arg Phe Leu Pro Leu Pro Gly Pro Ala Ala Ser Pro Glu Leu
                165                 170                 175

Pro Gly Ile Leu Ala Leu Glu Pro Pro Asp Val Gly Ser Ser Asp Pro
                180                 185                 190

Leu Ser Met Val Gly Pro Ser Gln Gly Arg Ser Pro Ser Tyr Ala Ser
                195                 200                 205
```

```
<210> SEQ ID NO 119
<211> LENGTH: 208
<212> TYPE: PRT
<213> ORGANISM: Rattus norvegicus

<400> SEQUENCE: 119

Met Asp Trp Met Lys Ser Arg Val Gly Ala Pro Gly Leu Trp Val Cys
1               5                   10                  15

Leu Leu Leu Pro Val Phe Leu Leu Gly Val Cys Glu Ala Tyr Pro Ile
                20                  25                  30

Ser Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
    50                  55                  60

Arg Glu Asp Gly Thr Val Val Gly Thr Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Thr Leu Tyr
                100                 105                 110

Gly Ser Pro His Phe Asp Pro Glu Ala Cys Ser Phe Arg Glu Leu Leu
                115                 120                 125

Leu Lys Asp Gly Tyr Asn Val Tyr Gln Ser Glu Ala His Gly Leu Pro
            130                 135                 140

Leu Arg Leu Pro Gln Lys Asp Ser Gln Asp Pro Ala Thr Arg Gly Pro
145                 150                 155                 160

Val Arg Phe Leu Pro Met Pro Gly Leu Pro His Glu Pro Gln Glu Gln
                165                 170                 175

Pro Gly Val Leu Pro Pro Glu Pro Pro Asp Val Gly Ser Ser Asp Pro
            180                 185                 190

Leu Ser Met Val Glu Pro Leu Gln Gly Arg Ser Pro Ser Tyr Ala Ser
            195                 200                 205

<210> SEQ ID NO 120
<211> LENGTH: 210
<212> TYPE: PRT
<213> ORGANISM: Mus musculus

<400> SEQUENCE: 120

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
                20                  25                  30

Pro Asp Ser Ser Pro Leu Leu Gln Phe Gly Gly Gln Val Arg Gln Arg
            35                  40                  45

Tyr Leu Tyr Thr Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
                100                 105                 110

Gly Ser Pro His Phe Asp Pro Glu Ala Cys Ser Phe Arg Glu Leu Leu
                115                 120                 125

Leu Glu Asp Gly Tyr Asn Val Tyr Gln Ser Glu Ala His Gly Leu Pro
```

```
            130                 135                 140
Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
                180                 185                 190

Asp Pro Leu Ser Met Val Glu Pro Leu Gln Gly Arg Ser Pro Ser Tyr
                195                 200                 205

Ala Ser
    210

<210> SEQ ID NO 121
<211> LENGTH: 107
<212> TYPE: PRT
<213> ORGANISM: Vicugna pacos

<400> SEQUENCE: 121

Met Asp Trp Asp Glu Ala Lys Phe Glu His Arg Gly Leu Trp Val Pro
1               5                   10                  15

Val Leu Thr Val Leu Leu Leu Gly Ala Cys Gln Ala Arg Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
        50                  55                  60

Ala Asp Gly Thr Val Val Gly Val Ala Arg Gln Pro Glu Gly Ile Pro
65                  70                  75                  80

Pro Glu Pro Pro Asp Val Gly Ser Ser Asp Pro Leu Ser Met Val Gly
                85                  90                  95

Pro Ser Tyr Ser Arg Ser Pro Ser Tyr Thr Ser
            100                 105

<210> SEQ ID NO 122
<211> LENGTH: 211
<212> TYPE: PRT
<213> ORGANISM: Anolis carolinensis

<400> SEQUENCE: 122

Cys Lys Ser Lys Gly Gly Gly Lys Gly Gly Glu Arg Met Trp Val Asp
1               5                   10                  15

Leu Val Phe Trp Ala Ala Leu Leu Arg Thr Ala Pro Ala Leu Pro Leu
                20                  25                  30

Arg Asn Ser Asn Pro Ile Tyr Gln Phe Asp Gly Gln Val Arg Leu Arg
            35                  40                  45

His Leu Tyr Thr Ala Asp Glu Gln Thr His Leu His Leu Glu Ile Leu
        50                  55                  60

Pro Asp Gly Thr Val Gly Gly Ser Arg Phe Gln Asn Pro Phe Ser Leu
65                  70                  75                  80

Met Glu Ile Lys Ala Val Lys Pro Gly Val Ile Arg Met Gln Ala Lys
                85                  90                  95

Lys Thr Ser Arg Phe Leu Cys Met Lys Pro Asn Gly Arg Leu Tyr Gly
            100                 105                 110

Ser Leu Phe Tyr Ser Glu Glu Ala Cys Asn Phe His Glu Lys Val Leu
        115                 120                 125

Ser Asp Gly Tyr Asn Leu Tyr Tyr Ser Glu Asn Tyr Asn Ile Pro Val
```

```
                130                 135                 140
Ser Leu Ser Ser Ala Gly Asn Leu Gly Gln Ser Arg Gln Leu Pro Pro
145                 150                 155                 160

Phe Ser Gln Phe Leu Pro Leu Val Asn Lys Ile Pro Leu Glu Pro Val
                165                 170                 175

Leu Glu Asp Phe Asp Phe Tyr Gly His Gln Leu Asp Val Glu Ser Ala
            180                 185                 190

Asp Pro Leu Ser Ile Leu Gly Gln Asn Pro Gly Phe Met Ser Pro Ser
        195                 200                 205

Tyr Val Phe
    210

<210> SEQ ID NO 123
<211> LENGTH: 188
<212> TYPE: PRT
<213> ORGANISM: Gadus morhua

<400> SEQUENCE: 123

Leu Leu Leu Ala Thr Leu Leu His Ile Gly Leu Ser Phe Tyr Val Pro
1               5                   10                  15

Asp Ser Gly Pro Leu Leu Trp Leu Gly Asp Gln Val Arg Glu Arg His
            20                  25                  30

Leu Tyr Thr Ala Glu Ser His Arg Arg Gly Leu Phe Leu Glu Met Ser
        35                  40                  45

Pro Asp Gly Gln Val Thr Gly Ser Ala Ala Gln Thr Pro Leu Ser Val
    50                  55                  60

Leu Glu Leu Arg Ser Val Arg Ala Gly Asp Thr Val Ile Arg Ala Arg
65                  70                  75                  80

Leu Ser Ser Leu Tyr Leu Cys Val Asp Arg Ala Gly His Leu Thr Gly
                85                  90                  95

Gln Arg Gln Tyr Thr Glu Ser Asp Cys Thr Phe Arg Glu Val Ile Leu
            100                 105                 110

Glu Asp Gly Tyr Thr His Phe Leu Ser Val His His Gly Leu Pro Ile
        115                 120                 125

Ser Leu Ala Pro Arg His Ser Pro Gly Arg Gln Gly Leu Arg Phe Ser
    130                 135                 140

Arg Phe Leu Pro Leu Arg Ser Ser Leu Ser Glu Asp Arg Val Ala Glu
145                 150                 155                 160

Pro Pro Asp Ser Pro Leu Asn Leu Asp Ser Glu Asp Pro Leu Gly Met
                165                 170                 175

Gly Leu Gly Ser Leu Leu Ser Pro Ala Phe Ser Met
            180                 185

<210> SEQ ID NO 124
<211> LENGTH: 216
<212> TYPE: PRT
<213> ORGANISM: Latimeria chalumnae

<400> SEQUENCE: 124

Met Leu Cys Gln Ser Phe Val Ile Leu Ser Gln Lys Phe Ile Phe Gly
1               5                   10                  15

Leu Phe Leu Thr Gly Leu Gly Leu Thr Gly Leu Ala Trp Thr Arg Pro
            20                  25                  30

Phe Gln Asp Ser Asn Pro Ile Leu Gln Tyr Ser Asp Ser Ile Arg Leu
        35                  40                  45

Arg His Leu Tyr Thr Ala Ser Glu Ser Arg His Leu His Leu Gln Ile
```

```
                     50                  55                  60
Asn Ser Asp Gly Gln Val Gly Thr Thr Lys Gln Ser Pro Tyr Ser
 65                  70                  75                  80

Leu Leu Glu Met Lys Ala Val Lys Thr Gly Phe Val Val Ile Arg Gly
                 85                  90                  95

Lys Lys Ser Ala Arg Tyr Leu Cys Met Glu Arg Ser Gly Arg Leu Tyr
                100                 105                 110

Gly Ser Leu Gln Tyr Thr Glu Lys Asp Cys Thr Phe Lys Glu Val Val
                115                 120                 125

Leu Ala Asp Gly Tyr Asn Leu Tyr Val Ser Glu Glu His Gln Ala Thr
                130                 135                 140

Val Thr Leu Ser Pro Met Arg Ala Arg Ile Ala Gln Gly Lys Lys Ile
145                 150                 155                 160

Pro Pro Phe Ser His Phe Leu Pro Met Val Asn Lys Val Pro Val Glu
                165                 170                 175

Asp Val Ala Ala Glu Met Glu Phe Val Gln Val Leu Arg Glu Met Thr
                180                 185                 190

Ala Asp Val Asp Ser Pro Asp Pro Phe Gly Met Thr Trp Glu Glu Ser
                195                 200                 205

Val His Ser Pro Ser Phe Phe Ala
                210                 215

<210> SEQ ID NO 125
<211> LENGTH: 192
<212> TYPE: PRT
<213> ORGANISM: Tursiops truncates

<400> SEQUENCE: 125

Met Gly Trp Asp Lys Thr Lys Leu Glu His Leu Gly Leu Trp Val Pro
  1               5                  10                  15

Val Leu Ala Val Leu Leu Gly Pro Cys Gln Ala His Pro Ile Pro Asp
                 20                  25                  30

Ser Ser Pro Leu Leu Gln Phe Gly Gly Gln Val Arg Gln Arg Tyr Leu
                 35                  40                  45

Tyr Thr Asp Asp Ala Gln Glu Thr Glu Ala His Leu Glu Ile Arg Ala
                 50                  55                  60

Asp Gly Thr Val Val Gly Thr Ala Arg Arg Ser Pro Glu Gly Val Lys
 65                  70                  75                  80

Thr Ser Arg Phe Leu Cys Gln Gly Pro Glu Gly Arg Leu Tyr Gly Ser
                 85                  90                  95

Leu His Phe Asn Pro Gln Ala Cys Ser Phe Arg Glu Leu Leu Leu Glu
                100                 105                 110

Asp Gly Tyr Asn Val Tyr Gln Ser Glu Ala Leu Gly Ile Pro Leu Arg
                115                 120                 125

Leu Pro Pro His Arg Ser Ser Asn Trp Asp Leu Ala Pro Arg Gly Pro
                130                 135                 140

Ala Arg Phe Leu Pro Leu Pro Gly Phe Leu Pro Pro Leu Glu Pro
145                 150                 155                 160

Pro Gly Ile Leu Ala Pro Glu Pro Asn Val Gly Ser Ser Asp Pro
                165                 170                 175

Leu Ser Met Val Gly Pro Ser His Gly Arg Ser Pro Ser Tyr Thr Ser
                180                 185                 190

<210> SEQ ID NO 126
<211> LENGTH: 209
```

<212> TYPE: PRT
<213> ORGANISM: Mustela putorius furo

<400> SEQUENCE: 126

Met Gly Trp Glu Glu Ala Arg Ser Glu His Leu Gly Leu Trp Val Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asn Gly Thr Leu Tyr Gly
            100                 105                 110

Ser Phe His Phe Asp Pro Val Ala Cys Ser Phe Arg Glu Val Leu Leu
        115                 120                 125

Glu Asp Gly Tyr Asn Ile Tyr His Ser Glu Thr Leu Gly Leu Pro Leu
    130                 135                 140

Arg Leu Pro Pro His Asn Ser Pro His Arg Asp Leu Ala Pro Arg Gly
145                 150                 155                 160

Pro Ala Arg Phe Leu Pro Leu Pro Gly Leu Leu Pro Ala Thr Pro Glu
                165                 170                 175

Ser Arg Gly Ile Pro Ala Pro Glu Pro Pro Asn Val Gly Ser Ser Asp
            180                 185                 190

Pro Leu Ser Met Val Gly Pro Leu Gln Gly Gln Ser Pro Ser Tyr Thr
        195                 200                 205

Ser

<210> SEQ ID NO 127
<211> LENGTH: 198
<212> TYPE: PRT
<213> ORGANISM: Takifugu rubripes

<400> SEQUENCE: 127

Phe Ile Tyr Leu Phe Ile Gln Thr Ala Leu Phe Ser Pro Ser Lys Trp
1               5                   10                  15

Phe Asn Phe Tyr Leu Pro Asp Ser Asn Pro Leu Leu Ser Phe Asp Ser
            20                  25                  30

His Gly Arg Gly Ile His Leu Tyr Thr Asp Asn Gln Arg Arg Gly Met
        35                  40                  45

Tyr Leu Gln Met Ser Thr Asp Gly Ser Val Ser Gly Ser Asp Val Gln
    50                  55                  60

Thr Ala Asn Ser Val Leu Glu Leu Lys Ser Val Arg Asn Gly His Val
65                  70                  75                  80

Val Ile Arg Gly Lys Ser Ser Ser Leu Phe Leu Cys Met Asp Ser Arg
                85                  90                  95

Gly Arg Leu Trp Gly Gln Arg His Pro Thr Glu Ala Asp Cys Thr Phe
            100                 105                 110

Arg Glu Val Leu Leu Ala Asp Gly Tyr Thr Arg Phe Leu Ser Leu His
        115                 120                 125

Asn Gly Thr Pro Val Ser Leu Ala Pro Lys Gln Ser Pro Asp Gln His

```
                130                 135                 140
Thr Val Pro Phe Thr Arg Phe Leu Pro Leu Arg Asn Thr Leu Ala Glu
145                 150                 155                 160

Glu Ser Met Ser Glu Pro Pro Ser Asn Gln Gln Arg Tyr Phe Asn Ile
                165                 170                 175

Asp Ser Asp Asp Leu Leu Gly Met Asp Leu Asn Ala Met Val Ser Pro
            180                 185                 190

Gln Phe Ser Gly Asp Lys
            195
```

<210> SEQ ID NO 128
<211> LENGTH: 203
<212> TYPE: PRT
<213> ORGANISM: Dipodomys ordii

<400> SEQUENCE: 128

```
Met Asp Gln Ala Lys Thr Arg Val Gly Ala Arg Gly Leu Gly Gly Leu
1               5                   10                  15

Val Leu Ala Val Ile Ile Leu Gly Ala Cys Lys Ala Arg Pro Ile Pro
                20                  25                  30

Asp Ser Ser Pro Leu Leu Gln Phe Gly Gly Gln Val Arg Leu Arg His
            35                  40                  45

Leu Tyr Thr Asp Asp Thr Gln Glu Thr Glu Ala His Leu Glu Ile Arg
    50                  55                  60

Ala Asp Gly Thr Val Val Gly Thr Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Lys Thr Ser Arg Phe Leu Cys Gln Arg Pro Asp Gly Thr Leu Tyr Gly
                100                 105                 110

Ser Leu His Phe Asp Pro Glu Val Cys Ser Phe Gln Glu Leu Leu Leu
            115                 120                 125

Glu Asp Gly Tyr Asn Ile Tyr Arg Ser Glu Ala Leu Gly Leu Pro Leu
    130                 135                 140

Arg Leu Ser Pro Asp Pro Ala Pro Trp Gly Pro Ala Arg Phe Leu Pro
145                 150                 155                 160

Leu Pro Gly Val Pro Pro Ala Pro Pro Glu Pro Pro Gly Ile Leu Ala
                165                 170                 175

Pro Glu Pro Pro Asp Val Gly Ser Ser Asp Pro Leu Ser Met Val Gly
            180                 185                 190

Leu Leu Gln Gly Arg Ser Pro Ser Tyr Ala Ser
            195                 200
```

<210> SEQ ID NO 129
<211> LENGTH: 184
<212> TYPE: PRT
<213> ORGANISM: Echinops telfairi

<400> SEQUENCE: 129

```
Met Gly Cys Thr Lys Ser Gly Trp Lys Ser Pro Gly Leu Trp Val Pro
1               5                   10                  15

Val Leu Ala Ser Leu Leu Gly Gly Cys Gly Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Thr Thr Glu Ala His Leu Glu Ile Arg
```

-continued

```
            50                  55                  60
Ala Asp Gly Thr Val Gly Val Ala His Gln Ser Pro Glu Lys Phe
 65                  70                  75                  80

Leu Ser Gln Trp Arg Glu Lys Pro Leu Arg Ser Leu His Phe Asp Pro
                 85                  90                  95

Ala Ala Cys Ser Phe Arg Glu Lys Leu Leu Glu Asp Gly Tyr Asn Leu
            100                 105                 110

Tyr His Ser Glu Thr His Gly Leu Pro Leu Arg Leu Pro Pro Arg Gly
                115                 120                 125

Gly Asp Pro Ser Ser Gln Pro Gly Ala Arg Phe Pro Pro Leu Pro Gly
            130                 135                 140

Gln Leu Pro Gln Leu Gln Glu Thr Pro Gly Val Leu Ala Pro Glu Pro
145                 150                 155                 160

Pro Asp Val Gly Ser Ser Asp Pro Leu Ser Met Val Gly Pro Trp Arg
                165                 170                 175

Gly Gln Ser Pro Ser Tyr Ala Ser
                180
```

<210> SEQ ID NO 130
<211> LENGTH: 210
<212> TYPE: PRT
<213> ORGANISM: Macaca mulatta

<400> SEQUENCE: 130

```
Met Asp Ser Asp Glu Thr Gly Phe Glu His Ser Gly Leu Trp Val Pro
  1               5                  10                  15

Val Leu Ala Gly Leu Leu Leu Gly Ala Cys Gln Ala His Pro Ile Pro
                 20                  25                  30

Asp Ser Ser Pro Leu Leu Gln Phe Gly Gly Gln Val Arg Gln Arg Tyr
             35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala His Gln Ser Pro Glu Ser Glu
 65                  70                  75                  80

Cys Gly Pro Glu Pro Gly Ser Glu Gly Gly Ala Val Gly Gly Ala
                 85                  90                  95

Glu Gly Pro Gly Leu Leu Gly Leu Arg Glu Ala Gly Leu Gly Pro Gly
            100                 105                 110

Ser Trp Leu His Phe Asp Pro Glu Ala Cys Ser Phe Arg Glu Leu Leu
                115                 120                 125

Leu Glu Asn Gly Tyr Asn Val Tyr Gln Ser Glu Ala His Gly Leu Pro
            130                 135                 140

Leu His Leu Pro Gly Asn Lys Ser Pro His Arg Asp Pro Ala Ser Gln
145                 150                 155                 160

Gly Pro Ala Arg Phe Leu Pro Leu Pro Gly Leu Pro Pro Ala Pro Pro
                165                 170                 175

Glu Pro Pro Gly Ile Leu Ala Pro Gln Pro Pro Asp Val Gly Ser Ser
            180                 185                 190

Asp Pro Leu Ser Met Val Gly Pro Ser Gln Ala Arg Ser Pro Ser Tyr
                195                 200                 205

Ala Ser
 210
```

<210> SEQ ID NO 131
<211> LENGTH: 193

<212> TYPE: PRT
<213> ORGANISM: Microcebus murinus

<400> SEQUENCE: 131

```
Met Gly Trp Asp Glu Ala Gly Ala Gly Phe Glu His Pro Gly Leu Trp
1               5                   10                  15

Phe Pro Met Leu Gly Val Leu Leu Gly Ala Cys Gln Ala Tyr Pro
            20                  25                  30

Ile Pro Asp Ser Ser Pro Leu Leu Gln Phe Gly Gly Gln Val Arg Gln
        35                  40                  45

Arg His Leu Tyr Thr Asp Asp Ile Gln Glu Thr Glu Ala His Leu Glu
    50                  55                  60

Ile Arg Ala Asp Gly Thr Val Val Gly Ala Ala Arg Gln Ser Pro Glu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Cys Ser Phe Arg Glu Leu Leu Leu Glu
        115                 120                 125

Asp Gly Tyr Asn Val Tyr Cys Pro Tyr Leu Pro His Leu Ser Pro
    130                 135                 140

Arg Ile Glu Leu Ala Gly Ser Arg Ser Ala Leu Pro Leu Pro Pro Ala
145                 150                 155                 160

Pro Glu Arg Arg Ile Leu Ala Pro Glu Pro Pro Asp Gly Ser Ser Asp
                165                 170                 175

Pro Leu Ser Met Val Gly Pro Ser Gln Gly Arg Ser Pro Ser Tyr Ala
            180                 185                 190

Ser
```

<210> SEQ ID NO 132
<211> LENGTH: 204
<212> TYPE: PRT
<213> ORGANISM: Ochotona princeps

<400> SEQUENCE: 132

```
Lys Asp Met Asp Gly Leu Gln Pro Pro Gly Leu Arg Val Pro Val Leu
1               5                   10                  15

Ala Ala Leu Leu Leu Gly Val Gly Gln Ala Arg Pro Ile Pro Asp Ser
                20                  25                  30

Ser Pro Leu Leu Gln Phe Gly Gly Gln Val Arg Gln Arg His Leu Tyr
            35                  40                  45

Thr Asp Asp Ala Gln Glu Ser Glu Val His Leu Glu Ile Arg Ala Asp
        50                  55                  60

Gly Thr Val Ala Gly Thr Ala Arg Arg Ser Pro Glu Ser Leu Leu Glu
65                  70                  75                  80

Met Lys Ala Leu Lys Pro Gly Val Ile Gln Ile Leu Gly Val His Thr
                85                  90                  95

Ser Arg Phe Leu Cys Gln Arg Pro Asp Gly Thr Leu Tyr Gly Ser Leu
            100                 105                 110

His Phe Asp His Lys Ala Cys Ser Phe Arg Glu Gln Leu Leu Glu Asp
        115                 120                 125

Gly Tyr Asn Val Tyr His Ser Glu Thr His Gly Leu Pro Leu Arg Leu
    130                 135                 140

Ser Pro Asp Arg Ala Pro Arg Gly Pro Ala Arg Phe Leu Pro Leu Pro
```

```
                145                 150                 155                 160
Gly Pro Pro Pro Asp Leu Leu Val Pro Pro Leu Pro Pro Asp Val Leu
                    165                 170                 175

Ala Pro Glu Pro Pro Asp Val Asp Ser Pro Asp Pro Leu Ser Met Val
                    180                 185                 190

Gly Pro Leu Gln Gly Gln Ser Pro Ser Tyr Thr Ser
                    195                 200
```

<210> SEQ ID NO 133
<211> LENGTH: 182
<212> TYPE: PRT
<213> ORGANISM: Xiphophorus maculates

<400> SEQUENCE: 133

```
Cys Pro Phe Pro Phe Leu Phe Leu Ile Leu Ser Leu Pro Phe Phe Ser
1               5                   10                  15

Ser Ser Phe Tyr Ile Pro Glu Ser Asn Pro Ile Phe Ala Phe Arg Asn
                20                  25                  30

Gln Leu Arg Glu Val His Leu Tyr Thr Glu Asn His Arg Arg Gly Leu
            35                  40                  45

Tyr Val Glu Ile His Leu Asp Gly Arg Val Thr Gly Ser Asp Ala Gln
    50                  55                  60

Ser Pro Tyr Ser Val Leu Gln Ile Lys Ser Val Lys Pro Gly His Val
65                  70                  75                  80

Val Ile Lys Gly Gln Thr Ser Ser Leu Phe Leu Cys Met Asp Asp Ser
                85                  90                  95

Gly Asn Leu Arg Gly Gln Thr Thr Tyr Asp Glu Ala Asp Cys Ser Phe
            100                 105                 110

Arg Glu Leu Leu Leu Ala Asp Gly Tyr Thr Arg Phe Leu Asn Ser Gln
        115                 120                 125

His Gly Val Pro Leu Ser Leu Ala Ser Arg Asn Ser Pro Asp Arg His
    130                 135                 140

Ser Val Pro Phe Thr Arg Phe Leu Pro Leu Arg Asn Thr Leu Thr Val
145                 150                 155                 160

Ser Glu Glu Ser Thr Lys Thr Gln Arg Asp Phe Asn Leu Asp Ser Asp
                165                 170                 175

Asp Leu Leu Gly Met Gly
            180
```

<210> SEQ ID NO 134
<211> LENGTH: 192
<212> TYPE: PRT
<213> ORGANISM: Gasterosteus aculeatus

<400> SEQUENCE: 134

```
Ser Leu Leu Leu Met Val Pro Leu Pro Phe Cys Ser Ser Phe Tyr Leu
1               5                   10                  15

Thr Asp Ser Ser Pro Leu Leu Pro Phe Asn Asn Gln Val Lys Glu Val
                20                  25                  30

His Leu Tyr Thr Ala Glu Asn His Arg Arg Ala Met Tyr Leu Gln Ile
            35                  40                  45

Ala Leu Asp Gly Ser Val Gly Ser Asp Ala Arg Ser Thr Tyr Ser
    50                  55                  60

Val Leu Gln Leu Lys Ser Ile Gln Pro Gly His Val Val Ile Arg Gly
65                  70                  75                  80

Lys Ala Ser Ser Met Phe Leu Cys Val Asp Ser Gly Gly Arg Leu Arg
```

```
                    85                  90                  95
Gly Gln Gly Pro Tyr Ser Glu Ala Asp Cys Ser Phe Arg Glu Leu Leu
            100                 105                 110

Leu Gly Asp Gly Tyr Thr Arg Phe Leu Ser Ser Gln His Gly Ser Pro
            115                 120                 125

Leu Ser Leu Ala Ser Arg Pro Ser Pro Asp Pro Asn Ser Val Pro Phe
        130                 135                 140

Thr Arg Phe Leu Pro Ile Arg Thr Ala Pro Glu Ala Glu Ser Val Ile
145                 150                 155                 160

Glu Glu Pro Pro Ser Asn Gln Arg Tyr Val Asn Val Asp Ser Glu Asp
                165                 170                 175

Leu Leu Gly Met Gly Leu Asn Thr Val Val Ser Pro Gln Phe Ser Ala
            180                 185                 190

<210> SEQ ID NO 135
<211> LENGTH: 165
<212> TYPE: PRT
<213> ORGANISM: Sarcophilus harrisii

<400> SEQUENCE: 135

Val Ser Ala Met Gly Leu Arg Glu Arg Ala Pro Arg Tyr Leu Ala Pro
1               5                   10                  15

Leu Leu Ser Leu Leu Ala Cys Arg Ala Ser Gly His Pro Leu Pro
            20                  25                  30

Asp Ser Ser Pro Met Leu Leu Phe Gly Gly Gln Val Arg Leu Arg His
        35                  40                  45

Leu Tyr Thr Asp Val Gly Gln Glu Ala Glu Ala His Val Glu Leu Ala
    50                  55                  60

Ser Asp Gly Thr Val Arg Ala Ala Ala Arg Arg Ser Pro Asn Ser Leu
65                  70                  75                  80

Leu Glu Leu Lys Ala Val Lys Pro Gly Ile Val Arg Ile Leu Ala Val
                85                  90                  95

His Ser Ser Arg Phe Leu Cys Met Arg Pro Asn Gly Glu Leu Tyr Gly
            100                 105                 110

Ala Ile His Tyr Asp Pro Ser Ala Cys Asn Phe Arg Glu Arg Leu Leu
        115                 120                 125

Gly Asp Gly Tyr Asn Val Tyr Glu Ser Glu Ala His Gly Arg Thr Leu
    130                 135                 140

Arg Leu Pro Pro Lys Ala Ala Pro Gly Pro Ala Gly Pro Ser Arg Phe
145                 150                 155                 160

Leu Pro Leu Pro Gly
                165

<210> SEQ ID NO 136
<211> LENGTH: 208
<212> TYPE: PRT
<213> ORGANISM: Macropus eugenii

<400> SEQUENCE: 136

Thr Glu Glu Pro Ser Thr Gly Ser Arg His Leu Gly Gln Trp Ala Pro
1               5                   10                  15

Gly Leu Pro Gly Pro Leu Leu Ser Leu Leu Ala Tyr Arg Gly Trp
            20                  25                  30

Gly Ser Pro Ile Pro Asp Ser Ser Pro Met Leu Leu Phe Gly Gly Gln
        35                  40                  45

Val Arg Leu Arg His Leu Tyr Thr Asp Asp Gly Gln Asp Thr Glu Ala
```

```
                50                  55                  60
His Val Glu Leu Gly Pro Asp Gly Val Arg Ala Val Ala Glu Arg
 65                  70                  75                  80

Ser Pro Asn Ser Leu Leu Glu Leu Lys Ala Val Lys Pro Gly Val Ile
                 85                  90                  95

Arg Ile Leu Ala Val Gln Ser Ser Arg Phe Leu Cys Met Arg Pro Asn
                100                 105                 110

Gly Glu Leu Tyr Gly Ala Val His Tyr Asp Pro Ser Ala Cys Asn Phe
                115                 120                 125

Arg Glu His Leu Leu Gly Asp Gly Tyr Asn Val Tyr Glu Ser Glu Thr
                130                 135                 140

His Arg Arg Thr Leu Arg Leu Ser Pro Ser Leu Gly Gln Ala Gly Pro
145                 150                 155                 160

Ser Arg Phe Leu Pro Leu Pro Gly Asp Trp Leu Pro Gly Pro Asp Pro
                165                 170                 175

Pro Trp Ala Gln Gly Pro Glu Pro Pro Asp Val Gly Ser Ala Asp Pro
                180                 185                 190

Leu Ser Met Val Gly Ala Val Gln Gly Leu Ser Pro Ser Tyr Ser Ser
                195                 200                 205
```

<210> SEQ ID NO 137
<211> LENGTH: 160
<212> TYPE: PRT
<213> ORGANISM: Xenopus tropicalis

<400> SEQUENCE: 137

```
Arg Gly Gly Arg Thr Lys Lys Thr Leu Leu Arg Lys Trp Leu Cys
  1               5                  10                  15

Leu Leu Ala Ile Met Leu Ser Arg Ser Arg Phe Ser Leu Ala Asn Pro
                 20                  25                  30

Ile Gln Asn Ser Asn Pro Ile Leu Ser Asn Asp Asn Gln Val Arg Thr
                 35                  40                  45

Gln Tyr Leu Tyr Thr Asp Asn Asn Met His Leu Tyr Leu Gln Ile
 50                  55                  60

Thr His Asn Gly Val Val Thr Gly Thr Glu Glu Lys Asn Asp Tyr Gly
 65                  70                  75                  80

Val Leu Glu Ile Lys Ala Val Lys Ala Gly Val Val Ile Lys Gly
                 85                  90                  95

Ile Arg Ser Asn Leu Tyr Leu Cys Met Asp Ser Arg His Gln Leu Tyr
                100                 105                 110

Ala Ser Ala Tyr Asp Lys Asp Cys His Phe His Glu Lys Ile Thr
                115                 120                 125

Pro Asp Asn Tyr Asn Met Tyr Ser Ser Glu Lys His Ser Glu Tyr Val
                130                 135                 140

Ser Leu Ala Pro Leu Lys Gly Ser Gln Met Ala Arg Phe Leu Pro Ile
145                 150                 155                 160
```

<210> SEQ ID NO 138
<211> LENGTH: 194
<212> TYPE: PRT
<213> ORGANISM: Danio rerio

<400> SEQUENCE: 138

```
Met Leu Leu Ala Cys Phe Phe Ile Phe Phe Ala Leu Phe Pro His Leu
  1               5                  10                  15

Arg Trp Cys Met Tyr Val Pro Ala Gln Asn Val Leu Leu Gln Phe Gly
```

```
                    20                  25                  30
Thr Gln Val Arg Glu Arg Leu Leu Tyr Thr Asp Gly Leu Phe Leu Glu
             35                  40                  45
Met Asn Pro Asp Gly Ser Val Lys Gly Ser Pro Glu Lys Asn Leu Asn
         50                  55                  60
Cys Val Leu Glu Leu Arg Ser Val Lys Ala Gly Glu Thr Val Ile Gln
 65                  70                  75                  80
Ser Ala Ala Thr Ser Leu Tyr Leu Cys Val Asp Asp Gln Asp Lys Leu
                 85                  90                  95
Lys Gly Gln His His Tyr Ser Ala Leu Asp Cys Thr Phe Gln Glu Leu
                100                 105                 110
Leu Leu Asp Gly Tyr Ser Phe Phe Leu Ser Pro His Thr Asn Leu Pro
            115                 120                 125
Val Ser Leu Leu Ser Lys Arg Gln Lys His Gly Asn Pro Leu Ser Arg
        130                 135                 140
Phe Leu Pro Val Ser Arg Ala Glu Asp Ser Arg Thr Gln Glu Val Lys
145                 150                 155                 160
Gln Tyr Ile Gln Asp Ile Asn Leu Asp Ser Asp Pro Leu Gly Met
                165                 170                 175
Gly His Arg Ser His Leu Gln Thr Val Phe Ser Pro Ser Leu His Thr
            180                 185                 190
Lys Lys

<210> SEQ ID NO 139
<211> LENGTH: 209
<212> TYPE: PRT
<213> ORGANISM: Bos grunniens mutus

<400> SEQUENCE: 139

Met Gly Trp Asp Glu Ala Lys Phe Lys His Leu Gly Leu Trp Val Pro
 1               5                  10                  15
Val Leu Ala Val Leu Leu Leu Gly Thr Cys Arg Ala His Pro Ile Pro
                 20                  25                  30
Asp Ser Ser Pro Leu Leu Gln Phe Gly Gly Gln Val Arg Gln Arg Tyr
             35                  40                  45
Leu Tyr Thr Asp Asp Ala Gln Glu Thr Glu Ala His Leu Glu Ile Arg
         50                  55                  60
Ala Asp Gly Thr Val Val Gly Ala Ala Arg Gln Ser Pro Glu Ser Leu
 65                  70                  75                  80
Leu Glu Leu Lys Ala Leu Lys Pro Gly Val Ile Gln Ile Leu Gly Val
                 85                  90                  95
Lys Thr Ser Arg Phe Leu Cys Gln Gly Pro Asp Gly Lys Leu Tyr Gly
                100                 105                 110
Ser Leu His Phe Asp Pro Lys Ala Cys Ser Phe Arg Glu Leu Leu Leu
            115                 120                 125
Glu Asp Gly Tyr Asn Val Tyr Gln Ser Glu Thr Leu Gly Leu Pro Leu
        130                 135                 140
Arg Leu Pro Pro Gln Arg Ser Asn Arg Asp Pro Ala Pro Arg Gly
145                 150                 155                 160
Pro Ala Arg Phe Leu Pro Leu Pro Gly Leu Pro Ala Glu Pro Pro Asp
                165                 170                 175
Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
```

-continued

```
            195                 200                 205
Ser

<210> SEQ ID NO 140
<211> LENGTH: 209
<212> TYPE: PRT
<213> ORGANISM: Saimiri boliviensis boliviensis

<400> SEQUENCE: 140

Met Gly Ser Glu Glu Val Ala Leu Glu Arg Pro Ala Leu Trp Val Ser
1               5                   10                  15

Val Leu Ala Gly Leu Leu Leu Gly Thr Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Ala Gly Ala Ala His Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu Tyr Phe Asp Pro Glu Ala Cys Ser Phe Arg Glu Leu Leu Leu
        115                 120                 125

Glu Asp Gly Tyr Asn Val Tyr Gln Ser Val Ala His Ser Leu Pro Leu
    130                 135                 140

His Leu Pro Gly Gly Arg Ser Pro Pro Trp Asp Pro Ala Pro Arg Gly
145                 150                 155                 160

Pro Ala Arg Phe Leu Pro Leu Pro Gly Leu Pro Glu Pro Pro Glu
                165                 170                 175

Ala Pro Gly Ile Leu Ala Pro Glu Pro Pro Asp Val Gly Ser Ser Asp
            180                 185                 190

Pro Leu Ser Met Val Gly Pro Ser Gln Gly Gln Ser Pro Ser Tyr Thr
        195                 200                 205

Ser

<210> SEQ ID NO 141
<211> LENGTH: 210
<212> TYPE: PRT
<213> ORGANISM: Callithrix jacchus
<220> FEATURE:
<221> NAME/KEY: misc_feature
<222> LOCATION: (64)..(64)
<223> OTHER INFORMATION: Xaa can be any naturally occurring amino acid

<400> SEQUENCE: 141

Met Gly Ser Glu Glu Val Gly Leu Glu His Pro Ala Leu Trp Val Ser
1               5                   10                  15

Val Leu Ala Gly Leu Leu Leu Gly Thr Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Lys Glu Ala His Leu Glu Ile Xaa
    50                  55                  60

Glu Asp Gly Thr Val Ala Gly Ala Ala Thr Lys Val Pro Lys Val Ser
65                  70                  75                  80
```

```
Leu Leu Gln Leu Lys Ala Leu Lys Pro Gly Val Ile Gln Ile Leu Gly
                85                  90                  95

Val Lys Thr Ser Arg Phe Leu Cys Gln Arg Pro Asp Gly Ala Leu Tyr
            100                 105                 110

Gly Ser Leu His Phe Asp Pro Glu Ala Cys Ser Phe Arg Glu Leu Leu
        115                 120                 125

Leu Glu Asp Gly Tyr Asn Val Tyr Gln Ser Val Ala His Gly Leu Pro
130                 135                 140

Leu His Leu Pro Glu Ser Arg Ser Pro Pro Arg Asp Pro Ala Pro Arg
145                 150                 155                 160

Gly Pro Ala Arg Phe Leu Pro Leu Pro Gly Leu Pro Pro Glu Pro Pro
                165                 170                 175

Glu Pro Pro Gly Ile Leu Ala Pro Glu Pro Pro Asp Val Gly Ser Ser
            180                 185                 190

Asp Pro Leu Ser Met Val Gly Pro Ser Gln Gly Gln Ser Pro Ser Tyr
                195                 200                 205

Ala Ser
    210

<210> SEQ ID NO 142
<211> LENGTH: 209
<212> TYPE: PRT
<213> ORGANISM: Tupaia chinensis

<400> SEQUENCE: 142

Met Gly Trp Asp Lys Ala Arg Phe Glu His Leu Gly Ala Trp Ala Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
    50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
130                 135                 140

Arg Leu Pro Pro His Asp Ser Pro His Arg Asp Arg Thr Pro Gln Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
            180                 185                 190

Pro Leu Ser Met Met Gly Pro Ser Gln Gly Gln Ser Pro Ser Tyr Ala
        195                 200                 205

Ser

<210> SEQ ID NO 143
```

```
<211> LENGTH: 188
<212> TYPE: PRT
<213> ORGANISM: Papio anubis

<400> SEQUENCE: 143

Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Ala Gln Gln Thr Glu Ala His Leu Glu Ile Arg
50                  55                  60

Glu Asp Gly Thr Val Gly Gly Ala Ala His Gln Ser Pro Glu Ser Lys
65                  70                  75                  80

Cys Gly Pro Glu Pro Gly Ser Glu Gly Gly Ala Leu His Phe Asp
                85                  90                  95

Pro Glu Ala Cys Ser Phe Arg Glu Leu Leu Glu Asn Gly Tyr Asn
                100                 105                 110

Val Tyr Gln Ser Glu Ala His Gly Leu Pro Leu His Leu Pro Gly Asn
            115                 120                 125

Lys Ser Pro His Arg Asp Pro Ala Ser Arg Gly Pro Ala Arg Phe Leu
130                 135                 140

Pro Leu Pro Gly Leu Pro Ala Pro Pro Glu Pro Gly Ile Leu
145                 150                 155                 160

Ala Pro Gln Pro Pro Asp Val Gly Ser Ser Asp Pro Leu Ser Met Val
                165                 170                 175

Gly Pro Ser Gln Ala Arg Ser Pro Ser Tyr Ala Ser
            180                 185

<210> SEQ ID NO 144
<211> LENGTH: 208
<212> TYPE: PRT
<213> ORGANISM: Pteropus alecto

<400> SEQUENCE: 144

Met Gly Trp Gly Lys Ala Arg Leu Gln His Pro Gly Leu Trp Gly Pro
1               5                   10                  15

Val Leu Ala Val Leu Leu Gly Ala Cys Gln Ala His Pro Ile Leu Asp
            20                  25                  30

Ser Ser Pro Leu Phe Gln Phe Gly Ser Gln Val Arg Arg Tyr Leu
            35                  40                  45

Tyr Thr Asp Asp Ala Gln Asp Thr Glu Ala His Leu Glu Ile Arg Ala
50                  55                  60

Asp Gly Thr Val Ala Gly Ala Ala Arg Arg Ser Pro Glu Ser Leu Leu
65                  70                  75                  80

Glu Leu Lys Ala Leu Lys Pro Gly Val Ile Gln Val Leu Gly Val Lys
                85                  90                  95

Thr Ser Arg Phe Leu Cys Gln Arg Pro Asp Gly Thr Leu Tyr Gly Ser
                100                 105                 110

Leu His Phe Asp Pro Ala Ala Cys Ser Phe Arg Glu Leu Leu Leu Lys
            115                 120                 125

Asp Gly Tyr Asn Val Tyr Gln Ser Glu Ala Leu Ala Arg Pro Leu Arg
130                 135                 140

Leu Pro Pro Tyr Ser Ser Pro Ser Ser Asp Pro Ala Arg Arg Gly Pro
145                 150                 155                 160
```

```
Ala Arg Phe Leu Pro Leu Pro Gly Pro Pro Glu Pro Pro Gln Pro
            165                 170                 175

Pro Gly Arg Leu Ala Pro Glu Pro Pro Asp Val Gly Ser Ser Asp Pro
        180                 185                 190

Leu Ser Met Val Trp Pro Ser Arg Gly Arg Ser Pro Ser Tyr Thr Ser
        195                 200                 205
```

<210> SEQ ID NO 145
<211> LENGTH: 210
<212> TYPE: PRT
<213> ORGANISM: Heterocephalus glaber

<400> SEQUENCE: 145

```
Met Asp Trp Ala Arg Ala Glu Ser Glu Arg Pro Gly Leu Trp Val Pro
1               5                   10                  15

Ala Val Leu Ala Val Leu Leu Leu Gly Ala Cys Gln Ala His Pro Ile
            20                  25                  30

Pro Asp Ser Ser Pro Leu Leu Gln Phe Gly Gly Gln Val Arg Gln Arg
        35                  40                  45

His Leu Tyr Thr Asp Asp Ala Gln Asp Thr Glu Val His Leu Glu Ile
    50                  55                  60

Arg Ala Asp Gly Ser Val Gly Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Arg Thr Ser Arg Phe Leu Cys Gln Arg Pro Asp Gly Thr Leu Tyr
            100                 105                 110

Gly Ser Leu His Phe Asp Pro Glu Ala Cys Ser Phe Arg Glu Leu Leu
        115                 120                 125

Leu Ala Asp Gly Tyr Asn Ile Tyr Gln Ser Glu Ala Tyr Gly Leu Pro
    130                 135                 140

Leu Arg Met Leu Pro Ser Asp Ser Ala Ser Arg Asp Pro Val Pro Pro
145                 150                 155                 160

Gly Pro Ala Arg Phe Leu Pro Leu Pro Gly Leu His Pro Pro Leu
                165                 170                 175

Glu Pro Pro Gly Met Leu Pro Glu Pro Pro Asp Val Gly Ser Ser
        180                 185                 190

Asp Pro Leu Ser Met Val Gly Pro Leu Gln Gly Arg Ser Pro Ser Tyr
    195                 200                 205

Ala Phe
    210
```

<210> SEQ ID NO 146
<211> LENGTH: 209
<212> TYPE: PRT
<213> ORGANISM: Cricetulus griseus

<400> SEQUENCE: 146

```
Met Asp Trp Met Lys Ser Gly Val Gly Val Pro Gly Leu Trp Val Pro
1               5                   10                  15

Leu Leu Pro Ile Phe Leu Leu Gly Val Ser Gln Ala His Pro Ile Pro
            20                  25                  30

Asp Ser Ser Pro Leu Leu Gln Phe Gly Gly Gln Val Arg His Arg His
        35                  40                  45

Leu Tyr Thr Asp Asp Asn Gln Glu Thr Glu Val His Leu Glu Ile Arg
    50                  55                  60
```

Gln Asp Gly Thr Val Ile Gly Thr Thr His Arg Ser Pro Glu Ser Leu
65                  70                  75                  80

Leu Glu Leu Lys Ala Leu Lys Pro Glu Val Ile Pro Val Leu Gly Val
                85                  90                  95

Lys Ala Ser Arg Phe Leu Cys Gln Gln Pro Asp Gly Thr Leu Tyr Gly
                100                 105                 110

Ser Pro His Phe Asp Pro Glu Ala Cys Ser Phe Arg Glu Leu Leu Leu
                115                 120                 125

Glu Asp Gly Tyr Asn Val Tyr Gln Ser Glu Val His Gly Leu Pro Leu
                130                 135                 140

Arg Leu Pro Gln Arg Asp Ser Pro Asn Gln Ala Pro Ala Ser Trp Gly
145                 150                 155                 160

Pro Val Pro Pro Leu Pro Val Pro Gly Leu Leu His Gln Pro Gln Glu
                165                 170                 175

Leu Pro Gly Phe Leu Ala Pro Glu Pro Pro Asp Val Gly Ser Ser Asp
                180                 185                 190

Pro Leu Ser Met Val Gly Pro Leu Gln Gly Arg Ser Pro Ser Tyr Ala
                195                 200                 205

Ser

<210> SEQ ID NO 147
<211> LENGTH: 192
<212> TYPE: PRT
<213> ORGANISM: Ovis aries

<400> SEQUENCE: 147

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
                20                  25                  30

Asp Ser Ser Pro Leu Leu Gln Phe Gly Gly Gln Val Arg Gln Arg Tyr
                35                  40                  45

Leu Tyr Thr Asp Asp Ala Gln Glu Thr Glu Ala His Leu Glu Ile Arg
50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Phe Gly Val
                85                  90                  95

Lys Thr Ser Arg Phe Leu Cys Gln Gly Pro Asp Gly Lys Leu Tyr Gly
                100                 105                 110

Ser Leu His Phe Asp Pro Lys Ala Cys Ser Phe Arg Glu Leu Leu Leu
                115                 120                 125

Glu Asp Gly Tyr Asn Val Tyr Gln Ser Glu Thr Leu Gly Leu Pro Leu
                130                 135                 140

Arg Leu Pro Pro Gln Arg Ser Ser Asn Arg Asp Pro Ala Pro Arg Gly
145                 150                 155                 160

Pro Pro Lys Pro Gln Leu His Phe Leu Lys Thr Ser Ala Val Gln Tyr
                165                 170                 175

Trp Pro Arg Tyr Glu Lys Val Pro Ala Phe Leu His Pro Phe Pro Gly
                180                 185                 190

<210> SEQ ID NO 148
<211> LENGTH: 135
<212> TYPE: PRT
<213> ORGANISM: Pan paniscus -continued

<400> SEQUENCE: 148

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Val Ser Phe Gln Asp Pro Pro His His Pro Cys Ser Ser Tyr
            115                 120                 125

Met Ser Pro Ser Gln Pro Gly
    130                 135

<210> SEQ ID NO 149
<211> LENGTH: 116
<212> TYPE: PRT
<213> ORGANISM: Macaca fascicularis

<400> SEQUENCE: 149

Met Asp Ser Asp Glu Thr Gly Phe Glu His Ser Gly Leu Trp Val Pro
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
50                  55                  60

Glu Asp Gly Thr Val Gly Gly Ala Ala His Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Lys Pro Asp Gly Ala Leu Tyr Gly
            100                 105                 110

Ser Val Ser Phe
        115

<210> SEQ ID NO 150
<211> LENGTH: 104
<212> TYPE: PRT
<213> ORGANISM: Mesocricetus auratus

<400> SEQUENCE: 150

Val Ile Gln Ile Leu Gly Val Lys Ala Ala Arg Phe Pro Cys Gln Gln
1               5                   10                  15

Pro Asp Gly Ser Leu Tyr Gly Ser Pro His Phe Asp Pro Glu Ala Cys
            20                  25                  30

Ser Phe Arg Glu Leu Leu Leu Glu Asp Gly Tyr Asn Val Tyr Gln Ser
        35                  40                  45

Glu Ala His Gly Leu Pro Leu Arg Leu Pro Gln Arg Asp Ala Pro Ser
 50                  55                  60

Gln Pro Pro Ala Ser Trp Gly Pro Val Arg Phe Leu Pro Val Pro Gly
 65                  70                  75                  80

Leu Phe Gln Pro Pro His Asp Leu Pro Gly Arg Pro Ala Pro Glu Pro
                 85                  90                  95

Pro Asp Val Gly Ser Ser Asp Pro
            100

<210> SEQ ID NO 151
<211> LENGTH: 151
<212> TYPE: PRT
<213> ORGANISM: Oreochromis niloticus

<400> SEQUENCE: 151

Met Tyr Leu Gln Met Asn Met Asp Gly Arg Val Thr Gly Ser Asp Ala
 1               5                  10                  15

Gln Thr Pro Tyr Ser Leu Met Gln Leu Lys Ser Val Lys Pro Gly His
                 20                  25                  30

Val Ile Ile Lys Gly Pro Ser Ser Leu Phe Leu Cys Val Asp Ser
             35                  40                  45

Glu Gly Asn Leu Arg Gly Gln Ser His Tyr Ser Glu Thr Ser Cys Thr
 50                  55                  60

Phe Arg Glu Met Leu Leu Ala Asp Gly Tyr Thr Arg Phe Ile Ser Ser
 65                  70                  75                  80

Gln Tyr Gly Phe Pro Met Ser Leu Ala Ser Arg His Ser Pro Asp Arg
                 85                  90                  95

His Ala Leu Pro Phe Thr Arg Phe Leu Pro Leu Arg Asn Asn Leu Lys
            100                 105                 110

Thr Asp Ser Val Ser Glu Gln Leu Pro Asn Asn Gln Arg Leu Phe Asn
            115                 120                 125

Val Asp Ser Asp Asp Leu Leu Gly Met Gly Leu Asn Ser Met Gly Ser
130                 135                 140

Pro Gln Phe Ser Met Asp Lys
145                 150

<210> SEQ ID NO 152
<211> LENGTH: 209
<212> TYPE: PRT
<213> ORGANISM: Homo sapiens

<400> SEQUENCE: 152

Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
                 20                  25                  30

Asp Ser Ser Pro Leu Leu Gln Phe Gly Gly Gln Val Arg Gln Arg Tyr
             35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Met Arg Pro Asp Gly Ala Leu Tyr Gly
            100                 105                 110

```
Ser Leu His Phe Asp Pro Glu Ala Cys Ser Phe Arg Glu Leu Leu Leu
            115                 120                 125
Glu Asp Gly Tyr Asn Val Tyr Gln Ser Glu Ala His Gly Leu Pro Leu
        130                 135                 140
His Leu Pro Gly Asn Lys Ser Pro His Arg Asp Pro Ala Pro Arg Gly
145                 150                 155                 160
Pro Ala Arg Phe Leu Pro Leu Pro Gly Leu Pro Ala Leu Pro Glu
                165                 170                 175
Pro Pro Gly Ile Leu Ala Pro Gln Pro Pro Asp Val Gly Ser Ser Asp
                180                 185                 190
Pro Leu Ser Met Val Gly Pro Ser Gln Gly Arg Ser Pro Ser Tyr Ala
                195                 200                 205
Ser
```

<210> SEQ ID NO 153
<211> LENGTH: 630
<212> TYPE: DNA
<213> ORGANISM: Homo sapiens

<400> SEQUENCE: 153

```
atggactcgg acgagaccgg gttcgagcac tcaggactgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct gggagtcaa gacatccagg    300
ttcctgtgcc agcggccaga tggggccctg tatggatcgc tccactttga ccctgaggcc    360
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg ccccccgcac tcccggagcc acccggaatc    540
ctggcccccc agccccccga tgtgggctcc tcggaccctc tgagcatggt gggaccttcc    600
cagggccgaa gccccagcta cgcttcctga                                     630
```

<210> SEQ ID NO 154
<211> LENGTH: 630
<212> TYPE: DNA
<213> ORGANISM: Pongo abelii

<400> SEQUENCE: 154

```
atggactcgg acgagaccgg gttcgagcac tcaggactgt gggttcctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct gggagtcaa gacatccagg    300
ttcctgtgcc agaggccaga tggggccctg tatggatcgc tccactttga ccctgaggcc    360
tgcagcttcc gggagctgct tcttgaggac ggatacaatg tttatcagtc cgaggcccat    420
ggcctcccgc tgcacctgcc gggaaacaag tccccacacc gggaccctgc accccgagga    480
ccagctcgct tcctgccact accaggcctg ccccccgcac cccagagcc gcccggaatc    540
ctggcccccc agccccccga tgtgggctcc tcggaccctc tgagcatggt gggaccttcc    600
cagggccgaa gccccagcta tgcttcctga                                     630
```

<210> SEQ ID NO 155
<211> LENGTH: 630
<212> TYPE: DNA
<213> ORGANISM: Pan troglodytes

<400> SEQUENCE: 155

| | | | | | | |
|---|---|---|---|---|---|---|
| atggactcgg | acgagaccgg | gttcgagcac | tcaggactgt | gggtttctgt | gctggctggt | 60 |
| cttctgctag | gagcctgcca | ggcacacccc | atccctgact | ccagtcctct | cctgcaattc | 120 |
| gggggccaag | tccggcagcg | gtacctctac | acagatgatg | cccagcagac | agaagcccac | 180 |
| ctggagatca | ggaggatgg | gacggtgggg | ggcgctgctg | accagagccc | cgaaagtctc | 240 |
| ctgcagctga | aagccttgaa | gccgggagtt | attcaaatct | gggagtcaa | gacatccagg | 300 |
| ttcctgtgcc | agaggccaga | tggggccctg | tatggatcgc | tccactttga | ccctgaggcc | 360 |
| tgcagcttcc | gggagctgct | tcttgaggac | ggatacaatg | tttaccagtc | cgaggcccac | 420 |
| ggcctcccgc | tgcacctgcc | ggggaacaag | tccccacacc | gggaccctgc | accccgagga | 480 |
| ccagctcgct | tcctgccact | accaggcctg | cccccgcac | cccggagcc | acccggaatc | 540 |
| ctggccccc | agccccccga | tgtgggctcc | tcagaccctc | tgagcatggt | gggaccttcc | 600 |
| cagggccgaa | gccccagcta | cacttcctga | | | | 630 |

<210> SEQ ID NO 156
<211> LENGTH: 630
<212> TYPE: DNA
<213> ORGANISM: Canis lupus familiaris

<400> SEQUENCE: 156

| | | | | | | |
|---|---|---|---|---|---|---|
| atgggctggg | ccgaggccgg | gttcgagcac | ctgggactgt | gggtccctgt | gctggctgtg | 60 |
| cttttgctgg | aagcctgccg | ggcacatccg | atccctgact | ccagccccct | cctacaattt | 120 |
| ggaggtcaag | ttcgacagcg | gtacctctac | accgacgatg | cccaggagac | agaggcccac | 180 |
| ctagagatca | gggccgatgg | cacagtggtg | ggggctgccc | gccagagccc | tgaaagtctc | 240 |
| ctggagctga | aagccctaaa | gccagggtc | attcaaatct | gggagtcaa | acatccagg | 300 |
| ttcctgtgcc | agggcccaga | tggacacta | tatggctcgc | tccatttcga | ccctgtggcc | 360 |
| tgcagtttcc | gagaactgct | tcttgaggat | gggtacaaca | tctaccactc | gagacccttt | 420 |
| ggtctcccgc | ttcgcctgcg | ccccacaac | tccgcatacc | gggacttggc | accccgcggg | 480 |
| cctgcccgct | tcctgccact | gccaggcctg | cttccagcac | cccagagcc | tccagggatc | 540 |
| ctggccccga | agcctcctga | cgtgggctcc | tcggaccctc | tgagcatggt | ggggccttca | 600 |
| cagggccgga | gtcccagcta | tgcttcctaa | | | | 630 |

<210> SEQ ID NO 157
<211> LENGTH: 630
<212> TYPE: DNA
<213> ORGANISM: Bos taurus

<400> SEQUENCE: 157

| | | | | | | |
|---|---|---|---|---|---|---|
| atgggctggg | acgaggccaa | gttcaagcac | ttgggactgt | gggtccctgt | gctggctgtc | 60 |
| ctcctgctag | gaacctgccg | ggcgcatccc | attccagact | ccagccccct | cctccagttt | 120 |
| gggggccaag | tccgccagcg | gtacctctac | acggatgatg | cccaggagac | agaggcccac | 180 |
| ctggagatca | gggccgatgg | cacagtggtg | ggggcagccc | gccagagccc | cgaaagtctc | 240 |
| ttggagctga | aagccctgaa | gccaggcgtc | attcagatct | gggagttaa | aacatccagg | 300 |

| | |
|---|---|
| tttctctgcc aggggccaga tgggaagctg tacggatcgc tgcactttga ccccaaagcc | 360 |
| tgcagctttc gggagctgct tcttgaagat ggatacaacg tctaccagtc ggagaccctg | 420 |
| ggccttccac tccgcctgcc ccccagcgc tcgtccaacc gggacccggc ccgcgggga | 480 |
| cctgctcgct tccttccact gccgggcctg cccgcggcgc ccccggatcc tccagggatc | 540 |
| ttggcccccg agcctcccga cgtgggctcc tcggatcccc tgagtatggt gggaccctcg | 600 |
| tatggccgaa gccccagcta cacttcttga | 630 |

<210> SEQ ID NO 158
<211> LENGTH: 630
<212> TYPE: DNA
<213> ORGANISM: Equus caballus

<400> SEQUENCE: 158

| | |
|---|---|
| atggactggg acaagacggg gttcaagtac cagggactgt gggtccctgt gctggctgtc | 60 |
| cttctgctgg gagcctgcca gtcacacccc atccctgact ccagtcccct cctccaattc | 120 |
| gggggccaag tcaggcagcg ccacctctac acagatgatg cccaggagac agaggcgcac | 180 |
| ctggagatca gggctgacgg cactgtggca ggggctgtcc accggagccc agaaagtctc | 240 |
| ttggagctga aagccctgaa gccaggggta attcaaatct tggagtcaa gacatccagg | 300 |
| tttctgtgcc aggggccaga cgggacgctg tacggatcgc tccacttcga ccccgtggcc | 360 |
| tgcagcttcc gggagctgct tctcgaagac ggctacaacg tttaccagtc tgagacccttt | 420 |
| ggcctcccac tccgcctgcc ccaccacagc tccccatacc aggatccggc cctcgggca | 480 |
| cccgcccgct cctgccgct gccaggcttt ccccagcac cccgagcc tccagggatc | 540 |
| ccggcccccg agccccgga cgtgggctcc tcggaccccc tgagcatggt ggggccttca | 600 |
| cgcagccgga gccccagcta cacttcctga | 630 |

<210> SEQ ID NO 159
<211> LENGTH: 630
<212> TYPE: DNA
<213> ORGANISM: Ailuropoda melanoleuca

<400> SEQUENCE: 159

| | |
|---|---|
| atgggctggg acgaggccag gtccgagcag ctggggctgt gggtccctgt gctggctgtc | 60 |
| cttttgctgg aagcttgcca ggcacaccct atccctgact ccagcccccct cctccaattc | 120 |
| ggaggccaag ttcgacagcg gtacctctac acggacgatg cccaggagac agaggcccac | 180 |
| ctagcgatca gggctgatgg cacagtggtg ggggctgcca gccggagccc agaaagtctc | 240 |
| ttggagctga aagccctgaa accgggggtc attcaaatcc tgggagtgaa aacatctagg | 300 |
| ttcctgtgcc agggcccaga tgggacactg tacggatcgg tccgcttcga ccccgtagcc | 360 |
| tgcagcttcc gggaactgct cctggaggat gggtacaaca tctaccactc tgagaccctc | 420 |
| ggcctcccac ttcgcctgcc cgccacaac tctccatacc gggactcggc gccccggggg | 480 |
| cctgcccgct cctgccccct gccaggcctg cttccggtcc ccccggaccc cccagggatc | 540 |
| ctgggcccg agcctcccga cgtgggctcc tcggaccccc tgagcatggt ggggccttca | 600 |
| cagggccgaa gtcccagcta cgcttcctga | 630 |

<210> SEQ ID NO 160
<211> LENGTH: 630
<212> TYPE: DNA
<213> ORGANISM: Oryctolagus cuniculus

<400> SEQUENCE: 160

```
atggactggg gcaaggccaa gtgccggccc ccggggctgt gggtccccgc gctcgctgcc      60
ctgctgctgg gggcctgcca ggcacacccc atccccgact ccagcccccT cctccagttt     120
ggggaccaag tgcggcagca gcacctgtac acggacgatg cgcaggaaac agaagcccac     180
ctggagatca gggcggatgg cacggtggtg ggggctgccc ggaggagccc agaaagtctc     240
ttgcagatga aagccttaca accggggatc attcagatct ggggggtcca gacgtccagg     300
ttcctctgcc agaggccgga tggcacgctc tacggctcgc tccacttcga ccgcgaggcc     360
tgcagcttcc gggagctgct cgtgaggat gggtacaacg tttacctctc ggaggccctg     420
ggcctgcccg tgcgcctgtc ccccggcagc tccccacgca gggcgccggc ccccggggga     480
ccagcccgct tcctgccgct gcccggcctg ccgccagacc ttccggaacc gccaggcctc     540
ctggccgccg cgcccccga tgtcgactcc ccggacccc tgagcatggt gcagcctgcg     600
ctggaccaga gccccagcta cacctcctga                                     630

<210> SEQ ID NO 161
<211> LENGTH: 630
<212> TYPE: DNA
<213> ORGANISM: Gorilla gorilla

<400> SEQUENCE: 161
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggtgctgctg accagagccc tgaaagtctc     240
ctgcagctga aagccttgaa gccgggagtt attcaaatct tgggagtcaa gacatccagg     300
ttcctgtgcc agaggccaga tggggccctg tatggatcgc tccactttga ccctgaggcc     360
tgcagcttcc gggagctgct tcttgaggac ggatacaatg tttaccagtc cgaggcccac     420
ggcctcccgc tgcacctgcc ggggaacaag tccccacacc gggaccctgc accccgagga     480
ccagctcgct tcctgccact accaggcctg cccccgcac ccccggagcc acccggaatc     540 ctggccccc agcccccga tgtgggctcc tcggaccctc tgagcatggt gggaccttcc     600
cagggccgaa gccccagcta cgcttcctga                                     630

<210> SEQ ID NO 162
<211> LENGTH: 630
<212> TYPE: DNA
<213> ORGANISM: Nomascus leucogenys

<400> SEQUENCE: 162
atggactcgg acgagaccgg gttcgagcac tcaggactgt gggttcctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc tgaaagtctc     240
ctgcagctga aagccttgaa gccgggagtt attcaaatct tgggagtcaa gacatccagg     300
ttcctatgcc agaggccaga tggggccctg tatggatcgc tccactttga ccctgaggcc     360
tgcagcttcc gggagctgct tcttgaggac ggatacaatg tttaccagtc cgaggcccat     420
ggcctcccgc tgcacctgcc ggggaacaag tccccacacc gggaccctgc accccgagga     480
ccagctcgct tcctgccact accaggcctg cccctgcac ccccagagcc gcccggaatc     540
```

```
ctggccccc  agcccccga   tgtgggctcc  tcggaccctc  tgagcatggt  gggaccttcc        600
cagggccgaa  gccccagcta  cgcttcctga                                           630
```

<210> SEQ ID NO 163
<211> LENGTH: 630
<212> TYPE: DNA
<213> ORGANISM: Procavia capensis

<400> SEQUENCE: 163

```
atggactggg  ccaagtttgg  gatcgagcac  ccgggactgt  gggtcccggt  gatggcagta        60
cttctgctgg  gagcctgcca  aggataccct  attcctgact  ccagcccct   tctccaattc       120 ggaggccagg  tccggcaacg  ttacctctac  acagatgacg  cgcaggagac  cgaggcccac      180
ctggagatcc  gagcagacgg  cacggtggtg  ggggctgccc  accggagccc  cgagagtctc      240
ttggagctga  aagctttgaa  gcccggcata  attcagatct  gggagtcaa   gacatccaga      300 ttcctctgcc  agggtcctga  tggggtgctg  tatggatcgc  tccgttttga  cccagtggcc      360
tgcagcttcc  gggagctgct  tcttgaagat  ggatacaatg  tttaccagtc  tgaggcccac      420
ggcctcccgc  ttcgcctacc  atcccacaat  tccccacaga  gggacctggc  gtcccgggtg      480
ccagcccgct  tcctgccact  gccaggccgg  ctcacggtgc  tcccagaacc  ttcggggtc       540 ctgggccctg  agcccccga   tgtggactcc  tcagaccccc  tgagcatggt  ggggccttcg      600
cagggccgaa  gccccagtta  cgcctcctga                                          630
```

<210> SEQ ID NO 164
<211> LENGTH: 630
<212> TYPE: DNA
<213> ORGANISM: Cavia porcellus

<400> SEQUENCE: 164

```
atggactggg  cccggactga  gtgtgagcgc  ccaaggctgt  gggtctccat  gctggccatc       60
cttctggtgg  gagcctgcca  ggcacaccct  atccctgact  ccagcccct   cctccagttt      120 gggggccagg  tccggcagcg  gtacctctac  acagatgatg  ctcaggacac  tgaagtgcac      180
ctggagatca  gggccgatgg  ctcagtacgg  ggcattgccc  acaggagccc  tgaaagtctc      240
ctggagctga  aagccttgaa  gccaggagtc  attcagatct  gggaatcag   gacttccagg      300 ttcctgtgcc  agaggcccga  tggagtctg   tatggatcac  tccactttga  tcctgaggcc      360
tgcagcttcc  gggagctgct  gcttgctgat  ggctacaatg  tctacaagtc  tgaagcccac      420
ggcctccctc  tgcacctgct  gcgcggtgac  tctctatcgc  aggaaccagc  acccccagga      480
ccagcccgat  ttctgccact  accaggcctg  cccgcaacac  cccggagcc   acccaggatg      540 ctgcccccag  ggcccccaga  tgtgggctcc  tcggaccctt  tgagcatggt  ggggcctta       600 tgggaccgaa  gccccagcta  tacttcctga                                          630
```

<210> SEQ ID NO 165
<211> LENGTH: 583
<212> TYPE: DNA
<213> ORGANISM: Tupaia belangeri

<400> SEQUENCE: 165

```
atgggctggg  acaaggcccg  gttcgagcac  ctgggagcgt  gggctcctgt  gctggctgtc       60
ctcctcctgg  gagcctgcca  ggcataccc   atccctgact  ccagcccct   cctacaattc      120 gggggccagg  tccggcagcg  gtacctctac  acggacgaca  cgcaggacac  agaagcccac      180
cttgagatca  gggccgacgg  caccgtggtg  ggggccgccc  accaaagccc  ggaaagtctc      240
```

```
ctggagctga aagccttgaa gccgggggtc attcaaatcc tgggagtcaa gacctccagg    300
ttcctgtgcc agaggccaga cggggccctg tacgggtcgc ttcacttcga ccccgaggcc    360
tgcagcttcc gggagctgct tctcgaggat ggatacaaca tttaccagtc tgaggctcgt    420
ggcctccccc tgcgcctgcc gccccacgac tccccacatc gggaccggac ccctcgggga    480
ccagctcgtt tcctgccgct gcctggcctg cccctggttc ctccagagct gccaggggtc    540
ctggcccttg agccccccga cgtgggctcc tcagacccgc tga                     583
```

<210> SEQ ID NO 166
<211> LENGTH: 586
<212> TYPE: DNA
<213> ORGANISM: Sorex araneus

<400> SEQUENCE: 166

```
atggtctggg acaaggccag ggggcagcag ttgggactgt gggcccccat gctgctgggc     60
ttgctgctgg gtgcctgcca ggcacacccc ctccctgact ccagccccct cctccaattt    120
gggggccaag tccgactgag gttcctgtac accgacgatg cccagaggac aggggcgcac    180
ctggagatca gggccgacgg cacagtgcag ggtgcggccc acaggacccc agaatgtctc    240
ctggagctga aagccttgaa gccaggcgta attcaaatcc ttggggtcag cacatccaga    300
ttcctgtgcc agcggcccga tggggtcctg tatggatcgc ttcgctttga cccagaggcc    360
tgcagtttcc gggaacttct tctccaggat ggatataacg tttaccagtc tgaggccctg    420
ggtctcccgc tctacctaca cccgcccagt gccccagtgt cccaggaacc agcctcacgg    480
ggcgccgtcc gcttcctgcc actgccagga ctgccacctg cctccctgga gccccccagg    540 cccccgccc cggtgcctcc agacgtgggt tcctcagacc ccctga                   586
```

<210> SEQ ID NO 167
<211> LENGTH: 546
<212> TYPE: DNA
<213> ORGANISM: Ictidomys tridecemlineatus

<400> SEQUENCE: 167

```
atgtacccca tccctgactc aagcccccctc ctccaatttg ggggccaagt ccggcagcgg     60
tacctgtaca cagatgatgc caggagact gaggcccacc tggagatcag ggctgatggc    120
accgtggtgg gggctgccca tcaaagcccg gaaagtctct tggaactgaa agccttgaag    180
cctggggtca ttcaaatctt gggggtcaaa acatccaggt tcctgtgcca gaggccagat    240
ggagtgctgt atggatcgct ccactttgac cctgaggcct gcagcttccg ggagcagctt    300
ctggaggacg ggtacaacgt ttaccagtca gaatcccacg gcctccccgt gcgcctgccc    360
cctaactcac ataccgggga cccagcgccg ccaggaccag cccgcttcct tccactgcca    420
ggcctgcccc cagcagccct ggagccgcca gggatcctgg gccctgagcc cctgatgtg    480 ggctcctccg acccactcag catggtgggg cctttgcagg gccgaagccc cagttacgct    540
tcctga                                                              546
```

<210> SEQ ID NO 168
<211> LENGTH: 627
<212> TYPE: DNA
<213> ORGANISM: Loxodonta africana

<400> SEQUENCE: 168

```
atggactggg ccaagtttgg gttggagcac ccaggactgt gggtccctgt gatggctgtc     60
```
cttctgctgg gagcctgcca gggacacccc atccctgact ccagcccct cctccaattc    120 gggggccagg tccggcaacg ttacctctac acagatgatc aggagaccga ggcccacctg    180
gagatcagag cagatggcac agtggcggga gccgctcacc ggagctctga gagtctcttg    240
gagctgaaag ctttgaagcc tggaataatt cagatcttgg gggtcaagac atcccggttc    300
ctgtgccagg ggcctgatgg ggtgctgtac ggatcgctcc atttcgaccc agccgcctgc    360
agcttccggg agctgcttct tgaagatgga tacaatgttt actggtccga ggcccatgga    420
ctcccaatcc gcctgccctc ccacaactcc ccatataggg acccagcatc ccgggtacca    480
gcccgcttcc tgccactgcc aggcctgctc ccaatgctcc aagaacctcc aggggtcctg    540
gcccctgagc cccctgatgt ggactcctca gaccccctga gcatggtggg gccttcacag    600
ggccgaagcc ccagctatgc ctcctga                                       627

<210> SEQ ID NO 169
<211> LENGTH: 627
<212> TYPE: DNA
<213> ORGANISM: Sus scrofa

<400> SEQUENCE: 169
atgggctggg ccgaggccaa gttcgagcgc ttgggactgt gggtccctgt gctggctgtc     60
ctgctgggag cctgccaggc acgtcccatt cctgactcca ccccctcct ccaatttggg    120 ggccaagtgc gccaacgata cctctacacg gatgatgccc aggaaactga agcccacctg    180
gagatcagag ctgatggcac cgtggcaggg gtagcccgcc agagccctga aagtctcttg    240
gagctgaaag ccctgaagcc aggggtcatt caaattttgg gagtccagac atcccggttc    300
ctgtgccagg ggccagacgg gagactgtac ggatcgctcc acttcgaccc tgaggcctgc    360
agcttccggg agctgcttct tgaggatggc tacaacgttt accagtctga ggcccttggc    420
ctcccactcc ggctgcctcc gcaccgctcc tccaaccggg acctggcccc cggggacct    480 gctcgcttcc tgccactgcc aggcctgccc cggcaccccc ggagccgcc agggatcttg    540 gcccctgaac ctcccgacgt gggctcctcg gaccccctga gcatggtggg gccttcacac    600
ggccggagcc ccagctacac ttcttga                                       627

<210> SEQ ID NO 170
<211> LENGTH: 627
<212> TYPE: DNA
<213> ORGANISM: Felis catus

<400> SEQUENCE: 170
atgggctggg acgaggccgg gtcccagcgc ctggactgt gggtcgtgct ggggtccctt     60
ttgccggaag cctgccaggc acaccctatc cctgactcca gcccctcct ccaattcggg    120 ggccaagttc gacagcggtt cctctacacg gacgacgccc aggagacaga ggtccacctc    180
gagatcaagg ctgatggcac agtggtgggg accgctcgcc ggagccctga gagtctcttg    240
gagctaaaag ccctgaagcc gggggtaatt caaatcttgg gggtcaaaac gtccaggttc    300
ctgtgccagg gccagatgg gacactgtat ggatcgctcc gctttgaccc cgcagcctgc    360
agcttccggg aactgctcct ggaggacgga tacaacatct accactcgga gaccctcggg    420
ctcccactcc gcctgccccc ccacaactcc ccatccgggg acttggcccc ccgggcacct    480
gcccgcttcc tgccgctgcc aggcctgctt ccggcacccc cggagcctcc aggatcctg    540 gccccgagc cccggacgt gggctcctcg gaccctctga gcatggtggg gccttcccag    600
ggccgaagtc ccagctacgc ttcctga                                       627

<210> SEQ ID NO 171
<211> LENGTH: 627
<212> TYPE: DNA
<213> ORGANISM: Otolemur garnettii

<400> SEQUENCE: 171

```
gacaaggcca ggactgggtt caagcaccca ggaccatggt ttcccctgct ggctgtactt      60
ttgttgggag cctgccaggc acaccctatc cctgactcca gccccctact ccagtttggt     120
ggccaagtcc ggcagcggta cctctacaca gatgatgccc aggagacaga agcccacctg     180
gagatcaggg aagatggcac agtggtgggg gctgcacaac agagccctga aagtctcttg     240
gagctgaaag ctttaaagcc aggggtcatt caaatcttgg gagtcaagac atccaggttc     300
ctgtgccaga ggccagatgg gggcctatat ggatcgctct actttgaccc caaggcctgc     360
agtttccggg agctgcttct tgaggatgga tacaacgttt actggtctga acctatggc      420
ctcccactgc acctgcctcc tgccaattcc ccatactggg gcccatccct tcggagccca     480
gcccgcttcc tgccactgcc aggccctcct gcagcatccc cagagctgcc ggggatcttg     540
gccctggaac cccccgatgt gggctcctcg gaccctctga gcatggtggg gccttcgcag     600
ggccgaagcc ccagctatgc ttcctga                                         627
```

<210> SEQ ID NO 172
<211> LENGTH: 627
<212> TYPE: DNA
<213> ORGANISM: Rattus norvegicus

<400> SEQUENCE: 172

```
atggactgga tgaaatctag agttggggcc ccgggactgt gggtctgtct cctgctgcct      60
gtcttcctgc tgggggtgtg cgaggcatac cccatctctg actccagccc cctcctccag     120
tttggggtc aagtccgaca gaggtatctc tacacagatg acgaccagga caccgaagcc     180
cacctggaga tcagggagga cggaacagtg gtgggcacag cacaccgcag tccagaaagt     240
ctcctggagc tcaaagcctt gaagccaggg gtcattcaaa tcctgggtgt caaagcctct     300
aggtttcttt gccaacaacc agatggaact ctctatggat cgcctcactt tgatcctgag     360
gcctgcagtt tcagagagct gctgcttaag gacggataca atgtgtacca gtctgaggcc     420
catggcctgc cctgcgtct gccccagaag gactcccagg atccagcaac ccggggacct     480
gtgcgcttcc tgcccatgcc aggcctgccc cacgagcccc aagagcaacc aggagtcctt     540
cccccagagc cccagatgt gggttcctcc gacccctga gcatggtaga gccttgcaa       600
ggccgaagcc ccagctatgc atcttga                                         627
```

<210> SEQ ID NO 173
<211> LENGTH: 633
<212> TYPE: DNA
<213> ORGANISM: Mus musculus

<400> SEQUENCE: 173

```
atggaatgga tgagatctag agttgggacc ctgggactgt gggtccgact gctgctggct      60
gtcttcctgc tggggtcta ccaagcatac cccatccctg actccagccc cctcctccag     120
tttggggtc aagtccggca gaggtacctc tacacagatg acgaccaaga cactgaagcc     180
cacctggaga tcagggagga tggaacagtg gtaggcgcag cacaccgcag tccagaaagt     240
ctcctggagc tcaaagcctt gaagccaggg gtcattcaaa tcctgggtgt caaagcctct     300
```

```
aggtttcttt gccaacagcc agatggagct ctctatggat cgcctcactt tgatcctgag    360
gcctgcagct tcagagaact gctgctggag gacggttaca atgtgtacca gtctgaagcc    420
catggcctgc ccctgcgtct gcctcagaag gactccccaa accaggatgc aacatcctgg    480
ggacctgtgc gcttcctgcc catgccaggc ctgctccacg agcccaaga ccaagcagga     540 ttcctgcccc cagagccccc agatgtgggc tcctctgacc ccctgagcat ggtagagcct    600
ttacagggcc gaagcccag ctatgcgtcc tga                                   633
```

```
<210> SEQ ID NO 174
<211> LENGTH: 324
<212> TYPE: DNA
<213> ORGANISM: Vicugna pacos

<400> SEQUENCE: 174
atggactggg acgaggccaa gttcgagcat cggggactgt gggtcccagt gctcactgtc     60
cttctgctgg agcctgcca ggcacgcccc attcctgact ccagcccct cctccaattc      120 gggggccaag tccggcagcg gtacctctac acggatgacg cccaggagac agaagcccac    180
ctggagatca gggctgatgg cacagtggtg ggggtggccc gccagcccga aggaattcct    240
cccgagcctc ctgacgtggg ctcctcagac ccctgagca tggtggggcc ttcatacagc     300
agaagcccca gctacacttc ctga                                           324
```

```
<210> SEQ ID NO 175
<211> LENGTH: 633
<212> TYPE: DNA
<213> ORGANISM: Anolis carolinensis

<400> SEQUENCE: 175
tgtaaaagca agggaggagg gaaggggga gagaggatgt gggtagacct agttttctgg      60
gctgccttgc tccgcacagc tcctgctctt cccttgcgga attcaacccc atctaccaa     120 tttgatgggc aggtccggct tcggcacctc tacacagcag atgaacagac gcacctccac    180
ttggagatct tgccagacgg taccgtgggt ggatccaggt ttcagaatcc cttcagtttg    240
atggagatca aagctgtgaa gccaggagtc attcgcatgc aggccaagaa gacctctaga    300
tttctctgta tgaaacccaa tggacgactg tatggctcgc tgttctactc tgaggaggca    360
tgcaacttcc atgagaaggt tctcagcgat ggctacaacc tctactattc tgaaaactac    420
aacatacctg tcagcctcag ctcggcaggg aacctgggtc agagccgtca gttgcctccc    480
ttctcccaat tcctgccgtt agtcaacaaa attcctcttg agcctgtgct tgaagacttt    540
gacttctatg gacatcaatt ggatgttgaa tcagctgatc ctttgagcat tttaggacaa    600
aaccctggtt tcatgagtcc gagctatgtc ttc                                 633
```

```
<210> SEQ ID NO 176
<211> LENGTH: 564
<212> TYPE: DNA
<213> ORGANISM: Gadus morhua

<400> SEQUENCE: 176
ctcctcctcg ccaccctcct ccacatcggc ctctccttct acgtccccga ctccggcccc     60
ctgctgtggc tgggcgacca ggtcaggag agacacctct acacagcaga gagccaccgg    120 aggggctgt tcctggagat gagccccgac ggtcaggtga caggaagtgc tgctcagacg    180
ccgctcagtg ttctggagct gaggtcggtc agagcaggag atacggtcat cagagcgcgc    240
ctctcctctc tctacctgtg tgtggacagg gcaggtcacc tgacaggaca gagacagtac    300
```

-continued

| | |
|---|---|
| acagagtccg actgcacctt cagagaggtc atccttgagg acggctacac ccacttcctg | 360 |
| tccgtgcacc acggacttcc tatttcgctg gcgccgagac actccccagg gagacagggg | 420 |
| ctgcgcttca gcaggttcct cccgctgagg agcagtctgt cagaggatag ggtcgccgag | 480 |
| cccccagaca gcccactgaa cctgactct gaagaccccc tggggatggg tctgggttcg | 540 |
| ctcctcagcc cggccttctc catg | 564 |

<210> SEQ ID NO 177
<211> LENGTH: 648
<212> TYPE: DNA
<213> ORGANISM: Latimeria chalumnae

<400> SEQUENCE: 177

| | |
|---|---|
| atgttatgcc agagttttgt gatattaagt cagaaattca ttttttgggct cttttttgact | 60 |
| ggattggggc taacaggatt ggcttggaca aggcccttcc aggattccaa tcccatcctg | 120 |
| cagtattccg attccatccg gctccgacat ctgtacactg ccagtgagag tcggcaccttt | 180 |
| cacctacaaa tcaactcgga tggacaggtg ggagggacaa ccaagcaaag cccttacagt | 240 |
| ctgttggaga tgaaggcggt gaagacaggt tttgtggtca tcaggggcaa gaaaagcgcc | 300 |
| cgttacctct gtatggaacg tagtggacgg ctctatggat cgctgcagta tacagaaaaa | 360 |
| gactgcacct tcaaagaggt tgtgttggca gatggataca acctgtatgt ctcagaggaa | 420 |
| caccaggcca cagtgacgct gagccccatg agggcgagga tagcgcaagg gaaaaagatc | 480 |
| ccacccttt cccatttcct tccaatggtg aacaaggtgc ctgtggagga tgttgccgct | 540 |
| gagatggagt ttgtccaggt gctgcgggaa atgacggccg acgtggactc tccggatccc | 600 |
| tttggaatga cctgggaaga atcggttcac agtccgagct ttttttgcc | 648 |

<210> SEQ ID NO 178
<211> LENGTH: 579
<212> TYPE: DNA
<213> ORGANISM: Tursiops truncatus

<400> SEQUENCE: 178

| | |
|---|---|
| atgggctggg acaagaccaa actcgagcac ctgggactgt gggtccctgt gctagctgtc | 60 |
| ctgctgggac cctgccaggc acatcccatt cctgactcca gccccctcct ccaatttggg | 120 |
| ggccaagtcc gccagcgata cctctacacg gatgacgccc aggagacgga ggcccacctg | 180 |
| gagatcaggg ctgatggcac agtggtgggg acggcccgcc ggagccccga aggagttaaa | 240 |
| acatccaggt tcctgtgcca gggcagag gggaggctgt atggatcgct ccacttcaac | 300 |
| ccccaggcct gcagcttccg ggagctgctt cttgaggatg gatacaacgt ttaccagtct | 360 |
| gaggctcttg gcattcccct ccgcctgccc ccgcaccgct cctccaactg ggacctggcc | 420 |
| cccgggac ctgctcgctt cctgccgctg ccaggcttcc tcccgccacc cctggagcct | 480 |
| ccagggatct tggcccccga gcctccccaa cgtaggttcct cggacccctt gagcatggtg | 540 |
| ggaccttcac atggccgaag ccccagctac acttcctga | 579 |

<210> SEQ ID NO 179
<211> LENGTH: 630
<212> TYPE: DNA
<213> ORGANISM: Mustela putorius furo

<400> SEQUENCE: 179

| | |
|---|---|
| atgggctggg aagaggccag gtccgagcac ctggggctgt gggtccctgt gctggcggtc | 60 |

| | |
|---|---|
| cttttgctgg gagcctgcca ggcatacect attcctgact ccagcccct cctccaattt | 120 |
| ggaggccaag ttcgacagcg gtacctctac acagacgacg ctcaggagac ggaggcccac | 180 |
| ctagagatca gggctgatgg cacggtggtg ggggctgccc gccggagccc cgaaagtctc | 240 |
| ttggagctga aagccctgaa gccaggggtc attcagatct tgggagtgaa acatccagg | 300 |
| ttcctgtgcc agggcccgaa tgggacactg tacggatcgt tccacttcga ccccgtagcc | 360 |
| tgcagcttcc gggaagtgct tctggaagat ggatacaaca tctaccactc tgagaccctg | 420 |
| ggcctcccac tgcgcctgcc cccccacaac tccccacaca gggacctggc gccccggggg | 480 |
| cctgcccgct tcctgcccct gccaggcctg cttccggcca ccccggagtc ccgggggatc | 540 |
| ccagccccg agcctcccaa cgtgggctcc tcagacccc tgagcatggt ggggcctttg | 600 |
| cagggtcaaa gtcccagcta cacttcctga | 630 |

<210> SEQ ID NO 180
<211> LENGTH: 597
<212> TYPE: DNA
<213> ORGANISM: Takifugu rubripes

<400> SEQUENCE: 180

| | |
|---|---|
| tttatttatt tatttattca aactgcactt ttttccccctt ccaaatggtt caacttttat | 60 |
| ctccctgact ccaacccgct cttatccttt gacagtcatg gcagaggcat ccacctctac | 120 |
| acagataatc aaaggcgagg gatgtatctg cagatgagca cagatggaag cgtttccggg | 180 |
| agtgatgtcc agacggcgaa cagtgtgctg gaactgaagt cagtcagaaa cggccacgtc | 240 |
| gtcatccgag gaaaatcgtc ttctctgttt ctctgtatgg acagcagagg ccgtttatgg | 300 |
| gggcagaggc accccactga ggccgactgc actttcaggg aagtgttgct ggcagatgga | 360 |
| tacactcgct tcctgtccct gcacaacgga actcctgtgt ctctggcacc taaacaatct | 420 |
| ccagaccagc acacagtccc cttcactcgt ttcctgccgc tcaggaatac actggcagag | 480 |
| gagagcatgt ctgaaccacc atcaaaccaa cagagatatt ttaacattga ctctgatgat | 540 |
| cttcttggaa tggatttaaa tgcgatggtc agtcctcagt tttcagggga caagtga | 597 |

<210> SEQ ID NO 181
<211> LENGTH: 612
<212> TYPE: DNA
<213> ORGANISM: Dipodomys ordii

<400> SEQUENCE: 181

| | |
|---|---|
| atggaccagg caaagaccag ggttgggggcc cggggctgg ggggccttgt gctggctgtc | 60 |
| ataattctgg gagcatgcaa ggcacggcct atccctgact ccagcccct cctccaattt | 120 |
| ggggtcaag ttcggcttcg gcacctctac acagatgaca ctcaggagac ggaagcccat | 180 |
| ctggagatca gggcagatgg cacggtagtg gggactgccc accggagccc tgaaagtctc | 240 |
| ttggagctga aagccttgaa gccaggagtc attcaaatct tagggatcaa gacatccaga | 300 |
| ttcttatgcc agagaccaga cgggacactg tatggatcac ccactttga ccctgaggtt | 360 |
| tgcagcttcc aggagctgct tctggaagat ggatacaaca tttaccgttc tgaagccctg | 420 |
| ggtctccccc tgcgcctgtc cccagatcca gcacctggg ggccagcccg cttcctgccc | 480 |
| ctgcctggtg tgcccccgc accgccggag ccccccggga tcctggctcc cgaaccccct | 540 |
| gatgtcggct cctccgaccc tctgagtatg gtgggactgt tgcagggccg aagcccagc | 600 |
| tatgcatcct ga | 612 |

<210> SEQ ID NO 182
<211> LENGTH: 555
<212> TYPE: DNA
<213> ORGANISM: Echinops telfairi

<400> SEQUENCE: 182

| | | | | | |
|---|---|---|---|---|---|
| atgggttgca | ccaaatctgg | gtggaagtcc | ccgggactgt | gggtccctgt | gctggccagc | 60 |
| cttctgctgg | gaggctgcgg | agcacacccc | atccctgact | ccagcccct | cctccaattc | 120 |
| gggggccaag | tccggcagcg | atacctctat | acggatgacg | cccagaccac | cgaggcccac | 180 |
| ctggagatca | gagcggatgg | cacagtgggg | ggcgtcgccc | accagagccc | agagaagttc | 240 |
| ctgagtcaat | ggcgtgaaaa | gcccctgaga | tcactccatt | tcgacccagc | cgcctgcagc | 300 |
| ttccgggaga | agcttctaga | agacggatac | aacttgtacc | actctgagac | ccacggcctc | 360 |
| cccctccgcc | tcccaccccg | tggggcgac | ccctcttctc | agcctggggc | cgcttccca | 420 |
| ccgctgccgg | ccagctccc | acaactccaa | gagacgccag | gggtcctcgc | cccgaaccc | 480 |
| cccgacgtgg | gctcttcaga | cccctgagc | atggtggggc | cttggcgagg | gcaaagtccc | 540 |
| agttatgcct | cctga | | | | | 555 |

<210> SEQ ID NO 183
<211> LENGTH: 633
<212> TYPE: DNA
<213> ORGANISM: Macaca mulatta

<400> SEQUENCE: 183

| | | | | | |
|---|---|---|---|---|---|
| atggactcgg | acgagaccgg | gttcgagcac | tcaggactgt | gggttcctgt | gctggctggt | 60 |
| cttctgctgg | gagcctgcca | ggcacacccc | atccctgact | ccagtcctct | cctgcaattc | 120 |
| gggggccaag | tccggcaacg | gtacctctac | acagatgatg | cccagcagac | agaagcccac | 180 |
| ctggagatca | gggaggatgg | gacagtgggg | ggcgctgctc | accagagccc | cgaaagtgag | 240 |
| tgtgggccag | agcctgggtc | tgagggagga | ggggctgtgg | gaggtgctga | gggacctgga | 300 |
| ctcctgggtc | tgagggaggc | agggctgggg | cctggatcct | ggctccactt | tgaccctgag | 360 |
| gcctgcagct | tccgggagct | gcttcttgag | aacggataca | atgtttacca | gtccgaggcc | 420 |
| cacggcctcc | cactgcacct | gccgggaaac | aagtccccac | accgggaccc | tgcatcccaa | 480 |
| ggaccagctc | gcttcctgcc | actaccaggc | ctgcccccg | cacccccgga | gccgccagga | 540 |
| atcctcgccc | ccagccccc | cgatgtgggc | tcctcggacc | ctctgagcat | ggtgggacct | 600 |
| tcccaggccc | gaagcccag | ctatgcttcc | tga | | | 633 |

<210> SEQ ID NO 184
<211> LENGTH: 582
<212> TYPE: DNA
<213> ORGANISM: Microcebus murinus

<400> SEQUENCE: 184

| | | | | | |
|---|---|---|---|---|---|
| atgggctggg | acgaggccgg | cgccgggttc | gagcacccag | gactgtggtt | tcccatgctg | 60 |
| ggtgtcctgc | tgctgggagc | ctgccaggcg | taccccatcc | ctgactccag | ccccctcctc | 120 |
| caatttggcg | gccaagtccg | gcagcggcac | ctctacacag | acgatatcca | ggagacagaa | 180 |
| gcccacctgg | agatcaggc | ggacggcaca | gtggtggggg | ccgcccgaca | gagccctgag | 240 |
| ttggagctga | agcccttaaa | gccaggggtc | attcaaatct | gggagtcaa | gacctccagg | 300 |
| ttcctgtgcc | agaggccaga | cggggccctg | tacggatcgc | tccactttga | ccccgagtgc | 360 |
| agcttccggg | agctgcttct | tgaggatgga | tacaacgtct | actgtcccta | cctcccgctg | 420 |

```
cacctgtccc cacgcatcga actggccgga tcacgctctg cgctgccact gcccccagca    480
cctgaacgca ggattttggc cccggagccc ccggatggct cctcggaccc tctgagcatg    540
gtggggcctt cgcagggccg aagtcccagc tatgcttcct ga                      582

<210> SEQ ID NO 185
<211> LENGTH: 615
<212> TYPE: DNA
<213> ORGANISM: Ochotona princeps

<400> SEQUENCE: 185
aaagacatgg acgggctcca gcctccgggg ctgcgggttc ctgtgctggc tgccctgctt    60
ttgggagttg gccaggcacg ccccatccct gattctagcc ctctcctcca attcgggggc   120
caggtccggc agaggcacct ctacacggat gacgcccagg aatcggaagt acacctggag   180
atccgggcag acggcaccgt ggcagggact gcccgccgga gccctgaaag tctcttagaa   240
atgaaagcgt tgaagccagg cgtcattcag atcctggggg tccacacatc caggttcctg   300
tgccagagac cagacgggac gctgtacggc tcgctccact tcgaccacaa ggcctgcagc   360
ttccgggagc agctgctgga ggatgggtac aacgtgtacc actcagagac cacggcctc    420 ccgctgcgcc tgtctccaga ccgagccccc cggggcccag cccgcttcct gccactgcca    480
ggccctcctc ctgacctcct ggtgccaccc ctgccaccgg acgtcctagc ccctgagccc    540
cccgacgtgg actccccaga cccctgagc atggtggggc ccttgcaggg ccaaagcccc    600
agctacactt cctga                                                   615

<210> SEQ ID NO 186
<211> LENGTH: 546
<212> TYPE: DNA
<213> ORGANISM: Xiphophorus maculatus

<400> SEQUENCE: 186
tgcccgttcc ccttccttt cttaatcctc tctcttccct ttttctcttc ctcgttttac     60
atcccagaat ccaacccaat ctttgccttc aggaatcagc tcagagaggt gcatctctac   120
acagaaaatc acagacgggg tttgtatgtg gagatacatc tggatgggag agtgactgga   180
agtgatgctc agagtcctta tagtgtgttg cagataaagt ctgttaaacc gggtcatgtg   240
gtcataaagg gacagacatc gtccctgttc ctctgcatgg acgactccgg gaatctaaga   300
ggacagacaa cctatgacga ggctgactgc tccttcaggg aactgctgct ggccgatggc   360
tacacccgtt tcctgaactc acaacatggc gttcctttat cactggcatc cagaaactct   420
ccagatcgac actccgttcc tttcacaaga ttttacctc tcaggaatac tttaacggtt     480
tcagaagaat caacaaaaac tcagagggac ttcaacctgg actcggacga ccttctcggg   540
atggga                                                             546

<210> SEQ ID NO 187
<211> LENGTH: 576
<212> TYPE: DNA
<213> ORGANISM: Gasterosteus aculeatus

<400> SEQUENCE: 187
tctctcctcc tcatggtccc acttcctttc tgttcatcct tttatctcac tgactccagc    60
ccacttctac ccttcaataa tcaagtcaaa gaggtgcacc tctacacagc agagaatcac   120
agaagagcga tgtacctgca gatcgctctg gacgggagcg tgtcgggaag cgacgctcgg   180
tccacttaca gtgtgctgca gctgaaatct atccagccgg ccacgtggt catcagaggg    240
```

```
aaggcctcct ccatgttcct ctgcgtggac agcgggggcc gtttgagagg acaggggccg      300
tactcagagg ccgactgcag cttcaggagc ctgctgctgg gggatggcta cacccggttc      360
ctgtcctcgc agcacgggtc cccgctgtct ctggcgtcga ggccttcccc ggatcccaac      420
tcggtgccct tcactcgatt cctacccatc cggaccgccc cgaggctga gagcgtgatc       480 gaagagccac cgagcaatca gagatacgtc aacgtggact ccgaggatct tcttggaatg      540
ggcctgaaca ctgtggtcag tcctcagttc tcggcg                                576

<210> SEQ ID NO 188
<211> LENGTH: 495
<212> TYPE: DNA
<213> ORGANISM: Sarcophilus harrisii

<400> SEQUENCE: 188
gtgtctgcca tgggcctgag ggagcgagct cccaggtacc tggccccgct gctgtccttg       60
ctcttggcct gcagggcctc gggtcacccc ctcccggatt ccagcccat gctcctgttt       120 gggggggcagg tccgcctccg gcacctctac acggatgtgg gccaggaggc cgaggcccac     180
gtggaactgg cgtccgacgg cacagtccgg cggcagcgc ggaggagtcc caacagtctc       240
ctggagctga aggctgtgaa gccgggcatc gtccgaatcc tggccgtcca cagctctcgg     300
tttctgtgta tgaggcccaa cggggagctg tacggagcga tacactacga cccttccgcc      360
tgcaactttc gggagcgcct gctggggggac ggctacaacg tgtacgagtc cgaggctcac     420
gggaggaccc tccgcctgcc ccccaaggcc gcaccgggac ccgccggacc ttctcgcttc      480
ctgccgctcc ccggc                                                        495

<210> SEQ ID NO 189
<211> LENGTH: 627
<212> TYPE: DNA
<213> ORGANISM: Macropus eugenii

<400> SEQUENCE: 189
acagaggagc cttctactgg gtccaggcac ctgggacaat gggctcccgg gctgcctggt       60
cctctgctgt ccttgctcct ggcctacagg ggctggggct cccccatccc tgattccagc      120
cccatgctcc tgtttggtgg ccaggtccgc ctccgacacc tgtacacaga tgatggccag      180
gacacggagg cccatgtgga gctggggcca gatggagtgg ttcgagctgt ggctgagagg      240
agccccaaca gtcttctgga actgaaggcg gtgaagcctg gagtcatccg aatcctcgct      300
gtccagagct ctcggtttct gtgtatgagg cccaacgggg aactgtatgg agcggtacac      360
tatgacccct ctgcctgcaa ctttcgggaa catctgctgg gggatggtta taatgtgtat      420
gaatcagaga ctcacagaag gaccctccgt ctgtccccat ccctgggtca ggctggcccc      480
tctcgcttcc tgccacttcc aggcgactgg ctgcccggcc tgatccacc ttgggcacag       540 ggccctgagc cccagacgt gggctctgca gacccctga gcatggtggg ggccgtgcag       600
ggcctcagcc ccagctactc ctcctga                                          627

<210> SEQ ID NO 190
<211> LENGTH: 480
<212> TYPE: DNA
<213> ORGANISM: Xenopus tropicalis

<400> SEQUENCE: 190
agagggggta ggaccaaaaa aaagacgtta ctcaggaaat ggctttgcct tttagccatt       60
```

```
atgttgagta ggtcaaggtt ttctttagca aatcctatcc agaattcgaa cccaatctta    120
tccaacgaca accaagtacg gactcagtat ttatacacag ataacaataa catgcacctg    180
tatcttcaga tcacccacaa tggagtagta actggtaccg aagaaaagaa tgactatggt    240
gtgctggaaa taaaggcagt aaaagctggg gttgtagtta taaaaggaat tcgaagcaat    300
ctctacctat gcatggattc tagacaccaa ttgtatgcgt cggcatatga taaagatgac    360
tgccatttcc atgaaaagat cacaccagat aattacaaca tgtatagctc agagaagcat    420
tcagaatacg tgtccttagc tccattaaaa ggaagccaga tggctcgttt tctacctata    480
```

<210> SEQ ID NO 191
<211> LENGTH: 585
<212> TYPE: DNA
<213> ORGANISM: Danio rerio

<400> SEQUENCE: 191

```
atgcttcttg cctgcttttt tatattttt gctcttttc ctcatcttcg gtggtgtatg     60
tatgttcctg cacagaacgt gcttctgcag tttggcacac aagtcaggga acgcctgctt    120
tacacagatg ggttgtttct tgaaatgaat ccagatggct ccgtcaaagg ctctcctgaa    180
aagaatctaa attgtgtgct ggagctgcgt tcagtcaaag cgggtgaaac cgtcatccag    240
agtgcagcta catctctcta cctctgcgtc gatgatcaag acaagctgaa aggacagcat    300
cattactctg cactagactg cacctttcag gaattgctac tggatggata ttcgtttttc    360
ctttctccac acactaatct tcccgtatcg ctcctctcga aacgtcagaa acacggcaat    420 cctcttttctc gcttcctccc tgttagcaga gcagaggaca gccggacaca ggaggtgaaa    480
cagtatattc aggatataaa cctggactct gacgacccac taggaatggg acatcggtca    540
cacttacaga ccgtcttcag tcccagtctg catactaaaa aatga                   585
```

<210> SEQ ID NO 192
<211> LENGTH: 630
<212> TYPE: DNA
<213> ORGANISM: Bos grunniens mutus

<400> SEQUENCE: 192

```
atgggctggg atgaagcgaa atttaaacat ctgggcctgt gggtgccggt gctggcggtg     60
ctgctgctgg gcacctgccg cgcgcatccg attccggata gcagcccgct gctgcagttt    120
ggcggccagg tgcgccagcg ctatctgtat accgatgatg cgcaggaaac cgaagcgcat    180
ctggaaattc gcgcggatgg caccgtggtg ggcgcggcgc gccagagccc ggaaaagcctg   240 ctggaactga aagcgctgaa accgggcgtg attcagattc tgggcgtgaa aaccagccgc    300
tttctgtgcc agggcccgga tggcaaactg tatggcagcc tgcattttga tccgaaaagcg   360 tgcagctttc gcgaactgct gctggaagat ggctataacg tgtatcagag cgaaaccctg    420
ggcctgccgc tgcgcctgcc gccgcagcgc agcagcaacc gcgatccggc gccgcgcggc    480
ccggcgcgct ttctgccgct gccgggcctg ccggcggaaa cgccggatcc gccgggcatt    540
ctggcgccgg aaccgccgga tgtgggcagc agcgatccgc tgagcatggt gggcccgagc    600
tatggccgca gcccgagcta taccagctaa                                   630
```

<210> SEQ ID NO 193
<211> LENGTH: 630
<212> TYPE: DNA
<213> ORGANISM: Saimiri boliviensis boliviensis

<400> SEQUENCE: 193

```
atgggctcgg aggaggtcgc gttggagcgc cctgcactgt gggtctctgt gttggctggt        60
ctcctgctgg gaacctgcca ggcataccc  atccctgact ctagtcccct cctgcaattt       120
ggaggccaag tccggcagcg gtacctctac acagatgacg ctcagcagac agaagcccac       180
ctggagatca gggaagatgg cacggtggcg ggggctgccc accagagccc cgaaagtctc       240
ttgcagctga agccttaaa  gccagggggtt attcaaatct tgggagtcaa gacctccagg       300
ttcctgtgcc agaggccgga cggggccctg tacggatcgc tctactttga ccccgaggcc       360
tgcagcttcc gggagctgct tcttgaggac ggatacaatg tgtaccagtc cgtggcccac       420
agcctcccgc tgcacctgcc aggggggcagg tccccaccct gggaccctgc acctcgagga      480
ccagctcgct tcctgccgct accaggcctg cccccgaac  cccccgaggc gccaggaatc       540
ctggcccccg agccccccga tgtgggctcc tcagaccctc tgagcatggt ggggccttcc       600
caaggccaaa gccccagcta cacttcctga                                        630

<210> SEQ ID NO 194
<211> LENGTH: 633
<212> TYPE: DNA
<213> ORGANISM: Callithrix jacchus
<220> FEATURE:
<221> NAME/KEY: misc_feature
<222> LOCATION: (190)..(190)
<223> OTHER INFORMATION: n is a, c, g, or t

<400> SEQUENCE: 194
atgggctcgg aggaggtcgg gttggagcac cctgcactgt gggtttctgt gctggctggt        60
ctcctgctgg gaacctgcca ggcgcacccc atccctgact ccagtcccct cctgcaattt       120
ggaggccaag tccggcagcg gtacctctac acagatgacg cccagcagaa agaagcccac       180
ctggagatcn aggaagatgg cacagtggcc ggggctgcca ccaaagtccc gaaagtgagt       240
ctcttgcagc tgaaagcctt aaagccaggg gttattcaaa tcttgggagt caagacatcc       300
aggttcctgt gccagaggcc agacggggcg ctgtatggat cgctccactt tgaccccgag       360
gcctgcagct ccgggagct  gcttcttgag gacggataca atgtgtacca gtctgtggcc       420
cacggcctcc cgctgcacct gccagagagc aggtcaccac cccgggaccc tgcaccccga       480
ggaccagctc gcttcctgcc actaccaggc ctgcccccctg aacccccaga gccgccagga      540
atcctggccc ctgagccccc cgacgtgggc tcctcagacc ctctgagcat ggtgggggcct       600 tcccaaggcc aaagccccag ctacgcttcc tga                                    633

<210> SEQ ID NO 195
<211> LENGTH: 630
<212> TYPE: DNA
<213> ORGANISM: Tupaia chinensis

<400> SEQUENCE: 195
atgggctggg ataaagcgcg ctttgaacat ctgggcgcgt gggcgccggt gctggcggtg        60
ctgctgctgg gcgcgtgcca ggcgtatccg attccggata gcagcccgct gctgcagttt       120
ggcggccagg tgcgccagcg ctatctgtat accgatgata cccaggatac cgaagcgcat       180
ctggaaattc gcgcggatgg caccgtggtg gcgcggcgc  atcagagccc ggaaagcctg       240
ctggaactga aagcgctgaa accgggcgtg attcagattc tgggcgtgaa accagccgc       300 tttctgtgcc agcgcccgga tggcgcgctg tatggcagcc tgcattttga tccggaagcg       360
tgcagctttc gcgaactgct gctggaagat ggctataaca tttatcagag cgaagcgcgc       420
```

| | |
|---|---|
| ggcctgccgc tgcgcctgcc gccgcatgat agcccgcatc gcgatcgcac cccgcagggc | 480 |
| ccggcgcgct ttctgccgct gccgggcctg ccgctggtgc cgccggaact gccgggcgtg | 540 |
| ctggcgctgg aaccgccgga tgtgggcagc agcgatccgc tgagcatgat gggcccgagc | 600 |
| cagggccaga gcccgagcta tgcgagctaa | 630 |

<210> SEQ ID NO 196
<211> LENGTH: 567
<212> TYPE: DNA
<213> ORGANISM: Papio anubis

<400> SEQUENCE: 196

| | |
|---|---|
| atggactcgg acgagaccgg gttcgagcac tcaggactgt gggttcctgt gctggctggt | 60 |
| cttctgctgg gagcctgcca ggcacacccc atccctgact ccagtcctct cctgcaattc | 120 |
| gggggccaag tccggcaacg gtacctctac acagatgatg cccagcagac agaagcccac | 180 |
| ctggagatca ggaggatggg acagtgggg ggcgctgctc accagagccc gaaagtaag | 240 |
| tgtgggccag agcctgggtc tgaggagga ggggctctcc actttgaccc tgaggcctgc | 300 |
| agcttccgcg agctgcttct tgagaacgga tacaatgttt accagtccga ggcccacggc | 360 |
| ctcccactgc acctgccggg aaacaagtcc ccacaccggg accctgcatc ccgaggacca | 420 |
| gctcgcttcc tgccactacc aggcctgccc ccgcaccccc cagagccacc aggaatcctc | 480 |
| gccccccagc ccccgatgt gggctcctcg acctctga gcatggtggg accttcccag | 540 |
| gccccgaagcc ctagctacgc ttcctga | 567 |

<210> SEQ ID NO 197
<211> LENGTH: 627
<212> TYPE: DNA
<213> ORGANISM: Pteropus alecto

<400> SEQUENCE: 197

| | |
|---|---|
| atgggctggg gcaaagcgcg cctgcagcat ccgggcctgt ggggcccggt gctggcggtg | 60 |
| ctgctgggcg cgtgccaggc gcatccgatt ctggatagca gcccgctgtt tcagtttggc | 120 |
| agccaggtgc gccgccgcta tctgtatacc gatgatgcgc aggataccga agcgcatctg | 180 |
| gaaattcgcg cggatggcac cgtggcgggc gcggcgcgcc gcagcccgga aagcctgctg | 240 |
| gaactgaaag cgctgaaacc gggcgtgatt caggtgctgg cgtgaaaac cagccgcttt | 300 |
| ctgtgccagc gcccggatgg caccctgtat ggcagcctgc attttgatcc ggcggcgtgc | 360 |
| agctttcgcg aactgctgct gaaagatggc tataacgtgt atcagagcga agcgctggcg | 420 |
| cgcccgctgc gcctgccgcc gtatagcagc ccgagcagcg atccggcgcg ccgcggcccg | 480 |
| gcgcgctttc tgccgctgcc gggcccgccg ccggaaccgc cgcagccgcc gggccgcctg | 540 |
| gcgccggaac cgccggatgt gggcagcagc gatccgctga gcatggtgtg gccgagccgc | 600 |
| ggccgcagcc cgagctatac cagctaa | 627 |

<210> SEQ ID NO 198
<211> LENGTH: 633
<212> TYPE: DNA
<213> ORGANISM: Heterocephalus glaber

<400> SEQUENCE: 198

| | |
|---|---|
| atggattggg cgcgcgcgga aagcgaacgc ccgggcctgt gggtgccggc ggtgctggcg | 60 |
| gtgctgctgc tgggcgcgtg ccaggcgcat ccgattccgg atagcagccc gctgctgcag | 120 |
| tttggcggcc aggtgcgcca cgccatctg tataccgatg atgcgcagga taccgaagtg | 180 |

```
catctggaaa ttcgcgcgga tggcagcgtg ggcggcgcgg cgcatcgcag cccggaaagc    240
ctgctggaac tgaaagcgct gaaaccgggc gtgattcaga ttctgggcgt gcgcaccagc    300
cgctttctgt gccagcgccc ggatggcacc ctgtatggca gcctgcattt tgatccggaa    360
gcgtgcagct ttcgcgaact gctgctggcg gatggctata acatttatca gagcgaagcg    420
tatggcctgc cgctgcgcat gctgccgagc gatagcgcga ccgcgatcc ggtgccgccg    480 ggcccggcgc gctttctgcc gctgccgggc ctgcatccgc cgccgctgga ccgccgggc    540 atgctgccgc cggaaccgcc ggatgtgggc agcagcgatc cgctgagcat ggtgggcccg    600
ctgcagggcc gcagcccgag ctatgcgttt taa                                 633

<210> SEQ ID NO 199
<211> LENGTH: 630
<212> TYPE: DNA
<213> ORGANISM: Cricetulus griseus

<400> SEQUENCE: 199
atggactgga tgaaatctgg agttggggtc ccgggactgt gggtccctct gctgcctatc     60
ttcctgctgg ggtctcccca ggcacacccc atccctgact ccagccccct cctccagttt    120
gggggtcaag tccggcacag gcacctctac acagatgaca accaggaaac tgaagtccac    180
ctggagatta ggcaggatgg cacggtgata gggaccacac accgcagccc agaaagtctc    240
ctggagctca aagccttgaa gccagaggtc atcccagtgc tgggtgtcaa ggcctccagg    300
tttctttgcc aacaaccaga cggaaccctg tatggatcgc tcactttga tcctgaggcc    360 tgcagtttca gggagctctt gcttgaggat ggatacaatg tgtaccaatc tgaagtccat    420
ggcctgcccc tgcgcctgcc ccagaggac tctccaaacc aggccccagc atcctgggga    480
cctgtgcccc cctgccagt gccaggactg ctccaccagc ccaggagct accagggttc    540 ctggccccag aacctccaga tgtgggctcc tctgacccac tgagcatggt gggacctttg    600
cagggccgaa gccccagcta tgcttcctga                                     630

<210> SEQ ID NO 200
<211> LENGTH: 579
<212> TYPE: DNA
<213> ORGANISM: Ovis aries

<400> SEQUENCE: 200
atgggctggg acgaggccaa gttcaagcac ttgggactgt gggtccctgt gctggctgtc     60
ctcctgctag gaacctgccg ggcgcatcca attccagact ccagccccct cctccagttt    120
gggggccaag tccgccagcg gtacctctac acggatgatg cccaggagac agaggcccac    180
ctggagatca gggccgatgg cacagtggtg gggcggccc gccagagtcc cgaaagtctc    240
ttggagctga aagccctgaa gccaggagtc attcagatct ttggagttaa acatccagg    300 ttcctgtgcc aggggccaga tgggaagctg tatggatcgc tgcactttga ccccaaagcc    360
tgcagcttcc gggagctgct tcttgaagat gggtacaatg tctaccagtc ggagaccctg    420
ggccttccac tccgcctgcc gccgcagcgc tcatccaacc gggacccggc cccgcgggga    480
cctccgaagc cccagctaca cttcttgaag acgtccgctg tgcagtactg gccacgttat    540
gagaaggtcc cagcttttct gcacccctttc cccggctga                          579

<210> SEQ ID NO 201
<211> LENGTH: 405
<212> TYPE: DNA
```

```
<213> ORGANISM: Pan paniscus

<400> SEQUENCE: 201
atggactcgg acgagaccgg gttcgagcac tcaggactgt gggtttctgt gctggctggt    60
cttctgctgg gagcctgcca ggcacacccc atccctgact ccagtcctct cctgcaattc   120
gggggccaag tccggcagcg gtacctctac acagatgatg cccagcagac agaagcccac   180
ctggagatca ggaggatgg gacggtgggg ggcgctgctg accagagccc cgaaagtctc    240
ctgcagctga aagccttgaa gccgggagtt attcaaatct gggagtcaa gacatccagg    300 ttcctgtgcc agaggccaga tggggccctg tatggatcgg tgagtttcca ggaccctcct   360
caccacccac catgctcctc ctatatgtcg ccctcacagc ctggg                   405

<210> SEQ ID NO 202
<211> LENGTH: 351
<212> TYPE: DNA
<213> ORGANISM: Macaca fascicularis

<400> SEQUENCE: 202
atggatagcg atgaaaccgg ctttgaacat agcggcctgt gggtgccggt gctggcgggc    60
ctgctgctgg gcgcgtgcca ggcgcatccg attccggata gcagcccgct gctgcagttt   120
ggcggccagg tgcgccagcg ctatctgtat accgatgatg cgcagcagac cgaagcgcat   180
ctggaaattc gcgaagatgg caccgtgggc ggcgcggcgc atcagagccc ggaaagcctg   240
ctgcagctga aagcgctgaa accgggcgtg attcagattc tgggcgtgaa aaccagccgc   300
tttctgtgcc agaaaccgga tggcgcgctg tatggcagcg tgagcttta a             351

<210> SEQ ID NO 203
<211> LENGTH: 314
<212> TYPE: DNA
<213> ORGANISM: Mesocricetus auratus

<400> SEQUENCE: 203
ggtcatccaa atcctgggtg tcaaggctgc taggtttcct tgccagcaac cagacggaag    60
cctgtacgga tcgcctcact tcgatcccga ggcctgcagt ttccgggagc tcctgcttga   120
ggatggatac aatgtgtacc agtcggaagc ccacggcctg cccctgcgcc tgccccagag   180
ggacgctccg agccagcccc cagcatcctg ggaccggtg cgcttcctgc agtgcccgg     240 actgttccag ccgccccacg acctcccagg gcgcccggcc ccagagcctc cggacgtggg   300
ctcctccgac ccac                                                     314

<210> SEQ ID NO 204
<211> LENGTH: 456
<212> TYPE: DNA
<213> ORGANISM: Nile tilapia

<400> SEQUENCE: 204
atgtatttgc agatgaacat ggatgggaga gtcacaggaa gtgatgctca gacaccttac    60
agtttgatgc agctgaaatc agttaaacca ggccatgtaa tcattaaagg accatcatca   120
tctctttttc tctgtgtgga cagcgaaggc aatctgagag gcagagtca ctactcagaa     180 accagctgca ccttcagaga aatgctgctg gctgacggat acaccgtttt catttcctca   240
caatatggat ttcccatgtc actggcatca agacattccc cagatcgaca cgcgcttccc   300
tttacgcggt tcctaccact gaggaataac ttgaaaacgg atagcgtatc agagcagctg   360
ccaaacaatc agagactctt caacgtggac tctgatgacc ttcttggaat gggtctaaat   420
```
tctatgggca gtcctcagtt ttctatggac aaataa                                  456

<210> SEQ ID NO 205
<211> LENGTH: 182
<212> TYPE: PRT
<213> ORGANISM: Artificial
<220> FEATURE:
<223> OTHER INFORMATION: Chimeric Protein

<400> SEQUENCE: 205

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Phe Glu Lys
            180

<210> SEQ ID NO 206
<211> LENGTH: 182
<212> TYPE: PRT
<213> ORGANISM: Artificial
<220> FEATURE:
<223> OTHER INFORMATION: Chimeric Protein

<400> SEQUENCE: 206

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Thr Gly Leu Glu Ala Val Arg
                165                 170                 175

Ser Pro Ser Phe Glu Lys
            180

<210> SEQ ID NO 207
<211> LENGTH: 187
<212> TYPE: PRT
<213> ORGANISM: Artificial
<220> FEATURE:
<223> OTHER INFORMATION: Chimeric Protein

<400> SEQUENCE: 207

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 208
<211> LENGTH: 182
<212> TYPE: PRT
<213> ORGANISM: Artificial
<220> FEATURE:
<223> OTHER INFORMATION: Chimeric Protein

<400> SEQUENCE: 208

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser

```
            35                  40                  45
Pro Glu Ser Leu Leu Gln Leu Lys Ala Leu Lys Pro Gly Val Ile Gln
        50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Thr Gly Leu Glu Ala Val Arg
                165                 170                 175
Ser Pro Ser Phe Glu Lys
            180

<210> SEQ ID NO 209
<211> LENGTH: 182
<212> TYPE: PRT
<213> ORGANISM: Artificial
<220> FEATURE:
<223> OTHER INFORMATION: Chimeric Protein

<400> SEQUENCE: 209

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Met Asp Pro Phe Gly Leu Val Thr Gly Leu Glu Ala Val Arg
                165                 170                 175
Ser Pro Ser Phe Glu Lys
            180

<210> SEQ ID NO 210
<211> LENGTH: 187
<212> TYPE: PRT
```

<213> ORGANISM: Artificial
<220> FEATURE:
<223> OTHER INFORMATION: Chimeric Protein

<400> SEQUENCE: 210

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185
```

<210> SEQ ID NO 211
<211> LENGTH: 546
<212> TYPE: DNA
<213> ORGANISM: Artificial
<220> FEATURE:
<223> OTHER INFORMATION: Nucleic Acid Molecule Encoding a Chimeric Protein

<400> SEQUENCE: 211

| | | | | |
|---|---|---|---|---|
| cacccccatcc | ctgactccag | tcctctcctg | caattcgggg | gccaagtccg gcagcggtac | 60 |
| ctctacacag | atgatgccca | gcagacagaa | gcccacctgg | agatcaggga ggatgggacg | 120 |
| gtgggggggcg | ctgctgacca | gagccccgaa | agtctcctgc | agctgaaagc cttgaagccg | 180 |
| ggagttattc | aaatcttggg | agtcaagaca | tccaggttcc | tgtgccagcg gccagatggg | 240 |
| gccctgtatg | gatcgctcca | ctttgaccct | gaggcctgca | gcttccggga gctgcttctt | 300 |
| gaggacggat | acaatgttta | ccagtccgaa | gcccacggcc | tcccgctgca cctgccaggg | 360 |
| aacaagtccc | cacaccggga | ccctgcaccc | cgaggaccag | ctcgcttcct gccactacca | 420 |
| ggcctgcccc | ccgcactccc | ggagccaccc | ggaatcctgg | cccccagcc ccccgatgtg | 480 |
| ggctcctcgg | accctctgag | catggtggga | ctggaggccg | tgaggagtcc cagctttgag | 540 |
| aagtaa | | | | | 546 |

<210> SEQ ID NO 212
<211> LENGTH: 549
<212> TYPE: DNA
<213> ORGANISM: Artificial
<220> FEATURE:

<223> OTHER INFORMATION: Nucleic Acid Molecule Encoding a Chimeric
      Protein

<400> SEQUENCE: 212

| caccccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggggcg ctgctgacca gagccccgaa agtctcctgc agctgaaagc cttgaagccg | 180 |
| ggagttattc aaatcttggg agtcaagaca tccaggttcc tgtgccagcg gccagatggg | 240 |
| gccctgtatg gatcgctcca ctttgaccct gaggcctgca gcttccggga gctgcttctt | 300 |
| gaggacggat acaatgttta ccagtccgaa gcccacggcc tcccgctgca cctgccaggg | 360 |
| aacaagtccc cacaccggga ccctgcaccc cgaggaccag ctcgcttcct gccactacca | 420 |
| ggcctgcccc ccgcactccc ggagccaccc ggaatcctgg cccccagcc cccgatgtg | 480 |
| ggctccatgg acccatttgg gcttgtcacc ggactggagg ccgtgaggag tcccagcttt | 540 |
| gagaagtaa | 549 |

<210> SEQ ID NO 213
<211> LENGTH: 564
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 213

| caccccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggggcg ctgctgacca gagccccgaa agtctcctgc agctgaaagc cttgaagccg | 180 |
| ggagttattc aaatcttggg agtcaagaca tccaggttcc tgtgccagcg gccagatggg | 240 |
| gccctgtatg gatcgctcca ctttgaccct gaggcctgca gcttccggga gctgcttctt | 300 |
| gaggacggat acaatgttta ccagtccgaa gcccacggcc tcccgctgca cctgccaggg | 360 |
| aacaagtccc cacaccggga ccctgcaccc cgaggaccag ctcgcttcct gccactactg | 420 |
| cccatggtcc cagaggagcc tgaggacctc aggggccact ggaatctga catgttctct | 480 |
| tcgcccctgg agaccgacag catggaccca tttgggcttg tcaccggact ggaggccgtg | 540 |
| aggagtccca gctttgagaa gtaa | 564 |

<210> SEQ ID NO 214
<211> LENGTH: 546
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 214

| caccccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggggcg ctgctgacca gagccccgaa agtctcctgc agctgaaagc cttgaagccg | 180 |
| ggagttattc aaatcttggg agtcaagaca tccaggttcc tgtgccaatg gccagatggg | 240 |
| gccctgtatg gatcgctcca ctttgaccct gaggcctgca gcttccggga gctgcttctt | 300 |
| gaggacggat acaatgttta ccagtccgaa gcccacggcc tcccgctgca cctgccaggg | 360 |

```
aacaagtccc cacaccggga ccctgcaccc cgaggaccag ctcgcttcct gccactacca    420
ggcctgcccc ccgcactccc ggagccaccc ggaatcctgg cccccagcc cccgatgtg     480 ggctcctcgg accctctgag catggtggga ctggaggccg tgaggagtcc cagctttgag   540
aagtaa                                                               546

<210> SEQ ID NO 215
<211> LENGTH: 549
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 215
caccccatcc ctgactccag tcctctcctg caattcgggg gccaagtccg gcagcggtac    60
ctctacacag atgatgccca gcagacagaa gcccacctgg agatcaggga ggatgggacg   120 gtgggggggcg ctgctgacca gagccccgaa agtctcctgc agctgaaagc cttgaagccg   180
ggagttattc aaatcttggg agtcaagaca tccaggttcc tgtgccaatg ccagatggg    240 gccctgtatg gatcgctcca cttttgaccct gaggcctgca gcttccggga gctgcttctt   300
gaggacggat acaatgttta ccagtccgaa gcccacggcc tcccgctgca cctgccaggg   360
aacaagtccc cacaccggga ccctgcaccc cgaggaccag ctcgcttcct gccactacca   420
ggcctgcccc ccgcactccc ggagccaccc ggaatcctgg cccccagcc cccgatgtg    480 ggctccatgg acccatttgg gcttgtcacc ggactggagg ccgtgaggag tcccagcttt   540
gagaagtaa                                                             549

<210> SEQ ID NO 216
<211> LENGTH: 564
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 216
caccccatcc ctgactccag tcctctcctg caattcgggg gccaagtccg gcagcggtac    60
ctctacacag atgatgccca gcagacagaa gcccacctgg agatcaggga ggatgggacg   120 gtgggggggcg ctgctgacca gagccccgaa agtctcctgc agctgaaagc cttgaagccg   180
ggagttattc aaatcttggg agtcaagaca tccaggttcc tgtgccaatg ccagatggg    240 gccctgtatg gatcgctcca cttttgaccct gaggcctgca gcttccggga gctgcttctt   300
gaggacggat acaatgttta ccagtccgaa gcccacggcc tcccgctgca cctgccaggg   360
aacaagtccc cacaccggga ccctgcaccc cgaggaccag ctcgcttcct gccactactg   420
cccatggtcc cagaggagcc tgaggacctc aggggccact ggaatctga catgttctct    480 tcgcccctgg agaccgacag catggaccca tttgggcttg tcaccggact ggaggccgtg   540
aggagtccca gctttgagaa gtaa                                           564

<210> SEQ ID NO 217
<211> LENGTH: 1044
<212> TYPE: PRT
<213> ORGANISM: Homo sapiens

<400> SEQUENCE: 217

Met Lys Pro Gly Cys Ala Ala Gly Ser Pro Gly Asn Glu Trp Ile Phe
```

-continued

```
 1               5                  10                 15
Phe Ser Thr Asp Glu Ile Thr Thr Arg Tyr Arg Asn Thr Met Ser Asn
            20                  25                 30
Gly Gly Leu Gln Arg Ser Val Ile Leu Ser Ala Leu Ile Leu Leu Arg
            35                  40             45
Ala Val Thr Gly Phe Ser Asp Gly Arg Ala Ile Trp Ser Lys Asn
            50              55              60
Pro Asn Phe Thr Pro Val Asn Glu Ser Gln Leu Phe Leu Tyr Asp Thr
 65              70                  75                 80
Phe Pro Lys Asn Phe Phe Trp Gly Ile Gly Thr Gly Ala Leu Gln Val
                85                  90             95
Glu Gly Ser Trp Lys Lys Asp Gly Lys Gly Pro Ser Ile Trp Asp His
               100             105                110
Phe Ile His Thr His Leu Lys Asn Val Ser Ser Thr Asn Gly Ser Ser
               115                 120             125
Asp Ser Tyr Ile Phe Leu Glu Lys Asp Leu Ser Ala Leu Asp Phe Ile
            130                 135             140
Gly Val Ser Phe Tyr Gln Phe Ser Ile Ser Trp Pro Arg Leu Phe Pro
145             150                 155                160
Asp Gly Ile Val Thr Val Ala Asn Ala Lys Gly Leu Gln Tyr Tyr Ser
                165             170                 175
Thr Leu Leu Asp Ala Leu Val Leu Arg Asn Ile Glu Pro Ile Val Thr
            180                 185                 190
Leu Tyr His Trp Asp Leu Pro Leu Ala Leu Gln Glu Lys Tyr Gly Gly
            195             200             205
Trp Lys Asn Asp Thr Ile Ile Asp Ile Phe Asn Asp Tyr Ala Thr Tyr
 210                 215             220
Cys Phe Gln Met Phe Gly Asp Arg Val Lys Tyr Trp Ile Thr Ile His
225                 230             235                 240
Asn Pro Tyr Leu Val Ala Trp His Gly Tyr Gly Thr Gly Met His Ala
                245             250                 255
Pro Gly Glu Lys Gly Asn Leu Ala Ala Val Tyr Thr Val Gly His Asn
            260             265                 270
Leu Ile Lys Ala His Ser Lys Val Trp His Asn Tyr Asn Thr His Phe
            275             280             285
Arg Pro His Gln Lys Gly Trp Leu Ser Ile Thr Leu Gly Ser His Trp
            290             295             300
Ile Glu Pro Asn Arg Ser Glu Asn Thr Met Asp Ile Phe Lys Cys Gln
305             310             315                 320
Gln Ser Met Val Ser Val Leu Gly Trp Phe Ala Asn Pro Ile His Gly
                325             330                 335
Asp Gly Asp Tyr Pro Glu Gly Met Arg Lys Lys Leu Phe Ser Val Leu
            340             345             350
Pro Ile Phe Ser Glu Ala Glu Lys His Glu Met Arg Gly Thr Ala Asp
            355             360             365
Phe Phe Ala Phe Ser Phe Gly Pro Asn Asn Phe Lys Pro Leu Asn Thr
            370             375             380
Met Ala Lys Met Gly Gln Asn Val Ser Leu Asn Leu Arg Glu Ala Leu
385             390             395             400
Asn Trp Ile Lys Leu Glu Tyr Asn Asn Pro Arg Ile Leu Ile Ala Glu
            405             410                 415
Asn Gly Trp Phe Thr Asp Ser Arg Val Lys Thr Glu Asp Thr Thr Ala
            420             425             430
```

```
Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
        595                 600                 605

Thr Gly Asn Leu Ser Ala Val Asn Arg Gln Ala Leu Arg Tyr Tyr Arg
    610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845
```

```
Phe Leu Gln Asp Ile Thr Arg Leu Ser Ser Pro Thr Arg Leu Ala Val
        850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 218
<211> LENGTH: 1043
<212> TYPE: PRT
<213> ORGANISM: Mus musculus

<400> SEQUENCE: 218

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65              70                  75                  80

Phe Pro Lys Asn Phe Ser Trp Gly Val Gly Thr Gly Ala Phe Gln Val
            85                  90                  95

Glu Gly Ser Trp Lys Thr Asp Gly Arg Gly Pro Ser Ile Trp Asp Arg
        100                 105                 110

Tyr Val Tyr Ser His Leu Arg Gly Val Asn Gly Thr Asp Arg Ser Thr
    115                 120                 125

Asp Ser Tyr Ile Phe Leu Glu Lys Asp Leu Leu Ala Leu Asp Phe Leu
130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
            165                 170                 175
```

```
Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
            195                 200             205

Trp Lys Asn Ala Thr Met Ile Asp Leu Phe Asn Asp Tyr Ala Thr Tyr
            210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
            275                 280                 285

Arg Pro His Gln Lys Gly Trp Leu Ser Ile Thr Leu Gly Ser His Trp
            290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
            355                 360                 365

Ala Phe Ser Phe Gly Pro Asn Asn Phe Arg Pro Ser Asn Thr Val Val
            370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
                405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
            435                 440                 445

Glu Ile Arg Val Phe Gly Tyr Thr Ala Trp Thr Leu Leu Asp Gly Phe
450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr
            500                 505                 510

Pro Asp Met Lys Gly Arg Phe Pro Cys Asp Phe Ser Trp Gly Val Thr
            515                 520                 525

Glu Ser Val Leu Lys Pro Glu Phe Thr Val Ser Ser Pro Gln Phe Thr
            530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                565                 570                 575

Tyr Val Ser Ile Lys Lys Arg Val Glu Met Leu Ala Lys Met Lys Val
            580                 585                 590
```

-continued

Thr His Tyr Gln Phe Ala Leu Asp Trp Thr Ser Ile Leu Pro Thr Gly
            595                 600                 605

Asn Leu Ser Lys Val Asn Arg Gln Val Leu Arg Tyr Tyr Arg Cys Val
    610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
        645                 650                 655

Gly Gly Trp Leu Asn Met Asn Thr Ala Lys Ala Phe Gln Asp Tyr Ala
            660                 665                 670

Glu Leu Cys Phe Arg Glu Leu Gly Asp Leu Val Lys Leu Trp Ile Thr
        675                 680                 685

Ile Asn Glu Pro Asn Arg Leu Ser Asp Met Tyr Asn Arg Thr Ser Asn
    690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
            725                 730                 735

Ser Leu Ser Leu His Cys Asp Trp Ala Glu Pro Ala Asn Pro Phe Val
        740                 745                 750

Asp Ser His Trp Lys Ala Ala Glu Arg Phe Leu Gln Phe Glu Ile Ala
    755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
            805                 810                 815

Asp Phe Tyr Ala Leu Asn His Phe Thr Thr Arg Phe Val Ile His Lys
        820                 825                 830

Gln Leu Asn Thr Asn Arg Ser Val Ala Asp Arg Asp Val Gln Phe Leu
    835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
            885                 890                 895

Asp Asp Gln Ile Arg Lys Tyr Tyr Leu Glu Lys Tyr Val Gln Glu Ala
        900                 905                 910

Leu Lys Ala Tyr Leu Ile Asp Lys Val Lys Ile Lys Gly Tyr Tyr Ala
    915                 920                 925

Phe Lys Leu Thr Glu Glu Lys Ser Lys Pro Arg Phe Gly Phe Phe Thr
930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
            965                 970                 975

Pro Ala Glu Asp Thr Asp Cys Thr Ile Cys Ser Phe Leu Val Glu Lys
        980                 985                 990

Lys Pro Leu Ile Phe Phe Gly Cys Cys Phe Ile Ser Thr Leu Ala Val
    995                 1000                1005

Leu Leu Ser Ile Thr Val Phe His His Gln Lys Arg Arg Lys Phe

Gln Lys Ala Arg Asn Leu Gln Asn Ile Pro Leu Lys Lys Gly His
1025                1030                1035

Ser Arg Val Phe Ser
1040

<210> SEQ ID NO 219
<211> LENGTH: 3135
<212> TYPE: DNA
<213> ORGANISM: Homo sapiens

<400> SEQUENCE: 219

| | |
|---|---|
| atgaagccag gctgtgcggc aggatctcca gggaatgaat ggatttctt cagcactgat | 60 |
| gaaataacca cacgctatag gaatacaatg tccaacgggg gattgcaaag atctgtcatc | 120 |
| ctgtcagcac ttattctgct acgagctgtt actggattct ctggagatgg aagagctata | 180 |
| tggtctaaaa atcctaattt tactccggta atgaaagtc agctgttct ctatgacact | 240 |
| ttccctaaaa acttttctg gggtattggg actggagcat gcaagtgga agggagttgg | 300 |
| aagaaggatg gaaaaggacc ttctatatgg gatcatttca tccacacaca ccttaaaaat | 360 |
| gtcagcagca cgaatggttc cagtgacagt tatatttttc tggaaaaaga cttatcagcc | 420 |
| ctggatttta taggagttc ttttatcaa ttttcaattt cctggccaag gcttttcccc | 480 |
| gatgaatag taacagttgc caacgcaaaa ggtctgcagt actacagtac tcttctggac | 540 |
| gctctagtgc ttagaaacat tgaacctata gttactttat accactggga tttgcctttg | 600 |
| gcactacaag aaaaatatgg ggggtggaaa atgatacca taatagatat cttcaatgac | 660 |
| tatgccacat actgtttcca gatgtttggg accgtgtca atattggat tacaattcac | 720 |
| aacccatatc tagtggcttg gcatgggtat gggacaggta tgcatgcccc tggagagaag | 780 |
| ggaaatttag cagctgtcta cactgtggga cacaacttga tcaaggctca ctcgaaagtt | 840 |
| tggcataact acaacacaca tttccgccca catcagaagg gttggttatc gatcacgttg | 900 |
| ggatctcatt ggatcgagcc aaaccggtcg gaaaacacga tggatatatt caaatgtcaa | 960 |
| caatccatgg tttctgtgct tggatggttt gccaacccta tccatgggga tggcgactat | 1020 |
| ccagagggga tgagaaagaa gttgttctcc gttctaccca ttttctctga agcagagaag | 1080 |
| catgagatga gaggcacagc tgatttcttt gccttttctt ttggacccaa caacttcaag | 1140 |
| cccctaaaca ccatggctaa aatgggacaa atgttcac ttaatttaag agaagcgctg | 1200 |
| aactggatta aactggaata caacaaccct cgaatcttga ttgctgagaa tggctggttc | 1260 |
| acagacagtc gtgtgaaaac agaagacacc acggccatct acatgatgaa gaatttcctc | 1320 |
| agccaggtgc ttcaagcaat aaggttagat gaaatacgag tgtttggtta actgcctgg | 1380 |
| tctctcctgg atggctttga atggcaggat gcttacacca tccgccgagg attattttat | 1440 |
| gtggatttta acagtaaaca gaaagagcgg aaacctaagt cttcagcaca ctactacaaa | 1500 |
| cagatcatac gagaaaatgg ttttcttta aaagagtcca cgccagatgt gcagggccag | 1560 |
| tttccctgtg acttctcctg gggtgtcact gaatctgttc ttaagcccga gtctgtggct | 1620 |
| tcgtccccac agttcagcga tcctcatctg tacgtgtgga acgccactgg caacagactg | 1680 |
| ttgcaccgag tggaagggt gaggctgaaa acacgacccg ctcaatgcac agattttgta | 1740 |
| aacatcaaaa acaacttga gatgttggca agaatgaaag tcacccacta ccggtttgct | 1800 |
| ctggattggg cctcggtcct tcccactggc aacctgtccg cggtgaaccg acaggccctg | 1860 |
| aggtactaca ggtgcgtggt cagtgagggg ctgaagcttg gcatctccgc gatggtcacc | 1920 |

```
ctgtattatc cgacccacgc ccacctaggc ctccccgagc ctctgttgca tgccgacggg   1980
tggctgaacc catcgacggc cgaggccttc caggcctacg ctgggctgtg cttccaggag   2040
ctgggggacc tggtgaagct ctggatcacc atcaacgagc ctaaccggct aagtgacatc   2100
tacaaccgct ctggcaacga cacctacggg gcggcgcaca acctgctggt ggcccacgcc   2160
ctggcctggc gcctctacga ccggcagttc aggccctcac agcgcgggggc cgtgtcgctg   2220 tcgctgcacg cggactgggc ggaacccgcc aaccccatg ctgactcgca ctggagggcg   2280
gccgagcgct tcctgcagtt cgagatcgcc tggttcgccg agccgctctt caagaccggg   2340
gactaccccg cggccatgag ggaatacatt gcctccaagc accgacgggg gctttccagc   2400
tcggccctgc cgcgcctcac cgaggccgaa aggaggctgc tcaagggcac ggtcgacttc   2460
tgcgcgctca accacttcac cactaggttc gtgatgcacg agcagctggc cggcagccgc   2520
tacgactcgg acagggacat ccagtttctg caggacatca cccgcctgag ctcccccacg   2580
cgcctggctg tgattccctg gggggtgcgc aagctgctgc ggtgggtccg gaggaactac   2640
ggcgacatgg acatttacat caccgccagt ggcatcgacg accaggctct ggaggatgac   2700
cggctccgga gtactaccct agggaagtac cttcaggagg tgctgaaagc atacctgatt   2760
gataaagtca gaatcaaagg ctattatgca ttcaaactgg ctgaagagaa atctaaaccc   2820
agatttggat tcttcacatc tgattttaaa gctaaatcct caatacaatt ttacaacaaa   2880
gtgatcagca gcagggcgtt cccttttgag aacagtagtt ctagatgcag tcagacccaa   2940
gaaaatacag agtgcactgt ctgcttattc cttgtgcaga gaaaccact gatattcctg   3000 ggttgttgct tcttctccac cctggttcta ctcttatcaa ttgccatttt tcaaaggcag   3060
aagagaagaa agttttggaa agcaaaaaac ttacaacaca taccattaaa gaaaggcaag   3120
agagttgtta gctaa                                                   3135
```

<210> SEQ ID NO 220
<211> LENGTH: 3132
<212> TYPE: DNA
<213> ORGANISM: Mus musculus

<400> SEQUENCE: 220

```
atgaagacag gctgtgcagc agggtctccg gggaatgaat ggattttctt cagctctgat     60
gaaagaaaca cacgctctag gaaaacaatg tccaacaggg cactgcaaag atctgccgtg    120
ctgtctgcgt tgttctgct gcgagctgtt accggcttct ccggagacgg gaaagcaata    180
tgggataaaa aacagtacgt gagtccggta aacccaagtc agctgttcct ctatgacact    240
ttccctaaaa acttttcctg gggcgttggg accggagcat tcaagtggaa agggagttgg    300
aagacagatg gaagaggacc ctcgatctgg gatcggtacg tctactcaca cctgagaggt    360
gtcaacggca cagacagatc cactgacagt tacatctttc tggaaaaaga cttgttggct    420
ctggattttt taggagtttc tttttatcag ttctcaatct cctggccacg gttgtttccc    480
aatggaacag tagcagcagt gaatgcgcaa ggtctccggt actaccgtgc acttctggac    540
tcgctggtac ttaggaatat cgagcccatt gttaccttgt accattggga tttgcctctg    600
acgctccagg aagaatatgg gggctggaaa aatgcaacta tgatagatct cttcaacgac    660
tatgccacat actgcttcca gacctttgga gaccgtgtca atattggat tacaattcac    720 aacccttacc ttgttgcttg gcatgggttt ggcacaggta tgcatgcacc aggagagaag    780
ggaaatttaa cagctgtcta cactgtggga cacaacctga tcaaggcaca ttcgaaagtg    840
```

```
tggcataact acgacaaaaa cttccgccct catcagaagg gttggctctc catcaccttg      900
gggtcccatt ggatagagcc aaacagaaca gacaacatgg aggacgtgat caactgccag      960
cactccatgt cctctgtgct tggatggttc gccaacccca tccacgggga cggcgactac     1020
cctgagttca tgaagacggg cgccatgatc cccgagttct ctgaggcaga aaggaggag      1080
gtgaggggca cggctgattt cttttgcctt tccttcgggc ccaacaactt caggccctca     1140
aacaccgtgg tgaaaatggg acaaaatgta tcactcaact taaggcaggt gctgaactgg     1200
attaaactgg aatacgatga ccctcaaatc ttgatttcgg agaacggctg gttcacagat     1260
agctatataa agacagagga caccacggcc atctacatga tgaagaattt cctaaaccag     1320
gttcttcaag caataaaatt tgatgaaatc cgcgtgtttg gttatacggc ctggactctc     1380
ctggatggct ttgagtggca ggatgcctat acgacccgac gagggctgtt ttatgtggac     1440
tttaacagtg agcagaaaga gaggaaaccc aagtcctcgg ctcattacta caagcagatc     1500
atacaagaca acggcttccc tttgaaagag tccacgccag acatgaaggg tcggttcccc     1560
tgtgatttct cttggggagt cactgagtct gttcttaagc ccgagtttac ggtctcctcc     1620
ccgcagttta ccgatcctca cctgtatgtg tggaatgtca ctggcaacag attgctctac     1680
cgagtggaag gggtaaggct gaaaacaaga ccatcccagt gcacagatta tgtgagcatc     1740
aaaaaacgag ttgaaatgtt ggcaaaaatg aaagtcaccc actaccagtt tgctctggac     1800
tggacctcta tccttcccac tggcaatctg tccaaagtta acagacaagt gttaaggtac     1860
tataggtgtg tggtgagcga aggactgaag ctgggcgtct tccccatggt gacgttgtac     1920
cacccaaccc actcccatct cggcctcccc ctgccacttc tgagcagtgg ggggtggcta     1980
aacatgaaca cagccaaggc cttccaggac tacgctgagc tgtgcttccg ggagttgggg     2040
gacttggtga agctctggat caccatcaat gagcctaaca ggctgagtga catgtacaac     2100
cgcacgagta atgacaccta ccgtgcagcc cacaacctga tgatcgccca tgcccaggtc     2160
tggcacctct atgataggca gtataggccg gtccagcatg gggctgtgtc gctgtcctta     2220
cattgcgact gggcagaacc tgccaacccc tttgtggatt cacactggaa ggcagccgag     2280
cgcttcctcc agtttgagat cgcctggttt gcagatccgc tcttcaagac tggcgactat     2340
ccatcggtta tgaaggaata catcgcctcc aagaaccagc gagggctgtc tagctcagtc     2400
ctgccgcgct tcaccgcgaa ggagagcagg ctggtgaagg gtaccgtcga cttctacgca     2460
ctgaaccact tcactacgag gttcgtgata cacaagcagc tgaacaccaa ccgctcagtt     2520
gcagacaggg acgtccagtt cctgcaggac atcacccgcc taagctcgcc cagccgcctg     2580
gctgtaacac cctggggagt gcgcaagctc cttgcgtgga tccggaggaa ctacagagac     2640
agggatatct acatcacagc caatggcatc gatgacctgg ctctagagga tgatcagatc     2700
cgaaagtact acttggagaa gtatgtccag gaggctctga agcatatct cattgacaag     2760
gtcaaaatca aaggctacta tgcattcaaa ctgactgaag agaaatctaa gcctagattt     2820
ggattttca cctctgactt cagagctaag tcctctgtcc agtttttacag caagctgatc     2880
agcagcagtg gcctccccgc tgagaacaga agtcctgcgt gtggtcagcc tgcggaagac     2940
acagactgca ccatttgctc atttctcgtg gagaagaaac cactcatctt cttcggttgc     3000
tgcttcatct ccactctggc tgtactgcta tccatcaccg ttttttcatca tcaaaagaga     3060
agaaaattcc agaaagcaag gaacttacaa aatataccat tgaagaaagg ccacagcaga     3120
gttttcagct aa                                                         3132
```

<210> SEQ ID NO 221
<211> LENGTH: 822
<212> TYPE: PRT
<213> ORGANISM: Homo sapiens

<400> SEQUENCE: 221

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

-continued

```
Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
        420                 425                 430

Ser Ser Ala Ser Met Asn Ser Gly Val Leu Leu Val Arg Pro Ser Arg
    435                 440                 445

Leu Ser Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Met Pro Leu Asp Gln Tyr Ser Pro Ser Phe Pro Asp Thr Arg
    770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
```

Gly Gly Leu Lys Arg Arg
                820

<210> SEQ ID NO 222
<211> LENGTH: 2469
<212> TYPE: DNA
<213> ORGANISM: Homo sapiens

<400> SEQUENCE: 222

```
atgtggagct ggaagtgcct cctcttctgg gctgtgctgg tcacagccac actctgcacc      60
gctaggccgt ccccgacctt gcctgaacaa gcccagccct ggggagcccc tgtggaagtg     120
gagtccttcc tggtccaccc cggtgacctg ctgcagcttc gctgtcggct gcgggacgat     180
gtgcagagca tcaactggct gcgggacggg gtgcagctgg cggaaagcaa ccgcaccccgc    240
atcacagggg aggaggtgga ggtgcaggac tccgtgcccg cagactccgg cctctatgct     300
tgcgtaacca gcagcccctc gggcagtgac accacctact tctccgtcaa tgtttcagat     360
gctctcccct cctcggagga tgatgatgat gatgatgact cctcttcaga ggagaaagaa     420
acagataaca ccaaaccaaa ccgtatgccc gtagctccat attggacatc cccagaaaag     480
atggaaaaga aattgcatgc agtgccggct gccaagacag tgaagttcaa atgcccttcc     540
agtgggaccc caaaccccac actgcgctgg ttgaaaaatg caaagaatt caaacctgac     600
cacagaattg gaggctacaa ggtccgttat gccacctgga gcatcataat ggactctgtg     660
gtgccctctg acaagggcaa ctacacctgc attgtggaga tgagtacgg cagcatcaac     720
cacacatacc agctggatgt cgtggagcgg tcccctcacc ggcccatcct gcaagcaggg     780
ttgcccgcca acaaaacagt ggccctgggt agcaacgtgg agttcatgtg taagtgtac     840
agtgacccgc agccgcacat ccagtggcta agcacatcg aggtgaatgg gagcaagatt     900
ggcccagaca acctgcctta gtccagatc ttgaagactg ctggagttaa taccaccgac     960
aaagagatgg aggtgcttca cttaagaaat gtctccttg aggacgcagg ggagtatacg    1020
tgcttggcgg gtaactctat cggactctcc catcactctg catggttgac cgttctggaa    1080
gccctggaag agaggccggc agtgatgacc tcgcccctgt acctggagat catcatctat    1140
tgcacagggg ccttcctcat ctcctgcatg gtgggtcgg tcatcgtcta caagatgaag    1200
agtggtacca gaagagtga cttccacagc cagatggctg tgcacaagct ggccaagagc    1260
atccctctgc gcagacaggt aacagtgtct gctgactcca gtgcatccat gaactctggg    1320
gttcttctgg ttcggccatc acggctctcc tccagtggga ctcccatgct agcaggggtc    1380
tctgagtatg agcttcccga agaccctcgc tgggagctgc ctcgggacag actggtctta    1440
ggcaaacccc tgggagaggg ctgctttggg caggtggtgt ggcagaggc tatcgggctg    1500
gacaaggaca aacccaaccg tgtgaccaaa gtggctgtga gatgttgaa gtcggacgca    1560
acagagaaag acttgtcaga cctgatctca gaaatggaga tgatgaagat gatcgggaag    1620
cataagaata tcatcaacct gctgggggcc tgcacgcagg atggtccctt gtatgtcatc    1680
gtggagtatg cctccaaggg caacctgcgg gagtacctgc aggcccggag gcccccaggg    1740
ctggaatact gctacaaccc cagccacaac ccagaggagc agctctcctc caaggacctg    1800
gtgtcctgcg cctaccaggt ggcccgaggc atggagtatc tggcctccaa gaagtgcata    1860
caccgagacc tggcagccag gaatgtcctg gtgacagagg acaatgtgat gaagatagca    1920
gactttggcc tcgcacggga cattcaccac atcgactact ataaaaagac aaccaacggc    1980
```

```
cgactgcctg tgaagtggat ggcacccgag gcattatttg accggatcta cacccaccag    2040
agtgatgtgt ggtcttttcgg ggtgctcctg tgggagatct tcactctggg cggctcccca    2100
taccccggtg tgcctgtgga ggaacttttc aagctgctga aggagggtca ccgcatggac    2160
aagcccagta actgcaccaa cgagctgtac atgatgatgc gggactgctg gcatgcagtg    2220
ccctcacaga gacccacctt caagcagctg gtggaagacc tggaccgcat cgtggccttg    2280
acctccaacc aggagtacct ggacctgtcc atgcccctgg accagtactc ccccagcttt    2340
cccgacaccc ggagctctac gtgctcctca ggggaggatt ccgtcttctc tcatgagccg    2400
ctgcccgagg agccctgcct gccccgacac ccagcccagc ttgccaatgg cggactcaaa    2460
cgccgctga                                                             2469
```

<210> SEQ ID NO 223
<211> LENGTH: 251
<212> TYPE: PRT
<213> ORGANISM: Homo sapiens

<400> SEQUENCE: 223

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
                20                  25                  30

Gly Ser Ser Trp Gly Gly Leu Ile His Leu Tyr Thr Ala Thr Ala Arg
            35                  40                  45

Asn Ser Tyr His Leu Gln Ile His Lys Asn Gly His Val Asp Gly Ala
        50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 224
<211> LENGTH: 251
<212> TYPE: PRT
<213> ORGANISM: Homo sapiens

```
<400> SEQUENCE: 224

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Thr
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 225
<211> LENGTH: 825
<212> TYPE: PRT
<213> ORGANISM: Homo sapiens

<400> SEQUENCE: 225

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110
```

```
Tyr Phe Ser Val Asn Val Ser Val Pro Ile Asp Ala Leu Pro Ser Ser
            115                 120                 125

Glu Asp Asp Asp Asp Asp Asp Ser Ser Glu Glu Lys Glu Thr
130                 135                 140

Asp Asn Thr Lys Pro Asn Pro Val Ala Pro Tyr Trp Thr Ser Pro Glu
145                 150                 155                 160

Lys Met Glu Lys Lys Leu His Ala Val Pro Ala Ala Lys Thr Val Lys
                165                 170                 175

Phe Lys Cys Pro Ser Ser Gly Thr Pro Asn Pro Thr Leu Arg Trp Leu
                180                 185                 190

Lys Asn Gly Lys Glu Phe Lys Pro Asp His Arg Ile Gly Gly Tyr Lys
                195                 200                 205

Val Arg Tyr Ala Thr Trp Ser Ile Ile Met Asp Ser Val Val Pro Ser
            210                 215                 220

Asp Lys Gly Asn Tyr Thr Cys Ile Val Glu Asn Glu Tyr Gly Ser Ile
225                 230                 235                 240

Asn His Thr Tyr Gln Leu Asp Val Val Glu Arg Ser Pro His Arg Pro
                245                 250                 255

Ile Leu Gln Ala Gly Leu Pro Ala Asn Lys Thr Val Ala Leu Gly Ser
            260                 265                 270

Asn Val Glu Phe Met Cys Lys Val Tyr Ser Asp Pro Gln Pro His Ile
            275                 280                 285

Gln Trp Leu Lys His Ile Glu Val Asn Gly Ser Lys Ile Gly Pro Asp
            290                 295                 300

Asn Leu Pro Tyr Val Gln Ile Leu Lys His Ser Gly Ile Asn Ser Ser
305                 310                 315                 320

Asp Ala Glu Val Leu Thr Leu Phe Asn Val Thr Glu Ala Gln Ser Gly
                325                 330                 335

Glu Tyr Val Cys Lys Val Ser Asn Tyr Ile Gly Glu Ala Asn Gln Ser
            340                 345                 350

Ala Trp Leu Thr Val Thr Arg Pro Val Ala Lys Ala Leu Glu Glu Arg
            355                 360                 365

Pro Ala Val Met Thr Ser Pro Leu Tyr Leu Glu Ile Ile Ile Tyr Cys
            370                 375                 380

Thr Gly Ala Phe Leu Ile Ser Cys Met Val Gly Ser Val Ile Val Tyr
385                 390                 395                 400

Lys Met Lys Ser Gly Thr Lys Lys Ser Asp Phe His Ser Gln Met Ala
                405                 410                 415

Val His Lys Leu Ala Lys Ser Ile Pro Leu Arg Arg Gln Val Thr Val
                420                 425                 430

Ser Ala Asp Ser Ser Ala Ser Met Asn Ser Gly Val Leu Leu Val Arg
            435                 440                 445

Pro Ser Arg Leu Ser Ser Ser Gly Thr Pro Met Leu Ala Gly Val Ser
450                 455                 460

Glu Tyr Glu Leu Pro Glu Asp Pro Arg Trp Glu Leu Pro Arg Asp Arg
465                 470                 475                 480

Leu Val Leu Gly Lys Pro Leu Gly Glu Gly Cys Phe Gly Gln Val Val
                485                 490                 495

Leu Ala Glu Ala Ile Gly Leu Asp Lys Asp Lys Pro Asn Arg Val Thr
                500                 505                 510

Lys Val Ala Val Lys Met Leu Lys Ser Asp Ala Thr Glu Lys Asp Leu
            515                 520                 525
```

Ser Asp Leu Ile Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Gln Ala Arg Arg Pro Gly Leu Glu Tyr Cys Tyr Asn Pro Ser His
            580                 585                 590

Asn Pro Glu Glu Gln Leu Ser Ser Lys Asp Leu Val Ser Cys Ala Tyr
            595                 600                 605

Gln Val Ala Arg Gly Met Glu Tyr Leu Ala Ser Lys Lys Cys Ile His
            610                 615                 620

Arg Asp Leu Ala Ala Arg Asn Val Leu Val Thr Glu Asp Asn Val Met
625                 630                 635                 640

Lys Ile Ala Asp Phe Gly Leu Ala Arg Asp Ile His His Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Ile Tyr Thr His Gln Ser Asp Val Trp Ser
            675                 680                 685

Phe Gly Val Leu Leu Trp Glu Ile Phe Thr Leu Gly Gly Ser Pro Tyr
690                 695                 700

Pro Gly Val Pro Val Glu Glu Leu Phe Lys Leu Leu Lys Glu Gly His
705                 710                 715                 720

Arg Met Asp Lys Pro Ser Asn Cys Thr Asn Glu Leu Tyr Met Met Met
            725                 730                 735

Arg Asp Cys Trp His Ala Val Pro Ser Gln Arg Pro Thr Phe Lys Gln
            740                 745                 750

Leu Val Glu Asp Leu Asp Arg Ile Val Ala Leu Thr Ser Asn Gln Glu
            755                 760                 765

Tyr Leu Asp Leu Ser Met Pro Leu Asp Gln Tyr Ser Pro Ser Phe Pro
770                 775                 780

Asp Thr Arg Ser Ser Thr Cys Ser Ser Gly Glu Asp Ser Val Phe Ser
785                 790                 795                 800

His Glu Pro Leu Pro Glu Glu Pro Cys Leu Pro Arg His Pro Ala Gln
            805                 810                 815

Leu Ala Asn Gly Gly Leu Lys Arg Arg
            820                 825

<210> SEQ ID NO 226
<211> LENGTH: 821
<212> TYPE: PRT
<213> ORGANISM: Homo sapiens

<400> SEQUENCE: 226

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
            50                  55                  60

Lys Asp Ala Ala Val Ile Ser Trp Thr Lys Asp Gly Val His Leu Gly
65                  70                  75                  80

-continued

```
Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
    355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495
```

```
Met Ala Glu Ala Val Gly Ile Asp Lys Asp Lys Pro Lys Glu Ala Val
                500                 505                 510
Thr Val Ala Val Lys Met Leu Lys Asp Asp Ala Thr Glu Lys Asp Leu
            515                 520                 525
Ser Asp Leu Val Ser Glu Met Glu Met Met Lys Met Ile Gly Lys His
530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
            580                 585                 590
Val Pro Glu Glu Gln Met Thr Phe Lys Asp Leu Val Ser Cys Thr Tyr
            595                 600                 605
Gln Leu Ala Arg Gly Met Glu Tyr Leu Ala Ser Gln Lys Cys Ile His
            610                 615                 620
Arg Asp Leu Ala Ala Arg Asn Val Leu Val Thr Glu Asn Asn Val Met
625                 630                 635                 640
Lys Ile Ala Asp Phe Gly Leu Ala Arg Asp Ile Asn Asn Ile Asp Tyr
                645                 650                 655
Tyr Lys Lys Thr Thr Asn Gly Arg Leu Pro Val Lys Trp Met Ala Pro
                660                 665                 670
Glu Ala Leu Phe Asp Arg Val Tyr Thr His Gln Ser Asp Val Trp Ser
            675                 680                 685
Phe Gly Val Leu Met Trp Glu Ile Phe Thr Leu Gly Gly Ser Pro Tyr
            690                 695                 700
Pro Gly Ile Pro Val Glu Glu Leu Phe Lys Leu Leu Lys Glu Gly His
705                 710                 715                 720
Arg Met Asp Lys Pro Ala Asn Cys Thr Asn Glu Leu Tyr Met Met Met
                725                 730                 735
Arg Asp Cys Trp His Ala Val Pro Ser Gln Arg Pro Thr Phe Lys Gln
            740                 745                 750
Leu Val Glu Asp Leu Asp Arg Ile Leu Thr Leu Thr Thr Asn Glu Glu
            755                 760                 765
Tyr Leu Asp Leu Ser Gln Pro Leu Glu Gln Tyr Ser Pro Ser Tyr Pro
770                 775                 780
Asp Thr Arg Ser Ser Cys Ser Ser Gly Asp Asp Ser Val Phe Ser Pro
785                 790                 795                 800
Asp Pro Met Pro Tyr Glu Pro Cys Leu Pro Gln Tyr Pro His Ile Asn
                805                 810                 815
Gly Ser Val Lys Thr
            820

<210> SEQ ID NO 227
<211> LENGTH: 822
<212> TYPE: PRT
<213> ORGANISM: Homo sapiens

<400> SEQUENCE: 227

Met Val Ser Trp Gly Arg Phe Ile Cys Leu Val Val Val Thr Met Ala
1               5                   10                  15
Thr Leu Ser Leu Ala Arg Pro Ser Phe Ser Leu Val Glu Asp Thr Thr
            20                  25                  30
Leu Glu Pro Glu Glu Pro Pro Thr Lys Tyr Gln Ile Ser Gln Pro Glu
        35                  40                  45
```

-continued

```
Val Tyr Val Ala Ala Pro Gly Glu Ser Leu Glu Val Arg Cys Leu Leu
     50                  55                  60
Lys Asp Ala Ala Val Ile Ser Trp Thr Lys Asp Gly Val His Leu Gly
 65                  70                  75                  80
Pro Asn Asn Arg Thr Val Leu Ile Gly Glu Tyr Leu Gln Ile Lys Gly
                 85                  90                  95
Ala Thr Pro Arg Asp Ser Gly Leu Tyr Ala Cys Thr Ala Ser Arg Thr
            100                 105                 110
Val Asp Ser Glu Thr Trp Tyr Phe Met Val Asn Val Thr Asp Ala Ile
        115                 120                 125
Ser Ser Gly Asp Asp Glu Asp Asp Thr Asp Gly Ala Glu Asp Phe Val
    130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
            260                 265                 270
Asp Val Glu Phe Val Cys Lys Val Tyr Ser Asp Ala Gln Pro His Ile
        275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
            340                 345                 350
Ala Trp Leu Thr Val Leu Pro Lys Gln Gln Ala Pro Gly Arg Glu Lys
        355                 360                 365
Glu Ile Thr Ala Ser Pro Asp Tyr Leu Glu Ile Ala Ile Tyr Cys Ile
    370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
            420                 425                 430
Ala Glu Ser Ser Ser Ser Met Asn Ser Asn Thr Pro Leu Val Arg Ile
        435                 440                 445
Thr Thr Arg Leu Ser Ser Thr Ala Asp Thr Pro Met Leu Ala Gly Val
    450                 455                 460
```

```
Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
            485                 490                 495

Val Met Ala Glu Ala Val Gly Ile Asp Lys Asp Lys Pro Lys Glu Ala
        500                 505                 510

Val Thr Val Ala Val Lys Met Leu Lys Asp Asp Ala Thr Glu Lys Asp
    515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
            565                 570                 575

Leu Arg Ala Arg Arg Pro Pro Gly Met Glu Tyr Ser Tyr Asp Ile Asn
        580                 585                 590

Arg Val Pro Glu Glu Gln Met Thr Phe Lys Asp Leu Val Ser Cys Thr
    595                 600                 605

Tyr Gln Leu Ala Arg Arg Met Glu Tyr Leu Ala Ser Gln Lys Cys Ile
610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
        660                 665                 670

Pro Glu Ala Leu Phe Asp Arg Val Tyr Thr His Gln Ser Asp Val Trp
    675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
        740                 745                 750

Gln Leu Val Glu Asp Leu Asp Arg Ile Leu Thr Leu Thr Thr Asn Glu
    755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
            805                 810                 815

Asn Gly Ser Val Lys Thr
            820

<210> SEQ ID NO 228
<211> LENGTH: 806
<212> TYPE: PRT
<213> ORGANISM: Homo sapiens

<400> SEQUENCE: 228

Met Gly Ala Pro Ala Cys Ala Leu Ala Leu Cys Val Ala Val Ala Ile
1               5                   10                  15
```

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
                35                  40                  45

Leu Val Phe Gly Ser Gly Asp Ala Val Glu Leu Ser Cys Pro Pro Pro
 50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
            210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
                515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
                740                 745                 750

Thr Val Thr Ser Thr Asp Glu Tyr Leu Asp Leu Ser Ala Pro Phe Glu
                755                 760                 765

Gln Tyr Ser Pro Gly Gly Gln Asp Thr Pro Ser Ser Ser Ser Ser Gly
                770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 229
<211> LENGTH: 808
<212> TYPE: PRT
<213> ORGANISM: Homo sapiens

<400> SEQUENCE: 229

-continued

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65              70                  75                  80

Leu Val Pro Ser Glu Arg Val Leu Val Gly Pro Gln Arg Leu Gln Val
            85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
        260                 265                 270

Phe His Cys Lys Val Tyr Ser Asp Ala Gln Pro His Ile Gln Trp Leu
    275                 280                 285

Lys His Val Glu Val Asn Gly Ser Lys Val Gly Pro Asp Gly Thr Pro
290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
            325                 330                 335

Leu Cys Arg Ala Thr Asn Phe Ile Gly Val Ala Glu Lys Ala Phe Trp
        340                 345                 350

Leu Ser Val His Gly Pro Arg Ala Ala Glu Glu Glu Leu Val Glu Ala
    355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
            405                 410                 415
```

-continued

```
Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805
```

<210> SEQ ID NO 230
<211> LENGTH: 802
<212> TYPE: PRT

<213> ORGANISM: Homo sapiens

<400> SEQUENCE: 230

```
Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400
```

Arg Pro Pro Ala Thr Val Gln Lys Leu Ser Arg Phe Pro Leu Ala Arg
            405                 410                 415

Gln Phe Ser Leu Glu Ser Gly Ser Gly Lys Ser Ser Ser Leu
        420                 425                 430

Val Arg Gly Val Arg Leu Ser Ser Gly Pro Ala Leu Leu Ala Gly
        435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
            485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
            530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
            565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
            610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
            645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
            690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
            725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
            755                 760                 765

Gly Asp Ala Ser Ser Thr Cys Ser Ser Asp Ser Val Phe Ser His
            770                 775                 780

Asp Pro Leu Pro Leu Gly Ser Ser Ser Phe Pro Phe Gly Ser Gly Val
785                 790                 795                 800

Gln Thr

<210> SEQ ID NO 231

```
<211> LENGTH: 1014
<212> TYPE: PRT
<213> ORGANISM: Mus musculus

<400> SEQUENCE: 231
```

| | | | | | | | | | | | | | | |
|---|---|---|---|---|---|---|---|---|---|---|---|---|---|---|
|Met|Leu|Ala|Arg|Ala|Pro|Pro|Arg|Arg|Pro|Pro|Arg|Leu|Val|Leu|Leu|
|1| | |5| | | | |10| | | | |15| |

Arg Leu Leu Leu Leu His Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
        115                 120                 125

Asp Ser Tyr Asn Asn Val Tyr Arg Asp Thr Glu Gly Leu Arg Glu Leu
130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
        355                 360                 365

Phe Ala Leu Ser Phe Gly Pro Thr Leu Ser Phe Gln Leu Leu Asp Pro
370                 375                 380

Asn Met Lys Phe Arg Gln Leu Glu Ser Pro Asn Leu Arg Gln Leu Leu

```
                385                 390                 395                 400
            Ser Trp Ile Asp Leu Glu Tyr Asn His Pro Ile Phe Ile Val Glu
                            405                 410                 415

Asn Gly Trp Phe Val Ser Gly Thr Thr Lys Arg Asp Asp Ala Lys Tyr
                            420                 425                 430

Met Tyr Tyr Leu Lys Lys Phe Ile Met Glu Thr Leu Lys Ala Ile Arg
                            435                 440                 445

Leu Asp Gly Val Asp Val Ile Gly Tyr Thr Ala Trp Ser Leu Met Asp
                450                 455                 460

Gly Phe Glu Trp His Arg Gly Tyr Ser Ile Arg Arg Gly Leu Phe Tyr
            465                 470                 475                 480

Val Asp Phe Leu Ser Gln Asp Lys Glu Leu Leu Pro Lys Ser Ser Ala
                            485                 490                 495

Leu Phe Tyr Gln Lys Leu Ile Glu Asp Asn Gly Phe Pro Pro Leu Pro
                            500                 505                 510

Glu Asn Gln Pro Leu Glu Gly Thr Phe Pro Cys Asp Phe Ala Trp Gly
                            515                 520                 525

Val Val Asp Asn Tyr Val Gln Val Asp Thr Thr Leu Ser Gln Phe Thr
                530                 535                 540

Asp Pro Asn Val Tyr Leu Trp Asp Val His Ser Lys Arg Leu Ile
            545                 550                 555                 560

Lys Val Asp Gly Val Val Ala Lys Lys Arg Lys Pro Tyr Cys Val Asp
                            565                 570                 575

Phe Ser Ala Ile Arg Pro Gln Ile Thr Leu Leu Arg Glu Met Arg Val
                            580                 585                 590

Thr His Phe Arg Phe Ser Leu Asp Trp Ala Leu Ile Leu Pro Leu Gly
                            595                 600                 605

Asn Gln Thr Gln Val Asn His Thr Val Leu His Phe Tyr Arg Cys Met
                            610                 615                 620

Ile Ser Glu Leu Val His Ala Asn Ile Thr Pro Val Val Ala Leu Trp
            625                 630                 635                 640

Gln Pro Ala Ala Pro His Gln Gly Leu Pro His Ala Leu Ala Lys His
                            645                 650                 655

Gly Ala Trp Glu Asn Pro His Thr Ala Leu Ala Phe Ala Asp Tyr Ala
                            660                 665                 670

Asn Leu Cys Phe Lys Glu Leu Gly His Trp Val Asn Leu Trp Ile Thr
                            675                 680                 685

Met Asn Glu Pro Asn Thr Arg Asn Met Thr Tyr Arg Ala Gly His His
                690                 695                 700

Leu Leu Arg Ala His Ala Leu Ala Trp His Leu Tyr Asp Asp Lys Phe
            705                 710                 715                 720

Arg Ala Ala Gln Lys Gly Lys Ile Ser Ile Ala Leu Gln Ala Asp Trp
                            725                 730                 735

Ile Glu Pro Ala Cys Pro Phe Ser Gln Asn Asp Lys Glu Val Ala Glu
                            740                 745                 750

Arg Val Leu Glu Phe Asp Ile Gly Trp Leu Ala Glu Pro Ile Phe Gly
                            755                 760                 765

Ser Gly Asp Tyr Pro Arg Val Met Arg Asp Trp Leu Asn Gln Lys Asn
                770                 775                 780

Asn Phe Leu Leu Pro Tyr Phe Thr Glu Asp Glu Lys Lys Leu Val Arg
            785                 790                 795                 800

Gly Ser Phe Asp Phe Leu Ala Val Ser His Tyr Thr Thr Ile Leu Val
                            805                 810                 815
```

```
Asp Trp Glu Lys Glu Asp Pro Met Lys Tyr Asn Asp Tyr Leu Glu Val
            820                 825                 830

Gln Glu Met Thr Asp Ile Thr Trp Leu Asn Ser Pro Ser Gln Val Ala
            835                 840                 845

Val Val Pro Trp Gly Leu Arg Lys Val Leu Asn Trp Leu Arg Phe Lys
    850                 855                 860

Tyr Gly Asp Leu Pro Met Tyr Val Thr Ala Asn Gly Ile Asp Asp
865                 870                 875                 880

Pro His Ala Glu Gln Asp Ser Leu Arg Ile Tyr Tyr Ile Lys Asn Tyr
                885                 890                 895

Val Asn Glu Ala Leu Lys Ala Tyr Val Leu Asp Asp Ile Asn Leu Cys
            900                 905                 910

Gly Tyr Phe Ala Tyr Ser Leu Ser Asp Arg Ser Ala Pro Lys Ser Gly
            915                 920                 925

Phe Tyr Arg Tyr Ala Ala Asn Gln Phe Glu Pro Lys Pro Ser Met Lys
            930                 935                 940

His Tyr Arg Lys Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
            980                 985                 990

Phe Thr Phe Ile Ile Ser Leu Ala  Leu Ile Phe His Tyr  Ser Lys Lys
            995                 1000                1005

Gly Gln  Arg Ser Tyr Lys
    1010

<210> SEQ ID NO 232
<211> LENGTH: 209
<212> TYPE: PRT
<213> ORGANISM: Homo sapiens

<400> SEQUENCE: 232

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
```

-continued

```
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Phe Ala
        195                 200                 205

Ser

<210> SEQ ID NO 233
<211> LENGTH: 209
<212> TYPE: PRT
<213> ORGANISM: Homo sapiens

<400> SEQUENCE: 233

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Phe Glu
        195                 200                 205

Lys

<210> SEQ ID NO 234
<211> LENGTH: 42
<212> TYPE: PRT
<213> ORGANISM: Artificial
<220> FEATURE:
<223> OTHER INFORMATION: FGF21 Variant

<400> SEQUENCE: 234

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Lys
        35                  40
```

```
<210> SEQ ID NO 235
<211> LENGTH: 42
<212> TYPE: PRT
<213> ORGANISM: Artificial
<220> FEATURE:
<223> OTHER INFORMATION: FGF21 Variant

<400> SEQUENCE: 235

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Ser
        35                  40

<210> SEQ ID NO 236
<211> LENGTH: 42
<212> TYPE: PRT
<213> ORGANISM: Artificial
<220> FEATURE:
<223> OTHER INFORMATION: FGF21 Variant

<400> SEQUENCE: 236

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Ala Ser
        35                  40

<210> SEQ ID NO 237
<211> LENGTH: 42
<212> TYPE: PRT
<213> ORGANISM: Artificial
<220> FEATURE:
<223> OTHER INFORMATION: FGF21 Variant

<400> SEQUENCE: 237

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Tyr Ala Ser
        35                  40

<210> SEQ ID NO 238
<211> LENGTH: 42
<212> TYPE: PRT
<213> ORGANISM: Artificial
<220> FEATURE:
<223> OTHER INFORMATION: FGF21 Variant

<400> SEQUENCE: 238

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Gly Arg Ser Pro Ser Tyr Ala Ser
        35                  40

<210> SEQ ID NO 239
<211> LENGTH: 42
<212> TYPE: PRT
```

```
<213> ORGANISM: Artificial
<220> FEATURE:
<223> OTHER INFORMATION: FGF21 Variant

<400> SEQUENCE: 239

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Glu Gln Gly Arg Ser Pro Ser Tyr Ala Ser
        35                  40

<210> SEQ ID NO 240
<211> LENGTH: 42
<212> TYPE: PRT
<213> ORGANISM: Artificial
<220> FEATURE:
<223> OTHER INFORMATION: FGF21 Variant

<400> SEQUENCE: 240

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Leu
            20                  25                  30

Ser Gln Gly Arg Ser Pro Ser Tyr Ala Ser
        35                  40

<210> SEQ ID NO 241
<211> LENGTH: 43
<212> TYPE: PRT
<213> ORGANISM: Artificial
<220> FEATURE:
<223> OTHER INFORMATION: FGF21 Variant

<400> SEQUENCE: 241

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Thr Gly
            20                  25                  30

Pro Ser Gln Gly Arg Ser Pro Ser Tyr Ala Ser
        35                  40

<210> SEQ ID NO 242
<211> LENGTH: 42
<212> TYPE: PRT
<213> ORGANISM: Artificial
<220> FEATURE:
<223> OTHER INFORMATION: FGF21 Variant

<400> SEQUENCE: 242

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Leu Val Gly Pro
            20                  25                  30

Ser Gln Gly Arg Ser Pro Ser Tyr Ala Ser
        35                  40

<210> SEQ ID NO 243
<211> LENGTH: 42
<212> TYPE: PRT
<213> ORGANISM: Artificial
<220> FEATURE:
<223> OTHER INFORMATION: FGF21 Variant
```

<400> SEQUENCE: 243

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Met Val Gly Pro
            20                  25                  30

Ser Gln Gly Arg Ser Pro Ser Tyr Ala Ser
        35                  40

<210> SEQ ID NO 244
<211> LENGTH: 42
<212> TYPE: PRT
<213> ORGANISM: Artificial
<220> FEATURE:
<223> OTHER INFORMATION: FGF21 Variant

<400> SEQUENCE: 244

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Ser Met Val Gly Pro
            20                  25                  30

Ser Gln Gly Arg Ser Pro Ser Tyr Ala Ser
        35                  40

<210> SEQ ID NO 245
<211> LENGTH: 42
<212> TYPE: PRT
<213> ORGANISM: Artificial
<220> FEATURE:
<223> OTHER INFORMATION: FGF21 Variant

<400> SEQUENCE: 245

Pro Gly Leu Pro Pro Ala Leu Pro Glu Pro Pro Gly Ile Leu Ala Pro
1               5                   10                  15

Gln Pro Pro Asp Val Gly Ser Met Asp Pro Leu Ser Met Val Gly Pro
            20                  25                  30

Ser Gln Gly Arg Ser Pro Ser Tyr Ala Ser
        35                  40

<210> SEQ ID NO 246
<211> LENGTH: 42
<212> TYPE: PRT
<213> ORGANISM: Artificial
<220> FEATURE:
<223> OTHER INFORMATION: FGF21 Variant

<400> SEQUENCE: 246

Pro Gly Leu Pro Pro Ala Leu Pro Glu Pro Pro Gly Ile Leu Ala Pro
1               5                   10                  15

Gln Pro Pro Asp Val Asp Ser Ser Asp Pro Leu Ser Met Val Gly Pro
            20                  25                  30

Ser Gln Gly Arg Ser Pro Ser Tyr Ala Ser
        35                  40

<210> SEQ ID NO 247
<211> LENGTH: 42
<212> TYPE: PRT
<213> ORGANISM: Artificial
<220> FEATURE:
<223> OTHER INFORMATION: FGF21 Variant

<400> SEQUENCE: 247

-continued

Pro Gly Leu Pro Pro Ala Leu Pro Glu Pro Gly Ile Leu Ala Pro
1               5                   10                  15

Gln Pro Pro Asp Thr Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 248
<211> LENGTH: 42
<212> TYPE: PRT
<213> ORGANISM: Artificial
<220> FEATURE:
<223> OTHER INFORMATION: FGF21 Variant

<400> SEQUENCE: 248

Pro Gly Leu Pro Pro Ala Leu Pro Glu Pro Gly Ile Leu Ala Pro
1               5                   10                  15

Gln Pro Pro Glu Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 249
<211> LENGTH: 42
<212> TYPE: PRT
<213> ORGANISM: Artificial
<220> FEATURE:
<223> OTHER INFORMATION: FGF21 Variant

<400> SEQUENCE: 249

Pro Gly Leu Pro Pro Ala Leu Pro Glu Pro Gly Ile Leu Ala Pro
1               5                   10                  15

Gln Pro Leu Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 250
<211> LENGTH: 42
<212> TYPE: PRT
<213> ORGANISM: Artificial
<220> FEATURE:
<223> OTHER INFORMATION: FGF21 Variant

<400> SEQUENCE: 250

Pro Gly Leu Pro Pro Ala Leu Pro Glu Pro Gly Ile Leu Ala Pro
1               5                   10                  15

Ser Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 251
<211> LENGTH: 42
<212> TYPE: PRT
<213> ORGANISM: Artificial
<220> FEATURE:
<223> OTHER INFORMATION: FGF21 Variant

<400> SEQUENCE: 251

Pro Gly Leu Pro Pro Ala Leu Pro Glu Pro Gly Ile Leu Ala Ser
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 252
<211> LENGTH: 42
<212> TYPE: PRT
<213> ORGANISM: Artificial
<220> FEATURE:
<223> OTHER INFORMATION: FGF21 Variant

<400> SEQUENCE: 252

Pro Gly Leu Pro Pro Ala Leu Pro Glu Pro Pro Gly Ile Leu Phe Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 253
<211> LENGTH: 42
<212> TYPE: PRT
<213> ORGANISM: Artificial
<220> FEATURE:
<223> OTHER INFORMATION: FGF21 Variant

<400> SEQUENCE: 253

Pro Gly Leu Pro Pro Ala Leu Pro Glu Pro Pro Gly Ile Met Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 254
<211> LENGTH: 42
<212> TYPE: PRT
<213> ORGANISM: Artificial
<220> FEATURE:
<223> OTHER INFORMATION: FGF21 Variant

<400> SEQUENCE: 254

Pro Gly Leu Pro Pro Ala Leu Pro Glu Pro Pro Gly Asp Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 255
<211> LENGTH: 42
<212> TYPE: PRT
<213> ORGANISM: Artificial
<220> FEATURE:
<223> OTHER INFORMATION: FGF21 Variant

<400> SEQUENCE: 255

Pro Gly Leu Pro Pro Ala Leu Pro Glu Pro Pro Ser Ile Leu Ala Pro
1               5                   10                  15

Gln Pro Pro Asp Val Gly Ser Ser Asp Pro Leu Ser Met Val Gly Pro
            20                  25                  30

```
Ser Gln Gly Arg Ser Pro Ser Tyr Ala Ser
        35                  40
```

<210> SEQ ID NO 256
<211> LENGTH: 42
<212> TYPE: PRT
<213> ORGANISM: Artificial
<220> FEATURE:
<223> OTHER INFORMATION: FGF21 Variant

<400> SEQUENCE: 256

```
Pro Gly Leu Pro Pro Ala Leu Pro Glu Pro Glu Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40
```

<210> SEQ ID NO 257
<211> LENGTH: 42
<212> TYPE: PRT
<213> ORGANISM: Artificial
<220> FEATURE:
<223> OTHER INFORMATION: FGF21 Variant

<400> SEQUENCE: 257

```
Pro Gly Leu Pro Pro Ala Leu Pro Glu Leu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40
```

<210> SEQ ID NO 258
<211> LENGTH: 43
<212> TYPE: PRT
<213> ORGANISM: Artificial
<220> FEATURE:
<223> OTHER INFORMATION: FGF21 Variant

<400> SEQUENCE: 258

```
Pro Gly Leu Pro Pro Ala Leu Pro Glu His Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40
```

<210> SEQ ID NO 259
<211> LENGTH: 43
<212> TYPE: PRT
<213> ORGANISM: Artificial
<220> FEATURE:
<223> OTHER INFORMATION: FGF21 Variant

<400> SEQUENCE: 259

```
Pro Gly Leu Pro Pro Ala Leu Pro Glu Gly Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40
```

<210> SEQ ID NO 260
<211> LENGTH: 43
<212> TYPE: PRT
<213> ORGANISM: Artificial
<220> FEATURE:
<223> OTHER INFORMATION: FGF21 Variant

<400> SEQUENCE: 260

Pro Gly Leu Pro Pro Ala Leu Pro Glu Arg Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 261
<211> LENGTH: 43
<212> TYPE: PRT
<213> ORGANISM: Artificial
<220> FEATURE:
<223> OTHER INFORMATION: FGF21 Variant

<400> SEQUENCE: 261

Pro Gly Leu Pro Pro Ala Leu Pro Glu Leu Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 262
<211> LENGTH: 43
<212> TYPE: PRT
<213> ORGANISM: Artificial
<220> FEATURE:
<223> OTHER INFORMATION: FGF21 Variant

<400> SEQUENCE: 262

Pro Gly Leu Pro Pro Ala Leu Pro Glu Asp Pro Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 263
<211> LENGTH: 42
<212> TYPE: PRT
<213> ORGANISM: Artificial
<220> FEATURE:
<223> OTHER INFORMATION: FGF21 Variant

<400> SEQUENCE: 263

Pro Gly Leu Pro Pro Ala Glu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 264
<211> LENGTH: 42

```
<212> TYPE: PRT
<213> ORGANISM: Artificial
<220> FEATURE:
<223> OTHER INFORMATION: FGF21 Variant

<400> SEQUENCE: 264

Pro Gly Leu Pro Pro Glu Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 265
<211> LENGTH: 42
<212> TYPE: PRT
<213> ORGANISM: Artificial
<220> FEATURE:
<223> OTHER INFORMATION: FGF21 Variant

<400> SEQUENCE: 265

Pro Gly Leu Val Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 266
<211> LENGTH: 42
<212> TYPE: PRT
<213> ORGANISM: Artificial
<220> FEATURE:
<223> OTHER INFORMATION: FGF21 Variant

<400> SEQUENCE: 266

Pro Gly Met Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 267
<211> LENGTH: 42
<212> TYPE: PRT
<213> ORGANISM: Artificial
<220> FEATURE:
<223> OTHER INFORMATION: FGF21 Variant

<400> SEQUENCE: 267

Pro Pro Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 268
<211> LENGTH: 42
<212> TYPE: PRT
<213> ORGANISM: Artificial
<220> FEATURE:
```

<223> OTHER INFORMATION: FGF21 Variant

<400> SEQUENCE: 268

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Lys
        35                  40

<210> SEQ ID NO 269
<211> LENGTH: 42
<212> TYPE: PRT
<213> ORGANISM: Artificial
<220> FEATURE:
<223> OTHER INFORMATION: FGF21 Variant

<400> SEQUENCE: 269

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Glu Lys
        35                  40

<210> SEQ ID NO 270
<211> LENGTH: 42
<212> TYPE: PRT
<213> ORGANISM: Artificial
<220> FEATURE:
<223> OTHER INFORMATION: FGF21 Variant

<400> SEQUENCE: 270

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Phe Glu Lys
        35                  40

<210> SEQ ID NO 271
<211> LENGTH: 42
<212> TYPE: PRT
<213> ORGANISM: Artificial
<220> FEATURE:
<223> OTHER INFORMATION: FGF21 Variant

<400> SEQUENCE: 271

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Val Arg Ser Pro Ser Phe Glu Lys
        35                  40

<210> SEQ ID NO 272
<211> LENGTH: 42
<212> TYPE: PRT
<213> ORGANISM: Artificial
<220> FEATURE:
<223> OTHER INFORMATION: FGF21 Variant

<400> SEQUENCE: 272

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Ala Val Arg Ser Pro Ser Phe Glu Lys
        35                  40

<210> SEQ ID NO 273
<211> LENGTH: 42
<212> TYPE: PRT
<213> ORGANISM: Artificial
<220> FEATURE:
<223> OTHER INFORMATION: FGF21 Variant

<400> SEQUENCE: 273

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Glu Ala Val Arg Ser Pro Ser Phe Glu Lys
        35                  40

<210> SEQ ID NO 274
<211> LENGTH: 42
<212> TYPE: PRT
<213> ORGANISM: Artificial
<220> FEATURE:
<223> OTHER INFORMATION: FGF21 Variant

<400> SEQUENCE: 274

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Thr Gly
            20                  25                  30

Leu Glu Ala Val Arg Ser Pro Phe Glu Lys
        35                  40

<210> SEQ ID NO 275
<211> LENGTH: 43
<212> TYPE: PRT
<213> ORGANISM: Artificial
<220> FEATURE:
<223> OTHER INFORMATION: FGF21 Variant

<400> SEQUENCE: 275

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Thr Gly
            20                  25                  30

Leu Glu Ala Val Arg Ser Pro Ser Phe Glu Lys
        35                  40

<210> SEQ ID NO 276
<211> LENGTH: 43
<212> TYPE: PRT
<213> ORGANISM: Artificial
<220> FEATURE:
<223> OTHER INFORMATION: FGF21 Variant

<400> SEQUENCE: 276

Pro Gly Leu Pro Pro Ala Leu Pro Glu Pro Pro Gly Ile Leu Ala Pro
1               5                   10                  15

```
Gln Pro Pro Asp Val Gly Ser Ser Asp Pro Leu Gly Leu Val Thr Gly
            20                  25                  30

Leu Glu Ala Val Arg Ser Pro Ser Phe Glu Lys
        35                  40
```

<210> SEQ ID NO 277
<211> LENGTH: 43
<212> TYPE: PRT
<213> ORGANISM: Artificial
<220> FEATURE:
<223> OTHER INFORMATION: FGF21 Variant

<400> SEQUENCE: 277

```
Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Gly Leu Val Thr Gly
            20                  25                  30

Leu Glu Ala Val Arg Ser Pro Ser Phe Glu Lys
        35                  40
```

<210> SEQ ID NO 278
<211> LENGTH: 43
<212> TYPE: PRT
<213> ORGANISM: Artificial
<220> FEATURE:
<223> OTHER INFORMATION: FGF21 Variant

<400> SEQUENCE: 278

```
Pro Gly Leu Pro Pro Ala Leu Pro Glu Pro Pro Gly Ile Leu Ala Pro
1               5                   10                  15

Gln Pro Pro Asp Val Gly Ser Met Asp Pro Phe Gly Leu Val Thr Gly
            20                  25                  30

Leu Glu Ala Val Arg Ser Pro Ser Phe Glu Lys
        35                  40
```

<210> SEQ ID NO 279
<211> LENGTH: 43
<212> TYPE: PRT
<213> ORGANISM: Artificial
<220> FEATURE:
<223> OTHER INFORMATION: FGF21 Variant

<400> SEQUENCE: 279

```
Pro Gly Leu Pro Pro Ala Leu Pro Glu Pro Pro Gly Ile Leu Ala Pro
1               5                   10                  15

Gln Pro Pro Asp Val Asp Ser Met Asp Pro Phe Gly Leu Val Thr Gly
            20                  25                  30

Leu Glu Ala Val Arg Ser Pro Ser Phe Glu Lys
        35                  40
```

<210> SEQ ID NO 280
<211> LENGTH: 43
<212> TYPE: PRT
<213> ORGANISM: Artificial
<220> FEATURE:
<223> OTHER INFORMATION: FGF21 Variant

<400> SEQUENCE: 280

```
Pro Gly Leu Pro Pro Ala Leu Pro Glu Pro Pro Gly Ile Leu Ala Pro
1               5                   10                  15

Gln Pro Pro Asp Thr Asp Ser Met Asp Pro Phe Gly Leu Val Thr Gly
            20                  25                  30
```

Leu Glu Ala Val Arg Ser Pro Ser Phe Glu Lys
        35                  40

<210> SEQ ID NO 281
<211> LENGTH: 43
<212> TYPE: PRT
<213> ORGANISM: Artificial
<220> FEATURE:
<223> OTHER INFORMATION: FGF21 Variant

<400> SEQUENCE: 281

Pro Gly Leu Pro Pro Ala Leu Pro Glu Pro Pro Gly Ile Leu Ala Pro
1               5                   10                  15

Gln Pro Pro Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 282
<211> LENGTH: 43
<212> TYPE: PRT
<213> ORGANISM: Artificial
<220> FEATURE:
<223> OTHER INFORMATION: FGF21 Variant

<400> SEQUENCE: 282

Pro Gly Leu Pro Pro Ala Leu Pro Glu Pro Pro Gly Ile Leu Ala Pro
1               5                   10                  15

Gln Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 283
<211> LENGTH: 43
<212> TYPE: PRT
<213> ORGANISM: Artificial
<220> FEATURE:
<223> OTHER INFORMATION: FGF21 Variant

<400> SEQUENCE: 283

Pro Gly Leu Pro Pro Ala Leu Pro Glu Pro Pro Gly Ile Leu Ala Pro
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 284
<211> LENGTH: 43
<212> TYPE: PRT
<213> ORGANISM: Artificial
<220> FEATURE:
<223> OTHER INFORMATION: FGF21 Variant

<400> SEQUENCE: 284

Pro Gly Leu Pro Pro Ala Leu Pro Glu Pro Pro Gly Ile Leu Ala Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 285
<211> LENGTH: 43
<212> TYPE: PRT
<213> ORGANISM: Artificial
<220> FEATURE:
<223> OTHER INFORMATION: FGF21 Variant

<400> SEQUENCE: 285

Pro Gly Leu Pro Pro Ala Leu Pro Glu Pro Pro Gly Ile Leu Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 286
<211> LENGTH: 43
<212> TYPE: PRT
<213> ORGANISM: Artificial
<220> FEATURE:
<223> OTHER INFORMATION: FGF21 Variant

<400> SEQUENCE: 286

Pro Gly Leu Pro Pro Ala Leu Pro Glu Pro Pro Gly Ile Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 287
<211> LENGTH: 43
<212> TYPE: PRT
<213> ORGANISM: Artificial
<220> FEATURE:
<223> OTHER INFORMATION: FGF21 Variant

<400> SEQUENCE: 287

Pro Gly Leu Pro Pro Ala Leu Pro Glu Pro Pro Gly Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 288
<211> LENGTH: 43
<212> TYPE: PRT
<213> ORGANISM: Artificial
<220> FEATURE:
<223> OTHER INFORMATION: FGF21 Variant

<400> SEQUENCE: 288

Pro Gly Leu Pro Pro Ala Leu Pro Glu Pro Pro Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 289

<211> LENGTH: 43
<212> TYPE: PRT
<213> ORGANISM: Artificial
<220> FEATURE:
<223> OTHER INFORMATION: FGF21 Variant

<400> SEQUENCE: 289

Pro Gly Leu Pro Pro Ala Leu Pro Glu Pro Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 290
<211> LENGTH: 43
<212> TYPE: PRT
<213> ORGANISM: Artificial
<220> FEATURE:
<223> OTHER INFORMATION: FGF21 Variant

<400> SEQUENCE: 290

Pro Gly Leu Pro Pro Ala Leu Pro Glu Leu Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 291
<211> LENGTH: 44
<212> TYPE: PRT
<213> ORGANISM: Artificial
<220> FEATURE:
<223> OTHER INFORMATION: FGF21 Variant

<400> SEQUENCE: 291

Pro Gly Leu Pro Pro Ala Leu Pro Glu His Leu Glu Ser Asp Met Phe
1               5                   10                  15

Ser Ser Pro Leu Glu Thr Asp Ser Met Asp Pro Phe Gly Leu Val Thr
            20                  25                  30

Gly Leu Glu Ala Val Arg Ser Pro Ser Phe Glu Lys
        35                  40

<210> SEQ ID NO 292
<211> LENGTH: 45
<212> TYPE: PRT
<213> ORGANISM: Artificial
<220> FEATURE:
<223> OTHER INFORMATION: FGF21 Variant

<400> SEQUENCE: 292

Pro Gly Leu Pro Pro Ala Leu Pro Glu Gly His Leu Glu Ser Asp Met
1               5                   10                  15

Phe Ser Ser Pro Leu Glu Thr Asp Ser Met Asp Pro Phe Gly Leu Val
            20                  25                  30

Thr Gly Leu Glu Ala Val Arg Ser Pro Ser Phe Glu Lys
        35                  40                  45

<210> SEQ ID NO 293
<211> LENGTH: 46
<212> TYPE: PRT
<213> ORGANISM: Artificial

<220> FEATURE:
<223> OTHER INFORMATION: FGF21 Variant

<400> SEQUENCE: 293

Pro Gly Leu Pro Pro Ala Leu Pro Glu Arg Gly His Leu Glu Ser Asp
1               5                   10                  15

Met Phe Ser Ser Pro Leu Glu Thr Asp Ser Met Asp Pro Phe Gly Leu
            20                  25                  30

Val Thr Gly Leu Glu Ala Val Arg Ser Pro Ser Phe Glu Lys
        35                  40                  45

<210> SEQ ID NO 294
<211> LENGTH: 47
<212> TYPE: PRT
<213> ORGANISM: Artificial
<220> FEATURE:
<223> OTHER INFORMATION: FGF21 Variant

<400> SEQUENCE: 294

Pro Gly Leu Pro Pro Ala Leu Pro Glu Leu Arg Gly His Leu Glu Ser
1               5                   10                  15

Asp Met Phe Ser Ser Pro Leu Glu Thr Asp Ser Met Asp Pro Phe Gly
            20                  25                  30

Leu Val Thr Gly Leu Glu Ala Val Arg Ser Pro Ser Phe Glu Lys
        35                  40                  45

<210> SEQ ID NO 295
<211> LENGTH: 48
<212> TYPE: PRT
<213> ORGANISM: Artificial
<220> FEATURE:
<223> OTHER INFORMATION: FGF21 Variant

<400> SEQUENCE: 295

Pro Gly Leu Pro Pro Ala Leu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 296
<211> LENGTH: 48
<212> TYPE: PRT
<213> ORGANISM: Artificial
<220> FEATURE:
<223> OTHER INFORMATION: FGF21 Variant

<400> SEQUENCE: 296

Pro Gly Leu Pro Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 297
<211> LENGTH: 48
<212> TYPE: PRT
<213> ORGANISM: Artificial
<220> FEATURE:
<223> OTHER INFORMATION: FGF21 Variant

```
<400> SEQUENCE: 297

Pro Gly Leu Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 298
<211> LENGTH: 48
<212> TYPE: PRT
<213> ORGANISM: Artificial
<220> FEATURE:
<223> OTHER INFORMATION: FGF21 Variant

<400> SEQUENCE: 298

Pro Gly Leu Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 299
<211> LENGTH: 48
<212> TYPE: PRT
<213> ORGANISM: Artificial
<220> FEATURE:
<223> OTHER INFORMATION: FGF21 Variant

<400> SEQUENCE: 299

Pro Gly Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 300
<211> LENGTH: 48
<212> TYPE: PRT
<213> ORGANISM: Artificial
<220> FEATURE:
<223> OTHER INFORMATION: FGF21 Variant

<400> SEQUENCE: 300

Pro Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 301
<211> LENGTH: 48
<212> TYPE: PRT
<213> ORGANISM: Artificial
<220> FEATURE:
<223> OTHER INFORMATION: FGF19 Variant

<400> SEQUENCE: 301

Leu Pro Met Val Pro Glu Glu Pro Glu Asp Leu Arg Gly His Leu Glu
```

```
                1               5                  10                 15
Ser Asp Met Phe Ser Ser Pro Leu Glu Thr Asp Ser Met Asp Pro Phe
                20                 25                 30

Gly Leu Val Thr Gly Leu Glu Ala Val Arg Ser Pro Ser Phe Ala Lys
            35                 40                 45
```

<210> SEQ ID NO 302
<211> LENGTH: 48
<212> TYPE: PRT
<213> ORGANISM: Artificial
<220> FEATURE:
<223> OTHER INFORMATION: FGF19 Variant

<400> SEQUENCE: 302

```
Leu Pro Met Val Pro Glu Glu Pro Glu Asp Leu Arg Gly His Leu Glu
1               5                  10                 15

Ser Asp Met Phe Ser Ser Pro Leu Glu Thr Asp Ser Met Asp Pro Phe
                20                 25                 30

Gly Leu Val Thr Gly Leu Ser Ala Val Arg Ser Pro Ser Phe Glu Lys
            35                 40                 45
```

<210> SEQ ID NO 303
<211> LENGTH: 48
<212> TYPE: PRT
<213> ORGANISM: Artificial
<220> FEATURE:
<223> OTHER INFORMATION: FGF19 Variant

<400> SEQUENCE: 303

```
Leu Pro Met Val Pro Glu Glu Pro Glu Asp Leu Arg Gly His Leu Glu
1               5                  10                 15

Ser Asp Met Phe Ser Ser Pro Leu Glu Thr Asp Ser Met Asp Pro Phe
                20                 25                 30

Gly Met Val Thr Gly Leu Glu Ala Val Arg Ser Pro Ser Phe Glu Lys
            35                 40                 45
```

<210> SEQ ID NO 304
<211> LENGTH: 48
<212> TYPE: PRT
<213> ORGANISM: Artificial
<220> FEATURE:
<223> OTHER INFORMATION: FGF19 Variant

<400> SEQUENCE: 304

```
Leu Pro Met Val Pro Glu Glu Pro Glu Asp Leu Arg Gly His Leu Glu
1               5                  10                 15

Ser Asp Leu Phe Ser Ser Pro Leu Glu Thr Asp Ser Met Asp Pro Phe
                20                 25                 30

Gly Leu Val Thr Gly Leu Glu Ala Val Arg Ser Pro Ser Phe Glu Lys
            35                 40                 45
```

<210> SEQ ID NO 305
<211> LENGTH: 48
<212> TYPE: PRT
<213> ORGANISM: Artificial
<220> FEATURE:
<223> OTHER INFORMATION: FGF19 Variant

<400> SEQUENCE: 305

```
Leu Pro Met Val Pro Glu Glu Pro Glu Asp Leu Arg Gly His Pro Glu
1               5                  10                 15

Ser Asp Met Phe Ser Ser Pro Leu Glu Thr Asp Ser Met Asp Pro Phe
```

20                  25                  30

Gly Leu Val Thr Gly Leu Glu Ala Val Arg Ser Pro Ser Phe Glu Lys
         35                  40                  45

<210> SEQ ID NO 306
<211> LENGTH: 47
<212> TYPE: PRT
<213> ORGANISM: Artificial
<220> FEATURE:
<223> OTHER INFORMATION: FGF19 Variant

<400> SEQUENCE: 306

Leu Pro Met Val Pro Glu Glu Pro Glu Asp Leu Arg His Leu Glu Ser
1               5                   10                  15

Asp Met Phe Ser Ser Pro Leu Glu Thr Asp Ser Met Asp Pro Phe Gly
                20                  25                  30

Leu Val Thr Gly Leu Glu Ala Val Arg Ser Pro Ser Phe Glu Lys
         35                  40                  45

<210> SEQ ID NO 307
<211> LENGTH: 47
<212> TYPE: PRT
<213> ORGANISM: Artificial
<220> FEATURE:
<223> OTHER INFORMATION: FGF19 Variant

<400> SEQUENCE: 307

Leu Pro Met Val Pro Glu Glu Pro Glu Asp Leu Gly His Leu Glu Ser
1               5                   10                  15

Asp Met Phe Ser Ser Pro Leu Glu Thr Asp Ser Met Asp Pro Phe Gly
                20                  25                  30

Leu Val Thr Gly Leu Glu Ala Val Arg Ser Pro Ser Phe Glu Lys
         35                  40                  45

<210> SEQ ID NO 308
<211> LENGTH: 48
<212> TYPE: PRT
<213> ORGANISM: Artificial
<220> FEATURE:
<223> OTHER INFORMATION: FGF19 Variant

<400> SEQUENCE: 308

Leu Pro Met Val Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys
         35                  40                  45

<210> SEQ ID NO 309
<211> LENGTH: 48
<212> TYPE: PRT
<213> ORGANISM: Artificial
<220> FEATURE:
<223> OTHER INFORMATION: FGF19 Variant

<400> SEQUENCE: 309

Leu Pro Met Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
                20                  25                  30

Gly Leu Val Thr Gly Leu Glu Ala Val Arg Ser Pro Ser Phe Glu Lys 35                  40                  45

<210> SEQ ID NO 310
<211> LENGTH: 48
<212> TYPE: PRT
<213> ORGANISM: Artificial
<220> FEATURE:
<223> OTHER INFORMATION: FGF19 Variant

<400> SEQUENCE: 310

Leu Pro Leu Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 311
<211> LENGTH: 48
<212> TYPE: PRT
<213> ORGANISM: Artificial
<220> FEATURE:
<223> OTHER INFORMATION: FGF19 Variant

<400> SEQUENCE: 311

Leu Gly Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 312
<211> LENGTH: 187
<212> TYPE: PRT
<213> ORGANISM: Artificial
<220> FEATURE:
<223> OTHER INFORMATION: Chimeric Protein

<400> SEQUENCE: 312

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 313
<211> LENGTH: 187
<212> TYPE: PRT
<213> ORGANISM: Artificial
<220> FEATURE:
<223> OTHER INFORMATION: Chimeric Protein

<400> SEQUENCE: 313

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 314
<211> LENGTH: 187
<212> TYPE: PRT
<213> ORGANISM: Artificial
<220> FEATURE:
<223> OTHER INFORMATION: Chimeric Protein

<400> SEQUENCE: 314

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg

```
                        85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Val Pro
        130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 315
<211> LENGTH: 187
<212> TYPE: PRT
<213> ORGANISM: Artificial
<220> FEATURE:
<223> OTHER INFORMATION: Chimeric Protein

<400> SEQUENCE: 315

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 316
<211> LENGTH: 187
<212> TYPE: PRT
<213> ORGANISM: Artificial
<220> FEATURE:
<223> OTHER INFORMATION: Chimeric Protein

<400> SEQUENCE: 316

His Pro Ile Pro Asp Ser Ser Pro Leu Leu Gln Phe Gly Gly Gln Val
1               5                   10                  15
```

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 317
<211> LENGTH: 187
<212> TYPE: PRT
<213> ORGANISM: Artificial
<220> FEATURE:
<223> OTHER INFORMATION: Chimeric Protein

<400> SEQUENCE: 317

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

```
<210> SEQ ID NO 318
<211> LENGTH: 187
<212> TYPE: PRT
<213> ORGANISM: Artificial
<220> FEATURE:
<223> OTHER INFORMATION: Chimeric Protein

<400> SEQUENCE: 318

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
                180                 185

<210> SEQ ID NO 319
<211> LENGTH: 186
<212> TYPE: PRT
<213> ORGANISM: Artificial
<220> FEATURE:
<223> OTHER INFORMATION: Chimeric Protein

<400> SEQUENCE: 319

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125
```

```
Ala Pro Arg Gly Pro Ala Arg Phe Leu Pro Leu Pro Gly Leu Pro Pro
    130                 135                 140

Ala Leu Pro Glu Pro Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 320
<211> LENGTH: 185
<212> TYPE: PRT
<213> ORGANISM: Artificial
<220> FEATURE:
<223> OTHER INFORMATION: Chimeric Protein

<400> SEQUENCE: 320

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
            180                 185

<210> SEQ ID NO 321
<211> LENGTH: 184
<212> TYPE: PRT
<213> ORGANISM: Artificial
<220> FEATURE:
<223> OTHER INFORMATION: Chimeric Protein

<400> SEQUENCE: 321

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
```

```
            50                  55                  60
Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
                130                 135                 140

Ala Leu Pro Glu Pro His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
                180

<210> SEQ ID NO 322
<211> LENGTH: 183
<212> TYPE: PRT
<213> ORGANISM: Artificial
<220> FEATURE:
<223> OTHER INFORMATION: Chimeric Protein

<400> SEQUENCE: 322

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
                 35                  40                  45

Pro Glu Ser Leu Leu Gln Leu Lys Ala Leu Lys Pro Gly Val Ile Gln
             50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
                130                 135                 140

Ala Leu Pro Glu Pro Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
                180

<210> SEQ ID NO 323
<211> LENGTH: 182
<212> TYPE: PRT
<213> ORGANISM: Artificial
<220> FEATURE:
<223> OTHER INFORMATION: Chimeric Protein
```

<400> SEQUENCE: 323

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Glu Ser Asp Met Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180
```

<210> SEQ ID NO 324
<211> LENGTH: 182
<212> TYPE: PRT
<213> ORGANISM: Artificial
<220> FEATURE:
<223> OTHER INFORMATION: Chimeric Protein

<400> SEQUENCE: 324

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Ser Asp Met Phe Ser Ser Pro Leu Glu Thr
145                 150                 155                 160
```

```
Asp Ser Met Asp Pro Phe Gly Leu Val Thr Gly Leu Glu Ala Val Arg
                165                 170                 175
Ser Pro Ser Phe Glu Lys
            180

<210> SEQ ID NO 325
<211> LENGTH: 182
<212> TYPE: PRT
<213> ORGANISM: Artificial
<220> FEATURE:
<223> OTHER INFORMATION: Chimeric Protein

<400> SEQUENCE: 325

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Asp Met Phe Ser Ser Pro Leu Glu Thr
145                 150                 155                 160
Asp Ser Met Asp Pro Phe Gly Leu Val Thr Gly Leu Glu Ala Val Arg
                165                 170                 175
Ser Pro Ser Phe Glu Lys
            180

<210> SEQ ID NO 326
<211> LENGTH: 182
<212> TYPE: PRT
<213> ORGANISM: Artificial
<220> FEATURE:
<223> OTHER INFORMATION: Chimeric Protein

<400> SEQUENCE: 326

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
```

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Met Phe Ser Ser Pro Leu Glu Thr
145                 150                 155                 160

Asp Ser Met Asp Pro Phe Gly Leu Val Thr Gly Leu Glu Ala Val Arg
            165                 170                 175

Ser Pro Ser Phe Glu Lys
            180

<210> SEQ ID NO 327
<211> LENGTH: 182
<212> TYPE: PRT
<213> ORGANISM: Artificial
<220> FEATURE:
<223> OTHER INFORMATION: Chimeric Protein

<400> SEQUENCE: 327

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Phe Ser Ser Pro Leu Glu Thr
145                 150                 155                 160

Asp Ser Met Asp Pro Phe Gly Leu Val Thr Gly Leu Glu Ala Val Arg
            165                 170                 175

Ser Pro Ser Phe Glu Lys
            180

<210> SEQ ID NO 328
<211> LENGTH: 182
<212> TYPE: PRT
<213> ORGANISM: Artificial
<220> FEATURE:
<223> OTHER INFORMATION: Chimeric Protein

<400> SEQUENCE: 328

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His

```
                20                  25                  30
Leu Glu Ile Arg Glu Asp Gly Thr Val Gly Gly Ala Ala Asp Gln Ser
            35                  40                  45
Pro Glu Ser Leu Leu Gln Leu Lys Ala Leu Lys Pro Gly Val Ile Gln
        50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Ser Ser Pro Leu Glu Thr
145                 150                 155                 160
Asp Ser Met Asp Pro Phe Gly Leu Val Thr Gly Leu Glu Ala Val Arg
                165                 170                 175
Ser Pro Ser Phe Glu Lys
            180

<210> SEQ ID NO 329
<211> LENGTH: 182
<212> TYPE: PRT
<213> ORGANISM: Artificial
<220> FEATURE:
<223> OTHER INFORMATION: Chimeric Protein

<400> SEQUENCE: 329

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
                20                  25                  30
Leu Glu Ile Arg Glu Asp Gly Thr Val Gly Gly Ala Ala Asp Gln Ser
            35                  40                  45
Pro Glu Ser Leu Leu Gln Leu Lys Ala Leu Lys Pro Gly Val Ile Gln
        50                  55                  60
Ile Leu Gly Val Lys Thr Ser Arg Phe Leu Cys Met Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Ser Pro Leu Glu Thr
145                 150                 155                 160
Asp Ser Met Asp Pro Phe Gly Leu Val Thr Gly Leu Glu Ala Val Arg
                165                 170                 175
Ser Pro Ser Phe Glu Lys
            180
```

```
<210> SEQ ID NO 330
<211> LENGTH: 182
<212> TYPE: PRT
<213> ORGANISM: Artificial
<220> FEATURE:
<223> OTHER INFORMATION: Chimeric Protein

<400> SEQUENCE: 330

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 331
<211> LENGTH: 182
<212> TYPE: PRT
<213> ORGANISM: Artificial
<220> FEATURE:
<223> OTHER INFORMATION: Chimeric Protein

<400> SEQUENCE: 331

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125
```

```
Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 332
<211> LENGTH: 182
<212> TYPE: PRT
<213> ORGANISM: Artificial
<220> FEATURE:
<223> OTHER INFORMATION: Chimeric Protein

<400> SEQUENCE: 332

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 333
<211> LENGTH: 182
<212> TYPE: PRT
<213> ORGANISM: Artificial
<220> FEATURE:
<223> OTHER INFORMATION: Chimeric Protein

<400> SEQUENCE: 333

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60
```

```
Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Asp Ser Met Asp Pro Phe Gly Leu Val Thr Gly Leu Glu Ala Val Arg
                165                 170                 175

Ser Pro Ser Phe Glu Lys
            180
```

```
<210> SEQ ID NO 334
<211> LENGTH: 182
<212> TYPE: PRT
<213> ORGANISM: Artificial
<220> FEATURE:
<223> OTHER INFORMATION: Chimeric Protein

<400> SEQUENCE: 334

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Phe Gly Leu Val Thr Gly Leu Glu Ala Val Arg
                165                 170                 175

Ser Pro Ser Phe Glu Lys
            180
```

```
<210> SEQ ID NO 335
<211> LENGTH: 182
<212> TYPE: PRT
<213> ORGANISM: Artificial
<220> FEATURE:
<223> OTHER INFORMATION: Chimeric Protein
```

```
<400> SEQUENCE: 335

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Gly Leu Val Thr Gly Leu Glu Ala Val Arg
                165                 170                 175

Ser Pro Ser Phe Glu Lys
            180

<210> SEQ ID NO 336
<211> LENGTH: 182
<212> TYPE: PRT
<213> ORGANISM: Artificial
<220> FEATURE:
<223> OTHER INFORMATION: Chimeric Protein

<400> SEQUENCE: 336

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160
```

-continued

```
Gly Ser Ser Asp Pro Leu Ser Leu Val Thr Gly Leu Glu Ala Val Arg
                165                 170                 175
Ser Pro Ser Phe Glu Lys
            180
```

FGF21 PROTEIN WITH ENHANCED BINDING AFFINITY FOR β-KLOTHO FOR THE TREATMENT OF TYPE II DIABETES, OBESITY, AND RELATED METABOLIC DISORDERS

This application is a continuation of U.S. patent application Ser. No. 13/784,289 filed Mar. 4, 2013, now issued as U.S. Pat. No. 9,475,856, which claims the benefit of U.S. Provisional Patent Application Ser. No. 61/605,961 filed Mar. 2, 2012, which is hereby incorporated by reference in its entirety.

This invention was made with government support under DE13686, DK077276, AG019712, DK091392, and DK067158 awarded by the National Institutes of Health. The Government has certain rights in the invention.

FIELD OF THE INVENTION

This invention relates to chimeric FGF21 proteins and their use for the treatment of diabetes, obesity, and related metabolic disorders.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet N° 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet N° 311, January 2011). Until the end of the $20^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet N° 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet N° 312, January 2011). Diabetic neuropathy, which affects up to half of all patients with diabetes worldwide (World Health Organization, Diabetes Fact Sheet N° 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414 (6865):821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®), which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356(24):2457-2471 (2007)). Of all diabetic complications, cardiovascular disease is the main cause of morbidity and mortality in patients with diabetes (World Health Organization, Diabetes Fact Sheet N° 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new anti-diabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6):1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12): 6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6):1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6):1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21," *Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21 therapeutics.

The present invention overcomes these and other deficiencies in the art.

SUMMARY OF THE INVENTION

One aspect of the present invention relates to a chimeric protein that includes an N-terminus coupled to a C-terminus. The N-terminus includes an N-terminal portion of fibroblast growth factor 21 ("FGF21") having a core domain and the C-terminus includes a C-terminal portion of fibroblast growth factor 19 ("FGF19"), where either (i) the N-terminal portion of FGF21 comprises at least one amino acid residue substitution to increase stability of the FGF21 core domain compared to the wild type FGF21; (ii) the C-terminal portion of FGF19 begins at a residue corresponding to any one of residues 169 to 204 of SEQ ID NO:1 and comprises amino acid residues TGLEAV(R/N)SPSFEK (SEQ ID NO: 49); or (iii) both (i) and (ii).

Another aspect of the present invention relates to a pharmaceutical composition that includes a chimeric protein according to the present invention and a pharmaceutically acceptable carrier.

Another aspect of the present invention relates to a method of treating a subject suffering from diabetes, obesity, or metabolic syndrome. This method includes selecting a subject suffering from diabetes, obesity, or metabolic syndrome and administering to this selected subject a therapeutically effective amount of a chimeric protein according to the present invention.

Another aspect of the present invention relates to a method of treating a subject in need of increased FGF21-βKlotho-FGF receptor ("FGFR") complex formation. This method includes selecting a subject in need of increased FGF21-βKlotho-FGFR complex formation and administering to the selected subject a chimeric FGF21 protein, where the chimeric FGF21 protein comprises an FGF21 core domain and a C-terminal portion of FGF19, thereby treating a subject in need of increased FGF21-βKlotho-FGFR complex formation.

Yet another aspect of the present invention relates to a method of causing increased FGF21 receptor agonist-βKlotho-FGFR complex formation. This method comprises providing a cell comprising βKlotho and an FGFR and providing an FGF21 receptor agonist, where the agonist comprises a chimeric protein comprising a C-terminal portion of FGF19. This method also includes contacting the cell and the FGF21 receptor agonist under conditions effective to cause increased FGF21 receptor agonist-βKlotho-FGFR complex formation relative to contacting the cell with FGF21 alone, where the FGF21 has a core domain.

A further aspect of the present invention relates to a method of screening for compounds with enhanced binding affinity for βKlotho suitable for fusion to the C-terminus of an N-terminal portion of FGF21 to generate an FGF21 agonist. The method includes providing FGF21, providing βKlotho, and providing one or more candidate compounds; combining the FGF21, the βKlotho, and the candidate compounds under conditions effective for FGF21 and βKlotho to form a binary complex if present by themselves; and identifying the candidate compounds which diminish binary complex formation, compared to when the candidate compound is absent, as being potentially suitable for fusion to the C-terminus of an N-terminal portion of FGF21 to generate an FGF21 agonist.

Yet a further aspect of the present invention relates to a method of screening for compounds with enhanced binding affinity for the βKlotho-FGFR complex suitable for treatment of diabetes, obesity, or related metabolic disorders. This method includes providing FGF21, providing a binary βKlotho-FGFR complex, and providing one or more candidate compounds. This method also includes combining the FGF21, the binary βKlotho-FGFR complex, and the candidate compounds under conditions effective for the FGF21 and the βKlotho-FGFR complex to form a ternary complex if present by themselves and identifying the candidate compounds which diminish ternary complex formation compared to when the candidate compound is absent as being potentially suitable for treatment of diabetes, obesity, or related metabolic disorders.

FGF21 depends on the co-receptor βKlotho to activate its cognate FGFR (FGFR1c) in its target tissues including white adipose tissue (Ogawa et al., "βKlotho is Required for Metabolic Activity of Fibroblast Growth Factor 21," *Proc Natl Acad Sci USA* 104(18):7432-7437 (2007); Ding et al., "βKlotho is Required for Fibroblast Growth Factor 21 Effects on Growth and Metabolism," *Cell Metab* 16:387-393 (2012), which are hereby incorporated by reference in their entirety). In the course of deciphering the molecular details of how FGF21 forms a signaling complex on the cell surface with FGFR1c and βKlotho, two discoveries were made that provided the basis for the rational design of an FGF21 agonist. It was found that βKlotho promotes binding of FGF21 to its cognate FGFR by engaging ligand and receptor simultaneously through two distinct binding sites (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). βKlotho plays the same role in promoting binding of FGF19, an endocrine regulator of bile acid homeostasis, to its cognate FGFR (Goetz et al., "Klotho Coreceptors Inhibit Signaling by Paracrine Fibroblast Growth Factor 8 Subfamily Ligands,"*Mol Cell Biol* 32:1944-1954 (2012), which is hereby incorporated by reference in its entirety). The binding site for βKlotho was mapped on FGF21 and FGF19 to the C-terminal region of each ligand that follows the β-trefoil core domain (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). In the course of these studies, it was found that the C-terminal tail peptides of FGF21 and FGF19 share a common binding site on βKlotho, and that the C-terminal tail of FGF19 binds tighter than the C-terminal tail of FGF21 to this site (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). As described herein, chimeric FGF21 proteins were made in which C-terminal sequences in FGF21 were replaced with the corresponding sequences of FGF19, which was found to confer greater binding affinity of βKlotho to the chimeras, and, hence, enhance agonistic properties.

In another approach of engineering an FGF21 agonist, residues in the β-trefoil core domain of FGF21 were mutated in order to increase the stability of FGF21. Based on extensive knowledge of the structures of FGF ligands, including the structures of FGF19 and FGF23, Q104 of FGF21 was selected for mutagenesis. As described herein, it was found that replacing Q104 with methionine, which is found in all other FGF ligands at the corresponding position (Mohammadi et al., "Structural Basis for Fibroblast Growth Factor Receptor Activation," *Cytokine & Growth Factor Rev* 16(2):107-137 (2005), which is hereby incorporated by reference in its entirety) increases the stability of FGF21 without affecting ligand-binding affinity for receptor. This enhanced affinity for βKlotho, together with the enhanced stability, make these chimeric proteins particularly suitable for use as a therapeutic.

BRIEF DESCRIPTION OF THE DRAWINGS

FIG. 1A shows a size-exclusion chromatogram of the 1:1 FGFR1c-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 1B shows a size-exclusion chromatogram of the ternary FGF21-FGFR1c-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 1C shows a representative surface plasmon resonance (SPR) sensorgram illustrating binding of FGF21 to the binary FGFR1c-βKlotho complex. FGF21 was immobilized on a biosensor chip, and increasing concentrations of FGFR1c-βKlotho complex were passed over the chip. FIG. 1D shows a representative SPR sensorgram illustrating no interaction between FGF21 and the binary FGFR1c-αKlotho complex. FGF21 was immobilized on a biosensor chip, and two concentrations of FGFR1c-αKlotho complex were passed over the chip.

FIG. 2A shows a size-exclusion chromatogram of the 1:1 FGFR4-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 2B shows a size-exclusion chromatogram of the ternary FGF19-FGFR4-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue.

FIG. 3A shows an overlay of SPR sensorgrams of FGFR1c binding to βKlotho, and fitted saturation binding curve. FIG. 3B shows an overlay of SPR sensorgrams of FGFR2c binding to βKlotho, and fitted saturation binding curve. FIG. 3C shows an overlay of SPR sensorgrams of FGFR3c binding to βKlotho. FIG. 3D shows an overlay of SPR sensorgrams of FGFR4 binding to βKlotho, and fitted saturation binding curve. FIG. 3E shows an overlay of SPR sensorgrams of FGFR1b binding to βKlotho. FIG. 3F shows an overlay of SPR sensorgrams of FGFR2b binding to βKlotho. FIG. 3G shows an overlay of SPR sensorgrams of FGFR3b binding to βKlotho. βKlotho ectodomain was immobilized on a biosensor chip, and increasing concentrations of the ligand-binding domain of each of the seven principal human FGFRs were passed over the chip. Where binding was observed, the dissociation constant ($K_D$) was calculated from the saturation binding curve. The data shown in FIGS. 3A-G are representative of two to five independent experiments.

FIG. 4A shows an overlay of SPR sensorgrams illustrating βKlotho binding to FGF19. FGF19 was immobilized on a biosensor chip, and increasing concentrations of βKlotho ectodomain were passed over the chip. FIG. 4B shows an overlay of SPR sensorgrams illustrating βKlotho binding to FGF21. FGF21 was immobilized on a biosensor chip, and increasing concentrations of βKlotho ectodomain were passed over the chip. Note that for any given concentration of βKlotho, the binding response is greater on the FGF19 chip surface than on the FGF21 chip surface. Also note that the FGF19-βKlotho complex dissociates more slowly than the FGF21-βKlotho complex (compare the dissociation phases of the sensorgrams shown in (A) and (B)). FIG. 4C shows an overlay of SPR sensorgrams illustrating no interaction between βKlotho and FGF23. FGF23 was immobilized on a biosensor chip, and increasing concentrations of βKlotho ectodomain were passed over the chip. FIG. 4D shows an overlay of SPR sensorgrams illustrating no interaction between αKlotho and FGF19. FGF19 was immobilized on a biosensor chip, and increasing concentrations of αKlotho ectodomain were passed over the chip. FIG. 4E shows an overlay of SPR sensorgrams illustrating no interaction between αKlotho and FGF21. FGF21 was immobilized on a biosensor chip, and increasing concentrations of αKlotho ectodomain were passed over the chip. The data shown in FIGS. 4A-E are representative of two to three independent experiments.

FIGS. 5A-5G show that the C-terminal tail peptides of FGF19 and FGF21 share a common binding site on βKlotho, and that the C-terminal tail peptide of FGF19 has greater affinity for this site than the C-terminal tail peptide of FGF21. FIG. 5A shows an alignment of the C-terminal tail sequences of human FGF19 (SEQ ID NO:1), FGF21 (SEQ ID NO:100), and FGF23 (SEQ ID NO:223). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence. FIG. 5B shows an overlay of SPR sensorgrams illustrating inhibition by the FGF19 C-terminal tail peptide (M171 to K216 of SEQ ID NO:1; FGF19$^{C\text{-}tail}$) of βKlotho binding to FGF19. FGF19 was immobilized on a biosensor chip, and mixtures of a fixed concentration of βKlotho ectodomain with increasing concentrations of FGF19$^{C\text{-}tail}$ were passed over the chip. FIG. 5C shows an overlay of SPR sensorgrams illustrating inhibition by the FGF21 C-terminal tail peptide (P168 to 5209 of SEQ ID NO:100; FGF21$^{C\text{-}tail}$) of βKlotho binding to FGF19. Mixtures of a fixed concentration of βKlotho ectodomain with increasing concentrations of FGF21$^{C\text{-}tail}$ were passed over a biosensor chip onto which FGF19 had been immobilized. FIG. 5D shows an overlay of SPR sensorgrams illustrating no inhibition by the FGF23 C-terminal tail peptide (S180 to 1251 of SEQ ID NO:223; FGF23$^{C\text{-}tail}$) of βKlotho binding to FGF19. βKlotho ectodomain and FGF23$^{C\text{-}tail}$ were mixed at a molar ratio of 1:2, and the mixture was injected over a biosensor chip onto which FGF19 had been immobilized. FIG. 5E shows an overlay of SPR sensorgrams illustrating inhibition by the FGF21 C-terminal tail peptide (P168 to 5209 of SEQ ID NO:100; FGF21$^{C\text{-}tail}$) of βKlotho binding to FGF21. FGF21 was immobilized on a biosensor chip, and mixtures of a fixed concentration of βKlotho ectodomain with increasing concentrations of FGF21$^{C\text{-}tail}$ were passed over the chip. FIG. 5F shows an overlay of SPR sensorgrams illustrating inhibition by the FGF19 C-terminal tail peptide (M171 to K216 of SEQ ID NO:1; FGF19$^{C\text{-}tail}$) of βKlotho binding to FGF21. Mixtures of a fixed concentration of βKlotho ectodomain with increasing concentrations of FGF19$^{C\text{-}tail}$ were passed over a biosensor chip onto which FGF21 had been immobilized. FIG. 5G shows an overlay of SPR sensorgrams illustrating no inhibition by the FGF23 C-terminal tail peptide (S180 to 1251 of SEQ ID NO:223; FGF23$^{C\text{-}tail}$) of βKlotho binding to FGF21. βKlotho ectodomain and FGF23$^{C\text{-}tail}$ were mixed at a molar ratio of 1:2, and the mixture was injected over a biosensor chip onto which FGF21 had been immobilized. The data shown in FIGS. 5B-G are representative of two to three independent experiments.

FIG. 6A shows an immunoblot analysis for phosphorylation of FRS2α (pFRS2α) and 44/42 MAP kinase (p44/42 MAPK) in the rat hepatoma cell line H4IIE, which had been stimulated with either FGF19 or FGF19$^{C\text{-}tail}$ alone, or with mixtures of FGF19 with increasing concentrations of FGF19$^{C\text{-}tail}$. Numbers above the lanes give the amounts of protein/peptide added in ng ml$^{-1}$. To control for equal sample loading, the protein blots were probed with an antibody recognizing both phosphorylated and nonphosphorylated (total) 44/42 MAP kinase (44/42 MAPK). FIG. 6B shows an immunoblot analysis for phosphorylation of FRS2a (pFRS2a) and 44/42 MAP kinase (p44/42 MAPK) in the rat hepatoma cell line H4IIE, which had been stimulated with either FGF19 or FGF21$^{C\text{-}tail}$ alone, or with mixtures of FGF19 with increasing concentrations of FGF21$^{C\text{-}tail}$. Numbers above the lanes give the amounts of protein/peptide added in ng ml$^{-1}$. To control for equal sample loading, the protein blots were probed with an antibody recognizing both phosphorylated and nonphosphorylated (total) 44/42 MAP kinase (44/42 MAPK). The data shown in FIGS. 6A-B are representative of two independent experiments. Note that while FGF21$^{C\text{-}tail}$ can inhibit FGF19 signaling in H4IIE cells, this cell line is otherwise not responsive to FGF21.

FIG. 7A shows an overlay of SPR sensorgrams illustrating inhibition by FGF21 in solution of βKlotho binding to FGF21 immobilized on a biosensor chip. Increasing concentrations of FGF21 were mixed with a fixed concentration of βKlotho ectodomain, and the mixtures were passed over a FGF21 chip. FIG. 7B shows an overlay of SPR sensorgrams illustrating inhibition by the FGF21$^{29\text{-}190}$/FGF19$^{197\text{-}216}$ chimera of βKlotho binding to FGF21 immobilized on a biosensor chip. Increasing concentrations of FGF21$^{29\text{-}190}$/FGF19$^{197\text{-}216}$ chimera were mixed with a fixed concentration of βKlotho ectodomain, and the mixtures were passed over a FGF21 chip. FIG. 7C shows an overlay of SPR sensorgrams illustrating inhibition by the FGF21$^{29\text{-}190}$/FGF19$^{197\text{-}216}$ chimera or FGF21 of βKlotho binding to immobilized FGF21. The figure was created from the data shown in FIGS. 7A-B, which are representative of two independent experiments.

FIGS. 8A-8B show a schematic of one of the FGF21/FGF19 chimeras claimed in this invention and an alignment of the primary sequences of FGF19 and FGF21. FIG. 8A shows a schematic of the FGF21$^{29\text{-}167}$/FGF19$^{169\text{-}216}$ chimera claimed as an FGF21 agonist herein. The amino acid boundaries of each component of the chimera are labeled. The FGF19 portion of the chimera is shaded gray. FIG. 8B shows a sequence alignment of human FGF19 and FGF21. Residue numbers are in parenthesis to the left of the alignment. The secondary structure elements known for FGF19 (β1-β12, α11) are indicated above the alignment, and FGF19 residues containing these elements are boxed. A dashed line across the alignment marks the junction between the FGF homology core domain and the C-terminal tail of FGF19 and FGF21. Gaps (dashes) were introduced to optimize the sequence alignment. Residues that are identical between FGF19 and FGF21 are shaded gray.

FIG. 11 shows an alignment of the C-terminal tail sequences of human FGF21 (SEQ ID NO: 100), FGF19 (SEQ ID NO: 1), and variants of FGF21 harboring a single amino acid substitution or insertion for a residue unique to FGF19. Residue numbers for the sequences of native or wildtype FGF21 (SEQ ID NO: 100) and FGF19 (SEQ ID NO: 1) are in parenthesis to the left of the alignment. Gaps (dashes) were introduced to optimize the alignment. In the sequence of native or wildtype FGF19 (SEQ ID NO: 1), residues unique to FGF19 are bold and boxed, and in the sequences of the variants of the FGF21 C-terminal tail, introduced FGF19 residues are highlighted in the same manner.

FIG. 12 shows an alignment of the C-terminal tail sequences of human FGF21 (SEQ ID NO: 100), FGF19 (SEQ ID NO: 1), and variants of FGF21 in which residues unique to FGF19 progressively replace the corresponding residues of FGF21 or are inserted into the FGF21 sequence. Residue numbers for the sequences of native FGF21 (SEQ ID NO: 100) and FGF19 (SEQ ID NO: 1) are in parenthesis to the left of the alignment. Gaps (dashes) were introduced to optimize the alignment. In the sequence of native FGF19 (SEQ ID NO: 1), residues unique to FGF19 are bold and boxed, and in the sequences of variants of the FGF21 C-terminal tail, introduced FGF19 residues are highlighted in the same manner.

FIG. 13 shows an alignment of the C-terminal tail sequences of human FGF19 (SEQ ID NO: 1), FGF21 (SEQ ID NO: 100), and variants of FGF19 harboring a single amino acid deletion or substitution for a residue unique to FGF21. Residue numbers for the sequences of native FGF19 (SEQ ID NO: 1) and FGF21 (SEQ ID NO: 100) are in parenthesis to the left of the alignment. Gaps (dashes) were introduced to optimize the alignment. In the sequence of native or wildtype FGF21 (SEQ ID NO: 100), residues unique to FGF21 are bold and boxed, and in the sequences of the variants of the FGF19 C-terminal tail, introduced FGF21 residues are also bold and boxed and deleted FGF19 residues are indicated by a dash (bold and boxed).

FIG. 14A shows an overlay of SPR sensorgrams illustrating inhibition by FGF21 in solution of FGFR1c-βKlotho binding to FGF21 immobilized on a biosensor chip. Increasing concentrations of FGF21 were mixed with a fixed concentration of FGFR1c-βKlotho complex, and the mixtures were passed over a FGF21 chip. FIG. 14B shows an overlay of SPR sensorgrams illustrating inhibition by single mutant FGF21 or wild-type FGF21 of FGFR1c-βKlotho binding to FGF21 immobilized on a biosensor chip. FIG. 14C shows an overlay of SPR sensorgrams illustrating inhibition by triple mutant FGF21 or wild-type FGF21 of FGFR1c-βKlotho binding to FGF21 immobilized on a biosensor chip. FIG. 14D shows an overlay of SPR sensorgrams illustrating inhibition by single mutant FGF21 or triple mutant FGF21 of FGFR1c-βKlotho binding to immobilized FGF21. In the experiments shown in FIGS. 14B-14C, FGFR1c-βKlotho complex was mixed with either mutant FGF21 or wild-type FGF21 at a molar ratio of 1:2 or 1:6, and the mixtures were injected over a FGF21 chip. The data shown in FIGS. 14A-14C are representative of two to three independent experiments. FIG. 14D was created from the data shown in FIGS. 14B-14C. Note that the mutants are less potent than wild-type FGF21 at inhibiting binding of the FGFR1c-βKlotho complex to immobilized FGF21. Also note that the triple mutant exhibits a greater reduction of inhibitory potency than the single mutant.

FIG. 15A shows an overlay of SPR sensorgrams illustrating inhibition by FGF21 in solution of FGFR1c-βKlotho binding to FGF21 immobilized on a biosensor chip. FIG. 15B shows an overlay of SPR sensorgrams illustrating inhibition by the FGF21$^{29-197}$/FGF19$^{204-216}$ chimera of FGFR1c-βKlotho binding to FGF21 immobilized on a biosensor chip. FIG. 15C shows an overlay of SPR sensorgrams illustrating inhibition by the FGF21$^{29-167}$/FGF19$^{169-216}$ chimera of FGFR1c-βKlotho binding to FGF21 immobilized on a biosensor chip. In the experiments shown in FIGS. 15A-15C, increasing concentrations of either an FGF21/FGF19 chimera or wild-type FGF21 were mixed with a fixed concentration of FGFR1c-βKlotho complex, and the mixtures were passed over a FGF21 chip. FIG. 15D shows an overlay of SPR sensorgrams illustrating inhibition by either of two FGF21/FGF19 chimeras or wild-type FGF21 of FGFR1c-βKlotho binding to immobilized FGF21. FIG. 15E shows an overlay of SPR sensorgrams illustrating inhibition by either of three FGF21/FGF19 chimeras of FGFR1c-βKlotho binding to immobilized FGF21. FIG. 15F shows an overlay of SPR sensorgrams illustrating inhibition by either of three FGF21/FGF19 chimeras of FGFR1c-βKlotho binding to immobilized FGF21. The data shown in FIGS. 15A-15C are representative of two to three independent experiments. FIGS. 15D-15F were created from the data shown in FIGS. 15A-15C. Included in FIGS. 15E-15F are SPR sensorgrams obtained from injecting mixtures of the FGF21$^{29-190}$/FGF19$^{197-216}$ chimera with the FGFR1c-βKlotho complex over a FGF21 chip.

FIG. 16A shows a molecular surface representation of the FGF23 crystal structure (PDB ID: 2P39; Goetz et al., "Molecular Insights into the Klotho-Dependent, Endocrine Mode of Action of Fibroblast Growth Factor 19 Subfamily Members," *Mol Cell Biol* 27:3417-3428 (2007), which is hereby incorporated by reference in its entirety). A close-up view into the hydrophobic interior core of FGF23's n-trefoil core domain showing some of the key hydrophobic side chains is shown on the right, and a view of the whole structure is shown on the left. Note that M96 makes numerous hydrophobic contacts with its neighboring residues such as I102, F115, and V136 in the n-trefoil core of FGF23. The M96T substitution would weaken these hydrophobic contacts leading to thermal instability of the FGF23 protein. FIG. 16B shows a size-exclusion chromatogram of the M96T mutant of FGF23 analyzed immediately after Ni-chelating affinity purification. FIG. 16C shows a size-exclusion chromatogram of the M96T mutant of FGF23 analyzed following incubation at 4° C. for 24 hours. FIG. 16D shows a size-exclusion chromatogram of wild-type FGF23 immediately following protein purification. FIG. 16E shows a size-exclusion chromatogram of purified wild-type FGF23 following incubation at 4° C. for 24 hours. Arrows in FIGS. 16B-16E indicate the retention times of molecular size standards, the void volume ($V_v$) and the column volume ($V_c$). Note that in contrast to wild-type FGF23, there is a substantial increase in the portion of M96T mutant protein eluting in the void volume indicating that the mutant protein unfolds over time.

FIG. 17A shows an immunoblot analysis for early growth response 1 (Egr1) expression in HEK293-βKlotho cells stimulated with $FGF21^{29-167}/FGF19^{169-216}$ chimera, $FGF21^{Q104M}$ mutant, or wild-type FGF21. Numbers above the lanes give the amounts of protein added in ng $ml^{-1}$. To control for equal sample loading, the protein blots were probed with an antibody to glyceraldehyde 3-phosphate dehydrogenase (GAPDH). The data are representative of two independent experiments. FIG. 17B shows the dose-response curve for induction of Egr1 protein expression in HEK293-βKlotho cells by the $FGF21^{29-167}/FGF19^{169-216}$ chimera or wild-type FGF21. The intensity of the protein bands on the immunoblots shown in FIG. 17A was quantified and the ratio of Egr1 to GAPDH was calculated. The ratio of Egr1 to GAPDH is plotted as a function of FGF21 ligand concentration. FIG. 17C shows the dose-response curve for induction of Egr1 protein expression in HEK293-βKlotho cells by the $FGF21^{Q104M}$ mutant or wild-type FGF21. The intensity of the protein bands on the immunoblots shown in FIG. 17A was quantified and the ratio of Egr1 to GAPDH was calculated. The ratio of Egr1 to GAPDH is plotted as a function of FGF21 ligand concentration.

FIG. 18A shows changes in blood glucose levels in healthy mice in response to injection of insulin alone or insulin plus FGF21 or vehicle. FIG. 18B shows changes in blood glucose levels in healthy mice in response to injection of insulin alone or insulin plus $FGF21^{29-167}/FGF19^{169-216}$ chimera or vehicle. FIG. 18C shows changes in blood glucose levels in healthy mice in response to injection of insulin alone or insulin plus $FGF21^{Q104M}$ mutant or vehicle. Blood glucose concentrations were measured before and at the indicated time points after the injection of protein(s) or vehicle. Blood glucose concentrations are expressed as percent of pre-injection values. Error bars denote standard deviation from mean.

DETAILED DESCRIPTION OF THE INVENTION

Figures 1A, 1B, 1C, 1D:
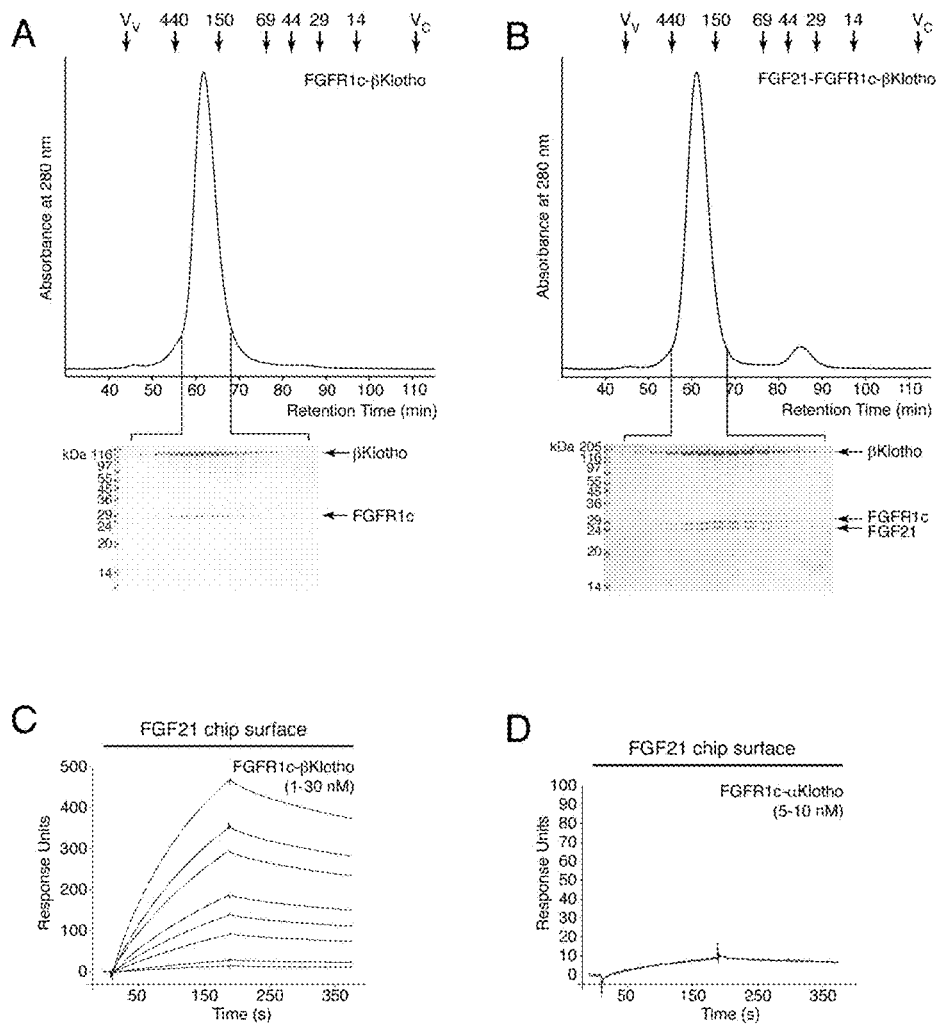
FIGS. 1A-1D show that the ternary complex of FGF21 with its cognate FGFR and βKlotho coreceptor can be reconstituted in solution using the ectodomains of βKlotho and FGFR1c.

One aspect of the present invention relates to a chimeric protein that includes an N-terminus coupled to a C-terminus. The N-terminus includes an N-terminal portion of fibroblast growth factor 21 ("FGF21") having a core domain and the C-terminus includes a C-terminal portion of fibroblast growth factor 19 ("FGF19"), where either (i) the N-terminal portion of FGF21 comprises at least one amino acid residue substitution to increase stability of the FGF21 core domain compared to the wild type FGF21; (ii) the C-terminal portion of FGF19 begins at a residue corresponding to any one of residues 169 to 204 of SEQ ID NO:1 and comprises amino acid residues TGLEAV(R/N)SPSFEK (SEQ ID NO:49); or (iii) both (i) and (ii).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer.

In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion of FGF21 and/or C-terminal portion of FGF19, respectively. In some embodiments, the N-terminal portion and/or the C-terminal portion having such additional portion(s) will have enhanced and/or prolonged activity compared to the corresponding naturally occurring N-terminal portion of FGF21 and/or C-terminal portion of FGF19, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149: 121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331: 1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115: 1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

Of particular interest is FGF19, which has been shown to target and have effects on both adipocytes and hepatocytes. For example, mice harboring a FGF19 transgene, despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment (Tomlinson et al., "Transgenic Mice Expressing Human Fibroblast Growth Factor-19 Display Increased Metabolic Rate and Decreased Adiposity," *Endocrinology* 143(5), 1741-1747 (2002), which is hereby incorporated by reference in its entirety). Obese mice that lacked leptin but harbored a FGF19 transgene showed weight loss, lowered cholesterol and triglycerides, and did not develop diabetes. Obese, diabetic mice that lacked leptin, when injected with recombinant human FGF19, showed reversal of their metabolic characteristics in the form of weight loss and lowered blood glucose (Fu et al., "Fibroblast Growth Factor 19 Increases Metabolic Rate and Reverses Dietary and Leptin-deficient Diabetes," *Endocrinology* 145(6), 2594-2603 (2004), which is hereby incorporated by reference in its entirety).

In one embodiment of the present invention, FGF19 is human FGF19 and has an amino acid sequence of SEQ ID NO: 1 (GenBank Accession No. NP_005108, which is hereby incorporated by reference in its entirety), or a portion thereof, as follows:

(SEQ ID NO: 1)
```
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```

In one embodiment, the C-terminal portion of FGF19 of the chimeric protein of the present invention does not include any of residues 1 to 168 of SEQ ID NO: 1. In certain embodiments of the present invention, the chimeric protein of the present invention does not include residues corresponding to residues spanning residues 1 to 168 of SEQ ID NO:1. In one embodiment, the C-terminal portion of FGF19 begins at a residue corresponding to any one of residues 169, 197, or 204 of SEQ ID NO: 1.

In another embodiment, the C-terminal portion of FGF19 of the chimeric protein of the present invention comprises an amino acid sequence spanning residues corresponding to residues selected from the group consisting of from position 204 to 216 of SEQ ID NO: 1, from position 197 to 216 of SEQ ID NO: 1, and from position 169 to 216 of SEQ ID NO: 1. In yet another embodiment, the C-terminal portion of FGF19 of the chimeric protein of the present invention comprises an amino acid sequence spanning residues of SEQ ID NO:1, which correspond to residues 191 to 206 or 191 to 209 of SEQ ID NO: 100.

In one embodiment of the present invention, FGF19 or a portion thereof is from a mammalian FGF19. In one embodiment of the present invention, FGF19 or a portion thereof is or is from a vertebrate FGF19. In one embodiment, FGF19 or a portion thereof is or is from a non-human vertebrate FGF19. It will be understood that this includes orthologs of human FGF19, or a polypeptide or protein obtained from one species that is the functional counterpart of a polypeptide or protein from a different species. In one embodiment, the C-terminal portion of FGF19 of the chimeric protein of the present invention is from human FGF19. In one embodiment, the C-terminal portion of FGF19 is from an ortholog of human FGF19 from gorilla gorilla, pan troglodytes, *macaca mulatta, pongo abelii, nomascus leucogenys, callithrix jacchus, microcebus murinus, choloepus hoffmanni, ailuropoda melanoleuca, sus scrofa, bos taurus, canis lupus familiaris, oryctolagus, pteropus vampyrus, tursiops truncates, myotis lucifugus, ornithorhynchus anatinus, monodelphis domestica, anolis carolinensis, ochotona princeps, cavia porcellus, tupaia belangeri, rattus norvegicus, mus musculus, gallus gallus, taeniopygia guttata, danio rerio, xenopus (silurana) tropicalis, otolemur garnettii, felis catus, pelodiscus sinensis, latimeria chalumnae, mustela putorius furo, takifugu rubripes, equus caballus, oryzias latipes, xiphophorus maculatus, ictidomys tridecemlineatus, gasterosteus aculeatus, oreochromis niloticus, meleagris gallopavo, papio anubis, saimiri boliviensis boliviensis, pteropus alecto, myotis davidii, tupaia chinensis*, or *heterocephalus glaber*.

Figure 10:
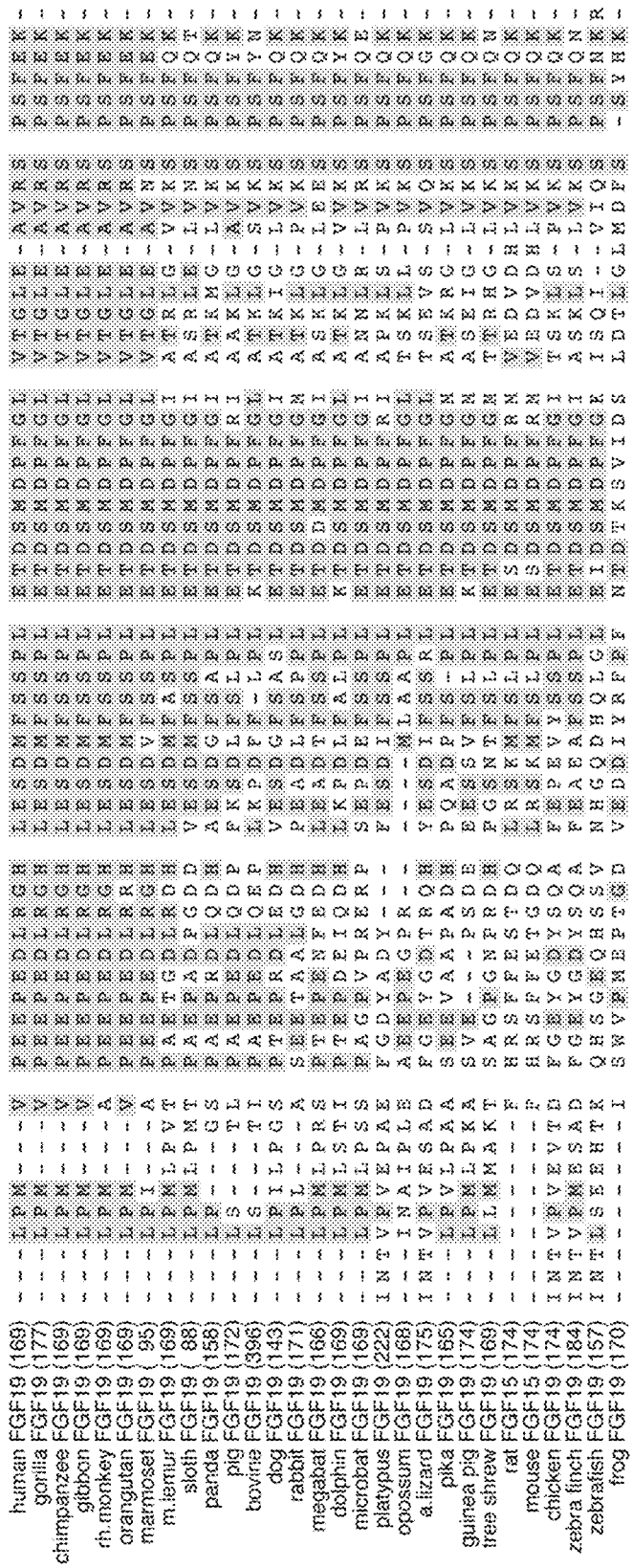
FIG. 10 shows a sequence alignment of the C-terminal tail of FGF19 orthologs (including human (SEQ ID NO: 1), gorilla (SEQ ID NO: 2), chimpanzee (SEQ ID NO: 3), gibbon (SEQ ID NO: 6), rhesus monkey (SEQ ID NO: 4), orangutan (SEQ ID NO: 5), marmoset (SEQ ID NO: 7), mouse lemur (SEQ ID NO: 8), sloth (SEQ ID NO: 9), panda (SEQ ID NO: 10), pig (SEQ ID NO: 11), bovine (SEQ ID NO: 12), dog (SEQ ID NO: 13), rabbit (SEQ ID NO: 14), megabat (SEQ ID NO: 15), dolphin (SEQ ID NO: 16), microbat (SEQ ID NO: 17), platypus (SEQ ID NO: 18), opossum (SEQ ID NO: 19), anole lizard (SEQ ID NO: 20), pika (SEQ ID NO: 21), guinea pig (SEQ ID NO: 22), tree shrew (SEQ ID NO: 23), rat (SEQ ID NO: 24), mouse (SEQ ID NO: 25), chicken (SEQ ID NO: 26), zebra finch (SEQ ID NO: 27), zebrafish (SEQ ID NO: 28), and frog (SEQ ID NO: 29)). Residue numbers are in parenthesis to the left of the alignment. Gaps (dashes) were introduced to optimize the alignment. Ortholog residues identical to human FGF19 are shaded gray.

In other embodiments of the present invention, the portion of FGF19 of the chimeric protein of the present invention is from an ortholog of human FGF19 having an amino acid sequence as shown in Table 1. The portions of an ortholog of human FGF19 of a chimeric protein according to the present invention include portions corresponding to the above-identified amino acid sequences of human FGF19. Corresponding portions may be determined by, for example, sequence analysis and structural analysis. The high degree of FGF19 sequence conservation among orthologs is shown in FIG. 10.

TABLE 1

*Gorilla gorilla* (gorilla) FGF19 (Ensembl Accession No. ENSGGOP00000021055, which is hereby incorporated by reference in its entirety) (SEQ ID NO: 2)
```
  1 MRSGCVVVHV WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Pan troglodytes* (chimpanzee) FGF19 (Ensembl Accession No. ENSPTRP00000006877, which is hereby incorporated by reference in its entirety) (SEQ ID NO: 3)
```
  1 MRNGCVVVHV WILAGLWLAV AGRPLAFSDA GRHVHYCWGD PIPLRHLYTS GPHGLSSCFL
 61 RIPANCVMNC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Macaca mulatta* (Rhesus monkey) FGF19 (GenBank Accession No. XP_001100825, which is hereby incorporated by reference in its entirety) (SEQ ID NO: 4)
```
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MAPEEPEDLR
181 GHLESDMFSS PLETDSMDPF GLVTGLEAVR SPSFEK
```

*Pongo abelii* (Sumatran orangutan) FGF19 (GenBank Accession No. XP_002821459, which is hereby incorporated by reference in its entirety) (SEQ ID NO: 5)
```
  1 MRSGCVVVHA WILAGLWLAV AGRPLAFSDS GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 RHLESDMFSS PLETDSMDPF GLVTGLEAVR SPSFEK
```

*Nomascus leucogenys* (Northern white-cheeked gibbon) FGF19 (Genbank Accession No. XP_003278071, which is hereby incorporated by reference in its entirety) (SEQ ID NO: 6)
```
  1 MRSECVVVHA WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

*Callithrix jacchus* (white-tufted-ear marmoset) FGF19 (GenBank Accession No. XP_002763730, which is hereby incorporated by reference in its entirety) (SEQ ID NO: 7)
```
  1 MWKATAGGQQ GQSEAQMSTC PHVPRPLWIA QSCLFSLQLQ YSEEDCAFEE EIRPDGYNVY
 61 WSEKHRLPVS LSSAKQRQLY KKRGFLPLSH FLPMLPIAPE EPEDLRGHLE SDVFSSPLET
121 DSMDPFGLVT GLEAVNSPSF EK
```

*Microcebus murinus* (mouse lemur) FGF19 (Ensembl Accession No. ENSMICP00000002788, which is hereby incorporated by reference in its entirety) (SEQ ID NO: 8)
```
  1 MPSGQSGCVA ARALILAGLW LTAAGRPLAF SDAGPHVHYG WGEPIRLRHL YTAGPHGLSS
 61 CFLRIRADGS VDCARGQSAH SLLEIRAVAL RTVAIKGVHS VRYLCMGADG RMQGLLRYSE
121 EDCAFEEEIR PDGYNVYRSE KHRLPVSLSS ARQRQLYKGR GFLPLSHFLP MLPVTPAETG
181 DLRDHLESDM FASPLETDSM DPFGIATRLG VVKSPSFQK
```

*Choloepus hoffmanni* (sloth) FGF19 (Ensembl Accession No. ENSCHOP00000002044, which is hereby incorporated by reference in its entirety) (SEQ ID NO: 9) (partial amino acid sequence corresponding to human FGF19 residues 79 to 216)
```
  1 LLEMKAVALR AVAIKGVHSA LYLCMNADGS LHGLPRYSAE DCAFEEEIRP DGYNVYWSRK
 61 HGLPVSLSSA KQRQLYKGRG FLPLSHFLPM LPMTPAEPAD PGDDVESDMF SSPLETDSMD
121 PFGIASRLEL VNSPSFQT
```

*Ailuropoda melanoleuca* (giant panda) FGF19 (GenBank Accession No. XP_002927952, which is hereby incorporated by reference in its entirety) (SEQ ID NO: 10) (partial amino acid sequence corresponding to human FGF19 residues 12 to 216)
```
124    VLAGLCL AVAGRPLAFS DAGPHVHYGW GEPIRLRHLY TAGPHGLSSC FLRIRADGGV
181 DCARGQSAHS LVEIRAVALR TVAIKGVHSV RYLCMGADGR MQGLPQYSAG DCAFEEEIRP
241 DGYNVYRSKK HRLPVSLSGA KQRQLYKDRG FLPLSHFLPM LPGSPAEPRD LQDHAESDGF
301 SAPLETDSMD PFGIATKMGL VKSPSFQK
```

*Sus scrofa* (pig) FGF19 (Ensembl Accession No. ENSSSCP00000013682, which is hereby incorporated by reference in its entirety) (SEQ ID NO: 11)
```
  1 MRSAPSRCAV VRALVLAGLW LAAAGRPLAF SDAGPHVHYG WGESVRLRHL YTASPHGVSS
 61 CFLRIHSDGP VDCAPGQSAH SLMEIRAVAL STVAIKGERS RYLCMGADGK MQGQTQYSDE
121 DCAFEEEIRP DGYNVYWSKK HHLPVSLSSA RQRQLYKGRG FLPLSHFLPM LSTLPAEPED
181 LQDPFKSDLF SLPLETDSMD PFRIAAKLGA VKSPSFYK
```

TABLE 1-continued

*Bos taurus* (bovine) FGF19 (GenBank Accession No. XP_599739, which is hereby incorporated by reference in its entirety) (SEQ ID NO: 12)

```
136             MRSAP SRCAVARALV LAGLWLAAAG RPLAFSDAGP HVHYGWGESV
181RLRHLYTAGP QGLYSCFLRI HSDGAVDCAQ VQSAHSLMEI RAVALSTVAI KGERSVLYLC
241MDADGKMQGL TQYSAEDCAF EEEIRPDGYN VYWSRKHHLP VSLSSSRQRQ LFKSRGFLPL
301SHFLPMLSTI PAEPEDLQEP LKPDFFLPLK TDSMDPFGLA TKLGSVKSPS FYN
```

*Canis lupus familiaris* (dog) FGF19 (GenBank Accession No. XP_540802, which is hereby incorporated by reference in its entirety) (SEQ ID NO: 13) (partial amino acid sequence corresponding to human FGF19 residues 25 to 216)

```
  1LAFSDAGPHV HSFWGEPIRL RHLYTAGPHG LSSCFLRIRA DGGVDCARGQ SAHSLMEMRA
 61VALRTVAIKG VHSGRYLCMG ADGRMQGLPQ YSAGDCTFEE EIRPDGYNVY WSKKHHLPIS
121LSSAKQRQLY KGRGFLPLSH FLPILPGSPT EPRDLEDHVE SDGFSASLET DSMDPFGIAT
181KIGLVKSPSF QK
```

*Oryctolagus cuniculus* (rabbit) FGF19 (GenBank Accession No. XP_002724495, which is hereby incorporated by reference in its entirety) (SEQ ID NO: 14)

```
  1MRRAPSGGAA ARALVLAGLW LAAAARPLAL SDAGPHLHYG WGEPVRLRHL YATSAHGVSH
 61CFLRIRADGA VDCERSQSAH SLLEIRAVAL RTVAFKGVHS SRYLCMGADG RMRGQLQYSE
121EDCAFQEEIS SGYNVYRSTT HHLPVSLSSA KQRHLYKTRG FLPLSHFLPV LPLASEETAA
181LGDHPEADLF SPPLETDSMD PFGMATKLGP VKSPSFQK
```

*Pteropus vampyrus* (megabat) FGF19 (Ensembl Accession No. ENSPVAP00000009339, which is hereby incorporated by reference in its entirety) (SEQ ID NO: 15)

```
  1MRSPCAVARA LVLAGLWLAS AAGPLALSDA GPHVHYGWGE AIRLRHLYTA GPHGPSSCFL
 61RIRADGAVDC ARGQSAHSLV EIRAVALRNV AIKGVHSVRY LCMGADGRML GLLQYSADDC
121AFEEEIRPDG YNVYHSKKHH LPVSLSSAKQ RQLYKDRGFL PLSHFLPMLP RSPTEPENFE
181DHLEADTFSS LETDDMDPFG IASKLGLEES PSFQK
```

*Tursiops truncatus* (dolphin) FGF19 (Ensembl Accession No. ENSTTRP00000000061, which is hereby incorporated by reference in its entirety) (SEQ ID NO: 16)

```
  1MRSAPSRCAV ARALVLAGLW LAAAGRPLAF SDAGPHVHYG WGESVRLRHL YTAGPQGLSS
 61CFLRIHSDGA VDCAPVQSAH SLMEIRAVAL STVAIKGERS VLYLCMGADG KMQGLSQYSA
121EDCAFEEEIR PDGYNVYWSK KHHLPVSLSS ARQRQLFKGR GFLPLSHFLP MLSTIPTEPD
181EIQDHLKPDL FALPLKTDSM DPFGLATKLG VVKSPSFYK
```

*Myotis lucifugus* (microbat) FGF19 (Ensembl Accession No. ENSMLUP00000002279, which is hereby incorporated by reference in its entirety) (SEQ ID NO: 17)

```
  1MQSAWSRRVV ARALVLASLG LASAGGPLGL SDAGPHVHYG WGESIRLRHL YTSGPHGPSS
 61CFLRIRADGA VDCARGQSAH SLVEIRAVAL RKVAIKGVHS ALYLCMGGDG RMLGLPQFSP
121EDCAFEEEIR PDGYNVYRSQ KHQLPVSLSS ARQRQLFKAR GFLPLSHFLP MLPSSPAGPV
181PRERPSEPDE FSSPLETDSM DPFGIANNLR LVRSPSFQE
```

*Ornithorhynchus anatinus* (platypus) FGF19 (GenBank Accession No. XP_001506714, which is hereby incorporated by reference in its entirety) (SEQ ID NO: 18) (partial amino acid sequence corresponding to human FGF19 residues 79 to 216)

```
  1MLSCVVLPSL LEIKAVAVRT VAIKGVHISR YLCMEEDGKT PWARLLEIKA VAVRTVAIKG
 61VHSSRYLCME EDGKLHGQIW YSAEDCAFEE EIRPDGYNVY KSKKYGVPVS LSSAKQRQQF
121KGRDFLPLSR FLPMINTVPV EPAEFGDYAD YFESDIFSSP LETDSMDPFR IAPKLSPVKS
181PSFQK
```

*Monodelphis domestica* (opossum) FGF19 (GenBank Accession No. XP_001506714, which is hereby incorporated by reference in its entirety) (SEQ ID NO: 19)

```
  1MAQLLAPLLT LAALWLAPTA RARPLVDAGP HVYYGWGEPI RLRHLYTANR HGLASFSFLR
 61IHRDGRVDGS RSQSALSLLE IKAVALRMVA IKGVHSSRYL CMGDAGKLQG SVRFSAEDCT
121FEEQIRPDGY NVYQSPKYNL PVSLCTDKQR QQAHGKEHLP LSHFLPMINA IPLEAEEPEG
181PRMLAAPLET DSMDPFGLTS KLLPVKSPSF QK
```

*Anolis carolinensis* (anole lizard) FGF19 (GenBank Accession No. XP_003214715, which is hereby incorporated by reference in its entirety) (SEQ ID NO: 20)

```
  1MCRRALPLLG ALLGLAAVAS RALPLTDAGP HVSYGWGEPV RLRHLYTAGR QGLFSQFLRI
 61HADGRVDGAG SQNRQSLLEI RAVSLRAVAL KGVHSSRYLC MEEDGRLRGM LRYSAEDCSF
121EEEMRPDGYN IYKSKKYGVL VSLSNARQRQ QFKGKDFLPL SHFLPMINTV PVESADFGEY
181GDTRQHYESD IFSSRLETDS MDPFGLTSEV SSVQSPSFGK
```

*Ochotona princeps* (pika) FGF19 (Ensembl Accession No. ENSOPRP00000009838, which is hereby incorporated by reference in its entirety) (SEQ ID NO: 21) (partial amino acid sequence corresponding to human FGF19 residues 12 to 77 and 113 to 216)

```
  1VRSRGAMARA LVLATLWLAA TGRPLALSDA GPHLHYGWGE PIRLRHLYAT SAHGLSHCFL
 61RIRTDGTVDC ERSQSAH--- ---------- ---------- ---------- --LQYSEEDC
```

TABLE 1-continued

```
121AFEEEISSGY NVYRSRRYQL PVSLGSARQR QLQRSRGFLP LSHFLPVLPA ASEEVAAPAD
181HPQADPFSPL ETDSMDPFGM ATKRGLVKSP SFQK
```

*Cavia porcellus* (guinea pig) FGF19 (Ensembl Accession No. ENSCPOP00000007325, which is hereby incorporated by reference in its entirety) (SEQ ID NO: 22)

```
  1MWSAPSGCVV IRALVLAGLW LAVAGRPLAR RSLALSDQGP HLYYGWDQPI RLRHLYAAGP
 61YGRSRCFLRI HTDGAVDCVE EQSEHCLLEI RAVALETVAI KDINSVRYLC MGPDGRMRGL
121PWYSEEDCAF KEEISYPGYS VYRSQKHHLP IVLSSVKQRQ QYQSKGVVPL SYFLPMLPKA
181SVEPSDEEES SVFSLPLKTD SMDPFGMASE IGLVKSPSFQ K
```

*Tupaia belangeri* (tree shrew) FGF19 (Ensembl Accession No. ENSTBEP00000000264, which is hereby incorporated by reference in its entirety) (SEQ ID NO: 23) (partial amino acid sequence corresponding to human FGF19 (residues 1 to 112 and 136 to 216)

```
  1MRRTPSGFAV ARVLFLGSLW LAAAGSPLAL SDAGPHVNYG WDESIRLRHL YTASPHGSTS
 61CFLRIDDGS VDCARGQSLH SLLEIKAVAL QTVAIKGVYS VRYLCMDADG RMQGL-----
121---------- --------ST KHGLPVSLSS AKQRQLLTVR GFPSLPHFLL MMAKTSAGPG
181NPRDHPGSNT FSLPLETDSM DPFGMTTRHG LVKSPSFQN
```

*Rattus norvegicus* (Norway rat) FGF15 (GenBank Accession No. NP_570109, which is hereby incorporated by reference in its entirety) (SEQ ID NO: 24)

```
  1MARKWSGRIV ARALVLATLW LAVSGRPLVQ QSQSVSDEGP LFLYGWGKIT RLQYLYSAGP
 61YVSNCFLRIR SDGSVDCEED QNERNLLEFR AVALKTIAIK DVSSVRYLCM SADGKIYGLI
121RYSEEDCTFR EEMDCLGYNQ YRSMKHHLHI IFIKAKPREQ LQGQKPSNFI PIFHRSFFES
181TDQLRSKMFS LPLESDSMDP FRMVEDVDHL VKSPSFQK
```

*Mus musculus* (house mouse) FGF15 (GenBank Accession No. NP_032029, which is hereby incorporated by reference in its entirety) (SEQ ID NO: 25)

```
  1MARKWNGRAV ARALVLATLW LAVSGRPLAQ QSQSVSDEDP LFLYGWGKIT RLQYLYSAGP
 61YVSNCFLRIR SDGSVDCEED QNERNLLEFR AVALKTIAIK DVSSVRYLCM SADGKIYGLI
121RYSEEDCTFR EEMDCLGYNQ YRSMKHHLHI IFIQAKPREQ LQDQKPSNFI PVFHRSFFET
181GDQLRSKMFS LPLESDSMDP FRMVEDVDHL VKSPSFQK
```

*Gallus gallus* (chicken) FGF19 (GenBank Accession No. NP_990005, which is hereby incorporated by reference in its entirety) (SEQ ID NO: 26)

```
  1MGPARPAAPG AALALLGIAA AAAAARSLPL PDVGGPHVNY GWGEPIRLRH LLHRPGKHGL
 61FSCFLRIGGD GRVDAVGSQS PQSLLEIRAV AVRTVAIKGV QSSRYLCMDE AGRLHGQLSY
121SIEDCSFEEE IRPDGYNVYK SKKYGISVSL SSAKQRQQFK GKDFLPLSHF LPMINTVPVE
181VTDFGEYGDY SQAFEPEVYS SPLETDSMDP FGITSKLSPV KSPSFQK
```

*Taeniopygia guttata* (zebra finch) FGF19 (GenBank Accession No. XP_002194493, which is hereby incorporated by reference in its entirety) (SEQ ID NO: 27)

```
  1MVIISNLYLM QNDVMMNMRR APLRVHAARS SATPASALPL PPPDAGPHLK YGWGEPIRLR
 61HLYTASKHGL FSCFLRIGAD GRVDAAGSQS PQSLLEIRAV AVRTVAIKGV QSSRYLCMDE
121AGRLHGQLRN STEDCSFEEE IRPDGYNVYR SKKHGISVSL SSAKQRQQFK GKDFLPLSHF
181LPMINTVPME SADFGEYGDY SQAFEAEAFS SPLETDSMDP FGIASKLSLV KSPSFQN
```

*Danio rerio* (zebrafish) FGF19 (GenBank Accession No. NP_001012246, which is hereby incorporated by reference in its entirety) (SEQ ID NO: 28)

```
  1MLLLLFVTVC GSIGVESLPL PDSGPHLAND WSEAVRLRHL YAARHGLHLQ INTDGEIIGS
 61TCKARTVSLM EIWPVDTGCV AIKGVASSRF LCMERLGNLY GSHIYTKEDC SFLERILPDG
121YNVYFSSKHG ALVTLSGAKN KLHSNDGTSA SQFLPMINTL SEEHTKQHSG EQHSSVNHGQ
181DHQLGLEIDS MDPFGKISQI VIQSPSFNKR
```

*Xenopus (Silurana) tropicalis* (western clawed frog) FGF19 (GenBank Accession No. NP_001136297, which is hereby incorporated by reference in its entirety) (SEQ ID NO: 29)

```
  1MWKTLPWILV PMMVAVLYFL GGAESLPLFD AGPHMQNGWG ESIRIRHLYT ARRFGHDSYY
 61LRIHEDGRVD GDRQQSMHSL LEIRAIAVGI VAIKGYRSSL YLCMGSEGKL YGMHSYSQDD
121CSFEEELLPD GYNMYKSRKH GVAVSLSKEK QKQQYKGKGY LPLSHFLPVI SWVPMEPTGD
181VEDDIYRFPF NTDTKSVIDS LDTLGLMDFS SYHKK
```

*Otolemur garnettii* (bushbaby) FGF19 (Ensembl Accession No. ENSOGAP00000017975, which is hereby incorporated by reference in its entirety) (SEQ ID NO: 30)

```
  1MPSGLRGRVV AGALALASFW LAVAGRPLAF SDAGPHVHYG WGEPIRLRHL YTAGPHGLSS
 61CFLRVRTDGA VDCARGQSAH SLLEIRAVAL RTVAIKGVHS ARYLCMGADG RMQGLPQYSE
121EDCAFEEEIR PDGYNVYWSE KHRLPVSLSS ARQRQLYKGR GFLPLSHFLP MLPVTPAEPG
181DLRDHLESDM FSLPLETDSM DPFGIATRLG VVKSPSFQK
```

TABLE 1-continued

*Pelis catus* (cat) FGF19 (Ensembl Accession No. ENSFCAP00000022548, which is hereby incorporated by reference in its entirety) (SEQ ID NO: 31)
```
  1MRSAPSQCAV TRALVLAGLW LAAAGRPLAF SDAGPHVHYG WGEPIRLRHL YTAGPHGLSS
 61CFLRIRADGG VDCARSQSAH SLVEIRAVAL RTVAIKGVHS VRYLCMGADG RMQGLLQYSA
121GDCAFQEEIR PDGYNVYRSE KHRLPVSLSS AIQRQLYKGR GFLPLSHFLP MLPGSPAEPR
181DLQDHVESER FSSPLETDSM DPFGIATKMG LVKSPSFQK
```

*Pelodiscus sinensis* (Chinese softshell turtle) FGF19 (Ensembl Accession No. ENSPSIP00000010374, which is hereby incorporated by reference in its entirety) (SEQ ID NO: 32)
```
  1MWRSLCKSHT SLALLGLCFA VVVRSLPFSD AGPHVNYGWG EPIRLRHLYT ASRHGLFNYF
 61LRISSDGKVD GTSIQSPHSL LEIRAVAVRT VAIKGVHSSR YLCMEEDGKL HGLLRYSTED
121CSFEEEIRPD GYNVYKSKKY GISVSLSSAK QRQQFKGKDF LPLSHFLPMI NTVPVESMDF
181GEYGDYSHTF ESDLFSSPLE TDSMDPFGIT SKISPVKSPS FQK
```

*Latimeria chalumnae* (coelacanth) FGF19 (Ensembl Accession No. ENSLACP00000014596, which is hereby incorporated by reference in its entirety) (SEQ ID NO: 33)
```
  1MLQALYNLCT ALVLFKLPFA MVGYTLPSAN EGPHLNYDWG ESVRLKHLYT SSKHGLISYF
 61LQINDDGKVD GTTTRSCYSL LEIKSVGPGV LAIKGIQSSR YLCVEKDGKL HGSRTYSADD
121CSFKEDILPD GYTIYVSKKH GSVVNLSNHK QKRQRNRRTL PPFSQFLPLM DTIRVECMNC
181GEHCDDNLHD ELETGLSMDP FESTSKKSFQ SPSFHNR
```

*Mustela putorius furo* (ferret) FGF19 (Ensembl Accession No. ENSMPUP00000004571, which is hereby incorporated by reference in its entirety) (SEQ ID NO: 34)
```
  1MRSAASRCAV ARALVLAGLW LAAAGRPLAF SDAGPHVHYG WGEPIRLRHL YTAGPHGLSS
 61CFLRIRADGG VDCARGQSAH SLVEIRAVAL RTVAIKGVYS DRYLCMGADG RMQGLPQYSA
121GDCAFEEEIR PDGYNVYRSK KHRLPVSLSS AKQRQLYKDR GFLPLSHFLP MLPGSLAEPR
181DLQDHVEADG FSAPLETDSM DPFGIATKMG LVKSPSFQK
```

*Takifugu rubripes* (fugu) FGF19 (Ensembl Accession No. ENSTRUP00000007110, which is hereby incorporated by reference in its entirety) (SEQ ID NO: 35)
```
  1SSTRISGNMV LLMLPITVAN LFLCAGVLSL PLLDQGSHFP QGWEQVVRFR HLYAASAGLH
 61LLITEEGSIQ GSADPTLYSL MEIRPVDPGC VVIRGAATTR FLCIEGAGRL YSSQTYSKDD
121CTFREQILAD GYSVYRSVGH GALVSLGNYR QQLRGEDWSV PTLAQFLPRI SSLDQDFKAA
181LDETEKPEQT APQRSEPVDM VDSFGKLSQI IHSPSFHK
```

*Equus caballus* (horse) FGF19 (Ensembl Accession No. ENSECAP00000017705, which is hereby incorporated by reference in its entirety) (SEQ ID NO: 36); partial sequence corresponding to human FGF19 residues 20 to 113
```
  1AAGRPLALSD AGPHVHYGWG EPIRLRHLYT AGPHGLSSCF LRIRADGAVD CARGQSAHSL
 61VEIRAVALRT VAIKGVHSVR YLCMGADGRM QGLV
```

*Oryzias latipes* (medaka) FGF19 (Ensembl Accession No. ENSORLP00000000352, which is hereby incorporated by reference in its entirety) (SEQ ID NO: 37)
```
  1TMLLIVVTIS TMVFSDSGVS SMPLSDHGPH ITHSWSQVVR LRHLYAVKPG QHVQIREDGH
 61IHGSAEQTLN SLLEIRPVAP GRVVFRGVAT SRFLCMESDG RLFSSHTFDK DNCVFREQIL
121ADGYNIYISD QHGTLLSLGN HRQQQGLDRV DVPALAQFLP RISTLQQGVY PVPDPPHQMR
181TMQTEKTLDA TDTFGQLSKI IHSPSFNKR
```

*Xiphophorus maculatus* (platyfish) FGF19 (Ensembl Accession No. ENSXMAP00000001516, which is hereby incorporated by reference in its entirety) (SEQ ID NO: 38)
```
  1MFVFILCIAG ELFTLGVFCM PMMDQGPLVT HGWGQVVRHR HLYAAKPGLH LLISEDGQIH
 61GSADQTLYSL LEIQPVGPGR VVIKGVATTR FLCMESDGRL YSTETYSRAD CTFREQIQAD
121GYNVYTSDSH GALLSLGNNQ QRHSGSDRGV PALARFLPRL NTLQQAVPTE PDVPDQLSPE
181KVQQTVDMVA SFGKLSHIIH SPSFHKR
```

*Ictidomys tridecemlineatus* (squirrel) FGF19 (Ensembl Accession No. ENSSTOP00000021639, which is hereby incorporated by reference in its entirety) (SEQ ID NO: 39)
```
  1MRSAPSGRAL ARALVLASLW LAVAGRPLAR RSLALSDQGP HLYYGWDQPI RLRHLYAAGP
 61YGFSNCFLRI RTDGAVDCEE KQSERSLMEI RAVALETVAI KDINSVRYLC MGADGRIQGL
121PRYSEEECTF KEEISYDGYN VYRSQKYHLP VVLSSAKQRQ LYQSKGVVPL SYFLPMLPLA
181SAETRDRLES DVFSLPLETD SMDPFGMASE VGLKSPSFQK
```

*Gasterosteus aculeatus* (stickleback) FGF19 (Ensembl Accession No. ENSGACP00000018732, which is hereby incorporated by reference in its entirety) (SEQ ID NO: 40)
```
  1MLLLLVPAYV ASVFLALGVV CLPLTDQGLH MADDWGQSVR LKHLYAASPG LHLLIGEDGR
 61IQGSAQQSPY SLLEISAVDP GCVVIRGVAT ARFLCIEGDG RLYSSDTYSR DDCTFREQIL
121PDGYSVYVSH GHGALLSLGN HRQRLQGRDH GVPALAQFLP RVSTMDQASA PDAPGQTATE
181TEEPVDSFGK LSQIIHSPSF HER
```

TABLE 1-continued

*Oreochromis niloticus* (tilapia) FGF19 (Ensembl Accession No.
ENSONIP00000022796, which is hereby incorporated by reference in its
entirety) (SEQ ID NO: 41)
```
  1 MLLLLIVSIV NMLFGVGMVC MPLSDNGPHI AHGWAQVVRL RHLYATRPGM HLLISEGGQI
 61 RGSAVQTLHS LMEIRPVGPG RVVIRGVATA RFLCIEDDGT LYSSHAYSRE DCIFREQILP
121 DGYNIYISDR HGVLLSLGNH RQRLQGLDRG DPALAQFLPR ISTLNQIPSP GANIGDHMKV
181 AKTEEPVDTI DSFGKFSQII DSPSFHKR
```

*Meleagris gallopavo* (turkey) FGF19 (Ensembl Accession No.
ENSMGAP00000010265, which is hereby incorporated by reference in its
entirety) (SEQ ID NO: 42); partial sequence corresponding to human
FGF19 residues 71 to 216
```
  1 VGNQSPQSIL EITAVDVGIV AIKGLFSGRY LAMNKRGRLY ASLSYSIEDC SFEEEIRPDG
 61 YNVYKSKKYG ISVSLSSAKQ RQQFKGKDFL PLSHFLPMIN TVPVEVTDFG EYGDYSQAFE
121 PEVYSSPLET DSMDPFGITS KLSPVKSPSF QK
```

*Papio anubis* (olive baboon) FGF19 (GenBank Accession No.
XP_003909471, which is hereby incorporated by reference in its
entirety) (SEQ ID NO: 43)
```
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSQKHR LPVSLSSAKQ RQLYKNRGFL PLSHFLPMLP MAPEEPEDLR
181 GPLESDMFSS PLETDSMDPF GLVTGLEAVR SPSFEK
```

*Saimiri boliviensis boliviensis* (Bolivian squirrel monkey) FGF19
(GenBank Accession No. XP_003941214, which is hereby incorporated by
reference in its entirety) (SEQ ID NO: 44)
```
  1 MRSGCVVVHA WILAGLWLAV VGRPLAFSDA GPHVHYGWGD PIRLRHLYTS SPHGLSSCFL
 61 RIRSDGVVDC ARGQSAHSLL EIKAVALRTV AIKGVHSSRY LCMGADGRLQ GLFQYSEEDC
121 AFEEEIRPDG YNVYLSEKHR LPVSLSSAKQ RQLYKKRGFL PLSHFLPMLP RAPEEPDDLR
181 GHLESDVFSS PLETDSMDPF GLVTGLEAVN SPSFEK
```

*Pteropus alecto* (black flying fox) FGF19 (GenBank Accession No.
ELK13233, which is hereby incorporated by reference in its entirety)
(SEQ ID NO: 45)
```
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS PLETDDMDPF GIASKLGLEE SPSFQK
```

*Myotis davidii* (David's myotis) FGF19 (GenBank Accession No.
ELK24234, which is hereby incorporated by reference in its entirety)
(SEQ ID NO: 46)
```
  1 MSGQNSGRHG SRPGLDEEPE PGPLELRALG STRADPQLCD FLENHFLGYT CLELDICLAT
 61 YLGVSHWGES IRLRHLYTSG PHGPSSCFLR IRVDGAVDCA RGQSAHSLVE IRAVALRKVA
121 IKGVHSALYL CMEGDGRMRG LPQFSPEDCA FEEEIRPDGY NVYRSQKHQL PVSLSSARQR
181 QLFKARGFLP LSHFLPMLPS SPAEPVHRER PLEPDAFSSP LETDSMDPFG IANNLRLVKS
241 PSFQK
```

*Tupaia chinensis* (Chinese tree shrew) FGF19 (GenBank Accession No.
ELW64990, which is hereby incorporated by reference in its entirety)
(SEQ ID NO: 47); residues 1-257, excluding 13-19
```
  1 MRRTWSGFAV AT-------R AGSPLALADA GPHVNYGWDE SIRLRHLYTA SLHGSTSCFL
 61 RIRDDGSVGC ARGQSMHSLL EIKAVALQTV AIKGVYSVRY LCMDTDGRMQ GLPQYSEEDC
121 TFEEEIRSDG HNVYRSKKHG LPVSLSSAKQ RQLYKGRGFL SLSHFLLMMP KTSAGPGNPR
181 DQRNPRDQRD PNTFSLPLET DSMDPFGMTT RHGLLLDSCC ASLVLLNIST DGEFSPYGNI
241 LRPSFRFKLF KMKKVTN
```

*Heterocephalus glaber* (naked mole-rat) FGF19 (GenBank Accession No.
EHB12332, which is hereby incorporated by reference in its entirety)
(SEQ ID NO: 48)
```
  1 MRFSKSTCGF FNHQRLQALW LSLSSVKWVL DAAVEGRPIR LRHLYAAGPY GRSRCFLRIH
 61 TDGAVDCVEE QSEHCLLEIR AVALETVAIK DINSVRYLCM GPDGRMQGLP WYSEEDCAFK
121 EEISYPGYSV YRSQKHHLPI VLSSVKQRQQ YQSKGVVPLS YFLPMLPKAS VEPGDEEESA
181 FSLPLKTDSM DPFGMASEIG LAKSPSFQK
```

In one embodiment, a C-terminal portion of FGF19 of the chimeric protein of the present invention comprises the conserved amino acid sequence TGLEAV(R/N)SPSFEK (SEQ ID NO: 49). In one embodiment, a C-terminal portion of FGF19 comprises the conserved amino acid sequence MDPFGLVTGLEAV(R/N)SPSFEK (SEQ ID NO: 50). In one embodiment, the C-terminal portion of FGF19 of the chimeric protein of the present invention comprises the conserved amino acid sequence LP(M/I)(V/A)PEEPEDLR(G/R)HLESD(MN)FSSPLETDSMDPFGLVTGLEAV(R/N)SPSFEK (SEQ ID NO: 51).

In one embodiment, the C-terminal portion of FGF19 of the chimeric protein of the present invention consists of an amino acid sequence selected from the group consisting of TGLEAV(R/N)SPSFEK (SEQ ID NO: 49); MDPFGLVTGLEAV(R/N)SPSFEK (SEQ ID NO: 50); and LP(M/I)(V/A)PEEPEDLR(G/R)HLESD(MN)FSSPLETDSMDPFGLVTGLEAV(R/N)SPSFEK (SEQ ID NO: 51).

In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence identity to the amino acid sequences of any of SEQ ID NOs: 49 to 51. In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence homology to the amino acid sequences of any of SEQ ID NOs: 49 to 51.

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

It will be understood that the portion from FGF19 of the chimeric protein of the present invention may be from a nucleotide sequence that encodes an FGF19 protein (e.g., those encoding orthologs) from a mammal or even a non-mammalian species. For example, a nucleotide sequence encoding a mammalian or non-mammalian FGF19 protein according to the present invention may include, but is not limited to, those FGF-encoding nucleotide sequences shown in Table 2.

TABLE 2

```
Human FGF19 gene coding sequence (SEQ ID NO: 52) (GenBank Accession
No. NM_005117, which is hereby incorporated by reference in its
entirety)
   464    ATGCGGA GCGGGTGTGT GGTGGTCCAC GTATGGATCC TGGCCGGCCT CTGGCTGGCC
   521 GTGGCCGGGC GCCCCCTCGC CTTCTCGGAC GCGGGGCCCC ACGTGCACTA CGGCTGGGGC
   581 GACCCCATCC GCCTGCGGCA CCTGTACACC TCCGGCCCCC ACGGGCTCTC CAGCTGCTTC
   641 CTGCGCATCC GTGCCGACGG CGTCGTGGAC TGCGCGCGGG GCCAGAGCGC GCACAGTTTG
   701 CTGGAGATCA AGGCAGTCGC TCTGCGGACC GTGGCCATCA AGGGCGTGCA CAGCGTGCGG
   761 TACCTCTGCA TGGGCGCCGA CGGCAAGATG CAGGGGCTGC TTCAGTACTC GGAGGAAGAC
   821 TGTGCTTTCG AGGAGGAGAT CCGCCCAGAT GGCTACAATG TGTACCGATC CGAAGCAC
   881 CGCCTCCCGG TCTCCCTGAG CAGTGCCAAA CAGCGGCAGC TGTACAAGAA CAGAGGCTTT
   941 CTTCCACTCT CTCATTTCCT GCCCATGCTG CCCATGGTCC CAGAGGAGCC TGAGGACCTC
  1001 AGGGGCCACT TGGAATCTGA CATGTTCTCT TCGCCCCTGG AGACCGACAG CATGGACCCA
  1061 TTTGGGCTTG TCACCGGACT GGAGGCCGTG AGGAGTCCCA GCTTTGAGAA GTAA Gorilla FGF19 gene coding sequence (SEQ ID NO: 53) (Ensembl Accession
No. ENSGGOT00000028361, which is hereby incorporated by reference in
its entirety)
   463    ATGCGGAG CGGGTGTGTG GTGGTCCACG TCTGGATCCT GGCCGGCCTC TGGCTGGCCG
   521 TGGCCGGGCG CCCCCTCGCC TTCTCGGACG CGGGGCCCCA CGTGCACTAC GGCTGGGGCG
   581 ACCCCATCCG CCTGCGGCAC CTGTACACCT CCGGCCCCCA CGGGCTCTCC AGCTGCTTCC
   641 TGCGCATCCG TGCCGACGGC GTCGTGGACT GCGCGCGGGG CCAGAGCGCG CACAGTTTGC
   701 TGGAGATCAA GGCAGTCGCT CTGCGGACCG TGGCCATCAA GGGCGTGCAC AGCGTGCGGT
   761 ACCTCTGCAT GGGCGCCGAC GGCAAGATGC AGGGGCTGCT TCAGTACTCG GAGGAAGACT
   821 GTGCTTTCGA GGAGGAGATC CGCCCAGATG GCTACAATGT GTACCGATCT GAGAAGCACC
   881 GCCTCCCGGT CTCCCTGAGC AGTGCCAAAC AGCGGCAGCT GTACAAGAAC AGAGGCTTTC
   941 TTCCGCTCTC TCATTTCCTG CCCATGCTGC CCATGGTCCC AGAGGAGCCT GAGGACCTCA
  1001 GGGGCCACTT GGAATCTGAC ATGTTCTCTT CACCCCTGGA GACCGACAGC ATGGACCCAT
  1061 TTGGGCTTGT CACCGGACTG GAGGCCGTGA GGAGTCCTAG CTTTGAGAAG TAA Pan troglodytes gene coding sequence (chimpanzee) FGF19 (SEQ ID NO:
54) (Ensembl Accession No. ENSPTRT00000007454, which is hereby
incorporated by reference in its entirety)
     1 ATGCGGAACG GGTGTGTGGT GGTCCACGTC TGGATCCTGG CCGGCCTCTG GCTGGCCGTG
    61 GCCGGGCGCC CCCTCGCCTT CTCGGACGCG GGGCGCCACG TGCACTACTG CTGGGGCGAC
   121 CCCATCCCCC TGCGGCACCT GTACACCTCC GGCCCCCATG GGCTCTCCAG CTGCTTCCTG
   181 CGCATCCCTG CGAACTGCGT CATGAACTGC GCGCGGGGCC AGAGCGCGCA CAGTTTGCTG
   241 GAGATCAAGG CAGTCGCTCT GCGGACCGTG GCCATCAAGG GCGTGCACAG CGTGCGGTAC
   301 CTCTGCATGG GCGCCGACGG CAAGATGCAG GGGCTGCTTC AGTACTCGGA GGAAGACTGT
   361 GCTTTCGAGG AGGAGATCCG CCCAGATGGC TACAATGTGT ACCGATCCGA GAAGCACCGC
   421 CTCCCGGTCT CCCTGAGCAG TGCCAAACAG CGGCAGCTGT ACAAGAACAG AGGCTTTCTT
   481 CCACTCTCTC ATTTCCTGCC CATGCTGCCC ATGGTCCCAG AGGAGCCTGA GGACCTCAGG
   541 GGCCACTTGG AATCTGACAT GTTCTCTTCG CCCCTGGAGA CCGACAGCAT GGACCCATTT
   601 GGGCTTGTCA CCGGACTGGA GGCCGTGAGG AGTCCCAGCT TTGAGAAGTA A Macaca mulatta gene coding sequence (Rhesus monkey) FGF19 (SEQ ID NO:
55) (GenBank Accession No. XM_001100825, which is hereby incorporated
by reference in its entirety)
   758       ATG AGGAGCGGGT GTGTGGTGGT CCACGCCTGG ATCCTGGCCA GCCTCTGGCT
   811 GGCCGTGGCC GGGCGTCCCC TCGCCTTCTC GGACGCGGGG CCCCACGTGC ACTACGGCTG
   871 GGGCGACCCC ATCCGCCTGC GGCACCTGTA CACCTCCGGC CCCCATGGGC TCTCCAGCTG
   931 CTTCCTGCGC ATCCGCACCG ACGGCGTCGT GGACTGCGCG CGGGGCCAAA GCGCGCACAG
```

TABLE 2-continued

```
 991 TTTGCTGGAG ATCAAGGCAG TAGCTCTGCG GACCGTGGCC ATCAAGGGCG TGCACAGCGT
1051 GCGGTACCTC TGCATGGGCG CCGACGGCAA GATGCAGGGG CTGCTTCAGT ACTCAGAGGA
1111 AGACTGTGCT TTCGAGGAGG AGATCCGCCC TGATGGCTAC AATGTATACC GATCCGAGAA
1171 GCACCGCCTC CCGGTCTCTC TGAGCAGTGC CAAACAGAGG CAGCTGTACA AGAACAGAGG
1231 CTTTCTTCCG CTCTCTCATT TCCTACCCAT GCTGCCCATG GCCCCAGAGG AGCCTGAGGA
1291 CCTCAGGGGC CACTTGGAAT CTGACATGTT CTCTTCGCCC CTGGAGACTG ACAGCATGGA
1351 CCCCATTTGGG CTTGTCACCG GACTGGAGGC GGTGAGGAGT CCCAGCTTTG AGAAATAA
```

*Pongo abelii* gene coding sequence (Sumatran orangutan) FGF19 (SEQ ID NO: 56) (GenBank Accession No. XM_002821413, which is hereby incorporated by reference in its entirety)

```
 763    ATGCGGAG CGGGTGTGTG GTGGTCCACG CCTGGATCCT GGCCGGCCTC TGGCTGGCCG
 821 TGGCCGGGCG CCCCCTCGCC TTCTCGGACT CGGGGCCCCA CGTGCACTAC GGCTGGGGCG
 881 ACCCCATCCG CCTGCGGCAC CTGTACACCT CCGGCCCCCA CGGGCTCTCC AGCTGCTTCC
 941 TGCGCATCCG TGCCGACGGC GTCGTGGACT GCGCGCGGGG CCAGAGCGCG CACAGTTTGC
1001 TGGAGATCAA GGCAGTGCTC CTGCGGACCG TGGCCATCAA GGGCGTGCAC AGCGTGCGGT
1061 ACCTCTGCAT GGGCGCCGAC GGCAAGATGC AGGGGCTGCT TCAGTACTCG GAGGAAGACT
1121 GTGCTTTCGA GGAGGAGATC CGCCCAGATG CTACAATGT GTACCGATCC GAGAAGCACC
1181 GCCTCCCGGT CTCCCTGAGC AGTGCCAAAC AGCGGCAGCT GTACAAGAAC AGGGGCTTTC
1241 TTCCGCTCTC TCATTTCCTG CCCATGCTGC CCATGGTCCC AGAGGAGCCT GAGGACCTCA
1301 GGCGCCACTT GGAATCCGAC ATGTTCTCTT CGCCCCTGGA GACCGACAGC ATGGACCCAT
1361 TTGGGCTTGT CACCGGACTG GAGGCCGTGA GGAGTCCCAG CTTTGAGAAA TAA
```

*Nomascus leucogenys* gene coding sequence (Northern white-cheeked gibbon) FGF19 (SEQ ID NO: 57) (Genbank Accession No. XM_003278023, which is hereby incorporated by reference in its entirety)

```
 456       ATGCG GAGCGAGTGT GTGGTGGTCC ACGCCTGGAT CCTGGCCGGC CTCTGGCTGG
 511 CAGTGGCCGG GCGCCCCCTC GCCTTTTCGG ACGCGGGGCC CCACGTGCAC TACGGCTGGG
 571 GCGACCCCAT CCGTCTGCGG CACCTGTACA CCTCCGGCCC CCACGGGCTC TCCAGCTGCT
 631 TCCTGCGCAT CCGTGCCGAC GGCGTCGTGG ACTGCGCGCG GGGCCAGAGC GCGCACAGTT
 691 TGCTGGAGAT CAAGGCAGTC GCTCTGCGGA CCGTGCCCAT AAAGGGCGTG CACAGCGTGC
 751 GGTACCTCTG CATGGGCGCC GACGGCAAGA TGCAGGGGCT GCTTCAGTAT TCGGAGGAAG
 811 ACTGTGCTTT CGAGGAGGAG ATCCGCCCAG ATGGCTACAA TGTGTACCGA TCCGAGAAGC
 871 ACCGCCTCCC CGTCTCCCTG AGCAGTGCCA ACAGCGGCA GCTGTATAAG AACAGAGGCT
 931 TTCTTCCACT CTCTCATTTC CTGCCCATGC TGCCCATGGT CCCAGAGGAG CCTGAGGACC
 991 TCAGGGGCCA CTTGGAATCT GACATGTTCT CTTCGCCCCT GGAGACCGAC AGCATGGACC
1051 CATTTGGGCT TGTCACCGGA CTGGAGGCCG TGAGGAGTCC CAGCTTTGAG AAATAA
```

*Callithrix jacchus* gene coding sequence (white-tufted-ear marmoset) FGF19 (SEQ ID NO: 58) (GenBank Accession No. XM_002763684, which is hereby incorporated by reference in its entirety)

```
   1 ATGTGGAAGG CCACCGCTGG TGGCCAGCAG GGACAGTCCG AAGCACAAAT GTCCACATGT
  61 CCCCATGTTC CTCGTCCTCT GTGGATTGCT CAGAGCTGCC TGTTTTCTCT GCAGCTCCAG
 121 TACTCGGAGG AAGACTGTGC TTTCGAGGAG GAGATCCGCC CTGATGGCTA CAATGTGTAC
 181 TGGTCCGAGA AGCACCGCCT CCCGGTCTCC CTGAGCAGCG CCAAACAGCG GCAGCTGTAC
 241 AAGAAACGAG GCTTTCTTCC ACTGTCCCAT TTCCTGCCCA TGCTGCCCAT AGCCCCAGAA
 301 GAGCCTGAGG ACCTCAGGGG ACACCTGGAA TCTGACGTGT TCTCTTCACC CCTGGAGACT
 361 GACAGCATGG ACCCATTTGG GCTTGTCACG GGACTGGAGG CGGTGAACAG TCCCAGCTTT
 421 GAGAAGTAA
```

*Microcebus murinus* gene coding sequence (mouse lemur) FGF19 (SEQ ID NO: 59) (Ensembl Accession No. ENSMICT00000003065, which is hereby incorporated by reference in its entirety)

```
   1 ATGCCGAGCG GCAAAGCGG TTGTGTGGCG GCCCGCGCCC TGATCCTGGC CGGCCTCTGG
  61 CTGACCGCGG CCGGGCGCCC GCTGGCCTTC TCCGACGCGG GCCCGCACGT GCACTACGGC
 121 TGGGGCGAGC CCATCCGCCT GCGGCACCTG TACACCGCCG GCCCCCACGG CCTCTCCAGC
 181 TGCTTCCTGC GCATCCGCGC AGACGGCTCC GTGGACTGCG CGCGGGGCCA GAGCGCACAC
 241 AGTTTGCTGG AGATCAGGGC GGTCGCTCTT CGGACTGTGG CCATCAAGGG CGTGCACACG
 301 GTGCGGTACC TCTGCATGGG CGCAGACGGC AGGATGCAGG GCTGCTCCG GTACTCGGAG
 361 GAAGACTGTG CCTTCGAGGA GGAGATCCGC CCCGATGGCT ACAACGTGTA CCGGTCTGAG
 421 AAGCACCGCC TGCCGGTGTC TCTGAGCAGC GCCAGGCAGA GGCAGCTGTA CAAGGGCAGG
 481 GGCTTCCTGC CGCTCTCTCA CTTCCTGCCC ATGCTGCCCG TGACCCCGGC AGAGACCGGG
 541 GACCTCAGGG ACCACTTGGA GTCCGACATG TTCGCTTCGC CCCTGGAGAC CGACAGCATG
 601 GACCCGTTTG GGATCGCCAC CAGACTTGGG GTGGTGAAGA GTCCCAGCTT TCAGAAATGA
```

*Choloepus hoffmanni* gene coding sequence (sloth) FGF19 (SEQ ID NO: 60) (Ensembl Accession No. ENSCHOT00000002324, which is hereby incorporated by reference in its entirety)

```
   1 TTGCTCGAAA TGAAGGCAGT GGCGCTGCGG GCCGTGGCCA TCAAGGGCGT GCACAGTGCT
  61 CTGTACCTCT GCATGAACGC CGACGGCAGT CTGCACGGGC TGCCTCGGTA CTCTGCAGAA
 121 GACTGTGCTT TGAGGAGGA AATCCGCCCC GACGGCTACA ATGTGTACTG GTCTAGGAAG
 181 CACGGCCTCC CTGTCTCTTT GAGCAGTGCA AACAGAGGC AGCTGTACAA AGGCAGAGGC
 241 TTTCTGCCCC TGTCCCACTT CCTGCCCATG CTGCCCATGA CGCCGGCCGA GCCCGCAGAC
 301 CCCGGGGATG ACGTGGAGTC GGACATGTTC TCTTCACCTC TGGAAACCGA CAGCATGGAT
 361 CCTTTTGGAA TTGCCTCCAG ACTTGAGCTT GTGAACAGTC CAGCTTTCAG CATAA
```

TABLE 2-continued

*Ailuropoda melanoleuca* gene coding sequence (giant panda) FGF19 (SEQ ID NO: 61) (GenBank Accession No. XM_002927906, which is hereby incorporated by reference in its entirety)

```
  69          GG TCCTAGCCGG CCTCTGCCTG GCGGTAGCCG GGCGCCCCCT AGCCTTCTCG
 421 GACGCGGGGC CGCACGTGCA CTACGGCTGG GGTGAGCCCA TCCGCCTACG GCACCTGTAC
 481 ACCGCCGGCC CCCACGGCCT CTCCAGCTGC TTCCTGCGCA TCCGTGCCGA CGGCGGGGTT
 541 GACTGCGCGC GGGGCCAGAG CGCGCACAGT TTGGTGGAGA TCAGGGCAGT CGCTCTGCGG
 601 ACCGTGGCCA TCAAGGGTGT GCACAGCGTC CGGTACCTCT GCATGGGCGC GGACGGCAGG
 661 ATGCAAGGGC TGCCTCAGTA CTCTGCAGGG GACTGTGCTT TCGAGGAGGA GATCCGCCCC
 721 GACGGCTACA ATGTGTACCG GTCCAAGAAG CACCGTCTCC CCGTCTCTCT GAGCGGTGCC
 781 AAACAGAGGC AGCTTTACAA AGACAGAGGC TTTCTGCCCC TGTCCCACTT CTTGCCCATG
 841 CTGCCCGGGA GCCCAGCAGA GCCCAGGGAC CTCCAGGACC ATGCGGAGTC GGACGGGTTT
 901 TCTGCACCCC TAGAAACAGA CAGCATGGAC CCTTTTGGGA TCGCCACCAA AATGGGACTA
 961 GTGAAGAGTC CCAGCTTCCA GAAATAA
```

*Sus scrofa* gene coding sequence (pig) FGF19 (SEQ ID NO: 62) (Ensembl Accession No. ENSSSCT00000014068, which is hereby incorporated by reference in its entirety)

```
   1 ATGCGGAGCG CTCCGAGCCG GTGCGCGGTG GTCCGCGCCC TGGTCCTGGC CGGCCTCTGG
  61 CTGGCCGCAG CCGGGCGCCC CCTAGCCTTC TCGGATGCTG GGCCGCACGT GCACTACGGC
 121 TGGGGCGAGT CGGTCCGGCC GCGGCACCTG TACACTGCGA GTCCCCACGG CGTCTCCAGC
 181 TGCTTCCTGC GCATCCACTC AGACGGCCCC GTGGACTGCG CGCCGGGACA GAGCGCGCAC
 241 AGTTTGATGG AGATCAGGGC AGTCGCGCTG AGTACCGTGG CGATCAAGGG CGAGCGCAGC
 301 GGCCGTTACC TCTGCATGGG CGCCGACGGC AAGATGCAAG GCAGACTCA GTACTCGGAT
 361 GAGGACTGTG CTTTCGAGGA GGAGATCCGC CCTGATGGCT ACAACGTGTA CTGGTCCAAG
 421 AAACACCATC TGCCCGTCTC TCTGAGCAGC GCCAGGCAGA GGCAGCTGTA CAAAGGCAGG
 481 GGCTTCCTGC CGCTGTCCCA CTTTCTGCCC ATGCTGTCCA CTCTCCCAGC CGAGCCGGAG
 541 GACCTCCAGG ACCCCTTCAA GTCCGACCTG TTTTCTTTGC CCTGGAAAC GGACAGCATG
 601 GACCCTTTCC GGATCGCCGC CAAACTGGGA GCGGTGAAGA GTCCCAGCTT CTATAAATAA
```

*Bos taurus* gene coding sequence (bovine) FGF19 (SEQ ID NO: 63) (GenBank Accession No. XM_599739, which is hereby incorporated by reference in its entirety)

```
 406 ATGCG GAGCGCTCCG
 421 AGCCGGTGCG CCGTGGCCCG CGCCCTGGTC CTGGCTGGCC TCTGGCTGGC CGCAGCCGGG
 481 CGCCCCCTGG CCTTCTCGGA TGCGGGGCCG CACGTGCACT ACGGCTGGGG CGAGTCGGTT
 541 CGCTTGCGGC ACCTGTATAC CGCGGGCCCG CAGGGCCTCT ACAGCTGCTT TCTGCGCATC
 601 CACTCCGACG GCGCCGTGGA CTGCGCGCAG GTCCAGAGCG CGCACAGTTT GATGGAGATC
 661 AGGGCGGTCG CTCTGAGCAC CGTAGCCATC AAGGGCGAGC GCAGCGTGCT GTACCTCTGC
 721 ATGGACGCCG ACGGCAAGAT GCAAGGACTG ACCCAGTACT CAGCCGAGGA CTGTGCTTTC
 781 GAGGAGGAGA TCCGTCCTGA CGGCTACAAC GTGTACTGGT CCAGGAAGCA CCATCTCCCG
 841 GTCTCCCTGA GCAGCTCCAG GCAGAGGCAG CTGTTCAAAA GCAGGGGCTT CCTGCCGCTG
 901 TCTCACTTCC TGCCCATGCT GTCCACCATC CCAGCCGAAC CTGAAGACCT CCAGGAACCC
 961 CTGAAGCCTG ATTTCTTTCT GCCCCTGAAA ACAGATAGCA TGGACCCTTT CGGGCTCGCC
1021 ACCAAACTGG GATCGGTGAA GAGTCCCAGC TTCTATAATT AA
```

*Canis lupus familiaris* gene coding sequence (dog) FGF19 (SEQ ID NO: 64) (GenBank Accession No. XM_540802, which is hereby incorporated by reference in its entirety)

```
   1 CTAGCCTTCT CCGACGCGGG GCCGCACGTG CACTCCTTCT GGGGGGAGCC CATCCGCCTG
  61 CGGCACCTGT ACACCGCCGG CCCCCACGGC CTCTCCAGCT GCTTCCTGCG CATCCGCGCC
 121 GACGGCGGGG TGGACTGCGC GCGGGGCCAG AGCGCGCACA GTCTGATGGA GATGAGGGCG
 181 GTCGCTCTGC GGACCGTGGC CATCAAGGGC GTGCACAGCG GCCGGTACCT CTGCATGGGC
 241 GCCGACGGCA GGATGCAAGG GCTGCCTCAG TACTCCGCGG GAGACTGTAC TTTCGAGGAG
 301 GAGATCCGTC CCGATGGCTA CAATGTGTAC TGGTCCAAGA AGCACCATCT CCCCATCTCT
 361 CTGAGTAGTG CCAAACAGAG GCAGCTCTAC AAGGGCAGGG GCTTTTTTGCC CCTGTCCCAC
 421 TTCTTACCTA TCTTGCCCGG GAGCCCAACA GAGCCCAGGG ACCTGGAAGA CCATGTGGAG
 481 TCTGACGGGT TTTCTGCATC CCTGGAAACA GACAGCATGG ACCCTTTTGG GATCGCCACC
 541 AAAATTGGAC TAGTGAAGAG TCCCAGTTTC CAAAAATAA
```

*Oryctolagus cuniculus* gene coding sequence (rabbit) FGF19 (SEQ ID NO: 65) (GenBank Accession No. XM_002724449, which is hereby incorporated by reference in its entirety)

```
   1 ATGCGCCGCG CGCCGAGCGG AGGTGCCGCG GCCCGCGCCT TGGTCCTGGC CGGCCTCTGG
  61 CTGGCCGCGG CCGCGCGCCC CTTGGCCTTG TCCGACGCGG GCCCGCATCT GCACTACGGC
 121 TGGGGCGAGC CCGTCCGCCT GCGGCACCTG TACGCCACCA GCGCCCACGG CGTCTCGCAC
 181 TGCTTCCTGC GTATACGCGC GACGGCGCC GTGGACTGCG AGGAGCCA GAGCGCACAC
 241 AGCTTGCTGG AGATCCGAGC GGTCGCCCTG CGCACCGTGG CCTTCAAGGG CGTGCACAGC
 301 TCCCGCTACC TCTGCATGGG CGCCGACGGC AGGATGCGGG GCAGCTGCA GTACTCGGAG
 361 GAGGACTGTG CCTTCCAGGA GGAGATCAGC TCCGGCTACA ACGTGTACCG CTCCACGACG
 421 CACCACCTGC CCGTGTCTCT GAGCAGTGCC AAGCAGAGAC ACCTGTACAA GACCAGAGGC
 481 TTCCTGCCCC TCTCCCACTT CCTGCCCGTG CTGCCCCTGG CCTCCGAGGA GACCGCGGCC
 541 CTCGGCGACC ACCCTGAAGC CGACCTGTTC TCCCCGCCCC TGGAAACCGA CAGCATGGAC
 601 CCCTTCGGCA TGGCCACCAA GCTCGGGCCG GTGAAGAGCC CCAGCTTTCA GAAGTAG
```

*Pteropus vampyrus* gene coding sequence (megabat) FGF19 (SEQ ID NO: 66) (Ensembl Accession No. ENSPVAT00000009907, which is hereby incorporated by reference in its entirety)

```
   1 ATGCGGAGCC CGTGCGCTGT GGCCCGCGCC TTGGTCCTGG CCGGCCTCTG GCTGGCCTCA
  61 GCTGCGGGCC CCCTCGCCCT CTCGGACGCG GGGCCGCACG TGCACTACGG CTGGGGCGAG
```

TABLE 2-continued

```
121 GCCATCCGCC TGCGGCACCT GTACACCGCC GGCCCCACG GCCCCTCCAG CTGCTTCCTG
181 CGCATCCGCG CGGATGGGGC GGTGGACTGC GCGCGGGGCC AGAGCGCGCA CAGTTTGGTG
241 GAAATCCGGG CTGTCGCCCT GCGGAACGTG GCTATCAAGG GCGTGCACAG CGTCCGATAC
301 CTCTGCATGG GAGCCGACGG CAGGATGCTA GGGCTGCTTC AGTACTCCGC TGACGACTGC
361 GCCTTCGAGG AGGAGATCCG CCCGGACGGC TACAACGTGT ACCACTCCAA GAAGCACCAC
421 CTCCCGGTCT CTCTGAGCAG TGCCAAGCAG AGGCAACTGT ACAAGGACAG GGGCTTCCTG
481 CCCCTGTCCC ATTTCCTGCC CATGCTGCCC AGGAGCCCGA CAGAGCCCGA GAACTTCGAA
541 GACCACTTGG AGGCCGACAC GTTTTCCTCG CCCCTGGAGA CAGACGACAT GGACCCTTTT
601 GGGATTGCCA GTAAATTGGG GCTGGAGGAA AGTCCCAGCT TCCAGAAGTA A
```

*Tursiops truncatus* gene coding sequence (dolphin) FGF19 (SEQ ID NO: 67) (Ensembl Accession No. ENSTTRT00000000066, which is hereby incorporated by reference in its entirety)

```
  1 ATGCGGAGCG CTCCGAGCCG GTGCGCCGTG GCCCGCGCCC TGGTCCTGGC CGGCCTCTGG
 61 CTGGCTGCAG CCGGGCGCCC CCTAGCCTTC TCGGATGCCG GGCCGCACGT GCACTACGGC
121 TGGGGCGAGT CCGTCCGCCT GCGGCACCTG TACACCGCGG GTCCCCAGGG CCTCTCCAGC
181 TGCTTCCTGC GCATCCACTC AGACGGCGCC GTGGACTGCG CGCCGGTTCA GAGCGCGCAC
241 AGTTTGATGG AGATCAGGGC AGTCGCTCTG AGTACCGTGG CCATCAAGGG CGAACGCAGC
301 GTCCTGTACC TCTGCATGGG CGCCGACGGC AAAATGCAAG GGCTGAGTCA GTACTCAGCT
361 GAGGACTGTG CCTTTGAGGA GGAAATCCGT CCGGACGGCT ACAACGTGTA CTGGTCCAAG
421 AAACACCACC TCCCGGTGTC CCTGAGCAGC GCCAGGCAGC GGCAGCTGTT CAAAGGCAGG
481 GGTTTCCTGC CGCTGTCTCA CTTCCTTCCC ATGCTGTCCA CCATCCCCAC AGAGCCCGAT
541 GAAATCCAGG ACCACTTGAA GCCCGATTTG TTTGCTTTGC CCCTGAAAAC AGATAGCATG
601 GACCCATTTG GGCTCGCCAC CAAACTGGGA GTGGTGAAGA GTCCCAGCTT CTATAAGTAA
```

*Myotis lucifugus* gene coding sequence (microbat) FGF19 (SEQ ID NO: 68) (Ensembl Accession No. ENSMLUT00000002508, which is hereby incorporated by reference in its entirety)

```
  1 ATGCAAAGCG CGTGGAGCCG ACGCGTTGTG GCCCGAGCCC TGGTCTTGGC CAGCCTCGGG
 61 CTGGCCTCAG CCGGGGGGCC CCTCGGTCTT TCGGACGCTG GGCCGCACGT GCACTACGGC
121 TGGGGGGAGT CCATCCGCCT GCGCCACCTG TACACCTCCG GCCCCACGG CCCATCCAGC
181 TGCTTCCTGC GCATCCGCGC TGACGGCGCA GTGGACTGCG CGCGGGGCCA GAGCGCGCAC
241 AGTTTGGTGG AGATCAGGGC CGTCGCCTTG CGGAAAGTGG CCATCAAGGG CGTGCACAGC
301 GCCCTGTACC TCTGCATGGG AGGCGACGGC AGGATGCTGG GGCTGCCTCA GTTCTCGCCC
361 GAGGACTGTG CTTTCGAGGA GGAGATCCGC CCGGACGGCT ACAACGTGTA CCGGTCCCAG
421 AAGCACCAGC TGCCCGTCTC GCTGAGCAGT GCCCGGCAGA GGCAGCTGTT CAAGGCCCGG
481 GGCTTCCTGC CGCTGTCCCA CTTCCTGCCC ATGCTGCCCA GCAGCCCGC GGGACCCGTG
541 CCCCGAGAGC GCCCCTCGGA CCGGACGAG TTCTCTTCGC CCCTGAAAAC AGACAGCATG
601 GACCCTTTTG GGATTGCCAA CAACCTGAGG CTGGTGAGAA GTCCCAGCTT TCAGGAATAA
```

*Ornithorhynchus anatinus* gene coding sequence (platypus) FGF19 (SEQ ID NO: 69) (GenBank Accession No. XM_001506664, which is hereby incorporated by reference in its entirety)

```
  1 ATGCTTTCCT GTGTGGTTTT GCCTAGTCTG CTGGAGATCA AGGCGGTGGC CGTGCGCACG
 61 GTGGCCATCA AAGGGGTCCA CATCTCTCGG TACCTCTGCA TGGAAGAGGA TGGGAAAACT
121 CCATGGGCAC GTCTGCTGGA GATCAAGGCG GTGGCCGTGC GCACGGTGGC CATCAAAGGG
181 GTCCACAGCT CTCGGTACCT CTGCATGGAA GAGGATGGAA AACTCCATGG GCAGATTTGG
241 TATTCTGCAG AAGACTGTGC TTTTGAAGAG GAAATACGTC CAGATGGCTA CAATGTGTAT
301 AAATCTAAGA AATATGGTGT TCCTGTTTCT TTAAGCAGCG CCAAACAAAG GCAGCAATTC
361 AAAGGAAGAG ACTTTCTGCC TCTTTCTCGT TTCTTGCCAA TGATCAACAC AGTGCCTGTG
421 GAGCCAGCAG AGTTTGGGGA CTATGCCGAT TACTTTGAAT CAGATATATT TTCCTCACCT
481 CTGGAAACTG ACAGCATGGA CCCATTTAGA ATTGCCCCTA AACTGTCCCC TGTAAAGAGC
541 CCCAGCTTTC AGAAATAA
```

*Monodelphis domestica* gene coding sequence (opossum) FGF19 (SEQ ID NO: 70) (GenBank Accession No. XM_001373653, which is hereby incorporated by reference in its entirety)

```
  1 ATGGCCCAGC TCCTGGCCCC GCTCCTCACC CTGGCTGCTC TCTGGCTGGC CCGACGGCG
 61 CGTGCCCGAC CGCTGGTGGA CGCCGGGCCT CACGTCTACT ACGGCTGGGG GGAGCCCATT
121 CGTCTGCGGC ATCTCTACAC GGCCAATCGG CACGGGCTCG CCAGCTTCTC CTTCCTCCGG
181 ATCCACCGCG ACGGCGCGT GGACGGCAGC CGGAGTCAGA GCGCGCTCAG TTTGCTGGAG
241 ATCAAGGCGG TAGCTCTTCG GATGGTGGCG ATCAAAGGTG TCCATAGCTC TCGGTACCTG
301 TGTATGGGAG ACGCCGGGAA ACTCCAGGGA TCGGTGAGGT TCTCGGCCGA GGACTGCGCC
361 TTCGAGGAGC AGATTCGCCC CGACGGCTAC AACGTGTACC AGTCCCCCAA GTACAACCTC
421 CCCGTCTCGC TCTGCACTGA CAAGCAGAGG CAGCAGGCCC ACGGCAAGGA GCACCTGCCC
481 CTGTCCCACT TCCTGCCCAT GATCAATGCT ATTCCTTTGG AGGCCGAGGA GCCCGAGGGC
541 CCCAGGATGT TGGCGGCGCC TCTGGAGACG GACAGCATGG ACCCCTTCGG CCTCACCTCC
601 AAGCTGTTGC CGGTCAAGAG CCCCAGCTTT CAGAAATAA
```

*Anolis carolinensis* gene coding sequence (anole lizard) FGF19 (SEQ ID NO: 71) (GenBank Accession No. XM_003214667, which is hereby incorporated by reference in its entirety)

```
  1 ATGTGTCGGC GGGCGTTGCC TCTGCTGGGG GCCCTTCTGG GCTTGGCGGC CGTGGCCTCC
 61 CGCGCCCTCC CGCTCACCGA CGCCGGGCCC CACGTCAGCT ACGGCTGGGG GGAGCCCGTC
121 CGGCTCAGGC ACCTCTACAC GGCCAACGGA CAGGGCTCT TCAGCCAGTT CCTCCGCATC
181 CACGCCGACG GGAGAGTCGA CGGCGCCGGC AGCCAGAACC GGCAGAGTTT GCTGGAGATC
241 CGCGCGGTCT CGTTGCGCGC CGTGCCCCTC AAAGGCGTGC ACAGCTCCCG CTACCTCTGC
301 ATGGAGGAGG ACGGCCGGCT CCGCGGGATG CTCAGATATT CTGCAGAAGA CTGTTCCTTT
361 GAAGAGGAGA TGCGTCCAGA TGGCTACAAT ATCTACAAGT CAAAGAAATA CGGAGTTTTG
421 GTCTCCCTAA GTAATGCCAG ACAAAGACAG CAATTCAAAG GGAAAGATTT TCTTCCTTTG
```

TABLE 2-continued

```
481 TCTCATTTCT TGCCGATGAT CAACACTGTG CCAGTGGAGT CTGCAGACTT TGGAGAGTAT
541 GGTGACACCA GGCAGCATTA TGAATCGGAT ATTTTCAGTT CACGTCTTGA AACTGACAGC
601 ATGGACCCTT TTGGCCTCAC TTCAGAAGTG TCATCAGTAC AAAGTCCTAG CTTTGGGAAA
661 TAA
```

*Ochotona princeps* gene coding sequence (pika) FGF19 (SEQ ID NO: 72)
(Ensembl Accession No. ENSOPRT00000010769, which is hereby
incorporated by reference in its entirety) (1-214, excluding 78-112)

```
  1 GTGCGGAGCA GGGGAGCCAT GGCCCGCGCT CTGGTTCTAG CCACTCTCTG GCTGGCCGCG
 61 ACGGGGCGGC CGCTGGCCTT GTCCGACGCG GGGCCGCACC TGCACTACGG CTGGGGCGAG
121 CCCATCCGCC TGCGGCACCT GTACGCCACC AGCGCCCACG GCCTCTCGCA CTGCTTTTTG
181 CGCATCCGTA CCGACGGCAC CGTGGACTGC GAGCGCAGCC AGAGCGCGCA CA--------
    ---------- ---------- ---------- ---------- ---------- ----------
242 ---------- ---------- ---------- ---------- ------CTAC AGTACTCGGA GGAGGACTGC
266 GCCTTCGAAG AGGAGATCAG CTCTGGCTAT AACGTGTACC GCTCCAGGAG GTACCAGCTG
326 CCCGTGTCCC TGGGCAGCGC CAGGCAGAGG CAGCTGCAGC GGAGCCGTGG CTTCCTGCCC
386 CTGTCCCACT TCCTGCCGGT GCTGCCCGCG GCCTCGGAGG AGGTGGCGGC CCCCGCTGAC
446 CACCCGCAAG CAGACCCTTT CTCGCCCCTG GAGACCGACA GCATGGACCC ATTTGGAATG
506 GCCACCAAGC GGGGGCTGGT GAAGAGCCCC AGCTTCCAGA AGTGA
```

*Cavia porcellus* gene coding sequence (guinea pig) FGF19 (SEQ ID NO:
73) (Ensembl Accession No. ENSCPOT00000008222, which is hereby
incorporated by reference in its entirety)

```
  1 ATGTGGAGTG CGCCGAGCGG ATGTGTGGTG ATCCGCGCCC TGGTCCTGGC TGGCCTGTGG
 61 CTGGCCGTGG CGGGGCGCCC CCTGGCCCGG CGGTCTCTGA CCAGGGGCCG CGTCTATCTGA CCAGGAGGCCG
121 CACTTGTACT ACGGCTGGGA CCAGCCGATC CGCCTTCGGC ACCTGTACGC CGCGGGCCCC
181 TACGGCCGCT CGCGCTGCTT CCTGCGCATT CACACGGACG GCGCGGTGGA CTGCGTCGAG
241 GAACAGAGCG AGCACTGTTT GCTGGAGATC AGAGCAGTCG CTCTGGAGAC CGTGGCCATC
301 AAGGACATAA ACAGCGTCCG GTACCTGTGC ATGGGCCCCG ACGGCAGGAT GCGGGGCCTG
361 CCCTGGTATT CGGAGGAGGA CTGTGCCTTC AAGGAAGAGA TCAGCTACCC GGGCTACAGC
421 GTGTACCGCT CCCAGAAGCA CCACCTCCCC ATCGTGCTGA GCAGTGTCAA GCAGAGGCAG
481 CAGTACCAGA GCAAGGGGGT GGTGCCCCTG TCCTACTTCC TGCCCATGCT GCCCAAGGCC
541 TCTGTGGAGC CCAGCGACGA GGAGGAATCC AGCGTGTTCT CGTTGCCCCT GAAGACGGAC
601 AGCATGGACC CCTTTGGGAT GGCCAGTGAG ATCGGGCTGG TGAAGAGTCC CAGCTTTCAG
661 AAGTAA
```

*Tupaia belangeri* gene coding sequence (tree shrew) FGF19 (SEQ ID NO:
74) (from Ensembl Accession No. ENSTBET00000000307, which is hereby
incorporated by reference in its entirety) (1-219, excluding 116-138)

```
  1 ATGAGGAGAA CACCTGAGCGG GTTTGCAGTG GCCCGTGTCC TCTTCCTGGG CAGCCTTTGG
 61 CTGGCCGCAG CCGGGAGCCC CTTGGCCCTG TCCGACGCCG GGCCGCATGT GAACTACGGC
121 TGGGATGAGT CCATACGCCT GCGACACTTG TACACCGCCA GCGCCCACGG CTTCCACCGAG
181 TGCTTCTTGC GCATCCGTGA CGACGGCTCA GTGGACTGCG CGCGGGGCCA GAGTTTGCAC
241 AGTTTGCTGG AGATCAAGGC AGTCGCTTTG CAGACCGTGG CCATCAAAGG CGTGTACAGT
301 GTCCGCTACC TCTGCATGGA CGCCGACGGC AGGATGCAGG GGCTG----- ----------
361 ---------- ---------- ---------- ---------- NNGGTCCACG
369 AAGCACGGCC TCCCAGTCTC CCTGAGCAGT GCCAAGCAGA GGCAGCTGTT AACGGTTAGG
429 GGCTTTCCTT CCCTTCCCCA CTTCCTGCTC ATGATGGCCA AGACTTCAGC AGGGCCTGGA
489 AACCCCAGGG ACCACCCAGG GTCTAACACT TTCTCGTTGC CCCTGGAAAC TGATAGCATG
549 GACCCATTTG GGATGACCAC CAGACATGGG CTGGTGAAGA GTCCCAGCTT TCAAAACTAA
```

*Rattus norvegicus* gene coding sequence (Norway rat) FGF15 (SEQ ID NO:
75) (GenBank Accession No. NM_130753, which is hereby incorporated by
reference in its entirety) (SEQ ID NO: 56)

```
  1 ATGGCGAGAA AGTGGAGTGG GCGTATTGTG GCCCGAGCTC TGGTCCTGGC CACTCTGTGG
 61 CTGGCCGTGT CTGGGCGTCC CCTGGTCCAG CAATCCCAGT CTGTGTCGGA TGAAGGTCCA
121 CTCTTTCTCT ATGGCTGGGG CAAGATTACC CGCCTGCAGT ACCTGTACTC TGCTGGTCCC
181 TACGTCTCCA ACTGCTTCCT GCGTATCCGG AGTGACGGCT CTGTGGACTG CGAGGAGGAC
241 CAGAACGAAC GAAATCTGTT GGAGTTCCGC GCGGTTGCTC TGAAGACAAT TGCCATCAAG
301 GACGTCAGCA GCGTCGGTA CCTCTGCATG AGCGCCGACG GCAAGATATA CGGGCTGATT
361 CGCTACTCGG AGGAAGACTG TACCTTCAGG GAGGAAATGG ACTGTTTGGG CTACAACCAG
421 TACAGGTCCA TGAAGCACCA CCTCCACATC ATCTTCATCA AGGCCAAGCC CAGAGAGCAG
481 CTCCAGGGCC AGAAACCTTC AAACTTTATC CCCATATTTC ACCGGTCTTT CTTTGAATCC
541 ACGGACCAGC TGAGGTCTAA AATGTTCTCT CTGCCCCTGG AGAGCGACAG CATGGATCCG
601 TTCAGAATGG TGGAGGATGT GGACCACCTA GTGAAGAGTC CAGCTTCCA GAAATGA
```

*Mus musculus* gene coding sequence (house mouse) FGF15 (SEQ ID NO: 76)
(GenBank Accession No. NM_008003, which is hereby incorporated by
reference in its entirety)

```
148                          ATG GCGAGAAAGT GGAACGGGCG TGCGGTGGCC
181 CGAGCCCTGG TCCTGGCCAC TCTGTGGCTG GCTGTGTCTG GCGTCCCCT GGCTCAGCAA
241 TCCCAGTCTG TGTCAGATGA AGATCCACTC TTTCTCTACG GCTGGGGCAA GATTACCCGC
301 CTGCAGTACC TGTACTCCGC TGGTCCCTAT GTCTCCAACT GCTTCCTCCG AATCCGGAGC
361 GACGGCTCTG TGGACTGCGA GGAGGACCAA AACGAACGAA ATTTGTTGGA ATTCCGCGCG
421 GTCGCTCTGA AGACGATTGC CATCAAGGAC GTCAGCAGCG TGCGGTACCT CTGCATGAGC
481 GCGGACGGCA AGATATACGG GCTGATTCGC TACTCGGAGG AAGACTGTAC CTTCAGGGAG
541 GAAATGGACT GTTTAGGCTA CAACCAGTAC AGATCCATGA AGCACCATCT CCATATCATC
601 TTCATCCAGG CCAAGCCCAG AGAACAGCTC CAGGACCAGA AACCCTCAAA CTTTATCCCC
661 GTGTTTCACC GCTCCTTCTT TGAAACCGGG GACCAGCTGA GGTCTAAAAT GTTCTCCCTG
```

TABLE 2-continued

```
721 CCCCTGGAGA GTGACAGCAT GGATCCGTTC AGGATGGTGG AGGATGTAGA CCACCTAGTG
781 AAGAGTCCCA GCTTCCAGAA ATGA
```

*Gallus gallus* gene coding sequence (chicken) FGF19 (SEQ ID NO: 77)
(GenBank Accession No. NM_204674, which is hereby incorporated by
reference in its entirety)
```
127       ATGG GGCCGGCCCG CCCCGCCGCA CCCGGCGCTG CCCTGGCGCT GCTGGGGATC
181 GCCGCCGCCG CCGCCGCCGC CAGGTCCCTG CCGCTGCCCG ACGTCGGGGG TCCGCACGTC
241 AACTACGGCT GGGGGGAACC CATCCGGCTG CGGCACCTAC TACACCGCCC AGGCAAGCAC
301 GGGCTCTTCA GCTGCTTCCT GCGCATCGGC GGCGACGGCC GGGTGGACGC TGTCGGTAGC
361 CAGAGCCCGC AGAGTCTGTT GGAGATCCGC GCCGTGGCGG TGCGCACCGT GGCCATCAAG
421 GGCGTGCAGA GCTCCCGCTA CCTCTGCATG GACGAGGCGG GGCGGCTGCA CGGGCAGCTC
481 AGCTATTCCA TTGAGGACTG TTCCTTTGAA GAGGAGATTC GTCCAGACGG CTACAACGTG
541 TATAAATCAA AGAAATACGG GGATATCGGT TCTTTGAGCA GTGCCAAACA AAGACAGCAA
601 TTCAAAGGAA AAGATTTTCT CCCGCTGTCT CACTTCTTAC CCATGATCAA CACTGTGCCA
661 GTGGAGGTGA CAGACTTTGG TGAATATGGT GATTACAGCC AGGCTTTTGA GCCAGAGGTC
721 TACTCATCGC CTCTCGAAAC GGACAGCATG GATCCCTTTG GATCACTTCA AACTGTCT
781 CCAGTGAAGA GCCCCAGCTT TCAGAAATGA
```

*Taeniopygia guttata* gene coding sequence (zebra finch) FGF19 (SEQ ID
NO: 78) (GenBank Accession No. XM_002194457, which is hereby
incorporated by reference in its entirety)
```
  1 ATGGTTATCA TAAGCAATCT ATATCTGATG CAGAACGATG TTATGATGAA TATGAGGCGA
 61 GCACCCCTTC GCGTTCACGC TGCTCGCTCT TCGGCCACCC CTGCCTCCGC GCTGCCGCTG
121 CCGCCGCCCG ACGCCGGCCC GCACCTCAAA TACGGCTGGA GAGAGCCCAT CCGGCTGCGG
181 CACCTCTACA CCGCCAGCAA GCACGGGCTC TTCAGCTGCT TCCTGCGTAT CGGCGCTGAC
241 GGCCGGGTGG ACGCGCCGG CAGCCAGAGC CCGCAGAGCC TGCTAGAGAT CCGCGCCGTG
301 GCCGTGCGCA CCGTGGCCAT CAAGGGCGTG CAGAGCTCCC GGTACCTGTG CATGGACGAG
361 GCGGGGCGGC TGCACGGGCA GCTCAGGAAT TCCACTGAAG ACTGCTCCTT TGAGGAGGAG
421 ATTCGCCCAG ACGGCTACAA TGTGTATAGA TCTAAAAAAC ATGGAATATC GGTGTCTTTG
481 AGCAGTGCCA AACAAAGACA GCAGTTCAAG GGGAAAGATT TCCTTCCCCT GTCTCACTTC
541 TTGCCCATGA TCAACACTGT GCCCATGGAG TCAGCAGACT TTGGTGAATA TGGTGATTAC
601 AGCCAGGCCT TTGAGGCAGA GGCCTTCTCC TCACCTCTGG AGACGGACAG CATGGACCCC
661 TTTGGCATCG CCTCCAAACT GTCCCTAGTG AAGAGCCCTA GCTTCCAAAA CTGA
```

*Danio rerio* gene coding sequence (zebrafish) FGF19 (SEQ ID NO: 79)
(GenBank Accession No. NM_001012246, which is hereby incorporated by
reference in its entirety)
```
  1 ATGCTCCTCT TACTCTTTGT CACTGTTTGT GGAAGTATCG GCGTGGAGAG CCTCCCGTTG
 61 CCCGACTCTG GTCCACATTT GGCAAATGAC TGGAGTGAAG CCGTCCGGCT ACGACATCTG
121 TACGCAGCCA GACATGGCTT ACATCTGCAA ATAAACACAG ACGGAGAAAT CATTGGATCC
181 ACATGCAAAG CTCGGACAGT AAGTTTGATG GAGATATGGC CGGTGGACAC AGGCTGCGTA
241 GCCATTAAGG GAGTTGCAAG CTCCCGATTT CTTTGCATGG AAAGACTGGG AAACCTGTAC
301 GGATCGCACA TTTACACTAA AGAGGACTGC TCTTTTTTGG AACGCATCCT TCCAGACGGC
361 TACAACGTCT ACTTCTCGAG CAAACACGGA GCTCTTGTGA CTTTAAGTGG TGCGAAAAAC
421 AAGTTGCACA GTAACGATGG GACTTCTGCA TCCCAGTTCC TCCCCATGAT CAACACATTT
481 TCAGAGGAAC ACACTAAACA GCACTCAGGG GAACAGCACT CTTCTGTTAA CCATGGACAG
541 GACCATCAGT TGGGCCTTGA AATAGACAGT ATGGACCCTT TCGGAAAGAT CTCTCAAATA
601 GTGATCCAGA GTCCCAGCTT CAACAAAGA TGA
```

*Xenopus (Silurana) tropicalis* gene coding sequence (Western clawed
frog) FGF19 (SEQ ID NO: 80) (GenBank Accession No. NM_001142825, which
is hereby incorporated by reference in its entirety)
```
  1 ATGTGGAAGA CCCTGCCTTG GATTTTGGTT CCCATGGCTG TGGCCGTGCT GTATTTCCTC
 61 GGAGGGGCGG AAAGTCTGCC GCTTTTTGAT GCCGGGCCGC ACATGCAGAA CGGCTGGGGG
121 GAGTCGATCA GAATTCGGCA CCTGTATACG GCCAGGAGGT TCGGGCACGA CAGCTACTAC
181 CTCCGGATAC ACGAGGATGG CAGAGTCGAT GGTGACAGGC AACAAAGCAT GCACAGTTTA
241 TTGGAAATCA GAGCAATTGC AGTTGGAATT GTTGCCATTA AAGGGTATCG CAGCTCTCTG
301 TACCTGTGCA TGGGGTCCGA GGGAAAACTC TATGGAATGC ACAGTTACTC CCAGGATGAT
361 TGCTCTTTTG AAGAGGAGCT TCTCCCGGAT GGATACAACA TGTATAAATC AAGGAAACAT
421 GGCGTTGCTG TCTCCCTAAG CAAGGAGAAG CAGAAGCAAC AATACAAAGG AAAGGGCTAC
481 CTCCCGTTGT CCCATTTCCT ACCCGTGATA AGCTGGGTGC CATGGAGCC CACCGGAGAT
541 GTAGAAGATG ATATCTACAG GTTTCCATTC AATACGGACA CAAAAAGTGT CATTGACAGC
601 CTTGATACCC TGGGACTAAT GGATTTTTCG AGTTATCACA GAAATAG
```

*Otolemur garnettii* (bushbaby) FGF19 gene coding sequence (SEQ ID NO:
81) (Ensembl accession no. ENSOGAT00000031686, which is hereby
incorporated by reference in its entirety)
```
  1 ATGCCCAGCG GGCTGAGAGG GCGTGTGGTA GCCGGCGCCC TGGCCCTGGC CAGCTTCTGG
 61 CTGGCCGTGG CCGGGCGCCC GCTGGCCTTC TCGGATGCCG GCCCTCACGT GCACTACGGC
121 TGGGGTGAGC CCATCCGCCT GCGACACCTG TACACCGCCG CCCCCACGG CCTCTCCAGC
181 TGCTTCCTGC GCGTACGCAC CGACGGTGCG GTAGACTGCG CGCGGGGCCA GAGCGCACAC
241 AGTTTGCTGG AAATCAGGGC CGTCGCTCTC CGGACCGTGG CCATCAAAGG CGTGCACAGC
301 GCGCGGTACC TCTGCATGGG CGCCGACGGC AGGATGCAGG GCTGCCTCA GTACTCGGAG
361 GAAGACTGTG CCTTTGAGGA GGAGATCCGG CCAGACGGCT ACAACGTCTA CTGGTCTGGA
421 AAGCACCGCC TGCCGGTGTC TCTGAGCAGT GCCCGGACAGA GGCAGCTGTA CAAGGGCAGG
481 GGCTTTCTGC CGCTCTCTCA CTTCCTGCCC ATGCTGCCTG TGACCCCAGC CGAGCCCGGG
541 GACCTCAGAG ACCACCTGGA ATCCGACATG TTCTCTTTGC CCTGGAAAC TGACAGCATG
601 GATCCATTTG GGATCGCCAC CAGACTGGGC GTGGTGAAGA GTCCCAGCTT TCAGAAATGA
```

TABLE 2-continued

*Felis catus* (cat) FGF19 gene coding sequence (SEQ ID NO: 82) (Ensembl accession no. ENSFCAT00000026317, which is hereby incorporated by reference in its entirety)

```
   1 ATGCGGAGCG CGCCGAGCCA GTGCGCGGTA ACCCGCGCCC TGGTCCTAGC CGGTCTCTGG
  61 CTGGCAGCAG CCGGGCGCCC CCTAGCCTTC TCGGACGCGG GGCCTCACGT GCACTACGGC
 121 TGGGGTGAGC CCATCCGCCT GCGGCACCTG TACACCGCCG GCCCCCACGG CCTCTCCAGC
 181 TGCTTCCTGC GCATCCGAGC CGACGGGGGG GTTGACTGCG CGCGGAGCCA GAGCGCGCAC
 241 AGTTTGGTGG AGATCAGGGC AGTCGCTCTG CGGACCGTGG CCATCAAGGG CGTGCACAGC
 301 GTCCGGTACC TCTGCATGGG CGCCGACGGC AGGATGCAAG GGCTGCTTCA GTACTCTGCT
 361 GGGGACTGTG CCTTCCAAGA GGAGATCCGC CCCGACGGCT ACAATGTGTA CCGGTCCGAG
 421 AAGCACCGTC TCCCCGTCTC TTTGAGTAGT GCCATACAGA GGCAGCTGTA CAAGGGCAGA
 481 GGGTTTTTGC CCCTGTCCCA TTTCTTGCCC ATGCTGCCCG GCAGCCCAGC AGAGCCCAGG
 541 GACCTCCAGG ACCACGTGGA GTCGGAGAGG TTTTCTTCAC CCCTGGAAAC AGACAGCATG
 601 GACCCTTTTG GGATTGCCAC CAAATGGGG TTAGTGAAGA GTCCCAGCTT CCAAAAGTAA
```

*Pelodiscus sinensis* (Chinese softshell turtle) FGF19 gene coding sequence (SEQ ID NO: 83) (Ensembl accession no. ENSPSIT00000010427, which is hereby incorporated by reference in its entirety)

```
 241                     ATGTGGAG GAGCCTGTGC AAATCTCACA
 301 CGTCTCTGGC TCTGCTGGGA CTCTGCTTTG CGGTGGTCGT GAGATCTCTG CCTTTCTCGG
 361 ATGCAGGGCC ACATGTGAAC TATGGCTGGG GGAGCCTAT TCGATTAAGG CACCTATACA
 421 CCGCCAGCAG ACACGGGCTG TTCAATTACT TCCTGAGGAT CAGCAGTGAT GGCAAAGTGG
 481 ATGGCACCAG CATTCAGAGT CCTCACAGTC TGCTGGAAAT CAGGGCTGTG GCAGTTCGCA
 541 CCGTGGCGAT CAAGGGCGTC CACAGTTCCC GGTACCTCTG CATGGAAGAA GACGGGAAGC
 601 TGCATGGACT TCTCAGGTAT TCTACAGAAG ATTGCTCCTT TGAAGAGGAG ATACGCCCAG
 661 ATGGCTACAA TGTATATAAA TCAAAGAAAT ATGGAATCTC TGTGTCCTTA AGTAGTGCCA
 721 AACAAAGACA ACAATTCAAA GGAAAAGACT TCTTCCATT GTCTCACTTC TTGCCTATGA
 781 TCAATACAGT ACCTGTGGAG TCAATGGATT TTGGAGAATA TGGTGATTAT AGTCATACTT
 841 TTGAATCAGA TCTATTCTCT TCACCTCTCG AAACTGACAG CATGGATCCC TTTGAATCA
 901 CCTCTAAAAT ATCTCCAGTG AAGAGCCCCA GCTTTCAGAA ATAA
```

*Latimeria chalumnae* (coelacanth) FGF19 gene coding sequence (SEQ ID NO: 84) (Ensembl accession no. ENSLACT00000014697, which is hereby incorporated by reference in its entirety)

```
   1 ATGTTACAGG CACTGTACAA TCTCTGTACA GCTCTAGTTT TGTTTAAGCT TCCTTTTGCA
  61 ATGGTGGGGT ACACCCTGCC TTCTGCCAAT GAAGGGCCCC ATCTGAACTA TGACTGGGGA
 121 GAATCTGTAA GACTCAAACA TCTGTACACA TCTAGCAAGC ATGGATTGAT CAGTTACTTT
 181 TTACAGATCA ATGATGATGG CAAAGTAGAT GGGACCACTA CACGAAGCTG TTATAGTTTG
 241 CTCGAAATAA AATCAGTGGG GCCAGGAGTT TTGGCAATTA AAGGCATACA GAGCTCCAGA
 301 TACCTTTGTG TCGAGAAGGA TGGAAAATTG CATGGATCGC GCACTTATTC AGCAGACGAT
 361 TGCTCCTTCA AGAGGATAT ACTCCCAGAT GGTTACACTA TCTACGTGTC AAAGAAACAT
 421 GGATCTGTTG TTAATCTGAG CAACCACAAA CAGAAACGTC AGAGAAATCG CAGAACCCTG
 481 CCTCCATTTT CTCAGTTCCT ACCGCTTATG GACACCATTC GTGTGGAGTG CATGAACTGC
 541 GGGGAGCACT GTGACGACAA CCTGCATGAC GAGCTAGAAA CAGGACTGTC CATGGATCCC
 601 TTTGAAAGTA CATCCAAAAA ATCCTTTCAG AGTCCCAGCT TCACAATAG ATAA
```

*Mustela putorius furo* (ferret) FGF19 gene coding sequence (SEQ ID NO: 85) (Ensembl accession no. ENSMPUT00000004650, which is hereby incorporated by reference in its entirety)

```
 421      ATGCGG AGCGCCGCGA GTCGGTGCGC GGTAGCCCGC GCGCTGGTCC TAGCCGGCCT
 481 TTGGCTGGCC GCAGCCGGGC GCCCCCTAGC CTTCTCGGAC GCGGGGCCGC ACGTGCACTA
 541 TGGCTGGGGT GAGCCCATCC GCCTACGGCA CCTGTACACC GCCGGCCCCC ACGGCCTCTC
 601 CAGCTGCTTC CTGCGCATCC GTGCCGACGG CGGGGTTGAC TGCGCGCGGG GCCAGAGCGC
 661 GCACAGTTTG GTGGAGATCC GGGCAGTCGC TCTGCGGACG GTGGCCATCA AGGGCGTGTA
 721 CAGCGACCGC TATCTCTGCA TGGGTGCGGA CGGCAGGATG CAAGGGCTGC CTCAGTACTC
 781 CGCCGGAGAC TGTGCTTTCG AGGAGGAGAT CCGCCCTGAT GGCTACAACG TGTACCGGTC
 841 CAAGAAGCAC CGTCTCCCCG TCTCCCTGAG CAGTGCGAAA CAAAGGCAGC TGTACAAGGA
 901 CCGGGGCTTT TTGCCTCTGT CCCATTTCTT GCCCATGCTG CCCGGGAGCC TGGCGGAGCC
 961 CAGGGACCTC CAGGACCACG TGGAGGCTGA TGGGTTTTCT GCCCCCCTAG AAACAGACAG
1021 CATGGACCCT TTTGGGATTG CCACCAAAAT GGGACTAGTG AAGAGTCCCA GCTTCCAAAA
1081 ATGA
```

*Takifugu rubripes* (fugu) FGF19 gene coding sequence (SEQ ID NO: 86) (Ensembl accession no. ENSTRUT00000007155, which is hereby incorporated by reference in its entirety)

```
   1 TCATCTACAA GGATTAGTGG AAACATGGTT CTCCTCATGC TCCCCATCAC CGTTGCAAAC
  61 CTCTTCCTCT GTGCTGGAGT TCTCTCCTTG CCTTTGTTGG ATCAAGGGTC TCATTTTCCC
 121 CAAGGCTGGG AACAGGTAGT CCGCTTCAGG CACCTGTATG CTGCCAGTGC AGGGCTGCAC
 181 CTGCTGATCA CTGAAGAGGG CTCGATCCAA GGCTCTGCAG ATCCAACTTT ATACAGCCTG
 241 ATGGAGATCC GTCCGGTGGA CCCAGGCTGT GTTGTCATTA GAGGAGCAGC AACCACACGA
 301 TTCCTCTGCA TAGAAGGTGC TGGAAGACTG TACTCATCAC AGACCTACAG CAAAGACGAC
 361 TGTACCTTCA GAGAGCAAAT CCTAGCAGAC GGCTACAGCG TCTACAGATC TGTCGGACAC
 421 GGAGCTCTGG TCAGTCTGGG AAACTACCGG CAGCAGCTGA GGGGGAGGA CTGGAGCGTT
 481 CCGACACTGG CTCAGTTCCT CCCCAGAATA AGTTCACTGG ATCAGGACTT TAAAGCTGCT
 541 CTTGACGAGA CTGAGAAGCC AGAACAAACT GCACCTCAAA GATCGGAACC TGTCGACATG
 601 GTGGACTCAT TTGAAAAGCT CTCTCAGATC ATCCACAGTC CCAGTTTTCA CAAG
```

TABLE 2-continued

*Equus caballus* (horse) FGF19 gene coding sequence (SEQ ID NO: 87)
(Ensembl accession no. ENSECAT00000021494, which is hereby
incorporated by reference in its entirety) (1-216, excluding 1-19 and
114-216)
```
  1 ---------- ---------- ---------- ---------- ---------- -------GCG
  4 GCCGGGCGCC CCCTAGCCTT GTCCGACGCT GGGCCGCACG TGCACTACGG CTGGGGCGAG
 64 CCGATCCGCC TGCGGCACCT GTACACCGCC GGCCCCCACG GCCTCTCCAG CTGCTTCCTG
124 CGCATCCGCG CCGATGGCGC CGTGGACTGC GCGCGGGGCC AGAGCGCGCA CAGTTTGGTG
184 GAGATCAGAG CAGTCGCTCT GCGCACCGTG GCCATCAAGG GCGTGCACAG CGTCCGGTAC
244 CTCTGCATGG GCGCCGACGG CAGGATGCAA GGGCTGGTA
```

*Oryzias latipes* (medaka) FGF19 gene coding sequence (SEQ ID NO: 88)
(Ensembl accession no. ENSORLT00000000352, which is hereby
incorporated by reference in its entirety)
```
  1 ACCATGCTGC TCATTGTGGT CACCATTTCC ACAATGGTGT TTTCTGACTC TGGAGTTTCC
 61 AGCATGCCGC TCTCTGATCA TGGACCCCAC ATCACTCACA GCTGGAGCCA AGTGGTCCGC
121 CTCCGGCACC TGTACGCGGT CAAGCCTGGA CAACATGTCC AGATCAGAGA GGATGGACAC
181 ATCCACGGCT CAGCAGAACA AACTCTGAAC AGCCTGCTGG AGATCCGTCC GGTTGCTCCG
241 GGACGGGTGG TCTTCAGAGG AGTAGCCACC TCAAGGTTTC TGTGCATGGA GAGCGACGGC
301 AGACTCTTCT CCTCACACAC ATTTGACAAG GACAACTGCG TCTTCAGAGA GCAGATCTTG
361 GCAGACGGCT ACAACATCTA CATTTCAGAT CAGCATGGAA CCCTGCTTAG TTTGGGAAAC
421 CACCGGCAAA GGCAGCAGGG TTTAGACCGG GATGTTCCAG CCCTGGCTCA GTTCCTCCCC
481 AGGATCAGCA CCCTGCAGCA GGGCGTGTAC CCAGTGCCAG ACCCCCCCA CCAGATGAGA
541 ACAATGCAAA CAGAGAAGAC TCTAGATGCC ACGGACACAT TGGGCAACT CTCTAAAATC
601 ATTCACAGTC CCAGCTTCAA CAAAAGATGA
```

*Xiphophorus maculatus* (platyfish) FGF19 gene coding sequence (SEQ ID
NO: 89) (Ensembl accession no. ENSXMAT00000001519, which is hereby
incorporated by reference in its entirety)
```
  1                                                                ATG
  4 TTTGTGTTCA TTCTATGCAT TGCTGGTGAA CTTTTTACTC TGGGAGTATT TTGCATGCCA
 64 ATGATGGACC AGGGGCCACT TGTCACCCAT GGCTGGGGCC AGGTGGTCCG GCACCGGCAT
124 CTGTATGCAG CCAAGCCAGG ACTGCACCTA CTGATCAGTG AGGATGGACA AATCCACGGT
184 TCCGCAGATC AAACTCTTTA CAGCCTGCTG GAGATCCAAC CTGTTGGCCC CGGACGTGTT
244 GTGATCAAAG GAGTGGCAAC CACACGCTTC CTCTGCATGG AGAGCGACGG CAGATTGTAC
304 TCAACTGAAA CATACAGCAG AGCTGACTGC ACCTTCAGAG AACAGATCCA GGCAGACGGC
364 TACAACGTCT ACACCTCTGA TAGCCATGGA GCCCTCCTCA GTTGGGAAA CAACCAGCAA
424 AGACACAGCG GCTCAGACCG TGGTGTTCCA GCTCTGGCCC GCTTTCTTCC CAGGTTAAAC
484 ACCCTTCAGC AGGCCGTCCC CACAGAGCCG GATGTTCCTG ATCAGCTCAG TCCAGAGAAA
544 GTACAACAGA CTGTGGACAT GGTGGCCTCC TTTGGCAAGC TCTCTCATAT AATTCACAGT
604 CCCAGCTTCC ATAAGAGATG A
```

*Ictidomys tridecemlineatus* (squirrel) FGF19 gene coding sequence (SEQ
ID NO: 90) (Ensembl accession no. ENSSTOT00000026298, which is hereby
incorporated by reference in its entirety)
```
  1 ATGCGGAGCG CGCCGAGCGG ACGTGCCTTA GCCCGCGCCC TGGTGCTGGC CAGCCTCTGG
 61 TTGGCAGTGG CCGGACGACC CCTGGCCCGG CGCTCTCTGG CTCTCTCCGA CCAGGGGCCA
121 CACTTGTACT ATGGCTGGGA TCAGCCCATC CGCCTCCGGC ACCTGTACGC CGCGGGCCCC
181 TACGGCTTCT CCAACTGTTT CCTGCGCATC CGCACCGACG GCGCCGTGGA CTGCGAGGAG
241 AAGCAGAGCG AGCGTAGTTT GATGGAGATC AGGGCGGTCG CTCTGGAGAC TGTGGCCATC
301 AAGGACATAA ACAGCGTCCG GTACCTCTGC ATGGGCGCCG ACGGCAGGAT ACAGGGACTG
361 CCTCGGTACT CGGAGGAAGA GTGCACGTTC AAGGAGGAGA TCAGCTATGA CGGCTACAAC
421 GTGTACCGGT CCCAGAAGTA CCACCTTCCC GTGGTGCTCA GCAGTGCCAA GCAGCGGCAG
481 CTGTACCAGA GCAAGGGCGT GGTTCCCCTG TCCTACTTCC TGCCCATGCT GCCCCTGGCC
541 TCTGCGGAGA CCAGGGACCG CTTGGAATCC GATGTGTTCT CTTTACCTCT GGAAACTGAC
601 AGCATGGACC CGTTTGGGAT GGCCAGTGAA GTGGGCCTGA AGAGCCCCAG CTTCCAGAAG
661 TAA
```

*Gasterosteus aculeatus* (stickleback) FGF19 gene coding sequence (SEQ
ID NO: 91) (Ensembl accession no. ENSGACT00000018770, which is hereby
incorporated by reference in its entirety)
```
  1 ATGCTGCTGC TGCTGGTCCC CGCGTACGTT GCCAGTGTGT TTTTAGCTCT CGGGGTTGTT
 61 TGCTTGCCCC TAACAGATCA GGGTCTCCAC ATGGCCGACG ACTGGGGCCA GTCGGTCCGA
121 CTCAAGCACC TGTACGCCGC CAGCCCGGGA CTCCACCTGC TGATCGGGGA GGATGGTCGG
181 ATCCAAGGCT CGGCGCAGCA AAGCCCCTAC AGCCTGCTGG AGATCAGTGC AGTGGATCCG
241 GGCTGTGTGG TCATCAGAGG AGTAGCAACC GCACGGTTTC TCTGCATCGA AGGCGATGGA
301 AGACTGTACT CATCGGACAC CTACAGCAGA GACGACTGCA CCTTCAGGGA GCAGATCCTC
361 CCGGACGGCT ACAGCGTCTA CGTCTCCCAT GGACACGGGG CCCTGCTCAG CCTGGGGAAC
421 CACAGGCAGA GGCTGCAGGG TCGAGACCAC GGCGTGCCGG CTCTGGCCCA GTTCCTCCCG
481 AGGGTCAGCA CCATGGATCA GGCCTCGGCC CCCGACGCGC CGGGCAGAC CGCCACCGAG
541 ACGGAAGAGC CCGTGGACTC GTTTGGAAAG CTCTCTCAGA TCATTCACAG TCCCAGCTTC
601 CACGAGAGAT GA
```

*Oreochromis niloticus* (tilapia) FGF19 gene coding sequence (SEQ ID NO:
92) (Ensembl accession no. ENSONIT00000022816, which is hereby
incorporated by reference in its entirety)
```
 55                                                             ATGCTG
 61 CTGCTCCTCA TCGTATCCAT TGTCAATATG CTTTTTGGTG TTGGAATGGT TTGCATGCCC
121 CTGTCAGACA ACGGGCCCCA CATCGCCCAC GGCTGGGCCC AGGTGGTCCG GCTCAGGCAC
181 CTTTACGCCA CCAGACCGGG AATGCACCTG CTGATCAGTG AGGGTGGACA GATCCGTGGT
```

TABLE 2-continued

```
241 TCTGCCGTCC AGACTCTGCA CAGCCTAATG GAGATTCGTC CAGTCGGTCC AGGCCGTGTT
301 GTCATCAGAG GGGTAGCAAC CGCAAGGTTT CTCTGCATAG AAGACGACGG CACACTGTAC
361 TCATCGCACG CCTACAGCAG AGAGGACTGC ATCTTCAGAG AGCAGATCTT GCCAGATGGG
421 TACAACATCT ACATCTCTGA CAGACATGGA GTCCTGCTCA GTCTGGGAAA CCACCGGCAA
481 AGACTGCAGG GCTTAGACCG AGGAGATCCA GCCCTGGCCC AGTTCCTCCC CAGGATCAGC
541 ACTCTGAATC AAATCCCTTC CCCTGGGGCA ACATCGGTG ACCACATGAA AGTAGCAAAA
601 ACAGAAGAAC CTGTGGACAC AATAGATTCA TTTGGAAAGT TCTCTCAGAT CATTGACAGT
607 CCCAGCTTCC ATAAGAGATG A
```

*Meleagris gallopavo* (turkey) FGF19 gene coding sequence (SEQ ID NO: 93) (Ensembl accession no. ENSMGAT00000011114, which is hereby incorporated by reference in its entirety) (1-216, excluding 1-70)
```
  1 GTAGGCAATC AATCACCACA GAGCATCCTT GAAATAACTG CTGTTGATGT CGGGATCGTC
 61 GCTATCAAGG GCTTGTTCTC TGGCAGATAC CTGGCCATGA ACAAAAGGGG CAGGCTTTAT
121 GCATCACTCA GCTATTCCAT TGAGGACTGT TCCTTTGAAG AGGAGATTCG TCCAGATGGC
181 TATAACGTGT ATAAATCAAA GAAATACGGA ATATCAGTGT CTTTGAGCAG TGCCAAACAA
241 AGACAACAAT TCAAAGGAAA AGATTTTCTC CCACTGTCTC ACTTCTTACC CATGATCAAC
301 ACTGTGCCAG TGGAGGTGAC AGACTTTGGT GAATACGGTG ATTACAGCCA GGCTTTTGAG
361 CCAGAGGTCT ACTCATCGCC TCTCGAAACG GACAGCATGG ATCCCTTTGG GATCACTTCC
421 AAACTGTCTC CAGTGAAGAG CCCCAGCTTT CAGAAA
```

*Papio anubis* (olive baboon) FGF19 gene coding sequence (SEQ ID NO: 94) (GenBank accession no. XM_003909422, which is hereby incorporated by reference in its entirety)
```
 758                                            ATG AGGAGCGGGT GTGTGGTGGT
 781 CCACGCCTGG ATCCTGGCCA GCCTCTGGCT GGCCGTGGCC GGGCGTCCCC TCGCCTTCTC
 841 GGACGCGGGG CCCCACGTGC ACTACGGCTG GGGCGACCCC ATCCGCCTGC GGCACCTGTA
 901 CACCTCCGGC CCCCACGGGC TCTCCAGCTG CTTCCTGCGC ATCCGCACCG ACGGCGTCGT
 961 GGACTGCGCG CGGGGCCAAA GCGCGCACAG TTTGCTGGAG ATCAAGGCAG TAGCTCTGCG
1021 GACCGTGGCC ATCAAGGGCG TGCACAGCGT GCGGTACCTC TGCATGGGCG CCGACGGCAA
1081 GATGCAGGGG CTGCTTCAGT ACTCAGAGGA AGACTGTGCT TTCGAGGAGG AGATCCGCCC
1141 TGATGGCTAC AATGTATACC GATCCCAGAA GCACCGCCTC CCGGTCTCCC TGAGCAGTGC
1201 CAAACAGCGG CAGCTGTACA AGAACAGAGG CTTTCTTCCG CTGTCTCATT TCCTGCCCAT
1261 GCTGCCCATG GCCCCAGAGG AGCCTGAGGA CCTCAGGGGC CCCTTGGAAT CTGACATGTT
1321 CTCTTCGCCC CTGGAGACTG ACAGCATGGA CCCATTTGGG CTTGTCACCG GACTGGAGGC
1381 GGTGAGGAGT CCCAGCTTTG AGAAATAA
```

*Saimiri boliviensis boliviensis* (Bolivian squirrel monkey) FGF19 gene coding sequence (SEQ ID NO: 95) (GenBank accession no. XM_003941165, which is hereby incorporated by reference in its entirety)
```
 231                                                      ATGCGGAGCG
 241 GGTGTGTGGT GGTCCACGCC TGGATCCTGG CTGGCCTCTG GCTGGCTGTG GTCGGGCGCC
 301 CCCTCGCCTT CTCCGATGCG GGGCCGCATG TGCATTACGG CTGGGGCGAC CCCATTCGCC
 361 TGCGGCACCT GTACACCTCC AGCCCCCACG GCCTCTCCAG CTGCTTCCTG CGCATCCGCA
 421 GCGACGGCGT CGTGGACTGC GCGCGGGGCC AGAGCGCGCA CAGTTTGCTG GAGATCAAGG
 481 CAGTCGCTCT AAGGACCGTG GCCATCAAGG GCGTGCACAG CTCGCGGTAC CTCTGCATGG
 541 GCGCCGACGG CAGGCTGCAG GGGCTGTTCC AGTACTCGGA GGAAGACTGT GCTTTCGAGG
 601 AGGAGATCCG CCCCGACGGC TACAATGTGT ACCTATCCGA GAAGCACCGC CTCCCGGTCT
 661 CCCTGAGCAG CGCCAAACAG CGGCAGCTGT ACAAGAAACG AGGCTTTCTT CCGCTGTCCC
 721 ATTTCCTGCC CATGCTGCCC AGAGCCCCAG AGGAGCCTGA TGACCTCAGG GGCCACTTGG
 781 AATCTGACGT GTTCTCTTCA CCCCTGGAGA CTGATAGCAT GGACCCCATTT GGGCTTGTCA
 841 CGGGACTGGA GGCGGTGAAC AGTCCCAGCT TTGAGAAGTA A
```

*Pteropus alecto* (black flying fox) FGF19 gene coding sequence (SEQ ID NO: 96) (generated using SMS Reverse Translate tool on the ExPASy Bioinformatics Resource website (www.expasy.org))
```
  1 ATGCGCAGCC CGTGCGCGGT GGCGCGCGCG CTGGTGCTGG CGGGCCTGTG GCTGGCGAGC
 61 GCGGCGGGCC CGCTGGCGCT GAGCGATGCG GGCCCCGCATG TGCATTATGG CTGGGGCGAA
121 GCGATTCGCC TGCGCCATCT GTATACCGCG GGCCCGCATG GCCCGAGCAG CTGCTTTCTG
181 CGCATTCGCG CGGATGGCGC GGTGATTGC GCGCGCGGCC AGAGCGCGCA TAGCCTGGTG
241 GAAATTCGCG CGGTGGCGCT GCGCAACGTG GCGATTAAAG GCGTGCATAG CGTGCGCTAT
301 CTGTGCATGG GCGCGGATGG CCGCATGCTG GGCCTGCTGC AGTATAGCGG GGATGATTGC
361 GCGTTTGAAG AAGAAATTCG CCCCGATGGC TATAACGTGT ATCATAGCAA AAAACATCAT
421 CTGCCGGTGA GCCTGAGCAG CGCGAAACAG CGCCAGCTGT ATAAAGATCG CGGCTTTCTG
481 CCGCTGAGCC ATTTTCTGCC GATGCTGCCG CGCAGCCCGA CCGAACCGGA AAACTTTGAA
541 GATCATCTGG AAGCGGATAC CTTTAGCAGC CCGCTGGAAA CCGATGATAT GGATCCGTTT
601 GGCATTGCGA GCAAACTGGG CCTGGAAGAA AGCCCGAGCT TCAGAAA
```

*Myotis davidii* (David's myotis) FGF19 gene coding sequence (SEQ ID NO: 97) (generated using SMS Reverse Translate tool on the ExPASy Bioinformatics Resource website (www.expasy.org))
```
  1 ATGAGCGGCC AGAACAGCGG CCGCCATGGC AGCCGCCCGG GCCTGGATGA AGAACCGGAA
 61 CCGGGCCCGC TGGAACTGCG CGCGCTGGGC AGCACCCCGG CGGATCCGCA GCTGTGCGAT
121 TTTCTGGAAA ACCATTTTCT GGGCTATACC TGCCTGGAAC TGGATATTTG CCTGGCGACC
181 TATCTGGGCG TGAGCCATTG GGGCGAAAGC ATTCGCCATC TGTA TACCAGCGGC
241 CCGCATGGCC CGAGCAGCTG CTTTCTGCGC ATTCGCGTGG ATGGCGCGGT GGATTGCGCG
301 CGCGGCCAGA GCGCGCATAG CCTGGTGGAA ATTCGCGCGG TGGCGCTGCG CAAAGTGGCG
361 ATTAAAGGCG TGCATAGCGC GCTGTATCTG TGCATGGAAG GCGATGGCCG CATGCGCGGC
421 CTGCCGCAGT TTAGCCCGGA AGATTGCGCG TTTGAAGAAG AAATTCGCCC GGATGGCTAT
481 AACGTGTATC GCAGCCAGAA ACATCAGCTG CCGGTGAGCC TGAGCAGCGC GCCAGCGC
```

TABLE 2-continued

```
541 CAGCTGTTTA AAGCGCGCGG CTTTCTGCCG CTGAGCCATT TTCTGCCGAT GCTGCCGAGC
601 AGCCCGGCGG AACCGGTGCA TCGCGAACGC CCGCTGGAAC CGGATGCGTT TAGCAGCCCG
661 CTGGAAACCG ATAGCATGGA TCCGTTTGGC ATTGCGAACA ACCTGCGCCT GGTGAAAAGC
721 CCGAGCTTTC AGAAA
```

*Tupaia chinensis* (Chinese tree shrew) FGF19 gene coding sequence (SEQ ID NO: 98) (generated using SMS Reverse Translate tool on the ExPASy Bioinformatics Resource website (www.expasy.org)) (1-257, excluding 13-19)

```
  1 ATGCGCCGCA CCTGGAGCGG CTTTGCGGTG GCGACC---- ---------- ----CGCGCG
 61 GGCAGCCCGC TGGCGCTGGC GGATGCGGGC CCGCATGTGA ACTATGGCTG GGATGAAAGC
121 ATTCGCCTGC GCCATCTGTA TACCGCGAGC CTGCATGGCA GCACCAGCTG CTTTCTGCGC
181 ATTCGCGATG ATGGCAGCGT GGGCTGCGCG CGCGGCCAGA GCATGCATAG CCTGCTGGAA
241 ATTAAAGCGG TGGCGCTGCA GACCGTGGCG ATTAAAGGCG TGTATAGCGT GCGCTATCTG
301 TGCATGGATA CCGATGGCCG CATGCAGGGC CTGCCGCAGT ATAGCGAAGA AGATTGCACC
361 TTTGAAGAAG AAATTCGCAG CGATGGCCAT AACGTGTATC GCAGCAAAAA ACATGGCCTG
421 CCGGTGAGCC TGAGCAGCGC GAAACAGCGC CAGCTGTATA AAGGCCGCGG CTTTCTGAGC
481 CTGAGCCATT TTCTGCTGAT GATGCCGAAA ACCAGCGCGG GCCCGGGCAA CCCGCGCGAT
541 CAGCGCAACC CGCGCGATCA GCGCGATCCG AACACCTTTA GCCTGCCGCT GGAAACCGAT
601 AGCATGGATC CGTTTGGCAT GACCACCCGC CATGGCCTGC TGCTGGATAG CTGCTGCGCG
661 AGCCTGGTGC TGCTGAACAT TAGCACCGAT GGCGAATTTA GCCCGTATGG CAACATTCTG
721 CGCCCGAGCT TTCGCTTTAA ACTGTTTAAA ATGAAAAAAG TGACCAAC
```

*Heterocephalus glaber* (naked mole-rat) FGF19 gene coding sequence (SEQ ID NO: 99) (generated using SMS Reverse Translate tool on the ExPASy Bioinformatics Resource website (www.expasy.org))

```
  1 ATGCGCTTTA GCAAAAGCAC CTGCGGCTTT TTTAACCATC AGCGCCTGCA GGCGCTGTGG
 61 CTGAGCCTGA GCAGCGTGAA ATGGGTGCTG GATGCGGCGG TGGAAGGCCG CCCGATTCGC
121 CTGCGCCATC TGTATGCGGC GGGCCCGTAT GGCCGCAGCC GCTGCTTTCT GCGCATTCAT
181 ACCGATGGCG CGGTGGATTG CGTGGAAGAA CAGAGCGAAC ATTGCCTGCT GGAAATTCGC
241 GCGGTGGCGC TGGAAACCGT GGCGATTAAA GATATTAACA GCGTGCGCTA TCTGTGCATG
301 GGCCCGGATG GCCGCATGCA GGGCCTGCCG TGGTATAGCC AAGAAGATTG CGCGTTTAAA
361 GAAGAAATTA GCTATCCGGG CTATAGCGTG TATCGCAGCC AGAAACATCA TCTGCCGATT
421 GTGCTGAGCA GCGTGAAACA GCGCCAGCAG TATCAGAGCA AAGGCGTGGT GCCGCTGAGC
481 TATTTTCTGC CGATGCTGCC GAAAGCGAGC GTGGAACCGG GCGATGAAGA AGAAAGCGCG
541 TTTAGCCTGC CGCTGAAAAC CGATAGCATG GATCCGTTTG GCATGGCGAG CGAAATTGGC
601 CTGGCGAAAA GCCCGAGCTT TCAGAAA
```

Another member of the FGF19 subfamily, FGF21, is expressed primarily by the pancreas (Fon Tacer et al., "Research Resource: Comprehensive Expression Atlas of the Fibroblast Growth Factor System in Adult Mouse," *Mol Endocrinol* 24(10):2050-2063 (2010), which is hereby incorporated by reference in its entirety) and has metabolic effects similar to that of FGF19, such as increased energy metabolism, weight loss, lowered blood glucose levels, and resistance to obesity and diabetes (Kharitonenkov et al., "FGF-21 as a Novel Metabolic Regulator," *J Clin Invest* 115(6), 1627-1635 (2005), which is hereby incorporated by reference in its entirety).

In one embodiment of the present invention, the FGF21 portion of the chimeric protein of the present invention is from human FGF21 protein having an amino acid sequence of SEQ ID NO: 100 (GenBank Accession No. NP_061986, which is hereby incorporated by reference in its entirety) or a portion thereof, as follows:

(SEQ ID NO: 100)

```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPALPEPPGI
181 LAPQPPDVGS SDPLSMVGPS QGRSPSYAS
```

"FGF-21 as a Novel Metabolic Regulator," *J Clin Invest* 115(6), 1627-1635 (2005); Coskun et al., "Fibroblast growth factor 21 corrects obesity in mice," *Endocrinology* 149(12): 6018-6027 (2008), which are hereby incorporated by reference in their entirety). Transgenic mice overexpressing FGF21 are also resistant to diet-induced obesity (Kharitonenkov et al., "FGF-21 as a Novel Metabolic Regulator," *J Clin Invest* 115(6), 1627-1635 (2005), which is hereby incorporated by reference in its entirety). Moreover, in diabetic rodent models, FGF21 administration lowers blood glucose and triglyceride levels (Kharitonenkov et al., "FGF- In one embodiment of the present invention, the N-terminal portion of FGF21 of the chimeric protein of the present invention comprises an amino acid sequence spanning residues corresponding to residues from position 29 to 167 of SEQ ID NO: 100, from position 29 to 190 of SEQ ID NO: 100, or from position 29 to 197 of SEQ ID NO: 100.

In one embodiment of the present invention, the N-terminal portion of the chimeric protein according to the present invention is or is derived from a mammalian FGF21. In one embodiment of the present invention, the N-terminal portion of the chimeric protein according to the present invention is or is derived from a vertebrate FGF21. In one embodiment, the N-terminal portion of the chimeric protein according to the present invention is derived from a non-human vertebrate FGF21. It will be understood that this includes orthologs of human FGF21, or a polypeptide or protein obtained from one species that is the functional counterpart of a polypeptide or protein from a different species. In one embodiment of the present invention, the N-terminal portion of FGF21 of the chimeric protein according to the present invention is derived from human, *pongo abelii, pan troglodytes, canis lupus familiaris, bos taurus, equus caballus, ailuropoda melanoleuca, oryctolagus cuniculus, gorilla gorilla, nomascus leucogenys, procavia capensis, cavia porcellus, tupaia belangeri, sorex araneus, ictidomys tridecemlineatus, loxodonta africana, sus scrofa, felis catus, otolemur garnettii, rattus norvegicus, mus musculus, vicugna pacos, anolis carolinensis, gadus morhua, latimeria chalumnae, tursiops truncatus, mustela putorius furo, takifugu rubripes, dipodomys ordii, echinops telfairi, macaca mulatta, microcebus murinus, ochotona princeps, xiphophorus maculatus, gasterosteus aculeatus, sarcophilus harrisii, macropus eugenii, xenopus tropicalis, danio rerio, bos grunniens mutus, saimiri boliviensis boliviensis, callithrix jacchus, tupaia chinensis, papio anubis, pteropus alecto, heterocephalus glaber, cricetulus griseus, ovies aries, pan paniscus, macaca fascicularis, mesocricetus auratus*, or *oreochromis niloticus*.

Figure 9:
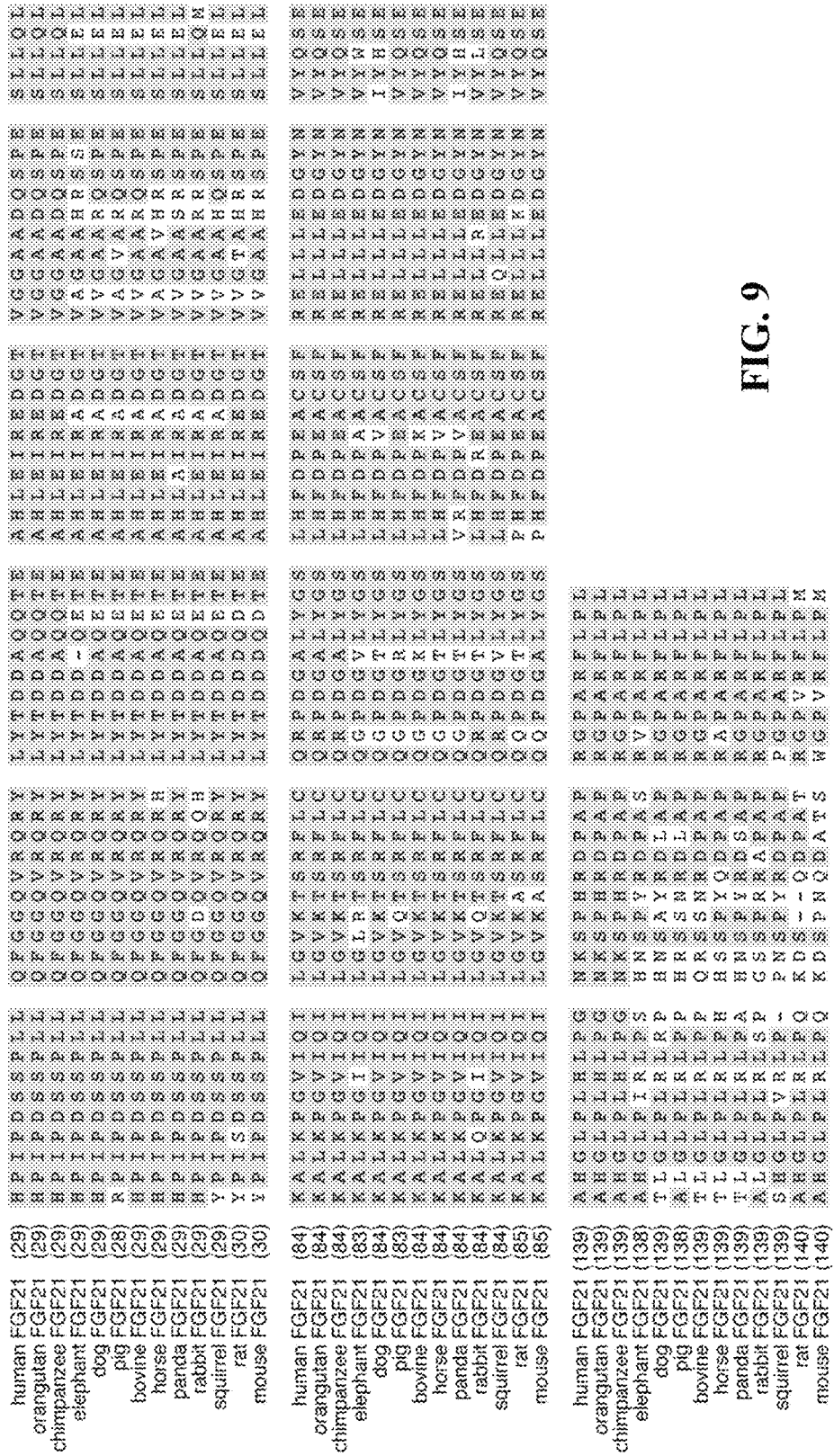
FIG. 9 shows a sequence alignment of the FGF homology core domain and its N-terminal extension of FGF21 orthologs (including human (SEQ ID NO: 100), orangutan (SEQ ID NO: 101), chimpanzee (SEQ ID NO: 102), elephant (SEQ ID NO: 115), dog (SEQ ID NO: 103), pig (SEQ ID NO: 116), bovine (SEQ ID NO: 104), horse (SEQ ID NO: 105), panda (SEQ ID NO: 106), rabbit (SEQ ID NO: 107), squirrel (SEQ ID NO: 114), rat (SEQ ID NO: 119), and mouse (SEQ ID NO: 120)). Residue numbers are in parenthesis to the left of the alignment. Gaps (dashes) were introduced to optimize the alignment. Ortholog residues identical to human FGF21 (SEQ ID NO: 100) are shaded gray. This illustrates the high degree of sequence conservation among mammals.

In one embodiment of the present invention, the portion of FGF21 of the chimeric protein of the present invention is from an ortholog of human FGF21 having an amino acid sequence as shown in Table 3. The portions of an ortholog of human FGF21 of a chimeric protein according to the present invention include portions corresponding to the above-identified amino acid sequences of human FGF21. Corresponding portions may be determined by, for example, sequence analysis and structural analysis. The high degree of FGF21 sequence conservation among mammals is shown in FIG. 9.

TABLE 3

```
Pongo abelii (Sumatran orangutan) FGF21 (GenBank Accession No.
XP_002829565, which is hereby incorporated by reference in its
entirety) (SEQ ID NO: 101)
    1 MDSDETGFEH SGLWVPVLAG LLLGACQAHP IPDSSPLLQF GGQVRQRYLY TDDAQQTEAH
   61 LEIREDGTVG GAADQSPESL LQLKALKPGV IQILGVKTSR FLCQRPDGAL YGSLHFDPEA
  121 CSFRELLLED GYNVYQSEAH GLPLHLPGNK SPHRDPAPRG PARFLPLPGL PPAPPEPPGI
  181 LAPQPPDVGS SDPLSMVGPS QGRSPSYAS Pan troglodytes (chimpanzee) FGF21 (GenBank Accession No. XP_524333,
which is hereby incorporated by reference in its entirety)
(SEQ ID NO: 102)
    1 MDSDETGFEH SGLWVSVLAG LLLGACQAHP IPDSSPLLQF GGQVRQRYLY TDDAQQTEAH
   61 LEIREDGTVG GAADQSPESL LQLKALKPGV IQILGVKTSR FLCQRPDGAL YGSLHFDPEA
  121 CSFRELLLED GYNVYQSEAH GLPLHLPGNK SPHRDPAPRG PARFLPLPGL PPAPPEPPGI
  181 LAPQPPDVGS SDPLSMVGPS QGRSPSYTS Canis lupus familiaris (dog) FGF21 (GenBank Accession No. XP_541510,
which is hereby incorporated by reference in its entirety)
(SEQ ID NO: 103)
    1 MGWAEAGFEH LGLWVPVLAV LLLEACRAHP IPDSSPLLQF GGQVRQRYLY TDDAQETEAH
   61 LEIRADGTVV GAARQSPESL LELKALKPGV IQILGVKTSR FLCQGPDGTL YGSLHFDPVA
  121 CSFRELLLED GYNIYHSETL GLPLRLRPHN SAYRDLAPRG PARFLPLPGL LPAPPEPPGI
  181 LAPEPPDVGS SDPLSMVGPS QGRSPSYAS Bos taurus (bovine) FGF21 (GenBank Accession No. XP_001789639, which
is hereby incorporated by reference in its entirety)
(SEQ ID NO: 104)
    1 MGWDEAKFKH LGLWVPVLAV LLLGTCRAHP IPDSSPLLQF GGQVRQRYLY TDDAQETEAH
   61 LEIRADGTVV GAARQSPESL LELKALKPGV IQILGVKTSR FLCQGPDGKL YGSLHFDPKA
  121 CSFRELLLED GYNVYQSETL GLPLRLPPQR SSNRDPAPRG PARFLPLPGL PAAPPDPPGI
  181 LAPEPPDVGS SDPLSMVGPS YGRSPSYTS Equus caballus (horse) FGF21 (GenBank Accession No. XP_001489202,
which is hereby incorporated by reference in its entirety)
(SEQ ID NO: 105)
    1 MDWDKTGFKY QGLWVPVLAV LLLGACQSHP IPDSSPLLQF GGQVRQRHLY TDDAQETEAH
   61 LEIRADGTVA GAVHRSPESL LELKALKPGV IQILGVKTSR FLCQGPDGTL YGSLHFDPVA
  121 CSFRELLLED GYNVYQSETL GLPLRLPHHS SPYQDPAPRA PARFLPLPGF PPAPPEPPGI
  181 PAPEPPDVGS SDPLSMVGPS RSRSPSYTS Ailuropoda melanoleuca (giant panda) FGF21 (GenBank Accession No.
XP_002917910, which is hereby incorporated by reference in its
entirety) (SEQ ID NO: 106)
    1 MGWDEARSEQ LGLWVPVLAV LLLEACQAHP IPDSSPLLQF GGQVRQRYLY TDDAQETEAH
   61 LAIRADGTVV GAASRSPESL LELKALKPGV IQILGVKTSR FLCQGPDGTL YGSVRFDPVA
  121 CSFRELLLED GYNIYHSETL GLPLRLPAHN SPYRDSAPRG PARFLPLPGL LPVPPDPPGI
  181 LGPEPPDVGS SDPLSMVGPS QGRSPSYAS Oryctolagus cuniculus (rabbit) FGF21 (GenBank Accession No.
XP_002723745, which is hereby incorporated by reference in its
entirety)
(SEQ ID NO: 107)
    1 MDWGKAKCRP PGLWVPALAA LLLGACQAHP IPDSSPLLQF GDQVRQQHLY TDDAQETEAH
   61 LEIRADGTVV GAARRSPESL LQMKALQPGI IQILGVQTSR FLCQRPDGTL YGSLHFDREA
  121 CSFRELLRED GYNVYLSEAL GLPLRLSPGS SPRRAPAPRG PARFLPLPGL PPDLPEPPGL
  181 LAAAPPDVDS PDPLSMVQPA LDQSPSYTS
```

TABLE 3-continued

*Gorilla gorilla* (gorilla) FGF21 (Ensembl Accession No. ENSGGOP00000001229, which is hereby incorporated by reference in its entirety) (SEQ ID NO: 108)
```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPAPPEPPGI
181 LAPQPPDVGS SDPLSMVGPS QGRSPSYAS
```

*Nomascus leucogenys* (Northern white-cheeked gibbon) FGF21 (Ensembl Accession No. ENSNLEP00000005639, which is hereby incorporated by reference in its entirety) (SEQ ID NO: 109)
```
  1 MDSDETGFEH SGLWVPVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPAPPEPPGI
181 LAPQPPDVGS SDPLSMVGPS QGRSPSYAS
```

*Procavia capensis* (hyrax) FGF21 (Ensembl Accession No. ENSOGAG00000001210, which is hereby incorporated by reference in its entirety) (SEQ ID NO: 110)
```
  1 MDWAKFGIEH PGLWVPVMAV LLLGACQGYP IPDSSPLLQF GGQVRQRYLY TDDAQETEAH
 61 LEIRADGTVV GAAHRSPESL LELKALKPGI IQILGVKTSR FLCQGPDGVL YGSLRFDPVA
121 CSFRELLLED GYNVYQSEAH GLPLRLPSHN SPQRDLASRV PARFLPLPGR LTVLPEPSGV
181 LGPEPPDVDS SDPLSMVGPS QGRSPSYAS
```

*Cavia porcellus* (guinea pig) FGF21 (Ensembl Accession No. ENSCPOP00000000237, which is hereby incorporated by reference in its entirety) (SEQ ID NO: 111)
```
  1 MDWARTECER PRLWVSMLAI LLVGACQAHP IPDSSPLLQF GGQVRQRYLY TDDAQDTEVH
 61 LEIRADGSVR GIAHRSPESL LELKALKPGV IQILGIRTSR FLCQRPDGSL YGSLHFDPEA
121 CSFRELLLAD GYNVYKSEAH GLPLHLLRGD SLSQEPAPPG PARFLPLPGL PATPPEPPRM
181 LPPGPPDVGS SDPLSMVGPL WDRSPSYTS
```

*Tupaia belangeri* (tree shrew) FGF21 (Ensembl Accession No. ENSTBEP00000013946, which is hereby incorporated by reference in its entirety) (SEQ ID NO: 112)
```
  1 MGWDKARFEH LGAWAPVLAV LLLGACQAYP IPDSSPLLQF GGQVRQRYLY TDDTQDTEAH
 61 LEIRADGTVV GAAHQSPESL LELKALKPGV IQILGVKTSR FLCQRPDGAL YGSLHFDPEA
121 CSFRELLLED GYNIYQSEAR GLPLRLPPHD SPHRDRTPRG PARFLPLPGL PLVPPELPGV
181 LALEPPDVGS SDPLSMMGPS QGQSPSYAS
```

*Sorex araneus* (shrew) FGF21 (Ensembl Accession No. ENSSARP00000002784, which is hereby incorporated by reference in its entirety) (SEQ ID NO: 113)
```
  1 MVWDKARGQQ LGLWAPMLLG LLLGACQAHP LPDSSPLLQF GGQVRLRFLY TDDAQRTGAH
 61 LEIRADGTVQ GAAHRTPECL LELKALKPGV IQILGVSTSR FLCQRPDGVL YGSLRFDPEA
121 CSFRELLLQD GYNVYQSEAL GLPLYLHPPS APVSQEPASR GAVRFLPLPG LPPASLEPPR
181 PPAPVPPDVG SSDPLSMVGP PERHSPSYTS
```

*Ictidomys tridecemlineatus* (squirrel) FGF21 (SEQ ID NO: 114)
```
  1 MDWVKAKLEP LGLWVLVLAA LVLGACQAYP IPDSSPLLQF GGQVRQRYLY TDDAQETEAH
 61 LEIRADGTVV GAAHQSPESL LELKALKPGV IQILGVKTSR FLCQRPDGVL YGSLHFDPEA
121 CSFREQLLED GYNVYQSESH GLPVRLPPNS PYRDPAPPGP ARFLPLPGLP PAALEPPGIL
181 GPEPPDVGSS DPLSMVGPLQ GRSPSYAS
```

*Loxodonta africana* (elephant) FGF21 (Ensembl Accession No. ENSLAFP00000016854, which is hereby incorporated by reference in its entirety) (SEQ ID NO: 115)
```
  1 MDWAKFGLE HPGLWVPVMA VLLLGACQGH PIPDSSPLLQ FGGQVRQRYL YTDDQETEAH
 60 LEIRADGTVA GAAHRSSESL LELKALKPGI IQILGVKTSR FLCQGPDGVL YGSLHFDPAA
120 CSFRELLLED GYNVYWSEAH GLPIRLPSHN SPYRDPASRV PARFLPLPGL LPMLQEPPGV
180 LAPEPPDVDS SDPLSMVGPS QGRSPSYAS
```

*Sus scrofa* (pig) FGF21 (GenBank Accession No. NP_001156882, which is hereby incorporated by reference in its entirety) (SEQ ID NO: 116)
```
  1 MGWAEAKFER LGLWVPVLAV LLGACQARPI PDSSPLLQFG GQVRQRYLYT DDAQETEAHL
 61 EIRADGTVAG VARQSPESLL ELKALKPGVI QILGVQTSRF LCQGPDGRLY GSLHFDPEAC
121 SFRELLLEDG YNVYQSEALG LPLRLPPHRS SNRDLAPRGP ARFLPLPGLP PAPPEPPGIL
181 APEPPDVGSS DPLSMVGPSH GRSPSYTS
```

*Felis catus* (cat) FGF21 (Ensembl Accession No. ENSFCAP00000006832, which is hereby incorporated by reference in its entirety) (SEQ ID NO: 117)
```
  1 MDWDEAGSQ RLGLWVVLGV LLPEACQAHP IPDSSPLLQF GGQVRQRFLY TDDAQETEVH
 60 LEIKADGTVV GTARRSPESL LELKALKPGV IQILGVKTSR FLCQGPDGTL YGSLRFDPAA
120 CSFRELLLED GYNIYHSETL GLPLRLPPHN SPYRDLAPRA PARFLPLPGL LPAPPEPPGI
180 LAPEPPDVGS SDPLSMVGPS QGRSPSYAS
```

TABLE 3-continued

*Otolemur garnettii* (bushbaby) FGF21 (Ensembl Accession No.
ENSOGAG00000003581, which is hereby incorporated by reference in its
entirety) (SEQ ID NO: 118)
```
  1 DKARTGFKH PGPWFPLLAV LLLGACQAHP IPDSSPLLQF GGQVRQRYLY TDDAQETEAH
 60 LEIREDGTVV GAAQQSPESL LELKALKPGV IQILGVKTSR FLCQRPDGGL YGSLYFDPKA
120 CSFRELLLED GYNVYWSETY GLPLHLPPAN SPYWGPSLRS PARFLPLPGP PAASPELPGI
180 LALEPPDVGS SDPLSMVGPS QGRSPSYAS
```

*Rattus norvegicus* (Norway rat) FGF21 (GenBank Accession No.
NP_570108, which is hereby incorporated by reference in
its entirety) (SEQ ID NO: 119)
```
  1 MDWMKSRVGA PGLWVCLLLP VFLLGVCEAY PISDSSPLLQ FGGQVRQRYL YTDDDQDTEA
 61 HLEIREDGTV VGTAHRSPES LLELKALKPG VIQILGVKAS RFLCQQPDGT LYGSPHFDPE
121 ACSFRELLLK DGYNVYQSEA HGLPLRLPQK DSQDPATRGP VRFLPMPGLP HEPQEQPGVL
181 PPEPPDVGSS DPLSMVEPLQ GRSPSYAS
```

*Mus musculus* (house mouse) FGF21 (GenBank Accession No. NP_064397,
which is hereby incorporated by reference in its entirety)
(SEQ ID NO: 120)
```
  1 MEWMRSRVGT LGLWVRLLLA VFLLGVYQAY PIPDSSPLLQ FGGQVRQRYL YTDDDQDTEA
 61 HLEIREDGTV VGAAHRSPES LLELKALKPG VIQILGVKAS RFLCQQPDGA LYGSPHFDPE
121 ACSFRELLLE DGYNVYQSEA HGLPLRLPQK DSPNQDATSW GPVRFLPMPG LLHEPQDQAG
181 FLPPEPPDVG SSDPLSMVEP LQGRSPSYAS
```

*Vicugna pacos* (alpaca) FGF21 (Ensembl Accession No.
ENSVPAP00000005562, which is hereby incorporated by reference in its
entirety) (SEQ ID NO: 121); partial sequence corresponding to human
FGF21 residues 1 to 78, 169 to 171, and 183 to 209
```
  1 MDWDEAKFEH RGLWVPVLTV LLLGACQARP IPDSSPLLQF GGQVRQRYLY TDDAQETEAH
 61 LEIRADGTVV GVARQPE--- ---------- ---------- ---------- ----------
121 ---------- ---------- ---------- ---------- --------GI P---------
181 --PEPPDVGS SDPLSMVGPS YSRSPSYTS
```

*Anolis carolinensis* (anole lizard) FGF21 (Ensembl Accession No.
ENSACAP00000016895, which is hereby incorporated by reference in its
entirety) (SEQ ID NO: 122)
```
  1 CKSKGGGKGG ERMWVDLVFW AALLRTAPAL PLRNSNPIYQ FDGQVRLRHL YTADEQTHLH
 61 LEILPDGTVG GSRFQNPFSL MEIKAVKPGV IRMQAKKTSR FLCMKPNGRL YGSLFYSEEA
121 CNFHEKVLSD GYNLYYSENY NIPVSLSSAG NLGQSRQLPP FSQFLPLVNK IPLEPVLEDF
181 DFYGHQLDVE SADPLSILGQ NPGFMSPSYV F
```

*Gadus morhua* (cod) FGF21 (Ensembl Accession No. ENSGMOP00000013789,
which is hereby incorporated by reference in its entirety)
(SEQ ID NO: 123)
```
  1 LLLATLLHIG LSFYVPDSGP LLWLGDQVRE RHLYTAESHR RGLFLEMSPD GQVTGSAAQT
 61 PLSVLELRSV RAGDTVIRAR LSSLYLCVDR AGHLTGQRQY TESDCTFREV ILEDGYTHFL
121 SVHHGLPISL APRHSPGRQG LRFSRFLPLR SSLSEDRVAE PPDSPLNLDS EDPLGMGLGS
181 LLSPAFSM
```

*Latimeria chalumnae* (coelacanth) FGF21 (Ensembl Accession No.
ENSLACP00000003781, which is hereby incorporated by reference in its
entirety) (SEQ ID NO: 124)
```
  1 MLCQSFVILS QKIFIGLFLT GLGLTGLAWT RPFQDSNPIL QYSDSIRLRH LYTASESRHL
 61 HKLQINSDGQV GGTTKQSPYS LLEMKAVKTG FVVIRGKKSA RYLCMERSGR LYGSLQYTEK
121 DCTFKEVVLA DGYNLYVSEE HQATVTLSPM RARIAQGKKI PPFSHFLPMV NKVPVEDVAA
181 EMEFVQVLRE MTADVDSPDP FGMTWEESVH SPSFFA
```

*Tursiops truncatus* (dolphin) FGF21 (Ensembl Accession No.
ENSTTRP00000013808, which is hereby incorporated by reference in its
entirety) (SEQ ID NO: 125)
```
  1 MGWDKTKLEH LGLWVPVLAV LLGPCQAHPI PDSSPLLQFG GQVRQRYLYT DDAQETEAHL
 61 EIRADGTVVG TARRSPEGVK TSRFLCQGPE GRLYGSLHFN PQACSFRELL LEDGYNVYQS
121 EALGIPLRLP PHRSSNWDLA PRGPARFLPL PGFLPPPLEP PGILAPEPPN VGSSDPLSMV
181 GPSHGRSPSY TS
```

*Mustela putorius furo* (ferret) FGF21 (Ensembl Accession No.
ENSMPUP00000003687, which is hereby incorporated by reference in its
entirety) (SEQ ID NO: 126)
```
  1 MGWEEARSEH LGLWVPVLAV LLLGACQAYP IPDSSPLLQF GGQVRQRYLY TDDAQETEAH
 61 LEIRADGTVV GAARRSPESL LELKALKPGV IQILGVKTSR FLCQGPNGTL YGSFHFDPVA
121 CSFREVLLED GYNIYHSETL GLPLRLPPHN SPHRDLAPRG PARFLPLPGL LPATPESRGI
181 PAPEPPNVGS SDPLSMVGPL QGQSPSYTS
```

*Takifugu rubripes* (fugu) FGF21 (Ensembl Accession No.
ENSTRUP00000033950, which is hereby incorporated by reference in its
entirety) (SEQ ID NO: 127)
```
  1 FIYLFIQTAL FSPSKWFNFY LPDSNPLLSF DSHGRGIHLY TDNQRRGMYL QMSTDGSVSG
 61 SDVQTANSVL ELKSVRNGHV VIRGKSSSLF LCMDSRGRLW GQRHPTEADC TFREVLLADG
121 YTRFLSLHNG TPVSLAPKQS PDQHTVPFTR FLPLRNTLAE ESMSEPPSNQ QRYFNIDSDD
181 LLGMDLNAMV SPQFSGDK
```

TABLE 3-continued

*Dipodomys ordii* (kangaroo rat) FGF21 (Ensembl Accession No.
ENSDORP00000001155, which is hereby incorporated by reference in its
entirety) (SEQ ID NO: 128)
```
  1 MDQAKTRVGA RGLGGLVLAV IILGACKARP IPDSSPLLQF GGQVRLRHLY TDDTQETEAH
 61 LEIRADGTVV GTAHRSPESL LELKALKPGV IQILGIKTSR FLCQRPDGTL YGSLHFDPEV
121 CSFQELLLED GYNIYRSEAL GLPLRLSPDP APWGPARFLP LPGVPPAPPE PPGILAPEPP
181 DVGSSDPLSM VGLLQGRSPS YAS
```

*Echinops telfairi* (lesser hedgehog tenrec) FGF21 (Ensembl Accession
No. ENSETEP00000008707, which is hereby incorporated by reference in
its entirety) (SEQ ID NO: 129)
```
  1 MGCTKSGWKS PGLWVPVLAS LLLGGCGAHP IPDSSPLLQF GGQVRQRYLY TDDAQTTEAH
 61 LEIRADGTVG GVAHQSPEKF LSQWREKPLR SLHFDPAACS FREKLLEDGY NLYHSETHGL
121 PLRLPPRGGD PSSQPGARFP PLPGQLPQLQ ETPGVLAPEP PDVGSSDPLS MVGPWRGQSP
181 SYAS
```

*Macaca mulatta* (rhesus monkey) FGF21 (Ensembl Accession No.
ENSMMUP00000031540, which is hereby incorporated by reference in its
entirety) (SEQ ID NO: 130)
```
  1 MDSDETGFEH SGLWVPVLAG LLLGACQAHP IPDSSPLLQF GGQVRQRYLY TDDAQQTEAH
 61 LEIREDGTVG GAAHQSPESE CGPEPGSEGG GAVGGAEGPG LLGLREAGLG PGSWLHFDPE
121 ACSFRELLLE NGYNVYQSEA HGLPLHLPGN KSPHRDPASQ GPARFLPLPG LPPAPPEPPG
181 ILAPQPPDVG SSDPLSMVGP SQARSPSYAS
```

*Microcebus murinus* (mouse lemur) FGF21 (Ensembl Accession No.
ENSMICP00000012089, which is hereby incorporated by reference in its
entirety) (SEQ ID NO: 131)
```
  1 MGWDEAGAGF EHPGLWFPML GVLLLGACQA YPIPDSSPLL QFGGQVRQRH LYTDDIQETE
 61 AHLEIRADGT VVGAARQSPE LELKALKPGV IQILGVKTSR FLCQRPDGAL YGSLHFDPEC
121 SFRELLLEDG YNVYCPYLPL HLSPRIELAG SRSALPLPPA PERRILAPEP PDGSSDPLSM
181 VGPSQGRSPS YAS
```

*Ochotona princeps* (pika) FGF21 (Ensembl Accession No.
ENSOPRP00000006754, which is hereby incorporated by reference in its
entirety) (SEQ ID NO: 132)
```
  1 KDMDGLQPPG LRVPVLAALL LGVGQARPIP DSSPLLQFGG QVRQRHLYTD DAQESEVHLE
 61 IRADGTVAGT ARRSPESLLE MKALKPGVIQ ILGVHTSRFL CQRPDGTLYG SLHFDHKACS
121 FREQLLEDGY NVYHSETHGL PLRLSPDRAP RGPARFLPLP GPPPDLLVPP LPPDVLAPEP
181 PDVDSPDPLS MVGPLQGQSP SYTS
```

*Xiphophorus maculatus* (platyfish) FGF21 (Ensembl Accession No.
ENSXMAP00000001576, which is hereby incorporated by reference in its
entirety) (SEQ ID NO: 133)
```
  1 CPFPFLFLIL SLPFFSSSFY IPESNPIFAF RNQLREVHLY TENHRRGLYV EIHLDGRVTG
 61 SDAQSPYSVL QIKSVKPGHV VIKGQTSSLF LCMDDSGNLR GQTTYDEADC SFRELLLADG
121 YTRFLNSQHG VPLSLASRNS PDRHSVPFTR FLPLRNTLTV SEESTKTQRD FNLDSDDLLG
181 MG
```

*Gasterosteus aculeatus* (stickleback) FGF21 (Ensembl Accession No.
ENSGACP00000010703, which is hereby incorporated by reference in its
entirety) (SEQ ID NO: 134)
```
  1 SLLLMVPLPF CSSFYLTDSS PLLPFNNQVK EVHLYTAENH RRAMYLQIAL DGSVSGSDAR
 61 STYSVLQLKS IQPGHVVIRG KASSMFLCVD SGGRLRGQGP YSEADCSFRE LLLGDGYTRF
121 LSSQHGSPLS LASRPSPDPN SVPFTRFLPI RTAPEAESVI EEPPSNQRYV NVDSEDLLGM
181 GLNTVVSPQF SA
```

*Sarcophilus harrisii* (tasmanian devil) FGF21 (Ensembl Accession No.
ENSSHAP00000005963, which is hereby incorporated by reference in its
entirety) (SEQ ID NO: 135); partial sequence corresponding to human
FGF21 residues 3 to 172
```
  1 VSAMGLRERA PRYLAPLLSL LLACRASGHP LPDSSPMLLF GGQVRLRHLY TDVGQEAEAH
 61 VELASDGTVR AAARRSPNSL LELKAVKPGI VRILAVHSSR FLCMRPNGEL YGAIHYDPSA
121 CNFRERLLGD GYNVYESEAH GRTLRLPPKA APGPAGPSRF LPLPG
```

*Macropus eugenii* (wallaby) FGF21 (Ensembl Accession No.
ENSMEUP00000013936, which is hereby incorporated by reference in its
entirety) (SEQ ID NO: 136)
```
  1 TEEPSTGSRH LGQWAPGLPG PLLSLLLAYR GWGSPIPDSS PMLLFGGQVR LRHLYTDDGQ
 61 DTEAHVELGP DGVVRAVAER SPNSLLELKA VKPGVIRILA VQSSRFLCMR PNGELYGAVH
121 YDPSACNFRE HLLGDGYNVY ESETHRRTLR LSPSLGQAGP SRFLPLPGDW LPGPDPPWAQ
181 GPEPPDVGSA DPLSMVGAVQ GLSPSYSS
```

*Xenopus tropicalis* (Western clawed frog) FGF21 (Ensembl Accession
No. ENSXETP00000009917, which is hereby incorporated by reference
in its entirety) (SEQ ID NO: 137); partial sequence corresponding
to human FGF21 residues 1 to 169
```
  1 RGGRTKKKTL LRKWLCLLAI MLSRSRFSLA NPIQNSNPIL SNDNQVRTQY LYTDNNNMHL
 61 YLQITHNGVV TGTEEKNDYG VLEIKAVKAG VVVIKGIRSN LYLCMDSRHQ LYASAYDKDD
121 CHFHEKITPD NYNMYSSEKH SEYVSLAPLK GSQMARFLPI
```

TABLE 3-continued

*Danio rerio* (zebrafish) FGF21 (Ensembl Accession No.
ENSDARP00000094287, which is hereby incorporated by reference in its
entirety) (SEQ ID NO: 138)
```
  1MLLACFFIFF ALFPHLRWCM YVPAQNVLLQ FGTQVRERLL YTDGLFLEMN PDGSVKGSPE
 61KNLNCVLELR SVKAGETVIQ SAATSLYLCV DDQDKLKGQH HYSALDCTFQ ELLLDGYSFF
121LSPHTNLPVS LLSKRQKHGN PLSRFLPVSR AEDSRTQEVK QYIQDINLDS DDPLGMGHRS
181HLQTVFSPSL HTKK
```

*Bos grunniens mutus* (yak) FGF21 (GenBank Accession No. ELR56628,
which is hereby incorporated by reference in its entirety)
(SEQ ID NO: 139)
```
  1MGWDEAKFKH LGLWVPVLAV LLLGTCRAHP IPDSSPLLQF GGQVRQRYLY TDDAQETEAH
 61LEIRADGTVV GAARQSPESL LELKALKPGV IQILGVKTSR FLCQGPDGKL YGSLHFDPKA
121CSFRELLLED GYNVYQSETL GLPLRLPPQR SSNRDPAPRG PARFLPLPGL PAEPPDPPGI
181LAPEPPDVGS SDPLSMVGPS YGRSPSYTS
```

*Saimiri boliviensis boliviensis* (Bolivian squirrel monkey) FGF21
(GenBank Accession No. XP_003940375, which is hereby incorporated by
reference in its entirety) (SEQ ID NO: 140)
```
  1MGSEEVALER PALWVSVLAG LLLGTCQAYP IPDSSPLLQF GGQVRQRYLY TDDAQQTEAH
 61LEIREDGTVA GAAHQSPESL LQLKALKPGV IQILGVKTSR FLCQRPDGAL YGSLYFDPEA
121CSFRELLLED GYNVYQSVAH SLPLHLPGGR SPPWDPAPRG PARFLPLPGL PPEPPEAPGI
181LAPEPPDVGS SDPLSMVGPS QGQSPSYTS
```

*Callithrix jacchus* (white-tufted-ear marmoset) FGF21 (GenBank
Accession No. XP_003735669, which is hereby incorporated by
reference in its entirety) (SEQ ID NO: 141)
```
  1MGSEEVGLEH PALWVSVLAG LLLGTCQAHP IPDSSPLLQF GGQVRQRYLY TDDAQQKEAH
 61LEIXEDGTVA GAATKVPKVS LLQLKALKPG VIQILGVKTS RFLCQRPDGA LYGSLHFDPE
121ACSFRELLLE DGYNVYQSVA HGLPLHLPES RSPPRDPAPR GPARFLPLPG LPPEPPEPPG
181ILAPEPPDVG SSDPLSMVGP SQGQSPSYAS
```

*Tupaia chinensis* (Chinese tree shrew) FGF21 (GenBank Accession No.
ELW47159, which is hereby incorporated by reference in its entirety)
(SEQ ID NO: 142)
```
  1MGWDKARFEH LGAWAPVLAV LLLGACQAYP IPDSSPLLQF GGQVRQRYLY TDDTQDTEAH
 61LEIRADGTVV GAAHQSPESL LELKALKPGV IQILGVKTSR FLCQRPDGAL YGSLHFDPEA
121CSFRELLLED GYNIYQSEAR GLPLRLPPHD SPHRDRTPQG PARFLPLPGL PLVPPELPGV
181LALEPPDVGS SDPLSMMGPS QGQSPSYAS
```

*Papio anubis* (olive baboon) FGF21 (GenBank Accession No.
XP_003915900, which is hereby incorporated by reference
in its entirety) (SEQ ID NO: 143)
```
  1MDSDETGFEH SGLWVPVLAG LLLGACQAHP IPDSSPLLQF GGQVRQRYLY TDDAQQTEAH
 61LEIREDGTVG GAAHQSPESK CGPEPGSEGG GALHFDPEAC SFRELLLENG YNVYQSEAHG
121LPLHLPGNKS PHRDPASRGP ARFLPLPGLP PAPPEPPGIL APQPPDVGSS DPLSMVGPSQ
181ARSPSYAS
```

*Pteropus alecto* (black flying fox) FGF21 (GenBank Accession No.
ELK18566, which is hereby incorporated by reference in its entirety)
(SEQ ID NO: 144)
```
  1MGWGKARLQH PGLWGPVLAV LLGACQAHPI LDSSPLFQFG SQVRRRYLYT DDAQDTEAHL
 61EIRADGTVAG AARRSPESLL ELKALKPGVI QVLGVKTSRF LCQRPDGTLY GSLHFDPAAC
121SFRELLLKDG YNVYQSEALA RPLRLPPYSS PSSDPARRGP ARFLPLPGPP PEPPQPPGRL
181APEPPDVGSS DPLSMVWPSR GRSPSYTS
```

*Heterocephalus glaber* (naked mole-rat) FGF21 (GenBank Accession No.
EHB06286, which is hereby incorporated by reference in its entirety)
(SEQ ID NO: 145)
```
  1MDWARAESER PGLWVPAVLA VLLLGACQAH PIPDSSPLLQ FGGQVRQRHL YTDDAQDTEV
 61HLEIRADGSV GGAAHRSPES LLELKALKPG VIQILGVRTS RFLCQRPDGT LYGSLHFDPE
121ACSFRELLLA DGYNIYQSEA YGLPLRMLPS DSASRDPVPP GPARFLPLPG LHPPPLEPPG
181MLPPEPPDVG SSDPLSMVGP LQGRSPSYAF
```

*Cricetulus griseus* (Chinese hamster) FGF21 (GenBank Accession No.
XP_003508726, which is hereby incorporated by reference in its
entirety) (SEQ ID NO: 146)
```
  1MDWMKSGVGV PGLWVPLLPI FLLGVSQAHP IPDSSPLLQF GGQVRHRHLY TDDNQETEVH
 61LEIRQDGTVI GTTHRSPESL LELKALKPEV IPVLGVKASR FLCQQPDGTL YGSPHFDPEA
121CSFRELLLED GYNVYQSEVH GLPLRLPQRD SPNQAPASWG PVPPLPVPGL HQPQELPGF
181LAPEPPDVGS SDPLSMVGPL QGRSPSYAS
```

*Ovis aries* (sheep) FGF21 (GenBank Accession No. XP_004015845,
which is hereby incorporated by reference in its entirety)
(SEQ ID NO: 147)
```
  1MGWDEAKFKH LGLWVPVLAV LLLGTCRAHP IPDSSPLLQF GGQVRQRYLY TDDAQETEAH
 61LEIRADGTVV GAARQSPESL LELKALKPGV IQIFGVKTSR FLCQGPDGKL YGSLHFDPKA
121CSFRELLLED GYNVYQSETL GLPLRLPPQR SSNRDPAPRG PPKPQLHFLK TSAVQYWPRY
181EKVPAFLHPF PG
```

TABLE 3-continued

*Pan paniscus* (pygmy chimpanzee) FGF21 (GenBank Accession No.
XP_003814163, which is hereby incorporated by reference in its
entirety) (SEQ ID NO: 148); partial sequence corresponding to human
FGF21 residues 1 to 116 and 195 to 201
```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSVSF----
121 ---------- ---------- ---------- ----Q----- ---------- -----DPP--
181 --HHPP---C S---SYMSPS Q---PG---
```

*Macaca fascicularis* (crab-eating macaque) FGF21(GenBank
Accession No. EHH59757, which is hereby incorporated by reference
in its entirety) (SEQ ID NO: 149); partial sequence corresponding
to human FGF21 residues 1 to 116
```
  1 MDSDETGFEH SGLWVPVLAG LLLGACQAHP IPDSSPLLQF GGQVRQRYLY TDDAQQTEAH
 61 LEIREDGTVG GAAHQSPESL LQLKALKPGV IQILGVKTSR FLCQKPDGAL YGSVSF
```

*Mesocricetus auratus* (golden hamster) FGF21 (GenBank Accession No.
ACB30542, which is hereby incorporated by reference in its entirety)
(SEQ ID NO: 150); partial sequence corresponding to human FGF21
residues 90 to 193
```
  1 VIQILGVKAA RFPCQQPDGS LYGSPHFDPE ACSFRELLLE DGYNVYQSEA HGLPLRLPQR
 61 DAPSQPPASW GPVRFLPVPG LFQPPHDLPG RPAPEPPDVG SSDP
```

*Oreochromis niloticus* (Nile tilapia) FGF21 (GenBank Accession No.
XP_003438516, which is hereby incorporated by reference in its
entirety) (SEQ ID NO: 151); partial sequence corresponding to human
FGF21 residues 59 to 209
```
  1 MYLQMNMDGR VTGSDAQTPY SLMQLKSVKP GHVIIKGPSS SLFLCVDSEG NLRGQSHYSE
 61 TSCTFREMLL ADGYTRFISS QYGFPMSLAS RHSPDRHALP FTRFLPLRNN LKTDSVSEQL
121 PNNQRLFNVD SDDLLGMGLN SMGSPQFSMD K
```

In one embodiment of the present invention, the N-terminal portion of FGF21 of the chimeric protein of the present invention comprises an amino acid residue substitution to strengthen or increase the stability of the FGF21 core domain compared to wild type FGF21. In one embodiment of the present invention, the N-terminal portion of FGF21 of the chimeric protein of the present invention comprises an amino acid residue substitution to strengthen or increase the stability of the FGF21 core domain compared to that of SEQ ID NO: 100. In one particular embodiment, the N-terminal portion of FGF21 comprises a substitution at a residue corresponding to residue 104 of SEQ ID NO: 100. In one embodiment, the substitution is a glutamine to methionine substitution (i.e., Q104M).

The N-terminal portion of the chimeric protein according to the present invention may include a core domain, also referred to as, for example, an FGF21 core domain. In one embodiment, the core domain is the FGF n-trefoil core domain. In one embodiment, this region corresponds to H29 to L167 of human FGF21 of SEQ ID NO: 100.

Based on the inventors' extensive knowledge of the structures of FGF ligands, including the structures of FGF19 and FGF23, Q104 of FGF21 was selected for mutagenesis. Replacing Q104 with methionine, which is found in all other FGF ligands at the corresponding position (Mohammadi et al., "Structural Basis for Fibroblast Growth Factor Receptor Activation," *Cytokine & Growth Factor Rev* 16(2):107-137 (2005), which is hereby incorporated by reference in its entirety), increases the stability of FGF21 without affecting ligand-binding affinity for receptor.

In one embodiment of the present invention, FGF21 has an amino acid sequence corresponding to human FGF21 harboring a mutation at Q104. In one embodiment of the present invention, FGF21 has an amino acid sequence corresponding to human FGF21 harboring a Q104M mutation. In one embodiment the FGF21 having an amino acid sequence corresponding to human FGF21 and harboring a Q104M mutation, has the amino acid sequence of SEQ ID NO: 152, as follows:

```
                                                                  (SEQ ID NO: 152)
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCMRPDGAL YGSLHFDPEA

121 CSFRELLLED GYNVYQSEAH GLPLHLPGNK SPHRDPAPRG PARFLPLPGL PPALPEPPGI

181 LAPQPPDVGS SDPLSMVGPS QGRSPSYAS
```

In one embodiment, increasing the stability of the core domain includes an increase in thermal stability of the protein as compared to either wild type protein or a chimeric protein in which such a substitution is not made. In one embodiment, increasing the stability includes increasing the half-life of the protein in the blood circulation as compared to either wild type protein or a chimeric protein in which such a substitution is not made.

In one embodiment according to the present invention, the chimeric FGF21 protein comprises an N-terminal portion of FGF21 that contains at least one amino acid residue substitution to increase stability of the FGF21 core domain as compared to a sequence corresponding to SEQ ID NO: 100. In one embodiment of the present invention, the N-terminal portion of FGF21 comprises an amino acid sequence spanning residues corresponding to residues selected from the group consisting of from position 29 to 167 of SEQ ID NO: 152, from position 29 to 190 of SEQ ID NO: 152, or from position 29 to 197 of SEQ ID NO: 152. Exemplary chimeric proteins include those of SEQ ID NOs: 312-336.

In one particular embodiment of the present invention, the N-terminal portion of FGF21 of the chimeric protein of the present invention is a modified N-terminal portion of the FGF21 protein. In one embodiment, the N-terminal portion of the chimeric protein of the present invention comprises an amino acid sequence at least 85% identical to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion of FGF21 of the chimeric protein of the present invention is derived from a modified FGF21 protein, where the N-terminal portion of the chimeric protein of the present invention comprises an amino acid sequence that has at least 80%, at least 85%, at least 90%, at least 95%, at least 97% or at least 99% amino acid sequence identity to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion having such amino acid sequence similarity will maintain the activity of the corresponding naturally occurring N-terminal portion of FGF21. In one embodiment, the N-terminal portion of the chimeric protein of the present invention comprises an amino acid sequence at least 85% homologous to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion of FGF21 of the chimeric protein of the present invention is derived from a modified FGF21 protein, where the N-terminal portion of the chimeric protein of the present invention comprises an amino acid sequence that has at least 80%, at least 85%, at least 90%, at least 95%, at least 97% or at least 99% amino acid sequence homology to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion having such amino acid sequence homology will maintain the activity of the corresponding naturally occurring N-terminal portion of FGF21.

In one embodiment of the present invention, the N-terminal portion of FGF21 of the chimeric protein of the present invention is a modified N-terminal portion of the FGF21 protein. In one embodiment, the N-terminal portion of FGF21 of the chimeric protein of the present invention comprises an amino acid sequence at least 85% identical to the amino acid sequence corresponding to residues from position 29 to 167 of SEQ ID NO: 152, from position 29 to 190 of SEQ ID NO: 152, or from position 29 to 197 of SEQ ID NO: 152. In one embodiment, the N-terminal portion of FGF21 of the chimeric protein of the present invention comprises an amino acid sequence at least 85% homologous to the amino acid sequence corresponding to residues from position 29 to 167 of SEQ ID NO: 152, from position 29 to 190 of SEQ ID NO: 152, or from position 29 to 197 of SEQ ID NO: 152.

It will be understood that the portion of FGF21 of the chimeric protein of the present invention may be derived from a nucleotide sequence that encodes a vertebrate or a non-vertebrate FGF21 protein. In one embodiment, the portion of FGF21 of the chimeric protein of the present invention may be derived a nucleotide sequence that encodes a mammalian FGF21 protein. Nucleotide sequences encoding a vertebrate FGF21 protein according to the present invention may include, but are not limited to, those shown in Table 4.

TABLE 4

```
Human FGF21 gene coding sequence (SEQ ID NO: 153) (GenBank Accession
No. NM_019113, which is hereby incorporated by reference in its
entirety)
  151 ATGGACTCGG ACGAGACCGG GTTCGAGCAC TCAGGACTGT GGGTTTCTGT GCTGGCTGGT
  211 CTTCTGCTGG GAGCCTGCCA GGCACACCCC ATCCCTGACT CCAGTCCTCT CCTGCAATTC
  271 GGGGGCCAAG TCCGGCAGCG GTACCTCTAC ACAGATGATG CCCAGCAGAC AGAAGCCCAC
  331 CTGGAGATCA GGGAGGATGG GACGGTGGGG GGCGCTGCTG ACCAGAGCCC CGAAAGTCTC
  391 CTGCAGCTGA AAGCCTTGAA GCCGGGAGTT ATTCAAATCT TGGGAGTCAA GACATCCAGG
  451 TTCCTGTGCC AGCGGCCAGA TGGGGCCCTG TATGGATCGC TCCACTTTGA CCCTGAGGCC
  511 TGCAGCTTCC GGGAGCTGCT TCTTGAGGAC GGATACAATG TTTACCAGTC CGAAGCCCAC
  571 GGCCTCCCGC TGCACCTGCC AGGGAACAAG TCCCCACACC GGGACCCTGC ACCCCGAGGA
  631 CCAGCTCGCT TCCTGCCACT ACCAGGCCTG CCCCCCGCAC TCCCGGAGCC ACCCGGAATC
  691 CTGGCCCCCC AGCCCCCCGA TGTGGGCTCC TCGGACCCTC TGAGCATGGT GGGACCTTCC
  751 CAGGGCCGAA GCCCCAGCTA CGCTTCCTGA Pongo abelii (Sumatran orangutan) FGF21 gene coding sequence (SEQ ID
NO: 154) (GenBank Accession No. XM_002829519, which is hereby
incorporated by reference in its entirety)
  165     ATGGAC TCGGACGAGA CCGGGTTCGA GCACTCAGGA CTGTGGGTTC CTGTGCTGGC
  221 TGGTCTTCTG CTGGGAGCCT GCCAGGCACA CCCCATCCCT GACTCCAGTC CTCTCCTGCA
  281 ATTCGGGGGC CAAGTCCGGC AGCGGTACCT CTACACAGAT GATGCCCAGC AGACAGAAGC
  341 CCACCTGGAG ATCAGGGAGG ATGGGACGGT GGGGGCGCT GCTGACCAGA GCCCCGAAAG
  401 TCTCCTGCAG CTGAAAGCCT TGAAGCCGGG AGTTATTCAA ATCTTGGGAG TCAAGACATC
  461 CAGGTTCCTG TGCCAGAGGC CAGATGGGGC CCTGTATGGA TCGCTCCACT TTGACCCTGA
  521 GGCCTGCAGC TTCCGGGAGC TGCTTCTTGA GGACGGATAC AATGTTTATC AGTCCGAGGC
  581 CCATGGCCTC CCGCTGCACC TGCCGGGAAA CAAGTCCCCA CACCGGGACC CTGCACCCCG
  641 AGGACCAGCT CGCTTCCTGC CACTACCAGG CCTGCCCCCC GCACCCCCAG AGCCGCCCGG
  701 AATCCTGGCC CCCAGCCCC CCGATGTGGG CTCCTCGGAC CCTCTGAGCA TGGTGGGACC
  761 TTCCCAGGGC CGAAGCCCCA GCTATGCTTC CTGA Pan troglodytes (chimpanzee) FGF21 gene coding sequence (SEQ ID NO:
155) (GenBank Accession No. XM_524333, which is hereby incorporated
by reference in its entirety)
  573     ATGGACTC GGACGAGACC GGGTTCGAGC ACTCAGGACT GTGGGTTTCT GTGCTGGCTG
  631 GTCTTCTGCT AGGAGCCTGC CAGGCACACC CCATCCCTGA CTCCAGTCCT CTCCTGCAAT
```

TABLE 4-continued

```
 691 TCGGGGGCCA AGTCCGGCAG CGGTACCTCT ACACAGATGA TGCCCAGCAG ACAGAAGCCC
 751 ACCTGGAGAT CAGGGAGGAT GGGACGGTGG GGGGCGCTGC TGACCAGAGC CCCGAAAGTC
 811 TCCTGCAGCT GAAAGCCTTG AAGCCGGGAG TTATTCAAAT CTTGGGAGTC AAGACATCCA
 871 GGTTCCTGTG CCAGAGGCCA GATGGGGCCC TGTATGGATC GCTCCACTTT GACCCTGAGG
 931 CCTGCAGCTT CCGGGAGCTG CTTCTTGAGG ACGGATACAA TGTTTACCAG TCCGAGGCCA
 991 ACGGCCTCCC GCTGCACCTG CCGGGGAACA AGTCCCCACA CCGGGACCCT GCACCCCGAG
1051 GACCAGCTCG CTTCCTGCCA CTACCAGGCC TGCCCCCCGC ACCCCGGAG CCACCCGGAA
1111 TCCTGGCCCC CCAGCCCCCC GATGTGGGCT CCTCAGACCC TCTGAGCATG GTGGGACCTT
1171 CCCAGGGCCG AAGCCCCAGC TACACTTCCT GA
```

Canis lupus familiaris (dog) FGF21 gene coding sequence (SEQ ID NO: 156) (GenBank Accession No. XM_541510, which is hereby incorporated by reference in its entirety)
```
   1 ATGGGCTGGG CCGAGGCCGG GTTCGAGCAC CTGGGACTGT GGGTCCCTGT GCTGGCTGTG
  61 CTTTTGCTGG AAGCCTGCCG GGCACATCCG ATCCCTGACT CCAGCCCCCT CCTACAATTT
 121 GGAGGTCAAG TTCGACAGCG GTACCTCTAC ACCGACGATG CCCAGGAGAC AGAGGCCCAC
 181 CTAGAGATCA GGGCCGATGG CACAGTGGTG GGGGCTGCCC GCCAGAGCCC TGAAAGTCTC
 241 CTGGAGCTGA AGCCCTAAA GCCAGGGGTC ATTCAAATCT TGGGAGTCAA ACATCCAGG
 301 TTCCTGTGCC AGGGCCCAGA TGGGACACTA TATGGCTCGC TCCATTTCGA CCCTGTGGCC
 361 TGCAGTTTCC GAGAACTGCT TCTTGAGGAT GGGTACAACA TCTACCACTC CGAGACCCTT
 421 GGTCTCCCGC TTCGCCTGCG CCCCCACAAC TCCGCATACC GGGACTTGGC ACCCCGCGGG
 481 CCTGCCCGCT TCCTGCCACT GCCAGGCCTG CTTCCAGCAC CCCCAGAGCC TCCAGGGATC
 541 CTGGCCCCGG AGCCTCCTGA CGTGGGCTCC TCGGACCCTC TGAGCATGGT GGGGCCTTCA
 601 CAGGGCCGGA GTCCCAGCTA TGCTTCCTAA
```

Bos taurus (bovine) FGF21 gene coding sequence (SEQ ID NO: 157) (GenBank Accession No. XP_001789587, which is hereby incorporated by reference in its entirety)
```
   1 ATGGGCTGGG ACGAGGCCAA GTTCAAGCAC TTGGGACTGT GGGTCCCTGT GCTGGCTGTC
  61 CTCCTGCTAG GAACCTGCCG GGCGCATCCC ATTCCAGACT CCAGCCCCCT CCTCCAGTTT
 121 GGGGGCCAAG TCCGCCAGCG GTACCTCTAC ACGGATGATG CCCAGGAGAC AGAGGCCCAC
 181 CTGGAGATCA GGGCCGATGG CACAGTGGTG GGGGCAGCCC GCCAGAGCCC CGAAAGTCTC
 241 TTGGAGCTGA AGCCCTGAA GCCAGGCGTC ATTCAGATCT TGGGAGTTAA AACATCCAGG
 301 TTTCTCTGCC AGGGGCCAGA TGGGAAGCTG TACGGATCGC TGCACTTTGA CCCCAAAGCC
 361 TGCAGCTTTC GGGAGCTGCT TCTTGAAGAT GGATACAACG TCTACCAGTC GGAGACCCTG
 421 GGCCTTCCAC TCCGCCTGCC CCCCAGCGC TCGTCCAACC GGGACCCGGC CCCGCGGGGA
 481 CCTGCTCGCT TCCTTCCACT GCCGGGCCTG CCCGCGGCGC CCCCGGATCC TCCAGGGATC
 541 TTGGCCCCCG AGCCTCCCGA CGTGGGCTCC TCGGATCCCC TGAGTATGGT GGGACCCTCG
 601 TATGGCCGAA GCCCCAGCTA CACTTCTTGA
```

Equus caballus (horse) FGF21 gene coding sequence (SEQ ID NO: 158) (GenBank Accession No. XM_001489152, which is hereby incorporated by reference in its entirety)
```
   1 ATGGACTGGG ACAAGACGGG GTTCAAGTAC CAGGGACTGT GGGTCCCTGT GCTGGCTGTC
  61 CTTCTGCTGG GAGCCTGCCA GTCACACCCC ATCCCTGACT CCAGTCCCCT CCTCCAATTC
 121 GGGGGCCAAG TCAGGCAGCG CCACCTCTAC ACAGATGATG CCCAGGAGAC AGAGGCGCAC
 181 CTGGAGATCA GGGCTGACGG CACTGTGGCA GGGGCTGTCC ACCGGAGCCC AGAAAGTCTC
 241 TTGGAGCTGA AGCCCTGAA GCCAGGGGTA ATTCAAATCT TGGGAGTCAA GACATCCAGG
 301 TTTCTGTGCC AGGGGCCAGA CGGGACGCTG TACGGATCGC TCCACTTCGA CCCCGTGGCC
 361 TGCAGCTTCC GGGAGCTGCT TCTCGAAGAC GGCTACAACG TTTACCAGTC TGAGACCCTT
 421 GGCCTCCCAC TCCGCCTGCC CCACCACAGC TCCCCATACC AGGATCCGGC CCCTCGGGCA
 481 CCCGCCCGCT TCCTGCCGCT GCCAGGCTTT CCCCCAGCAC CCCCGGAGCC TCCAGGGATC
 541 CCGGCCCCCG AGCCCCCGGA CGTGGGCTCC TCGGACCCCC TGAGCATGGT GGGGCCTTCA
 601 CGCAGCCGGA GCCCCAGCTA CACTTCCTGA
```

Ailuropoda melanoleuca (giant panda) FGF21 gene coding sequence (SEQ ID NO: 159) (GenBank Accession No. XM_002917864, which is hereby incorporated by reference in its entirety)
```
   1 ATGGGCTGGG ACGAGGCCAG GTCCGAGCAG CTGGGGCTGT GGGTCCCTGT GCTGGCTGTC
  61 CTTTTGCTGG AAGCTTGCCA GGCACACCCT ATCCCTGACT CCAGCCCCCT CCTCCAATTC
 121 GGAGGCCAAG TTCGACAGCG GTACCTCTAC ACGGACGATG CCCAGGAGAC AGAGGCCCAC
 181 CTAGCGATCA GGGCTGATGG CACAGTGGTG GGGGCTGCCA GCCGGAGCCC AGAAAGTCTC
 241 TTGGAGCTGA AGCCCTGAA ACCGGGGGTC ATTCAAATCC TGGGAGTGAA AACATCTAGG
 301 TTCCTGTGCC AGGGCCCAGA TGGGACACTG TACGGATCGG TCCGCTTCGA CCCCGTAGCC
 361 TGCAGCTTCC GGGAACTGCT CCTGGAGGAT GGGTACAACA TCTACCACTC TGAGACCCTC
 421 GGCCTCCCAC TTCGCCTGCC CGCCCACAAC TCTCCATACC GGGACTCGGC GCCCCGGGGG
 481 CCTGCCCGCT TCCTGCCCCT GCCAGGCCTG CTTCCGGTCC CCCCGGACCC CCAGGGGATC
 541 CTGGGCCCCG AGCCTCCCGA CGTGGGCTCC TCGGACCCCC TGAGCATGGT GGGGCCTTCA
 601 CAGGGCCGAA GTCCCAGCTA CGCTTCCTGA
```

Oryctolagus cuniculus (rabbit) FGF21 gene coding sequence (SEQ ID NO: 160) (GenBank Accession No. XM_002723699, which is hereby incorporated by reference in its entirety)
```
   1 ATGGACTGGG GCAAGGCCAA GTGCCGGCCC CCGGGGCTGT GGGTCCCCGC GCTCGCTGCC
  61 CTGCTGCTGG GGGCCTGCCA GGCACACCCC ATCCCCGACT CCAGCCCCCT CCTCCAGTTT
 121 GGGGACCAAG TGCGGCAGCA GCACCTGTAC ACGGACGATG CGCAGGAAAC AGAAGCCCAC
 181 CTGGAGATCA GGGCGGATGG CACGGTGGTG GGGGCTGCCC GGAGGAGCCC AGAAAGTCTC
 241 TTGCAGATGA AAGCCTTACA ACCGGGGATC ATTCAGATCT TGGGGGTCCA GACGTCCAGG
 301 TTCCTCTGCC AGAGGCCGGA TGGCACGCTC TACGGCTCGC TCCACTTCGA CCGCGAGGCC
 361 TGCAGCTTCC GGGAGCTGCT GCGTGAGGAT GGGTACAACG TTTACCTCTC GGAGGCCCTG
```

TABLE 4-continued

```
421 GGCCTGCCCC TGCGCCTGTC CCCCGGCAGC TCCCCACGCA GGGCGCCGGC CCCCCGGGGA
481 CCAGCCCGCT TCCTGCCGCT GCCCGGCCTG CCGCCAGACC TTCCGGAACC GCCAGGCCTC
541 CTGGCCGCCG CGCCCCCCGA TGTCGACTCC CCGGACCCCC TGAGCATGGT GCAGCCTGCG
601 CTGGACCAGA GCCCCAGCTA CACCTCCTGA
```

Gorilla gorilla (gorilla) FGF21 gene coding sequence (SEQ ID NO:
161) (Ensembl Accession No. ENSGGOT00000001253, which is hereby
incorporat ed by reference in its entirety)

```
151 ATGGACTCGG ACGAGACCGG GTTCGAGCAC TCAGGACTGT GGGTTTCTGT GCTGGCTGGT
211 CTTCTGCTGG GAGCCTGCCA GGCACACCCC ATCCCTGACT CCAGTCCTCT CCTGCAATTC
271 GGGGGCCAAG TCCGGCAGCG GTACCTCTAC ACAGATGATG CCCAGCAGAC AGAAGCCCAC
331 CTGGAGATCA GGGAGGATGG GACGGTGGGG GGTGCTGCTG ACCAGAGCCC TGAAAGTCTC
391 CTGCAGCTGA AAGCCTTGAA GCCGGGAGTT ATTCAAATCT TGGGAGTCAA GACATCCAGG
451 TTCCTGTGCC AGAGGCCAGA TGGGGCCCTG TATGGATCGC TCCACTTTGA CCCTGAGGCC
511 TGCAGCTTCC GGGAGCTGCT TCTTGAGGAC GGATACAATG TTTACCAGTC CGAGGCCCAC
571 GGCCTCCCGC TGCACCTGCC GGGGAACAAG TCCCCACACC GGGACCCTGC ACCCCGAGGA
631 CCAGCTCGCT TCCTGCCACT ACCAGGCCTG CCCCCCGCAC CCCCGGAGCC ACCCGGAATC
691 CTGGCCCCCC AGCCCCCCGA TGTGGGCTCC TCGGACCCTC TGAGCATGGT GGGACCTTCC
751 CAGGGCCGAA GCCCCAGCTA CGCTTCCTGA
```

Nomascus leucogenys (Northern white-cheeked gibbon) FGF21 gene
coding sequence (SEQ ID NO: 162) (Ensembl Accession No.
ENSNLET00000005931, which is hereby incorporated by
reference in its entirety)

```
587       ATGG ACTCGGACGA GACCGGGTTC GAGCACTCAG GACTGTGGGT TCCTGTGCTG
647 GCTGGTCTTC TGCTGGGAGC CTGCCAGGCA CACCCCATCC CTGACTCCAG TCCTCTCCTG
707 CAATTCGGGG GCCAAGTCCG GCAGCGGTAC CTCTACACAG ATGATGCCCA GCAGACAGAA
767 GCCCACCTGG AGATCAGGGA GGATGGGACG GTGGGGGGCG CTGCTGACCA GAGCCCTGAA
831 AGTCTCCTGC AGCTGAAAGC CTTGAAGCCG GGAGTTATTC AAATCTTGGG AGTCAAGACA
891 TCCAGGTTCC TATGCCAGAG GCCAGATGGG GCCCTGTATG GATCGCTCCA CTTTGACCCT
951 GAGGCCTGCA GCTTCCGGGA GCTGCTTCTT GAGGACGGAT ACAATGTTTA CCAGTCCGAG
1011 GCCCATGGCC TCCCGCTGCA CCTGCCGGGG AACAAGTCCC CACACCGGGA CCCTGCACCC
1071 CGAGGACCAG CTCGCTTCCT GCCACTACCA GGCCTGCCCC CTGCACCCCC AGAGCCGCCC
1131 GGAATCCTGG CCCCCCAGCC CCCGATGTG GGCTCCTCGG ACCCTCTGAG CATGGTGGGA
1191 CCTTCCCAGG GCCGAAGCCC CAGCTACGCT TCCTGA
```

Procavia capensis (hyrax) FGF21 gene coding sequence (SEQ ID NO:
163) (Ensembl Accession No. ENSPCAT00000001288, which is hereby
incorporated by reference in its entirety)

```
  1 ATGGACTGGG CCAAGTTTGG GATCGAGCAC CCGGGACTGT GGGTCCCGGT GATGGCAGTA
 61 CTTCTGCTGG GAGCCTGCCA AGGATACCCT ATTCCTGACT CCAGCCCCCT TCTCCAATTC
121 GGAGGCCAGG TCCGGCAACG TTACCTCTAC ACAGATGACG CAGGAGAC CGAGGCCCAC
181 CTGGAGATCC GAGCAGACGG CACGGTGGTG GGGGCTGCCC ACCGGAGCCC CGAGAGTCTC
241 TTGGAGCTGA AAGCTTTGAA GCCCGGCATA ATTCAGATCT GGGAGTCAA GACATCCAGA
301 TTCCTCTGCC AGGGTCCTGA TGGGGTGCTG TATGGATCGC TCCGTTTTGA CCCAGTGGCC
361 TGCAGCTTCC GGGAGCTGCT TCTTGAAGAT GGATACAATG TTTACCAGTC TGAGGCCCAC
421 GGCCTCCCGC TTCGCCTACC ATCCCACAAT TCCCCACAGA GGGACCTGGC GTCCCGGGTG
481 CCAGCCCGCT TCCTGCCACT GCCAGGCCGG CTCACGGTGC TCCCAGAACC TTCGGGGGTC
541 CTGGGCCCTG AGCCCCCGA TGTGGACTCC TCAGACCCCC TGAGCATGGT GGGGCCTTCG
601 CAGGGCCGAA GCCCCAGTTA CGCCTCCTGA
```

Cavia porcellus (guinea pig) FGF21 gene coding sequence (SEQ ID NO:
164) (Ensembl Accession No. ENSCPOT00000000273, which is hereby
incorporated by reference in its entirety)

```
  1 ATGGACTGGG CCCGGACTGA GTGTGAGCGC CCAAGGCTGT GGGTCTCCAT GCTGGCCATC
 61 CTTCTGGTGG GAGCCTGCCA GGCACACCCT ATCCCTGACT CCAGCCCCCT CCTCCAGTTT
121 GGGGGCCAGG TCCGGCAGCG GTACCTCTAC ACAGATGATG CTCAGGACAC TGAAGTGCAC
181 CTGGAGATCA GGGCCGATGG CTCAGTACGG GGCATTGCCC ACAGGAGCCC TGAAAGTCTC
241 CTGGAGCTGA AAGCCTTGAA GCCAGGAGTC ATTCAGATCT GGGAATCAG GACTTCCAGG
301 TTCCTGTGCC AGAGGCCCGA TGGGAGTCTG TATGGATCAC TCCACTTTGA TCCTGAGGCC
361 TGCAGCTTCC GGGAGCTGCT GCTTGCTGAT GGCTACAATG TCTACAAGTC TGAAGCCCAC
421 GGCCTCCCTC TGCACCTGCT GCGCGGTGAC TCTCTATCGC AGGAACCAGC ACCCCCAGGA
481 CCAGCCCGAT TTCTGCCACT ACCAGGCCTG CCCGCAACAC CCCCGGAGCC ACCCAGGATG
541 CTGCCCCCAG GGCCCCCAGA TGTGGGCTCC TCGGACCCTT TGAGCATGGT GGGGCCTTTA
601 TGGGACCGAA GCCCCAGCTA TACTTCCTGA
```

Tupaia belangeri (tree shrew) FGF21 gene coding sequence (SEQ ID NO:
165) (Ensembl Accession No. ENSTBET00000016056, which is hereby
incorporated by reference in its entirety)

```
  1 ATGGGCTGGG ACAAGGCCCG GTTCGAGCAC CTGGGAGCGT GGGCTCCTGT GCTGGCTGTC
 61 CTCCTCCTGG GAGCCTGCCA GGCATACCCC ATCCCTGACT CCAGCCCCCT CCTACAATTC
121 GGGGGCCAGG TCCGGCAGCG GTACCTCTAC ACGGACGACA CGCAGGACAC AGAAGCCCAC
181 CTTGAGATCA GGGCCGACGG CACCGTGGTG GGGGCCGCCC ACCAAAGCCC GGAAAGTCTC
241 CTGGAGCTGA AAGCCTTGAA GCCGGGGGTC ATTCAAATCC TGGGAGTCAA GACCTCCAGG
301 TTCCTGTGCC AGAGGCCAGA CGGGGCCCTG TACGGGTCCG TTCACTTCGA CCCCGAGGCC
361 TGCAGCTTCC GGGAGCTGCT TCTCGAGGAT GGATACAACA TTTACCAGTC TGAGGCTCGT
421 GGCCTCCCCC TGCGCCTGCC GCCCACGAC TCCCCACATC GGGACCGGAC CCCTCGGGGA
481 CCAGCTCGTT TCCTGCCGCT GCCTGGCCTG CCCCTGGTTC CTCCAGAGCT GCCAGGGGTC
541 CTGGCCCTTG AGCCCCCGA CGTGGGCTCC TCAGACCCGC TGA
```

TABLE 4-continued

*Sorex araneus* (shrew) FGF21 gene coding sequence (SEQ ID NO: 166)
(Ensembl Accession No. ENSSART00000003074, which is hereby
incorporated by reference in its entirety)
     1 ATGGTCTGGG ACAAGGCCAG GGGGCAGCAG TTGGGACTGT GGGCCCCCAT GCTGCTGGGC
    61 TTGCTGCTGG GTGCCTGCCA GGCACACCCC CTCCCTGACT CCAGCCCCCT CCTCCAATTT
   121 GGGGGCCAAG TCCGACTGAG GTTCCTGTAC ACCGACGATG CCCAGAGGAC AGGGGCGCAC
   181 CTGGAGATCA GGGCCGACGG CACAGTGCAG GGTGCGGCCC ACAGGACCCC AGAATGTCTC
   241 CTGGAGCTGA AAGCCTTGAA GCCAGGCGTA ATTCAAATCC TTGGGGTCAG CACATCCAGA
   301 TTCCTGTGCC AGCGGCCCGA TGGGGTCCTG TATGGATCGC TTCGCTTTGA CCCAGAGGCC
   361 TGCAGTTTCC GGGAACTTCT TCTCCAGGAT GGATATAACG TTTACCAGTC TGAGGCCCTG
   421 GGTCTCCCGC TCTACCTACA CCCGCCCAGT GCCCCAGTGT CCCAGGAACC AGCCTCACGG
   481 GGCGCCGTCC GCTTCCTGCC ACTGCCAGGA CTGCCACCTG CCTCCCTGGA GCCCCCCAGG
   541 CCCCCCGCCC CGGTGCCTCC AGACGTGGGT TCCTCAGACC CCCTGA

*Ictidomys tridecemlineatus* (squirrel) FGF21 gene coding sequence
(SEQ ID NO: 167)
     1 ATGTACCCCA TCCCTGACTC AAGCCCCCTC CTCCAATTTG GGGGCCAAGT CCGGCAGCGG
    61 TACCTGTACA CAGATGATGC CCAGGAGACT GAGGCCCACC TGGAGATCAG GGCTGATGGC
   121 ACCGTGGTGG GGGCTGCCCA TCAAAGCCCG GAAAGTCTCT TGGAACTGAA AGCCTTGAAG
   181 CCTGGGGTCA TTCAAATCTT GGGGGTCAAA ACATCCAGGT TCCTGTGCCA GAGGCCAGAT
   241 GGGAGTGCTGT ATGGATCGCT CCACTTTGAC CCTGAGGCCT GCAGCTTCCG GGAGCAGCTT
   301 CTGGAGGACG GGTACAACGT TTACCAGTCA GAATCCCACG GCCTCCCCGT GCGCCTGCCC
   361 CCTAACTCAC CATACCGGGA CCCAGCGCCC CAGGACCAG CCCGCTTCCT TCCACTGCCA
   421 GGCCTGCCCC CAGCAGCCCT GGAGCCGCCA GGGATCCTGG CCCTGAGCC CCTGATGTG
   481 GGCTCCTCCG ACCCACTCAG CATGGTGGGG CCTTTGCAGG GCCGAAGCCC CAGTTACGCT
   541 TCCTGA

*Loxodonta africana* (elephant) FGF21 gene coding sequence (SEQ ID NO:
168) (Ensembl Accession No. ENSLAFT00000022429, which is hereby
incorporated by reference in its entirety)
     1 ATGGACTGGG CCAAGTTTGG GTTGGAGCAC CCAGGACTGT GGGTCCCTGT GATGGCTGTC
    61 CTTCTGCTGG GAGCCTGCCA GGGACACCCC ATCCCTGACT CCAGCCCCCT CCTCCAATTC
   121 GGGGGCCAGG TCCGGCAACG TTACCTCTAC ACAGATGATG AGGAGACCGA GGCCCACCTG
   181 GAGATCAGAG CAGATGGCAC AGTGGCGGGA GCCGCTCACC GGAGCTCTGA GAGTCTCTTG
   241 GAGCTGAAAG CTTTGAAGCC TGGAATAATT CAGATCTTGG GGTCAAGAC ATCCCGGTTC
   301 CTGTGCCAGG GGCCTGATGG GGTGCTGTAC GGATCGCTCC ATTTCGACCC AGCCGCCTGC
   361 AGCTTCCGGG AGCTGCTTCT TGAAGATGGA TACAATGTTT ACTGGTCCGA GGCCCATGGA
   421 CTCCCAATCC GCCTGCCCTC CCACAACTCC CCATATAGGG ACCCAGCATC CCGGGTACCA
   481 GCCCGCTTCC TGCCACTGCC AGGCCTGCTC CCAATGCTCC AAGAACCTCC AGGGGTCCTG
   541 GCCCCTGAGC CCCCTGATGT GGACTCCTCA GACCCCCTGA GCATGGTGGG GCCTTCACAG
   601 GGCCGAAGCC CCAGCTATGC CTCCTGA

*Sus scrofa* (pig) FGF21 gene coding sequence) (SEQ ID NO: 169)
(GenBank Accession No. NM_001163410, which is hereby incorporated by
reference in its entirety
   131 ATGGGCTGGG CCGAGGCCAA GTTCGAGCGC TTGGGACTGT GGGTCCCTGT GCTGGCTGTC
   191 CTGCTGGGAG CCTGCCAGGC ACGTCCCATT CCTGACTCCA GCCCCCTCCT CCAATTTGGG
   251 GGCCAAGTGC GCCAACGATA CCTCTACACG GATGATGCCC AGGAAACTGA AGCCCACCTG
   311 GAGATCAGAG CTGATGGCAC CGTGGCAGGG GTAGCCCGCC AGAGCCCTGA AAGTCTCTTG
   371 GAGCTGAAAG CCCTGAAGCC AGGGGTCATT CAAATTTTGG GAGTCCAGAC ATCCCGGTTC
   431 CTGTGCCAGG GGCCAGACGG GAGACTGTAC GGATCGCTCC ACTTCGACCC TGAGGCCTGC
   491 AGCTTCCGGG AGCTGCTTCT TGAGGATGGC TACAACGTTT ACCAGTCTGA GGCCCTTGGC
   551 CTCCCACTCC GGCTGCCTCC GCACCGCTCC TCCAACCGGG ACCTGGCCCC CGGGGACCT
   611 GCTCGCTTCC TGCCACTGCC AGGCCTGCCC CCGGCACCCC CGGAGCCGCC AGGGATCTTG
   671 GCCCCTGAAC CTCCCGACGT GGGCTCCTCG GACCCCCTGA GCATGGTGGG GCCTTCACAC
   731 GGCCGGAGCC CCAGCTACAC TTCTTGA

*Felis catus* (cat) FGF21 gene coding sequence (SEQ ID NO: 170)
(Ensembl Accession No. ENSFCAT00000007367, which is hereby
incorporated by reference in its entirety)
     1 ATGGGCTGGG ACGAGGCCGG GTCCCAGCGC CTGGGACTGT GGGTCGTGCT GGGGGTCCTT
    61 TTGCCGGAAG CCTGCCAGGC ACACCCTATC CCTGACTCCA GCCCCCTCCT CCAATTCGGG
   121 GGCCAAGTTC GACAGCGGTT CCTCTACACG GACGACGCCC AGGAGACAGA GGTCCACCTC
   181 GAGATCAAGG CTGATGGCAC AGTGGTGGGG ACCGCTCGCC GGAGCCCTGA GAGTCTCTTG
   241 GAGCTAAAAG CCCTGAAGCC GGGGGTAATT CAAATCTTGG GGTCAAAAC GTCCAGGTTC
   301 CTGTGCCAGG GCCCAGATGG GACACTGTAT GGATCGCTCC GCTTTGACCC CGCAGCCTGC
   361 AGCTTCCGGG AACTGCTCCT GGAGGACGGA TACAACATCT ACCACTCGGA GACCCTCGGG
   421 CTCCCACTCC GCCTGCCCCC CCACAACTCC CCATACCGGG ACTTGGCCCC CGGGCACCCT
   481 GCCCGCTTCC TGCCGCTGCC AGGCCTGCTT CCGGCACCCC CGGAGCCTCC AGGGATCCTG
   541 GCCCCCGAGC CCCCGGACGT GGGCTCCTCG GACCCTCTGA GCATGGTGGG GCCTTCCCAG
   601 GGCCGAAGTC CCAGCTACGC TTCCTGA

*Otolemur garnettii* (bushbaby) FGF21 gene coding sequence (SEQ ID NO:
171) (Ensembl Accession No. ENSOGAT00000003585, which is hereby
incorporated by reference in its entirety)
     1 GACAAGGCCA GGACTGGGTT CAAGCACCCA GGACCATGGT TCCCCTGCT GGCTGTACTT
    61 TTGTTGGGAG CCTGCCAGGC ACACCCTATC CCTGACTCCA GCCCCCTACT CCAGTTTGGT
   121 GGCCAAGTCC GGCAGCGGTA CCTCTACACA GATGATGCCC AGGAGACAGA AGCCCACCTG
   181 GAGATCAGGG AAGATGGCAC AGTGGTGGGG GCTCACAACAG AGAGCCCTGA AAGTCTCTTG
   241 GAGCTGAAAG CTTTAAAGCC AGGGGTCATT CAAATCTTGG GAGTCAAGAC ATCCAGGTTC TABLE 4-continued

```
301 CTGTGCCAGA GGCCAGATGG GGGCCTATAT GGATCGCTCT ACTTTGACCC CAAGGCCTGC
361 AGTTTCCGGG AGCTGCTTCT TGAGGATGGA TACAACGTTT ACTGGTCTGA GACCTATGGC
421 CTCCCACTGC ACCTGCCTCC TGCCAATTCC CCATACTGGG GCCCATCCCT TCGGAGCCCA
481 GCCCGCTTCC TGCCACTGCC AGGCCCTCCT GCAGCATCCC CAGAGCTGCC GGGGATCTTG
541 GCCCTGGAAC CCCCCGATGT GGGCTCCTCG GACCCTCTGA GCATGGTGGG GCCTTCGCAG
601 GGCCGAAGCC CCAGCTATGC TTCCTGA
```

*Rattus norvegicus* (Norway rat) FGF21 gene coding sequence (SEQ ID NO: 172) (GenBank Accession No. NM_130752, which is hereby incorporated by reference in its entirety)

```
  1 ATGGACTGGA TGAAATCTAG AGTTGGGGCC CCGGGACTGT GGGTCTGTCT CCTGCTGCCT
 61 GTCTTCCTGC TGGGGGTGTG CGAGGCATAC CCCATCTCTG ACTCCAGCCC CCTCCTCCAG
121 TTTGGGGGTC AAGTCCGACA GAGGTATCTC TACACAGATG ACGACCAGGA CACCGAAGCC
181 CACCTGGAGA TCAGGGAGGA CGGAACAGTG GTGGGCACAG CACACCGCAG TCCAGAAAGT
241 CTCCTGGAGC TCAAAGCCTT GAAGCCAGGG GTCATTCAAA TCCTGGGTGT CAAAGCCTCT
301 AGGTTTCTTT GCCAACAACC AGATGGAACT CTCTATGGAT CGCCTCACTT TGATCCTGAG
361 GCCTGCAGTT TCAGAGAGCT GCTGCTTAAG GACGGATACA ATGTGTACCA GTCTGAGGCC
421 CATGGCCTGC CCCTGCGTCT GCCCCAGAAG GACTCCCAGG ATCCAGCAAC CCGGGGACCT
481 GTGCGCTTCC TGCCCATGCC AGGCCTGCCC CACGAGCCCC AAGAGCAACC AGGAGTCCTT
541 CCCCCAGAGC CCCCAGATGT GGGTTCCTCC GACCCCCTGA GCATGGTAGA GCCTTTGCAA
601 GGCCGAAGCC CCAGCTATGC ATCTTGA
```

*Mus musculus* (house mouse) FGF21 gene coding sequence (SEQ ID NO: 173) (GenBank Accession No. NM_020013, which is hereby incorporated by reference in its entirety)

```
185     ATGGAA TGGATGAGAT CTAGAGTTGG GACCCTGGGA CTGTGGGTCC GACTGCTGCT
241 GGCTGTCTTC CTGCTGGGGG TCTACCAAGC ATACCCCATC CCTGACTCCA GCCCCCTCCT
301 CCAGTTTGGG GGTCAAGTCC GGCAGAGGTA CCTCTACACA GATGACGACC AAGACACTGA
361 AGCCCACCTG GAGATCAGGG AGGATGGAAC AGTGGTAGGC GCAGCACACC GCAGTCCAGA
421 AAGTCTCCTG GAGCTCAAAG CCTTGAAGCC AGGGGTCATT CAAATCCTGG GTGTCAAAGC
481 CTCTAGGTTT CTTTGCCAAC AGCCAGATGG AGCTCTCTAT GGATCGCCTC ACTTTGATCC
541 TGAGGCCTGC AGCTTCAGAG AACTGCTGCT GGAGGACGGT TACAATGTGT ACCAGTCTGA
601 AGCCCATGGC CTGCCCCTGC GTCTGCCTCA GAAGGACTCC CCAAACCAGG ATGCAACATC
661 CTGGGGACCT GTGCGCTTCC TGCCCATGCC AGGCCTGCTC CACGAGCCCC AAGACCAAGC
721 AGGATTCCTG CCCCCAGAGC CCCCAGATGT GGGCTCCTCT GACCCCCTGA GCATGGTAGA
781 GCCTTTACAG GGCCGAAGCC CCAGCTATGC GTCCTGA
```

*Vicugna pacos* (alpaca) FGF21 gene coding sequence (SEQ ID NO: 174) (Ensembl accession no. ENSVPAT00000005993, which is hereby incorporated by reference in its entirety) (1-209, excluding 79-168 and 172-182)

```
  1 ATGGACTGGG ACGAGGCCAA GTTCGAGCAT CGGGGACTGT GGGTCCCAGT GCTCACTGTC
 61 CTTCTGCTGG GAGCCTGCCA GGCACGCCCC ATTCCTGACT CCAGCCCCCT CCTCCAATTC
121 GGGGGCCAAG TCCGGCAGCG GTACCTCTAC ACGGATGACG CCCAGGAGAC AGAAGCCCAC
181 CTGGAGATCA GGGCTGATGG CACAGTGGTG GGGGTGGCCC GCCAG---CC CGAA------
241 ---------- ---------- ---------- ---------- ---------- ----------
301 ---------- ---------- ---------- ---------- ---------- ----------
361 ---------- ---------- ---------- ---------- ---------- ----------
421 ---------- ---------- ---------- ---------- ---------- ----------
481 ---------- ---------- ----GGAATT CCT------- ---------- ----------
541 ------CCCG AGCCTCCTGA CGTGGGCTCC TCAGACCCCC TGAGCATGGT GGGGCCTTCA
601 TACAGCAGAA GCCCCAGCTA CACTTCCTGA
```

*Anolis carolinensis* (anole lizard) FGF21 gene coding sequence (SEQ ID NO: 175) (Ensembl accession no. ENSACAT00000017230, which is hereby incorporated by reference in its entirety)

```
  1 TGTAAAGCA AGGGAGGAGG GAAGGGGGGA GAGAGGATGT GGGTAGACCT AGTTTTCTGG
 61 GCTGCCTTGC TCCGCACAGC TCCTGCTCTT CCCTTGCGGA ATTCCAACCC CATCTACCAA
121 TTTGATGGGC AGGTCCGGCT TCGGCACCTC TACACAGCAG ATGAACAGAC GCACCTCCAC
181 TTGGAGATCT TGCCAGACGG TACCGTGGGT GGATCCAGGT TTCAGAATCC CTTCAGTTTG
241 ATGGAGATCA AAGCTGTGAA GCCAGGAGTC ATTCGCATGC AGGCCAAGAA GACCTCTAGA
301 TTTCTCTGTA TGAAACCCAA TGGACGACTG TATGGCTCGC TGTTCTACTC TGAGGAGGCA
361 TGCAACTTCC ATGAGAAGGT TCTCAGCGAT GGCTACAACC TCTACTATTC TGAAAACTAC
421 AACATACCTG TCAGCCTCAG CTCGGCAGGG AACCTGGGTC AGAGCCGTCA GTTGCCTCCC
481 TTCTCCCAAT TCCTGCCGTT AGTCAACAAA ATTCCTCTTG AGCCTGTGCT TGAAGACTTT
541 GACTTCTATG GACATCAATT GGATGTTGAA TCAGCTGATC CTTTGAGCAT TTTAGGACAA
601 AACCCTGGTT TCATGAGTCC GAGCTATGTC TTC
```

*Gadus morhua* (cod) FGF21 gene coding sequence (SEQ ID NO: 176) (Ensembl accession no. ENSGMOT00000014151, which is hereby incorporated by reference in its entirety)

```
  1 CTCCTCCTCG CCACCCTCCT CCACATCGGC CTCTCCTTCT ACGTCCCCGA CTCCGGCCCC
 61 CTGCTGTGGC TGGGCGACCA GGTCAGGGAG GACACCTCT ACACAGCAGA GAGCCACCGG
121 AGGGGGCTGT TCCTGGAGAT GAGCCCGGAC GGTCAGGTGA CAGGAAGTGC TGCTCAGACG
181 CCGCTCAGTG TTCTGGAGCT GAGGTCGGTC AGAGCAGGAG ATACGGTCAT CAGAGCGCGC
241 CTCTCCTCTC TCTACCTGTG TGTGGACAGG CAGGTCACC TGACAGGACA GAGACAGTAC
301 ACAGAGTCCG ACTGCACCTT CAGAGAGGTC ATCCTTGAGG ACGGCTACAC CCACTTCCTG
361 TCCGTGCACC ACGGACTTCC TATTTCGCTG GCGCCGAGAC ACTCCCCAGG GAGACAGGGG
421 CTGCGCTTCA GCAGGTTCCT CCCGCTGAGG AGCAGTCTGT CAGAGGATAG GGTCGCCGAG
```

TABLE 4-continued

```
481 CCCCCAGACA GCCCACTGAA CCTGGACTCT GAAGACCCCC TGGGGATGGG TCTGGGTTCG
541 CTCCTCAGCC CGGCCTTCTC CATG
```

*Latimeria chalumnae* (coelacanth) FGF21 gene coding sequence (SEQ ID NO: 177) (Ensembl accession no. ENSLACT00000003815, which is hereby incorporated by reference in its entirety)
```
  1 ATGTTATGCC AGAGTTTTGT GATATTAAGT CAGAAATTCA TTTTTGGGCT CTTTTTGACT
 61 GGATTGGGGC TAACAGGATT GGCTTGGACA AGGCCCTTCC AGGATTCCAA TCCCATCCTG
121 CAGTATTCCG ATTCCATCCG GCTCCGACAT CTGTACACTG CCAGTGAGAG TCGGCACCTT
181 CACCTACAAA TCAACTCGGA TGGACAGGTG GGAGGGACAA CCAAGCAAAG CCCTTACAGT
241 CTGTTGGAGA TGAAGGCGGT GAAGACAGGT TTTGTGGTCA TCAGGGGCAA GAAAAGCGCC
301 CGTTACCTCT GTATGGAACG TAGTGGACGG CTCTATGGAT CGCTGCAGTA TACAGAAAAA
361 GACTGCACCT TCAAAGAGGT TGTGTTGGCA GATGGATACA ACCTGTATGT CTCAGAGGAA
421 CACCAGGCCA CAGTGACGCT GAGCCCCATG AGGGCGAGGA TAGCGCAAGG GAAAAAGATC
481 CCACCCTTTT CCCATTTCCT TCCAATGGTG AACAAGGTGC CTGTGGAGGA TGTTGCCGCT
541 GAGATGGAGT TTGTCCAGGT GCTGCGGGAA ATGACGGCCG ACGTGGACTC TCCGGATCCC
601 TTTGGAATGA CCTGGGAAGA ATCGGTTCAC AGTCCGAGCT TTTTTGCC
```

*Tursiops truncatus* (dolphin) FGF21 gene coding sequence (SEQ ID NO: 178) (Ensembl accession no. ENSTTRT00000014561, which is hereby incorporated by reference in its entirety)
```
  1 ATGGGCTGGG ACAAGACCAA ACTCGAGCAC CTGGGACTGT GGGTCCCTGT GCTAGCTGTC
 61 CTGCTGGGAC CCTGCCAGGC ACATCCCATT CCTGACTCCA GCCCCTCCT CCAATTTGGG
121 GGCCAAGTCC GCCAGCGATA CCTCTACACG GATGACGCCC AGGAGACGGA GGCCCACCTG
181 GAGATCAGGG CTGATGGCAC AGTGGTGGGG ACGGCCCGCC GGAGCCCCGA AGGAGTTAAA
241 ACATCCAGGT TCCTGTGCCA GGGGCCAGAG GGGAGGCTGT ATGGATCGCT CCACTTCAAC
301 CCCCAGGCCT GCAGCTTCCG GGAGCTGCTT CTTGAGGATG GATACAACGT TTACCAGTCA
361 GAGGCTCTTG GCATTCCCCT CCGCCTGCCC CCGCACCGCT CCTCCAACTG GGACCTGGCC
421 CCCCGGGGAC CTGCTCGCTT CCTGCCGCTG CCAGGCTTCC TCCCGCCACC CCTGGAGCCT
481 CCAGGGATCT TGGCCCCCGA GCCTCCCAAC GTAGGTTCCT CGGACCCCTT GAGCATGGTG
541 GGACCTTCAC ATGGCCGAAG CCCCAGCTAC ACTTCCTGA
```

*Mustela putorius furo* (ferret) FGF21 gene coding sequence (SEQ ID NO: 179) (Ensembl accession no. ENSMPUT00000003755, which is hereby incorporated by reference in its entirety)
```
188        ATG GGCTGGGAAG AGGCCAGGTC CGAGCACCTG GGGCTGTGGG TCCCTGTGCT
241 GGCGGTCCTT TTGCTGGGAG CCTGCCAGGC ATACCCTATT CCTGACTCCA GCCCCCTCCT
301 CCAATTTGGA GGCCAAGTTC GACAGCGGTA CCTCTACACA GACGACGCTC AGGAGACGGA
361 GGCCCACCTA GAGATCAGGG CTGATGGCAC GGTGGTGGGG GCTGCCCGCC GGAGCCCCGA
421 AAGTCTCTTG GAGCTGAAAG CCCTGAAGCC AGGGGTCATT CAGATCTTGG GAGTGAAAAC
481 ATCCAGGTTC CTGTGCCAGG GCCCGAATGG GACACTGTAC GGATCGTTCC ACTTCGACCC
541 CGTAGCCTGC AGCTTCCGGG AAGTGCTTCT GGAAGATGGA TACAACATCT ACCACTCTGA
601 GACCCTGGGC CTCCCACTGC GCCTGCCCCC CCACAACTCC CCACACAGGG ACCTGGCGCC
661 CCGGGGGCCT GCCCGCTTCC TGCCCCTGCC AGGCCTGCTT CCGGCCACCC CGGAGTCCCG
721 GGGGATCCCA GCCCCCGAGC CTCCCAACGT GGGCTCCTCA GACCCCCTGA GCATGGTGGG
781 GCCTTTGCAG GGTCAAAGTC CCAGCTACAC TTCCTGA
```

*Takifugu rubripes* (fugu) FGF21 gene coding sequence (SEQ ID NO: 180) (Ensembl accession no. ENSTRUT00000034076, which is hereby incorporated by reference in its entirety)
```
  1 TTTATTTATT TATTTATTCA AACTGCACTT TTTTCCCCTT CCAAATGGTT CAACTTTTAT
 61 CTCCCTGACT CCAACCCGCT CTTATCCTTT GACAGTCATG GCAGAGGCAT CCACCTCTAC
121 ACAGATAATC AAAGGCGAGG GATGTATCTG CAGATGAGCA CAGATGGAAG CGTTTCCGGG
181 AGTGATGTCC AGACGGCGAA CAGTGTGCTG GAACTGAAGT CAGTCAGAAA CGGCCACGTC
241 GTCATCCGAG GAAATCGTC TTCTCTGTTT CTCTGTATGG ACAGCAGAGG CCGTTTATGG
301 GGGCAGAGGC ACCCCACTGA GGCCGACTGC ACTTTCAGGG AAGTGTTGCT GGCAGATGGA
361 TACACTCGCT TCCTGTCCCT GCACAACGGA ACTCCTGTGT CTCTGGCACC TAAACAATCT
421 CCAGACCAGC ACACAGTCCC CTTCACTCGT TTCCTGCCGC TCAGGAATAC ACTGGCAGAG
481 GAGAGCATGT CTGAACCACC ATCAAACCAA CAGAGATATT TTAACATTGA CTCTGATGAT
541 CTTCTTGGAA TGGATTTAAA TGCGATGGTC AGTCCTCAGT TTTCAGGGGA CAAGTGA
```

*Dipodomys ordii* (kangaroo rat) FGF21 gene coding sequence (SEQ ID NO: 181) (Ensembl accession no. ENSDORT00000001234, which is hereby incorporated by reference in its entirety)
```
  1 ATGGACCAGG CAAAGACCAG GGTTGGGGCC CGGGGGCTGG GGGGCTTGT GCTGGCTGTC
 61 ATAATTCTGG GAGCATGCAA GGCACGGCCT ATCCCTGACT CCAGCCCCCT CCTCCAATTT
121 GGGGGTCAAG TTCGGCTTCG GCACCTCTAC ACAGATGACA CTCAGGAGAC GGAAGCCCAT
181 CTGGAGATCA GGGCAGATGG CACGGTAGTG GGGACTGCCC ACCGGAGCCC TGAAAGTCTC
241 TTGGAGCTGA AGCCTTGAA GCCAGGAGTC ATTCAAATCT TAGGGATCAA GACATCCAGA
301 TTCTTATGCC AGAGACCAGA CGGGACACTG TATGGATCAC TCCACTTTGA CCCTGAGGTT
361 TGCAGCTTCC AGGAGCTGCT TCTGAAGGAT GGATACAACA TTTACCGTTC TGAAGCCCTG
421 GGTCTCCCCC TGCGCCTGTC CCCAGATCCA GCACCCTGGG GGCCAGCCCG CTTCCTGCCC
481 CTGCCTGGTG TGCCCCCCGC ACCGCCGGAG CCCCCCGGGA TCCTGGCTCC CGAACCCCCT
541 GATGTCGGCT CCTCCGACCC TCTGAGTATG GTGGACTGT TGCAGGGCCG AAGCCCCAGC
601 TATGCATCCT GA
```

TABLE 4-continued

*Echinops telfairi* (lesser hedgehog tenrec) FGF21 gene coding
sequence (SEQ ID NO: 182) (Ensembl accession no. ENSETET00000010721,
which is hereby incorporated by reference in its entirety)
```
  1 ATGGGTTGCA CCAAATCTGG GTGGAAGTCC CCGGGACTGT GGGTCCCTGT GCTGGCCAGC
 61 CTTCTGCTGG GAGGCTGCGG AGCACACCCC ATCCCTGACT CCAGCCCCCT CCTCCAATTC
121 GGGGGCCAAG TCCGGCAGCG ATACCTCTAT ACGGATGACG CCCAGACCAC CGAGGCCCAC
181 CTGGAGATCA GAGCGGATGG CACAGTGGGG GGCGTCGCCC ACCAGAGCCC AGAGAAGTTC
241 CTGAGTCAAT GGCGTGAAAA GCCCCTGAGA TCACTCCATT TCGACCCAGC CGCCTGCAGC
301 TTCCGGGAGA AGCTTCTAGA AGACGGATAC AACTTGTACC ACTCTGAGAC CCACGGCCTC
361 CCCCTCCGCC TCCCACCCCG TGGGGGCGAC CCCTCTTCTC AGCCTGGGGC CCGCTTCCCA
421 CCGCTGCCGG GCCAGCTCCC ACAACTCCAA GAGACGCCAG GGGTCCTCGC CCCCGAACCC
481 CCCGACGTGG GCTCTTCAGA CCCCCTGAGC ATGGTGGGGC CTTGGCGAGG GCAAAGTCCC
541 AGTTATGCCT CCTGA
```

*Macaca mulatta* (rhesus monkey) FGF21 gene coding sequence (SEQ ID
NO: 183) (Ensembl accession no. ENSMMUT00000038440, which is hereby
incorporated by reference in its entirety)
```
  1 ATGGACTCGG ACGAGACCGG GTTCGAGCAC TCAGGACTGT GGGTTCCTGT GCTGGCTGGT
 61 CTTCTGCTGG GAGCCTGCCA GGCACACCCC ATCCCTGACT CCAGTCCTCT CCTGCAATTC
121 GGGGGCCAAG TCCGGCAACG GTACCTCTAC ACAGATGATG CCCAGCAGAC AGAAGCCCAC
181 CTGGAGATCA GGGAGGATGG GACAGTGGGG GGCGCTGCTC ACCAGAGCCC CGAAAGTGAG
241 TGTGGGCCAG AGCCTGGGTC TGAGGGAGGA GGGGCTGTGG GAGGTGCTGA GGGACCTGGA
301 CTCCTGGGTC TGAGGGAGGC AGGGCTGGGG CCTGGATCCT GGCTCCACTT TGACCCTGAG
361 GCCTGCAGCT TCCGGGAGCT GCTTCTTGAG AACGGATACA ATGTTTACCA GTCCGAGGCC
421 CACGGCCTCC CACTGCACCT GCCGGGAAAC AAGTCCCCAC ACCGGGACCC TGCATCCCAA
481 GGACCAGCTC GCTTCCTGCC ACTACCAGGC CTGCCCCCCG CACCCCCGGA GCCGCCAGGA
541 ATCCTCGCCC CCCAGCCCCC CGATGTGGGC TCCTCGGACC CTCTGAGCAT GGTGGGACCT
601 TCCCAGGCCC GAAGCCCCAG CTATGCTTCC TGA
```

*Microcebus murinus* (mouse lemur) FGF21 gene coding sequence (SEQ ID
NO: 184) (Ensembl accession no. ENSMICT00000013258, which is hereby
incorporated by reference in its entirety)
```
  1 ATGGGCTGGG ACGAGGCCGG CGCCGGGTTC GAGCACCCAG GACTGTGGTT TCCCATGCTG
 61 GGTGTCCTGC TGCTGGGAGC CTGCCAGGCG TACCCCATCC CTGACTCCAG CCCCCTCCTC
121 CAATTTGGCG GCCAAGTCCG GCAGCGGCAC CTCTACACAG ACGATATCCA GGAGACAGAA
181 GCCCACCTGG AGATCAGGGC GGACGGCACA GTGGTGGGGG CCGCCCGACA GAGCCCTGAG
241 TTGGAGCTGA AAGCCTTAAA GCCAGGGGTC ATTCAAATCT TGGGAGTCAA GACCTCCAGG
301 TTCCTGTGCC AGAGGCCAGA CGGGGCCCTG TACGGATCGC TCCACTTTGA CCCCGAGTGC
361 AGCTTCCGGG AGCTGCTTCT TGAGGATGGA TACAACGTCT ACTGTCCCTA CCTCCCGCTG
421 CACCTGTCCC CACGCATCGA ACTGGCCGGA TCACGCTCTG CGCTGCCACT GCCCCCAGCA
481 CCTGAACGCA GGATTTTGGC CCCGGAGCCC CCGGATGGCT CCTCGGACCC TCTGAGCATG
541 GTGGGGCCTT CGCAGGGCCG AAGTCCCAGC TATGCTTCCT GA
```

*Ochotona princeps* (pika) FGF21 gene coding sequence (SEQ ID NO: 185)
(Ensembl accession no. ENSOPRT00000007373, which is hereby
incorporated by reference in its entirety)
```
  1 AAAGACATGG ACGGGCTCCA GCCTCCGGGG CTGCGGGTTC CTGTGCTGGC TGCCCTGCTT
 61 TTGGGAGTTG GCCAGGCACG CCCCATCCCT GATTCTAGCC CTCTCCTCCA ATTCGGGGGC
121 CAGGTCCGGC AGAGGCACCT CTACACGGAT GACGCCCAGG AATCGGAAGT ACACCTGGAG
181 ATCCGGGCAG ACGGCACCGT GGCAGGGACT GCCCGCCGGA GCCCTGAAAG TCTCTTAGAA
241 ATGAAAGCGT TGAAGCCAGG CGTCATTCAG ATCCTGGGGG TCCACACATC CAGGTTCCTG
301 TGCCAGAGAC CAGACGGGAC GCTGTACGGC TCGCTCCACT TCGACCACAA GGCCTGCAGC
361 TTCCGGGAGC AGCTGCTGGA GGATGGGTAC AACGTGTACC ACTCAGAGAC ACACGGCCTC
421 CCGCTGCGCC TGTCTCCAGA CCGAGCCCCC CGGGGCCCAG CCCGCTTCCT GCCACTGCCA
481 GGCCCTCCTC CTGACCTCCT GGTGCCACCC CTGCCACCGG ACGTCCTAGC CCCTGAGCCC
541 CCCGACGTGG ACTCCCCAGA CCCCCTGAGC ATGGTGGGGC CCTTGCAGGG CCAAAGCCCC
601 AGCTACACTT CCTGA
```

*Xiphophorus maculatus* (platyfish) FGF21 gene coding sequence (SEQ ID
NO: 186) (Ensembl accession no. ENSXMAT00000001579, which is hereby
incorporated by reference in its entirety)
```
  1 TGCCCGTTCC CCTTCCTTTT CTTAATCCTC TCTCTTCCCT TTTTCTCTTC CTCGTTTTAC
 61 ATCCCAGAAT CCAACCCAAT CTTTGCCTTC AGGAATCAGC TCAGAGAGGT GCATCTCTAC
121 ACAGAAAATC ACAGACGGGG TTTGTATGTG GAGATACATC TGGATGGGAG AGTGACTGGA
181 AGTGATGCTC AGAGTCCTTA TAGTGTGTTG CAGATAAAGT CTGTTAAACC GGGTCATGTG
241 GTCATAAAGG GACAGACATC GTCCCTGTTC CTCTGACTAG ACGACTCCGG GAATCTAAGA
301 GGACAGACAA CCTATGACGA GGCTGACTGC TCCTTCAGGG AACTGCTGCT GGCCGATGGC
361 TACACCCGTT TCCTGAACTC ACAACATGGC GTTCCTTTAT CACTGGCATC CAGAAACTCT
421 CCAGATCGAC ACTCCGTTCC TTTCACAAGA TTTTTACCTC TCAGGAATAC TTTAACGGTT
481 TCAGAAGAAT CAACAAAAAC TCAGAGGGAC TTCAACCTGG ACTCGGACGA CCTTCTCGGG
541 ATGGGA
```

*Gasterosteus aculeatus* (stickleback) FGF21 gene coding sequence (SEQ
ID NO: 187) (Ensembl accession no. ENSGACT00000010725, which is
hereby incorporated by reference in its entirety)
```
  1 TCTCTCCTCC TCATGGTCCC ACTTCCTTTC TGTTCATCCT TTTATCTCAC TGACTCCAGC
 61 CCACTTCTAC CCTTCAATAA TCAAGTCAAA GAGGTGCACC TCTACACAGC AGAGAATCAC
121 AGAAGAGCGA TGTACCTGCA GATCGCTCTG GACGGGAGCG TGTCGGGAAG CGACGCTCGG
181 TCCACTTACA GTGTGCTGCA GCTGAAATCT ATCCAGCCGG GCCACGTGGT CATCAGAGGG
```

TABLE 4-continued

```
241 AAGGCCTCCT CCATGTTCCT CTGCGTGGAC AGCGGGGGCC GTTTGAGAGG ACAGGGGCCG
301 TACTCAGAGG CCGACTGCAG CTTCAGGGAG CTGCTGCTGG GGGATGGCTA CACCCGGTTC
361 CTGTCCTCGC AGCACGGGTC CCCGCTGTCT CTGGCGTCGA GGCCTTCCCC GGATCCCAAC
421 TCGGTGCCCT TCACTCGATT CCTACCCATC CGGACCGCCC CCGAGGCTGA GAGCGTGATC
481 GAAGAGCCAC CGAGCAATCA GAGATACGTC AACGTGGACT CCGAGGATCT TCTTGGAATG
541 GGCCTGAACA CTGTGGTCAG TCCTCAGTTC TCGGCG
```

*Sarcophilus harrisii* (Tasmanian devil) FGF21 gene coding sequence
(SEQ ID NO: 188) (Ensembl accession no. ENSSHAT00000006017, which
is hereby incorporated by reference in its entirety) (1-209,
excluding 1-2 and 173-209)
```
132             GTGTCTGCC ATGGGCCTGA GGGAGCGAGC TCCCAGGTAC CTGGCCCCGC
181 TGCTGTCCTT GCTCTTGGCC TGCAGGGCCT CGGGTCACCC CCTCCCGGAT TCCAGCCCCA
241 TGCTCCTGTT TGGGGGGCAG GTCCGCCTCC GGCACCTCTA CACGGATGTG GGCCAGGAGG
301 CCGAGGCCCA CGTGGAACTG GCGTCCGACG GCACAGTCCG GGCGGCAGCG CGGAGGAGTC
361 CCAACAGTCT CCTGGAGCTG AAGGCTGTGA AGCCGGGCAT CGTCCGAATC CTGGCCGTCC
421 ACAGCTCTCG GTTTCTGTGT ATGAGGCCCA ACGGGGAGCT GTACGGAGCG ATACACTACG
481 ACCCTTCCGC CTGCAACTTT CGGGAGCGCC TGCTGGGGGA CGGCTACAAC GTGTACGAGT
541 CCGAGGCTCA CGGGAGGACC CTCCGCCTGC CCCCCAAGGC CGCACCGGGA CCCGCCGGAC
601 CTTCTCGCTT CCTGCCGCTC CCCGGC
```

*Macropus eugenii* (wallaby) FGF21 gene coding sequence (SEQ ID NO:
189) (Ensembl accession no. ENSMEUT00000015309, which is hereby
incorporated by reference in its entirety)
```
  1 ACAGAGGAGC CTTCTACTGG GTCCAGGCAC CTGGGACAAT GGGCTCCCGG GCTGCCTGGT
 61 CCTCTGCTGT CCTTGCTCCT GGCCTACAGG GGCTGGGGCT CCCCCATCCC TGATTCCAGC
121 CCCATGCTCC TGTTTGGTGG CCAGGTCCGC CTCCGACACC TGTACACAGA TGATGGCCAG
181 GACACGGAGG CCCATGTGGA GCTGGGGCCA GATGGAGTGG TTCGAGCTGT GGCTGAGAGG
241 AGCCCCAACA GTCTTCTGGA ACTGAAGGCG GTGAAGCCTG GAGTCATCCG AATCCTCGCT
301 GTCCAGAGCT CTCGGTTTCT GTGTATGAGG CCCAACGGGG AACTGTATGG AGCGGTACAC
361 TATGACCCTT CTGCCTGCAA CTTTCGGGAA CATCTGCTGG GGGATGGTTA TAATGTGTAT
421 GAATCAGAGA CTCACAGAAG GACCCTCCGT CTGTCCCCAT CCCTGGGTCA GGCTGGCCCC
481 TCTCGCTTCC TGCCACTTCC AGGCGACTGG CTGCCCGGCC CTGATCCACC TTGGGCACAG
541 GGCCCTGAGC CCCCAGACGT GGGCTCTGCA GACCCCCTGA GCATGGTGGG GGCCGTGCAG
601 GGCCTCAGCC CCAGCTACTC CTCCTGA
```

*Xenopus tropicalis* (Western clawed frog) FGF21 gene coding sequence
(SEQ ID NO: 190) (Ensembl accession no. ENSXETT00000009917, which is
hereby incorporated by reference in its entirety) (1-209, excluding
170-209)
```
  1 AGAGGGGGTA GGACCAAAAA AAAGACGTTA CTCAGGAAAT GGCTTTGCCT TTTAGCCATT
 61 ATGTTGAGTA GGTCAAGGTT TTCTTTAGCA AATCCTATCC AGAATTCGAA CCCAATCTTA
121 TCCAACGACA ACCAAGTACG GACTCAGTAT TTATACACAG ATAACAATAA CATGCACCTG
181 TATCTTCAGA TCACCCACAA TGGAGTAGTA ACTGGTACCG AAGAAAAGAA TGACTATGGT
241 GTGCTGGAAA TAAAGGCAGT AAAAGCTGGG GTTGTAGTTA TAAAAGGAAT TCGAAGCAAT
301 CTCTACCTAT GCATGGATTC TAGACACCAA TTGTATGCGT CGGCATATGA TAAAGATGAC
361 TGCCATTTCC ATGAAAAGAT CACACCAGAT AATTACAACA TGTATAGCTC AGAGAAGCAT
421 TCAGAATACG TGTCCTTAGC TCCATTAAAA GGAAGCCAGA TGGCTCGTTT TCTACCTATA
```

*Danio rerio* (zebrafish) FGF21 gene coding sequence (SEQ ID NO: 191)
(Ensembl accession no. ENSDART00000103511, which is hereby
incorporated by reference in its entirety)
```
 30                         A TGCTTCTTGC CTGCTTTTTT ATATTTTTTG
 61 CTCTTTTTCC TCATCTTCGG TGGTGTATGT ATGTTCCTGC ACAGAACGTG CTTCTGCAGT
121 TTGGCACACA AGTCAGGGAA CGCCTGCTTT ACACAGATGG GTTGTTTCTT GAAATGAATC
181 CAGATGGCTC CGTCAAAGGC TCTCCTGAAA AGAATCTAAA TTGTGTGCTG GAGCTGCGTT
241 CAGTCAAAGC GGGTGAAACC GTCATCCAGA GTGCAGCTAC ATCTCTCTAC CTCTGCGTCG
301 ATGATCAAGA CAAGCTGAAA GGACAGCATC ATTACTCTGC ACTAGACTGC ACCTTTCAGG
361 AATTGCTACT GGATGGATAT TCGTTTTTCC TTTCTCCACA CACTAATCTT CCCGTATCGC
421 TCCTCTCGAA ACGTCAGAAA CACGGCAATC TCTTTCTCG CTTCCTCCCT GTTAGCAGAG
481 CAGAGGACAG CCGGACACAG GAGGTGAAAC AGTATATTCA GGATATAAAC CTGGACTCTG
541 ACGACCCACT AGGAATGGGA CATCGGTCAC ACTTACAGAC CGTCTTCAGT CCCAGTCTGC
572 ATACTAAAAA ATGA
```

*Bos grunniens mutus* (yak) FGF21 gene coding sequence (SEQ ID NO:
192) (generated using SMS Reverse Translate tool on the ExPASy
Bioinformatics Resource website (www.expasy.org))
```
  1 ATGGGCTGGG ATGAAGCGAA ATTTAAACAT CTGGGCCTGT GGGTGCCGGT GCTGGCGGTG
 61 CTGCTGCTGG GCACCTGCCG CGCGCATCCG ATTCCGGATA GCAGCCCGCT GCTGCAGTTT
121 GGCGGCCAGG TGCGCCAGCG CTATCTGTAT ACCGATGATG CGCAGGAAAC CGAAGCGCAT
181 CTGGAAATTC GCGCGGATGG CACCGTGGTG GGCGCGGCGC GCCAGAGCCC GGAAAGCCTG
241 CTGGAACTGA AAGCGCTGAA ACCGGGCGTG ATTCAGATTC TGGGCGTGAA AACCAGCCGC
301 TTTCTGTGCC AGGGCCCGGA TGGCAAACTG TATGCAGCGC TGCATTTTGA TCCGAAAGCG
361 TGCAGCTTTC GCGAACTGCT GCTGGAAGAT GGCTATAACG TGTATCAGAG CGAAACCCTG
421 GGCCTGCCGC TGCGCCTGCC GCCGCAGCGC AGCAGCAACC GCGATCCGGC CGCGCGCGGC
481 CCGGCGCGCT TTCTGCCGCT GCCGGGCCTG CCGGCGGAAC CGCCGGATCC GCCGGGCATT
541 CTGGCGCCGG AACCGCCGGA TGTGGGCAGC AGCGATCCGC TGAGCATGGT GGGCCCGAGC
601 TATGGCCGCA GCCCGAGCTA TACCAGCTAA
```

TABLE 4-continued

*Saimiri boliviensis boliviensis* (Bolivian squirrel monkey) FGF21
gene coding sequence (SEQ ID NO: 193) (GenBank accession no.
XM_003940326, which is hereby incorporated by
reference in its entirety)
```
 163                                            atgggctc ggaggaggtc
 181 GCGTTGGAGC GCCCTGCACT GTGGGTCTCT GTGTTGGCTG GTCTCCTGCT GGGAACCTGC
 241 CAGGCATACC CCATCCCTGA CTCTAGTCCC CTCCTGCAAT TTGGAGGCCA AGTCCGGCAG
 301 CGGTACCTCT ACACAGATGA CGCTCAGCAG ACAGAAGCCC ACCTGGAGAT CAGGGAAGAT
 361 GGCACGGTGG CGGGGGCTGC CACCAGAGC CCCGAAAGTC TCTTGCAGCT GAAAGCCTTA
 421 AAGCCAGGGG TTATTCAAAT CTTGGGAGTC AAGACCTCCA GGTTCCTGTG CCAGAGGCCG
 481 GACGGGGCCC TGTACGGATC GCTCTACTTT GACCCCGAGG CCTGCAGCTT CCGGGAGCTG
 541 CTTCTTGAGG ACGGATACAA TGTGTACCAG TCCGTGCCC ACAGCCTCCC GCTGCACCTG
 601 CCAGGGGGCA GGTCCCCACC CTGGGACCCT GCACCTCGAG GACCAGCTCG CTTCCTGCCG
 661 CTACCAGGCC TGCCCCCCGA ACCCCCCGAG GCGCCAGGAA TCCTGGCCCC CGAGCCCCCC
 721 GATGTGGGCT CCTCAGACCC TCTGAGCATG GTGGGGCCTT CCCAAGGCCA AAGCCCCAGC
 781 TACACTTCCT GA
```

*Callithrix jacchus* (white-tufted-ear marmoset) FGF21 gene coding
sequence (SEQ ID NO: 194) (GenBank accession no. XM_003735621, which
is hereby incorporated by reference in its entirety)
```
   1 ATGGGCTCGG AGGAGGTCGG GTTGGAGCAC CCTGCACTGT GGGTTTCTGT GCTGGCTGGT
  61 CTCCTGCTGG GAACCTGCCA GGCGCACCCC ATCCCTGACT CCAGTCCCCT CCTGCAATTT
 121 GGAGGCCAAG TCCGGCAGCG GTACCTCTAC ACAGATGACG CCCAGCAGAA AGAAGCCCAC
 181 CTGGAGATCN AGGAAGATGG CACAGTGGCC GGGGCTGCCA CCAAAGTCCC GAAAGTGAGT
 241 CTCTTGCAGC TGAAAGCCTT AAAGCCAGGG GTTATTCAAA TCTTGGGAGT CAAGACATCC
 301 AGGTTCCTGT GCCAGAGGCC AGACGGGGCG CTGTATGGAT CGCTCCACTT TGACCCCGAG
 361 GCCTGCAGCT TCCGGGAGCT GCTTCTTGAG GACGGATACA ATGTGTACCA GTCTGTGGCC
 421 CACGGCCTCC CGCTGCACCT CCAGAGAGC AGGTCACCAC CCCGGGACCC TGCACCCCGA
 481 GGACCAGCTC GCTTCCTGCC ACTACCAGGC CTGCCCCCTG AACCCCCAGA GCCGCCAGGA
 541 ATCCTGGCCC CTGAGCCCCC CGACGTGGGC TCCTCAGACC CTCTGAGCAT GGTGGGGCCT
 601 TCCCAAGGCC AAAGCCCCAG CTACGCTTCC TGA
```

*Tupaia chinensis* (Chinese tree shrew) FGF21 gene coding sequence
(SEQ ID NO: 195) (generated using SMS Reverse Translate tool on
the ExPASy Bioinformations Resource website (www.expasy.org))
```
   1 ATGGGCTGGG ATAAAGCGCG CTTTGAACAT CTGGGCGCGT GGGCGCCGGT GCTGGCGGTG
  61 CTGCTGCTGG GCGCGTGCCA GGCGTATCCG ATTCCGGATA GCAGCCCGCT GCTGCAGTTT
 121 GGCGGCCAGG TGCGCCAGCG CTATCTGTAT ACCGATGATA CCCAGGATAC CGAAGCGCAT
 181 CTGGAAATTC GCGCGGATGG CACCGTGGTG GGCGCGGCGC ATCAGAGCCC GGAAAGCCTG
 241 CTGGAACTGA AAGCGCTGAA ACCGGGCGTG ATTCAGATTC TGGGCGTGAA AACCAGCCGC
 301 TTTCTGTGCC AGCGCCCGGA TGGCGCGCTG TATGGCAGCC TGCATTTTGA TCCGGAAGCG
 361 TGCAGCTTTC GCGAACTGCT GCTGGAAGAT GGCTATAACA TTTATCAGAG CGAAGCGCGC
 421 GGCCTGCCGC TGCGCCTGCC GCCGCATGAT AGCCCGCATC GCGATCGCAC CCCGCAGGGC
 481 CCGGCGCGCT TTCTGCCGCT GCCGGGCCTG CCGCTGGTGC CGCCGGAACT GCCGGGCGTG
 541 CTGGCGCTGG AACCGCCGGA TGTGGGCAGC AGCGATCCGC TGAGCATGAT GGGCCCGAGC
 601 CAGGGCCAGA GCCCGAGCTA TGCGAGCTAA
```

*Papio anubis* (olive baboon) FGF21 gene coding sequence (SEQ ID NO:
196) (GenBank accession no. XM_003915851, which is hereby
incorporated by reference in its entirety)
```
   1 ATGGACTCGG ACGAGACCGG GTTCGAGCAC TCAGGACTGT GGGTTCCTGT GCTGGCTGGT
  61 CTTCTGCTGG GAGCCTGCCA GGCACACCCC ATCCCTGACT CCAGTCCTCT CCTGCAATTC
 121 GGGGGCCAAG TCCGGCAACG GTACCTCTAC ACAGATGATG CCCAGCAGAC AGAAGCCCAC
 181 CTGGAGATCA GGGAGGATGG GACAGTGGGG GGCGCTGCTC ACCAGAGCCC CGAAAGTAAG
 241 TGTGGGCCAG AGCCTGGGTC TGAGGGAGGA GGGGCTCTCC ACTTTGACCC TGAGGCCTGC
 301 AGCTTCCGCG AGCTGCTTCT TGAGAACGGA TACAATGTTT ACCAGTCCGA GGCCCACGGC
 361 CTCCCACTGC ACCTGCCGGG AAACAAGTCC CACACCGGG ACCCTGCATC CCGAGGACCA
 421 GCTCGCTTCC TGCCACTACC AGGCCTGCCC CCGCACCCC CAGAGCCACC AGGAATCCTC
 481 GCCCCCCAGC CCCCGATGT GGGCTCCTCG GACCCTCTGA GCATGGTGGG ACCTTCCCAG
 541 GCCCGAAGCC CTAGCTACGC TTCCTGA
```

*Pteropus alecto* (black flying fox) FGF21 gene coding sequence (SEQ
ID NO: 197) (generated using SMS Reverse Translate tool on
the ExPASy Bioinformatics Resource website (www.expasy.org))
```
   1 ATGGGCTGGG GCAAAGCGCG CCTGCAGCAT CCGGGCCTGT GGGGCCCGGT GCTGGCGGTG
  61 CTGCTGGGCG CGTGCCAGGC GCATCCGATT CTGGATAGCA GCCCGCTGTT TCAGTTTGGC
 121 AGCCAGGTGC GCCGCCGCTA TCTGTATACC GATGATGCGC AGGATACCGA AGCGCATCTG
 181 GAAATTCGCG CGGATGGCAC CGTGGCGGGC GCGGCGCGCC GCAGCCCGGA AAGCCTGCTG
 241 GAACTGAAAG CGCTGAAACC GGGCGTGATT CAGGTGCTGG CGTGAAAAC CAGCCGCTTT
 301 CTGTGCCAGC GCCCGGATGG CACCCTGTAT GGCAGCCTGC ATTTTGATCC GGCGGCGTGC
 361 AGCTTTCGCG AACTGCTGCT GAAAGATGGC TATAACGTGT ATCAGAGCGA AGCGCTGGCG
 421 CGCCCGCTGC GCCTGCCGCC GTATAGCAGC CCGAGCAGCG ATCCGGCGCG CCGCGGCCCG
 481 GCGCGCTTTC TGCCGCTGCC GGGCCCGCCG CCGGAACCGC CGCAGCCGCC GGGCCGCCTG
 541 GCGCCGGAAC CGCCGGATGT GGGCAGCAGC GATCCGCTGA GCATGGTGTG GCCGAGCCGC
 601 GGCCGCAGCC GAGCTATAC CAGCTAA
```

TABLE 4-continued

*Heterocephalus glaber* (naked mole-rat) FGF21 gene coding sequence
(SEQ ID NO: 198) (generated using SMS Reverse Translate tool on
the ExPASy Bioinformatics Resource website (www.expasy.org))
```
  1 ATGGATTGGG CGCGCGCGGA AAGCGAACGC CCGGGCCTGT GGGTGCCGGC GGTGCTGGCG
 61 GTGCTGCTGC TGGGCGCGTG CCAGGCGCAT CCGATTCCGG ATAGCAGCCC GCTGCTGCAG
121 TTTGGCGGCA AGGTGCGCCA GCGCCATCTG TATACCGATG ATGCGCAGGA TACCGAAGTG
181 CATCTGGAAA TTCGCGCGGA TGGCAGCGTG GGCGGCGCGG CGCATCGCAG CCCGGAAAGC
241 CTGCTGGAAC TGAAAGCGCT GAAACCGGGC GTGATTCAGA TTCTGGGCGT GCGCACCAGC
301 CGCTTTCTGT GCCAGCGCCC GGATGGCACC CTGTATGGCA GCCTGCATTT TGATCCGGAA
361 GCGTGCAGCT TCGCGAACT GCTGCTGGCG GATGGCTATA ACATTTATCA GAGCGAAGCG
421 TATGGCCTGC CGCTGCGCAT GCTGCCGAGC GATAGCGCGA GCCGCGATCC GGTGCCGCCG
481 GGCCCGGCGC GCTTTCTGCC GCTGCCGGGC CTGCATCCGC CGCCGCTGGA ACCGCCGGGC
541 ATGCTGCCGC CGGAACCGCC GGATGTGGGC AGCAGCGATC CGCTGAGCAT GGTGGGCCCG
601 CTGCAGGGCC GCAGCCCGAG CTATGCGTTT TAA
```

*Cricetulus griseus* (Chinese hamster) FGF21 gene coding sequence (SEQ
ID NO: 199) (GenBank accession no. XM_003508678, which is hereby
incorporated by reference in its entirety)
```
  1 ATGGACTGGA TGAAATCTGG AGTTGGGGTC CCGGGACTGT GGGTCCCTCT GCTGCCTATC
 61 TTCCTGCTGG GGGTCTCCCA GGCACACCCC ATCCCTGACT CCAGCCCCCT CCTCCAGTTT
121 GGGGGTCAAG TCCGGCACAG GCACCTCTAC ACAGATGACA ACCAGGAAAC TGAAGTCCAC
181 CTGGAGATTA GCAGGATGG CACGGTGATA GGGACCACAC ACCGCAGCCC AGAAAGTCTC
241 CTGGAGCTCA AAGCCTTGAA GCCAGAGGTC ATCCAGTGC TGGGTGTCAA GGCCTCCAGG
301 TTTCTTTGCC AACAACCAGA CGGAACCCTG TATGGATCGC CTCACTTTGA TCCTGAGGCC
361 TGCAGTTTCA GGGAGCTCTT GCTTGAGGAT GGATACAATG TGTACCAATC TGAAGTCCAT
421 GGCCTGCCCC TGCGCCTGCC CCAGAGGGAC TCTCCAAACC AGGCCCCAGC ATCCTGGGGA
481 CCTGTGCCCC CCTGCCAGT GCCAGGACTG CTCCACCAGC CCAGGAGCT ACCAGGGTTC
541 CTGGCCCCAG AACCTCCAGA TGTGGGCTCC TCTGACCCAC TGAGCATGGT GGGACCTTTG
601 CAGGGCCGAA GCCCCAGCTA TGCTTCCTGA
```

*Ovis aries* (sheep) FGF21 gene coding sequence (SEQ ID NO: 200)
(GenBank accession no. XM_004015796, which is hereby incorporated by
reference in its entirety)
```
  1 ATGGGCTGGG ACGAGGCCAA GTTCAAGCAC TTGGGACTGT GGGTCCCTGT GCTGGCTGTC
 61 CTCCTGCTAG GAACCTGCCG GGCGCATCCA ATTCCAGACT CCAGCCCCCT CCTCAGTTT
121 GGGGGCCAAG TCCGCCAGCG GTACCTCTAC ACGGATGATG CCCAGGAGAC AGAGGCCCAC
181 CTGGAGATCA GGGCCGATGG CACAGTGGTG GGGCGCGCG GCCAGAGTCC CGAAAGTCTC
241 TTGGAGCTGA AAGCCCTGAA GCCAGGAGTC ATTCAGATCT TTGGAGTTAA ACATCCAGG
301 TTCCTGTGCC AGGGGCCAGA TGGGAAGCTG TATGGATCGC TGCACTTTGA CCCCAAAGCC
361 TGCAGCTTCC GGGAGCTGCT TCTTGAAGAT GGGTACAATG TCTACCAGTC GGAGACCCTG
421 GGCCTTCCAC TCCGCCTGCC GCCGCAGCGC TCATCCAACC GGGACCCGGC CCCGCGGGGA
481 CCTCCGAAGC CCCAGCTACA CTTCTTGAAG ACGTCCGCTG TGCAGTACTG GCCACGTTAT
541 GAGAAGGTCC CAGCTTTTCT GCACCCCTTC CCCGGCTGA
```

*Pan paniscus* (pygmy chimpanzee) FGF21 gene coding sequence (SEQ ID
NO: 201) (GenBank accession no. XM_003814115, which is
hereby incorporated by reference in its entirety) (1-209,
excluding 117-194 and 202-209)
```
573                               ATGGACTC GGACGAGACC GGGTTCGAGC
601 ACTCAGGACT GTGGGTTTCT GTGCTGGCTG GTCTTCTGCT GGGAGCCTGC CAGGCACACC
661 CCATCCCTGA CTCCAGTCCT CTCCTGCAAT TCGGGGGCCA AGTCCGGCAG CGGTACCTCT
721 ACACAGATGA TGCCCAGCAG ACAGAAGCCC ACCTGGAGAT CAGGGAGGAT GGGACGGTGG
781 GGGGCGCTGC TGACCAGAGC CCCGAAAGTC TCCTGCAGCT GAAAGCCTTG AAGCCGGGAG
841 TTATTCAAAT CTTGGGAGTC AAGCACATCCA GGTTCCTGTG CCAGAGGCCA GATGGGGCCC
901 TGTATGGATC GGTGAGTTTC ---------- ---------- ---------- ----------
    ---------- ---------- ---------- ---------- ---------- ----------
921 ---------- ----CAG--- ---------- ---------- ---------- ----------
924 ---------- -------GAC CCTCCT---- --------CA CCACCCACCA ---------T
946 GCTCC----- ----TCCTAT ATGTCGCCCTCACAG------ ---CCTGGG
```

*Macaca fascicularis* (crab-eating macaque) FGF21 gene coding sequence
(SEQ ID NO: 202) (generated using SMS Reverse Translate tool on the
ExPASy Bioinformatics Resource website (www.expasy.org)) (1-209,
excluding 117-209)
```
  1 ATGGATAGCG ATGAAACCGG CTTTGAACAT AGCGGCCTGT GGGTGCCGGT GCTGGCGGGC
 61 CTGCTGCTGG GCGCGTGCCA GGCGCATCCG ATTCCGGATA GCAGCCCGCT GCTGCAGTTT
121 GGCGGCCAGG TGCGCCAGCG CTATCTGTAT ACCGATGATG CGCAGCAGAC CGAAGCGCAT
181 CTGGAAATTC GCGAAGATGG CACCGTGGGC GGCGCGGCGC ATCAGAGCCC GGAAAGCCTG
241 CTGCAGCTGA AAGCGCTGAA ACCGGGCGTG ATTCAGATTC TGGGCGTGAA AACCAGCCGC
301 TTTCTGTGCC AGAAACCGGA TGGCGCGCTG TATGGCAGCG TGAGCTTTTA A
```

*Mesocricetus auratus* (golden hamster) FGF21 gene coding sequence
(SEQ ID NO: 203) (GenBank accession no. EU497769, which is hereby
incorporated by reference in its entirety) (1-209, excluding 1-89
and 194-209)
```
  1 GGTCATCCAA ATCCTGGGTG TCAAGGCTGC TAGGTTTCCT TGCCAGCAAC CAGACGGAAG
 61 CCTGTACGGA TCGCCTCACT TCGATCCCGA GGCCTGCAGT TTCGGGAGC TCCTGCTTGA
121 GGATGGATAC AATGTGTACC AGTCGGAAGC CCACGGCCTG CCCCTGCGCC TGCCCCAGAG
181 GGACGCTCCG AGCCAGCCCC CAGCATCCTG GGACCGGTG CGCTTCCTGC CAGTGCCCGG
```

TABLE 4-continued

```
241 ACTGTTCCAG CCGCCCCACG ACCTCCCAGG GCGCCCGGCC CCAGAGCCTC CGGACGTGGG
301 CTCCTCCGAC CCAC
```

Nile tilapia FGF21 gene coding sequence (SEQ ID NO: 204) (GenBank
accession no. XM_003438468, which is hereby incorporated by
reference in its entirety) (1-209, excluding 1-58)

```
  1 ATGTATTTGC AGATGAACAT GGATGGGAGA GTCACAGGAA GTGATGCTCA GACACCTTAC
 61 AGTTTGATGC AGCTGAAATC AGTTAAACCA GGCCATGTAA TCATTAAAGG ACCATCATCA
121 TCTCTTTTTC TCTGTGTGGA CAGCGAAGGC AATCTGAGAG GGCAGAGTCA CTACTCAGAA
181 ACCAGCTGCA CCTTCAGAGA AATGCTGCTG GCTGACGGAT ACACCCGTTT CATTTCCTCA
241 CAATATGGAT TTCCCATGTC ACTGGCATCA AGACATTCCC CAGATCGACA CGCGCTTCCC
301 TTTACGCGGT TCCTACCACT GAGGAATAAC TTGAAAACGG ATAGCGTATC AGAGCAGCTG
361 CCAAACAATC AGAGACTCTT CAACGTGGAC TCTGATGACC TTCTTGGAAT GGGTCTAAAT
421 TCTATGGGCA GTCCTCAGTT TTCTATGGAC AAATAA
```

In one embodiment, the chimeric protein of the present invention comprises the amino acid sequence of SEQ ID NO: 205, SEQ ID NO: 206, SEQ ID NO: 207, SEQ ID NO: 208, SEQ ID NO: 209, or SEQ ID NO: 210, as shown in Table 5.

In one embodiment of the present invention, the chimeric protein may include one or more subsitutions for or additions of amino acids from another FGF molecule. In one embodiment, the C-terminal portion from FGF19 includes a modification that includes a substitution for or addition of

TABLE 5

Figure 11:
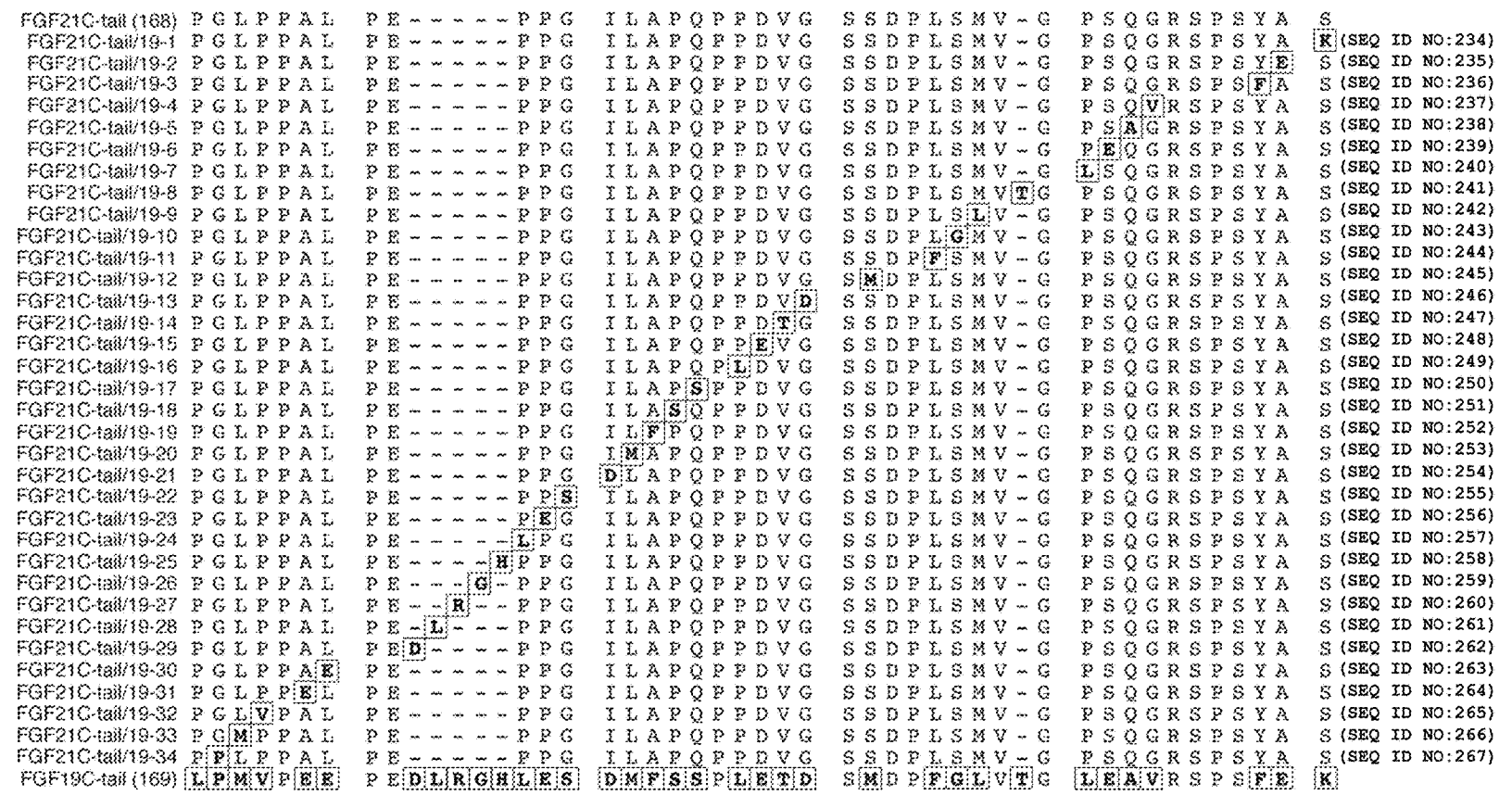
Figure 12:
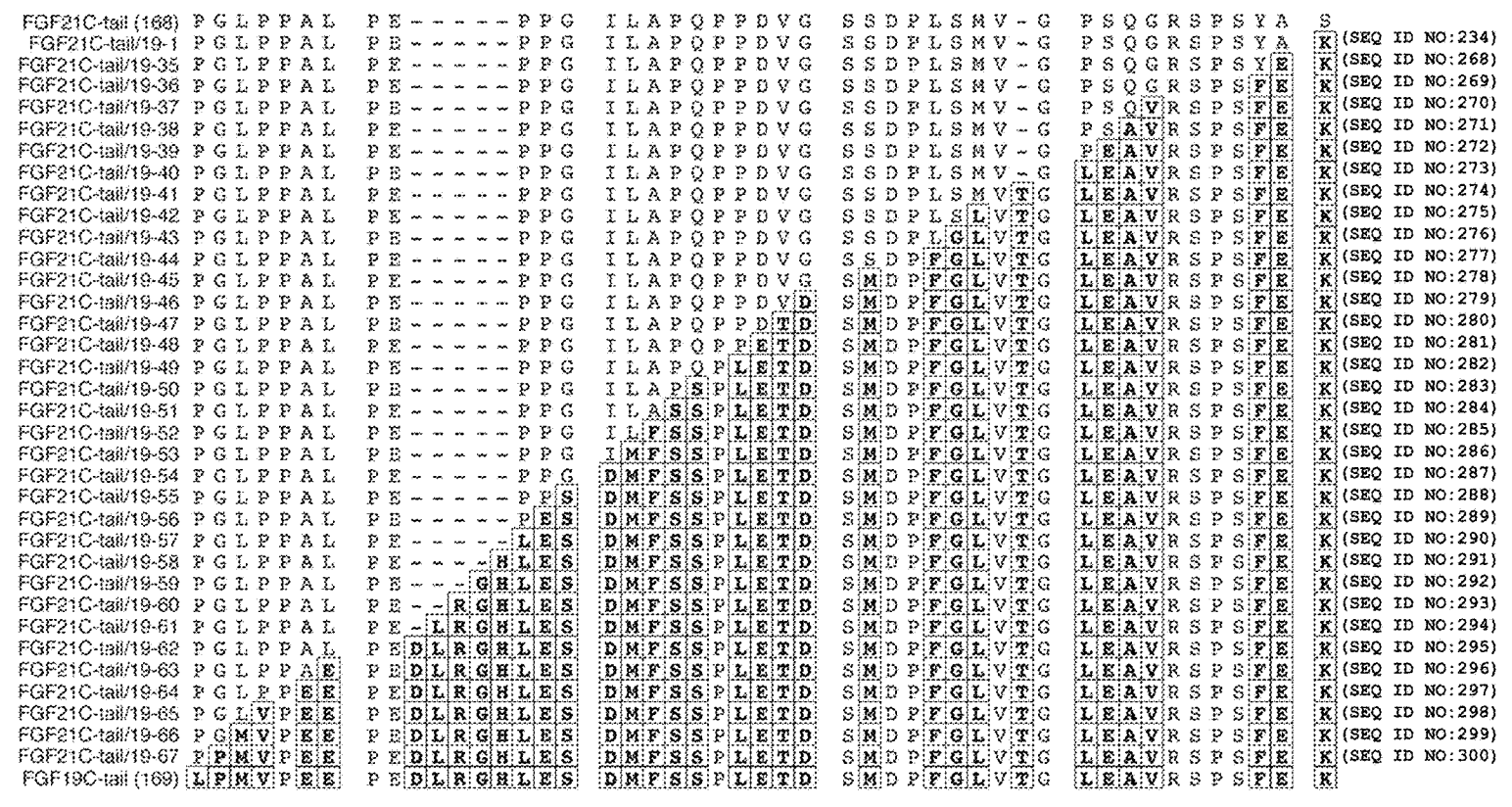
Figure 13:
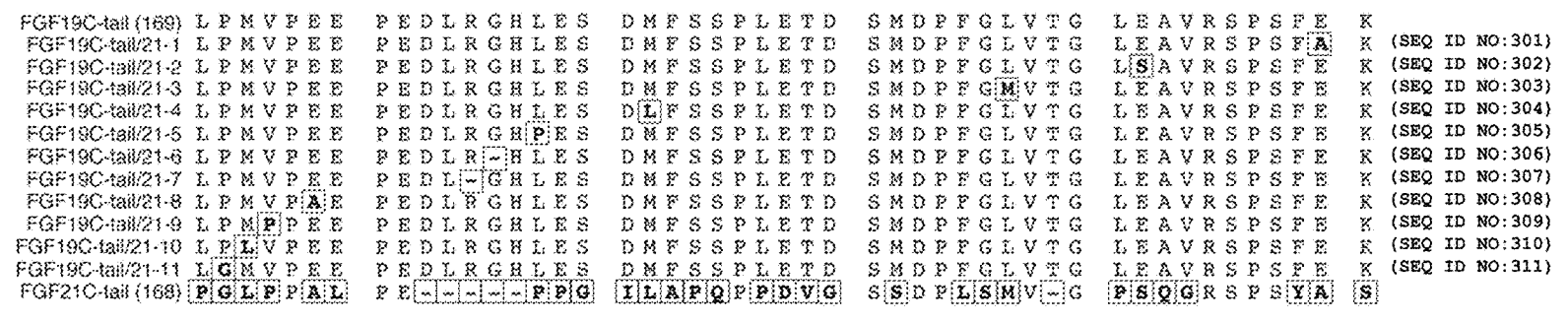

| Description of Chimeric Protein | Sequence |
| --- | --- |
| Amino acid sequence of a FGF21/19 chimera composed of residues H29 to V197 of human FGF21 and residues T204 to K216 of human FGF19 (bold) | SEQ ID NO: 205<br>HP IPDSSPLLQF GGQVRQRYLY TDDAQQTEAH<br>LEIREDGTVG GAADQSPESL LQLKALKPGV<br>IQILGVKTSR FLCQRPDGAL YGSLHFDPEA<br>CSFRELLLED GYNVYQSEAH GLPLHLPGNK<br>SPHRDPAPRG PARFLPLPGL PPALPEPPGI<br>LAPQPPPDVGS SDPLSMVTGL EAVRSPSFEK |
| Amino acid sequence of a FGF21/19 chimera composed of residues H29 to S190 of human FGF21 and residues M197 to K216 of human FGF19 (bold) | SEQ ID NO: 206<br>HP IPDSSPLLQF GGQVRQRYLY TDDAQQTEAH<br>LEIREDGTVG GAADQSPESL LQLKALKPGV<br>IQILGVKTSR FLCQRPDGAL YGSLHFDPEA<br>CSFRELLLED GYNVYQSEAH GLPLHLPGNK<br>SPHRDPAPRG PARFLPLPGL PPALPEPPGI<br>LAPQPPPDVGS MDPFGLVTGL EAVRSPSFEK |
| Amino acid sequence of a FGF21/19 chimera composed of the β-trefoil core domain of human FGF21 (residues H29 to L167) and the C-terminal tail of human FGF19 (residues L169 to K216) (bold) | SEQ ID NO: 207<br>HP IPDSSPLLQF GGQVRQRYLY TDDAQQTEAH<br>LEIREDGTVG GAADQSPESL LQLKALKPGV<br>IQILGVKTSR FLCQRPDGAL YGSLHFDPEA<br>CSFRELLLED GYNVYQSEAH GLPLHLPGNK<br>SPHRDPAPRG PARFLPLLPM VPEEPEDLRG<br>HLESDMFSSP LETDSMDPFG LVTGLEAVRS<br>PSFEK |
| Amino acid sequence of a FGF21/19 chimera composed of residues H29 to V197 of human FGF21 harboring Q104M mutation and residues T204 to K216 of human FGF19 (bold) | SEQ ID NO: 208<br>HP IPDSSPLLQF GGQVRQRYLY TDDAQQTEAH<br>LEIREDGTVG GAADQSPESL LQLKALKPGV<br>IQILGVKTSR FLCMRPDGAL YGSLHFDPEA<br>CSFRELLLED GYNVYQSEAH GLPLHLPGNK<br>SPHRDPAPRG PARFLPLPGL PPALPEPPGI<br>LAPQPPPDVGS SDPLSMVTGL EAVRSPSFEK |
| Amino acid sequence of a FGF21/19 chimera composed of residues H29 to S190 of human FGF21 harboring Q104M mutation and residues M197 to K216 of human FGF19 (bold) | SEQ ID NO: 209<br>HP IPDSSPLLQF GGQVRQRYLY TDDAQQTEAH<br>LEIREDGTVG GAADQSPESL LQLKALKPGV<br>IQILGVKTSR FLCMRPDGAL YGSLHFDPEA<br>CSFRELLLED GYNVYQSEAH GLPLHLPGNK<br>SPHRDPAPRG PARFLPLPGL PPALPEPPGI<br>LAPQPPPDVGS MDPFGLVTGL EAVRSPSFEK |
| Amino acid sequence of a FGF21/19 chimera composed of the β-trefoil core domain of human FGF21 (residues H29 to L167) harboring Q104M mutation and the C-terminal tail of human FGF19 (residues L169 to K216) (bold) | SEQ ID NO: 210<br>HP IPDSSPLLQF GGQVRQRYLY TDDAQQTEAH<br>LEIREDGTVG GAADQSPESL LQLKALKPGV<br>IQILGVKTSR FLCMRPDGAL YGSLHFDPEA<br>CSFRELLLED GYNVYQSEAH GLPLHLPGNK<br>SPHRDPAPRG PARFLPLLPM VPEEPEDLRG<br>HLESDMFSSP LETDSMDPFG LVTGLEAVRS<br>PSFEK | amino acid residues from an FGF21 molecule. Exemplary substitutions and additions of such residues are shown in FIGS. 11, 12, and 13.

In one embodiment, the C-terminal portion from FGF19 comprises a modification that includes a substitution of 5 amino acid residues from an FGF21 molecule. In one embodiment, the modification comprises a substitution for or addition of amino acid residues 168 to 209 of SEQ ID NO: 100. In one embodiment, the modification is a substitution of amino acid residues from SEQ ID NO: 100 for corresponding amino acid residues of SEQ ID NO: 1. As shown in FIGS. 5A, 8B, 11, 12, and 13, the corresponding residues of FGF molecules may be identified by sequence analysis and/or structural analysis. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid residues 168 to 209 of SEQ ID NO: 100 for the corresponding contiguous stretch of amino acid residues of SEQ ID NO: 1. In one embodiment, amino acid residues 169 to 173, 169 to 196, or 169 to 203 of SEQ ID NO: 1 are substituted with the corresponding amino acid residues selected from the sequence comprising amino acid residues 168 to 209 of SEQ ID NO: 100.

In one embodiment, the modification includes a substitution of one or more individual amino acid residues from residues 168 to 209 of SEQ ID NO: 100 for the corresponding amino acid residues of SEQ ID NO: 1. In one embodiment, the C-terminal portion includes substitutions of one or more of amino acid residues 169, 170, 171, 172, 174, 175, 183, 184, 185, 186, 187, 188, 189, 190, 192, 193, 194, 195, 197, 200, 201, 202, 206, 207, 208, 209, 214, 215, or 216 of SEQ ID NO: 1 for the corresponding amino acid residues of SEQ ID NO: 100.

In one embodiment of the present invention, the C-terminal portion from FGF19 includes a modification that includes a deletion of amino acid residues that are absent in the corresponding C-terminal portion from FGF21. As shown in FIGS. 5A, 8B, 11, 12, and 13, FGF19 residues that are absent in the corresponding C-terminal portion of FGF21 may be identified by sequence analysis and/or structural analysis. In one embodiment, the modification comprises a deletion of amino acid residues selected from residues 204 to 216, 197 to 216, 174 to 216, or 169 to 216 of SEQ ID NO: 1. In one embodiment, the modification comprises a deletion corresponding to amino acid residue 204 of SEQ ID NO: 1. In one embodiment, the modification includes a deletion of amino acid residues 178, 179, 180, 181, and/or 182 of SEQ ID NO: 1 individually or in combination.

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 211, SEQ ID NO: 212, SEQ ID NO: 213, SEQ ID NO: 214, SEQ ID NO: 215, or SEQ ID NO: 216 (as shown in Table 6). Another aspect of the present invention relates to a nucleic acid construct comprising a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

TABLE 6

| Description of Chimeric Protein | Sequence |
|---|---|
| Nucleotide sequence of a FGF21/19 chimera composed of residues H29 to V197 of human FGF21 and residues T204 to K216 of human FGF19 (bold) | SEQ ID NO: 211<br>cacccc atccctgact ccagtcctct<br>cctgcaattc gggggccaag tccggcagcg<br>gtacctctac acagatgatg cccagcagac<br>agaagcccac ctggagatca gggaggatgg<br>gacggtgggg ggcgctgctg accagagccc<br>cgaaagtctc ctgcagctga aagccttgaa<br>gccgggagtt attcaaatct tgggagtcaa<br>gacatccagg ttcctgtgcc agcggccaga<br>tggggccctg tatggatcgc tccactttga<br>ccctgaggcc tgcagcttcc gggagctgct<br>tcttgaggac ggatacaatg tttaccagtc<br>cgaagcccac ggcctcccgc tgcacctgcc<br>agggaacaag tccccacacc gggaccctgc<br>accccgagga ccagctcgct tcctgccact<br>accaggcctg ccccccgcac tcccggagcc<br>acccggaatc ctggcccccc agcccccga<br>tgtgggctcc tcggaccctc tgagcatggt<br>gggactggag gccgtgagga gtcccagctt tgagaagtaa |
| Nucleotide sequence of a FGF21/19 chimera composed of residues H29 to S190 of human FGF21 and residues M197 to K216 of human FGF19 (bold) | SEQ ID NO: 212<br>cacccc atccctgact ccagtcctct<br>cctgcaattc gggggccaag tccggcagcg<br>gtacctctac acagatgatg cccagcagac<br>agaagcccac ctggagatca gggaggatgg<br>gacggtgggg ggcgctgctg accagagccc<br>cgaaagtctc ctgcagctga aagccttgaa<br>gccgggagtt attcaaatct tgggagtcaa<br>gacatccagg ttcctgtgcc agcggccaga<br>tggggccctg tatggatcgc tccactttga |

TABLE 6-continued

| Description of Chimeric Protein | Sequence |
|---|---|
| | ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggcccccc agcccccccga tgtgggctcc atggacccat ttgggcttgt caccggactg gaggccgtga ggagtcccag ctttgagaag taa |
| Nucleotide sequence of a FGF21/19 chimera composed of the β-trefoil core domain of human FGF21 (residues H29 to L167) and the C-terminal tail of human FGF19 (residues L169 to K216) (bold) | SEQ ID NO: 213<br>cacccc atccctgact ccagtcctct cctgcaattc gggggccaag tccggcagcg gtacctctac acagatgatg cccagcagac agaagcccac ctggagatca gggaggatgg gacggtgggg ggcgctgctg accagagccc cgaaagtctc ctgcagctga aagccttgaa gccgggagtt attcaaatct tgggagtcaa gacatccagg ttcctgtgcc agcggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact actgcccatg gtcccagagg agcctgagga cctcaggggc cacttggaat ctgacatgtt ctcttcgccc ctggagaccg acagcatgga cccatttggg cttgtcaccg gactggaggc cgtgaggagt cccagctttg agaagtaa |
| Nucleotide sequence of a FGF21/19 chimera composed of residues H29 to V197 of human FGF21 harboring Q104M mutation and residues T204 to K216 of human FGF19 (bold) | SEQ ID NO: 214<br>cacccc atccctgact ccagtcctct cctgcaattc gggggccaag tccggcagcg gtacctctac acagatgatg cccagcagac agaagcccac ctggagatca gggaggatgg gacggtgggg ggcgctgctg accagagccc cgaaagtctc ctgcagctga aagccttgaa gccgggagtt attcaaatct tgggagtcaa gacatccagg ttcctgtgcc aatggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggcccccc agcccccccga tgtgggctcc tcggaccctc tgagcatggt gggactggag gccgtgagga gtcccagctt tgagaagtaa |
| Nucleotide sequence of a FGF21/19 chimera composed of residues H29 to S190 of human FGF21 harboring Q104M mutation and residues M197 to K216 of human FGF19 (bold) | SEQ ID NO: 215<br>cacccc atccctgact ccagtcctct cctgcaattc gggggccaag tccggcagcg gtacctctac acagatgatg cccagcagac agaagcccac ctggagatca gggaggatgg gacggtgggg ggcgctgctg accagagccc cgaaagtctc ctgcagctga aagccttgaa gccgggagtt attcaaatct tgggagtcaa gacatccagg ttcctgtgcc aatggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggcccccc agcccccccga tgtgggctcc atggacccat ttgggcttgt caccggactg gaggccgtga ggagtcccag ctttgagaag taa |
| Nucleotide sequence of a FGF21/19 chimera composed of the β-trefoil core domain of human FGF21 (residues H29 to | SEQ ID NO: 216<br>cacccc atccctgact ccagtcctct cctgcaattc gggggccaag tccggcagcg gtacctctac acagatgatg cccagcagac |

TABLE 6-continued

| Description of Chimeric Protein | Sequence | | |
|---|---|---|---|
| L167) harboring Q104M mutation and the C-terminal tail of human FGF19 (residues L169 to K216) (bold) | agaagcccac gacggtgggg cgaaagtctc gccgggagtt gacatccagg tggggccctg ccctgaggcc tcttgaggac cgaagcccac agggaacaag accccgagga actgcccatg cctcaggggc ctcttcgccc cccatttggg cgtgaggagt | ctggagatca ggcgctgctg ctgcagctga attcaaatct ttcctgtgcc tatggatcgc tgcagcttcc ggatacaatg ggcctcccgc tccccacacc ccagctcgct gtcccagagg cacttggaat ctggagaccg cttgtcaccg cccagctttg | gggaggatgg accagagccc aagccttgaa tggggagtcaa aatggccaga tccactttga gggagctgct tttaccagtc tgcacctgcc gggaccctgc tcctgccact agcctgagga ctgacatgtt acagcatgga gactggaggc agaagtaa |

Also encompassed are vectors or expression vectors comprising such nucleic acid molecules and host cells comprising such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," Methods in Enzymology 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is an anti-inflammatory agent, an antihypertensive agent, an anti-diabetic agent, and/or cholesterol-lowering drug such as a drug of the "statin" class. In one embodiment, the second agent is insulin. In one embodiment, the insulin is rapid acting, short acting, regular acting, intermediate acting, or long acting insulin. In one embodiment, the insulin is and/or comprises Humalog, Lispro, Novolog, Apidra, Humulin, Aspart, regular insulin, NPH, Lente, Ultralente, Lantus, Glargine, Levemir, or Detemir. In one embodiment, the second agent is a statin. In one embodiment, the statin is and/or comprises Atorvastatin (e.g., Lipitor or Torvast), Cerivastatin (e.g., Lipobay or Baycol), Fluvastatin (e.g., Lescol or Lescol), Lovastatin (e.g., Mevacor, Altocor, or Altoprev) Mevastatin, Pitavastatin (e.g., Livalo or Pitava), Pravastatin (e.g., Pravachol, Selektine, or Lipostat) Rosuvastatin (e.g., Crestor), Simvastatin (e.g., Zocor or Lipex), Vytorin, Advicor, Besylate Caduet or Simcor.

In one embodiment of the present invention, the pharmaceutical composition according to the present invention is administered with an anti-inflammatory agent, an antifibrotic agent, an antihypertensive agent, an antidiabetic agent, a triglyceride-lowering agent, and/or a cholesterol-lowering agent.

Another aspect of the present invention relates to a method of treating a subject suffering from diabetes, obesity, or metabolic syndrome. This method includes selecting a subject suffering from diabetes, obesity, or metabolic syndrome and administering to this selected subject a therapeutically effective amount of a chimeric protein according to the present invention.

In one embodiment, the selected subject is a mammal. In one particular embodiment, the selected subject is a human. In another embodiment, the selected subject is a rodent.

In one embodiment the selected subject has diabetes. As used herein, diabetes includes, but is not limited to, type I diabetes, type II diabetes, gestational diabetes, and drug-induced diabetes. In one embodiment, the subject has obesity. In one embodiment, the subject has metabolic syndrome.

The pharmaceutical compositions comprising a chimeric protein of the present invention provided herein can be used to treat a number of conditions. Preferably, the condition is one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, an improvement, or even a preservation, of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of type 1 diabetes, type 2 diabetes, gestational diabetes, drug-induced diabetes, high blood glucose, metabolic syndrome, lipodystrophy syndrome, dyslipidemia, insulin resistance, leptin resistance, atherosclerosis, vascular disease, inflammatory disease, fibrotic disease, hypercholesterolemia, hypertriglyceridemia, non-alcoholic fatty liver disease, overweight, and obesity.

The pharmaceutical composition according to the present invention can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions comprising the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 µg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. In one embodiment, the dosage is the same as that of a native FGF21 therapeutic. In one embodiment, the dosage is less than that of a native FGF21 therapeutic, but having the same effect as a higher dosage of a native FGF21 therapeutic. Guidance as to particular dosages and methods of delivery of proteins is provided in the literature; see, for example, U.S. Pat. Nos. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated.

Microencapsulation of recombinant proteins for sustained release has been successfully performed with human growth hormone (rhGH), interferon- (rhIFN-), interleukin-2, and MN rgp120. Johnson et al., "Preparation and Characterization of Poly(D,L-lactide-co-glycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The compositions according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

Another aspect of the present invention relates to a method of treating a subject in need of increased FGF21-βKlotho-FGF receptor ("FGFR") complex formation. This method includes selecting a subject in need of increased FGF21-βKlotho-FGFR complex formation and administering to the selected subject a chimeric FGF21 protein, where the chimeric FGF21 protein includes an FGF21 core domain and a C-terminal portion of FGF19, thereby treating a subject in need of increased FGF21-βKlotho-FGFR complex formation.

Suitable chimeric FGF21 proteins include chimeric proteins according to the present invention, as described above and throughout the present application.

FGF21 depends on the co-receptor βKlotho to activate its cognate FGFR (FGFR1c) in its target tissues including white adipose tissue (Ogawa et al., "BetaKlotho is Required for Metabolic Activity of Fibroblast Growth Factor 21," *Proc. Natl. Acad. Sci. USA* 104(18):7432-7437 (2007), which is hereby incorporated by reference in its entirety). In the course of deciphering the molecular details of how FGF21 forms a signaling complex on the cell surface with FGFR1c and βKlotho, two discoveries were made that provided the basis for the rational design of an FGF21 agonist. It was found that βKlotho promotes binding of FGF21 to its cognate FGFR by engaging ligand and receptor simultaneously through two distinct binding sites. βKlotho plays the same role in promoting binding of FGF19, an endocrine regulator of bile acid homeostasis, to its cognate FGFR. The binding site for βKlotho was mapped on FGF21 and FGF19 to the C-terminal region of each ligand that follows the n-trefoil core domain. In the course of these studies, it was found that the C-terminal tail peptides of FGF21 and FGF19 share a common binding site on βKlotho, and that the C-terminal tail of FGF19 binds tighter than the C-terminal tail of FGF21 to this site. Based on these findings, chimeric FGF21 proteins were made in which C-terminal sequences in FGF21 were replaced with the corresponding sequences of FGF19 in order to confer greater binding affinity to βKlotho, and enhance agonistic properties.

In one embodiment according to the present invention, βKlotho is mammalian βKlotho. In one embodiment, βKlotho is human or mouse βKlotho. In one particular embodiment of the present invention, βKlotho is human or mouse βKlotho comprising the amino acid sequence of SEQ ID NO: 217 (i.e., GenBank Accession No. NP_783864, which is hereby incorporated by reference in its entirety) or SEQ ID NO: 218 (i.e., GenBank Accession No. NP_112457, which is hereby incorporated by reference in its entirety), respectively, as follows:

```
SEQ ID NO: 217:
   1 MKPGCAAGSP GNEWIFFSTD EITTRYRNTM SNGGLQRSVI LSALILLRAV TGFSGDGRAI

61 WSKNPNFTPV NESQLFLYDT FPKNFFWGIG TGALQVEGSW KKDGKGPSIW DHFIHTHLKN

121 VSSTNGSSDS YIFLEKDLSA LDFIGVSFYQ FSISWPRLFP DGIVTVANAK GLQYYSTLLD

181 ALVLRNIEPI VTLYHWDLPL ALQEKYGGWK NDTIIDIFND YATYCFQMFG DRVKYWITIH

241 NPYLVAWHGY GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS VLPIFSEAEK

361 HEMRGTADFF AFSFGPNNFK PLNTMAKMGQ NVSLNLREAL NWIKLEYNNP RLIAENGWF

421 TDSRVKTEDT TAIYMMKNFL SQVLQAIRLD EIRVFGYTAW SLLDGFEWQD AYTIRRGLFY

481 VDFNSKQKER KPKSSAHYYK QIIRENGFSL KESTPDVQGQ FPCDFSWGVT ESVLKPESVA

541 SSPQFSDPHL YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG LPEPLLHADG

661 WLNPSTAEAF QAYAGLCFQE LGDLVKLWIT INEPNRLSDI YNRSGNDTYG AAHNLLVAHA

721 LAWRLYDRQF RPSQRGAVSL SLHADWAEPA NPYADSHWRA AERFLQFEIA WFAEPLFKTG

781 DYPAAMREYI ASKHRRGLSS SALPRLTEAE RRLLKGTVDF CALNHFTTRF VM HEQLAGSR

841 YDSDRDIQFL QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK AKSSIQFYNK

961 VISSRGPPFE NSSSRCSQTQ ENTECTVCLF LVQKKPLIFL GCCFFSTLVL LLSIAIFQRQ

1021 KRRKFWKAKN LQHIPLKKGK RVVS

SEQ ID NO: 218:
   1 MKTGCAAGSP GNEWIFFSSD ERNTRSRKTM SNRALQRSAV LSAFVLLRAV TGFSGDGKAI

61 WDKKQYVSPV NPSQLFLYDT FPKNFSWGVG TGAFQVEGSW KTDGRGPSIW DRYVYSHLRG

121 VNGTDRSTDS YIFLEKDLLA LDFLGVSFYQ FSISWPRLFP NGTVAAVNAQ GLRYYRALLD

181 SLVLRNIEPI VTLYHWDLPL TLQEEYGGWK NATMIDLFND YATYCFQTFG DRVKYWITIH

241 NPYLVAWHGF GTGMHAPGEK GNLTAVYTVG HNLIKAHSKV WHNYDKNFRP HQKGWLSITL

301 GSHWIEPNRT DNMEDVINCQ HSMSSVLGWF ANPIHGDGDY PEFMKTGAMI PEFSEAEKEE

361 VRGTADFFAF SFGPNNFRPS NTVVKMGQNV SLNLRQVLNW IKLEYDDPQI LISENGWF TD

421 SYIKTEDTTA IYMMKNFLNQ VLQAIKFDEI RVFGYTAWTL LDGFEWQDAY TTRRGLFYVD

481 FNSEQKERKP KSSAHYYKQI IQDNGFPLKE STPDMKGRFP CDFSWGVTES VLKPEFTVSS

541 PQFTDPHLYV WNVTGNRLLY RVEGVRLKTR PSQCTDYVSI KKRVEMLAKM KVTHYQFALD

601 WTSILPTGNL SKVNRQVLRY YRCVVSEGLK LGVFPMVTLY HPTHSHLGLP LPLLSSGGWL

661 NMNTAKAFQD YAELCFRELG DLVKLWITIN EPNRLSDMYN RTSNDTYRAA HNLMIAHAQV

721 WHLYDRQYRP VQHGAVSLSL HCDWAEPANP FVDSHWKAAE RFLQFEIAWF ADPLFKTGDY

781 PSVMKEYIAS KNQRGLSSSV LPRFTAKESR LVKGTVDFYA LNHFTTRFVI HKQLNTNRSV

841 ADRDVQFLQD ITRLSSPSRL AVTPWGVRKL LAWIRRNYRD RDIYITANGI DDLALEDDQI
```

-continued

```
 901 RKYYLEKYVQ EALKAYLIDK VKIKGYYAFK LTEEKSKPRF GFFTSDFRAK SSVQFYSKLI

961 SSSGLPAENR SPACGQPAED TDCTICSFLV EKKPLIFFGC CFISTLAVLL SITVFHHQKR

1021 RKFQKARNLQ NIPLKKGHSR VFS
```

In one particular embodiment of the present invention, βKlotho is human or mouse βKlotho encoded by a nucleotide sequence comprising the nucleotide sequences of SEQ ID NO: 219 (GenBank Accession No. NM_175737, which is hereby incorporated by reference in its entirety) and SEQ ID NO: 220 (GenBank Accession No. NM_031180, which is hereby incorporated by reference in its entirety), as follows:

```
SEQ ID NO: 219 (Human βKlotho gene coding sequence):
  98           atg aagccaggct gtgcggcagg atctccaggg aatgaatgga ttttcttcag 151 cactgatgaa ataaccacac gctataggaa tacaatgtcc aacggggat tgcaaagatc 211 tgtcatcctg tcagcactta ttctgctacg agctgttact ggattctctg gagatggaag 271 agctatatgg tctaaaaatc ctaattttac tccggtaaat gaaagtcagc tgtttctcta 331 tgacactttc cctaaaaact ttttctgggg tattgggact ggagcattgc aagtggaagg 391 gagttggaag aaggatggaa aaggaccttc tatatgggat catttcatcc acacacacct 451 taaaaatgtc agcagcacga atggttccga tgacagttat attttctgg aaaaagactt 511 atcagccctg gattttatag gagtttcttt ttatcaattt tcaattcct ggccaaggct 571 tttccccgat ggaatagtaa cagttgccaa cgcaaaaggt ctgcagtact acagtactct 631 tctggacgct ctagtgctta gaaacattga acctatagtt actttatacc actgggattt 691 gcctttggca ctacaagaaa atatgggg gtggaaaaat gataccataa tagatatctt 751 caatgactat gccacatact gtttccagat gtttggggac cgtgtcaaat attggattac 811 aattcacaac ccatatctag tggcttggca tgggtatggg acaggtatgc atgcccctgg 871 agagaaggga aatttagcag ctgtctacac tgtgggacac aacttgatca aggctcactc 931 gaaagtttgg cataactaca acacacattt ccgcccacat cagaagggtt ggttatcgat 991 cacgttggga tctcattgga tcgagccaaa ccggtcggaa aacacgatgg atatattcaa 1051 atgtcaacaa tccatggttt ctgtgcttgg atggtttgcc aaccctatcc atggggatgg 1111 cgactatcca gaggggatga gaaagaagtt gttctccgtt ctacccatt tctctgaagc 1171 agagaagcat gagatgagag gcacagctga ttttctttgcc ttttcttttg gacccaacaa 1231 cttcaagccc ctaaacacca tggctaaaat gggacaaaat gtttcactta atttaagaga 1291 agcgctgaac tggattaaac tggaatacaa caaccctcga atcttgattg ctgagaatgg 1351 ctggttcaca gacagtcgtg tgaaaacaga agacaccacg gccatctaca tgatgaagaa 1411 tttcctcagc caggtgcttc aagcaataag gttagatgaa atacgagtgt tggttatac 1471 tgcctggtct ctcctggatg gctttgaatg gcaggatgct tacaccatcc gccgaggatt 1531 attttatgtg gattttaaca gtaaacagaa agagcggaaa cctaagtctt cagcacacta 1591 ctacaaacag atcatacgag aaaatggttt tctttaaaa gagtccacgc cagatgtgca 1651 gggccagttt ccctgtgact tctcctgggg tgtcactgaa tctgttctta agcccgagtc 1711 tgtggcttcg tccccacagt tcagcgatcc tcatctgtac gtgtggaacg ccactggcaa 1771 cagactgttg caccgagtgg aagggtgag gctgaaaaca cgacccgctc aatgcacaga 1831 ttttgtaaac atcaaaaaac aacttgagat gttggcaaga atgaaagtca cccactaccg 1891 gtttgctctg gattgggcct cggtccttcc cactggcaac ctgtccgcgg tgaaccgaca 1951 ggccctgagg tactacaggt gcgtggtcag tgaggggctg aagcttggca tctccgcgat 2011 ggtcacctg tattatccga cccacgccca cctaggcctc cccgagcctc tgttgcatgc
```

-continued

```
2071 cgacgggtgg ctgaacccat cgacggccga ggccttccag gcctacgctg ggctgtgctt 2131 ccaggagctg ggggacctgg tgaagctctg gatcaccatc aacgagccta accggctaag 2191 tgacatctac aaccgctctg gcaacgacac ctacggggcg gcgcacaacc tgctggtggc 2251 ccacgccctg gcctggcgcc tctacgaccg gcagttcagg ccctcacagc gcggggccgt 2311 gtcgctgtcg ctgcacgcgg actgggcgga acccgccaac ccctatgctg actcgcactg 2371 gagggcggcc gagcgcttcc tgcagttcga gatcgcctgg ttcgccgagc cgctcttcaa 2431 gaccggggac taccccgcgg ccatgaggga atacattgcc tccaagcacc gacggggggct 2491 ttccagctcg gccctgccgc gcctcaccga ggccgaaagg aggctgctca agggcacggt 2551 cgacttctgc gcgctcaacc acttcaccac taggttcgtg atgcacgagc agctggccgg 2611 cagccgctac gactcggaca gggacatcca gtttctgcag gacatcaccc gcctgagctc 2671 ccccacgcgc ctggctgtga ttccctgggg ggtgcgcaag ctgctgcggt gggtccggag 2731 gaactacggc gacatggaca tttacatcac cgccagtggc atcgacgacc aggctctgga 2791 ggatgaccgg ctccggaagt actacctagg gaagtacctt caggaggtgc tgaaagcata 2851 cctgattgat aaagtcagaa tcaaaggcta ttatgcattc aaactggctg aagagaaatc 2911 taaacccaga tttggattct tcacatctga ttttaaagct aaatcctcaa tacaatttta 2971 caacaaagtg atcagcagca ggggcttccc ttttgagaac agtagttcta gatgcagtca 3031 gacccaagaa aatacagagt gcactgtctg cttattcctt gtgcagaaga aaccactgat 3091 attcctgggt tgttgcttct tctccaccct ggttctactc ttatcaattg ccattttca 3151 aaggcagaag agaagaaagt tttggaaagc aaaaaactta caacacatac cattaaagaa 3211 aggcaagaga gttgttagct aa
```

SEQ ID NO: 220 (House mouse βKlotho gene coding sequence):

```
  2 atgaagaca ggctgtgcag cagggtctcc ggggaatgaa tggattttct tcagctctga 61 tgaaagaaac acacgctcta ggaaaacaat gtccaacagg gcactgcaaa gatctgccgt 121 gctgtctgcg tttgttctgc tgcgagctgt taccggcttc tccggagacg ggaaagcaat 181 atgggataaa aaacagtacg tgagtccggt aaacccaagt cagctgttcc tctatgacac 241 tttccctaaa aacttttcct ggggcgttgg gaccggagca tttcaagtgg aagggagttg 301 gaagacagat ggaagaggac cctcgatctg ggatcggtac gtctactcac acctgagagg 361 tgtcaacggc acagacagat ccactgacag ttacatcttt ctggaaaaag acttgttggc 421 tctggatttt ttaggagttt ctttttatca gttctcaatc tcctggccac ggttgtttcc 481 caatggaaca gtagcagcag tgaatgcgca aggtctccgg tactaccgtg cacttctgga 541 ctcgctggta cttaggaata tcgagcccat tgttaccttg taccattggg atttgcctct 601 gacgctccag gaagaatatg ggggctgaaa aatgcaact atgatagatc tcttcaacga 661 ctatgccaca tactgcttcc agacctttgg agaccgtgtc aaatattgga ttacaattca 721 caacccttac cttgttgctt ggcatgggtt tggcacaggt atgcatgcac caggagagaa 781 gggaaattta acagctgtct acactgtggg acacaacctg atcaaggcac attcgaaagt 841 gtggcataac tacgacaaaa acttccgccc tcatcagaag ggttggctct ccatcacctt 901 ggggtcccat tggatagagc caaacagaac agacaacatg gaggacgtga tcaactgcca 961 gcactccatg tcctctgtgc ttggatggtt cgccaaccac atccacgggg acggcgacta 1021 ccctgagttc atgaagacgg cgccatgat ccccgagttc tctgaggcag agaaggagga 1081 ggtgaggggc acggctgatt tctttgcctt ttccttcggg cccaacaact tcaggccctc 1141 aaacaccgtg gtgaaaatgg gacaaaatgt atcactcaac ttaaggcagg tgctgaactg
```

```
-continued
1201 gattaaactg gaatacgatg accctcaaat cttgatttcg gagaacggct ggttcacaga 1261 tagctatata aagacagagg acaccacggc catctacatg atgaagaatt tcctaaacca 1321 ggttcttcaa gcaataaaat ttgatgaaat ccgcgtgttt ggttatacgg cctggactct 1381 cctggatggc tttgagtggc aggatgccta tacgacccga cgagggctgt tttatgtgga 1441 ctttaacagt gagcagaaag agaggaaacc caagtcctcg gctcattact acaagcagat 1501 catacaagac aacggcttcc ctttgaaaga gtccacgcca gacatgaagg gtcggttccc 1561 ctgtgatttc tcttggggag tcactgagtc tgttcttaag cccgagttta cggtctcctc 1621 cccgcagttt accgatcctc acctgtatgt gtggaatgtc actggcaaca gattgctcta 1681 ccgagtggaa ggggtaaggc tgaaaacaag accatcccag tgcacagatt atgtgagcat 1741 caaaaaacga gttgaaatgt tggcaaaaat gaaagtcacc cactaccagt ttgctctgga 1801 ctggacctct atccttccca ctggcaatct gtccaaagtt aacagacaag tgttaaggta 1861 ctataggtgt gtggtgagcg aaggactgaa gctgggcgtc ttccccatgg tgacgttgta 1921 ccacccaacc cactcccatc tcggcctccc cctgccactt ctgagcagtg gggggtggct 1981 aaacatgaac acagccaagg ccttccagga ctacgctgag ctgtgcttcc gggagttggg 2041 ggacttggtg aagctctgga tcaccatcaa tgagcctaac aggctgagtg acatgtacaa 2101 ccgcacgagt aatgacacct accgtgcagc ccacaacctg atgatcgccc atgcccaggt 2161 ctggcacctc tatgataggc agtataggcc ggtccagcat ggggctgtgt cgctgtcctt 2221 acattgcgac tgggcagaac ctgccaaccc ctttgtggat tcacactgga aggcagccga 2281 gcgcttcctc cagtttgaga tcgcctggtt tgcagatccg ctcttcaaga ctggcgacta 2341 tccatcggtt atgaaggaat acatcgcctc caagaaccag cgagggctgt ctagctcagt 2401 cctgccgcgc ttcaccgcga aggagagcag gctggtgaag ggtaccgtcg acttctacgc 2461 actgaaccac ttcactacga ggttcgtgat acacaagcag ctgaacacca accgctcagt 2521 tgcagacagg gacgtccagt tcctgcagga catcacccgc taagctcgc ccagccgcct 2581 ggctgtaaca ccctggggag tgcgcaagct ccttgcgtgg atccggagga actacagaga 2641 cagggatatc tacatcacag ccaatggcat cgatgacctg gctctagagg atgatcagat 2701 ccgaaagtac tacttggaga agtatgtcca ggaggctctg aaagcatatc tcattgacaa 2761 ggtcaaaatc aaaggctact atgcattcaa actgactgaa gagaaatcta agcctagatt 2821 tggatttttc acctctgact tcagagctaa gtcctctgtc cagttttaca gcaagctgat 2881 cagcagcagt ggcctcccccg ctgagaacag aagtcctgcg tgtggtcagc ctgcggaaga 2941 cacagactgc accatttgct catttctcgt ggagaagaaa ccactcatct tcttcggttg 3001 ctgcttcatc tccactctgg ctgtactgct atccatcacc gtttttcatc atcaaaagag 3061 aagaaaattc cagaaagcaa ggaacttaca aaatatacca ttgaagaaag gccacagcag 3121 agttttcagc taa
```

In one embodiment of the present invention, the FGF receptor is FGFR1c receptor. In one particular embodiment, the FGFR1c receptor is the human FGFR1c receptor comprising the amino acid sequence of SEQ ID NO: 221 (GenBank Accession No. NP 075598, which is hereby incorporated by reference in its entirety), as follows:

```
  1 MWSWKCLLFW AVLVTATLCT ARPSPTLPEQ AQPWGAPVEV ESFLVHPGDL LQLRCRLRDD

61 VQSINWLRDG VQLAESNRTR ITGEEVEVQD SVPADSGLYA CVTSSPSGSD TTYFSVNVSD

121 ALPSSEDDDD DDDSSSEEKE TDNTKPNRMP VAPYWTSPEK MEKKLHAVPA AKTVKFKCPS

181 SGTPNPTLRW LKNGKEFKPD HRIGGYKVRY ATWSIIMDSV VPSDKGNYTC IVENEYGSIN
```

```
241 HTYQLDVVER SPHRPILQAG LPANKTVALG SNVEFMCKVY SDPQPHIQWL KHIEVNGSKI

301 GPDNLPYVQI LKTAGVNTTD KEMEVLHLRN VSFEDAGEYT CLAGNSIGLS HHSAWLTVLE

361 ALEERPAVMT SPLYLEIIIY CTGAFLISCM VGSVIVYKMK SGTKKSDFHS QMAVHKLAKS

421 IPLRRQVTVS ADSSASMNSG VLLVRPSRLS SSGTPMLAGV SEYELPEDPR WELPRDRLVL

481 GKPLGEGCFG QVVLAEAIGL DKDKPNRVTK VAVKMLKSDA TEKDLSDLIS EMEMMKMIGK

541 HKNIINLLGA CTQDGPLYVI VEYASKGNLR EYLQARRPPG LEYCYNPSHN PEEQLSSKDL

601 VSCAYQVARG MEYLASKKCI HRDLAARNVL VTEDNVMKIA DFGLARDIHH IDYYKKTTNG

661 RLPVKWMAPE ALFDRIYTHQ SDVWSFGVLL WEIFTLGGSP YPGVPVEELF KLLKEGHRMD

721 KPSNCTNELY MMMRDCWHAV PSQRPTFKQL VEDLDRIVAL TSNQEYLDLS MPLDQYSPSF

781 PDTRSSTCSS GEDSVFSHEP LPEEPCLPRH PAQLANGGLK RR
```

In one particular embodiment of the present invention, the FGFR1c receptor is the human FGFR1c receptor encoded by a nucleotide sequence comprising the nucleotide sequence of SEQ ID NO: 222 (GenBank Accession No. NM 023110, which is hereby incorporated by reference in its entirety), as follows:

```
SEQ ID NO: 222 (Human FGFR1c gene coding sequence):
 943 atgtggag ctggaagtgc ctcctcttct gggctgtgct ggtcacagcc acactctgca 1001 ccgctaggcc gtccccgacc ttgcctgaac aagcccagcc ctggggagcc cctgtggaag 1061 tggagtcctt cctggtccac cccgtgacc tgctgcagct tcgctgtcgg ctgcgggacg 1121 atgtgcagag catcaactgg ctgcgggacg gggtgcagct ggcggaaagc aaccgcaccc 1181 gcatcacagg ggaggaggtg gaggtgcagg actccgtgcc cgcagactcc ggcctctatg 1241 cttgcgtaac cagcagcccc tcgggcagtg acaccaccta cttctccgtc aatgtttcag 1301 atgctctccc ctcctcggag gatgatgatg atgatgatga ctcctcttca gaggagaaag 1361 aaacagataa caccaaacca aaccgtatgc ccgtagctcc atattggaca tccccagaaa 1421 agatggaaaa gaaattgcat gcagtgccgg ctgccaagac agtgaagttc aaatgccctt 1481 ccagtgggac cccaaacccc acactgcgct ggttgaaaaa tggcaaagaa ttcaaacctg 1541 accacagaat tggaggctac aaggtccgtt atgccacctg gagcatcata atggactctg 1601 tggtgccctc tgacaagggc aactacacct gcattgtgga aatgagtac ggcagcatca 1661 accacacata ccagctggat gtcgtggagc ggtcccctca ccggcccatc ctgcaagcag 1721 ggttgcccgc caacaaaaca gtggccctgg gtagcaacgt ggagttcatg tgtaaggtgt 1781 acagtgaccc gcagccgcac atccagtggc taaagcacat cgaggtgaat gggagcaaga 1841 ttggcccaga caacctgcct tatgtccaga tcttgaagac tgctggagtt aataccaccg 1901 acaaagagat ggaggtgctt cacttaagaa atgtctcctt tgaggacgca ggggagtata 1961 cgtgcttggc gggtaactct atcggactct cccatcactc tgcatggttg accgttctgg 2021 aagccctgga agagaggccg gcagtgatga cctcgcccct gtacctggag atcatcatct 2081 attgcacagg ggccttcctc atctcctgca tggtggggtc ggtcatcgtc tacaagatga 2141 agagtggtac caagaagagt gacttccaca gccagatggc tgtgcacaag ctggccaaga 2201 gcatccctct gcgcagacag gtaacagtgt ctgctgactc cagtgcatcc atgaactctg 2261 gggttcttct ggttcggcca tcacggctct cctccagtgg gactcccatg ctagcagggg 2301 tctctgagta tgagcttccc gaagaccctc gctgggagct gcctcgggac agactggtct 2361 taggcaaacc cctgggagag ggctgctttg gcaggtggt gttggcagag gctatcgggc 2421 tggacaagga caaacccaac cgtgtgacca agtggctgt gaagatgttg aagtcggacg 2481 caacagagaa agacttgtca gacctgatct cagaaatgga gatgatgaag atgatcggga
```

```
2541 agcataagaa tatcatcaac ctgctggggg cctgcacgca ggatggtccc ttgtatgtca 2601 tcgtggagta tgcctccaag ggcaacctgc gggagtacct gcaggcccgg aggcccccag 2661 ggctggaata ctgctacaac cccagccaca acccagagga gcagctctcc tccaaggacc 2721 tggtgtcctg cgcctaccag gtggcccgag gcatggagta tctggcctcc aagaagtgca 2781 tacaccgaga cctggcagcc aggaatgtcc tggtgacaga ggacaatgtg atgaagatag 2841 cagactttgg cctcgcacgg gacattcacc acatcgacta ctataaaaag acaaccaacg 2901 gccgactgcc tgtgaagtgg atggcacccg aggcattatt tgaccggatc tacacccacc 2961 agagtgatgt gtggtctttc ggggtgctcc tgtgggagat cttcactctg ggcggctccc 3021 catacccccgg tgtgcctgtg gaggaacttt tcaagctgct gaaggagggt caccgcatgg 3081 acaagcccag taactgcacc aacgagctgt acatgatgat gcgggactgc tggcatgcag 3141 tgccctcaca gagacccacc ttcaagcagc tggtggaaga cctggaccgc atcgtggcct 3201 tgacctccaa ccaggagtac ctggacctgt ccatgccct ggaccagtac tcccccagct 3261 ttcccgacac ccggagctct acgtgctcct caggggagga ttccgtcttc tctcatgagc 3321 cgctgcccga ggagccctgc ctgccccgac acccagccca gcttgccaat ggcggactca 3381 aacgccgctg a
```

The FGFR1, transcript variant 1 protein is a member of the FGFR family, where amino acid sequences are highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting in motion a cascade of downstream signals, ultimately influencing a myriad of biological processes including mitogenesis and differentiation. This particular family member binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome. See, e.g., Dode et al., "Kallmann Syndrome: Fibroblast Growth Factor Signaling Insufficiency?" *J Mol Med* 82(11):725-34 (2004); Coumoul et al., "Roles of FGF Receptors in Mammalian Development and Congenital Diseases," *Birth Defects Res C Embryo Today* 69(4):286-304 (2003), which are hereby incorporated by reference in their entirety. Alternatively spliced variants, which encode different protein isoforms, have been described; however, not all variants have been fully characterized.

The nucleic acid and amino acid sequences for FGFR1 variants 2-6 may be found using the following reference sequence ID numbers on GenBank: FGFR1, transcript variant 2 (GenBank Accession No. NM_015850), FGFR1, transcript variant 3 (GenBank Accession No. NM_023105), FGFR1, transcript variant 4 (GenBank Accession No. NM_023106), FGFR1, transcript variant 5 (GenBank Accession No. NM_023107), FGFR1, transcript variant 6 (GenBank Accession No. NM_023108), and FGFR1, transcript variant 9, (GenBank Accession No. NM_023111). These sequences are hereby incorporated by reference in their entirety.

Yet another aspect of the present invention relates to a method of causing increased FGF21 receptor agonist-βKlotho-FGFR complex formation. This method comprises providing a cell comprising βKlotho and an FGFR and providing an FGF21 receptor agonist, where the agonist comprises a chimeric protein comprising a C-terminal portion of FGF19. This method also includes contacting the cell and the FGF21 receptor agonist under conditions effective to cause increased FGF21 receptor agonist-βKlotho-FGFR complex formation relative to contacting the cell with FGF21 alone, where the FGF21 has a core domain.

With respect to the FGF21 agonist, suitable chimeric proteins include those chimeric proteins according to the present invention that are described above and throughout the present application. Suitable N-terminal portions of FGF21 and C-terminal portions of FGF19 are also described above and throughout the present application.

In one embodiment, the method of causing increased FGF21 receptor agonist-βKlotho-FGFR complex formation is carried out in vitro. In one embodiment, the method is carried out in an adipocyte.

In one embodiment, the method of causing increased FGF21 receptor agonist-βKlotho-FGFR complex formation is carried out in vivo. In one embodiment, the method is carried out in a mammal. In one particular embodiment, the mammal is a mouse.

A further aspect of the present invention relates to a method of screening for compounds with enhanced binding affinity for βKlotho suitable for fusion to the C-terminus of an N-terminal portion of FGF21 to generate an FGF21 agonist. The method includes providing FGF21, providing βKlotho, and providing one or more candidate compounds; combining the FGF21, the βKlotho, and the candidate compounds under conditions effective for FGF21 and βKlotho to form a binary complex if present by themselves; and identifying the candidate compounds which diminish binary complex formation, compared to when the candidate compound is absent, as being potentially suitable for fusion to the C-terminus of an N-terminal portion of FGF21 to generate an FGF21 agonist. In one embodiment, the candidate compound out-competes FGF21 for binding to the βKlotho.

Yet a further aspect of the present invention relates to a method of screening for compounds with enhanced binding affinity for the βKlotho-FGFR complex suitable for treatment of diabetes, obesity, or related metabolic disorders. This method includes providing FGF21, providing a binary βKlotho-FGFR complex, and providing one or more candidate compounds. This method also includes combining the FGF21, the binary βKlotho-FGFR complex, and the candidate compounds under conditions effective for the FGF21 and the βKlotho-FGFR complex to form a ternary complex if present by themselves and identifying the candidate compounds which diminish ternary complex formation compared to when the candidate compound is absent as being potentially suitable for treatment of diabetes, obesity, or related metabolic disorders. In one embodiment, the candidate compound out-competes FGF21 for binding to the βKlotho-FGFR complex.

In one embodiment of the screening aspects of the present invention, the FGF21 has the amino acid sequence of SEQ ID NO: 100.

In one embodiment of the screening aspects of the present invention, βKlotho has the amino acid sequence of SEQ ID NO: 217 or SEQ ID NO: 218.

In one embodiment of the screening aspects of the present invention, the FGF receptor is FGFR1c. In one particular embodiment, the FGFR1c receptor has the amino acid sequence of SEQ ID NO: 221.

In one embodiment of the screening aspects of the present invention, a plurality of compounds is tested. In one embodiment, the candidate compounds are biomolecules. In one embodiment, the biomolecules are proteins. In one embodiment, the biomolecules are peptides. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with adipocytes. In one embodiment, the cell-based assay is carried out with skeletal muscle cells. In one embodiment, stimulation of glucose uptake is the assay readout. In one embodiment, induction of glucose transporter 1 gene expression is the assay readout. In one embodiment, a dose-response curve is generated for the stimulation of glucose uptake by a candidate compound to determine potency and efficacy of the candidate compound. In one embodiment, a dose-response curve is generated for the induction of glucose transporter 1 gene expression by a candidate compound to determine potency and efficacy of the candidate compound. For example, if the dose-response curve is shifted to the left compared to that obtained for native FGF21, the candidate compound has greater potency than native FGF21. In one embodiment, an $IC_{50}$ value is derived from the dose-response curve of a candidate compound to determine potency of the candidate compound. An $IC_{50}$ value smaller than that obtained for native FGF21 identifies a candidate compound as more potent than native FGF21.

In one embodiment of the screening aspects of the present invention, the cell-based assay is carried out with mammalian cells ectopically expressing βKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for βKlotho-dependent activation of FGF receptor by a candidate compound to determine potency and efficacy of the candidate compound. For example, if the dose-response curve is shifted to the left compared to that obtained for native FGF21, the candidate compound is more potent than native FGF21. In one embodiment, an $IC_{50}$ value is derived from the dose-response curve of a candidate compound to determine potency of the candidate compound. An $IC_{50}$ value smaller than that obtained for native FGF21 identifies a candidate compound as more potent than native FGF21.

In one embodiment of the screening aspects of the present invention, the surface plasmon resonance spectroscopy-based assay is carried out using FGF21 as ligand coupled to a biosensor chip. In one embodiment, mixtures of βKlotho ectodomain with increasing concentrations of a candidate compound are passed over a biosensor chip containing FGF21. In one embodiment, mixtures of the binary complex of FGFR ligand-binding domain and βKlotho ectodomain with increasing concentrations of a candidate compound are passed over a biosensor chip containing FGF21. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for native FGF21, the candidate compound has greater potency than native FGF21. In one embodiment, an $IC_{50}$ value is derived from the inhibition-binding curve of a candidate compound to determine potency of the candidate compound. An $IC_{50}$ value smaller than that obtained for native FGF21 identifies a candidate compound as more potent than native FGF21. In one embodiment, the inhibition constant $K_i$ is determined for a candidate compound to determine potency of the candidate compound. A $K_i$ value smaller than that obtained for native FGF21 identifies a candidate compound as more potent than native FGF21.

In one embodiment of the screening aspects of the present invention, the method is carried out in vivo. In one embodiment, the method is carried out in a mammal. In one particular embodiment, the mammal is a mouse. In one embodiment, the ability of a candidate compound to potentiate the hypoglycemic effect of insulin is used as readout for FGF21-like metabolic activity. This involves fasting the mammal for a period of time prior to insulin injection and measuring fasting blood glucose levels. The mammal is then injected with insulin alone or co-injected with insulin plus a candidate compound. Blood glucose levels are measured at several time points after the injection. If a candidate compound potentiates the hypoglycemic effect of insulin to a greater degree than native FGF21 does, the candidate compound exhibits enhanced efficacy. Likewise, if a candidate compound potentiates the hypoglycemic effect of insulin to a similar degree than native FGF21 does but at a lower dose compared to that of FGF21 and/or for a longer period of time compared to FGF21, the candidate compound has enhanced agonistic properties.

EXAMPLES

The following examples are provided to illustrate embodiments of the present invention but are by no means intended to limit its scope.

Materials and Methods Used in Examples 1-8

Purification of FGF19, FGF21, FGF23, FGFR, αKlotho, and βKlotho Proteins and Purification of FGF19, FGF21, and FGF23 Peptides The three endocrine FGF ligands, and mutants, chimeras, and C-terminal peptides thereof, as well as the ligand-binding domain of FGFRs were expressed in E. coli BL21 (DE3) cells. The secreted, bioactive form of human FGF19 (R23 to K216 of SEQ ID NO: 1), human FGF21 (H29 to 5209 of SEQ ID NO: 100), and human FGF23 (Y25 to 1251 of SEQ ID NO: 223) was refolded in vitro from inclusion bodies, and purified by published protocols (Ibrahimi et al., "Biochemical Analysis of Pathogenic Ligand-dependent FGFR2 Mutations Suggests Distinct Pathophysiological Mechanisms for Craniofacial and Limb Abnormalities," Hum Mol Genet 13(19):2313-2324 (2004), Plotnikov et al., "Crystal Structures of Two FGF-FGFR Complexes Reveal the Determinants of Ligand-receptor Specificity," Cell 101 (4):413-424 (2000), which are hereby incorporated by reference in their entirety). In order to minimize proteolysis of FGF23, arginine residues 176 and 179 of the proteolytic cleavage site $^{176}$RXXR$^{179}$ (with reference to SEQ ID NO: 223) were replaced with glutamine as it occurs in the phosphate wasting disorder "autosomal dominant hypophosphatemic rickets" (Anonymous, "Autosomal Dominant Hypophosphataemic Rickets is Associated with Mutations in FGF23," Nat Genet 26(3):345-348 (2000); White et al., "Autosomal-dominant Hypophosphatemic Rickets (ADHR) Mutations Stabilize FGF-23," Kidney Int 60(6):2079-2086 (2001), which are hereby incorporated by reference in their entirety).

Chimeras composed of a N-terminal portion of human FGF21 (H29 to V197, H29 to S190, or H29 to L167 of SEQ ID NO: 100) and a C-terminal portion of human FGF19 (T204 to K216, M197 to K216, or L169 to K216 of SEQ ID NO: 1), termed FGF21$^{29-197}$/FGF19$^{204-216}$ (SEQ ID NO: 205), FGF21$^{29-190}$/FGF19$^{197-216}$ (SEQ ID NO: 206), and FGF21$^{29-167}$/FGF19$^{169-216}$ (SEQ ID NO: 207), respectively, were purified from inclusion bodies by the same protocol as the wild-type protein.

Likewise, two single mutants (Q104M and Y207F, SEQ ID NOs: 152 and 232, respectively) and one triple mutant (Y207F/A208E/S209K, SEQ ID NO: 233) of human FGF21 were purified by the same protocol as the wild-type protein. The C-terminal tail peptide of human FGF19 (M171 to K216 of SEQ ID NO: 1, termed FGF19$^{C-tail}$) and the C-terminal tail peptide of human FGF21 (P168 to 5209 of SEQ ID NO: 100, termed FGF21$^{C-tail}$) were expressed as fusion peptides with a 50 residue-long N-terminal tag including a hexahistidine tag, and purified from the soluble cell lysate fraction by nickel affinity- and ion exchange chromatographies.

The N-terminally hexahistidine-tagged C-terminal tail peptide of human FGF23 (S180 to 1251 of SEQ ID NO: 223, termed FGF23$^{C-tail}$) was expressed and purified as described previously (Goetz et al., "Isolated C-terminal Tail of FGF23 Alleviates Hypophosphatemia by Inhibiting FGF23-FGFR-Klotho Complex Formation," Proc Natl Acad Sci USA 107(1):407-412 (2010), which is hereby incorporated by reference in its entirety).

A single mutant (M96T) of human FGF23 (SEQ ID NO: 224) was purified by the same protocol as the wild-type protein. The proteolytic cleavage site $^{176}$RXXR$^{179}$ was not mutated in the M96T mutant protein. The wild-type FGF23 protein used as a control in the experiments with the M96T mutant also did not contain mutations at the proteolytic cleavage site.

Full-length human FGF homologous factor 1B (FHF1B; M1 to T181), which was used as a negative control for surface plasmon resonance (SPR) spectroscopy, was purified by a published protocol (Olsen et al., "Fibroblast Growth Factor (FGF) Homologous Factors Share Structural but not Functional Homology with FGFs," J Biol Chem 278(36): 34226-34236 (2003), which is hereby incorporated by reference in its entirety).

The ligand-binding domain of each of the seven principal human FGFRs, namely FGFR1b (D142 to E374 of SEQ ID NO: 225), FGFR1c (D142 to R365 of SEQ ID NO: 221), FGFR2b (A140 to E366 of SEQ ID NO: 227), FGFR2c (N149 to E368 of SEQ ID NO: 226), FGFR3b (D147 to H358 of SEQ ID NO: 229), FGFR3c (D147 to E365 of SEQ ID NO: 228), and FGFR4 (Q144 to D355 of SEQ ID NO: 230), was refolded in vitro from inclusion bodies, and purified as described previously (Ibrahimi et al., "Biochemical Analysis of Pathogenic Ligand-dependent FGFR2 Mutations Suggests Distinct Pathophysiological Mechanisms for Craniofacial and Limb Abnormalities," Hum Mol Genet 13(19):2313-2324 (2004); Plotnikov et al., "Crystal Structures of Two FGF-FGFR Complexes Reveal the Determinants of Ligand-receptor Specificity," Cell 101(4):413-424 (2000), which are hereby incorporated by reference in their entirety).

The ectodomain of murine αKlotho (A35 to K982 of SEQ ID NO: 231) was purified from culture media of a HEK293 cell line ectopically expressing the αKlotho ectodomain as a fusion protein with a C-terminal FLAG tag (Kurosu et al., "Regulation of Fibroblast Growth Factor-23 Signaling by Klotho," J Biol Chem 281(10):6120-6123 (2006); Kurosu et al., "Suppression of Aging in Mice by the Hormone Klotho," Science 309(5742):1829-1833 (2005), which are hereby incorporated by reference in their entirety). Similarly, the ectodomain of murine βKlotho (F53 to L995 of SEQ ID NO: 218) was expressed in HEK293 cells as a fusion protein with a C-terminal FLAG tag and purified using the same protocol as for the αKlotho ectodomain. Purified bovine β-glucuronidase was obtained from Sigma-Aldrich.

Analysis of Ternary Complex Formation between FGF19/ FGF21, FGFR, and βKlotho by Size-Exclusion Chromatography Size-exclusion chromatography experiments were performed on a HiLoad™ 16/60 Superdex™ 200 prep grade column (GE Healthcare) mounted on an ÄKTApurifier (GE Healthcare). Because of poor solubility of the ligand-binding domain of FGFR1c in low salt buffer, the experiments were carried out with 25 mM HEPES-NaOH buffer, pH7.5, containing 1.0 M NaCl. Sample injection volume was 0.9 to 2.0 ml, and the flow rate was 1.0 ml min$^{-1}$. Protein retention times were determined by absorbance at 280 nm. The column was calibrated with ferritin (440 kDa), immunoglobulin G (150 kDa), albumin (69.3 kDa), ovalbumin (44.3 kDa), carbonic anhydrase (28.8 kDa), and ribonuclease A (13.7 kDa). The void volume was determined using blue dextran 2,000, and the column volume was measured with acetone. To examine ternary complex formation between FGF21, FGFR1c, and βKlotho, 2.72 μmol of the 1:1 binary complex of FGFR1c ligand-binding domain and βKlotho ectodomain were mixed with 9.25 μmol of FGF21, and the mixture was applied to the size-exclusion column. The retention time of the FGFR1c-βKlotho complex alone served as a reference point. To examine ternary complex formation between FGF19, FGFR4, and βKlotho, 2.46 μmol of the 1:1 binary complex of FGFR4 ligand-binding domain and βKlotho ectodomain were mixed with 8.51 μmol of FGF19, and the mixture was applied to the size-exclusion column. The retention time of the FGFR4-βKlotho complex alone served as a reference point. Proteins of column peak fractions were resolved on 14% SDS-polyacrylamide gels, and then stained with Coomassie Brilliant Blue R-250.

Analysis of Mutant and Wild-Type FGF23 Proteins by Size-Exclusion Chromatography Size-exclusion chromatography experiments were performed on a HiLoad™ 16/60 Superdex™ 75 prep grade column (GE Healthcare). Because of poor solubility of FGF23 in low salt buffer, the experiments were carried out with 25 mM HEPES-NaOH buffer, pH7.5, containing 1.0 M NaCl. Sample injection volume was 1.5 to 3.8 ml, and the flow rate was 1.0 ml min$^{-1}$. Protein retention times were determined by absorbance at 280 nm. The column was calibrated with albumin (69.3 kDa), ovalbumin (44.3 kDa), carbonic anhydrase (28.8 kDa), ribonuclease A (13.7 kDa), and aprotinin (6.5 kDa). The void volume was determined using blue dextran 2,000, and the column volume was measured with acetone. To assess stability of FGF23 harboring the M96T mutation, equal amounts of mutant protein were injected onto the column at different times after affinity purification of the mutant protein. As a control, the elution profile of wild-type FGF23 was studied.

Analysis of FGF19/21/23-α/βKlotho, FGFR-βKlotho, and FGF21-FGFR1c-βKlotho Interactions by Surface Plasmon Resonance Spectroscopy SPR experiments were performed on a Biacore 2000 instrument (Biacore AB), and all the protein-protein and protein-peptide interactions were studied at 25° C. in HBS-EP buffer (10 mM HEPES-NaOH, pH 7.4, 150 mM NaCl, 3 mM EDTA, 0.005% (v/v) polysorbate 20). Proteins were immobilized by amine coupling on flow channels of research grade CM5 chips (Biacore AB). Proteins were injected over a CM5 chip at a flow rate of 50 μl min$^{-1}$, and at the end of each protein injection (180 s), HBS-EP buffer (50 μl min$^{-1}$) was flowed over the chip to monitor dissociation for 180 s. In experiments where βKlotho binding to FGFR was analyzed, the chip surface was then regenerated by injecting 50 μl of 2.0 M NaCl in 10 mM sodium/potassium phosphate, pH 6.5. In experiments where α/βKlotho binding to FGF19/21/23 or binding of the FGFR1c-βKlotho complex to FGF21 was studied, 2.0 M NaCl in 10 mM sodium acetate, pH 4.5 was used for chip regeneration. To control for nonspecific binding in experiments where the ectodomain of αKlotho or βKlotho was immobilized on the chip, β-glucuronidase was coupled to the control flow channel of the chip (~43-68 fmol/mm$^2$). Like αKlotho and βKlotho, β-glucuronidase is a member of family 1 glycosidases (carbohydrate-active enzymes database at cazy's online website; Cantarel et al., "The Carbohydrate-Active EnZymes Database (CAZy): an Expert Resource for Glycogenomics," *Nucleic Acids Res* 37:D233-238 (2009), which is hereby incorporated by reference in its entirety), and hence structurally related to each of the two extracellular glycosidase-like domains of αKlotho and βKlotho, respectively. In experiments where an FGF ligand was immobilized on the chip, FHF1B, which shares structural similarity with FGFs, but does not exhibit any FGFR binding (Olsen et al., "Fibroblast Growth Factor (FGF) Homologous Factors Share Structural but not Functional Homology with FGFs," *J Biol Chem* 278(36):34226-34236 (2003), which is hereby incorporated by reference in its entirety), was coupled to the control flow channel of the chip (~17-101 fmol/mm$^2$). The data were processed with BiaEvaluation software (Biacore AB). For each protein injection over a chip onto which αKlotho or βKlotho had been immobilized, the nonspecific responses from the β-glucuronidase control flow channel were subtracted from the responses recorded for the α/βKlotho flow channel. Similarly, for each protein injection over a FGF chip, the nonspecific responses from the FHF1B control flow channel were subtracted from the responses recorded for the FGF flow channel. Each set of experiments was repeated at least twice.

To analyze FGF21 binding to the binary FGFR1c-βKlotho complex, FGF21 was immobilized on a chip (~20 fmol/mm$^2$ of flow channel), and increasing concentrations of 1:1 complex of FGFR1c ligand-binding domain and βKlotho ectodomain in HBS-EP buffer were passed over the chip. To test the specificity of the interaction between FGF21 and the FGFR1c-βKlotho complex, two concentrations of 1:1 complex of FGFR1c ligand-binding domain and αKlotho ectodomain in HBS-EP buffer were passed over the FGF21 chip. The results are shown in FIGS. 1C and 1D.

To measure binding of βKlotho to each of the seven principal FGFRs, the ectodomain of βKlotho was immobilized on a chip (~42-46 fmol/mm$^2$ of flow channel). Increasing concentrations of the ligand-binding domain of FGFR1b, FGFR1c, FGFR2b, FGFR2c, FGFR3b, FGFR3c, or FGFR4 in HBS-EP buffer were passed over the chip. Maximal equilibrium binding responses were plotted against the concentrations of FGFR ligand-binding domain, and from the fitted saturation binding curve the equilibrium dissociation constant ($K_D$) was calculated. The fitted binding curve was judged to be accurate based on the distribution of the residuals (even and near zero) and $\chi^2$ (<10% of $R_{max}$). The results are shown in FIGS. 3A to 3G.

To analyze binding of βKlotho to FGF19 and FGF21, FGF19 and FGF21 were coupled to two flow channels of a chip (~30 fmol/mm$^2$ of flow channel). As a control, FGF23 was also coupled to the chip (~29 fmol/mm$^2$ of flow channel). Increasing concentrations of the ectodomain of βKlotho in HBS-EP buffer were injected over the chip. As an additional control, binding of αKlotho to FGF19 and FGF21 was studied. The results are shown in FIGS. 4A to 4E.

To examine whether the isolated C-terminal tail peptide of FGF19 or FGF21 can compete with full-length FGF19 or FGF21 for binding to βKlotho, FGF19 and FGF21 were immobilized on two flow channels of a chip (~18-29 fmol/mm$^2$ of flow channel). Increasing concentrations of either FGF19$^{C-tail}$ (0-20 nM) or FGF21$^{C-tail}$ (0-200 nM) were mixed with a fixed concentration of βKlotho (10 nM) in HBS-EP buffer, and the mixtures were passed over the chip. To test the specificity of the interaction between βKlotho and the C-terminal tail of FGF19 or FGF21, βKlotho ectodomain was mixed with a 2-fold molar excess of FGF23$^{C\text{-}tail}$, and the mixture was injected over the chip. The results are shown in FIGS. 5B to 5G.

To examine whether mutants of FGF21 or chimeras composed of a N-terminal portion of FGF21 and a C-terminal portion of FGF19 can compete with wild-type ligand for binding to the FGFR1c-βKlotho complex, FGF21 was immobilized on a chip (~30 fmol/mm$^2$ of flow channel). Increasing concentrations of FGF21 mutant or chimera (0-60 nM) were mixed with a fixed concentration of 1:1 complex of FGFR1c ligand-binding domain and βKlotho ectodomain (10 nM), and the mixtures were passed over the chip. As a control, competition of FGF21 in solution with immobilized FGF21 for binding to the FGFR1c-βKlotho complex was studied. The results are shown in FIGS. 14A to 14D and 15A to 15F.

Figures 7A, 7B, 7C:
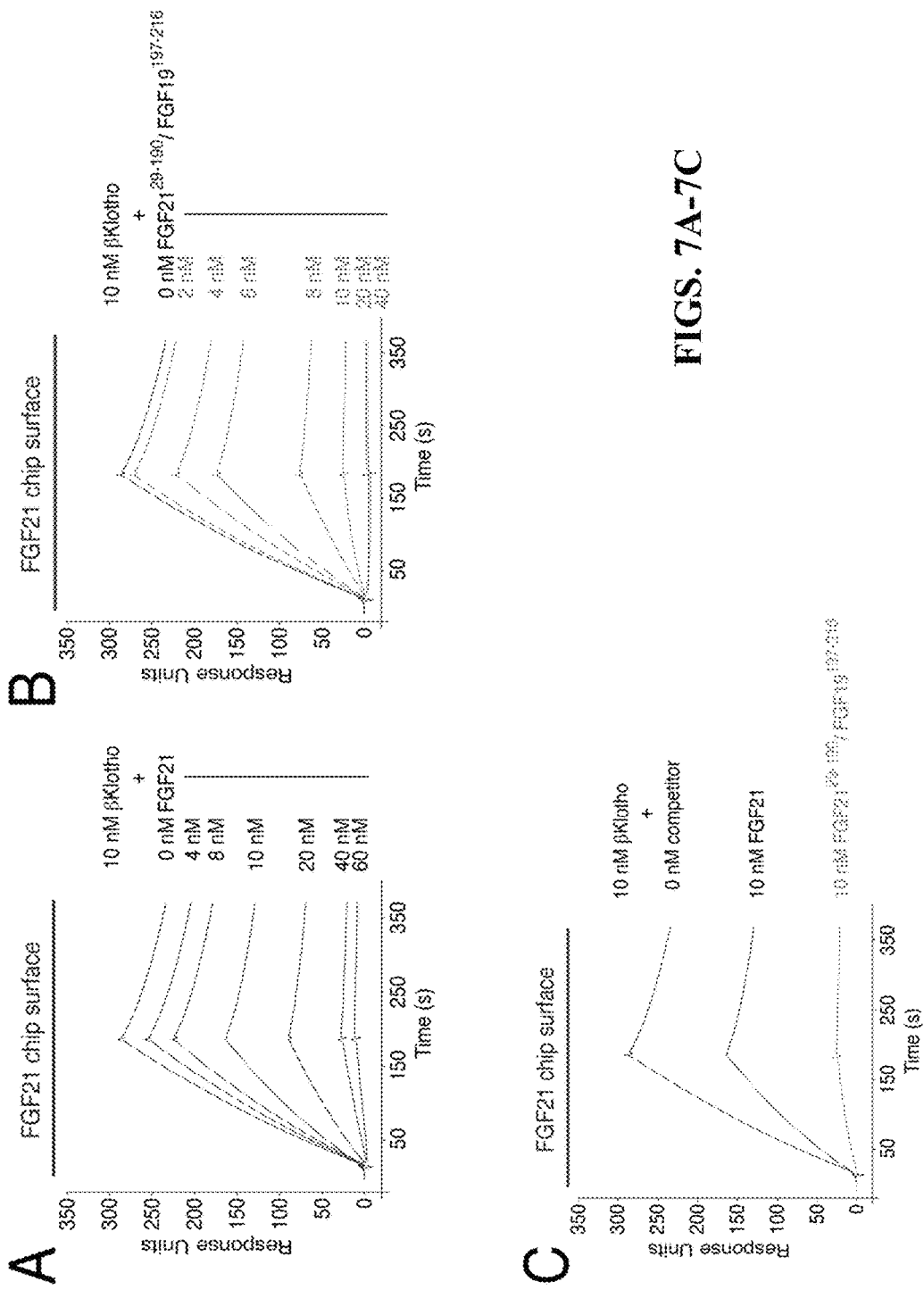
FIGS. 7A-7C show that a FGF21/FGF19 chimera has enhanced binding affinity for βKlotho.

To examine whether a chimera composed of a N-terminal portion of FGF21 and a C-terminal portion of FGF19 can compete with wild-type FGF21 for binding to βKlotho, FGF21 was immobilized on a chip (~29 fmol/mm$^2$ of flow channel). Increasing concentrations of chimera (0-40 nM) were mixed with a fixed concentration of βKlotho ectodomain (10 nM), and the mixtures were injected over the chip. As a control, competition of FGF21 in solution with immobilized FGF21 for binding to βKlotho was studied. The results are shown in FIGS. 7A to 7C.

Analysis of Phosphorylation of FRS2α and 44/42 MAP Kinase in a Hepatoma Cell Line To test whether the C-terminal tail peptides of FGF19 and FGF21 are interchangeable in inhibiting the signaling of FGF19, H4IIE rat hepatoma cells, which endogenously express βKlotho and FGFR4, were serum starved overnight and then pretreated for 60 min with either FGF19$^{C\text{-}tail}$ (10 to 1000 ng ml$^{-1}$) or FGF21$^{C\text{-}tail}$ (10 to 1000 ng ml$^{-1}$) prior to stimulation with FGF19 (30 ng ml$^1$) for 10 min. Cell stimulation with FGF19 (3 to 300 ng ml$^{-1}$), FGF19$^{C\text{-}tail}$ (10 to 1000 ng ml$^{-1}$), or FGF21$^{C\text{-}tail}$ (10 to 1000 ng ml$^{-1}$) alone served as controls.

Figures 6A, 6B:
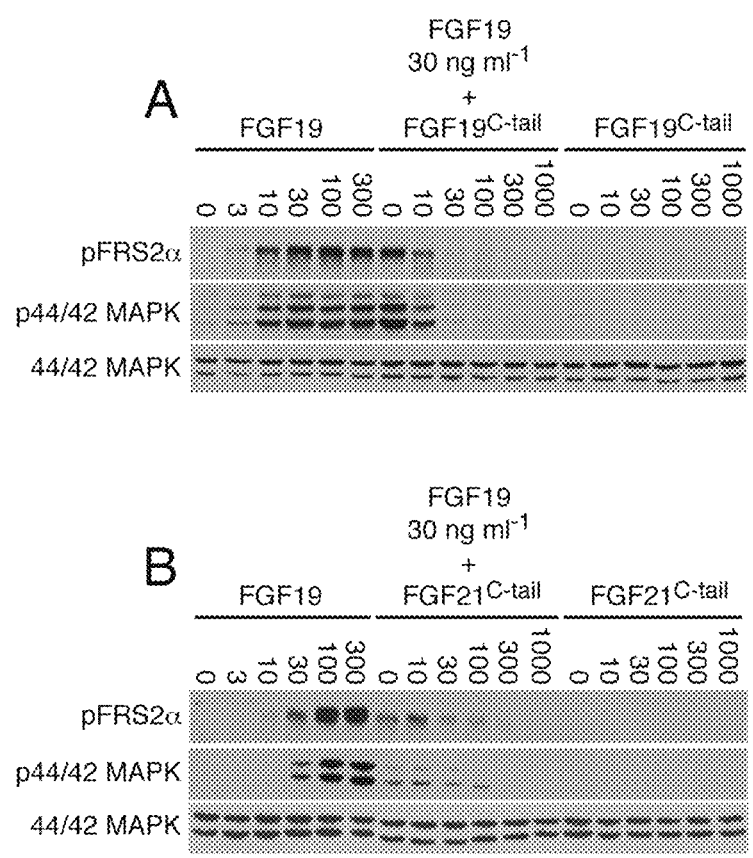
FIGS. 6A-6B show that the C-terminal tail peptides of FGF19 and FGF21 are interchangeable in inhibiting the signaling of FGF19.

After stimulation, the cells were lysed (Kurosu et al, "Suppression of Aging in Mice by the Hormone Klotho," *Science* 309(5742):1829-1833 (2005), which is hereby incorporated by reference in its entirety), and cellular proteins were resolved on SDS-polyacrylamide gels and transferred to nitrocellulose membranes. The protein blots were probed with an antibody to phosphorylated FGFR substrate-2α (FRS2α), and with antibodies recognizing only phosphorylated 44/42 MAP kinase or both phosphorylated and nonphosphorylated (total) 44/42 MAP kinase. All antibodies were from Cell Signaling Technology. The results are shown in FIGS. 6A and 6B.

Analysis of Egr1 Protein Expression in an Epithelial Cell Line

Figures 17A, 17B, 17C:
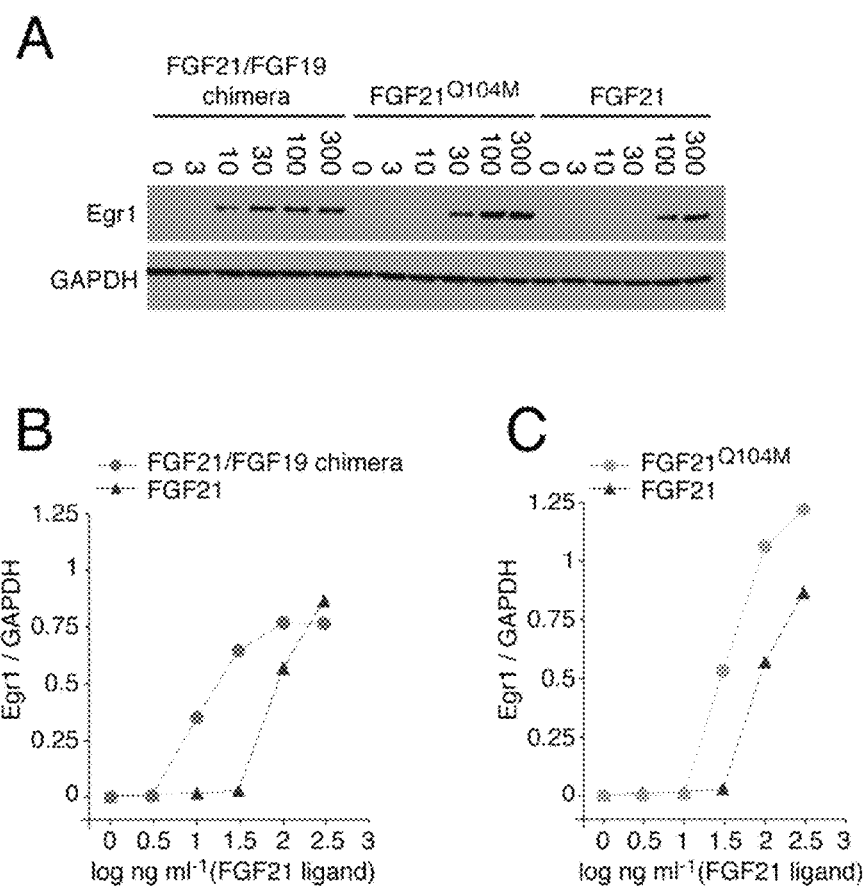
FIGS. 17A-17C show that a FGF21/FGF19 chimera and a single mutant of FGF21 harboring Q104M substitution in the core domain act as FGF21 agonists in a cell-based assay.

The ability of a single mutant of FGF21 and an FGF21/FGF19 chimera to activate FGFR1c in a βKlotho-dependent fashion was studied using induction of Egr1 expression as readout for FGFR1c activation. HEK293 cells, which endogenously express FGFR1c (Kurosu et al, "Regulation of Fibroblast Growth Factor-23 Signaling by Klotho," *J Biol Chem* 281:6120-6123 (2006), which is hereby incorporated by reference in its entirety), were transiently transfected with murine βKlotho. βKlotho HEK293 transfectants were serum starved overnight and then stimulated for 90 min with FGF21 mutant, chimera, or wild-type protein (3 to 300 ng ml$^{-1}$ each). After stimulation, the cells were lysed (Kurosu et al, "Suppression of Aging in Mice by the Hormone Klotho," *Science* 309(5742):1829-1833 (2005), which is hereby incorporated by reference in its entirety), and cellular proteins were resolved on SDS-polyacrylamide gels and transferred to nitrocellulose membranes. The protein blots were probed with antibodies to Egr1 and GAPDH. The intensity of the protein bands on the immunoblots was quantified and the ratio of Egr1 to GAPDH was calculated. The ratio of Egr1 to GAPDH was then plotted as a function of FGF21 ligand concentration. The anti-Egr1 antibody was from Cell Signaling Technology and the anti-GAPDH antibody was from Abcam. The results are shown in FIGS. 17A to 17C.

Insulin Tolerance Test in Mice

The metabolic activity of a single mutant of FGF21 and an FGF21/FGF19 chimera was studied in C57BL/6 mice. The ability of FGF21 mutant or chimera to potentiate the hypoglycemic effect of insulin was used as readout for FGF21-like metabolic activity (Ohnishi et al., "Dietary and Genetic Evidence for Enhancing Glucose Metabolism and Reducing Obesity by Inhibiting Klotho Functions," *FASEB J* 25, 2031-2039 (2011), which is hereby incorporated by reference in its entirety). Mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units per kilogram body weight) alone or insulin (0.5 units per kilogram body weight) plus either FGF21 mutant or FGF21/FGF19 chimera (0.3 mg per kilogram body weight). As controls, mice were injected with vehicle alone or co-injected with insulin plus FGF21. At the indicated time points after the injection (FIGS. 18A-18C), blood was drawn from the tail vein. Glucose concentrations in the blood samples were determined using Bayer Contour® blood glucose test strips (Bayer Corp.).

Figure 2A:
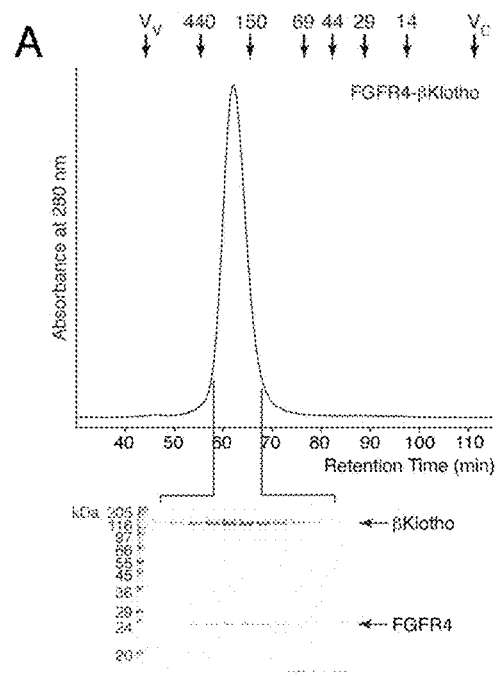
FIGS. 2A-2B show that the ternary complex of FGF19 with its cognate FGFR and βKlotho coreceptor can be reconstituted in solution using the ectodomains of βKlotho and FGFR4.
Figure 2B:
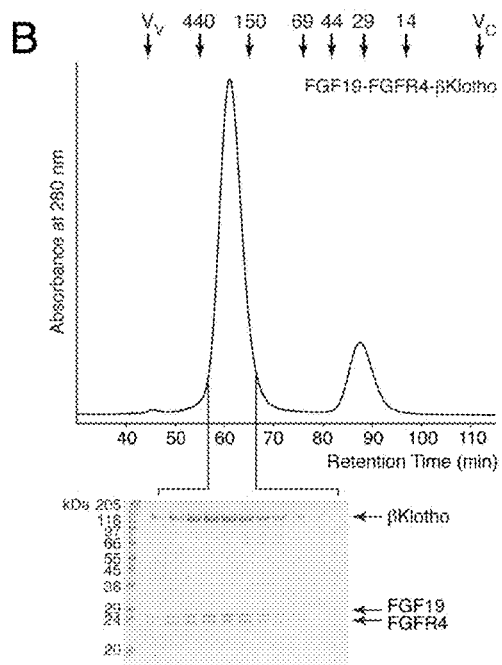
Figures 3A, 3B, 3C, 3D, 3E, 3F, 3G:
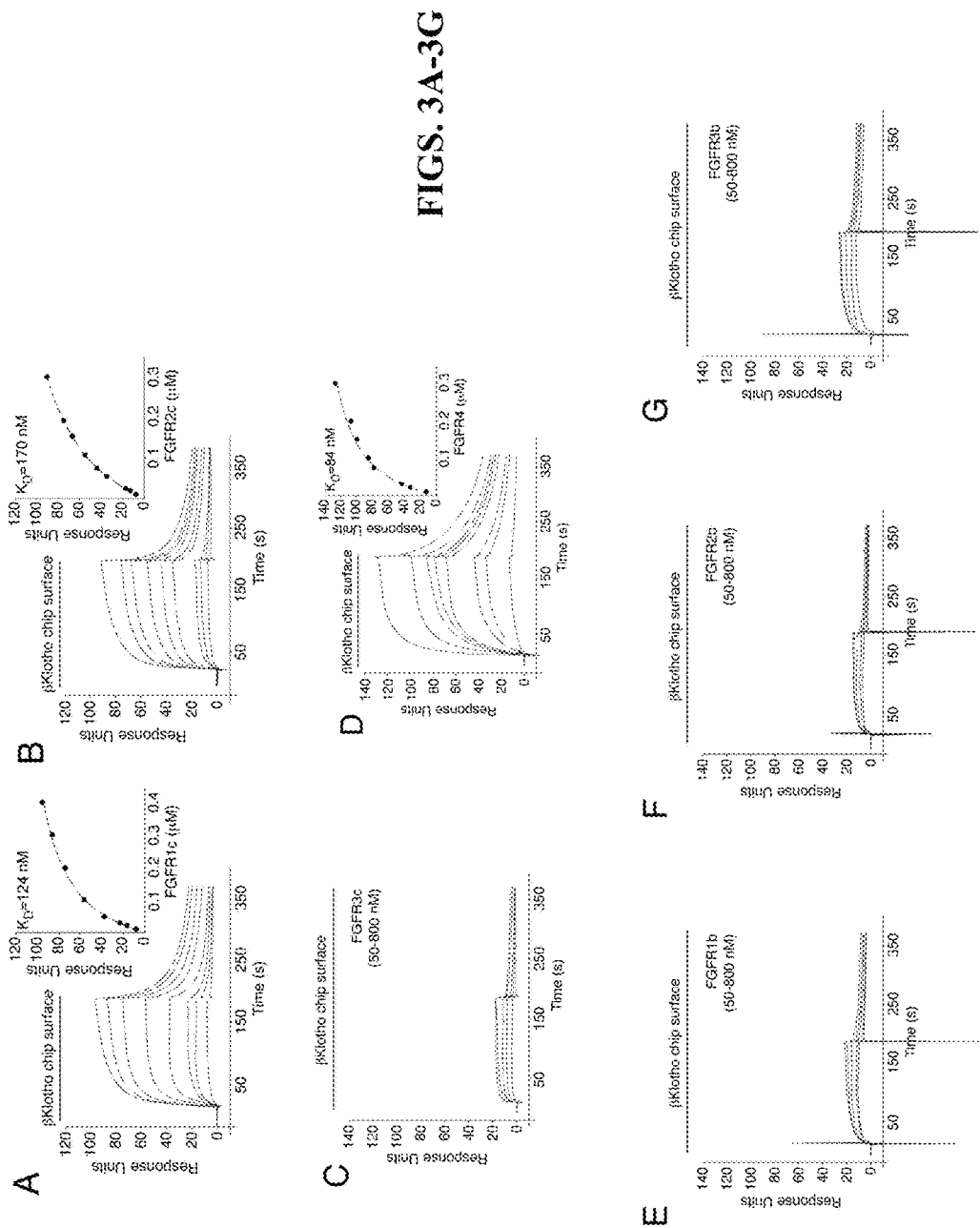
FIGS. 3A-3G show the FGFR binding specificity profile of βKlotho.

Example 1—Klotho Co-Receptors Use Different Mechanisms to Promote Binding of Endocrine FGF Ligands to Cognate FGFRs The protein-protein interactions leading to the formation of the ternary complex between FGF23, FGFR1c, and αKlotho were previously characterized (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). It was shown that the ectodomain of αKlotho possesses a high-affinity binding site for the ligand-binding domain of FGFR1c but not for the FGF23 ligand (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety), and that the preformed binary FGFR1c-αKlotho complex binds avidly to FGF23 (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). It was concluded that FGF23 binds to a de novo binding site generated at the composite FGFR1c-αKlotho interface. The region on FGF23 that binds to this site was mapped to the C-terminal tail that follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). Here it was explored whether βKlotho uses the same mechanism to promote binding of FGF19 and FGF21 to FGFR4 and FGFR1c, the principal cognate FGFRs of these ligands. It was first examined whether the FGF21-FGFR1c-βKlotho ternary complex can be reconstituted in solution in the same manner as the FGF23-FGFR1c-αKlotho complex. To form FGFR1c-βKlotho binary complex, conditioned media from a HEK293 cell line ectopically expressing murine βKlotho ectodomain (F53 to L995 of SEQ ID NO: 218) was applied to an affinity column containing the ligand-binding domain of FGFR1c (D142 to R365 of SEQ ID NO: 221). The FGFR1c-βKlotho complex eluted from the column was purified further by size-exclusion chromatography (FIG. 1A). To examine ternary complex formation, the FGFR1c-βKlotho complex was mixed with FGF21 (H29 to S209 of SEQ ID NO: 100), and the mixture was applied to a size-exclusion column. As shown in FIG. 1B, FGF21 coeluted with FGFR1c-βKlotho, demonstrating that, similar to FGF23, FGF21 forms a stable ternary complex with the ectodomain of βKlotho and the ligand-binding domain of FGFR1c. Consistent with the gel filtration data, analysis of ternary complex formation by SPR spectroscopy also showed that FGF21 binds the binary FGFR1c-βKlotho complex (FIG. 1C). The SPR analysis further showed that FGF21 does not interact with the FGFR1c-αKlotho complex demonstrating that the interaction between FGF21 and the FGFR1c-βKlotho complex is specific (FIG. 1D). Similar to FGF21, the ternary complex of FGF19 with its cognate receptor (FGFR4) and βKlotho co-receptor could be reconstituted in solution using the ectodomain of βKlotho and the ligand-binding domain of FGFR4 (FIGS. 2A and 2B).

Since the ectodomain of βKlotho forms stable binary complexes with the ligand-binding domains of FGFR1c and FGFR4, it was reasoned that it must contain a high affinity binding site for FGFR1c and FGFR4. To substantiate this and to measure the binding affinity of βKlotho for each of the two receptors, SPR spectroscopy was employed. βKlotho ectodomain was immobilized on a biosensor chip, and increasing concentrations of the ligand-binding domain of either FGFR1c or FGFR4 were passed over the chip. βKlotho bound both receptors with comparably high affinity (FIGS. 3A and 3D), demonstrating that similar to αKlotho, βKlotho contains a high-affinity binding site for its cognate FGFRs.

Figures 4A, 4B, 4C, 4D, 4E:
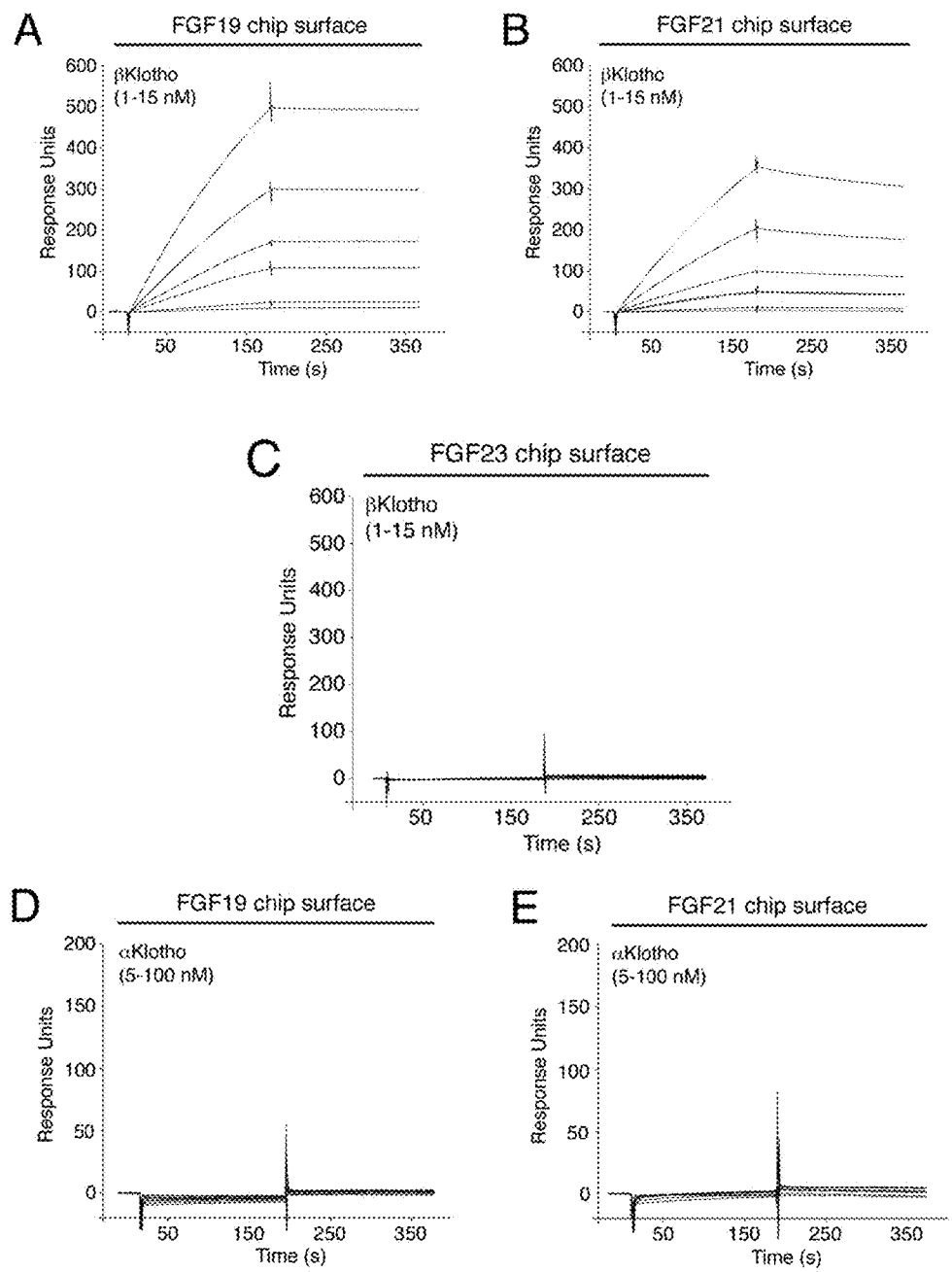
FIGS. 4A-4E show that βKlotho contains a high affinity binding site for FGF19 and FGF21.

For ternary complex formation with FGF19 or FGF21, two possible mechanisms remained open: one was that a de novo binding site for the ligand was generated in the context of the binary βKlotho-FGFR complex as in the case of ternary complex formation between αKlotho, FGF23, and FGFR; the other possibility was that βKlotho contained a distinct high affinity binding site for the ligand. In order to distinguish between these two mechanisms, it was examined, by SPR spectroscopy, whether βKlotho directly binds to FGF19 and FGF21, respectively. FGF19 and FGF21 and as a specificity control, FGF23 were immobilized on a biosensor chip, and increasing concentrations of the ectodomain of βKlotho were passed over the chip. Both FGF19 and FGF21 bound strongly to βKlotho (FIGS. 4A and 4B), whereas no interaction was observed between FGF23 and βKlotho (FIG. 4C). To further confirm the specificity of the interaction, increasing concentrations of the ectodomain of αKlotho were passed over the chip. Neither FGF19 nor FGF21 bound to αKlotho (FIGS. 4D and 4E). Together, the data show that in contrast to αKlotho, βKlotho possesses distinct high-affinity binding sites for cognate endocrine FGF ligand and FGFR, indicating that βKlotho promotes ternary complex formation by engaging FGF ligand and FGFR simultaneously.

Example 2—βKlotho Binding Site on FGF19 and FGF21 Maps to the C-Terminal Region of Each Ligand It was next investigated which sequences of FGF19 and FGF21 bind to βKlotho. A clue to the location of the βKlotho binding site on FGF19 and FGF21 came from the previous finding that the binding site on FGF23 for the binary FGFR-αKlotho complex resides in the C-terminal region of FGF23 that follows the n-trefoil core domain (Goetz et al., "Molecular Insights into the Klotho-Dependent, Endocrine Mode of Action of Fibroblast Growth Factor 19 Subfamily Members," *Mol Cell Biol* 27(9):3417-3428 (2007), which is hereby incorporated by reference in its entirety). Subsequent studies suggested that the same region in FGF19 and FGF21 mediates binding of these ligands to βKlotho. Specifically, it was shown that a chimera of FGF19 with the C-terminal tail of FGF21 was able to bind βKlotho and gradual deletion of C-terminal residues of FGF21 resulted in progressively reduced binding affinity for βKlotho (Wu et al., "C-terminal Tail of FGF19 Determines its Specificity Toward Klotho Co-receptors," *J Biol Chem* 283(48):33304-33309 (2008); Yie et al., "FGF21 N- and C-termini Play Different Roles in Receptor Interaction and Activation," *FEBS Lett* 583(1):19-24 (2009); Micanovic et al., "Different Roles of N- and C-termini in the Functional Activity of FGF21," *J Cell Physiol* 219(2):227-234 (2009), which are hereby incorporated by reference in their entirety). In order to unambiguously demonstrate that the βKlotho-binding site on FGF19 and FGF21 resides in the C-terminal region of each ligand, the C-terminal tail peptides of FGF19 (FGF19$^{C\text{-}tail}$; M171 to K216 of SEQ ID NO: 1) and FGF21 (FGF21$^{C\text{-}tail}$; P168 to S209 of SEQ ID NO: 100) were expressed and purified. It was then examined, by SPR spectroscopy, whether each peptide can compete with full-length ligand for binding to βKlotho. FGF19 and FGF21 were immobilized on a biosensor chip, and mixtures of a fixed concentration of βKlotho ectodomain with increasing concentrations of either FGF19$^{C\text{-}tail}$ or FGF21$^{C\text{-}tail}$ were passed over the chip. As shown in FIG. 5B, FGF19$^{C\text{-}tail}$ competed, in a dose-dependent fashion, with FGF19 for binding to βKlotho. Similarly, FGF21$^{C\text{-}tail}$ competed with FGF21 for binding to βKlotho (FIG. 5E). To confirm that the interaction between βKlotho and the C-terminal tail of FGF19 or FGF21 is specific, βKlotho ectodomain was mixed with a 2-fold molar excess of the C-terminal tail peptide of FGF23 (FGF23$^{C\text{-}tail}$), and the mixture was passed over the FGF19/21 chip. As expected, FGF23$^{C\text{-}tail}$ did not interfere with βKlotho binding to immobilized FGF19 or FGF21 (FIGS. 5D and 5G). Together, the data conclusively show that the C-terminal region of FGF19 and FGF21 contains the βKlotho-binding site.

Example 3—FGF19 and FGF21 Share a Common Binding Site on βKlotho

Since both FGF19 and FGF21 bind to βKlotho, it raised the question whether these ligands bind to a shared site on βKlotho or whether each ligand has its own distinct binding site. To answer this, an SPR-based competition binding assay as described above was employed to examine whether the isolated C-terminal tail peptide of FGF19 can compete with full-length FGF21 for binding to βKlotho, and conversely, whether the C-terminal tail peptide of FGF21 can compete with full-length FGF19 for binding to βKlotho. As shown in FIG. 5F, FGF19$^{C\text{-}tail}$ effectively competed with FGF21 for binding to βKlotho. Similarly, FGF21$^{C\text{-}tail}$ was capable of inhibiting βKlotho binding to FGF19 (FIG. 5C). These data show that FGF19 and FGF21 have overlapping binding sites on βKlotho.

To provide biological evidence for the in vitro finding that FGF19 and FGF21 bind to a shared binding site on βKlotho, it was next examined whether the FGF19$^{C\text{-}tail}$ peptide and the FGF21$^{C\text{-}tail}$ peptide are both able to block FGF19 signaling in cells. H4IIE hepatoma cells, which endogenously express βKlotho and FGFR4 (Kurosu et al., "Tissue-specific Expression of betaKlotho and Fibroblast Growth Factor (FGF) Receptor Isoforms Determines Metabolic Activity of FGF19 and FGF21," *J Biol Chem* 282:26687-26695 (2007), which is hereby incorporated by reference in its entirety), were pretreated with FGF19$^{C\text{-}tail}$ or FGF21$^{C\text{-}tail}$ and then stimulated with FGF19. As shown in FIGS. 6A and 6B, both FGF19$^{C\text{-}tail}$ and FGF21$^{C\text{-}tail}$ inhibited, in a dose-dependent fashion, FGF19-induced tyrosine phosphorylation of FRS2a and downstream activation of MAP kinase cascade. As expected, neither of the two peptides elicited any signaling response when applied alone (FIGS. 6A and 6B). These data show that the C-terminal tail peptides of FGF19 and FGF21 are interchangeable in inhibiting the signaling of FGF19, and provide cell-based evidence that FGF19 and FGF21 share a common binding site on βKlotho. Importantly, the binding site overlap may provide a molecular mechanism for why transgenic expression or therapeutic administration of FGF19 produces beneficial effects on glucose and lipid metabolism resembling those elicited by FGF21 (Fu et al., "Fibroblast Growth Factor 19 Increases Metabolic Rate and Reverses Dietary and Leptin-deficient Diabetes," *Endocrinology* 145:2594-2603 (2004); Tomlinson et al., "Transgenic Mice Expressing Human Fibroblast Growth Factor-19 Display Increased Metabolic Rate and Decreased Adiposity," *Endocrinology* 143:1741-1747 (2002), which are hereby incorporated by reference in their entirety).

Example 4—FGF19 Binds βKlotho with Greater Affinity than FGF21

It was next asked whether FGF19 and FGF21 bind with similar affinity to the common site on βKlotho or whether the two ligands have different binding affinities for βKlotho. A quantitative analysis of the SPR data shows that the FGF19 C-terminal tail peptide is more potent than the FGF21 C-terminal tail peptide at inhibiting binding of βKlotho to full-length FGF19 or FGF21. Specifically, an equimolar amount of FGF19$^{C\text{-}tail}$ relative to βKlotho already yielded nearly complete inhibition of βKlotho binding to FGF19 or FGF21 (FIGS. 5B and 5F), whereas a 10- to 20-fold molar excess of FGF21$^{C\text{-}tail}$ over βKlotho was needed to achieve a similar effect (FIGS. 5C and 5E). These data indicate that the C-terminal tail of FGF19 binds βKlotho with greater affinity than the C-terminal tail of FGF21 suggesting that primary sequence differences at this region account for the observed difference in binding affinity of the two ligands for βKlotho.

Comparison of the C-terminal tail sequences of FGF19 and FGF21 shows a significant degree of sequence similarity (40% amino acid identity) only in the last twenty residues (FIG. 5A; see also FIG. 8B), pointing to these residues as the major binding epitope for βKlotho. To test this possibility, the nineteen most C-terminal residues in FGF21 were swapped with the corresponding residues of FGF19, including a one-residue insertion (FIG. 12, FGF21$^{C\text{-}tail}$ variant 19-45), and it was examined, by SPR spectroscopy, whether the chimeric FGF21 protein (termed FGF21$^{29\text{-}190}$/FGF19$^{197\text{-}216}$; SEQ ID NO: 206) is more potent than wild-type FGF21 at inhibiting binding of βKlotho to immobilized FGF21. As shown in FIGS. 7B and 7C, an equimolar amount of FGF21$^{29\text{-}190}$/FGF19$^{197\text{-}216}$ chimera relative to βKlotho yielded nearly complete inhibition of βKlotho binding to immobilized FGF21, whereas the same molar ratio of wild-type FGF21 to βKlotho produced at best half-maximum inhibition (FIGS. 7A and 7C). These data show that the exchange of unique residues in the distal portion of the C-terminal tail of FGF21 for the corresponding residues of FGF19 confers increased binding affinity to βKlotho on FGF21. In other words, the sequence from M197 to K216 of FGF19 contains residues that contribute to the higher βKlotho-binding affinity of FGF19 compared to FGF21.

The biological significance of the differential binding affinities of FGF19 and FGF21 for βKlotho was next explored. Since FGF19 binds βKlotho with greater affinity than FGF21 does, FGF19 would out-compete FGF21 for βKlotho if both FGF ligands were present in target tissue at the same time. Under physiological conditions, FGF19 and FGF21 do not appear to equally coexist in the blood circulation (Badman et al., "Hepatic Fibroblast Growth Factor 21 is Regulated by PPARalpha and is a Key Mediator of Hepatic Lipid Metabolism in Ketotic States," *Cell Metab* 5:426-437 (2007); Galman et al., "The Circulating Metabolic Regulator FGF21 is Induced by Prolonged Fasting and PPARalpha Activation in Man," *Cell Metab* 8:169-174 (2008); Holt et al., "Definition of a Novel Growth Factor-dependent Signal Cascade for the Suppression of Bile Acid Biosynthesis," *Genes Dev* 17:1581-1591 (2003); Inagaki et al., "Fibroblast Growth Factor 15 Functions as an Enterohepatic Signal to Regulate Bile Acid Homeostasis," *Cell Metab* 2:217-225 (2005); Inagaki et al., "Endocrine Regulation of the Fasting Response by PPARalpha-mediated Induction of Fibroblast Growth Factor 21," *Cell Metab* 5:415-425 (2007); Tong et al., "Transcriptional Repressor E4-binding Protein 4 (E4BP4) Regulates Metabolic Hormone Fibroblast Growth Factor 21 (FGF21) During Circadian Cycles and Feeding," *J Biol Chem* 285:36401-36409 (2010), which are hereby incorporated by reference in their entirety). It was speculated that the high affinity interaction between FGF19 and βKlotho, together with the binding preference of βKlotho for FGFR4, ensure that most of the postprandially secreted FGF19 acts on the liver (and the gall bladder) and hence becomes trapped in the enterohepatic circulation. Importantly, these findings have provided for the rational design of an FGF21 agonist, as follows.

Figures 8A, 8B:
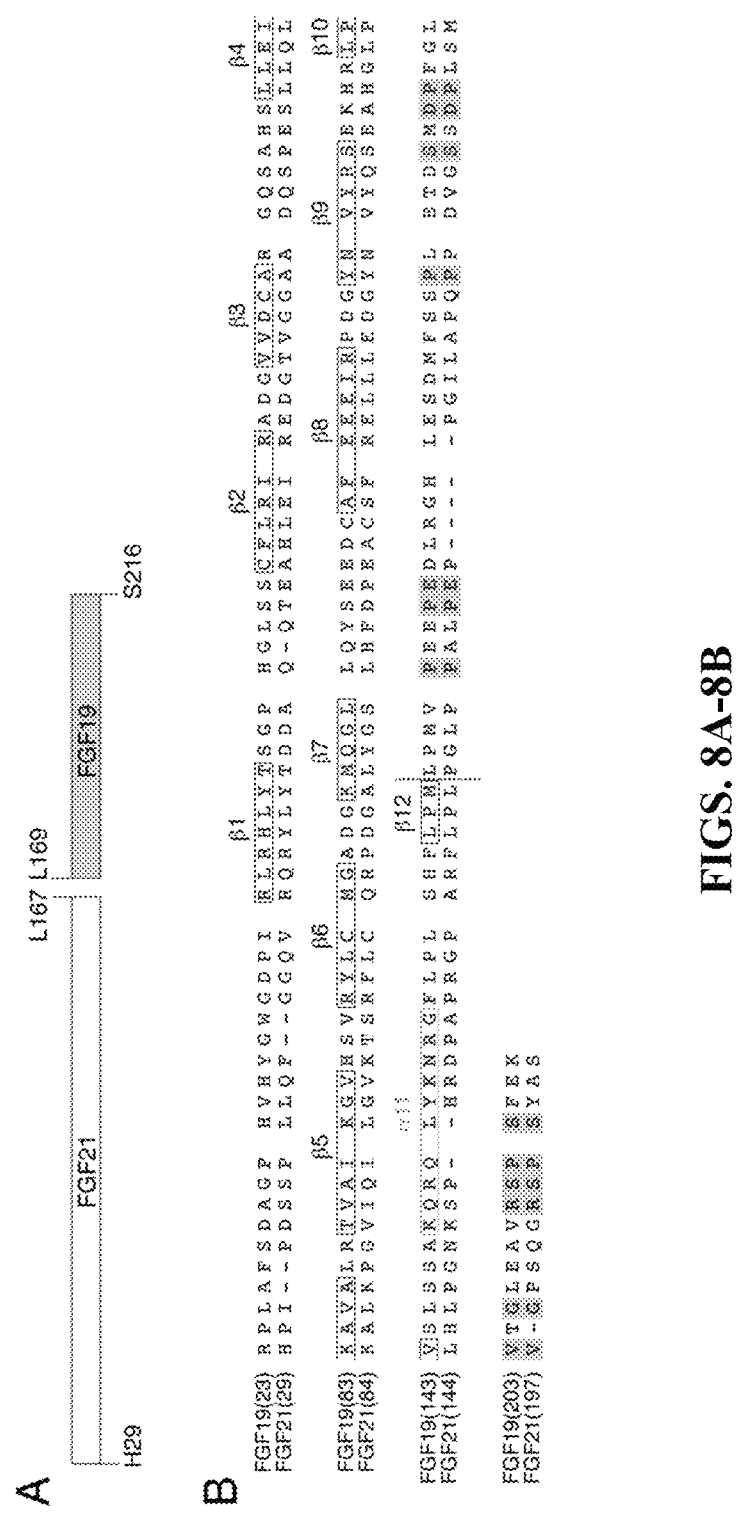

Example 5—Chimera Composed of a N-Terminal Portion of FGF21 and a C-Terminal Portion of FGF19 Exhibits Enhanced Binding Affinity for the FGFR1c-βKlotho Complex Based on these findings, it was reasoned that variants of FGF21 in which C-terminal residues unique to FGF21 were replaced with the corresponding residues of FGF19 should have enhanced binding affinity for βKlotho compared to native FGF21, and hence agonist potency. To begin to explore this, residues located in the distal portion of the C-terminal tail of FGF21 were progressively mutated, namely residues within the sequence from S191 to S209, since this region is essential in determining the ligand's binding affinity for βKlotho (FIG. 7). Specifically, a single mutant of FGF21 (Y207F; FIG. 11, FGF21$^{C\text{-}tail}$ variant 19-3), a triple mutant of FGF21 (Y207F/A208E/S209K; FIG. 12, FGF21$^{C\text{-}tail}$ variant 19-36), and a chimeric FGF21 protein in which the twelve most C-terminal residues in FGF21 were swapped with the corresponding residues of FGF19, including a one-residue insertion, (termed FGF21$^{29\text{-}197}$/FGF19$^{204\text{-}216}$; SEQ ID NO: 205; FIG. 12, FGF21$^{C\text{-}tail}$ variant 19-41) were made. The FGF21$^{29\text{-}190}$/FGF19$^{197\text{-}216}$ chimera (SEQ ID NO: 206; see FIG. 12, FGF21$^{C\text{-}tail}$ variant 19-45), which is discussed above, was also included in these studies. In this chimera, the entire sequence from S191 to S209 of FGF21 is replaced by the corresponding sequence of FGF19 (FIG. 12, FGF21$^{C\text{-}tail}$ variant 19-45), and it was shown that this chimera exhibits enhanced binding affinity for βKlotho compared to native FGF21 (FIG. 7). A chimera in which the entire C-terminal tail of FGF21 was exchanged for the corresponding region of FGF19 (termed FGF21$^{29\text{-}167}$/FGF19$^{169\text{-}216}$; SEQ ID NO: 207; FIG. 8A) was used as a control.

To test whether the FGF21 mutant or chimeric proteins exhibit agonist potency, a SPR-based competition binding assay was employed. A competition binding assay was selected over a direct binding assay because its binding data are not confounded by the effects that the coupling of one binding partner to the chip might have. Specifically, it was examined whether a mutant or chimera can compete with native FGF21 for binding to the FGFR1c-βKlotho complex. If a mutant or chimera had greater affinity for the FGFR1c-βKlotho complex than native FGF21, and hence agonist potency, it would out-compete native FGF21 for binding to FGFR1c-βKlotho. FGF21 was immobilized on a biosensor chip, and mixtures of a fixed concentration of FGFR1c-βKlotho complex with increasing concentrations of either FGF21 mutant or FGF21/FGF19 chimera were passed over the chip. As a control, competition of FGF21 in solution with immobilized FGF21 for binding to the FGFR1c-βKlotho complex was studied.

Figures 14A, 14B, 14C, 14D:
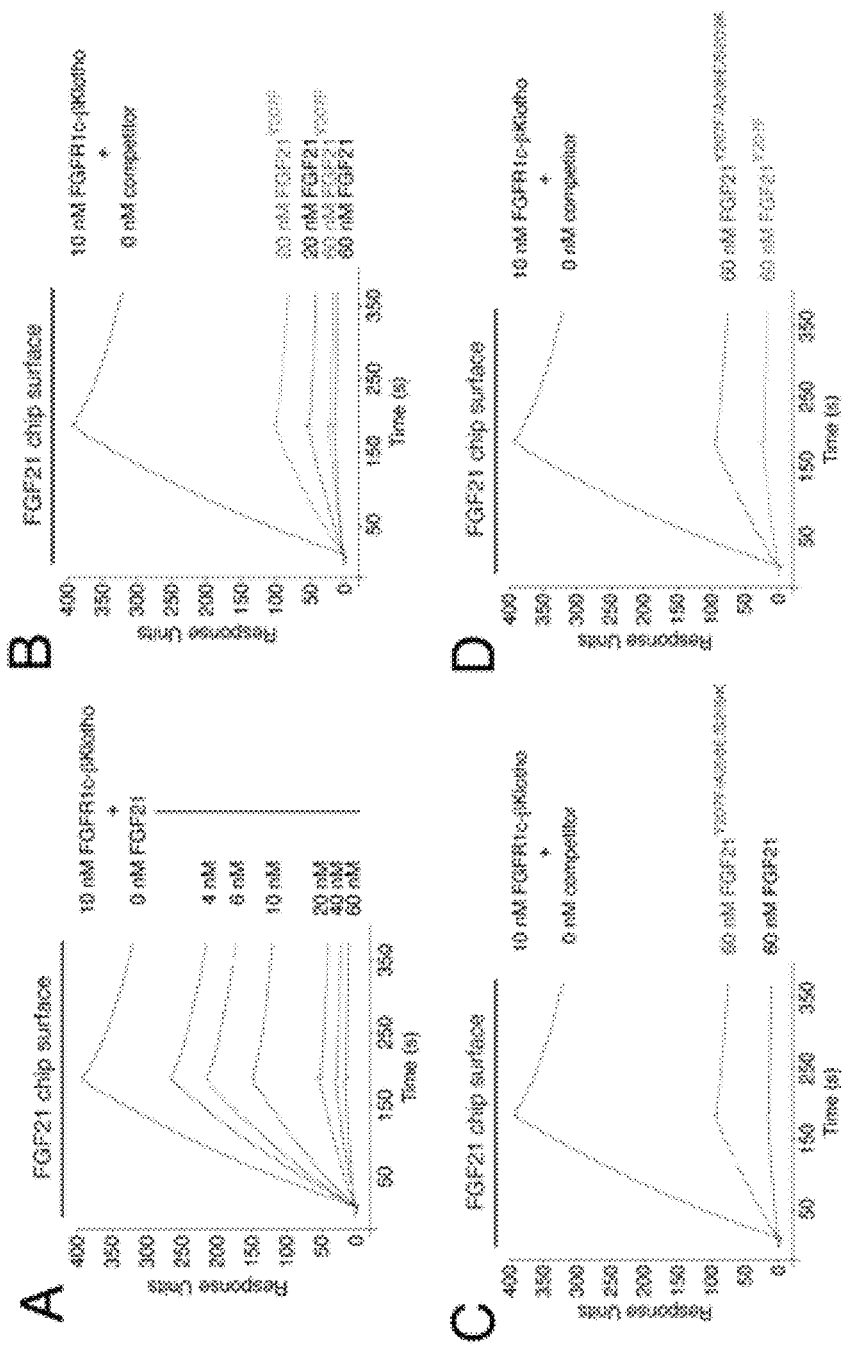
FIGS. 14A-14D show that substitution of the last three residues at the C-terminus of FGF21 for the corresponding residues of FGF19 reduces the binding affinity of FGF21 for the FGFR1c-βKlotho complex.
Figures 15A, 15B, 15C, 15D, 15E, 15F:
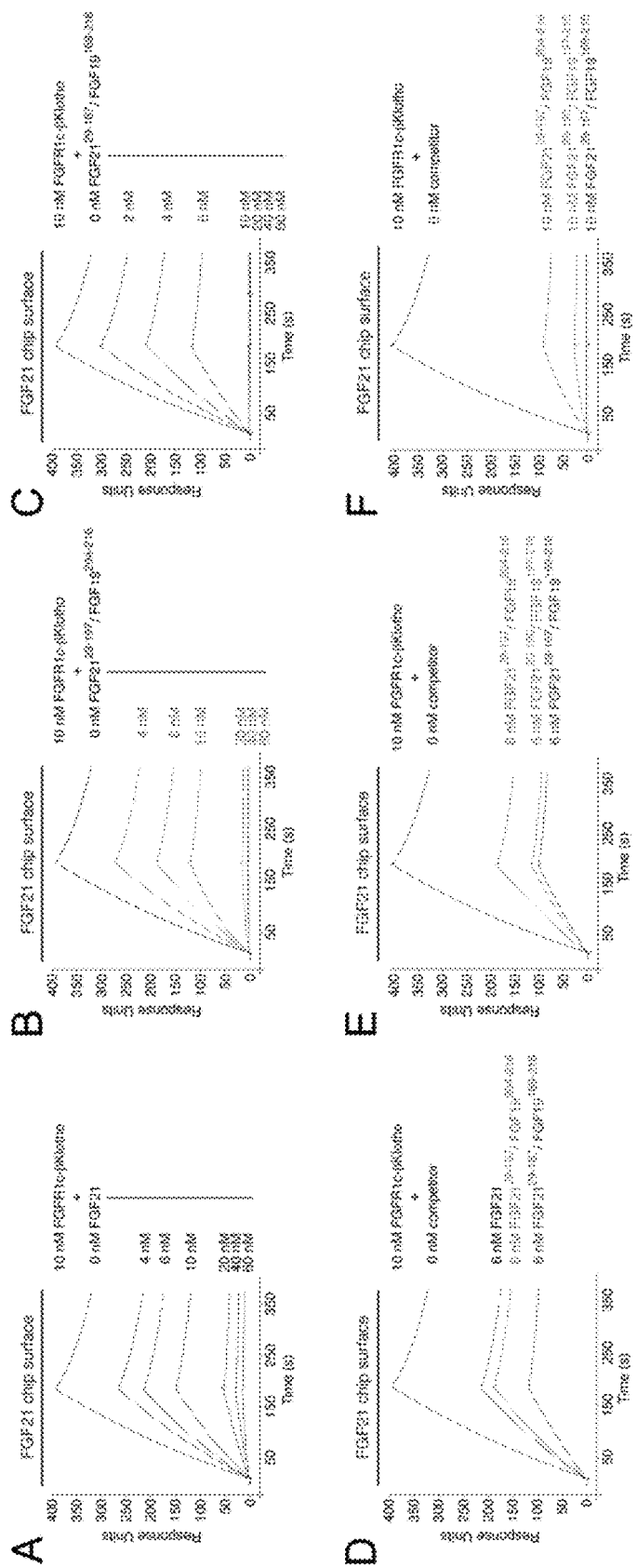
FIGS. 15A-15F show that FGF21/FGF19 chimeras have enhanced binding affinity for the FGFR1c-βKlotho complex.

As expected, FGF21 in solution competed, in a dose-dependent fashion, with immobilized FGF21 for binding to the FGFR1c-βKlotho complex (FIGS. 14A and 15A). The Y207F mutant of FGF21 was a weaker competitor than wild-type FGF21 for binding to the FGFR1c-βKlotho complex (FIG. 14B), suggesting that the mutant had reduced affinity for FGFR1c-βKlotho compared to wild-type FGF21. The Y207F/A208E/S209K triple mutant of FGF21 was even less potent than the Y207F single mutant at inhibiting binding of the FGFR1c-βKlotho complex to immobilized wild-type FGF21 (FIGS. 14C and 14D). These data indicate that the triple mutation causes an even greater loss in binding affinity of FGF21 for FGFR1c-βKlotho than the single mutation.

Based on these findings, it was concluded that replacing Y207 in FGF21 with phenylalanine of FGF19 reduces rather than enhances the binding affinity of FGF21 for βKlotho, and the combined replacement of Y207, A208, and S209 for the corresponding residues of FGF19 has an even greater negative impact on the binding affinity of FGF21 for βKlotho. In contrast to those two mutants of FGF21, all three FGF21/FGF19 chimeras proved to be more potent competitors than native FGF21 for binding to the FGFR1c-βKlotho complex (FIGS. 15A-15F). At any given concentration tested, the FGF21$^{29\text{-}197}$/FGF19$^{204\text{-}216}$ chimera caused greater inhibition of FGFR1c-βKlotho binding to the FGF21 chip surface than native FGF21 did (FIGS. 15A, 15B, and 15D), suggesting that it has increased affinity for FGFR1c-βKlotho compared to native FGF21. The FGF21$^{29\text{-}190}$/FGF19$^{197\text{-}216}$ chimera, which harbors four additional amino acid substitutions in the distal portion of the C-terminal tail of FGF21 compared to the FGF21$^{29\text{-}197}$/FGF19$^{204\text{-}216}$ chimera (FIG. 12), exhibited a further increased binding affinity for FGFR1c-βKlotho; at any given dose, it inhibited binding of FGFR1c-βKlotho to immobilized FGF21 to a substantially greater degree than the FGF21$^{29\text{-}197}$/FGF19$^{204\text{-}216}$ chimera (FIGS. 15E and 15F). For example, an equimolar amount of FGF21$^{29\text{-}190}$/FGF19$^{197\text{-}216}$ chimera relative to FGFR1c-βKlotho complex yielded nearly complete inhibition of FGFR1c-βKlotho binding to immobilized FGF21, whereas the same molar ratio of FGF21$^{29\text{-}197}$/FGF19$^{204\text{-}216}$ chimera to FGFR1c-βKlotho produced at best 75% inhibition (FIG. 15F). These data show that a substantial further increase in binding affinity for FGFR1c-βKlotho was achieved by introducing four amino acid substitutions in the FGF21 sequence from S191 to V197 in addition to replacing the unique residues C-terminal to V197 with the analogous residues of FGF19. The FGF21$^{167}$/FGF19$^{169\text{-}216}$ chimera in which the entire C-terminal tail of FGF21 was exchanged for the corresponding region of FGF19 was only slightly more potent than the FGF21$^{29\text{-}190}$/FGF19$^{197\text{-}216}$ chimera at inhibiting binding of FGFR1c-βKlotho to immobilized FGF21 (FIGS. 15E and 15F). Thus, the major increase in binding affinity for FGFR1c-βKlotho was obtained by replacing the C-terminal sequence from S191 to S209 in FGF21 with the analogous sequence of FGF19.

Together, the data show that an FGF21 agonist can be engineered by replacing C-terminal sequences in FGF21 with the corresponding sequences of FGF19. Increased binding affinity for βKlotho underlies the agonist potency of an FGF21/FGF19 chimera. Based on the findings with the triple mutant of FGF21, it was speculated that replacing the sequence from S191 to S206 in FGF21 with the analogous sequence of FGF19 might be sufficient to confer similar binding affinity for βKlotho on FGF21 as FGF19 has. Moreover, it is thought that replacing poorly conserved residues in the C-terminal region of FGF19 might further enhance the binding affinity of FGF19 itself for βKlotho (FIGS. 10 and 13).

Example 6—Chimera Composed of a N-Terminal Portion of FGF21 and a C-Terminal Portion of FGF19 Acts as an FGF21 Agonist in a Cell-Based Assay The FGF21$^{29\text{-}167}$/FGF19$^{169\text{-}216}$ chimera, which has proved the most potent among the three FGF21/FGF19 chimeras in the competition binding experiments, was then selected for analysis of agonist potency and efficacy in a cell-based assay. Specifically, the ability of the chimera to activate FGFR1c in a βKlotho-dependent fashion in HEK293 cells co-expressing FGFR1c and βKlotho was examined. Induction of protein expression of Egr1, a known downstream mediator of FGF signaling, was used as readout for FGFR1c activation. As shown in FIG. 17A, the FGF21$^{29\text{-}167}$/FGF19$^{169\text{-}216}$ chimera induced, in a dose-dependent fashion, Egr1 protein expression. The effect became evident at a 10-fold lower concentration of chimera than native FGF21 (FIG. 17A). The dose-response curve for the FGF21$^{29\text{-}167}$/FGF19$^{169\text{-}216}$ chimera obtained from quantitative analysis of the data shown in FIG. 17A was markedly shifted to the left compared to the dose-response curve for native FGF21 (FIG. 17B). The maximum signaling responses were similar, however. These data show that the FGF21/FGF19 chimera exhibits greater potency than native FGF21, which is consistent with the SPR results.

Figures 18A, 18B, 18C:
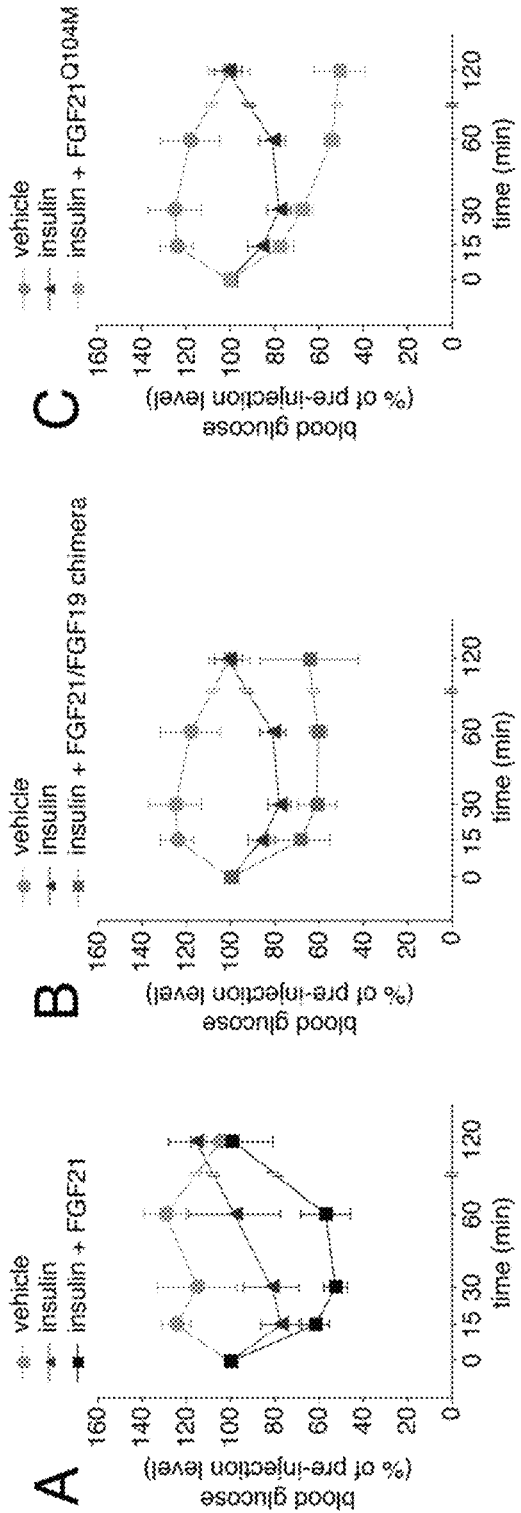
FIGS. 18A-18C show that a FGF21/FGF19 chimera and a single mutant of FGF21 harboring Q104M substitution in the core domain exhibit prolonged potentiating effects on insulin-induced hypoglycemia.

Example 7—Chimera Composed of a N-Terminal Portion of FGF21 and a C-Terminal Portion of FGF19 Acts as an FGF21 Agonist In Vivo These findings prompted examination of whether the FGF21$^{29\text{-}167}$/FGF19$^{169\text{-}216}$ chimera exhibits FGF21 agonist activity in vivo. Specifically, insulin tolerance was used as pharmacodynamic marker, and it was analyzed whether the chimera can potentiate the hypoglycemic effect of exogenous insulin in mice. As shown in FIGS. 18A and 18B, the FGF21$^{29\text{-}167}$/FGF19$^{169\text{-}216}$ chimera increased the hypoglycemic effect of insulin to a similar degree as native FGF21 did. However, the effect of the chimera persisted for at least twice as long as that of native FGF21 (FIGS. 18A and 18B). These data show that compared to native FGF21, the FGF21/FGF19 chimera has a prolonged potentiating effect on insulin-induced hypoglycemia, which is indicative of agonist potency.

Example 8—Mutant FGF21 Harboring Q104M Substitution in the Core Domain Acts as an FGF21 Agonist In Vitro and In Vivo In a second approach of engineering an FGF21 agonist, glutamine at position 104 in FGF21 was mutated to methionine in order to increase the thermal stability of the n-trefoil core domain of FGF21 (FGF21$^{Q104M}$, SEQ ID NO: 152). Except for FGF21, all FGF ligands have a methionine residue at the position analogous to Q104 of FGF21 (Mohammadi et al., "Structural Basis for Fibroblast Growth Factor Receptor Activation," *Cytokine & Growth Factor Rev* 16(2):107-137 (2005), which is hereby incorporated by reference in its entirety). Together with other hydrophobic residues, the methionine forms the interior hydrophobic core of an FGF ligand's n-trefoil core domain. The key role the methionine plays in providing stabilizing interactions in the hydrophobic core is evidenced by the fact that its replacement with threonine as it naturally occurs in FGF23 dramatically reduces protein stability (FIGS. 16A-E), and leads to disease (Chefetz et al., "A Novel Homozygous Missense Mutation in FGF23 Causes Familial Tumoral Calcinosis Associated with Disseminated Visceral Calcification," *Hum Genet* 118(2):261-266 (2005), which is hereby incorporated by reference in its entirety).

Figures 16A, 16B, 16C, 16D, 16E:
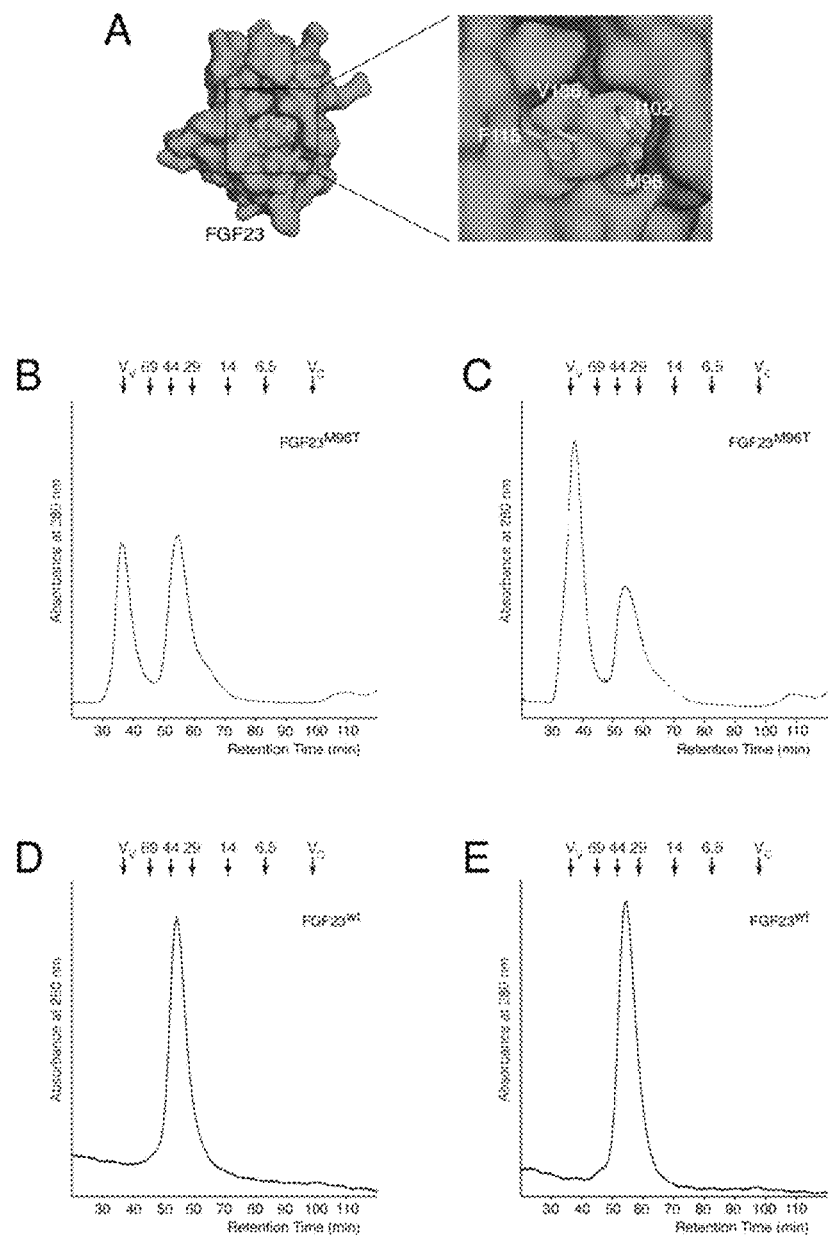
FIGS. 16A-16E show that substitution of methionine at position 96 for threonine in FGF23 (SEQ ID NO: 224), as it occurs in Familial Tumoral Calcinosis (Chefetz et al., "A Novel Homozygous Missense Mutation in FGF23 Causes Familial Tumoral Calcinosis Associated with Disseminated Visceral Calcification," *Hum Genet* 118(2):261-266 (2005), which is hereby incorporated by reference in its entirety), destabilizes the FGF23 protein.

In particular, as shown in FIGS. 16A-E, substitution of methionine at position 96 for threonine in FGF23 (SEQ ID NO: 224), as it occurs in Familial Tumoral Calcinosis (Chefetz et al., "A Novel Homozygous Missense Mutation in FGF23 Causes Familial Tumoral Calcinosis Associated with Disseminated Visceral Calcification," *Hum Genet* 118 (2):261-266 (2005), which is hereby incorporated by reference in its entirety), destabilizes the FGF23 protein. FIG. 16A shows a molecular surface representation of the FGF23 crystal structure (PDB ID: 2P39; Goetz et al., "Molecular Insights into the Klotho-Dependent, Endocrine Mode of Action of Fibroblast Growth Factor 19 Subfamily Members," *Mol Cell Biol* 27:3417-3428 (2007), which is hereby incorporated by reference in its entirety). A close-up view into the hydrophobic interior core of FGF23's n-trefoil core domain showing some of the key hydrophobic side chains is shown on the right, and a view of the whole structure is shown on the left. Note that M96 makes numerous hydrophobic contacts with its neighboring residues such as I102, F115, and V136 in the n-trefoil core of FGF23. The M96T substitution would weaken these hydrophobic contacts leading to thermal instability of the FGF23 protein. FIG. 16B shows a size-exclusion chromatogram of the M96T mutant of FGF23 analyzed immediately after Ni-chelating affinity purification. FIG. 16C shows a size-exclusion chromatogram of the M96T mutant of FGF23 analyzed following incubation at 4° C. for 24 hours. FIG. 16D shows a size-exclusion chromatogram of wild-type FGF23 immediately following protein purification. FIG. 16E shows a size-exclusion chromatogram of purified wild-type FGF23 following incubation at 4° C. for 24 hours. Arrows in FIGS. 16B-E indicate the retention times of molecular size standards, the void volume ($V_v$) and the column volume ($V_c$). Note that, in contrast to wild-type FGF23, there is a substantial increase in the portion of M96T mutant protein eluting in the void volume indicating that the mutant protein unfolds over time.

Thus, it was reasoned that substituting Q104 of FGF21 for methionine would confer greater stability on FGF21, and hence increase the half-life of the FGF21 protein in the blood circulation. Owing to its increased half-life compared to wild-type FGF21, the Q104M mutant might exhibit agonist potency.

To test this, a cell-based assay was first employed. Specifically, it was analyzed whether the mutant protein can activate FGFR1c in a βKlotho-dependent fashion in HEK293 cells co-expressing FGFR1c and βKlotho. Induction of protein expression of Egr1, a known downstream mediator of FGF signaling, was used as readout for FGFR1c activation. As shown in FIG. 17A, the Q104M mutant of FGF21 induced, in a dose-dependent fashion, Egr1 protein expression. The induction of Egr1 protein expression by the FGF21 mutant was already detectable at a concentration of 30 ng ml$^{-1}$, whereas a more than 3-fold greater concentration of wild-type FGF21 was needed to see a similar effect (FIG. 17A). The dose-response curve for the FGF21 mutant obtained from quantitative analysis of the data shown in FIG. 17A was shifted to the left compared to the dose-response curve for wild-type FGF21, and the maximum response for the mutant was greater than that for wild-type FGF21 (FIG. 17C). These data show that the Q104M mutant of FGF21 exhibits greater potency and efficacy than native FGF21.

These findings prompted examination of whether the Q104M mutant of FGF21 acts as an FGF21 agonist in vivo. Insulin tolerance was used as pharmacodynamic marker, and it was tested whether the mutant can potentiate the hypoglycemic effect of exogenous insulin in mice. As shown in FIGS. 18A and 18C, the Q104M mutant of FGF21 increased the hypoglycemic effect of insulin to a similar degree as wild-type FGF21 did. However, the effect of the mutant persisted for at least twice as long as that of wild-type FGF21, and tended to further increase with time (FIGS. 18A and 18C). These data show that compared to wild-type FGF21, the Q104M mutant of FGF21 has a prolonged potentiating effect on insulin-induced hypoglycemia, which is indicative of agonist potency.

Although the invention has been described in detail for the purposes of illustration, it is understood that such detail is solely for that purpose, and variations can be made therein by those skilled in the art without departing from the spirit and scope of the invention, which is defined by the following claims.

What is claimed:

1. A β-Klotho binding agent comprising:
   a fibroblast growth factor 21 (FGF21) protein comprising the amino acid sequence of amino acid residues 29 to 209 of SEQ ID NO: 152.

2. The agent according to claim 1, wherein the FGF21 protein consists of the amino acid sequence of amino acid residues 29 to 209 SEQ ID NO: 152.

3. The agent according to claim 2, wherein the agent consists of said FGF21 protein.

4. A pharmaceutical composition comprising:
   the agent of claim 1 and
   a pharmaceutically-acceptable carrier.

5. The pharmaceutical composition of claim 4 further comprising:
   an anti-inflammatory agent, an antifibrotic agent, an anti-hypertensive agent, an antidiabetic agent, a triglyceride-lowering agent, and/or a cholesterol-lowering agent.

6. A method for decreasing blood glucose level in a subject, said method comprising:
   selecting a subject and
   administering to said selected subject an effective amount of the agent of claim 1 to decrease blood glucose level in the selected subject.

7. The method according to claim 6, wherein the selected subject has diabetes, obesity, or metabolic syndrome.

8. The method according to claim 7, wherein the selected subject has diabetes.

9. The method according to claim 8, wherein the selected subject has type II diabetes, gestational diabetes, or drug-induced diabetes.

10. The method according to claim 8, wherein the selected subject has type I diabetes.

11. The method according to claim 7, wherein the selected subject has obesity.

12. The method according to claim 7, wherein the selected subject has metabolic syndrome.

13. The method according to claim 6, wherein said administering is carried out parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

14. The method according to claim 6, wherein the protein is administered with a pharmaceutically-acceptable carrier.

15. The method according to claim 6, wherein the selected subject is a mammal.

16. The method according to claim 15, wherein the selected subject is a human.

17. A β-Klotho binding agent comprising:
    a fibroblast growth factor 21 (FGF21) protein comprising the amino acid sequence of amino acid residues 29 to 209 of SEQ ID NO: 152 having a proline to valine substitution at amino acid residue 171.

18. The agent according to claim 17, wherein the FGF21 protein consists of the amino acid sequence of amino acid residues 29 to 209 SEQ ID NO: 152 having a proline to valine substitution at amino acid residue 171.

19. The agent according to claim 18, wherein the agent consists of said FGF21 protein.

20. A pharmaceutical composition comprising:
    the agent of claim 17 and
    a pharmaceutically-acceptable carrier.

21. The pharmaceutical composition of claim 20 further comprising:
    an anti-inflammatory agent, an antifibrotic agent, an anti-hypertensive agent, an antidiabetic agent, a triglyceride-lowering agent, and/or a cholesterol-lowering agent.

22. A method for decreasing blood glucose level in a subject, said method comprising:
    selecting a subject and
    administering to said selected subject an effective amount of the agent of claim 17 to decrease blood glucose level in the selected subject.

23. The method according to claim 22, wherein the selected subject has diabetes, obesity, or metabolic syndrome.

24. The method according to claim 23, wherein the selected subject has diabetes.

25. The method according to claim 24, wherein the selected subject has type II diabetes, gestational diabetes, or drug-induced diabetes.

26. The method according to claim 24, wherein the selected subject has type I diabetes.

27. The method according to claim 23, wherein the selected subject has obesity.

28. The method according to claim 23, wherein the selected subject has metabolic syndrome.

29. The method according to claim 22, wherein said administering is carried out parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

30. The method according to claim 22, wherein the protein is administered with a pharmaceutically-acceptable carrier.

31. The method according to claim 22, wherein the selected subject is a mammal.

32. The method according to claim 31, wherein the selected subject is a human.

* * * * *

UNITED STATES PATENT AND TRADEMARK OFFICE
CERTIFICATE OF CORRECTION

PATENT NO. : 10,174,090 B2
APPLICATION NO. : 15/283862
DATED : January 8, 2019
INVENTOR(S) : Mohammadi et al.

It is certified that error appears in the above-identified patent and that said Letters Patent is hereby corrected as shown below:

In the Specification

Column 1 at Lines 13-16, delete "This invention was made with government support under DE13686, DK077276, AG019712, DK091392, and KD067158 awarded by the National Institutes of Health. The Government has certain rights in the invention."

And insert:
--This invention was made with government support under R01 DK067158, DK077276, R01 DE013686, AG019712, and DK091392 awarded by the National Institutes of Health. The government has certain rights in the invention.--

Signed and Sealed this
Twenty-eighth Day of October, 2025

John A. Squires
*Director of the United States Patent and Trademark Office*